United States Patent
Jin et al.

(10) Patent No.: US 10,711,000 B2
(45) Date of Patent: Jul. 14, 2020

(54) AUTOTAXIN INHIBITORS AND USES THEREOF

(71) Applicant: Fronthera U.S. Pharmaceuticals LLC, San Diego, CA (US)

(72) Inventors: Bohan Jin, San Diego, CA (US); Qing Dong, San Diego, CA (US); Gene Hung, San Diego, CA (US); Yao Li, Chengdu (CN)

(73) Assignee: FRONTHERA U.S. PHARMACEUTICALS LLC, San Diego, CA (US)

( * ) Notice: Subject to any disclaimer, the term of this patent is extended or adjusted under 35 U.S.C. 154(b) by 0 days.

(21) Appl. No.: 16/509,300

(22) Filed: Jul. 11, 2019

(65) Prior Publication Data

US 2019/0367515 A1 Dec. 5, 2019

Related U.S. Application Data

(63) Continuation of application No. PCT/CN2019/089025, filed on May 29, 2019.

(60) Provisional application No. 62/731,003, filed on Sep. 13, 2018, provisional application No. 62/677,459, filed on May 29, 2018.

(51) Int. Cl.
| | | |
|---|---|---|
| *C07D 471/04* | (2006.01) | |
| *C07D 519/00* | (2006.01) | |
| *A61P 11/00* | (2006.01) | |
| *A61P 17/00* | (2006.01) | |
| *A61K 9/48* | (2006.01) | |
| *A61K 9/00* | (2006.01) | |
| *A61K 47/20* | (2006.01) | |

(52) U.S. Cl.
CPC .......... *C07D 471/04* (2013.01); *A61K 9/0019* (2013.01); *A61K 9/0056* (2013.01); *A61P 11/00* (2018.01); *A61P 17/00* (2018.01); *C07D 519/00* (2013.01)

(58) Field of Classification Search
CPC ..... C07D 471/04; C07D 519/00; A61P 17/00; A61P 11/00; A61K 9/0056; A61K 9/0019; A61K 9/4866; A61K 9/006; A61K 47/20
See application file for complete search history.

(56) References Cited

FOREIGN PATENT DOCUMENTS

| | | |
|---|---|---|
| WO | WO-2014139882 A1 | 9/2014 |
| WO | WO-2014202458 A1 | 12/2014 |
| WO | WO-2019014308 A1 | 1/2019 |
| WO | WO-2019158107 A1 | 8/2019 |
| WO | WO-2019223721 A1 | 11/2019 |

OTHER PUBLICATIONS

Wermuth, C. G.,"Molecular variations based on isosteric replacements." The Practice of Medicinal Chemistry 2 Ch. 13 (1996); p. 203-237.*
WO 2019/158107 A1; WIPO English Machine Translation; p. 1-520.*
Desroy et al. Discovery of 2-[]2-Ethyl-6-[4-[2-(3-hydroxyazetidin-1-yl)-2-oxoethyl]piperazin-1-yl]-8-methylimidazo[1,2-a]pyridin-3-yl]methylamino]-4-(4-fluorophenyl)thiazole-5-carbonitrile (GLPG1690), a First-in-Class Autotaxin Inhibitor Undergoing Clinical Evaluation for the Treatment of Idiopathic Pulmonary Fibrosis. J Med Chem 60(9):3580-3590 (2017).
PCT/CN2019/089025 International Search Report and Written Opinion dated Sep. 5, 2019.

* cited by examiner

*Primary Examiner* — John M Mauro
(74) *Attorney, Agent, or Firm* — Wilson Sonsini Goodrich & Rosati

(57) ABSTRACT

Described herein are methods and compositions for the treatment of conditions, diseases, or disorders associated with autotaxin activity. The methods and compositions disclosed herein include the use of at least one autotaxin inhibitor compound.

20 Claims, No Drawings

AUTOTAXIN INHIBITORS AND USES THEREOF

CROSS-REFERENCE

This application is a continuation of PCT International Application No. PCT/CN2019/089025, filed May 29, 2019, which claims the benefit of U.S. Provisional Application No. 62/677,459, filed May 29, 2018 and U.S. Provisional Application No. 62/731,003, filed Sep. 13, 2018; each of which is incorporated herein by reference in their entirety.

FIELD OF THE INVENTION

Described herein are methods of using autotaxin inhibitors, and pharmaceutical compositions and medicaments thereof, in the treatment of conditions, diseases, or disorders associated with autotaxin activity.

BACKGROUND OF THE INVENTION

Autotaxin (ATX), also known as ectonucleotide pyrophosphatase/phosphodiesterase family member 2 or ENPP2, is an adipocyte secreted lysophospholipase D that catalyzes the formation of the lipid mediator, lysophosphatidic acid (LPA). Autotaxin expression is enhanced in individuals with certain conditions or diseases.

BRIEF SUMMARY OF THE INVENTION

Autotaxin (ATX), also known as ectonucleotide pyrophosphatase/phosphodiesterase family member 2 (ENPP2), is a secreted lysophospholipase D (lysoPLD) that cleaves choline from lysophosphatidylcholine (LPC) forming lysophosphatidic acid (LPA), a potent mitogen and motily factor that has been implicated in the pathophysiology of cancer and many other biological processes such as vascular development lymphocyte homing and inflammation. LPA consists of a single fatty acyl chain, a glycerol backbone and a free phosphate group. The great variety of cellular and biological actions of LPA is explained by the fact that the six known LPA receptors show broad tissue expression and can couple to at least six distinct G proteins, which, in turn, feed into multiple effector systems.

ATX is processed along the classical export pathway and secreted as a catalytically active glycoprotein. ATX's major lipid substrate, LPC, is secreted by the liver and is abundantly present in plasma and interstitial fluids.

Disclosed herein is a compound of Formula (I'), or a pharmaceutically acceptable salt, solvate, or stereoisomer thereof:

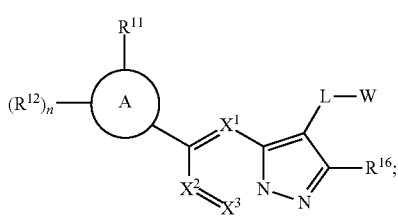

Formula (I')

wherein:
$X^1$ is N or $CR^{13}$;
$X^2$ is N or $CR^{14}$;
$X^3$ is N or $CR^{15}$;

W is

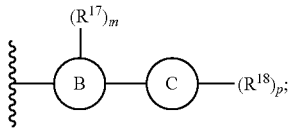

Ring A is cycloalkyl, heterocycloalkyl, aryl, or heteroaryl;
Ring B is cycloalkyl, heterocycloalkyl, aryl, or heteroaryl;
Ring C is cycloalkyl, heterocycloalkyl, aryl, or heteroaryl;
L is —O—, —S—, or —NR$^{19}$—;
$R^{11}$ is $L^1$-$R^{20}$;
$L^1$ is absent or $C_1$-$C_6$ alkylene optionally substituted with deuterium, halogen, —CN, —OR$^a$, —NR$^c$R$^d$, —C(=O)OR$^a$, or —C(=O)NR$^c$R$^d$;
$R^{20}$ is halogen, —CN, —OR$^{21}$, —SR$^{21}$, —S(=O)R$^{22}$, —S(=O)$_2$R$^{22}$, —NO$_2$, —NR$^{23}$R$^{24}$, —NR$^{21}$S(=O)$_2$R$^{22}$, —S(=O)$_2$NR$^{23}$R$^{24}$, —C(=O)R$^{22}$, —OC(=O)R$^{22}$, —C(=O)C(=O)R$^{22}$, —C(=O)OR$^{21}$, —C(=O)NR$^{21}$OR$^{21}$, —OC(=O)OR$^{21}$, —C(=O)NR$^{23}$R$^{24}$, —OC(=O)NR$^{23}$R$^{24}$, —NR$^{21}$C(=O)NR$^{23}$R$^{24}$, —NR$^{21}$S(=O)$_2$ NR$^{23}$R$^{24}$, —NR$^{21}$C(=O)R$^{22}$, —NR$^{21}$C(=O) OR$^{21}$, $C_1$-$C_6$ alkyl, cycloalkyl, heterocycloalkyl, aryl, or heteroaryl; wherein the alkyl, cycloalkyl, heterocycloalkyl, aryl, and heteroaryl are independently optionally substituted with one, two, or three $R^1$;
each $R^{21}$ is independently hydrogen, —CN, $C_1$-$C_6$ alkyl, cycloalkyl, heterocycloalkyl, aryl, or heteroaryl; wherein the alkyl, cycloalkyl, heterocycloalkyl, aryl, and heteroaryl are independently optionally substituted with one, two, or three $R^{1a}$;
$R^{22}$ is hydrogen, —CN, $C_1$-$C_6$ alkyl, cycloalkyl, heterocycloalkyl, aryl, or heteroaryl; wherein the alkyl, cycloalkyl, heterocycloalkyl, aryl, and heteroaryl are independently optionally substituted with one, two, or three $R^{1b}$;
$R^{23}$ and $R^{24}$ are independently hydrogen, $C_1$-$C_6$ alkyl, cycloalkyl, heterocycloalkyl, aryl, or heteroaryl;
wherein the alkyl, cycloalkyl, heterocycloalkyl, aryl, and heteroaryl are independently optionally substituted with one, two, or three $R^{1c}$;
or $R^{23}$ and $R^{24}$ are taken together with the nitrogen atom to which they are attached to form a heterocycloalkyl optionally substituted with one, two, or three $R^{1d}$;
each $R^{12}$ is independently deuterium, halogen, —CN, —OR$^a$, —NR$^c$R$^d$, —C(=O)OR$^a$, —C(=O)NR$^c$R$^d$, $C_1$-$C_6$ alkyl, cycloalkyl, heterocycloalkyl, aryl, or heteroaryl; wherein the alkyl, cycloalkyl, heterocycloalkyl, aryl, and heteroaryl are independently optionally substituted with one, two, or three $R^2$;
or two $R^{12}$ on the same carbon are taken together to form an oxo;
$R^{13}$ is hydrogen, deuterium, halogen, —CN, —OR$^a$, —NR$^c$R$^d$, —C(=O)OR$^a$, —C(=O)NR$^c$R$^d$, $C_1$-$C_6$ alkyl, cycloalkyl, heterocycloalkyl, aryl, or heteroaryl; wherein the alkyl, cycloalkyl, heterocycloalkyl, aryl, and heteroaryl are independently optionally substituted with one, two, or three $R^3$;
$R^{14}$ is hydrogen, deuterium, halogen, —CN, —OR$^a$, —NR$^c$R$^d$, —C(=O)OR$^a$, —C(=O)NR$^c$R$^d$, $C_1$-$C_6$ alkyl, cycloalkyl, heterocycloalkyl, aryl, or heteroaryl; wherein the alkyl, cycloalkyl, heterocycloalkyl, aryl, and heteroaryl are independently optionally substituted with one, two, or three $R^4$;

$R^{15}$ is hydrogen, deuterium, halogen, —CN, —OR$^a$, —NR$^c$R$^d$, —C(=O)OR$^a$, —C(=O)NR$^c$R$^d$, C$_1$-C$_6$ alkyl, cycloalkyl, heterocycloalkyl, aryl, or heteroaryl; wherein the alkyl, cycloalkyl, heterocycloalkyl, aryl, and heteroaryl are independently optionally substituted with one, two, or three R$^5$;

or R$^{14}$ and R$^{15}$ are taken together to form a cycloalkyl or heterocycloalkyl; wherein the cycloalkyl and heterocycloalkyl are independently optionally substituted with one, two, or three R$^6$;

$R^{16}$ is hydrogen, deuterium, halogen, —CN, —OR$^a$, —NR$^c$R$^d$, —C(=O)OR$^a$, —C(=O)NR$^c$R$^d$, C$_1$-C$_6$ alkyl, cycloalkyl, heterocycloalkyl, aryl, or heteroaryl; wherein the alkyl, cycloalkyl, heterocycloalkyl, aryl, and heteroaryl are independently optionally substituted with one, two, or three R$^7$;

each $R^{17}$ is independently deuterium, halogen, —CN, —OR$^a$, —NR$^c$R$^d$, —C(=O)R$^a$, —C(=O)OR$^a$, —C(=O)NR$^c$R$^d$, —NR$^a$C(=O)R$^b$, C$_1$-C$_6$ alkyl, cycloalkyl, heterocycloalkyl, aryl, or heteroaryl; wherein the alkyl, cycloalkyl, heterocycloalkyl, aryl, and heteroaryl are independently optionally substituted with one, two, or three R$^8$;

or two R$^{17}$ on the same carbon are taken together to form an oxo;

each $R^{18}$ is independently deuterium, halogen, —CN, —OR$^a$, —NR$^c$R$^d$, —C(=O)R$^a$, —C(=O)OR$^a$, —C(=O)NR$^c$R$^d$, —NR$^a$C(=O)R$^b$, C$_1$-C$_6$ alkyl, cycloalkyl, heterocycloalkyl, aryl, or heteroaryl; wherein the alkyl, cycloalkyl, heterocycloalkyl, aryl, and heteroaryl are independently optionally substituted with one, two, or three R$^9$;

or two R$^{18}$ on the same carbon are taken together to form an oxo;

$R^{19}$ is hydrogen, —S(=O)R$^b$, —S(=O)$_2$R$^b$, —S(=O)$_2$NR$^c$R$^d$, —C(=O)R$^b$, —C(=O)OR$^a$, —C(=O)NR$^c$R$^d$, C$_1$-C$_6$ alkyl, C$_1$-C$_6$ haloalkyl, C$_1$-C$_6$ heteroalkyl, cycloalkyl, or heterocycloalkyl;

each R$^{1a}$, R$^{1b}$, R$^{1c}$, and R$^{1d}$ are independently oxo, halogen, —CN, —OR$^a$, —S(=O)$_2$R$^b$, —NR$^c$R$^d$, —S(=O)$_2$NR$^c$R$^d$, —C(=O)R$^b$, —OC(=O)R$^b$, —C(=O)OR$^a$, —OC(=O)OR$^a$, —C(=O)NR$^c$R$^d$, —OC(=O)NR$^c$R$^d$, —NR$^a$C(=O)NR$^c$R$^d$, —NR$^a$C(=O)R$^b$, C$_1$-C$_6$ alkyl, C$_1$-C$_6$ haloalkyl, C$_1$-C$_6$ hydroxyalkyl, or phenyl;

each $R^1$ is independently oxo, halogen, —CN, —OR$^a$, —NR$^c$R$^d$, —C(=O)OR$^a$, —C(=O)R$^a$, —C(=O)NR$^c$R$^d$, —S(=O)$_2$R$^b$, C$_1$-C$_6$ alkyl, cycloalkyl, heterocycloalkyl, or phenyl; wherein the alkyl, cycloalkyl, heterocycloalkyl, and phenyl are independently optionally substituted with one, two, or three halogen, —OH, —NH$_2$, C$_1$-C$_6$ alkyl, or phenyl;

each $R^2$, $R^3$, $R^4$, $R^5$, $R^6$, $R^7$, $R^8$, and $R^9$ are independently oxo, halogen, —CN, —OR$^a$, —NR$^c$R$^d$, —C(=O)OR$^a$, —C(=O)R$^a$, —C(=O)NR$^c$R$^d$, —S(=O)$_2$R$^b$, C$_1$-C$_6$ alkyl, cycloalkyl, heterocycloalkyl, or phenyl; wherein the alkyl, cycloalkyl, heterocycloalkyl, and phenyl are independently optionally substituted with one, two, or three halogen, —OH, —NH$_2$, C$_1$-C$_6$ alkyl, or phenyl;

each R$^a$ is independently hydrogen, C$_1$-C$_6$ alkyl, cycloalkyl, heterocycloalkyl, aryl, or heteroaryl; wherein the alkyl, cycloalkyl, heterocycloalkyl, aryl, and heteroaryl are independently optionally substituted with one, two, or three halogen, —OH, —NH$_2$, or C$_1$-C$_6$ alkyl;

each R$^b$ is independently C$_1$-C$_6$ alkyl, cycloalkyl, heterocycloalkyl, aryl, or heteroaryl; wherein the alkyl, cycloalkyl, heterocycloalkyl, aryl, and heteroaryl are independently optionally substituted with one, two, or three halogen, —OH, —NH$_2$, or C$_1$-C$_6$ alkyl;

each R$^c$ and R$^d$ are independently hydrogen, C$_1$-C$_6$ alkyl, cycloalkyl, heterocycloalkyl, aryl, or heteroaryl; wherein the alkyl, cycloalkyl, heterocycloalkyl, aryl, and heteroaryl are independently optionally substituted with one, two, or three halogen, —OH, —NH$_2$, or C$_1$-C$_6$ alkyl;

or R$^c$ and R$^d$ are taken together with the nitrogen atom to which they are attached to form a heterocycloalkyl optionally substituted with one, two, or three halogen, —OH, —NH$_2$, or C$_1$-C$_6$ alkyl;

n is 0-3;

m is 0-3; and p is 0-3.

Also disclosed herein are compounds of Formula (Ia), or a pharmaceutically acceptable salt, solvate, or stereoisomer thereof:

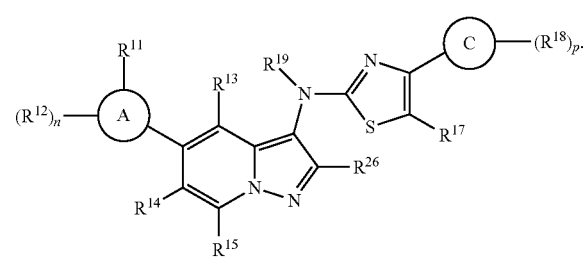

Formula (Ia)

Also disclosed herein are compounds of Formula (Ib), or a pharmaceutically acceptable salt, solvate, or stereoisomer thereof:

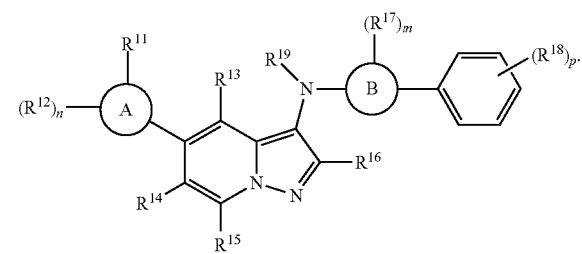

Formula (Ib)

Also disclosed herein are compounds of Formula (Ic), or a pharmaceutically acceptable salt, solvate, or stereoisomer thereof:

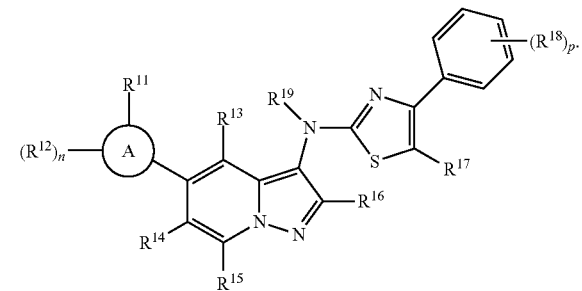

Formula (Ic)

Also disclosed herein are compounds of Formula (Id), or a pharmaceutically acceptable salt, solvate, or stereoisomer thereof:

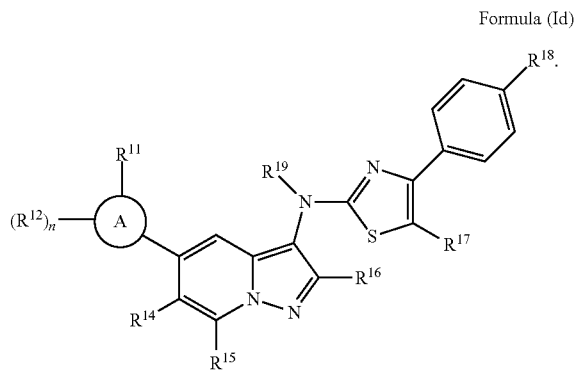

Formula (Id)

Also disclosed herein is a pharmaceutical composition comprising a therapeutically effective amount of a compound disclosed herein, and a pharmaceutically acceptable excipient.

Also disclosed herein is a method of treating fibrotic diseases, cancers, inflammatory diseases, autoimmune diseases, respiratory diseases, cardiovascular diseases, neurological diseases, and metabolic diseases, the method comprising administering a therapeutic amount of a compound disclosed herein or a pharmaceutical composition disclosed herein.

Also disclosed herein is a method of treating Idiopathic Pulmonary Fibrosis (IPF), scleroderma, or nonalcoholic steatohepatitis (NASH), the method comprising administering a therapeutic amount of a compound disclosed herein or a pharmaceutical composition disclosed herein.

Also disclosed herein is a method of treating Idiopathic Pulmonary Fibrosis (IPF), the method comprising administering a therapeutic amount of a compound disclosed herein or a pharmaceutical composition disclosed herein.

Also disclosed herein is a method of treating scleroderma, the method comprising administering a therapeutic amount of a compound disclosed herein or a pharmaceutical composition disclosed herein.

Also disclosed herein is a method of treating nonalcoholic steatohepatitis (NASH), the method comprising administering a therapeutic amount of a compound disclosed herein or a pharmaceutical composition disclosed herein.

INCORPORATION BY REFERENCE

All publications, patents, and patent applications mentioned in this specification are herein incorporated by reference for the specific purposes identified herein.

DETAILED DESCRIPTION OF THE INVENTION

Definitions

As used herein and in the appended claims, the singular forms "a," "and," and "the" include plural referents unless the context clearly dictates otherwise. Thus, for example, reference to "an agent" includes a plurality of such agents, and reference to "the cell" includes reference to one or more cells (or to a plurality of cells) and equivalents thereof known to those skilled in the art, and so forth. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range, in some instances, will vary between 1% and 15% of the stated number or numerical range. The term "comprising" (and related terms such as "comprise" or "comprises" or "having" or "including") is not intended to exclude that in other certain embodiments, for example, an embodiment of any composition of matter, composition, method, or process, or the like, described herein, "consist of" or "consist essentially of" the described features.

As used in the specification and appended claims, unless specified to the contrary, the following terms have the meaning indicated below.

"Alkyl" refers to a straight or branched chain hydrocarbon monoradical, which may be fully saturated or unsaturated, having from one to about ten carbon atoms, or from one to six carbon atoms. Examples of saturated hydrocarbon monoradical include, but are not limited to, methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, sec-butyl, t-butyl, n-pentyl, isopentyl, neopentyl, tert-amyl and hexyl, and longer alkyl groups, such as heptyl, octyl, and the like. Whenever it appears herein, a numerical range such as "$C_1$-$C_6$ alkyl" means that the alkyl group consists of 1 carbon atom, 2 carbon atoms, 3 carbon atoms, 4 carbon atoms, 5 carbon atoms or 6 carbon atoms, although the present definition also covers the occurrence of the term "alkyl" where no numerical range is designated. In some embodiments, the alkyl is a $C_1$-$C_{10}$ alkyl, a $C_1$-$C_9$ alkyl, a $C_1$-$C_8$ alkyl, a $C_1$-$C_7$ alkyl, a $C_1$-$C_6$ alkyl, a $C_1$-$C_5$ alkyl, a $C_1$-$C_4$ alkyl, a $C_1$-$C_3$ alkyl, a $C_1$-$C_2$ alkyl, or a $C_1$ alkyl. When the alkyl refers to an unsaturated straight or branched chain hydrocarbon monoradical it is known as an "alkenyl" or an "alkynyl". The alkenyl may be in either the cis or trans conformation about the double bond(s), and should be understood to include both isomers. Examples of alkenyls include, but are not limited to ethenyl (—CH=$CH_2$), 1-propenyl (—$CH_2$CH=$CH_2$), isopropenyl [—C($CH_3$)=$CH_2$], butenyl, 1,3-butadienyl and the like. Whenever it appears herein, a numerical range such as "$C_2$-$C_6$ alkenyl" means that the alkenyl group may consist of 2 carbon atoms, 3 carbon atoms, 4 carbon atoms, 5 carbon atoms or 6 carbon atoms, although the present definition also covers the occurrence of the term "alkenyl" where no numerical range is designated. In some embodiments, the alkenyl is a $C_2$-$C_{10}$ alkenyl, a $C_2$-$C_9$ alkenyl, a $C_2$-$C_8$ alkenyl, a $C_2$-$C_7$ alkenyl, a $C_2$-$C_6$ alkenyl, a $C_2$-$C_5$ alkenyl, a $C_2$-$C_4$ alkenyl, a $C_2$-$C_3$ alkenyl, or a $C_2$ alkenyl. Examples of alkynyl include, but are not limited to ethynyl, 2-propynyl, 2-butynyl, 1,3-butadiynyl and the like. Whenever it appears herein, a numerical range such as "$C_2$-$C_6$ alkynyl" means that the alkynyl group may consist of 2 carbon atoms, 3 carbon atoms, 4 carbon atoms, 5 carbon atoms or 6 carbon atoms, although the present definition also covers the occurrence of the term "alkynyl" where no numerical range is designated. In some embodiments, the alkynyl is a $C_2$-$C_{10}$ alkynyl, a $C_2$-$C_9$ alkynyl, a $C_2$-$C_8$ alkynyl, a $C_2$-$C_7$ alkynyl, a $C_2$-$C_6$ alkynyl, a $C_2$-$C_5$ alkynyl, a $C_2$-$C_4$ alkynyl, a $C_2$-$C_3$ alkynyl, or a $C_2$ alkynyl. Unless stated otherwise specifically in the specification, an alkyl group is optionally substituted as described below, for example, with oxo, halogen, amino, nitrile, nitro, hydroxyl, haloalkyl, alkoxy, aryl, cycloalkyl, heterocycloalkyl, heteroaryl, and the like. In some embodiments, the alkyl is optionally substituted with oxo, halogen, —CN, —CF$_3$, —OH, —OMe, —NH$_2$, or —NO$_2$. In some embodiments, the alkyl is optionally substituted with oxo, halogen, —CN, —CF$_3$, —OH, or —OMe. In some embodiments, the alkyl is optionally substituted with halogen.

"Alkylene" refers to a straight or branched divalent hydrocarbon chain. Whenever it appears herein, a numerical range such as "$C_1$-$C_6$ alkylene" means that the alkylene consists of 1 carbon atom, 2 carbon atoms, 3 carbon atoms, 4 carbon atoms, 5 carbon atoms, or 6 carbon atoms, although the present definition also covers the occurrence of the term "alkylene" where no numerical range is designated. In some embodiments, the alkylene is a $C_1$-$C_{10}$ alkylene, a $C_1$-$C_9$ alkylene, a $C_1$-$C_8$ alkylene, a $C_1$-$C_7$ alkylene, a $C_1$-$C_6$ alkylene, a $C_1$-$C_5$ alkylene, a $C_1$-$C_4$ alkylene, a $C_1$-$C_3$ alkylene, a $C_1$-$C_2$ alkylene, or a $C_1$ alkylene. Unless stated otherwise specifically in the specification, an alkylene group may be optionally substituted, for example, with oxo, halogen, amino, nitrile, nitro, hydroxyl, haloalkyl, alkoxy, aryl, cycloalkyl, heterocycloalkyl, heteroaryl, and the like. In some embodiments, an alkylene is optionally substituted with oxo, halogen, —CN, —CF$_3$, —OH, —OMe, —NH$_2$, or —NO$_2$. In some embodiments, an alkylene is optionally substituted with oxo, halogen, —CN, —CF$_3$, —OH, or —OMe. In some embodiments, the alkylene is optionally substituted with halogen.

"Alkoxy" refers to a radical of the formula —OR$_a$ where R$_a$ is an alkyl radical as defined. Unless stated otherwise specifically in the specification, an alkoxy group may be optionally substituted, for example, with oxo, halogen, amino, nitrile, nitro, hydroxyl, haloalkyl, alkoxy, aryl, cycloalkyl, heterocycloalkyl, heteroaryl, and the like. In some embodiments, an alkoxy is optionally substituted with oxo, halogen, —CN, —CF$_3$, —OH, —OMe, —NH$_2$, or —NO$_2$. In some embodiments, an alkoxy is optionally substituted with oxo, halogen, —CN, —CF$_3$, —OH, or —OMe. In some embodiments, the alkoxy is optionally substituted with halogen.

"Aryl" refers to a radical derived from a hydrocarbon ring system comprising hydrogen, 6 to 30 carbon atoms and at least one aromatic ring. The aryl radical may be a monocyclic, bicyclic, tricyclic or tetracyclic ring system, which may include fused (when fused with a cycloalkyl or heterocycloalkyl ring, the aryl is bonded through an aromatic ring atom) or bridged ring systems. In some embodiments, the aryl is a 6- to 10-membered aryl. In some embodiments, the aryl is a 6-membered aryl. Aryl radicals include, but are not limited to, aryl radicals derived from the hydrocarbon ring systems of anthrylene, naphthylene, phenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. In some embodiments, the aryl is phenyl. Unless stated otherwise specifically in the specification, an aryl may be optionally substituted, for example, with halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, an aryl is optionally substituted with halogen, methyl, ethyl, —CN, —CF$_3$, —OH, —OMe, —NH$_2$, or —NO$_2$. In some embodiments, an aryl is optionally substituted with halogen, methyl, ethyl, —CN, —CF$_3$, —OH, or —OMe. In some embodiments, the aryl is optionally substituted with halogen.

"Cycloalkyl" refers to a stable, partially or fully saturated, monocyclic or polycyclic carbocyclic ring, which may include fused (when fused with an aryl or a heteroaryl ring, the cycloalkyl is bonded through a non-aromatic ring atom) or bridged ring systems. Representative cycloalkyls include, but are not limited to, cycloalkyls having from three to fifteen carbon atoms ($C_3$-$C_{15}$ cycloalkyl), from three to ten carbon atoms ($C_3$-$C_{10}$ cycloalkyl), from three to eight carbon atoms ($C_3$-$C_8$ cycloalkyl), from three to six carbon atoms ($C_3$-$C_6$ cycloalkyl), from three to five carbon atoms ($C_3$-$C_5$ cycloalkyl), or three to four carbon atoms ($C_3$-$C_4$ cycloalkyl). In some embodiments, the cycloalkyl is a 3- to 6-membered cycloalkyl. In some embodiments, the cycloalkyl is a 5- to 6-membered cycloalkyl. Monocyclic cycloalkyls include, for example, cyclopropyl, cyclobutyl, cyclopentyl, cyclohexyl, cycloheptyl, and cyclooctyl. Polycyclic cycloalkyls or carbocycles include, for example, adamantyl, norbornyl, decalinyl, bicyclo[3.3.0]octane, bicyclo[4.3.0]nonane, cis-decalin, trans-decalin, bicyclo[2.1.1]hexane, bicyclo[2.2.1]heptane, bicyclo[2.2.2]octane, bicyclo[3.2.2]nonane, and bicyclo[3.3.2]decane, and 7,7-dimethyl-bicyclo[2.2.1]heptanyl. Partially saturated cycloalkyls include, for example cyclopentenyl, cyclohexenyl, cycloheptenyl, and cyclooctenyl. Unless stated otherwise specifically in the specification, a cycloalkyl is optionally substituted, for example, with oxo, halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, a cycloalkyl is optionally substituted with oxo, halogen, methyl, ethyl, —CN, —CF$_3$, —OH, —OMe, —NH$_2$, or —NO$_2$. In some embodiments, a cycloalkyl is optionally substituted with oxo, halogen, methyl, ethyl, —CN, —CF$_3$, —OH, or —OMe. In some embodiments, the cycloalkyl is optionally substituted with halogen.

"Halo" or "halogen" refers to bromo, chloro, fluoro or iodo. In some embodiments, halogen is fluoro or chloro. In some embodiments, halogen is fluoro.

"Haloalkyl" refers to an alkyl radical, as defined above, that is substituted by one or more halo radicals, as defined above, e.g., trifluoromethyl, difluoromethyl, fluoromethyl, trichloromethyl, 2,2,2-trifluoroethyl, 1,2-difluoroethyl, 3-bromo-2-fluoropropyl, 1,2-dibromoethyl, and the like.

"Heterocycloalkyl" refers to a stable 3- to 24-membered partially or fully saturated ring radical comprising 2 to 23 carbon atoms and from one to 8 heteroatoms selected from nitrogen, oxygen, phosphorous, and sulfur. Representative heterocycloalkyls include, but are not limited to, heterocycloalkyls having from two to fifteen carbon atoms ($C_2$-$C_{15}$ heterocycloalkyl), from two to ten carbon atoms ($C_2$-$C_{10}$ heterocycloalkyl), from two to eight carbon atoms ($C_2$-$C_8$ heterocycloalkyl), from two to six carbon atoms ($C_2$-$C_6$ heterocycloalkyl), from two to five carbon atoms ($C_2$-$C_5$ heterocycloalkyl), or two to four carbon atoms ($C_2$-$C_4$ heterocycloalkyl). In some embodiments, the heterocycloalkyl is a 3- to 6-membered heterocycloalkyl. In some embodiments, the heterocycloalkyl is a 5- to 6-membered heterocycloalkyl. In some embodiments, the heterocycloalkyl is a 5- to 11-membered spiroheterocycloalkyl. In some embodiments, the heterocycloalkyl is a 5- to 9-membered spiroheterocycloalkyl. In some embodiments, the heterocycloalkyl is a 5- to 7-membered spiroheterocycloalkyl. Unless stated otherwise specifically in the specification, the heterocycloalkyl radical may be a monocyclic, bicyclic, tricyclic or tetracyclic ring system, which may include fused (when fused with an aryl or a heteroaryl ring, the heterocycloalkyl is bonded through a non-aromatic ring atom) or bridged ring systems; and the nitrogen, carbon or sulfur atoms in the heterocycloalkyl radical may be optionally oxidized; the nitrogen atom may be optionally quaternized. Examples of such heterocycloalkyl radicals include, but are not limited to, aziridinyl, azetidinyl, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,1-dioxo-thiomorpholinyl, 1,3-dihydroisobenzofuran-1-yl, 3-oxo-1,3-dihydroisobenzofuran-1-yl, methyl-2-oxo-1,3-dioxol-4-yl, and 2-oxo-1,3-dioxol-4-yl. The term heterocycloalkyl also includes all ring forms of the carbohydrates, including but not limited to the monosaccharides, the disaccharides and the oligosaccharides. Unless otherwise noted, heterocycloalkyls have from 2 to 10 carbons in the ring. It is understood that when referring to the number of carbon atoms in a heterocycloalkyl, the number of carbon atoms in the heterocycloalkyl is not the same as the total number of atoms (including the heteroatoms) that make up the heterocycloalkyl (i.e. skeletal atoms of the heterocycloalkyl ring). Partially saturated heterocycloalkyls include, for example dihydropyrrolyl or tetrahydropyridine. Unless stated otherwise specifically in the specification, a heterocycloalkyl is optionally substituted, for example, with oxo, halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, a heterocycloalkyl is optionally substituted with oxo, halogen, methyl, ethyl, —CN, —CF$_3$, —OH, —OMe, —NH$_2$, or —NO$_2$. In some embodiments, a heterocycloalkyl is optionally substituted with oxo, halogen, methyl, ethyl, —CN, —CF$_3$, —OH, or —OMe. In some embodiments, the heterocycloalkyl is optionally substituted with halogen.

"Heteroalkyl" refers to an alkyl group in which one or more skeletal atoms of the alkyl are selected from an atom other than carbon, e.g., oxygen, nitrogen (e.g. —NH—, —N(alkyl)-), sulfur, or combinations thereof. A heteroalkyl is attached to the rest of the molecule at a carbon atom of the heteroalkyl. In one aspect, a heteroalkyl is a $C_1$-$C_6$ heteroalkyl wherein the heteroalkyl is comprised of 1 to 6 carbon atoms and one or more atoms other than carbon, e.g., oxygen, nitrogen (e.g. —NH—, —N(alkyl)-), sulfur, or combinations thereof wherein the heteroalkyl is attached to the rest of the molecule at a carbon atom of the heteroalkyl. Unless stated otherwise specifically in the specification, a heteroalkyl is optionally substituted, for example, with oxo, halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, a heteroalkyl is optionally substituted with oxo, halogen, methyl, ethyl, —CN, —CF$_3$, —OH, —OMe, —NH$_2$, or —NO$_2$. In some embodiments, a heteroalkyl is optionally substituted with oxo, halogen, methyl, ethyl, —CN, —CF$_3$, —OH, or —OMe. In some embodiments, the heteroalkyl is optionally substituted with halogen.

"Heteroaryl" refers to a 5- to 14-membered ring system radical comprising hydrogen atoms, one to thirteen carbon atoms, one to six heteroatoms selected from nitrogen, oxygen, phosphorous, and sulfur, and at least one aromatic ring. The heteroaryl radical may be a monocyclic, bicyclic, tricyclic or tetracyclic ring system, which may include fused (when fused with a cycloalkyl or heterocycloalkyl ring, the heteroaryl is bonded through an aromatic ring atom) or bridged ring systems; and the nitrogen, carbon or sulfur atoms in the heteroaryl radical may be optionally oxidized; the nitrogen atom may be optionally quaternized. In some embodiments, the heteroaryl is a 5- to 10-membered heteroaryl. In some embodiments, the heteroaryl is a 5- to 6-membered heteroaryl. In some embodiments, the heteroaryl is a 5-membered heteroaryl. In some embodiments, the heteroaryl is a 6-membered heteroaryl. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]clioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e., thienyl). Unless stated otherwise specifically in the specification, a heteroaryl is optionally substituted, for example, with halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, a heteroaryl is optionally substituted with halogen, methyl, ethyl, —CN, —CF$_3$, —OH, —OMe, —NH$_2$, or —NO$_2$. In some embodiments, a heteroaryl is optionally substituted with halogen, methyl, ethyl, —CN, —CF$_3$, —OH, or —OMe. In some embodiments, the heteroaryl is optionally substituted with halogen.

The terms "treat," "prevent," "ameliorate," and "inhibit," as well as words stemming therefrom, as used herein, do not necessarily imply 100% or complete treatment, prevention, amelioration, or inhibition. Rather, there are varying degrees of treatment, prevention, amelioration, and inhibition of which one of ordinary skill in the art recognizes as having a potential benefit or therapeutic effect. In this respect, the disclosed methods can provide any amount of any level of treatment, prevention, amelioration, or inhibition of the disorder in a mammal. For example, a disorder, including symptoms or conditions thereof, may be reduced by, for example, about 100%, about 90%, about 80%, about 70%, about 60%, about 50%, about 40%, about 30%, HTF %, or about 10%. Furthermore, the treatment, prevention, amelioration, or inhibition provided by the methods disclosed herein can include treatment, prevention, amelioration, or inhibition of one or more conditions or symptoms of the disorder, e.g., cancer or an inflammatory disease. Also, for purposes herein, "treatment," "prevention," "amelioration," or "inhibition" encompass delaying the onset of the disorder, or a symptom or condition thereof.

The terms "effective amount" or "therapeutically effective amount," as used herein, refer to a sufficient amount of a compound disclosed herein being administered which will relieve to some extent one or more of the symptoms of the disease or condition being treated, e.g., cancer or an inflammatory disease. In some embodiments, the result is a reduction and/or alleviation of the signs, symptoms, or causes of a disease, or any other desired alteration of a biological system. For example, an "effective amount" for therapeutic uses is the amount of the composition comprising a compound disclosed herein required to provide a clinically significant decrease in disease symptoms. In some embodiments, an appropriate "effective" amount in any individual case is determined using techniques, such as a dose escalation study.

Compounds

Described herein are compounds or pharmaceutically acceptable salts, solvates, or stereoisomers thereof, which are autotaxin inhibitors.

Disclosed herein is a compound of Formula (I'), or a pharmaceutically acceptable salt, solvate, or stereoisomer thereof:

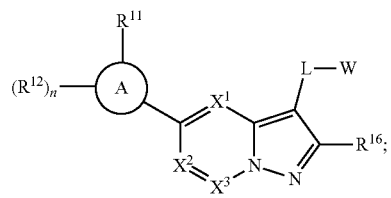

Formula (I')

wherein:
$X^1$ is N or $CR^{13}$;
$X^2$ is N or $CR^{14}$;
$X^3$ is N or $CR^{15}$;
W is

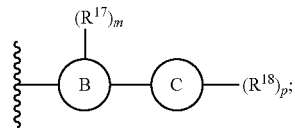

Ring A is cycloalkyl, heterocycloalkyl, aryl, or heteroaryl;
Ring B is cycloalkyl, heterocycloalkyl, aryl, or heteroaryl;
Ring C is cycloalkyl, heterocycloalkyl, aryl, or heteroaryl;
L is —O—, —S—, or —$NR^{19}$—;
$R^{11}$ is $L^1$-$R^{20}$;
$L^1$ is absent or $C_1$-$C_6$ alkylene optionally substituted with deuterium, halogen, —CN, —$OR^a$, —$NR^cR^d$, —C(=O) $OR^a$, or —C(=O)$NR^cR^d$;
$R^{20}$ is halogen, —CN, —$OR^{21}$, —$SR^{21}$, —S(=O)$R^{22}$, —S(=O)$_2R^{22}$, —$NO_2$, —$NR^{23}R^{24}$, —$NR^{21}$S(=O)$_2R^{22}$, —S(=O)$_2NR^{23}R^{24}$, —C(=O)$R^{22}$, —OC(=O)$R^{22}$, —C(=O)C(=O)$R^{22}$, —C(=O)$OR^{21}$, —C(=O) $NR^{21}OR^{21}$, —OC(=O)$OR^{21}$, —C(=O)$NR^{23}R^{24}$, —OC (=O)$NR^{23}R^{24}$, —$NR^{21}$C(=O)$NR^{23}R^{24}$, —$NR^{21}$S (=O)$_2$ $NR^{23}R^{24}$, —$NR^{21}$C(=O)$R^{22}$, —$NR^{21}$C(=O) $OR^{21}$, $C_1$-$C_6$ alkyl, cycloalkyl, heterocycloalkyl, aryl, or heteroaryl; wherein the alkyl, cycloalkyl, heterocycloalkyl, aryl, and heteroaryl are independently optionally substituted with one, two, or three $R^1$;
each $R^{21}$ is independently hydrogen, —CN, $C_1$-$C_6$ alkyl, cycloalkyl, heterocycloalkyl, aryl, or heteroaryl; wherein the alkyl, cycloalkyl, heterocycloalkyl, aryl, and heteroaryl are independently optionally substituted with one, two, or three $R^{1a}$;

$R^{22}$ is hydrogen, —CN, $C_1$-$C_6$ alkyl, cycloalkyl, heterocycloalkyl, aryl, or heteroaryl; wherein the alkyl, cycloalkyl, heterocycloalkyl, aryl, and heteroaryl are independently optionally substituted with one, two, or three $R^{1b}$;
$R^{23}$ and $R^{24}$ are independently hydrogen, $C_1$-$C_6$ alkyl, cycloalkyl, heterocycloalkyl, aryl, or heteroaryl; wherein the alkyl, cycloalkyl, heterocycloalkyl, aryl, and heteroaryl are independently optionally substituted with one, two, or three $R^{1c}$;
or $R^{23}$ and $R^{24}$ are taken together with the nitrogen atom to which they are attached to form a heterocycloalkyl optionally substituted with one, two, or three $R^{1d}$;
each $R^{12}$ is independently deuterium, halogen, —CN, —$OR^a$, —$NR^cR^d$, —C(=O)$OR^a$, —C(=O)$NR^cR^d$, $C_1$-$C_6$ alkyl, cycloalkyl, heterocycloalkyl, aryl, or heteroaryl; wherein the alkyl, cycloalkyl, heterocycloalkyl, aryl, and heteroaryl are independently optionally substituted with one, two, or three $R^2$;
or two $R^{12}$ on the same carbon are taken together to form an oxo;
$R^{13}$ is hydrogen, deuterium, halogen, —CN, —$OR^a$, —$NR^cR^d$, —C(=O)$OR^a$, —C(=O)$NR^cR^d$, $C_1$-$C_6$ alkyl, cycloalkyl, heterocycloalkyl, aryl, or heteroaryl; wherein the alkyl, cycloalkyl, heterocycloalkyl, aryl, and heteroaryl are independently optionally substituted with one, two, or three $R^3$;
$R^{14}$ is hydrogen, deuterium, halogen, —CN, —$OR^a$, —$NR^cR^d$, —C(=O)$OR^a$, —C(=O)$NR^cR^d$, $C_1$-$C_6$ alkyl, cycloalkyl, heterocycloalkyl, aryl, or heteroaryl; wherein the alkyl, cycloalkyl, heterocycloalkyl, aryl, and heteroaryl are independently optionally substituted with one, two, or three $R^4$;
$R^{15}$ is hydrogen, deuterium, halogen, —CN, —$OR^a$, —$NR^cR^d$, —C(=O)$OR^a$, —C(=O)$NR^cR^d$, $C_1$-$C_6$ alkyl, cycloalkyl, heterocycloalkyl, aryl, or heteroaryl; wherein the alkyl, cycloalkyl, heterocycloalkyl, aryl, and heteroaryl are independently optionally substituted with one, two, or three $R^5$;
or $R^{14}$ and $R^{15}$ are taken together to form a cycloalkyl or heterocycloalkyl; wherein the cycloalkyl and heterocycloalkyl are independently optionally substituted with one, two, or three $R^6$;
$R^{16}$ is hydrogen, deuterium, halogen, —CN, —$OR^a$, —$NR^cR^d$, —C(=O)$OR^a$, —C(=O)$NR^cR^d$, $C_1$-$C_6$ alkyl, cycloalkyl, heterocycloalkyl, aryl, or heteroaryl; wherein the alkyl, cycloalkyl, heterocycloalkyl, aryl, and heteroaryl are independently optionally substituted with one, two, or three $R^7$;
each $R^{17}$ is independently deuterium, halogen, —CN, —$OR^a$, —$NR^cR^d$, —C(=O)$R^a$, —C(=O)$OR^a$, —C(=O)$NR^cR^d$, —$NR^a$C(=O)$R^b$, $C_1$-$C_6$ alkyl, cycloalkyl, heterocycloalkyl, aryl, or heteroaryl; wherein the alkyl, cycloalkyl, heterocycloalkyl, aryl, and heteroaryl are independently optionally substituted with one, two, or three $R^8$;
or two $R^{17}$ on the same carbon are taken together to form an oxo;
each $R^{18}$ is independently deuterium, halogen, —CN, —$OR^a$, —$NR^cR^d$, —C(=O)$R^a$, —C(=O)$OR^a$, —C(=O)$NR^cR^d$, —$NR^a$C(=O)$R^b$, $C_1$-$C_6$ alkyl, cycloalkyl, heterocycloalkyl, aryl, or heteroaryl; wherein the alkyl, cycloalkyl, heterocycloalkyl, aryl, and heteroaryl are independently optionally substituted with one, two, or three $R^9$;
or two $R^{18}$ on the same carbon are taken together to form an oxo;

$R^{19}$ is hydrogen, —S(=O)$R^b$, —S(=O)$_2R^b$, —S(=O)$_2$ N$R^cR^d$, —C(=O)$R^b$, —C(=O)O$R^a$, —C(=O)N$R^cR^d$, $C_1$-$C_6$ alkyl, $C_1$-$C_6$ haloalkyl, $C_1$-$C_6$ heteroalkyl, cycloalkyl, or heterocycloalkyl;

each $R^{1a}$, $R^{1b}$, $R^{1c}$, and $R^{1d}$ are independently oxo, halogen, —CN, —O$R^a$, —S(=O)$_2R^b$, —N$R^cR^d$, —S(=O)$_2$ N$R^cR^d$, —C(=O)$R^b$, —OC(=O)$R^b$, —C(=O)O$R^a$, —OC(=O)O$R^a$, —C(=O)N$R^cR^d$, —OC(=O)N$R^cR^d$, —N$R^a$C(=O)N$R^cR^d$, —N$R^a$C(=O)$R^b$, $C_1$-$C_6$ alkyl, $C_1$-$C_6$ haloalkyl, $C_1$-$C_6$ hydroxyalkyl, or phenyl;

each $R^1$ is independently oxo, halogen, —CN, —O$R^a$, —N$R^cR^d$, —C(=O)O$R^a$, —C(=O)$R^a$, —C(=O)N$R^cR^d$, —S(=O)$_2R^b$, $C_1$-$C_6$ alkyl, cycloalkyl, heterocycloalkyl, or phenyl; wherein the alkyl, cycloalkyl, heterocycloalkyl, and phenyl are independently optionally substituted with one, two, or three halogen, —OH, —NH$_2$, $C_1$-$C_6$ alkyl, or phenyl;

each $R^2$, $R^3$, $R^4$, $R^5$, $R^6$, $R^7$, $R^8$, and $R^9$ are independently oxo, halogen, —CN, —O$R^a$, —N$R^cR^d$, —C(=O)O$R^a$, —C(=O)$R^a$, —C(=O)N$R^cR^d$, —S(=O)$_2R^b$, $C_1$-$C_6$ alkyl, cycloalkyl, heterocycloalkyl, or phenyl; wherein the alkyl, cycloalkyl, heterocycloalkyl, and phenyl are independently optionally substituted with one, two, or three halogen, —OH, —NH$_2$, $C_1$-$C_6$ alkyl, or phenyl;

each $R^a$ is independently hydrogen, $C_1$-$C_6$ alkyl, cycloalkyl, heterocycloalkyl, aryl, or heteroaryl; wherein the alkyl, cycloalkyl, heterocycloalkyl, aryl, and heteroaryl are independently optionally substituted with one, two, or three halogen, —OH, —NH$_2$, or $C_1$-$C_6$ alkyl;

each $R^b$ is independently $C_1$-$C_6$ alkyl, cycloalkyl, heterocycloalkyl, aryl, or heteroaryl; wherein the alkyl, cycloalkyl, heterocycloalkyl, aryl, and heteroaryl are independently optionally substituted with one, two, or three halogen, —OH, —NH$_2$, or $C_1$-$C_6$ alkyl;

each $R^c$ and $R^d$ are independently hydrogen, $C_1$-$C_6$ alkyl, cycloalkyl, heterocycloalkyl, aryl, or heteroaryl; wherein the alkyl, cycloalkyl, heterocycloalkyl, aryl, and heteroaryl are independently optionally substituted with one, two, or three halogen, —OH, —NH$_2$, or $C_1$-$C_6$ alkyl;

or $R^c$ and $R^d$ are taken together with the nitrogen atom to which they are attached to form a heterocycloalkyl optionally substituted with one, two, or three halogen, —OH, —NH$_2$, or $C_1$-$C_6$ alkyl;

n is 0-3;

m is 0-3; and p is 0-3.

In some embodiments of a compound of Formula (I'), $X^1$ is N. In some embodiments of a compound of Formula (I'), $X^1$ is N C$R^{13}$. In some embodiments of a compound of Formula (I'), $X^2$ is N. In some embodiments of a compound of Formula (I'), $X^2$ is C$R^{14}$. In some embodiments of a compound of Formula (I'), $X^3$ is N. In some embodiments of a compound of Formula (I'), $X^3$ is C$R^{15}$.

Disclosed herein is a compound of Formula (I), or a pharmaceutically acceptable salt, solvate, or stereoisomer thereof:

Formula (I)

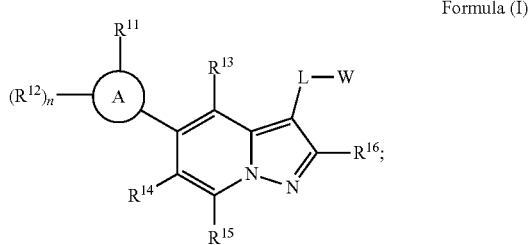

wherein:

W is

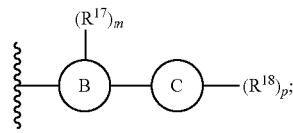

Ring A is cycloalkyl, heterocycloalkyl, aryl, or heteroaryl;
Ring B is cycloalkyl, heterocycloalkyl, aryl, or heteroaryl;
Ring C is cycloalkyl, heterocycloalkyl, aryl, or heteroaryl;
L is —O—, —S—, or —N$R^{19}$—;
$R^{11}$ is $L^1$-$R^{20}$;
$L^1$ is absent or $C_1$-$C_6$ alkylene optionally substituted with deuterium, halogen, —CN, —O$R^a$, —N$R^cR^d$, —C(=O)O$R^a$, or —C(=O)N$R^cR^d$;

$R^{20}$ is halogen, —CN, —O$R^{21}$, —S$R^{21}$, —S(=O)$R^{22}$, —S(=O)$_2R^{22}$, —NO$_2$, —N$R^{23}R^{24}$, —N$R^{21}$S(=O)$_2R^{22}$, —S(=O)$_2$N$R^{23}R^{24}$, —C(=O)$R^{22}$, —OC(=O)$R^{22}$, —C(=O)C(=O)$R^{22}$, —C(=O)O$R^{21}$, —C(=O) N$R^{21}$O$R^{21}$, —OC(=O)O$R^{21}$, —C(=O)N$R^{23}R^{24}$, —OC (=O)N$R^{23}R^{24}$, —N$R^{21}$C(=O)N$R^{23}R^{24}$, —N$R^{21}$S (=O)$_2$ N$R^{23}R^{24}$, —N$R^{21}$C(=O)$R^{22}$, —N$R^{21}$C(=O) O$R^{21}$, $C_1$-$C_6$ alkyl, cycloalkyl, heterocycloalkyl, aryl, or heteroaryl; wherein the alkyl, cycloalkyl, heterocycloalkyl, aryl, and heteroaryl are independently optionally substituted with one, two, or three $R^1$;

each $R^{21}$ is independently hydrogen, —CN, $C_1$-$C_6$ alkyl, cycloalkyl, heterocycloalkyl, aryl, or heteroaryl; wherein the alkyl, cycloalkyl, heterocycloalkyl, aryl, and heteroaryl are independently optionally substituted with one, two, or three $R^{1a}$;

$R^{22}$ is hydrogen, —CN, $C_1$-$C_6$ alkyl, cycloalkyl, heterocycloalkyl, aryl, or heteroaryl; wherein the alkyl, cycloalkyl, heterocycloalkyl, aryl, and heteroaryl are independently optionally substituted with one, two, or three $R^{1b}$;

$R^{23}$ and $R^{24}$ are independently hydrogen, $C_1$-$C_6$ alkyl, cycloalkyl, heterocycloalkyl, aryl, or heteroaryl; wherein the alkyl, cycloalkyl, heterocycloalkyl, aryl, and heteroaryl are independently optionally substituted with one, two, or three $R^{1c}$;

or $R^{23}$ and $R^{24}$ are taken together with the nitrogen atom to which they are attached to form a heterocycloalkyl optionally substituted with one, two, or three $R^{1d}$;

each $R^{12}$ is independently deuterium, halogen, —CN, —O$R^a$, —N$R^cR^d$, —C(=O)O$R^a$, —C(=O)N$R^cR^d$, $C_1$-$C_6$ alkyl, cycloalkyl, heterocycloalkyl, aryl, or heteroaryl; wherein the alkyl, cycloalkyl, heterocycloalkyl, aryl, and heteroaryl are independently optionally substituted with one, two, or three $R^2$;

or two $R^{12}$ on the same carbon are taken together to form an oxo;

$R^{13}$ is hydrogen, deuterium, halogen, —CN, —O$R^a$, —N$R^cR^d$, —C(=O)O$R^a$, —C(=O)N$R^cR^d$, $C_1$-$C_6$ alkyl, cycloalkyl, heterocycloalkyl, aryl, or heteroaryl; wherein the alkyl, cycloalkyl, heterocycloalkyl, aryl, and heteroaryl are independently optionally substituted with one, two, or three $R^3$;

$R^{14}$ is hydrogen, deuterium, halogen, —CN, —O$R^a$, —N$R^cR^d$, —C(=O)O$R^a$, —C(=O)N$R^cR^d$, $C_1$-$C_6$ alkyl, cycloalkyl, heterocycloalkyl, aryl, or heteroaryl; wherein the alkyl, cycloalkyl, heterocycloalkyl, aryl, and heteroaryl are independently optionally substituted with one, two, or three $R^4$;

$R^{15}$ is hydrogen, deuterium, halogen, —CN, —$OR^a$, —$NR^cR^d$, —C(=O)$OR^a$, —C(=O)$NR^cR^d$, $C_1$-$C_6$ alkyl, cycloalkyl, heterocycloalkyl, aryl, or heteroaryl; wherein the alkyl, cycloalkyl, heterocycloalkyl, aryl, and heteroaryl are independently optionally substituted with one, two, or three $R^5$;

or $R^{14}$ and $R^{15}$ are taken together to form a cycloalkyl or heterocycloalkyl; wherein the cycloalkyl and heterocycloalkyl are independently optionally substituted with one, two, or three $R^6$;

$R^{16}$ is hydrogen, deuterium, halogen, —CN, —$OR^a$, —$NR^cR^d$, —C(=O)$OR^a$, —C(=O)$NR^cR^d$, $C_1$-$C_6$ alkyl, cycloalkyl, heterocycloalkyl, aryl, or heteroaryl; wherein the alkyl, cycloalkyl, heterocycloalkyl, aryl, and heteroaryl are independently optionally substituted with one, two, or three $R^7$;

each $R^{17}$ is independently deuterium, halogen, —CN, —$OR^a$, —$NR^cR^d$, —C(=O)$R^a$, —C(=O)$OR^a$, —C(=O)$NR^cR^d$, —$NR^aC(=O)R^b$, $C_1$-$C_6$ alkyl, cycloalkyl, heterocycloalkyl, aryl, or heteroaryl; wherein the alkyl, cycloalkyl, heterocycloalkyl, aryl, and heteroaryl are independently optionally substituted with one, two, or three $R^8$;

or two $R^{17}$ on the same carbon are taken together to form an oxo;

each $R^{18}$ is independently deuterium, halogen, —CN, —$OR^a$, —$NR^cR^d$, —C(=O)$R^a$, —C(=O)$OR^a$, —C(=O)$NR^cR^d$, —$NR^aC(=O)R^b$, $C_1$-$C_6$ alkyl, cycloalkyl, heterocycloalkyl, aryl, or heteroaryl; wherein the alkyl, cycloalkyl, heterocycloalkyl, aryl, and heteroaryl are independently optionally substituted with one, two, or three $R^9$;

or two $R^{18}$ on the same carbon are taken together to form an oxo;

$R^{19}$ is hydrogen, —S(=O)$R^b$, —S(=O)$_2R^b$, —S(=O)$_2$ $NR^cR^d$, —C(=O)$R^b$, —C(=O)$OR^a$, —C(=O)$NR^cR^d$, $C_1$-$C_6$ alkyl, $C_1$-$C_6$ haloalkyl, $C_1$-$C_6$ heteroalkyl, cycloalkyl, or heterocycloalkyl;

each $R^{1a}$, $R^{1b}$, $R^{1c}$, and $R^{1d}$ are independently oxo, halogen, —CN, —$OR^a$, —S(=O)$_2R^b$, —$NR^cR^d$, —S(=O)$_2$ $NR^cR^d$, —C(=O)$R^b$, —OC(=O)$R^b$, —C(=O)$OR^a$, —OC(=O)$OR^a$, —C(=O)$NR^cR^d$, —OC(=O)$NR^cR^d$, —$NR^aC(=O)NR^cR^d$, —$NR^aC(=O)R^b$, $C_1$-$C_6$ alkyl, $C_1$-$C_6$ haloalkyl, $C_1$-$C_6$ hydroxyalkyl, or phenyl;

each $R^1$ is independently oxo, halogen, —CN, —$OR^a$, —$NR^cR^d$, —C(=O)$OR^a$, —C(=O)$R^a$, —C(=O) $NR^cR^d$, —S(=O)$_2R^b$, $C_1$-$C_6$ alkyl, cycloalkyl, heterocycloalkyl, or phenyl; wherein the alkyl, cycloalkyl, heterocycloalkyl, and phenyl are independently optionally substituted with one, two, or three halogen, —OH, —$NH_2$, $C_1$-$C_6$ alkyl, or phenyl;

each $R^2$, $R^3$, $R^4$, $R^5$, $R^6$, $R^7$, $R^8$, and $R^9$ are independently oxo, halogen, —CN, —$OR^a$, —$NR^cR^d$, —C(=O)$OR^a$, —C(=O)$R^a$, —C(=O)$NR^cR^d$, —S(=O)$_2R^b$, $C_1$-$C_6$ alkyl, cycloalkyl, heterocycloalkyl, or phenyl; wherein the alkyl, cycloalkyl, heterocycloalkyl, and phenyl are independently optionally substituted with one, two, or three halogen, —OH, —$NH_2$, $C_1$-$C_6$ alkyl, or phenyl;

each $R^a$ is independently hydrogen, $C_1$-$C_6$ alkyl, cycloalkyl, heterocycloalkyl, aryl, or heteroaryl; wherein the alkyl, cycloalkyl, heterocycloalkyl, aryl, and heteroaryl are independently optionally substituted with one, two, or three halogen, —OH, —$NH_2$, or $C_1$-$C_6$ alkyl;

each $R^b$ is independently $C_1$-$C_6$ alkyl, cycloalkyl, heterocycloalkyl, aryl, or heteroaryl; wherein the alkyl, cycloalkyl, heterocycloalkyl, aryl, and heteroaryl are independently optionally substituted with one, two, or three halogen, —OH, —$NH_2$, or $C_1$-$C_6$ alkyl;

each $R^c$ and $R^d$ are independently hydrogen, $C_1$-$C_6$ alkyl, cycloalkyl, heterocycloalkyl, aryl, or heteroaryl; wherein the alkyl, cycloalkyl, heterocycloalkyl, aryl, and heteroaryl are independently optionally substituted with one, two, or three halogen, —OH, —$NH_2$, or $C_1$-$C_6$ alkyl;

or $R^c$ and $R^d$ are taken together with the nitrogen atom to which they are attached to form a heterocycloalkyl optionally substituted with one, two, or three halogen, —OH, —$NH_2$, or $C_1$-$C_6$ alkyl;

n is 0-3;

m is 0-3; and p is 0-3.

In some embodiments of a compound of Formula (I) or (I'), or a pharmaceutically acceptable salt, solvate, or stereoisomer thereof, the compound is a compound of Formula (Ia):

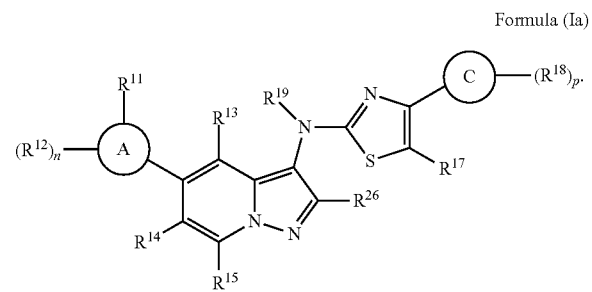

Formula (Ia)

In some embodiments of a compound of Formula (I) or (I'), or a pharmaceutically acceptable salt, solvate, or stereoisomer thereof, the compound is a compound of Formula (Ib):

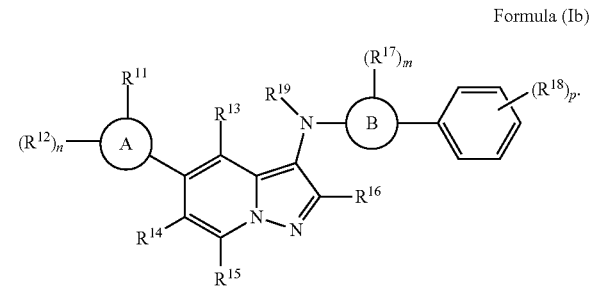

Formula (Ib)

In some embodiments of a compound of Formula (I) or (I'), or a pharmaceutically acceptable salt, solvate, or stereoisomer thereof, the compound is a compound of Formula (Ic):

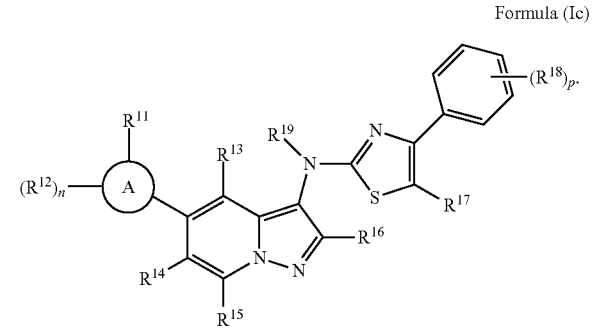

Formula (Ic)

In some embodiments of a compound of Formula (I) or (I'), or a pharmaceutically acceptable salt, solvate, or stereoisomer thereof, the compound is a compound of Formula (Id):

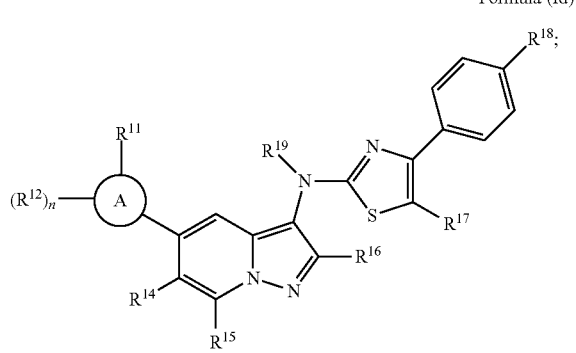

Formula (Id)

In some embodiments of a compound of Formula (I), (I'), (Ia), (Ib), (Ic), or (Id):
  Ring A is monocyclic heterocycloalkyl or spirocyclic heterocycloalkyl;
  $R^{11}$ is $L^1$-$R^{20}$;
  $L^1$ is absent or $C_1$-$C_6$ alkylene;
  $R^{14}$ is hydrogen or deuterium;
  $R^{15}$ is hydrogen, deuterium, or $C_1$-$C_6$ alkyl;
  $R^{16}$ is $C_1$-$C_6$ alkyl;
  $R^{17}$ is hydrogen or —CN;
  $R^{18}$ is halogen;
  $R^{19}$ is hydrogen or $C_1$-$C_6$ alkyl;
  $R^{20}$ is —C(O)NR$^{23}$R$^{24}$;
  $R^{23}$ and $R^{24}$ are taken together with the nitrogen atom to which they are attached to form a heterocycloalkyl optionally substituted with one, two, or three —OR$^a$ or $C_1$-$C_6$ hydroxyalkyl;
  $R^a$ is hydrogen or $C_1$-$C_6$ alkyl;
  $R^{12}$ is deuterium, halogen, $C_1$-$C_6$ alkyl, or $C_1$-$C_6$ haloalkyl; and
  n is 0 or 1.

In some embodiments of a compound of Formula (I), (I'), (Ia), (Ib), (Ic), or (Id):
  Ring A is monocyclic heterocycloalkyl or spirocyclic heterocycloalkyl;
  $R^{11}$ is $L^1$-$R^{20}$;
  $L^1$ is absent or $C_1$-$C_6$ alkylene;
  $R^{14}$ is hydrogen, halogen, or deuterium;
  $R^{15}$ is hydrogen, deuterium, or $C_1$-$C_6$ alkyl;
  $R^{16}$ is $C_1$-$C_6$ alkyl;
  $R^{17}$ is hydrogen or —CN;
  $R^{18}$ is halogen;
  $R^{19}$ is hydrogen or $C_1$-$C_6$ alkyl;
  $R^{20}$ is —C(=O)NR$^{23}$R$^{24}$;
  $R^{23}$ and $R^{24}$ are taken together with the nitrogen atom to which they are attached to form a heterocycloalkyl optionally substituted with one, two, or three —OR$^a$ or $C_1$-$C_6$ hydroxyalkyl;
  $R^a$ is hydrogen or $C_1$-$C_6$ alkyl;
  $R^{12}$ is deuterium, halogen, $C_1$-$C_6$ alkyl, or $C_1$-$C_6$ haloalkyl; and
  n is 0 or 1.

Also disclosed herein is compound of Formula (II), or a pharmaceutically acceptable salt, solvate, or stereoisomer thereof:

Formula (II)

wherein:
  $X^1$ is N or CR$^{13}$;
  $X^2$ is N or CR$^{14}$;
  $X^3$ is N or CR$^{15}$;
  W is Ring A is cycloalkyl, heterocycloalkyl, aryl, or heteroaryl;
Ring B is cycloalkyl, heterocycloalkyl, aryl, or heteroaryl;
Ring C is cycloalkyl, heterocycloalkyl, aryl, or heteroaryl;
L is —O—, —S—, or —NR$^{19}$—;
$R^{11}$ is $L^1$-$R^{20}$;
$L^1$ is absent or $C_1$-$C_6$ alkylene optionally substituted with deuterium, halogen, —CN, —OR$^a$, —NR$^c$R$^d$, —C(=O)OR$^a$, or —C(=O)NR$^c$R$^d$;
$R^{20}$ is halogen, —CN, —OR$^{21}$, —SR$^{21}$, —S(=O)R$^{22}$, —S(=O)$_2$R$^{22}$, —NO$_2$, —NR$^{23}$R$^{24}$, —NR$^{21}$S(=O)$_2$R$^{22}$, —S(=O)$_2$NR$^{23}$R$^{24}$, —C(=O)R$^{22}$, —OC(=O)R$^{22}$, —C(=O)C(=O)R$^{22}$, —C(=O)OR$^{21}$, —C(=O)NR$^{21}$OR$^{21}$, —OC(=O)OR$^{21}$, —C(=O)NR$^{23}$R$^{24}$, —OC(=O)NR$^{23}$R$^{24}$, —NR$^{21}$C(=O)NR$^{23}$R$^{24}$, —NR$^{21}$S(=O)$_2$NR$^{23}$R$^{24}$, —NR$^{21}$C(=O)R$^{22}$, —NR$^{21}$C(=O)OR$^{21}$, $C_1$-$C_6$ alkyl, cycloalkyl, heterocycloalkyl, aryl, or heteroaryl; wherein the alkyl, cycloalkyl, heterocycloalkyl, aryl, and heteroaryl are independently optionally substituted with one, two, or three $R^1$;
each $R^{21}$ is independently hydrogen, —CN, $C_1$-$C_6$ alkyl, cycloalkyl, heterocycloalkyl, aryl, or heteroaryl; wherein the alkyl, cycloalkyl, heterocycloalkyl, aryl, and heteroaryl are independently optionally substituted with one, two, or three $R^{1a}$;
$R^{22}$ is hydrogen, —CN, $C_1$-$C_6$ alkyl, cycloalkyl, heterocycloalkyl, aryl, or heteroaryl; wherein the alkyl, cycloalkyl, heterocycloalkyl, aryl, and heteroaryl are independently optionally substituted with one, two, or three $R^{1b}$;
$R^{23}$ and $R^{24}$ are independently hydrogen, $C_1$-$C_6$ alkyl, cycloalkyl, heterocycloalkyl, aryl, or heteroaryl; wherein the alkyl, cycloalkyl, heterocycloalkyl, aryl, and heteroaryl are independently optionally substituted with one, two, or three $R^{1c}$;
or $R^{23}$ and $R^{24}$ are taken together with the nitrogen atom to which they are attached to form a heterocycloalkyl optionally substituted with one, two, or three $R^{1d}$;
each $R^{12}$ is independently deuterium, halogen, —CN, —OR$^a$, —NR$^c$R$^d$, —C(=O)OR$^a$, —C(=O)NR$^c$R$^d$, $C_1$-$C_6$ alkyl, cycloalkyl, heterocycloalkyl, aryl, or heteroaryl; wherein the alkyl, cycloalkyl, heterocycloalkyl, aryl, and heteroaryl are independently optionally substituted with one, two, or three $R^2$;
or two $R^{12}$ on the same carbon are taken together to form an oxo;
$R^{13}$ is hydrogen, deuterium, halogen, —CN, —OR$^a$, —NR$^c$R$^d$, —C(=O)OR$^a$, —C(=O)NR$^c$R$^d$, $C_1$-$C_6$ alkyl, cycloalkyl, heterocycloalkyl, aryl, or heteroaryl; wherein the alkyl, cycloalkyl, heterocycloalkyl, aryl, and heteroaryl are independently optionally substituted with one, two, or three $R^3$;
$R^{14}$ is hydrogen, deuterium, halogen, —CN, —OR$^a$, —NR$^c$R$^d$, —C(=O)OR$^a$, —C(=O)NR$^c$R$^d$, $C_1$-$C_6$ alkyl, cycloalkyl, heterocycloalkyl, aryl, or heteroaryl; wherein the alkyl, cycloalkyl, heterocycloalkyl, aryl, and heteroaryl are independently optionally substituted with one, two, or three $R^4$;
$R^{15}$ is hydrogen, deuterium, halogen, —CN, —OR$^a$, —NR$^c$R$^d$, —C(=O)OR$^a$, —C(=O)NR$^c$R$^d$, $C_1$-$C_6$ alkyl, cycloalkyl, heterocycloalkyl, aryl, or heteroaryl; wherein the alkyl, cycloalkyl, heterocycloalkyl, aryl, and heteroaryl are independently optionally substituted with one, two, or three $R^5$;
or $R^{14}$ and $R^{15}$ are taken together to form a cycloalkyl or heterocycloalkyl; wherein the cycloalkyl and heterocycloalkyl are independently optionally substituted with one, two, or three $R^6$;
$R^{26}$ is hydrogen, —C(=O)OR$^a$, —C(=O)NR$^c$R$^d$, —S(=O)R$^b$, —S(=O)$_2$R$^b$, $C_1$-$C_6$ alkyl, cycloalkyl, heterocycloalkyl, aryl, or heteroaryl; wherein the alkyl, cycloalkyl, heterocycloalkyl, aryl, and heteroaryl are independently optionally substituted with one, two, or three $R^7$;
each $R^{17}$ is independently deuterium, halogen, —CN, —OR$^a$, —NR$^c$R$^d$, —C(=O)R$^a$, —C(=O)OR$^a$, —C(=O)NR$^c$R$^d$, —NR$^a$C(=O)R$^b$, $C_1$-$C_6$ alkyl, cycloalkyl, heterocycloalkyl, aryl, or heteroaryl; wherein the alkyl, cycloalkyl, heterocycloalkyl, aryl, and heteroaryl are independently optionally substituted with one, two, or three $R^8$;
or two $R^{17}$ on the same carbon are taken together to form an oxo;
each $R^{18}$ is independently deuterium, halogen, —CN, —OR$^a$, —NR$^c$R$^d$, —C(=O)R$^a$, —C(=O)OR$^a$, —C(=O)NR$^c$R$^d$, —NR$^a$C(=O)R$^b$, $C_1$-$C_6$ alkyl, cycloalkyl, heterocycloalkyl, aryl, or heteroaryl; wherein the alkyl, cycloalkyl, heterocycloalkyl, aryl, and heteroaryl are independently optionally substituted with one, two, or three $R^9$;
or two $R^{18}$ on the same carbon are taken together to form an oxo;
$R^{19}$ is hydrogen, —S(=O)R$^b$, —S(=O)$_2$R$^b$, —S(=O)$_2$NR$^c$R$^d$, —C(=O)R$^b$, —C(=O)OR$^a$, —C(=O)NR$^c$R$^d$, $C_1$-$C_6$ alkyl, $C_1$-$C_6$ haloalkyl, $C_1$-$C_6$ heteroalkyl, cycloalkyl, or heterocycloalkyl;
each $R^{1a}$, $R^{1b}$, $R^{1c}$, and $R^{1d}$ are independently oxo, halogen, —CN, —OR$^a$, —S(=O)$_2$R$^b$, —NR$^c$R$^d$, —S(=O)$_2$NR$^c$R$^d$, —C(=O)R$^b$, —OC(=O)R$^b$, —C(=O)OR$^a$, —OC(=O)OR$^a$, —C(=O)NR$^c$R$^d$, —OC(=O)NR$^c$R$^d$, —NR$^a$C(=O)NR$^c$R$^d$, —NR$^a$C(=O)R$^b$, $C_1$-$C_6$ alkyl, $C_1$-$C_6$ haloalkyl, $C_1$-$C_6$ hydroxyalkyl, or phenyl;
each $R^1$ is independently oxo, halogen, —CN, —OR$^a$, —NR$^c$R$^d$, —C(=O)OR$^a$, —C(=O)R$^a$, —C(=O)NR$^c$R$^d$, —S(=O)$_2$R$^b$, $C_1$-$C_6$ alkyl, cycloalkyl, heterocycloalkyl, or phenyl; wherein the alkyl, cycloalkyl, heterocycloalkyl, and phenyl are independently optionally substituted with one, two, or three halogen, —OH, —NH$_2$, $C_1$-$C_6$ alkyl, or phenyl;
each $R^2$, $R^3$, $R^4$, $R^5$, $R^6$, $R^7$, $R^8$, and $R^9$ are independently oxo, halogen, —CN, —NR$^c$R$^d$, —C(=O)OR$^a$, —C(=O)R$^a$, —C(=O)NR$^c$R$^d$, —S(=O)$_2$R$^b$, $C_1$-$C_6$ alkyl, cycloalkyl, heterocycloalkyl, or phenyl; wherein the alkyl, cycloalkyl, heterocycloalkyl, and phenyl are independently optionally substituted with one, two, or three halogen, —OH, —NH$_2$, $C_1$-$C_6$ alkyl, or phenyl;
each $R^a$ is independently hydrogen, $C_1$-$C_6$ alkyl, cycloalkyl, heterocycloalkyl, aryl, or heteroaryl; wherein the alkyl, cycloalkyl, heterocycloalkyl, aryl, and heteroaryl are independently optionally substituted with one, two, or three halogen, —OH, —NH$_2$, or $C_1$-$C_6$ alkyl;
each $R^b$ is independently $C_1$-$C_6$ alkyl, cycloalkyl, heterocycloalkyl, aryl, or heteroaryl; wherein the alkyl, cycloalkyl, heterocycloalkyl, aryl, and heteroaryl are independently optionally substituted with one, two, or three halogen, —OH, —NH$_2$, or $C_1$-$C_6$ alkyl;
each $R^c$ and $R^d$ are independently hydrogen, $C_1$-$C_6$ alkyl, cycloalkyl, heterocycloalkyl, aryl, or heteroaryl; wherein the alkyl, cycloalkyl, heterocycloalkyl, aryl, and heteroaryl are independently optionally substituted with one, two, or three halogen, —OH, —NH$_2$, or $C_1$-$C_6$ alkyl;
or $R^c$ and $R^d$ are taken together with the nitrogen atom to which they are attached to form a heterocycloalkyl optionally substituted with one, two, or three halogen, —OH, —NH$_2$, or $C_1$-$C_6$ alkyl;
n is 0-3;
m is 0-3; and
p is 0-3.

In some embodiments of a compound of Formula (II), or a pharmaceutically acceptable salt, solvate, or stereoisomer thereof wherein the compound is a compound of Formula (IIa):

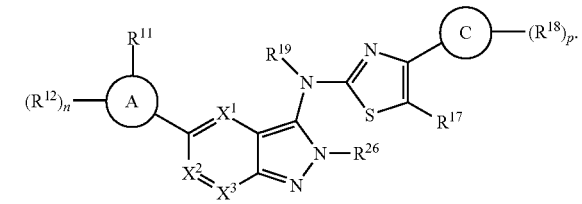

Formula (IIa)

In some embodiments of a compound of Formula (II), or a pharmaceutically acceptable salt, solvate, or stereoisomer thereof wherein the compound is a compound of Formula (IIb):

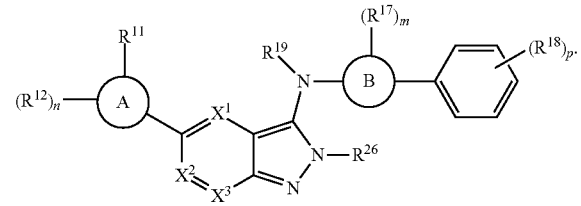

Formula (IIb)

In some embodiments of a compound of Formula (II), or a pharmaceutically acceptable salt, solvate, or stereoisomer thereof wherein the compound is a compound of Formula (IIc)

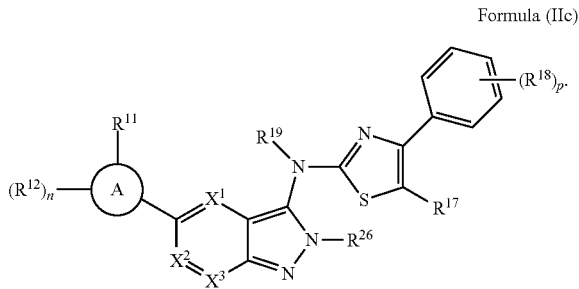

Formula (IIc)

In some embodiments of a compound of Formula (I), (I'), or (II), L is —O—. In some embodiments of a compound of Formula (I), L is —S—. In some embodiments of a compound of Formula (I) or (I'), L is —NR$^{19}$—.

In some embodiments of a compound of Formula (I), (I'), (Ia)-(Id), (II), or (IIa)-(IIc), R$^{19}$ is hydrogen, —S(=O)$_2$R$^b$, —S(=O)$_2$NR$^c$R$^d$, —C(=O)R$^b$, —C(=O)OR$^a$, —C(=O)NR$^c$R$^d$, C$_1$-C$_6$ alkyl, C$_1$-C$_6$ haloalkyl, C$_1$-C$_6$ heteroalkyl, cycloalkyl, or heterocycloalkyl. In some embodiments of a compound of Formula (I), (I'), (Ia)-(Id), (II), or (IIa)-(IIc), R$^{19}$ is hydrogen, C$_1$-C$_6$ alkyl, C$_1$-C$_6$ haloalkyl, C$_1$-C$_6$ heteroalkyl, cycloalkyl, or heterocycloalkyl. In some embodiments of a compound of Formula (I), (I'), (Ia)-(Id), (II), or (IIa)-(IIc), R$^{19}$ is hydrogen or C$_1$-C$_6$ alkyl.

In some embodiments of a compound of Formula (I), (I'), (Ib), (II), or (IIb), Ring B is heteroaryl. In some embodiments of a compound of Formula (I), (I'), (Ib), (II), or (IIb), Ring B is a 5-membered heteroaryl. In some embodiments of a compound of Formula (I), (I'), (Ib), (II), or (IIb), Ring B is thiophene, furan, pyrrole, thiazole, isothiazole, oxazole, isoxazole, pyrazole, imidazole, triazole, thiadiazole, or oxadiazole. In some embodiments of a compound of Formula (I), (I'), (Ib), (II), or (IIb), Ring B is thiazole. In some embodiments of a compound of Formula (I), (I'), (Ib), (II), or (IIb), Ring B is a 6-membered heteroaryl. In some embodiments of a compound of Formula (I), (I'), (Ib), (II), or (IIb), Ring B is pyridine, pyrimidine, or pyrazine. In some embodiments of a compound of Formula (I), (I'), (Ib), (II), or (IIb), Ring B is pyridine.

In some embodiments of a compound of Formula (I), (I'), (Ib), (II), or (IIb), Ring B is aryl. In some embodiments of a compound of Formula (I), (I'), (Ib), (II), or (IIb), Ring B is phenyl.

In some embodiments of a compound of Formula (I), (I'), (Ib), (II), or (IIb), Ring B is cycloalkyl. In some embodiments of a compound of Formula (I), (I'), (Ib), (II), or (IIb), Ring B is cyclopropyl, cyclobutyl, cyclopentyl, or cyclohexyl.

In some embodiments of a compound of Formula (I), (I'), (Ib), (II), or (IIb), Ring B is heterocycloalkyl. In some embodiments of a compound of Formula (I), (I'), (Ib), (II), or (IIb), Ring B is pyrrolidine, piperidine, or piperazine.

In some embodiments of a compound of Formula (I), (I'), (Ia), (II), or (IIa), Ring C is aryl. In some embodiments of a compound of Formula (I), (I'), (Ia), (II), or (IIa), Ring C is phenyl.

In some embodiments of a compound of Formula (I), (I'), (Ia), (II), or (IIa), Ring C is heteroaryl. In some embodiments of a compound of Formula (I), (I'), (Ia), (II), or (IIa), Ring C is pyridine, pyrimidine, or pyrazine.

In some embodiments of a compound of Formula (I), (I'), (Ia), (II), or (IIa), Ring C is cycloalkyl. In some embodiments of a compound of Formula (I), (I'), (Ia), (II), or (IIa), Ring C is cyclopropyl, cyclobutyl, cyclopentyl, or cyclohexyl.

In some embodiments of a compound of Formula (I), (I'), (Ia), (II), or (IIa), Ring C is heterocycloalkyl. In some embodiments of a compound of Formula (I), (I'), (Ia), (II), or (IIa), Ring C is a pyrrolidine, piperidine, or piperazine.

In some embodiments of a compound of Formula (I), (I'), (Ia)-(Ic), (II), or (IIa)-(IIc), R$^{13}$ is hydrogen, deuterium, halogen, —CN, —OR$^a$, —NR$^c$R$^d$, C$_1$-C$_6$ alkyl, cycloalkyl, heterocycloalkyl, aryl, or heteroaryl; wherein the alkyl, cycloalkyl, heterocycloalkyl, aryl, and heteroaryl are independently optionally substituted with one, two, or three R$^3$. In some embodiments of a compound of Formula (I), (I'), (Ia)-(Ic), (II), or (IIa)-(IIc), R$^{13}$ is hydrogen, deuterium, halogen, —CN, —OR$^a$, —NR$^c$R$^d$, C$_1$-C$_6$ alkyl, cycloalkyl, or heterocycloalkyl; wherein the alkyl, cycloalkyl, and heterocycloalkyl are independently optionally substituted with one, two, or three R$^3$. In some embodiments of a compound of Formula (I), (I'), (Ia)-(Ic), (II), or (IIa)-(IIc), R$^{13}$ is hydrogen, deuterium, halogen, —CN, —OR$^a$, —NR$^c$R$^d$, C$_1$-C$_6$ alkyl optionally substituted with one, two, or three R$^3$. In some embodiments of a compound of Formula (I), (I'), (Ia)-(Ic), (II), or (IIa)-(IIc), R$^{13}$ is hydrogen, deuterium, halogen, —CN, —OR$^a$, —NR$^c$R$^d$, C$_1$-C$_6$ alkyl, or C$_1$-C$_6$ haloalkyl. In some embodiments of a compound of Formula (I), (I'), (Ia)-(Ic), (II), or (IIa)-(IIc), R$^{13}$ is hydrogen, deuterium, halogen, C$_1$-C$_6$ alkyl, or C$_1$-C$_6$ haloalkyl. In some embodiments of a compound of Formula (I), (I'), (Ia)-(Ic), (II), or (IIa)-(IIc), R$^{13}$ is hydrogen, deuterium, or halogen. In some embodiments of a compound of Formula (I), (I'), (Ia)-(Ic), (II), or (IIa)-(IIc), R$^{13}$ is hydrogen or deuterium. In some embodiments of a compound of Formula (I), (I'), (Ia)-(Ic), (II), or (IIa)-(IIc), R$^{13}$ is hydrogen.

In some embodiments of a compound of Formula (I), (I'), (Ia)-(Id), (II), or (IIa)-(IIc), R$^{14}$ is hydrogen, deuterium, halogen, —CN, —OR$^a$, —NR$^c$R$^d$, C$_1$-C$_6$ alkyl, cycloalkyl, heterocycloalkyl, aryl, or heteroaryl; wherein the alkyl, cycloalkyl, heterocycloalkyl, aryl, and heteroaryl are independently optionally substituted with one, two, or three R$^4$. In some embodiments of a compound of Formula (I), (I'), (Ia)-(Id), (II), or (IIa)-(IIc), R$^{14}$ is hydrogen, deuterium, halogen, —CN, —OR$^a$, —NR$^c$R$^d$, C$_1$-C$_6$ alkyl, cycloalkyl, or heterocycloalkyl; wherein the alkyl, cycloalkyl, and heterocycloalkyl are independently optionally substituted with one, two, or three R$^4$. In some embodiments of a compound of Formula (I), (I'), (Ia)-(Id), (II), or (IIa)-(IIc), R$^{14}$ is hydrogen, deuterium, halogen, —CN, —OR$^a$, —NR$^c$R$^d$, C$_1$-C$_6$ alkyl optionally substituted with one, two, or three R$^4$. In some embodiments of a compound of Formula (I), (I'), (Ia)-(Id), (II), or (IIa)-(IIc), R$^{14}$ is hydrogen, deuterium, halogen, —CN, —OR$^a$, —NR$^c$R$^d$, C$_1$-C$_6$ alkyl, or C$_1$-C$_6$ haloalkyl. In some embodiments of a compound of Formula (I), (I'), (Ia)-(Id), (II), or (IIa)-(IIc), R$^{14}$ is hydrogen, deuterium, halogen, C$_1$-C$_6$ alkyl, or C$_1$-C$_6$ haloalkyl. In some embodiments of a compound of Formula (I), (I'), (Ia)-(Id), (II), or (IIa)-(IIc), R$^{14}$ is hydrogen, deuterium, halogen, or C$_1$-C$_6$ alkyl. In some embodiments of a compound of Formula (I), (I'), (Ia)-(Id), (II), or (IIa)-(IIc), R$^{14}$ is hydrogen, deuterium, or halogen. In some embodiments of a compound of Formula (I), (I'), (Ia)-(Id), (II), or (IIa)-(IIc), R$^{14}$ is hydrogen or deuterium. In some embodiments of a compound of Formula (I), (I'), (Ia)-(Id), (II), or (IIa)-(IIc), $R^{14}$ is hydrogen. In some embodiments of a compound of Formula (I), (I'), (Ia)-(Id), (II), or (IIa)-(IIc), $R^{14}$ is hydrogen, deuterium, or halogen. In some embodiments of a compound of Formula (I), (I'), (Ia)-(Id), (II), or (IIa)-(IIc), $R^{14}$ is halogen.

In some embodiments of a compound of Formula (I), (I'), (Ia)-(Id), (II), or (IIa)-(IIc), $R^{15}$ is hydrogen, deuterium, halogen, —CN, —OR$^a$, —NR$^c$R$^d$, $C_1$-$C_6$ alkyl, cycloalkyl, heterocycloalkyl, aryl, or heteroaryl; wherein the alkyl, cycloalkyl, heterocycloalkyl, aryl, and heteroaryl are independently optionally substituted with one, two, or three $R^5$. In some embodiments of a compound of Formula (I), (I'), (Ia)-(Id), (II), or (IIa)-(IIc), $R^{15}$ is hydrogen, deuterium, halogen, —CN, —OR$^a$, —NR$^c$R$^d$, $C_1$-$C_6$ alkyl, cycloalkyl, or heterocycloalkyl; wherein the alkyl, cycloalkyl, and heterocycloalkyl are independently optionally substituted with one, two, or three $R^5$. In some embodiments of a compound of Formula (I), (I'), (Ia)-(Id), (II), or (IIa)-(IIc), $R^{15}$ is hydrogen, deuterium, halogen, —CN, —OR$^a$, —NR$^c$R$^d$, $C_1$-$C_6$ alkyl optionally substituted with one, two, or three $R^5$. In some embodiments of a compound of Formula (I), (I'), (Ia)-(Id), (II), or (IIa)-(IIc), $R^{15}$ is hydrogen, deuterium, halogen, —CN, —OR$^a$, —NR$^c$R$^d$, $C_1$-$C_6$ alkyl, or $C_1$-$C_6$ haloalkyl. In some embodiments of a compound of Formula (I), (I'), (Ia)-(Id), (II), or (IIa)-(IIc), $R^{15}$ is hydrogen, deuterium, halogen, $C_1$-$C_6$ alkyl, or $C_1$-$C_6$ haloalkyl. In some embodiments of a compound of Formula (I), (I'), (Ia)-(Id), (II), or (IIa)-(IIc), $R^{15}$ is hydrogen, deuterium, or halogen. In some embodiments of a compound of Formula (I), (I'), (Ia)-(Id), (II), or (IIa)-(IIc), $R^{15}$ is hydrogen or deuterium. In some embodiments of a compound of Formula (I), (I'), (Ia)-(Id), (II), or (IIa)-(IIc), $R^{15}$ is hydrogen, deuterium, or $C_1$-$C_6$ alkyl. In some embodiments of a compound of Formula (I), (I'), (Ia)-(Id), (II), or (IIa)-(IIc), $R^{15}$ is hydrogen. In some embodiments of a compound of Formula (I), (I'), (Ia)-(Id), (II), or (IIa)-(IIc), $R^{15}$ is $C_1$-$C_6$ alkyl.

In some embodiments of a compound of Formula (I), (I'), (Ia)-(Id), (II), or (IIa)-(IIc), $R^{14}$ and $R^{15}$ are taken together to form a cycloalkyl or heterocycloalkyl; wherein the cycloalkyl and heterocycloalkyl are independently optionally substituted with one, two, or three $R^6$. In some embodiments of a compound of Formula (I), (I'), (Ia)-(Id), (II), or (IIa)-(IIc), $R^{14}$ and $R^{15}$ are taken together to form a cycloalkyl optionally substituted with one, two, or three $R^6$. In some embodiments of a compound of Formula (I), (I'), (Ia)-(Id), (II), or (IIa)-(IIc), $R^{14}$ and $R^{15}$ are taken together to form a heterocycloalkyl optionally substituted with one, two, or three $R^6$.

In some embodiments of a compound of Formula (I), (I'), (Ia)-(Id), (II), or (IIa)-(IIc), $R^{16}$ is hydrogen, deuterium, halogen, —CN, —OR$^a$, —NR$^c$R$^d$, $C_1$-$C_6$ alkyl, cycloalkyl, heterocycloalkyl, aryl, or heteroaryl; wherein the alkyl, cycloalkyl, heterocycloalkyl, aryl, and heteroaryl are independently optionally substituted with one, two, or three $R^7$. In some embodiments of a compound of Formula (I), (I'), (Ia)-(Id), (II), or (IIa)-(IIc), $R^{16}$ is hydrogen, deuterium, halogen, —CN, —OR$^a$, —NR$^c$R$^d$, $C_1$-$C_6$ alkyl, cycloalkyl, or heterocycloalkyl; wherein the alkyl, cycloalkyl, and heterocycloalkyl are independently optionally substituted with one, two, or three $R^7$. In some embodiments of a compound of Formula (I), (I'), (Ia)-(Id), (II), or (IIa)-(IIc), $R^{16}$ is hydrogen, deuterium, halogen, —CN, —OR$^a$, —NR$^c$R$^d$, $C_1$-$C_6$ alkyl optionally substituted with one, two, or three $R^7$. In some embodiments of a compound of Formula (I), (I'), (Ia)-(Id), (II), or (IIa)-(IIc), $R^{16}$ is hydrogen, deuterium, halogen, —CN, —OR$^a$, —NR$^c$R$^d$, $C_1$-$C_6$ alkyl, $C_1$-$C_6$ haloalkyl, or cycloalkyl. In some embodiments of a compound of Formula (I), (I'), (Ia)-(Id), (II), or (IIa)-(IIc), $R^{16}$ is hydrogen, deuterium, halogen, $C_1$-$C_6$ alkyl, $C_1$-$C_6$ haloalkyl, or cycloalkyl. In some embodiments of a compound of Formula (I), (I'), (Ia)-(Id), (II), or (IIa)-(IIc), $R^{16}$ is hydrogen, deuterium, $C_1$-$C_6$ alkyl, $C_1$-$C_6$ haloalkyl, or cycloalkyl. In some embodiments of a compound of Formula (I), (I'), (Ia)-(Id), (II), or (IIa)-(IIc), $R^{16}$ is hydrogen, $C_1$-$C_6$ alkyl, $C_1$-$C_6$ haloalkyl, or cycloalkyl. In some embodiments of a compound of Formula (I), (I'), (Ia)-(Id), (II), or (IIa)-(IIc), $R^{16}$ is $C_1$-$C_6$ alkyl or cycloalkyl. In some embodiments of a compound of Formula (I), (I'), (Ia)-(Id), (II), or (IIa)-(IIc), $R^{16}$ is $C_1$-$C_6$ alkyl.

In some embodiments of a compound of Formula (II), or (IIa)-(IIc), $R^{26}$ is hydrogen, deuterium, halogen, —CN, —OR$^a$, —NR$^c$R$^d$, $C_1$-$C_6$ alkyl, cycloalkyl, heterocycloalkyl, aryl, or heteroaryl; wherein the alkyl, cycloalkyl, heterocycloalkyl, aryl, and heteroaryl are independently optionally substituted with one, two, or three $R^7$. In some embodiments of a compound of Formula (II) or (IIa)-(IIc), $R^{26}$ is hydrogen, deuterium, halogen, —CN, —OR$^a$, —NR$^c$R$^d$, $C_1$-$C_6$ alkyl, cycloalkyl, or heterocycloalkyl; wherein the alkyl, cycloalkyl, and heterocycloalkyl are independently optionally substituted with one, two, or three $R^7$. In some embodiments of a compound of Formula (II) or (IIa)-(IIc), $R^{26}$ is hydrogen, deuterium, halogen, —CN, —OR$^a$, —NR$^c$R$^d$, $C_1$-$C_6$ alkyl optionally substituted with one, two, or three $R^7$. In some embodiments of a compound of Formula (II) or (IIa)-(IIc), $R^{26}$ is hydrogen, deuterium, halogen, —CN, —OR$^a$, —NR$^c$R$^d$, $C_1$-$C_6$ alkyl, $C_1$-$C_6$ haloalkyl, or cycloalkyl. In some embodiments of a compound of Formula (II) or (IIa)-(IIc), $R^{26}$ is hydrogen, deuterium, halogen, $C_1$-$C_6$ alkyl, $C_1$-$C_6$ haloalkyl, or cycloalkyl. In some embodiments of a compound of Formula (II) or (IIa)-(IIc), $R^{26}$ is hydrogen, deuterium, $C_1$-$C_6$ alkyl, $C_1$-$C_6$ haloalkyl, or cycloalkyl. In some embodiments of a compound of Formula (II) or (IIa)-(IIc) $R^{26}$ is hydrogen, $C_1$-$C_6$ alkyl, $C_1$-$C_6$ haloalkyl, or cycloalkyl. In some embodiments of a compound of Formula (II) or (IIa)-(IIc), $R^{26}$ is $C_1$-$C_6$ alkyl.

In some embodiments of a compound of Formula (I), (I'), (Ia)-(Id), (II), or (IIa)-(IIc), each $R^{17}$ is independently deuterium, halogen, —CN, —OR$^a$, —NR$^c$R$^d$, $C_1$-$C_6$ alkyl, cycloalkyl, heterocycloalkyl, aryl, or heteroaryl; wherein the alkyl, cycloalkyl, heterocycloalkyl, aryl, and heteroaryl are independently optionally substituted with one, two, or three $R^8$. In some embodiments of a compound of Formula (I), (I'), (Ia)-(Id), (II), or (IIa)-(IIc), each $R^{17}$ is independently deuterium, halogen, —CN, —OR$^a$, —NR$^c$R$^d$, $C_1$-$C_6$ alkyl, cycloalkyl, or heterocycloalkyl; wherein the alkyl, cycloalkyl, and heterocycloalkyl are independently optionally substituted with one, two, or three $R^8$. In some embodiments of a compound of Formula (I), (I'), (Ia)-(Id), (II), or (IIa)-(IIc), each $R^{17}$ is independently deuterium, halogen, —CN, —OR$^a$, —NR$^c$R$^d$, $C_1$-$C_6$ alkyl optionally substituted with one, two, or three $R^8$. In some embodiments of a compound of Formula (I), (I'), (Ia)-(Id), (II), or (IIa)-(IIc), each $R^{17}$ is independently deuterium, halogen, —CN, —OR$^a$, —NR$^c$R$^d$, $C_1$-$C_6$ alkyl, or $C_1$-$C_6$ haloalkyl. In some embodiments of a compound of Formula (I), (I'), (Ia)-(Id), (II), or (IIa)-(IIc), each $R^{17}$ is independently halogen, —CN, $C_1$-$C_6$ alkyl, or $C_1$-$C_6$ haloalkyl. In some embodiments of a compound of Formula (I), (I'), (Ia)-(Id), (II), or (IIa)-(IIc), each $R^{17}$ is —CN.

In some embodiments of a compound of Formula (I), (Ib), (II), or (IIb), m is 0. In some embodiments of a compound of Formula (I), (Ib), (II), or (IIb), m is 1. In some embodiments of a compound of Formula (I), (Ib), (II), or (IIb), m is 2. In some embodiments of a compound of Formula (I), (Ib), (II), or (IIb), m is 3. In some embodiments of a compound of Formula (I), m is 0 or 1. In some embodiments of a compound of Formula (I), (Ib), (II), or (IIb), m is 1 or 2. In some embodiments of a compound of Formula (I), (Ib), (II), or (IIb), m is 0-2.

In some embodiments of a compound of Formula (I), (I'), (Ia)-(Id), (II), or (IIa)-(IIc), each $R^{18}$ is independently deuterium, halogen, —CN, —$OR^a$, —$NR^cR^d$, $C_1$-$C_6$ alkyl, cycloalkyl, heterocycloalkyl, aryl, or heteroaryl; wherein the alkyl, cycloalkyl, heterocycloalkyl, aryl, and heteroaryl are independently optionally substituted with one, two, or three $R^9$. In some embodiments of a compound of Formula (I), (I'), (Ia)-(Id), (II), or (IIa)-(IIc), each $R^{18}$ is independently deuterium, halogen, —CN, —$OR^a$, —$NR^cR^d$, $C_1$-$C_6$ alkyl, cycloalkyl, or heterocycloalkyl; wherein the alkyl, cycloalkyl, and heterocycloalkyl are independently optionally substituted with one, two, or three $R^9$. In some embodiments of a compound of Formula (I), (I'), (Ia)-(Id), (II), or (IIa)-(IIc), each $R^{18}$ is independently deuterium, halogen, —CN, —$OR^a$, —$NR^cR^d$, $C_1$-$C_6$ alkyl optionally substituted with one, two, or three $R^9$. In some embodiments of a compound of Formula (I), (I'), (Ia)-(Id), (II), or (IIa)-(IIc), each $R^{18}$ is independently deuterium, halogen, —CN, —$OR^a$, —$NR^cR^d$, $C_1$-$C_6$ alkyl, or $C_1$-$C_6$ haloalkyl. In some embodiments of a compound of Formula (I), (I'), (Ia)-(Id), (II), or (IIa)-(IIc), each $R^{18}$ is independently halogen, $C_1$-$C_6$ alkyl, or $C_1$-$C_6$ haloalkyl. In some embodiments of a compound of Formula (I), (I'), (Ia)-(Id), (II), or (IIa)-(IIc), each $R^{18}$ is independently halogen.

In some embodiments of a compound of Formula (I), (I'), (Ia)-(Ic), (II), or (IIa)-(IIc), p is 0. In some embodiments of a compound of Formula (I), (I'), (Ia)-(Ic), (II), or (IIa)-(IIc), p is 1. In some embodiments of a compound of Formula (I), (I'), (Ia)-(Ic), (II), or (IIa)-(IIc), p is 2. In some embodiments of a compound of Formula (I), (I'), (Ia)-(Ic), (II), or (IIa)-(IIc), p is 3. In some embodiments of a compound of Formula (I), (I'), (Ia)-(Ic), (II), or (IIa)-(IIc), p is 0 or 1. In some embodiments of a compound of Formula (I), (I'), (Ia)-(Ic), (II), or (IIa)-(IIc), p is 1 or 2. In some embodiments of a compound of Formula (I), (Ia), (Ib), or (Ic), p is 0-2.

In some embodiments of a compound of Formula (I), (I'), (Ia)-(Id), (II), or (IIa)-(IIc), Ring A is aryl. In some embodiments of a compound of Formula (I), (I'), (Ia)-(Id), (II), or (IIa)-(IIc), Ring A is phenyl.

In some embodiments of a compound of Formula (I), (I'), (Ia)-(Id), (II), or (IIa)-(IIc), Ring A is cycloalkyl. In some embodiments of a compound of Formula (I), (I'), (Ia)-(Id), (II), or (IIa)-(IIc), Ring A is cyclopropyl, cyclobutyl, cyclopentyl, or cyclohexyl. In some embodiments of a compound of Formula (I), (I'), (Ia)-(Id), (II), or (IIa)-(IIc), Ring A is cyclohexyl.

In some embodiments of a compound of Formula (I), (I'), (Ia)-(Id), (II), or (IIa)-(IIc), Ring A is heteroaryl. In some embodiments of a compound of Formula (I), (I'), (Ia)-(Id), (II), or (IIa)-(IIc), Ring A is pyridine, pyrimidine, or pyrazine. In some embodiments of a compound of Formula (I), (I'), (Ia)-(Id), (II), or (IIa)-(IIc), Ring A is pyridine.

In some embodiments of a compound of Formula (I), (I'), (Ia)-(Id), (II), or (IIa)-(IIc), Ring A is heterocycloalkyl. In some embodiments of a compound of Formula (I), (I'), (Ia)-(Id), (II), or (IIa)-(IIc), Ring A is a monocyclic heterocycloalkyl. In some embodiments of a compound of Formula (I), (I'), (Ia)-(Id), (II), or (IIa)-(IIc), Ring A is a bicyclic heterocycloalkyl. In some embodiments of a compound of Formula (I), (I'), (Ia)-(Id), (II), or (IIa)-(IIc), Ring A is a spirocyclic heterocycloalkyl.

In some embodiments of a compound of Formula (I), (I'), (Ia)-(Id), (II), or (IIa)-(IIc), Ring A is pyrrolidine, piperidine, piperazine, tetrahydropyridine, dihydropyrrole, 2,7-diazaspiro[3.5]nonane, 6-azaspiro[2.5]octane, 2,8-diazaspiro[4.5]decane, 2-azaspiro[3.3]heptane, 5-azaspiro[2.3]hexane, 2,6-diazaspiro[3.4]octane, or 2,7-diazaspiro[4.4]nonane. In some embodiments of a compound of Formula (I), (I'), (Ia)-(Id), (II), or (IIa)-(IIc), Ring A is piperidine or piperazine. In some embodiments of a compound of Formula (I), (I'), (Ia)-(Id), (II), or (IIa)-(IIc), Ring A is piperazine. In some embodiments of a compound of Formula (I), (I'), (Ia)-(Id), (II), or (IIa)-(IIc), Ring A is 2,7-diazaspiro[3.5]nonane, 6-azaspiro[2.5]octane, 2,8-diazaspiro[4.5]decane, 2-azaspiro[3.3]heptane, 5-azaspiro[2.3]hexane, 2,6-diazaspiro[3.4]octane, or 2,7-diazaspiro[4.4]nonane.

In some embodiments of a compound of Formula (I), (I'), (Ia)-(Id), (II), or (IIa)-(IIc), Ring A is

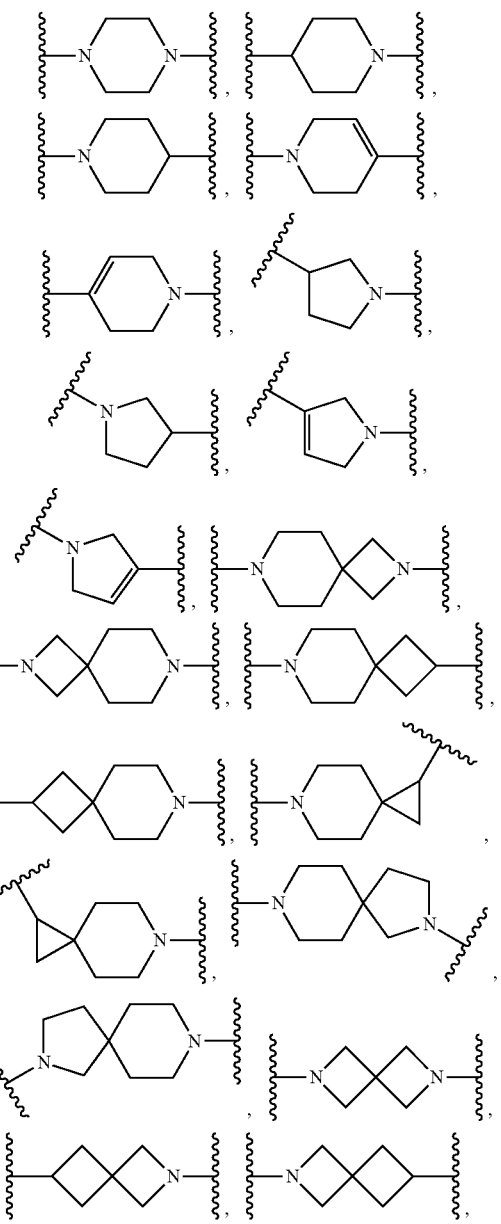

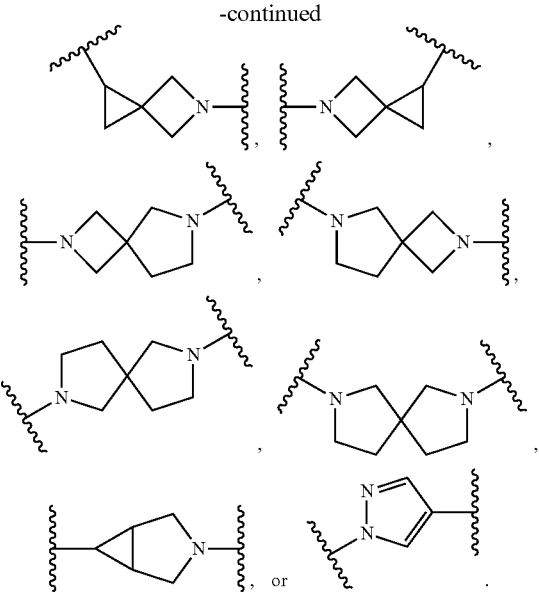

In some embodiments of a compound of Formula (I), (I'), (Ia)-(Id), (II), or (IIa)-(IIc), Ring A is

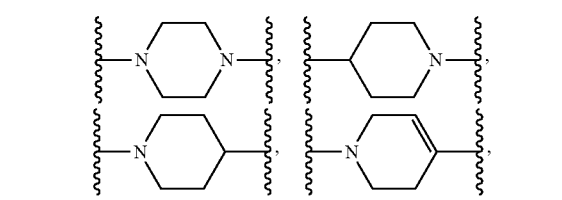

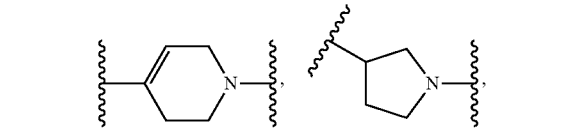

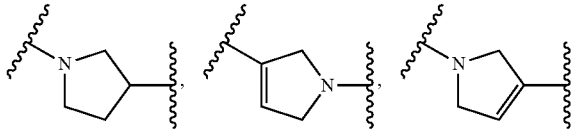

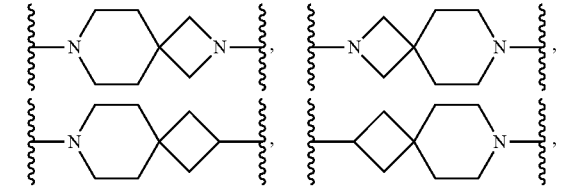

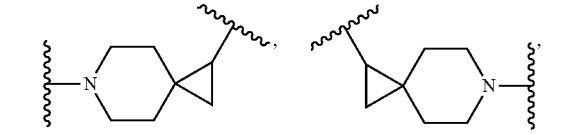

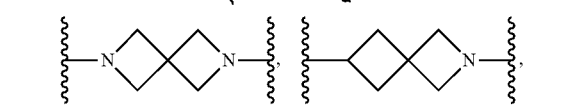

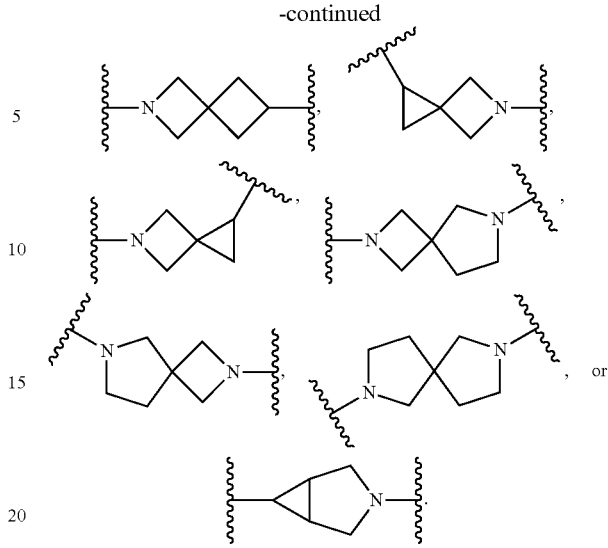

In some embodiments of a compound of Formula (I), (I'), (Ia)-(Id), (II), or (IIa)-(IIc), Ring A is

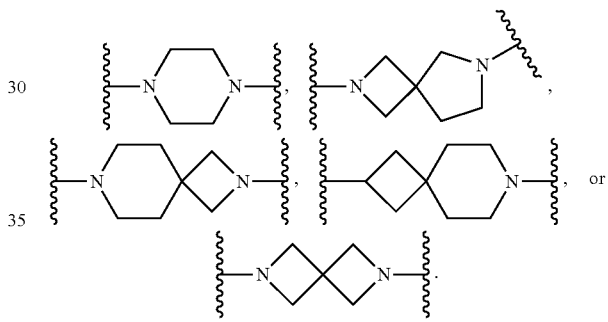

In some embodiments of a compound of Formula (I), (I'), (Ia)-(Id), (II), or (IIa)-(IIc), Ring A is

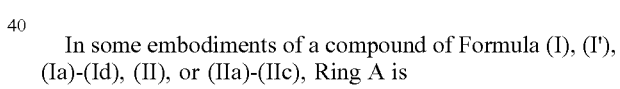
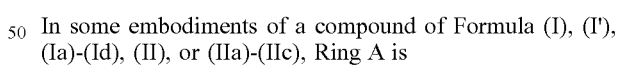

In some embodiments of a compound of Formula (I), (I'), (Ia)-(Id), (II), or (IIa)-(IIc), Ring A is

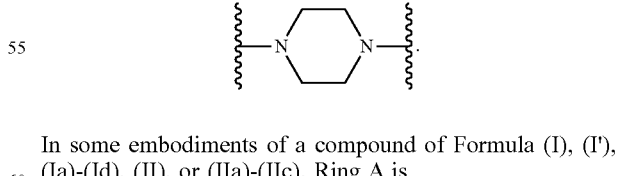

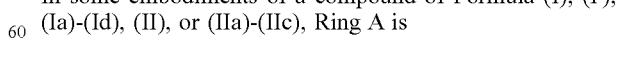

In some embodiments of a compound of Formula (I), (I'), (Ia)-(Id), (II), or (IIa)-(IIc), Ring A is

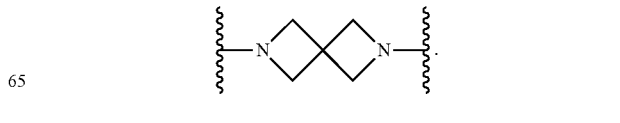

In some embodiments of a compound of Formula (I), (I'), (Ia)-(Id), (II), or (IIa)-(IIc), each $R^{12}$ is independently deuterium, halogen, —CN, —OR$^a$, —NR$^c$R$^d$, $C_1$-$C_6$ alkyl, cycloalkyl, heterocycloalkyl, aryl, or heteroaryl; wherein the alkyl, cycloalkyl, heterocycloalkyl, aryl, and heteroaryl are independently optionally substituted with one, two, or three $R^2$. In some embodiments of a compound of Formula (I), (I'), (Ia)-(Id), (II), or (IIa)-(IIc), each $R^{12}$ is independently deuterium, halogen, —CN, —OR$^a$, —NR$^c$R$^d$, $C_1$-$C_6$ alkyl, cycloalkyl, or heterocycloalkyl; wherein the alkyl, cycloalkyl, heterocycloalkyl, are independently optionally substituted with one, two, or three $R^2$. In some embodiments of a compound of Formula (I), (I'), (Ia)-(Id), (II), or (IIa)-(IIc), each $R^{12}$ is independently deuterium, halogen, —CN, —OR$^a$, —NR$^c$R$^d$, or $C_1$-$C_6$ alkyl optionally substituted with one, two, or three $R^2$. In some embodiments of a compound of Formula (I), (I'), (Ia)-(Id), (II), or (IIa)-(IIc), each $R^{12}$ is independently deuterium, halogen, —CN, —OR$^a$, —NR$^c$R$^d$, $C_1$-$C_6$ alkyl, or $C_1$-$C_6$ haloalkyl. In some embodiments of a compound of Formula (I), (I'), (Ia)-(Id), (II), or (IIa)-(IIc), each $R^{12}$ is independently deuterium, halogen, $C_1$-$C_6$ alkyl, or $C_1$-$C_6$ haloalkyl. In some embodiments of a compound of Formula (I), (I'), (Ia)-(Id), (II), or (IIa)-(IIc), each $R^{12}$ is independently deuterium or halogen. In some embodiments of a compound of Formula (I), (I'), (Ia)-(Id), (II), or (IIa)-(IIc), each $R^{12}$ is independently halogen. In some embodiments of a compound of Formula (I), (I'), (Ia)-(Id), (II), or (IIa)-(IIc), each $R^{12}$ is independently $C_1$-$C_6$ alkyl.

In some embodiments of a compound of Formula (I), (I'), (Ia)-(Id), (II), or (IIa)-(IIc), n is 0. In some embodiments of a compound of Formula (I), (I'), (Ia)-(Id), (II), or (IIa)-(IIc), n is 1. In some embodiments of a compound of Formula (I), (I'), (Ia)-(Id), (II), or (IIa)-(IIc), n is 2. In some embodiments of a compound of Formula (I), (I'), (Ia)-(Id), (II), or (IIa)-(IIc), n is 3. In some embodiments of a compound of Formula (I), (I'), (Ia)-(Id), (II), or (IIa)-(IIc), n is 0 or 1. In some embodiments of a compound of Formula (I), (I'), (Ia)-(Id), (II), or (IIa)-(IIc), n is 1 or 2. In some embodiments of a compound of Formula (I), (I'), (Ia)-(Id), (II), or (IIa)-(IIc), n is 0-2.

In some embodiments of a compound of Formula (I), (I'), (Ia)-(Id), (II), or (IIa)-(IIc), $L^1$ is absent. In some embodiments of a compound of Formula (I), (I'), (Ia)-(Id), (II), or (IIa)-(IIc), $L^1$ is $C_1$-$C_6$ alkylene. In some embodiments of a compound of Formula (I), (I'), (Ia)-(Id), (II), or (IIa)-(IIc), $L^1$ is $C_1$ alkylene.

In some embodiments of a compound of Formula (I), (I'), (Ia)-(Id), (II), or (IIa)-(IIc), $R^{20}$ is halogen, —CN, —OR$^{21}$, —S(=O)$_2$R$^{22}$, —NR$^{23}$R$^{24}$, —NR$^{21}$S(=O)$_2$R$^{22}$, —S(=O)$_2$ NR$^{23}$R$^{24}$, —C(=O)R$^{22}$, —C(=O)C(=O)R$^{22}$, —C(=O)OR$^{21}$, —C(=O)NR$^{21}$OR$^{21}$, —C(=O)NR$^{23}$R$^{24}$, $C_1$-$C_6$ alkyl, cycloalkyl, heterocycloalkyl, aryl, or heteroaryl; wherein the alkyl, cycloalkyl, heterocycloalkyl, aryl, and heteroaryl are independently optionally substituted with one, two, or three $R^1$. In some embodiments of a compound of Formula (I), (I'), (Ia)-(Id), (II), or (IIa)-(IIc), $R^{20}$ is halogen, —CN, —OR$^{21}$, —S(=O)$_2$R$^{22}$, —NR$^{23}$R$^{24}$, —NR$^{21}$S(=O)$_2$ R$^{22}$, —S(=O)$_2$NR$^{23}$R$^{24}$, —C(=O)R$^{22}$, —C(=O)C(=O)R$^{22}$, —C(=O)OR$^{21}$, —C(=O) NR$^{21}$OR$^{21}$, —C(=O)NR$^{23}$R$^{24}$, $C_1$-$C_6$ alkyl, cycloalkyl, heterocycloalkyl, aryl, or heteroaryl; wherein the alkyl, cycloalkyl, heterocycloalkyl, aryl, and heteroaryl are independently optionally substituted with one, two, or three $R^1$.

In some embodiments of a compound of Formula (I), (I'), (Ia)-(Id), (II), or (IIa)-(IIc), $R^{20}$ is halogen, —CN, —S(=O)$_2$ R$^{22}$, —NR$^{21}$S(=O)$_2$R$^{22}$, —S(=O)$_2$NR$^{23}$R$^{24}$, —C(=O)R$^{22}$, —C(=O)C(=O)R$^{22}$, —C(=O)OR$^{21}$, —C(=O)NR$^{23}$R$^{24}$, $C_1$-$C_6$ alkyl, cycloalkyl, heterocycloalkyl, aryl, or heteroaryl; wherein the alkyl, cycloalkyl, heterocycloalkyl, aryl, and heteroaryl are independently optionally substituted with one, two, or three $R^1$. In some embodiments of a compound of Formula (I), (I'), (Ia)-(Id), (II), or (IIa)-(IIc), $R^{20}$ is —CN, —S(=O)$_2$R$^{22}$, —C(=O) R$^{22}$, —C(=O)OR$^{21}$, —C(=O)NR$^{23}$R$^{24}$, $C_1$-$C_6$ alkyl, cycloalkyl, heterocycloalkyl, aryl, or heteroaryl; wherein the alkyl, cycloalkyl, heterocycloalkyl, aryl, and heteroaryl are independently optionally substituted with one, two, or three $R^1$. In some embodiments of a compound of Formula (I), (I'), (Ia)-(Id), (II), or (IIa)-(IIc), $R^{20}$ is —CN, —S(=O)$_2$R$^{22}$, —C(=O)R$^{22}$, —C(=O)OR$^{21}$, —C(=O)NR$^{23}$R$^{24}$, heterocycloalkyl, or heteroaryl; wherein the heterocycloalkyl and heteroaryl are independently optionally substituted with one, two, or three $R^1$. In some embodiments of a compound of Formula (I), (I'), (Ia)-(Id), (II), or (IIa)-(IIc), $R^{20}$ is —C(=O)NR$^{23}$R$^{24}$ or —C(=O)R$^{22}$. In some embodiments of a compound of Formula (I), (I'), (Ia)-(Id), (II), or (IIa)-(IIc), $R^{20}$ is —C(=O)NR$^{23}$R$^{24}$. In some embodiments of a compound of Formula (I), (I'), (Ia)-(Id), (II), or (IIa)-(IIc), $R^{20}$ is —C(=O)R$^{22}$.

In some embodiments of a compound of Formula (I), (I'), (Ia)-(Id), (II), or (IIa)-(IIc), each $R^{21}$ is independently hydrogen, —CN, $C_1$-$C_6$ alkyl, cycloalkyl, or heterocycloalkyl; wherein the alkyl, cycloalkyl, and heterocycloalkyl are independently optionally substituted with one, two, or three $R^{1a}$. In some embodiments of a compound of Formula (I), (I'), (Ia)-(Id), (II), or (IIa)-(IIc), each $R^{21}$ is independently hydrogen, —CN, or $C_1$-$C_6$ alkyl optionally substituted with one, two, or three $R^{1a}$. In some embodiments of a compound of Formula (I), (I'), (Ia)-(Id), (II), or (IIa)-(IIc), each $R^{21}$ is independently hydrogen, or $C_1$-$C_6$ alkyl optionally substituted with one, two, or three $R^{1a}$. In some embodiments of a compound of Formula (I), (I'), (Ia)-(Id), (II), or (IIa)-(IIc), each $R^{21}$ is independently hydrogen, $C_1$-$C_6$ alkyl, $C_1$-$C_6$ haloalkyl, or benzyl.

In some embodiments of a compound of Formula (I), (I'), (Ia)-(Id), (II), or (IIa)-(IIc), $R^{22}$ is hydrogen, —CN, $C_1$-$C_6$ alkyl, cycloalkyl, heterocycloalkyl, aryl, or heteroaryl; wherein the alkyl, cycloalkyl, heterocycloalkyl, aryl, and heteroaryl are independently optionally substituted with one, two, or three $R^{1b}$. In some embodiments of a compound of Formula (I), (I'), (Ia)-(Id), (II), or (IIa)-(IIc), $R^{22}$ is $C_1$-$C_6$ alkyl, heterocycloalkyl, or heteroaryl; wherein the alkyl, heterocycloalkyl, and heteroaryl are independently optionally substituted with one, two, or three $R^{1b}$. In some embodiments of a compound of Formula (I), (I'), (Ia)-(Id), (II), or (IIa)-(IIc), $R^{22}$ is hydrogen, $C_1$-$C_6$ alkyl, $C_1$-$C_6$ haloalkyl, $C_1$-$C_6$ hydroxyalkyl, cycloalkyl, heterocycloalkyl, aryl, or heteroaryl. In some embodiments of a compound of Formula (I), (I'), (Ia)-(Id), (II), or (IIa)-(IIc), $R^{22}$ is hydrogen, $C_1$-$C_6$ alkyl, $C_1$-$C_6$ haloalkyl, $C_1$-$C_6$ hydroxyalkyl, or heterocycloalkyl. In some embodiments of a compound of Formula (I), (I'), (Ia)-(Id), (II), or (IIa)-(IIc), $R^{22}$ is $C_1$-$C_6$ alkyl, $C_1$-$C_6$ haloalkyl, $C_1$-$C_6$ hydroxyalkyl, cycloalkyl, heterocycloalkyl, aryl, or heteroaryl. In some embodiments of a compound of Formula (I), (I'), (Ia)-(Id), (II), or (IIa)-(IIc), $R^{22}$ is $C_1$-$C_6$ alkyl, $C_1$-$C_6$ haloalkyl, $C_1$-$C_6$ hydroxyalkyl, or heterocycloalkyl. In some embodiments of a compound of Formula (I), (I'), (Ia)-(Id), (II), or (IIa)-(IIc), $R^{22}$ is heterocycloalkyl.

In some embodiments of a compound of Formula (I), (I'), (Ia)-(Id), (II), or (IIa)-(IIc), each $R^{23}$ and $R^{24}$ are independently hydrogen, $C_1$-$C_6$ alkyl, cycloalkyl, or heterocycloalkyl; wherein the alkyl, cycloalkyl, and heterocycloalkyl are independently optionally substituted with one, two, or three $R^{1c}$. In some embodiments of a compound of Formula (I), (I'), (Ia)-(Id), (II), or (IIa)-(IIc), each $R^{23}$ and $R^{24}$ are independently hydrogen, $C_1$-$C_6$ alkyl, cycloalkyl, or heterocycloalkyl; wherein the alkyl optionally substituted with one, two, or three $R^{1c}$. In some embodiments of a compound of Formula (I), (I'), (Ia)-(Id), (II), or (IIa)-(IIc), each $R^{23}$ and $R^{24}$ are independently hydrogen, $C_1$-$C_6$ alkyl, or $C_1$-$C_6$ haloalkyl.

In some embodiments of a compound of Formula (I), (I'), (Ia)-(Id), (II), or (IIa)-(IIc), $R^{23}$ and $R^{24}$ are taken together with the nitrogen atom to which they are attached to form a heterocycloalkyl optionally substituted with one, two, or three $R^{1d}$.

In some embodiments of a compound of Formula (I), (I'), (Ia)-(Id), (II), or (IIa)-(IIc), $R^{23}$ and $R^{24}$ are taken together with the nitrogen atom to which they are attached to form a heterocycloalkyl optionally substituted with one, two, or three oxo, halogen, —CN, —$OR^a$, —$S(=O)_2R^b$, —$NR^cR^d$, —$S(=O)_2NR^cR^d$, —$C(=O)R^b$, —$OC(=O)R^b$, —$C(=O)OR^a$, —$OC(=O)OR^a$, —$C(=O)NR^cR^d$, —$OC(=O)NR^cR^d$, —$NR^aC(=O)NR^cR^d$, —$NR^aC(=O)R^b$, $C_1$-$C_6$ alkyl, $C_1$-$C_6$ haloalkyl, or $C_1$-$C_6$ hydroxyalkyl. In some embodiments of a compound of Formula (I), (I'), (Ia)-(Id), (II), or (IIa)-(IIc), $R^{23}$ and $R^{24}$ are taken together with the nitrogen atom to which they are attached to form a heterocycloalkyl optionally substituted with one, two, or three oxo, halogen, —CN, —$OR^a$, —$NR^cR^d$, —$C(=O)OR^a$, —$C(=O)NR^cR^d$, $C_1$-$C_6$ alkyl, $C_1$-$C_6$ haloalkyl, or $C_1$-$C_6$ hydroxyalkyl. In some embodiments of a compound of Formula (I), (I'), (Ia)-(Id), (II), or (IIa)-(IIc), $R^{23}$ and $R^{24}$ are taken together with the nitrogen atom to which they are attached to form a heterocycloalkyl optionally substituted with one, two, or three —$OR^a$, $C_1$-$C_6$ alkyl, $C_1$-$C_6$ haloalkyl, or $C_1$-$C_6$ hydroxyalkyl.

In some embodiments of a compound of Formula (I), (I'), (Ia)-(Id), (II), or (IIa)-(IIc), $R^{23}$ and $R^{24}$ are taken together with the nitrogen atom to which they are attached to form an azetidine, pyrrolidine, piperidine, or piperazine; each optionally substituted with one, two, or three $R^{1d}$. In some embodiments of a compound of Formula (I), (I'), (Ia)-(Id), (II), or (IIa)-(IIc), $R^{23}$ and $R^{24}$ are taken together with the nitrogen atom to which they are attached to form an azetidine optionally substituted with one, two, or three $R^{1d}$.

In some embodiments of a compound of Formula (I), (I'), (Ia)-(Id), (II), or (IIa)-(IIc), each $R^a$ is independently hydrogen, $C_1$-$C_6$ alkyl, cycloalkyl, heterocycloalkyl; wherein the alkyl, cycloalkyl, and heterocycloalkyl are independently optionally substituted with one or more halogen, —OH, —$NH_2$, or $C_1$-$C_6$ alkyl. In some embodiments of a compound of Formula (I), (I'), (Ia)-(Id), (II), or (IIa)-(IIc), each $R^a$ is independently hydrogen, $C_1$-$C_6$ alkyl, cycloalkyl, heterocycloalkyl; wherein the alkyl, cycloalkyl, and heterocycloalkyl are independently optionally substituted with one or more halogen or $C_1$-$C_6$ alkyl. In some embodiments of a compound of Formula (I), (I'), (Ia)-(Id), (II), or (IIa)-(IIc), each $R^a$ is independently hydrogen, $C_1$-$C_6$ alkyl, $C_1$-$C_6$ haloalkyl, or cycloalkyl. In some embodiments of a compound of Formula (I), (I'), (Ia)-(Id), (II), or (IIa)-(IIc), each $R^a$ is independently hydrogen, $C_1$-$C_6$ alkyl, or cycloalkyl. In some embodiments of a compound of Formula (I), (I'), (Ia)-(Id), (II), or (IIa)-(IIc), each $R^a$ is independently hydrogen or $C_1$-$C_6$ alkyl.

In some embodiments of a compound of Formula (I), (I'), (Ia)-(Id), (II), or (IIa)-(IIc), each $R^b$ is independently $C_1$-$C_6$ alkyl, cycloalkyl, heterocycloalkyl; wherein the alkyl, cycloalkyl, and heterocycloalkyl are independently optionally substituted with one or more halogen, —OH, —$NH_2$, or $C_1$-$C_6$ alkyl. In some embodiments of a compound of Formula (I), (I'), (Ia)-(Id), (II), or (IIa)-(IIc), each $R^b$ is independently $C_1$-$C_6$ alkyl, cycloalkyl, heterocycloalkyl; wherein the alkyl, cycloalkyl, and heterocycloalkyl are independently optionally substituted with one or more halogen or $C_1$-$C_6$ alkyl. In some embodiments of a compound of Formula (I), (I'), (Ia)-(Id), (II), or (IIa)-(IIc), each $R^b$ is independently $C_1$-$C_6$ alkyl, $C_1$-$C_6$ haloalkyl, or cycloalkyl. In some embodiments of a compound of Formula (I), (I'), (Ia)-(Id), (II), or (IIa)-(IIc), each $R^b$ is independently $C_1$-$C_6$ alkyl or cycloalkyl. In some embodiments of a compound of Formula (I), (I'), (Ia)-(Id), (II), or (IIa)-(IIc), each $R^b$ is independently $C_1$-$C_6$ alkyl.

In some embodiments of a compound of Formula (I), (I'), (Ia)-(Id), (II), or (IIa)-(IIc), each $R^c$ and $R^d$ are independently hydrogen, $C_1$-$C_6$ alkyl, cycloalkyl, heterocycloalkyl; wherein the alkyl, cycloalkyl, and heterocycloalkyl are independently optionally substituted with one or more halogen, —OH, —$NH_2$, or $C_1$-$C_6$ alkyl. In some embodiments of a compound of Formula (I), (I'), (Ia)-(Id), (II), or (IIa)-(IIc), each $R^c$ and $R^d$ are independently hydrogen, $C_1$-$C_6$ alkyl, cycloalkyl, heterocycloalkyl; wherein the alkyl, cycloalkyl, and heterocycloalkyl are independently optionally substituted with one or more halogen or $C_1$-$C_6$ alkyl. In some embodiments of a compound of Formula (I), (I'), (Ia)-(Id), (II), or (IIa)-(IIc), each $R^c$ and $R^d$ are independently hydrogen, $C_1$-$C_6$ alkyl, $C_1$-$C_6$ haloalkyl, or cycloalkyl. In some embodiments of a compound of Formula (I), (I'), (Ia)-(Id), (II), or (IIa)-(IIc), each $R^c$ and $R^d$ are independently independently hydrogen, $C_1$-$C_6$ alkyl, or cycloalkyl. In some embodiments of a compound of Formula (I), (I'), (Ia)-(Id), (II), or (IIa)-(IIc), each $R^c$ and $R^d$ are independently independently hydrogen or $C_1$-$C_6$ alkyl.

In some embodiments of a compound of Formula (I), (I'), (Ia)-(Id), (II), or (IIa)-(IIc), $R^c$ and $R^d$ are taken together with the nitrogen atom to which they are attached to form a heterocycloalkyl optionally substituted with one or more halogen, —OH, —$NH_2$, or $C_1$-$C_6$ alkyl. In some embodiments of a compound of Formula (I), (I'), (Ia)-(Id), (II), or (IIa)-(IIc), $R^c$ and $R^d$ are taken together with the nitrogen atom to which they are attached to form a heterocycloalkyl optionally substituted with one or more halogen or $C_1$-$C_6$ alkyl.

In some embodiments of a compound of Formula (I), (I'), (Ia)-(Id), (II), or (IIa)-(IIc), each $R^1$ is independently halogen, —CN, —$OR^a$, —$C(=O)OR^a$, $C_1$-$C_6$ alkyl, cycloalkyl, or heterocycloalkyl; wherein the alkyl, cycloalkyl, or heterocycloalkyl are independently optionally substituted with one or more halogen, —OH, —$NH_2$, or $C_1$-$C_6$ alkyl. In some embodiments of a compound of Formula (I), (I'), (Ia)-(Id), (II), or (IIa)-(IIc), each $R^1$ is independently halogen, —CN, —$OR^a$, —$NR^cR^d$, —$C(=O)OR^a$, $C_1$-$C_6$ alkyl, or $C_1$-$C_6$ haloalkyl. In some embodiments of a compound of Formula (I), (I'), (Ia)-(Id), (II), or (IIa)-(IIc), each $R^1$ is independently halogen, —CN, —$OR^a$, —$NR^cR^d$, $C_1$-$C_6$ alkyl, or $C_1$-$C_6$ haloalkyl. In some embodiments of a compound of Formula (I), (I'), (Ia)-(Id), (II), or (IIa)-(IIc), each $R^1$ is independently halogen, $C_1$-$C_6$ alkyl, or $C_1$-$C_6$ haloalkyl. In some embodiments of a compound of Formula (I), (I'), (Ia)-(Id), (II), or (IIa)-(IIc), each $R^1$ is independently halogen or $C_1$-$C_6$ alkyl. In some embodiments of a compound of Formula (I), (I'), (Ia)-(Id), (II), or (IIa)-(IIc), each $R^1$ is independently halogen.

In some embodiments of a compound of Formula (I), (I'), (Ia)-(Id), (II), or (IIa)-(IIc), each $R^2$, $R^3$, $R^4$, $R^5$, $R^6$, $R^7$, $R^8$, and $R^9$ are independently halogen, —CN, —$OR^a$, —$NR^cR^d$, —C(=O)OR$^a$, C$_1$-C$_6$ alkyl, cycloalkyl, or heterocycloalkyl; wherein the alkyl, cycloalkyl, or heterocycloalkyl are independently optionally substituted with one or more halogen, —OH, —NH$_2$, or C$_1$-C$_6$ alkyl. In some embodiments of a compound of Formula (I), (I'), (Ia)-(Id), (II), or (IIa)-(IIc), each R$^2$, R$^3$, R$^4$, R$^5$, R$^6$, R$^7$, R$^8$, and R$^9$ are independently halogen, —CN, —OR$^a$, —NR$^c$R$^d$, —C(=O)OR$^a$, C$_1$-C$_6$ alkyl, or C$_1$-C$_6$ haloalkyl. In some embodiments of a compound of Formula (I), (I'), (Ia)-(Id), (II), or (IIa)-(IIc), each R$^2$, R$^3$, R$^4$, R$^5$, R$^6$, R$^7$, R$^8$, and R$^9$ are independently halogen, —CN, —OR$^a$, —NR$^c$R$^d$, C$_1$-C$_6$ alkyl, or C$_1$-C$_6$ haloalkyl. In some embodiments of a compound of Formula (I), (I'), (Ia)-(Id), (II), or (IIa)-(IIc), each R$^2$, R$^3$, R$^4$, R$^5$, R$^6$, R$^7$, R$^8$, and R$^9$ are independently halogen, C$_1$-C$_6$ alkyl, or C$_1$-C$_6$ haloalkyl. In some embodiments of a compound of Formula (I), (I'), (Ia)-(Id), (II), or (IIa)-(IIc), each R$^2$, R$^3$, R$^4$, R$^5$, R$^6$, R$^7$, R$^8$, and R$^9$ are independently halogen or C$_1$-C$_6$ alkyl. In some embodiments of a compound of Formula (I), (I'), (Ia)-(Id), (II), or (IIa)-(IIc), each R$^2$, R$^3$, R$^4$, R$^5$, R$^6$, R$^7$, R$^8$, and R$^9$ are independently halogen.

In some embodiments of a compound of Formula (I), (I'), (Ia)-(Id), (II), or (IIa)-(IIc), each R$^{1a}$, R$^{1b}$, R$^{1c}$, and R$^{1d}$ are independently oxo, halogen, —CN, —OR$^a$, —NR$^c$R$^d$, —C(=O)OR$^a$, —C(=O)NR$^c$R$^d$, C$_1$-C$_6$ alkyl, C$_1$-C$_6$ haloalkyl, or C$_1$-C$_6$ hydroxyalkyl. In some embodiments of a compound of Formula (I), (I'), (Ia)-(Id), (II), or (IIa)-(IIc), each R$^{1a}$, R$^{1b}$, R$^{1c}$, and R$^{1d}$ are independently halogen, —OR$^a$, C$_1$-C$_6$ alkyl, C$_1$-C$_6$ haloalkyl, or C$_1$-C$_6$ hydroxyalkyl. In some embodiments of a compound of Formula (I), (I'), (Ia)-(Id), (II), or (IIa)-(IIc), each R$^{1a}$, R$^{1b}$, R$^{1c}$, and R$^{1d}$ are independently —OR$^a$, C$_1$-C$_6$ alkyl, C$_1$-C$_6$ haloalkyl, or C$_1$-C$_6$ hydroxyalkyl. In some embodiments of a compound of Formula (I), (I'), (Ia)-(Id), (II), or (IIa)-(IIc), each R$^{1a}$, R$^{1b}$, R$^{1c}$, and R$^{1d}$ are independently halogen, —OR$^a$, C$_1$-C$_6$ alkyl, or C$_1$-C$_6$ haloalkyl. In some embodiments of a compound of Formula (I), (I'), (Ia)-(Id), (II), or (IIa)-(IIc), each R$^{1a}$, R$^{1b}$, R$^{1c}$, and R$^{1d}$ are independently halogen, C$_1$-C$_6$ alkyl, or C$_1$-C$_6$ haloalkyl. In some embodiments of a compound of Formula (I), (I'), (Ia)-(Id), (II), or (IIa)-(IIc), each R$^{1a}$, R$^{1b}$, R$^{1c}$, and R$^{1d}$ are independently halogen.

In some embodiments of a compound of Formula (I), (I'), (Ia)-(Id), (II), or (IIa)-(IIc), R$^{20}$ is optionally substituted with one or two R$^1$. In some embodiments of a compound of Formula (I), (I'), (Ia)-(Id), (II), or (IIa)-(IIc), R$^{20}$ is optionally substituted with one R$^1$. In some embodiments of a compound of Formula (I), (I'), (Ia)-(Id), (II), or (IIa)-(IIc), R$^{20}$ is optionally substituted with two R$^1$. In some embodiments of a compound of Formula (I), (I'), (Ia)-(Id), (II), or (IIa)-(IIc), R$^{20}$ is optionally substituted with three R$^1$.

In some embodiments of a compound of Formula (I), (I'), (Ia)-(Id), (II), or (IIa)-(IIc), each R$^{21}$ is independently optionally substituted with one or two R$^{1a}$. In some embodiments of a compound of Formula (I), (I'), (Ia)-(Id), (II), or (IIa)-(IIc), each R$^{21}$ is independently optionally substituted with one R$^{1a}$. In some embodiments of a compound of Formula (I), (I'), (Ia)-(Id), (II), or (IIa)-(IIc), each R$^{21}$ is independently optionally substituted with two R$^{1a}$. In some embodiments of a compound of Formula (I), (I'), (Ia)-(Id), (II), or (IIa)-(IIc), each R$^{21}$ is independently optionally substituted with three R$^{1a}$.

In some embodiments of a compound of Formula (I), (I'), (Ia)-(Id), (II), or (IIa)-(IIc), R$^{22}$ is optionally substituted with one or two R$^{1b}$. In some embodiments of a compound of Formula (I), (I'), (Ia)-(Id), (II), or (IIa)-(IIc), R$^{22}$ is optionally substituted with one R$^{1b}$. In some embodiments of a compound of Formula (I), (I'), (Ia)-(Id), (II), or (IIa)-(IIc), R$^{22}$ is optionally substituted with two R$^{1b}$. In some embodiments of a compound of Formula (I), (I'), (Ia)-(Id), (II), or (IIa)-(IIc), R$^{22}$ is optionally substituted with three R$^{1b}$.

In some embodiments of a compound of Formula (I), (I'), (Ia)-(Id), (II), or (IIa)-(IIc), R$^{23}$ and R$^{24}$ are independently optionally substituted with one or two R$^{1c}$. In some embodiments of a compound of Formula (I), (I'), (Ia)-(Id), (II), or (IIa)-(IIc), R$^{23}$ and R$^{24}$ are independently optionally substituted with one R$^{1c}$. In some embodiments of a compound of Formula (I), (I'), (Ia)-(Id), (II), or (IIa)-(IIc), R$^{23}$ and R$^{24}$ are independently optionally substituted with two R$^{1c}$. In some embodiments of a compound of Formula (I), (I'), (Ia)-(Id), (II), or (IIa)-(IIc), R$^{23}$ and R$^{24}$ are independently optionally substituted with three R$^{1c}$.

In some embodiments of a compound of Formula (I), (I'), (Ia)-(Id), (II), or (IIa)-(IIc), R$^{23}$ and R$^{24}$ are taken together with the nitrogen atom to which they are attached to form a heterocycloalkyl optionally substituted with one or two R$^{1d}$. In some embodiments of a compound of Formula (I), (I'), (Ia)-(Id), (II), or (IIa)-(IIc), R$^{23}$ and R$^{24}$ are taken together with the nitrogen atom to which they are attached to form a heterocycloalkyl optionally substituted one R$^{1d}$. In some embodiments of a compound of Formula (I), (I'), (Ia)-(Id), (II), or (IIa)-(IIc), R$^{23}$ and R$^{24}$ are taken together with the nitrogen atom to which they are attached to form a heterocycloalkyl optionally substituted with two R$^{1d}$. In some embodiments of a compound of Formula (I), (I'), (Ia)-(Id), (II), or (IIa)-(IIc), R$^{23}$ and R$^{24}$ are taken together with the nitrogen atom to which they are attached to form a heterocycloalkyl optionally substituted with three R$^{1d}$.

In some embodiments of a compound of Formula (I), (I'), (Ia)-(Id), (II), or (IIa)-(IIc), R$^{12}$ is optionally substituted with one or two R$^2$. In some embodiments of a compound of Formula (I), (I'), (Ia)-(Id), (II), or (IIa)-(IIc), R$^{12}$ is optionally substituted with one R$^2$. In some embodiments of a compound of Formula (I), (I'), (Ia)-(Id), (II), or (IIa)-(IIc), R$^{12}$ is optionally substituted with two R$^2$. In some embodiments of a compound of Formula (I), (I'), (Ia)-(Id), (II), or (IIa)-(IIc), R$^{12}$ is optionally substituted with three R$^2$.

In some embodiments of a compound of Formula (I), (I'), (Ia)-(Id), (II), or (IIa)-(IIc), R$^{13}$ is optionally substituted with one or two R$^3$. In some embodiments of a compound of Formula (I), (I'), (Ia)-(Id), (II), or (IIa)-(IIc), R$^{13}$ is optionally substituted with one R$^3$. In some embodiments of a compound of Formula (I), (I'), (Ia)-(Id), (II), or (IIa)-(IIc), R$^{13}$ is optionally substituted with two R$^3$. In some embodiments of a compound of Formula (I), (I'), (Ia)-(Id), (II), or (IIa)-(IIc), R$^{13}$ is optionally substituted with three R$^3$.

In some embodiments of a compound of Formula (I), (I'), (Ia)-(Id), (II), or (IIa)-(IIc), R$^{14}$ is optionally substituted with one or two R$^4$. In some embodiments of a compound of Formula (I), (I'), (Ia)-(Id), (II), or (IIa)-(IIc), R$^{14}$ is optionally substituted with one R$^4$. In some embodiments of a compound of Formula (I), (I'), (Ia)-(Id), (II), or (IIa)-(IIc), R$^{14}$ is optionally substituted with two R$^4$. In some embodiments of a compound of Formula (I), (I'), (Ia)-(Id), (II), or (IIa)-(IIc), R$^{14}$ is optionally substituted with three R$^4$.

In some embodiments of a compound of Formula (I), (I'), (Ia)-(Id), (II), or (IIa)-(IIc), R$^{15}$ is optionally substituted with one or two R$^5$. In some embodiments of a compound of Formula (I), (I'), (Ia)-(Id), (II), or (IIa)-(IIc), R$^{15}$ is optionally substituted with one R$^5$. In some embodiments of a compound of Formula (I), (I'), (Ia)-(Id), (II), or (IIa)-(IIc), R$^{15}$ is optionally substituted with two R$^5$. In some embodiments of a compound of Formula (I), (I'), (Ia)-(Id), (II), or (IIa)-(IIc), R$^{15}$ is optionally substituted with three R$^5$.

In some embodiments of a compound of Formula (I), (I'), or (Ia)-(Id), R$^{16}$ is optionally substituted with one or two R$^7$.

In some embodiments of a compound of Formula (I), (I'), or (Ia)-(Id), $R^{16}$ is optionally substituted with one $R^7$. In some embodiments of a compound of Formula (I), (I'), or (Ia)-(Id), $R^{16}$ is optionally substituted with two $R^7$. In some embodiments of a compound of Formula (I), (I'), or (Ia)-(Id), $R^{16}$ is optionally substituted with three $R^7$.

In some embodiments of a compound of Formula (II) or (IIa)-(IIc), $R^{26}$ is optionally substituted with one or two $R^7$. In some embodiments of a compound of Formula (II) or (IIa2-(IIc), $R^{26}$ is optionally substituted with one $R^7$. In some embodiments of a compound of Formula (II) or (IIa)-(IIc), $R^{26}$ is optionally substituted with two $R^7$. In some embodiments of a compound of Formula (II) or (IIa)-(IIc), $R^{26}$ is optionally substituted with three $R^7$.

In some embodiments of a compound of Formula (I), (I'), (Ia)-(Id), (II), or (IIa)-(IIc), $R^{17}$ is optionally substituted with one or two $R^8$. In some embodiments of a compound of Formula (I), (I'), (Ia)-(Id), (II), or (IIa)-(IIc), $R^{17}$ is optionally substituted with one $R^8$. In some embodiments of a compound of Formula (I), (I'), (Ia)-(Id), (II), or (IIa)-(IIc), $R^{17}$ is optionally substituted with two $R^8$. In some embodiments of a compound of Formula (I), (I'), (Ia)-(Id), (II), or (IIa)-(IIc), $R^{17}$ is optionally substituted with three $R^8$.

In some embodiments of a compound of Formula (I), (I'), (Ia)-(Id), (II), or (IIa)-(IIc), $R^{18}$ is optionally substituted with one or two $R^9$. In some embodiments of a compound of Formula (I), (I'), (Ia)-(Id), (II), or (IIa)-(IIc), $R^{18}$ is optionally substituted with one $R^9$. In some embodiments of a compound of Formula (I), (I'), (Ia)-(Id), (II), or (IIa)-(IIc), $R^{18}$ is optionally substituted with two $R^9$. In some embodiments of a compound of Formula (I), (I'), (Ia)-(Id), (II), or (IIa)-(IIc), $R^{19}$ is optionally substituted with three $R^9$.

In some embodiments, the compound or a pharmaceutically acceptable salt, solvate, or stereoisomer thereof is:

| Ex. | Structure |
|---|---|
| 1 | 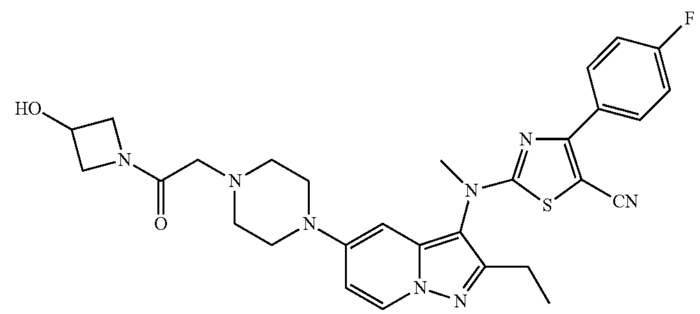 [SMILES: CCc1nn2ccc(N3CCN(CC(=O)N4CC(O)C4)CC3)cc2c1N(C)c1nc(-c2ccc(F)cc2)c(C#N)s1] |
| 2 | 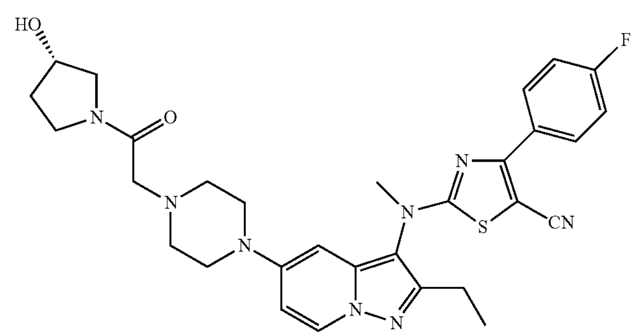 [SMILES: CCc1nn2ccc(N3CCN(CC(=O)N4CC[C@H](O)C4)CC3)cc2c1N(C)c1nc(-c2ccc(F)cc2)c(C#N)s1] |
| 3 | 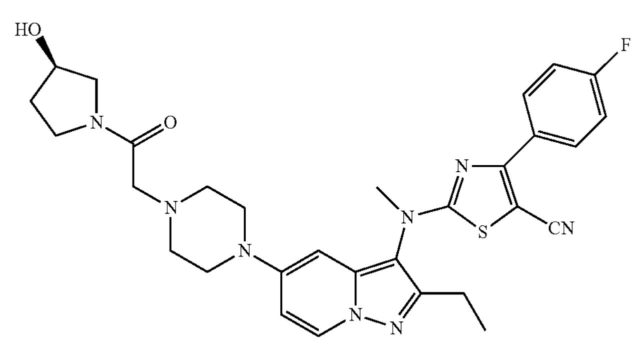 [SMILES: CCc1nn2ccc(N3CCN(CC(=O)N4CC[C@@H](O)C4)CC3)cc2c1N(C)c1nc(-c2ccc(F)cc2)c(C#N)s1] |

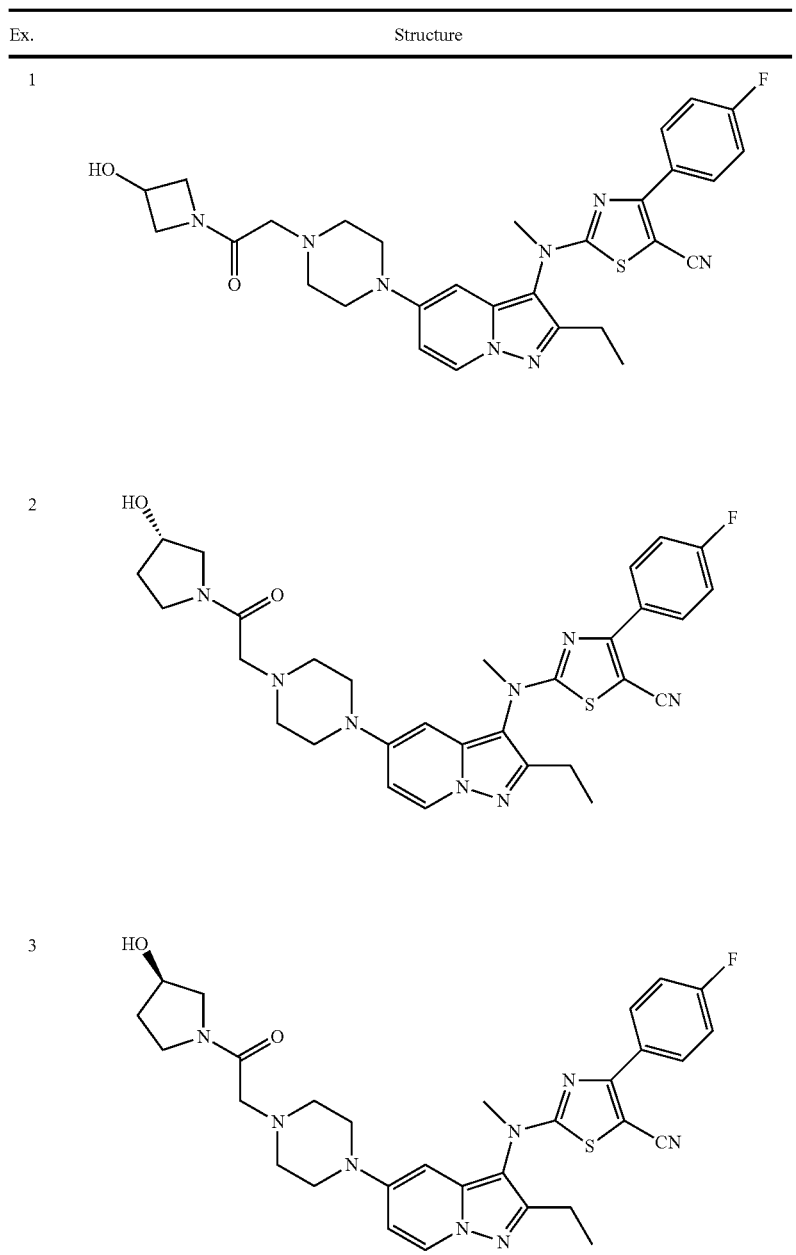

-continued

| Ex. | Structure |
|---|---|
| 4 | 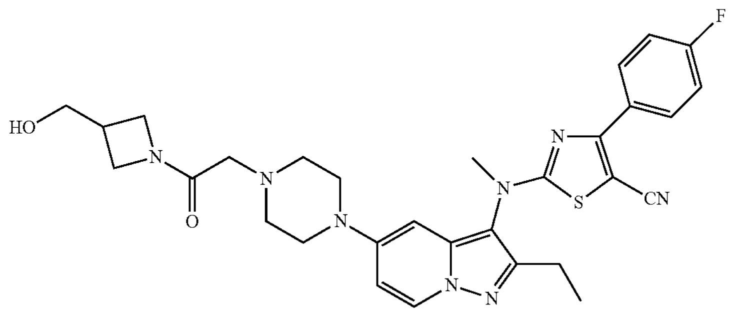 [SMILES: CCc1nn2ccc(N3CCN(CC(=O)N4CC(CO)C4)CC3)cc2c1N(C)c1nc(-c2ccc(F)cc2)c(C#N)s1] |
| 5 | 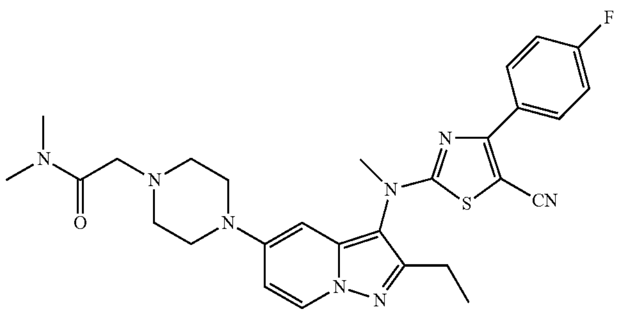 [SMILES: CCc1nn2ccc(N3CCN(CC(=O)N(C)C)CC3)cc2c1N(C)c1nc(-c2ccc(F)cc2)c(C#N)s1] |
| 6 | 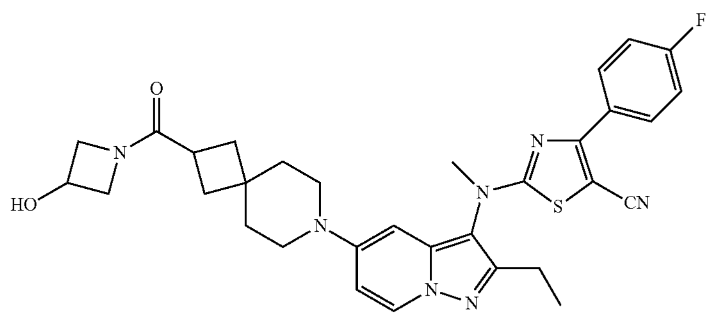 [SMILES: CCc1nn2ccc(N3CCC4(CC3)CC(C(=O)N3CC(O)C3)C4)cc2c1N(C)c1nc(-c2ccc(F)cc2)c(C#N)s1] |
| 7 | 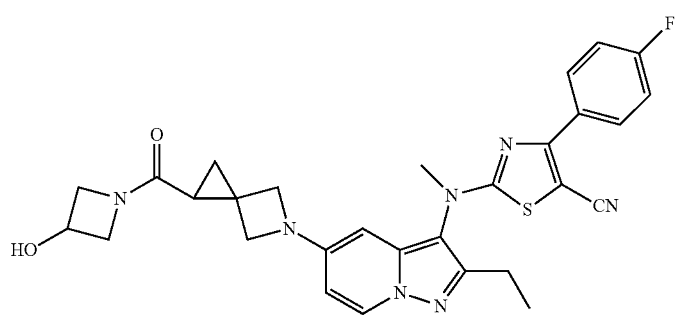 [SMILES: CCc1nn2ccc(N3CC4(CC4C(=O)N4CC(O)C4)C3)cc2c1N(C)c1nc(-c2ccc(F)cc2)c(C#N)s1] |
| 8 | 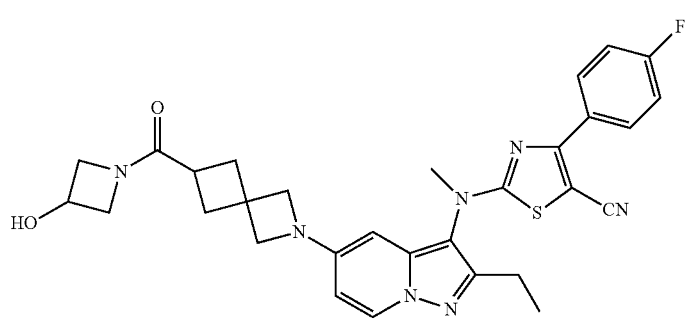 [SMILES: CCc1nn2ccc(N3CC4(CC(C(=O)N5CC(O)C5)C4)C3)cc2c1N(C)c1nc(-c2ccc(F)cc2)c(C#N)s1] |

| Ex. | Structure |
|---|---|
| 9 | 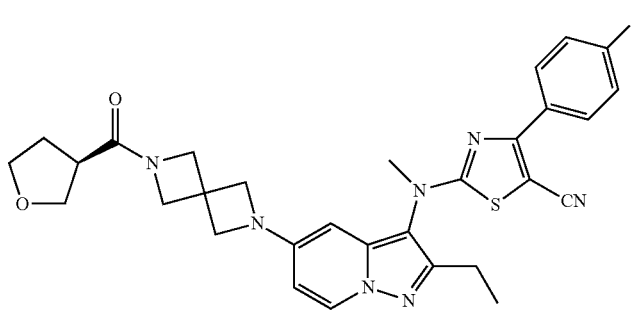 |
| 10 | 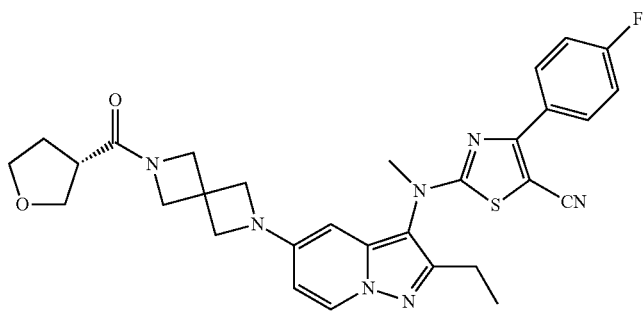 [SMILES: CCc1nn2ccc(N3CC4(CN(C(=O)[C@H]5CCOC5)C4)C3)cc2c1N(C)c1nc(-c2ccc(F)cc2)c(C#N)s1] |
| 11 | 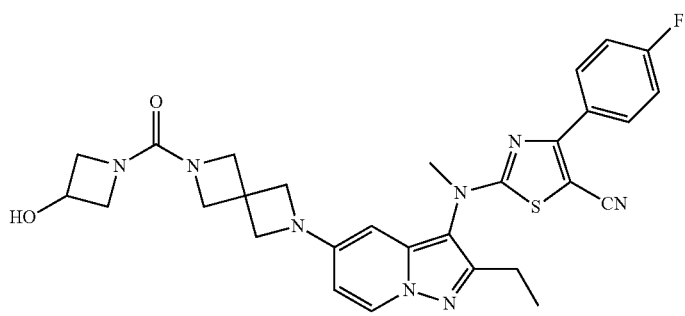 [SMILES: CCc1nn2ccc(N3CC4(CN(C(=O)N5CC(O)C5)C4)C3)cc2c1N(C)c1nc(-c2ccc(F)cc2)c(C#N)s1] |
| 12 | 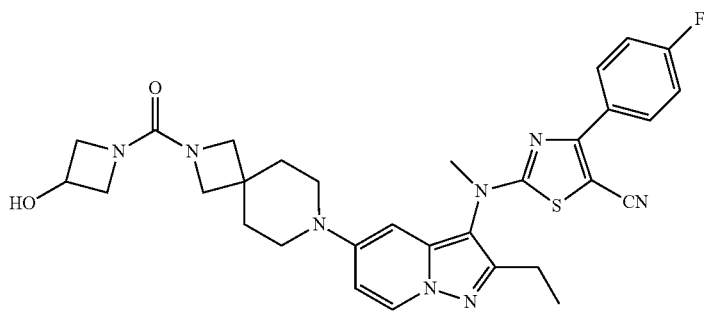 [SMILES: CCc1nn2ccc(N3CCC4(CC3)CN(C(=O)N3CC(O)C3)C4)cc2c1N(C)c1nc(-c2ccc(F)cc2)c(C#N)s1] |
| 13 | 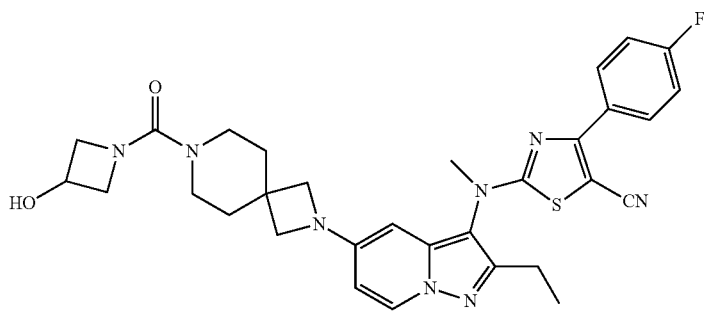 [SMILES: CCc1nn2ccc(N3CC4(CCN(C(=O)N5CC(O)C5)CC4)C3)cc2c1N(C)c1nc(-c2ccc(F)cc2)c(C#N)s1] |

| Ex. | Structure |
|---|---|
| 14 | 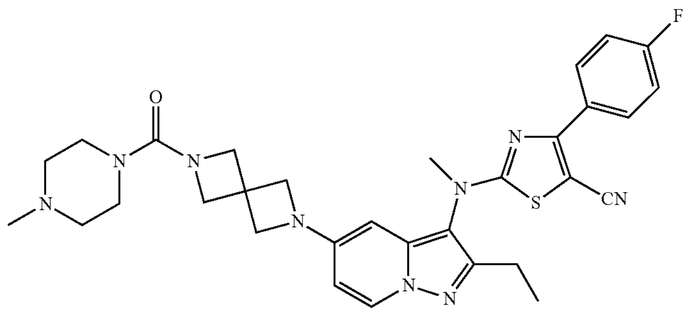 [SMILES: CCc1nn2ccc(N3CC4(CN(C(=O)N5CCN(C)CC5)C4)C3)cc2c1N(C)c1nc(-c2ccc(F)cc2)c(C#N)s1] |
| 15 | 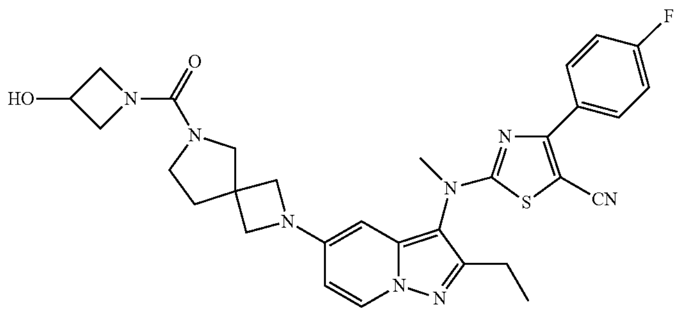 [SMILES: CCc1nn2ccc(N3CC4(CCN(C(=O)N5CC(O)C5)C4)C3)cc2c1N(C)c1nc(-c2ccc(F)cc2)c(C#N)s1] |
| 16 | 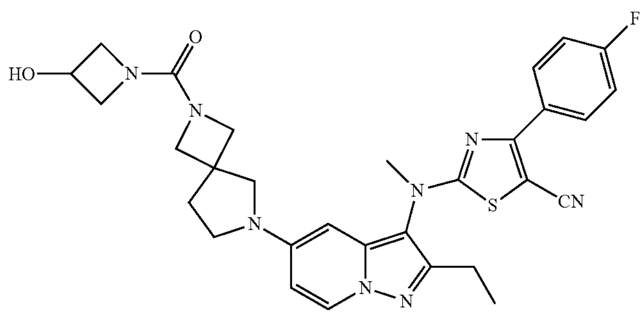 [SMILES: CCc1nn2ccc(N3CCC4(CN(C(=O)N5CC(O)C5)C4)C3)cc2c1N(C)c1nc(-c2ccc(F)cc2)c(C#N)s1] |
| 17 | 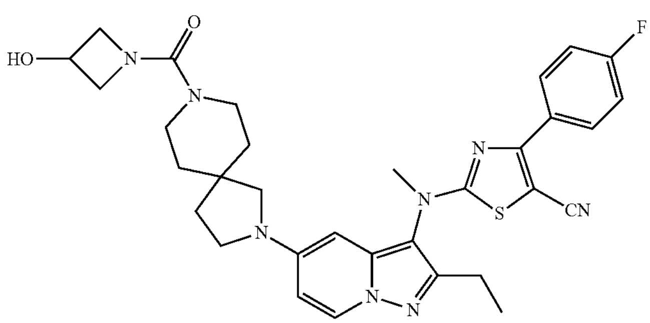 [SMILES: CCc1nn2ccc(N3CCC4(CCN(C(=O)N5CC(O)C5)CC4)C3)cc2c1N(C)c1nc(-c2ccc(F)cc2)c(C#N)s1] |
| 18 | 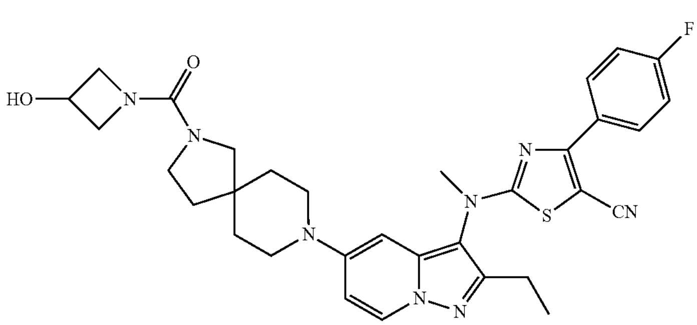 [SMILES: CCc1nn2ccc(N3CCC4(CCN(C(=O)N5CC(O)C5)C4)CC3)cc2c1N(C)c1nc(-c2ccc(F)cc2)c(C#N)s1] |

| Ex. | Structure |
|---|---|
| 19 | 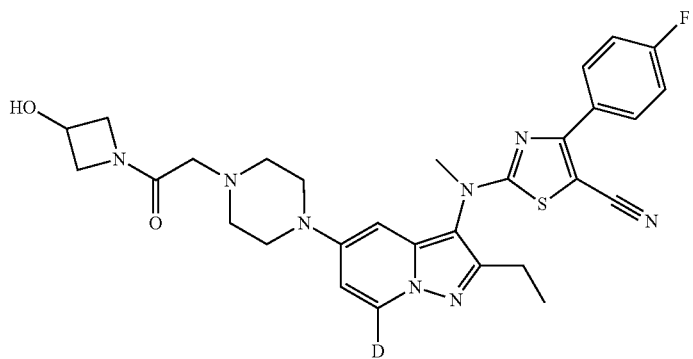 [SMILES: [2H]c1cc(N2CCN(CC(=O)N3CC(O)C3)CC2)cc2c(N(C)c3nc(-c4ccc(F)cc4)c(C#N)s3)c(CC)nn12] |
| 20 | 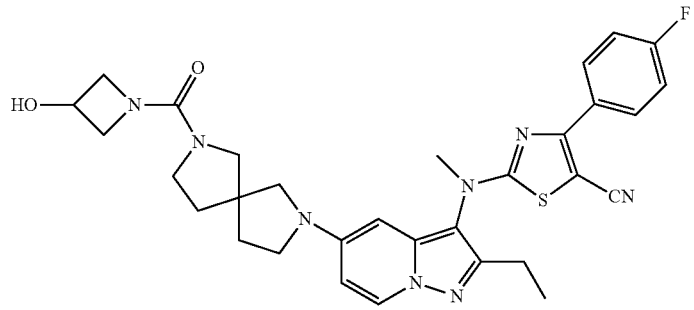 [SMILES: CCc1nn2ccc(N3CCC4(CCN(C(=O)N5CC(O)C5)C4)C3)cc2c1N(C)c1nc(-c2ccc(F)cc2)c(C#N)s1] |
| 21 | 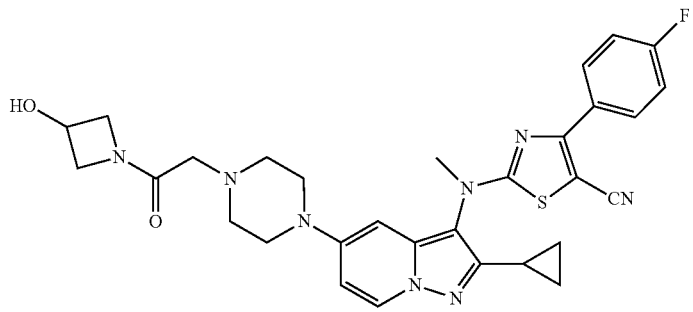 [SMILES: CN(c1nc(-c2ccc(F)cc2)c(C#N)s1)c1c(C2CC2)nn2ccc(N3CCN(CC(=O)N4CC(O)C4)CC3)cc12] |
| 22 | 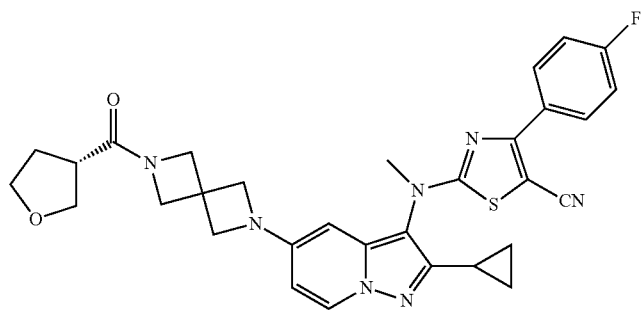 [SMILES: CN(c1nc(-c2ccc(F)cc2)c(C#N)s1)c1c(C2CC2)nn2ccc(N3CC4(CN(C(=O)[C@H]5CCOC5)C4)C3)cc12] |

-continued

| Ex. | Structure |
|---|---|
| 23 | 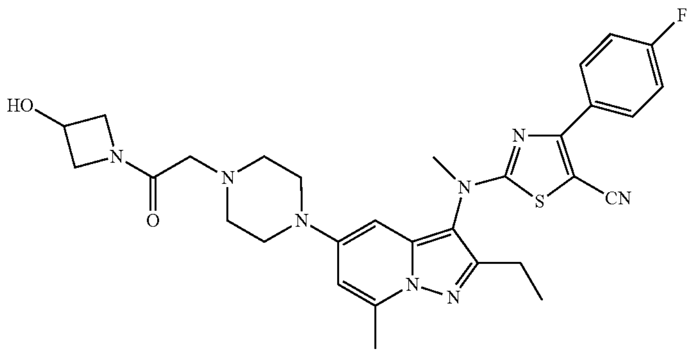 [SMILES: CCc1nn2c(C)cc(N3CCN(CC(=O)N4CC(O)C4)CC3)cc2c1N(C)c1nc(-c2ccc(F)cc2)c(C#N)s1] |
| 24 | 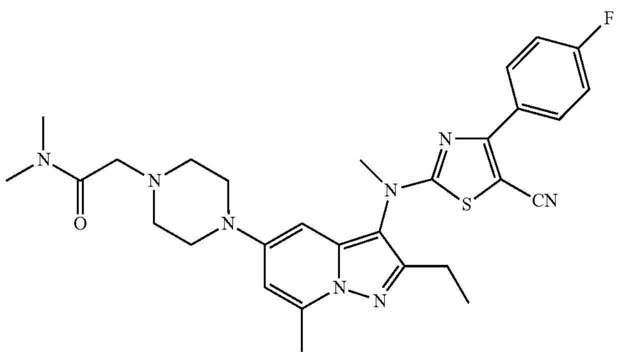 [SMILES: CCc1nn2c(C)cc(N3CCN(CC(=O)N(C)C)CC3)cc2c1N(C)c1nc(-c2ccc(F)cc2)c(C#N)s1] |
| 25 | 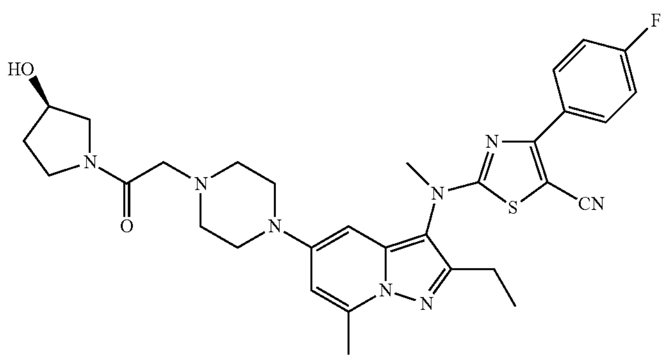 [SMILES: CCc1nn2c(C)cc(N3CCN(CC(=O)N4CC[C@@H](O)C4)CC3)cc2c1N(C)c1nc(-c2ccc(F)cc2)c(C#N)s1] |
| 26 | 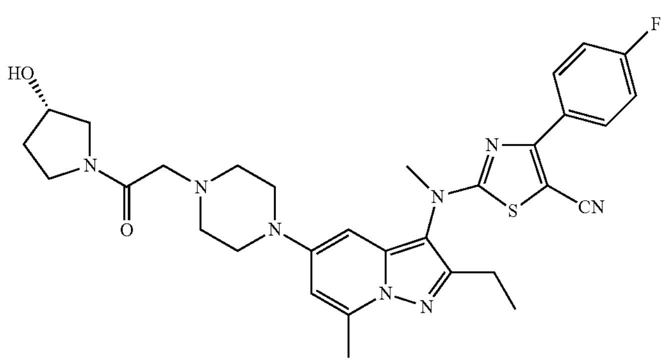 [SMILES: CCc1nn2c(C)cc(N3CCN(CC(=O)N4CC[C@H](O)C4)CC3)cc2c1N(C)c1nc(-c2ccc(F)cc2)c(C#N)s1] |

-continued
| Ex. | Structure |
|---|---|
| 27 | 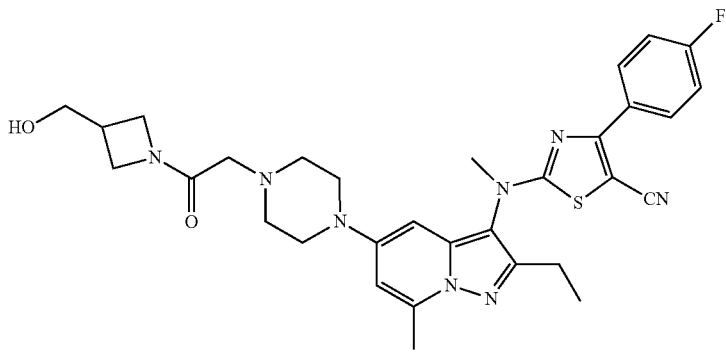 [SMILES: CCc1nn2c(C)cc(N3CCN(CC(=O)N4CC(CO)C4)CC3)cc2c1N(C)c1nc(-c2ccc(F)cc2)c(C#N)s1] |
| 28 | 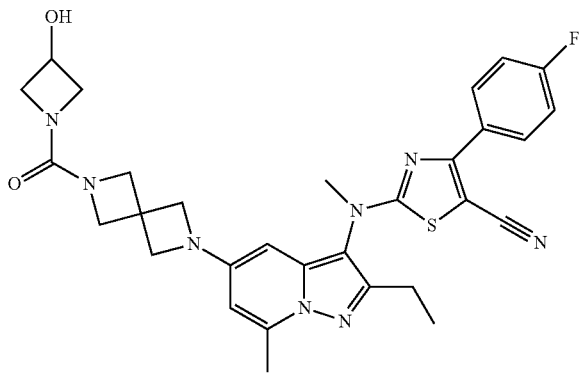 [SMILES: CCc1nn2c(C)cc(N3CC4(CN(C(=O)N5CC(O)C5)C4)C3)cc2c1N(C)c1nc(-c2ccc(F)cc2)c(C#N)s1] |
| 29 | 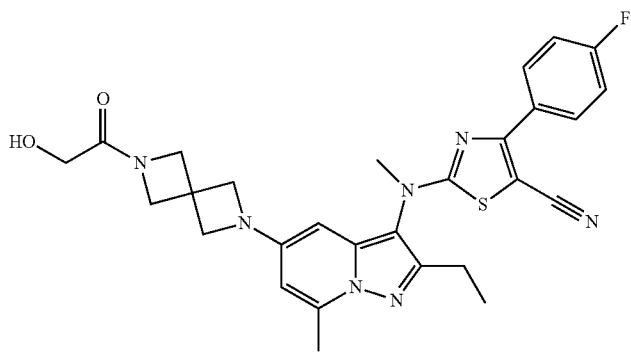 [SMILES: CCc1nn2c(C)cc(N3CC4(CN(C(=O)CO)C4)C3)cc2c1N(C)c1nc(-c2ccc(F)cc2)c(C#N)s1] |
| 30 | 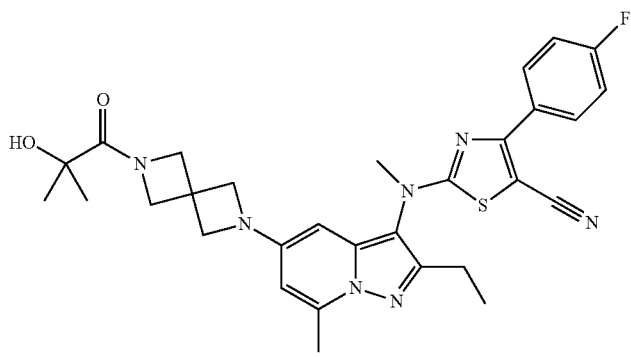 [SMILES: CCc1nn2c(C)cc(N3CC4(CN(C(=O)C(C)(C)O)C4)C3)cc2c1N(C)c1nc(-c2ccc(F)cc2)c(C#N)s1] |

-continued
| Ex. | Structure |
|---|---|
| 31 | 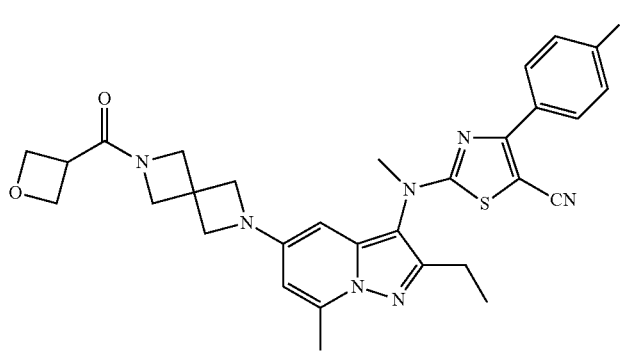 |
| 32 | 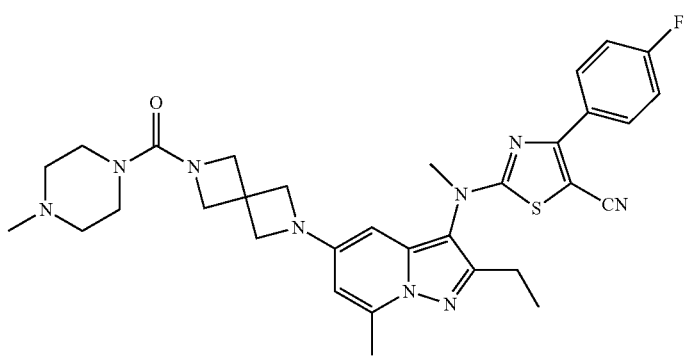 [SMILES: CCc1nn2c(C)cc(N3CC4(CN(C(=O)N5CCN(C)CC5)C4)C3)cc2c1N(C)c1nc(-c2ccc(F)cc2)c(C#N)s1] |
| 33 | 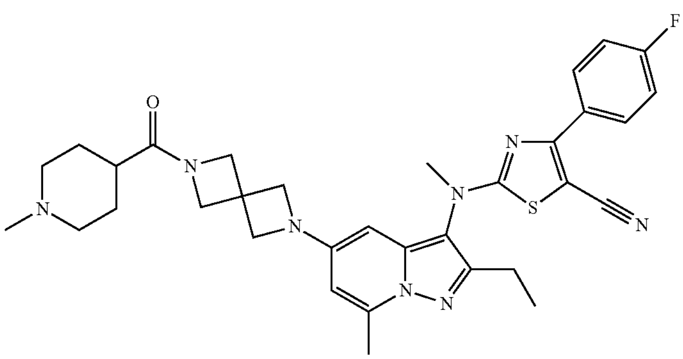 [SMILES: CCc1nn2c(C)cc(N3CC4(CN(C(=O)C5CCN(C)CC5)C4)C3)cc2c1N(C)c1nc(-c2ccc(F)cc2)c(C#N)s1] |
| 34 | 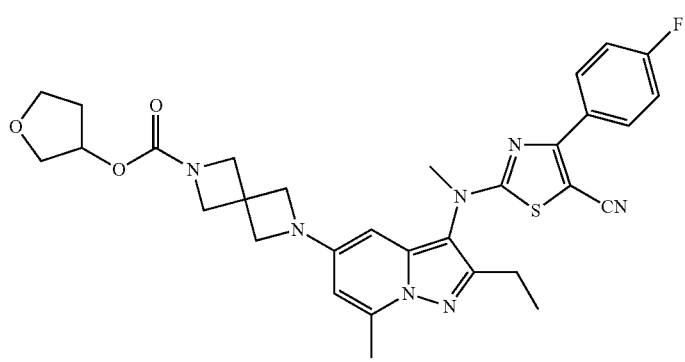 [SMILES: CCc1nn2c(C)cc(N3CC4(CN(C(=O)OC5CCOC5)C4)C3)cc2c1N(C)c1nc(-c2ccc(F)cc2)c(C#N)s1] |

-continued

| Ex. | Structure |
|---|---|
| 35 | 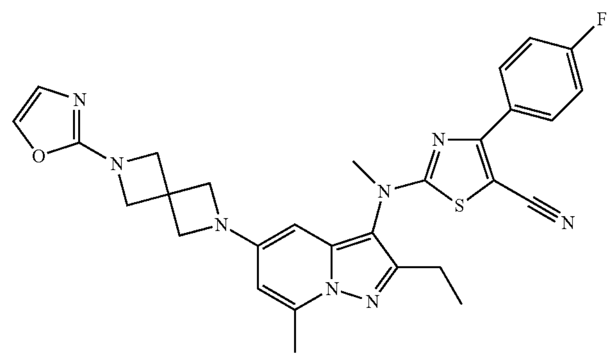 [SMILES: CCc1nn2c(C)cc(N3CC4(C3)CN(c3ncco3)C4)cc2c1N(C)c1nc(-c2ccc(F)cc2)c(C#N)s1] |
| 36 | 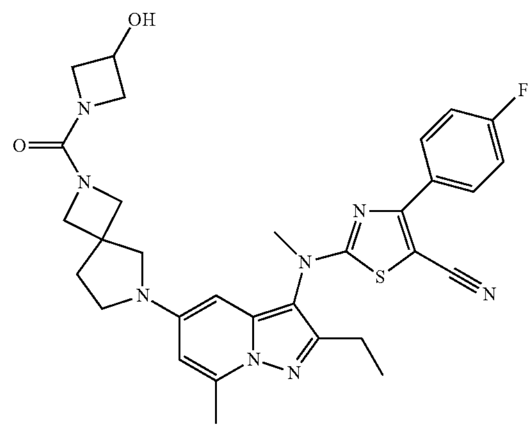 [SMILES: CCc1nn2c(C)cc(N3CCC4(CN(C(=O)N5CC(O)C5)C4)C3)cc2c1N(C)c1nc(-c2ccc(F)cc2)c(C#N)s1] |
| 37 | 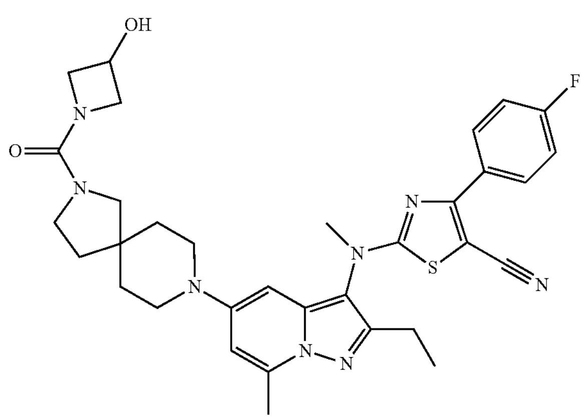 [SMILES: CCc1nn2c(C)cc(N3CCC4(CCN(C(=O)N5CC(O)C5)C4)CC3)cc2c1N(C)c1nc(-c2ccc(F)cc2)c(C#N)s1] |
| 38 | 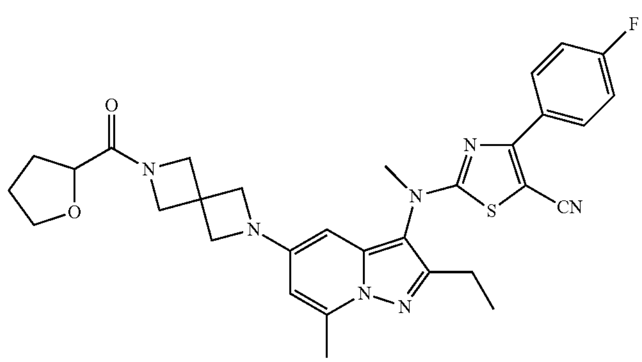 [SMILES: CCc1nn2c(C)cc(N3CC4(CN(C(=O)C5CCCO5)C4)C3)cc2c1N(C)c1nc(-c2ccc(F)cc2)c(C#N)s1] |

| Ex. | Structure |
|---|---|
| 39 | 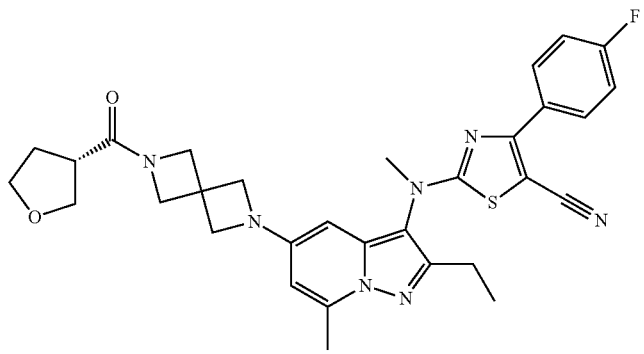 [SMILES: CCc1nn2c(C)cc(N3CC4(CN(C(=O)[C@H]5CCOC5)C4)C3)cc2c1N(C)c1nc(-c2ccc(F)cc2)c(C#N)s1] |
| 40 | 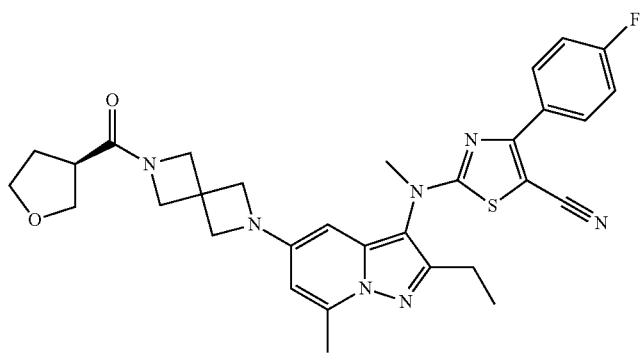 [SMILES: CCc1nn2c(C)cc(N3CC4(CN(C(=O)[C@@H]5CCOC5)C4)C3)cc2c1N(C)c1nc(-c2ccc(F)cc2)c(C#N)s1] |
| 41 | 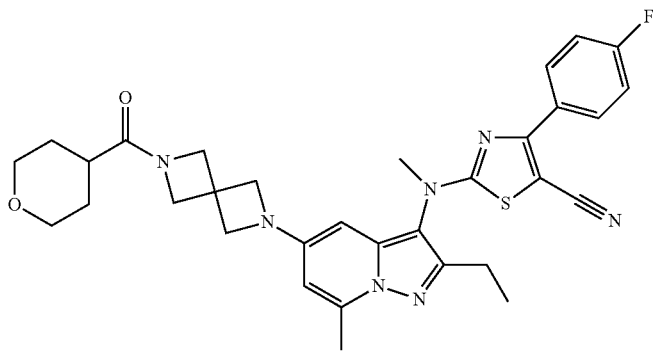 [SMILES: CCc1nn2c(C)cc(N3CC4(CN(C(=O)C5CCOCC5)C4)C3)cc2c1N(C)c1nc(-c2ccc(F)cc2)c(C#N)s1] |
| 42 | 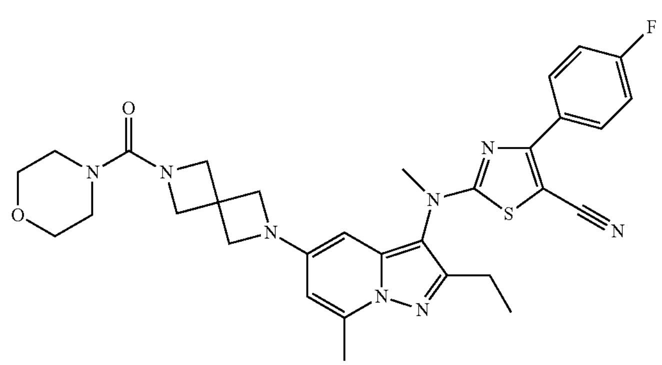 |

-continued
| Ex. | Structure |
|---|---|
| 43 | 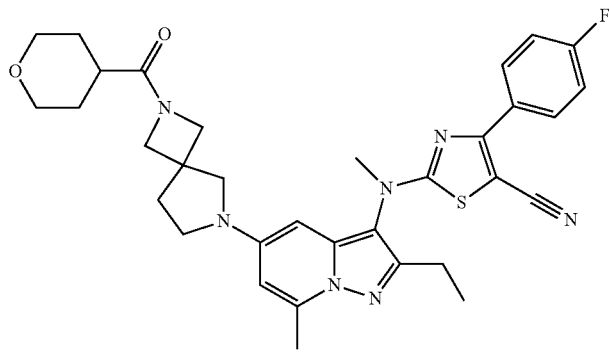 [SMILES: CCc1nn2c(C)cc(N3CCC4(CN(C(=O)C5CCOCC5)C4)C3)cc2c1N(C)c1nc(-c2ccc(F)cc2)c(C#N)s1] |
| 44 | 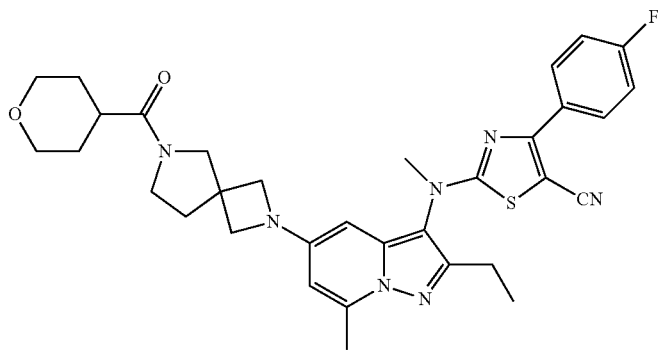 [SMILES: CCc1nn2c(C)cc(N3CC4(CCN(C(=O)C5CCOCC5)C4)C3)cc2c1N(C)c1nc(-c2ccc(F)cc2)c(C#N)s1] |
| 45 | 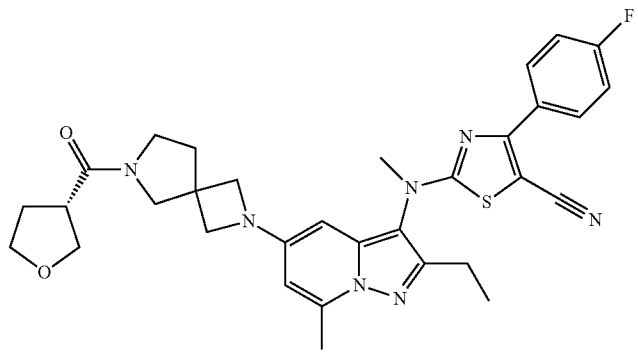 [SMILES: CCc1nn2c(C)cc(N3CC4(CCN(C(=O)[C@H]5CCOC5)C4)C3)cc2c1N(C)c1nc(-c2ccc(F)cc2)c(C#N)s1] |
| 46 | 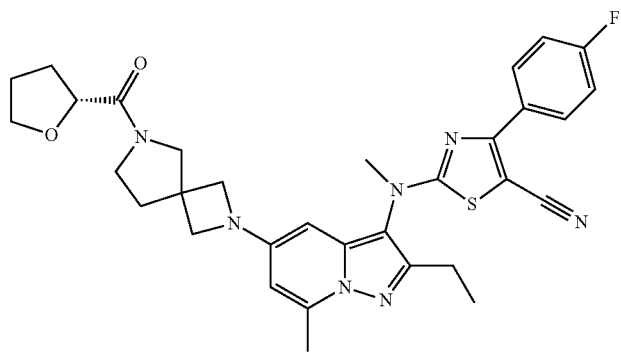 [SMILES: CCc1nn2c(C)cc(N3CC4(CCN(C(=O)[C@H]5CCCO5)C4)C3)cc2c1N(C)c1nc(-c2ccc(F)cc2)c(C#N)s1] |

-continued

| Ex. | Structure |
|---|---|
| 47 | 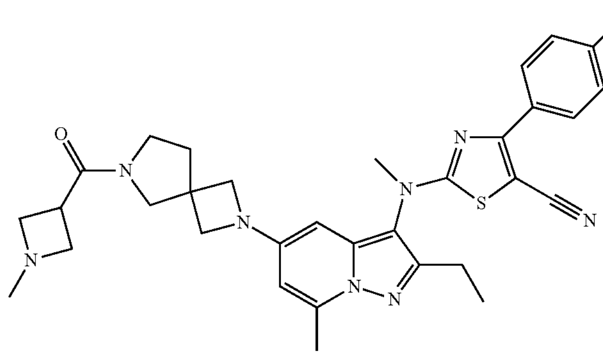 |
| 49 | 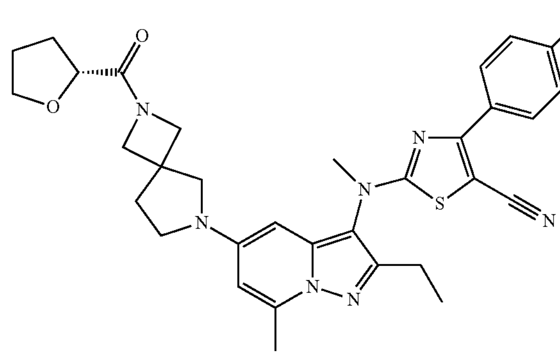 |
| 50 | 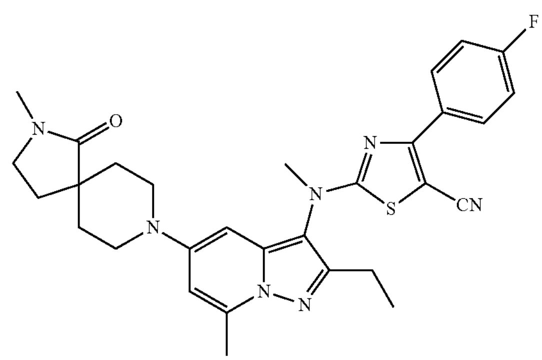 [SMILES: CCc1nn2c(C)cc(N3CCC4(CCN(C)C4=O)CC3)cc2c1N(C)c1nc(-c2ccc(F)cc2)c(C#N)s1] |
| 51 | 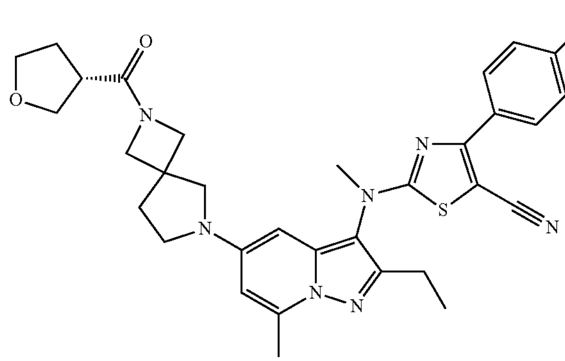 |

| Ex. | Structure |
|---|---|
| 52 | 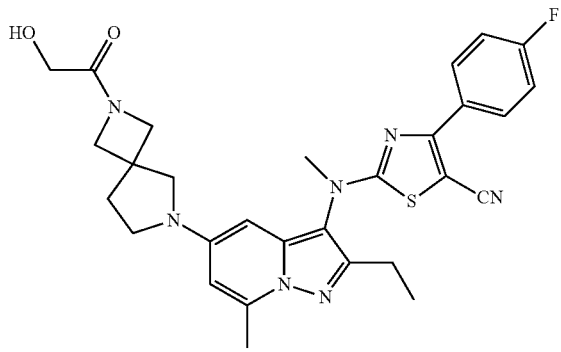 [SMILES: CCc1nn2c(C)cc(N3CCC4(CN(C(=O)CO)C4)C3)cc2c1N(C)c1nc(-c2ccc(F)cc2)c(C#N)s1] |
| 53 | 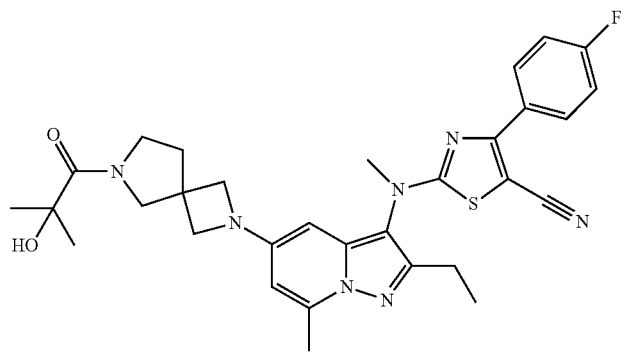 [SMILES: CCc1nn2c(C)cc(N3CC4(CCN(C(=O)C(C)(C)O)C4)C3)cc2c1N(C)c1nc(-c2ccc(F)cc2)c(C#N)s1] |
| 54 | 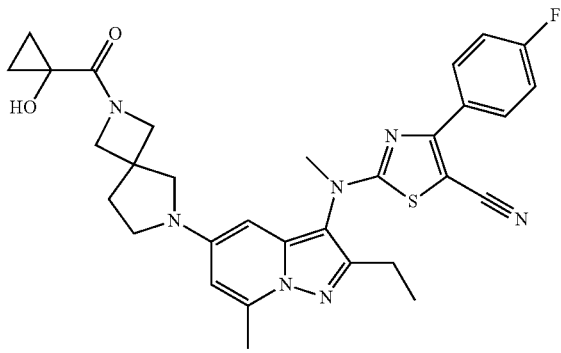 [SMILES: CCc1nn2c(C)cc(N3CCC4(CN(C(=O)C5(O)CC5)C4)C3)cc2c1N(C)c1nc(-c2ccc(F)cc2)c(C#N)s1] |
| 55 | 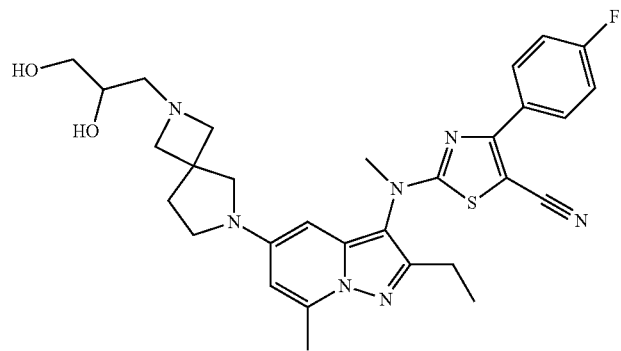 [SMILES: CCc1nn2c(C)cc(N3CCC4(CN(CC(O)CO)C4)C3)cc2c1N(C)c1nc(-c2ccc(F)cc2)c(C#N)s1] |

-continued
| Ex. | Structure |
|---|---|
| 56 | 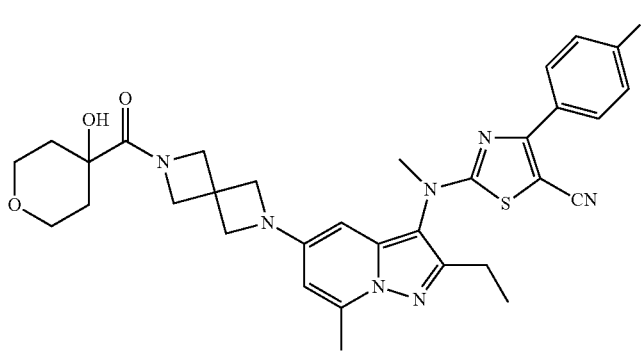 |
| 57 | 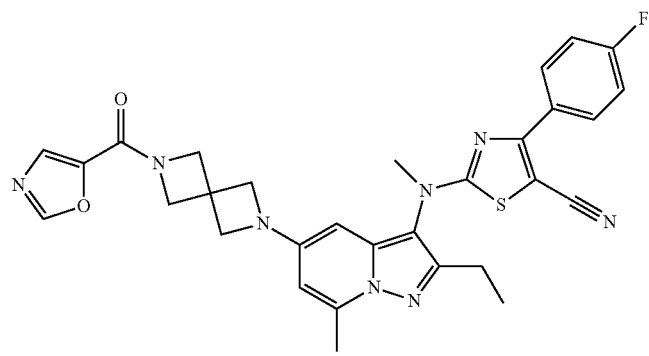 [SMILES: CCc1nn2c(C)cc(N3CC4(CN(C(=O)c5cnco5)C4)C3)cc2c1N(C)c1nc(-c2ccc(F)cc2)c(C#N)s1] |
| 59 | 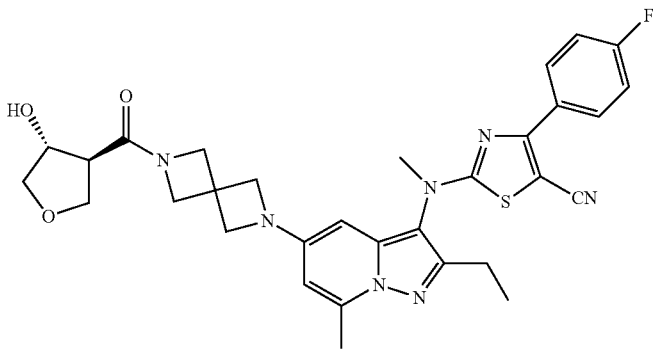 [SMILES: CCc1nn2c(C)cc(N3CC4(CN(C(=O)[C@H]5COC[C@@H]5O)C4)C3)cc2c1N(C)c1nc(-c2ccc(F)cc2)c(C#N)s1] |
| 60 | 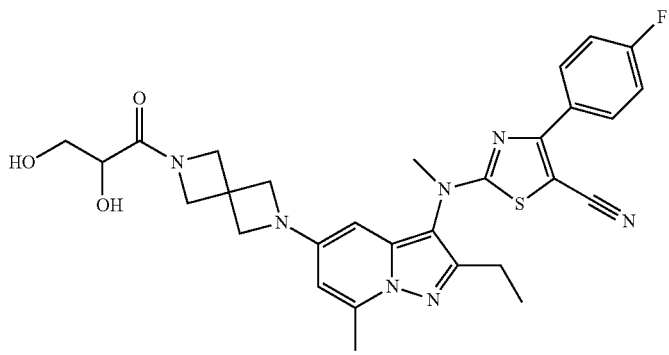 [SMILES: CCc1nn2c(C)cc(N3CC4(CN(C(=O)C(O)CO)C4)C3)cc2c1N(C)c1nc(-c2ccc(F)cc2)c(C#N)s1] |

-continued

| Ex. | Structure |
|-----|-----------|
| 61  | 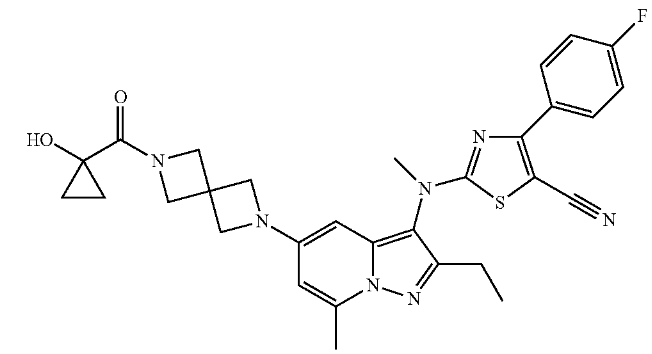 [SMILES: CCc1nn2c(C)cc(N3CC4(CN(C(=O)C5(O)CC5)C4)C3)cc2c1N(C)c1nc(-c2ccc(F)cc2)c(C#N)s1]          |
| 62  | 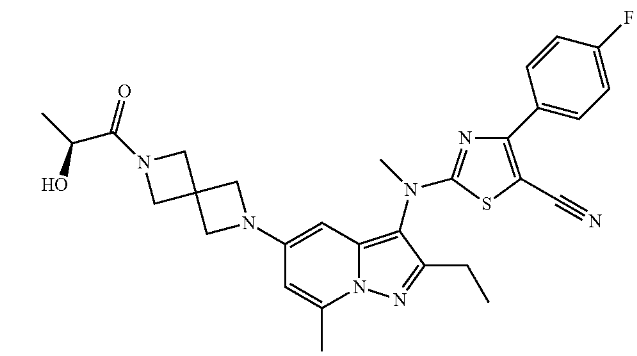 [SMILES: CCc1nn2c(C)cc(N3CC4(CN(C(=O)[C@H](C)O)C4)C3)cc2c1N(C)c1nc(-c2ccc(F)cc2)c(C#N)s1]          |
| 63  | 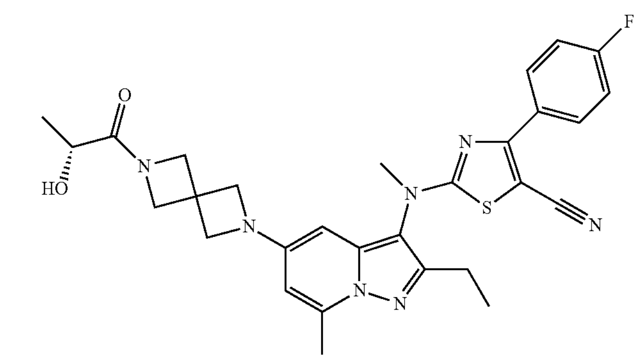 [SMILES: CCc1nn2c(C)cc(N3CC4(CN(C(=O)[C@@H](C)O)C4)C3)cc2c1N(C)c1nc(-c2ccc(F)cc2)c(C#N)s1]          |
| 64  | 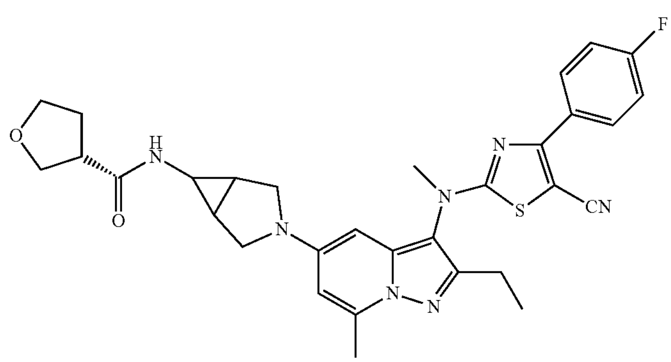          |

-continued
| Ex. | Structure |
|---|---|
| 66 | 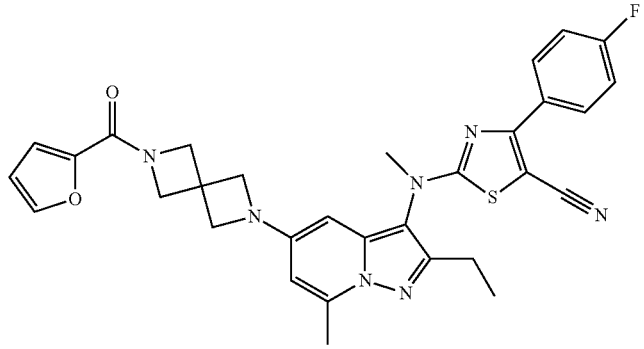 [SMILES: CCc1nn2c(C)cc(N3CC4(CN(C(=O)c5ccco5)C4)C3)cc2c1N(C)c1nc(-c2ccc(F)cc2)c(C#N)s1] |
| 67 | 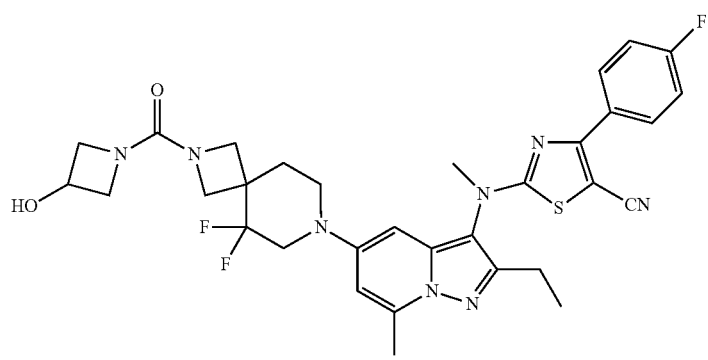 [SMILES: CCc1nn2c(C)cc(N3CCC4(CN(C(=O)N5CC(O)C5)C4)C(F)(F)C3)cc2c1N(C)c1nc(-c2ccc(F)cc2)c(C#N)s1] |
| 68 | 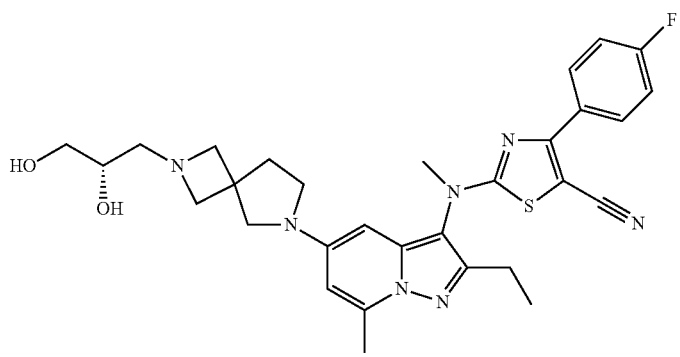 [SMILES: CCc1nn2c(C)cc(N3CCC4(CN(C[C@H](O)CO)C4)C3)cc2c1N(C)c1nc(-c2ccc(F)cc2)c(C#N)s1] |
| 69 | 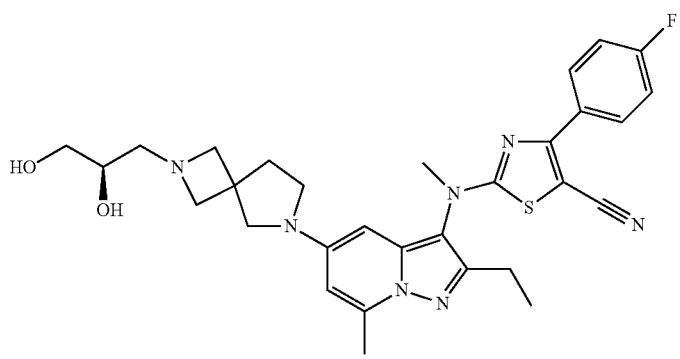 [SMILES: CCc1nn2c(C)cc(N3CCC4(CN(C[C@@H](O)CO)C4)C3)cc2c1N(C)c1nc(-c2ccc(F)cc2)c(C#N)s1] |

-continued
| Ex. | Structure |
|---|---|
| 70 | 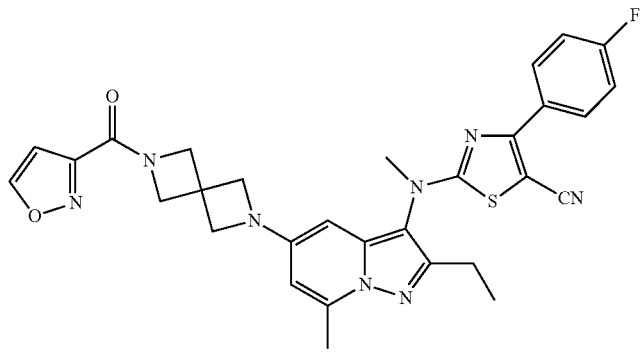 [SMILES: CCc1nn2c(C)cc(N3CC4(CN(C(=O)c5ccon5)C4)C3)cc2c1N(C)c1nc(-c2ccc(F)cc2)c(C#N)s1] |
| 71 | 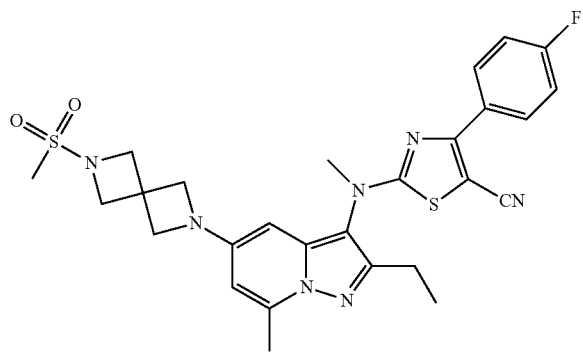 [SMILES: CCc1nn2c(C)cc(N3CC4(C3)CN(S(C)(=O)=O)C4)cc2c1N(C)c1nc(-c2ccc(F)cc2)c(C#N)s1] |
| 72 | 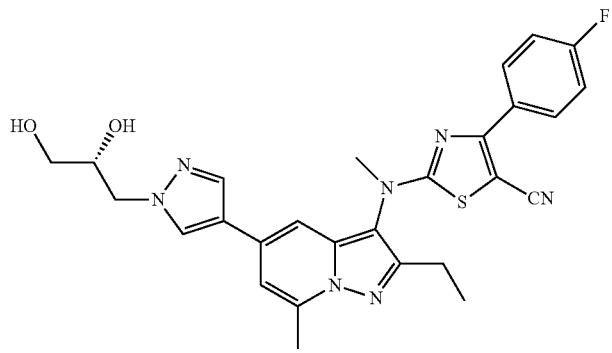 [SMILES: CCc1nn2c(C)cc(-c3cnn(C[C@@H](O)CO)c3)cc2c1N(C)c1nc(-c2ccc(F)cc2)c(C#N)s1] |
| 73 | 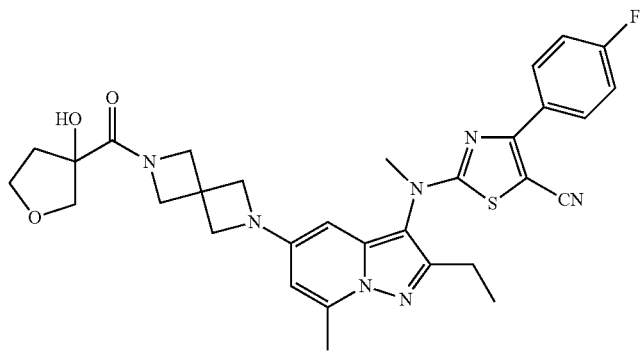 [SMILES: CCc1nn2c(C)cc(N3CC4(CN(C(=O)C5(O)CCOC5)C4)C3)cc2c1N(C)c1nc(-c2ccc(F)cc2)c(C#N)s1] |

| Ex. | Structure |
|---|---|
| 74 | 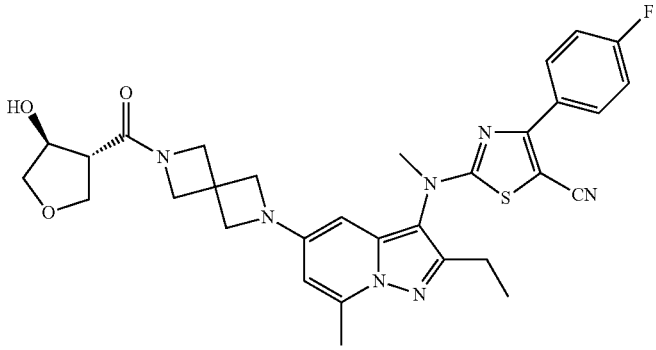 [SMILES: CCc1nn2c(C)cc(N3CC4(CN(C(=O)[C@@H]5COC[C@H]5O)C4)C3)cc2c1N(C)c1nc(-c2ccc(F)cc2)c(C#N)s1] |
| 75 | 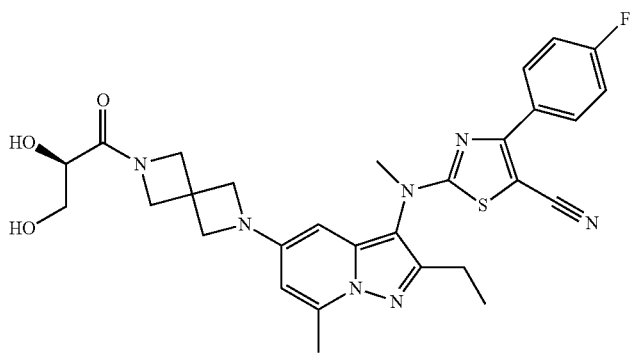 [SMILES: CCc1nn2c(C)cc(N3CC4(CN(C(=O)[C@H](O)CO)C4)C3)cc2c1N(C)c1nc(-c2ccc(F)cc2)c(C#N)s1] |
| 76 | 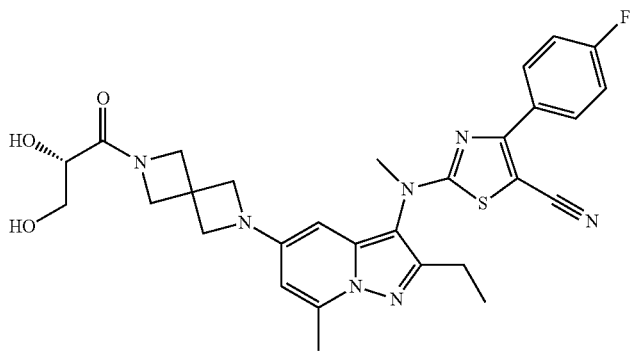 [SMILES: CCc1nn2c(C)cc(N3CC4(CN(C(=O)[C@@H](O)CO)C4)C3)cc2c1N(C)c1nc(-c2ccc(F)cc2)c(C#N)s1] |
| 77 | 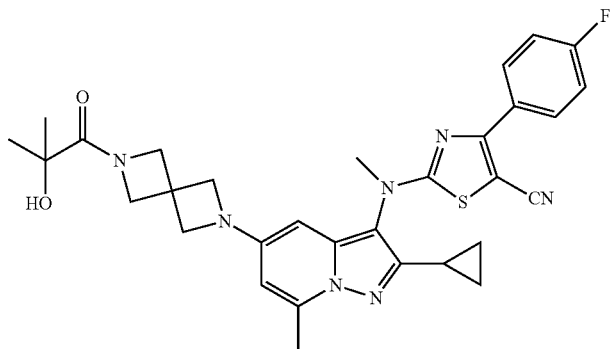 [SMILES: Cc1cc(N2CC3(CN(C(=O)C(C)(C)O)C3)C2)cc2c(N(C)c3nc(-c4ccc(F)cc4)c(C#N)s3)c(C3CC3)nn12] |

| Ex. | Structure |
|---|---|
| 78 | 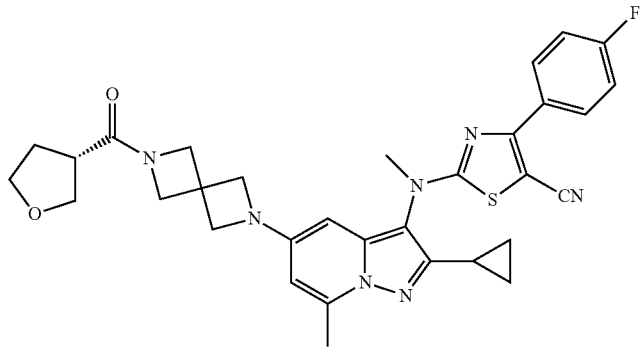 [SMILES: Cc1cc(N2CC3(CN(C(=O)[C@H]4CCOC4)C3)C2)cc2c(N(C)c3nc(-c4ccc(F)cc4)c(C#N)s3)c(C3CC3)nn12] |
| 79 | 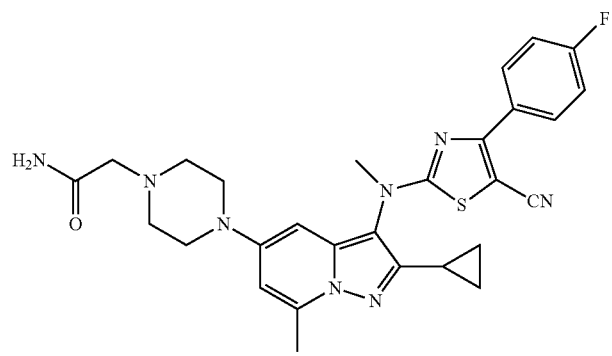 [SMILES: Cc1cc(N2CCN(CC(N)=O)CC2)cc2c(N(C)c3nc(-c4ccc(F)cc4)c(C#N)s3)c(C3CC3)nn12] |
| 80 | 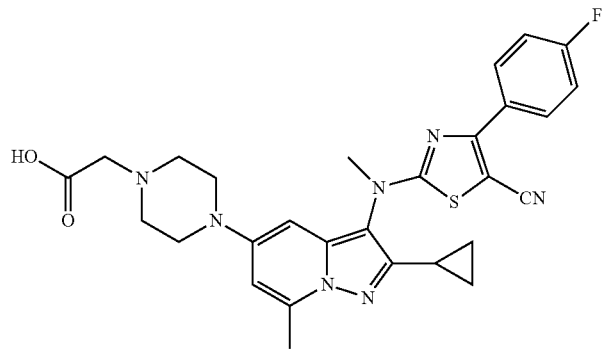 [SMILES: Cc1cc(N2CCN(CC(=O)O)CC2)cc2c(N(C)c3nc(-c4ccc(F)cc4)c(C#N)s3)c(C3CC3)nn12] |
| 82 | 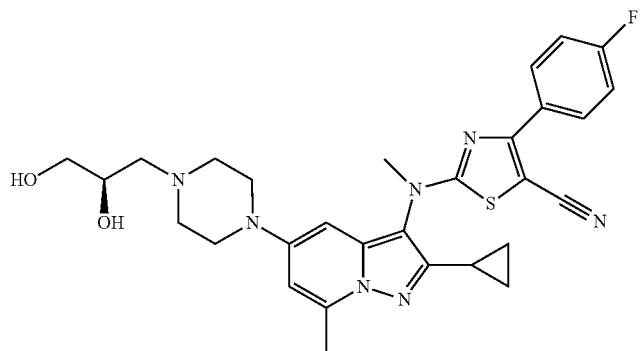 [SMILES: Cc1cc(N2CCN(C[C@@H](O)CO)CC2)cc2c(N(C)c3nc(-c4ccc(F)cc4)c(C#N)s3)c(C3CC3)nn12] |

-continued
| Ex. | Structure |
|---|---|
| 83 | 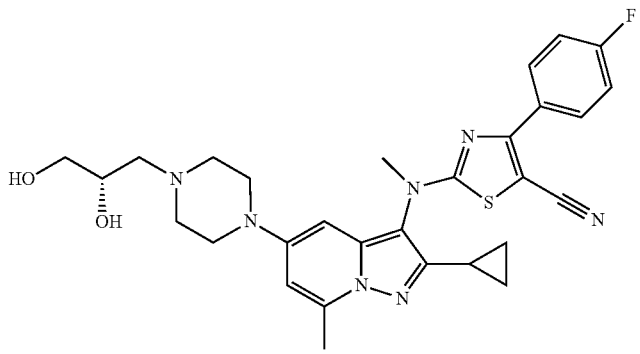 [SMILES: Cc1cc(N2CCN(C[C@H](O)CO)CC2)cc2c(N(C)c3nc(-c4ccc(F)cc4)c(C#N)s3)c(C3CC3)nn12] |
| 84 | 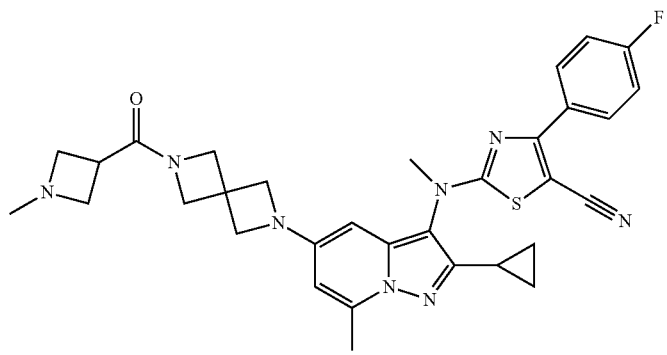 [SMILES: Cc1cc(N2CC3(CN(C(=O)C4CN(C)C4)C3)C2)cc2c(N(C)c3nc(-c4ccc(F)cc4)c(C#N)s3)c(C3CC3)nn12] |
| 85 | 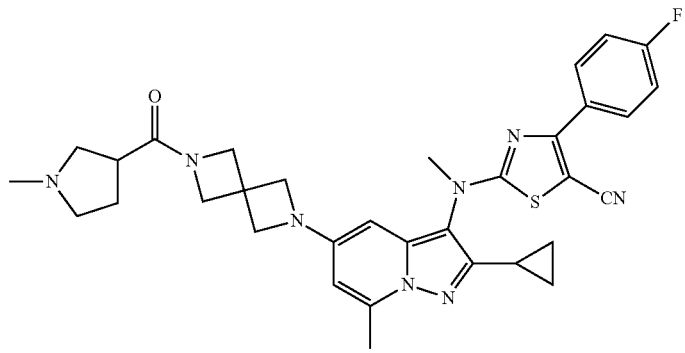 [SMILES: Cc1cc(N2CC3(CN(C(=O)C4CCN(C)C4)C3)C2)cc2c(N(C)c3nc(-c4ccc(F)cc4)c(C#N)s3)c(C3CC3)nn12] |
| 86 | 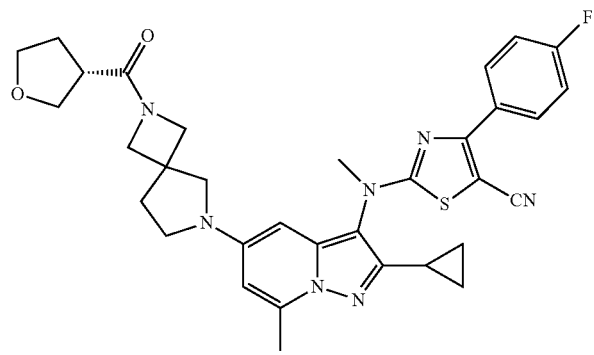 [SMILES: Cc1cc(N2CCC3(CN(C(=O)[C@H]4CCOC4)C3)C2)cc2c(N(C)c3nc(-c4ccc(F)cc4)c(C#N)s3)c(C3CC3)nn12] |

-continued
| Ex. | Structure |
|---|---|
| 87 | 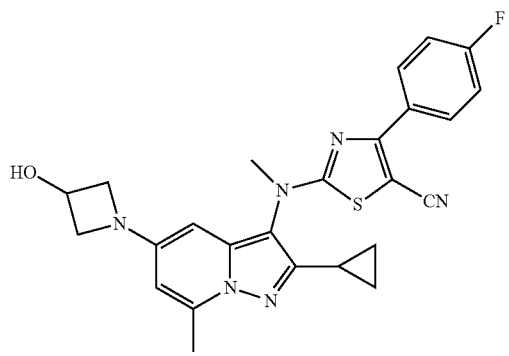 [SMILES: Cc1cc(N2CC(C#N)C2)cc2c(N(C)c3nc(-c4ccc(F)cc4)c(C#N)s3)c(C3CC3)nn12] |
| 88 | 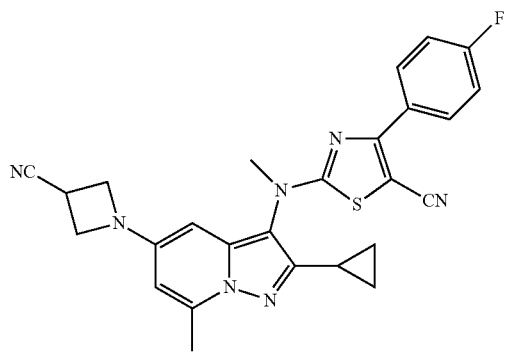 |
| 90 | 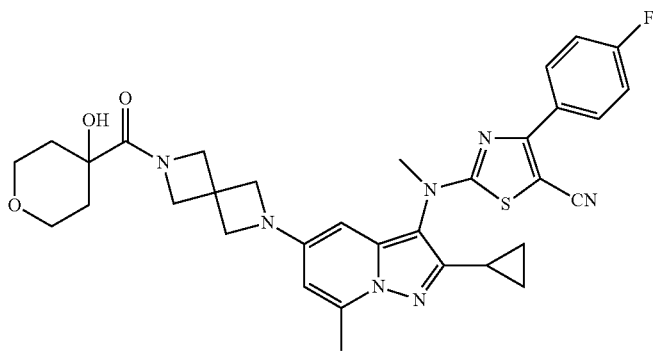 [SMILES: Cc1cc(N2CC3(CN(C(=O)C4(O)CCOCC4)C3)C2)cc2c(N(C)c3nc(-c4ccc(F)cc4)c(C#N)s3)c(C3CC3)nn12] |
| 91 | 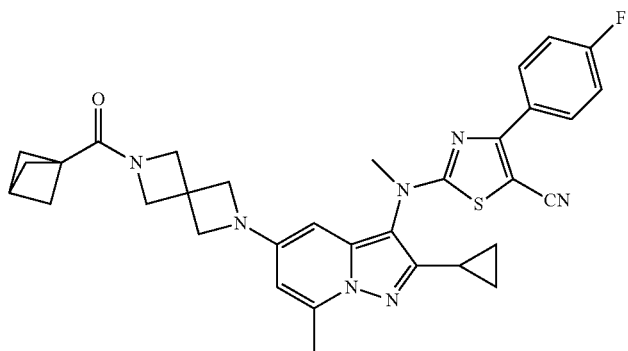 [SMILES: Cc1cc(N2CC3(CN(C(=O)C45CC(C4)C5)C3)C2)cc2c(N(C)c3nc(-c4ccc(F)cc4)c(C#N)s3)c(C3CC3)nn12] |

-continued
| Ex. | Structure |
|---|---|
| 92 | 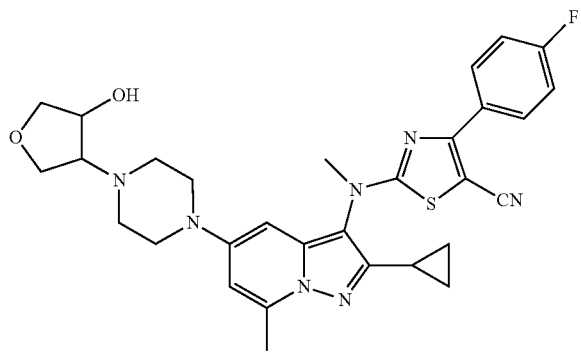 [SMILES: Cc1cc(N2CCN(C3COCC3O)CC2)cc2c(N(C)c3nc(-c4ccc(F)cc4)c(C#N)s3)c(C3CC3)nn12] |
| 93 | 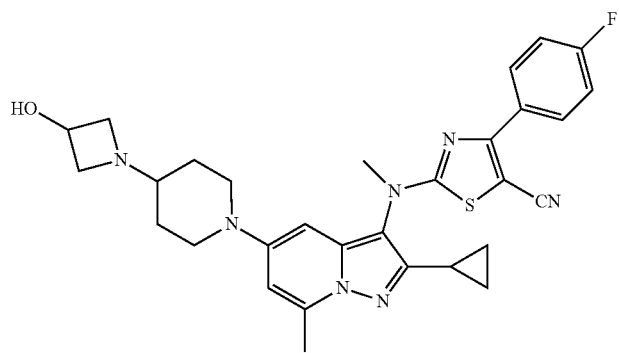 [SMILES: Cc1cc(N2CCC(N3CC(O)C3)CC2)cc2c(N(C)c3nc(-c4ccc(F)cc4)c(C#N)s3)c(C3CC3)nn12] |
| 94 | 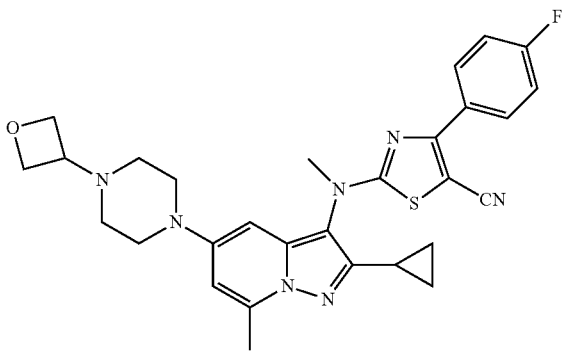 [SMILES: Cc1cc(N2CCN(C3COC3)CC2)cc2c(N(C)c3nc(-c4ccc(F)cc4)c(C#N)s3)c(C3CC3)nn12] |
| 95 | 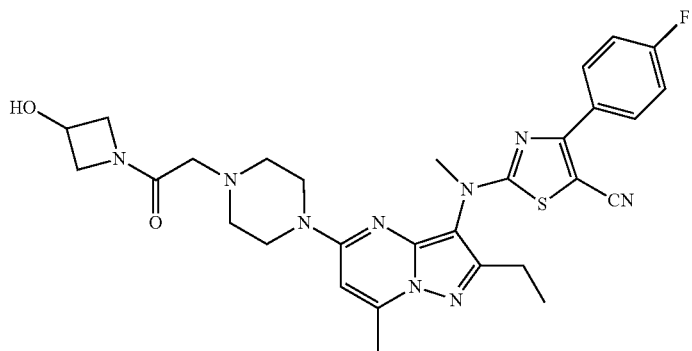 |

-continued
| Ex. | Structure |
|---|---|
| 96 | 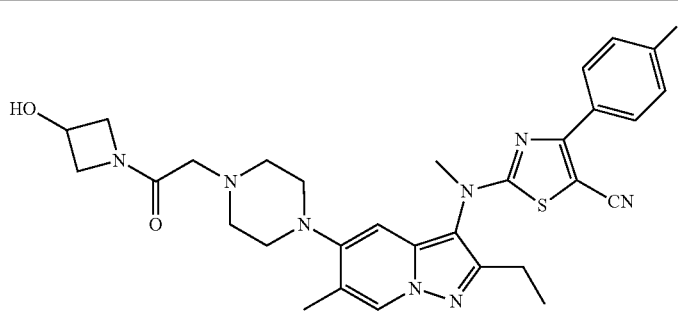 |
| 97 | 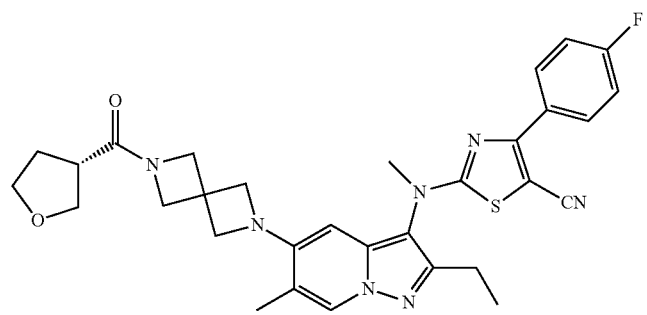 [SMILES: CCc1nn2cc(C)c(N3CC4(CN(C(=O)[C@H]5CCOC5)C4)C3)cc2c1N(C)c1nc(-c2ccc(F)cc2)c(C#N)s1] |
| 98 | 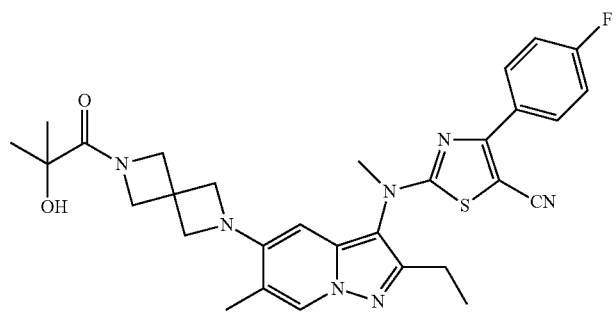 [SMILES: CCc1nn2cc(C)c(N3CC4(CN(C(=O)C(C)(C)O)C4)C3)cc2c1N(C)c1nc(-c2ccc(F)cc2)c(C#N)s1] |
| 99 | 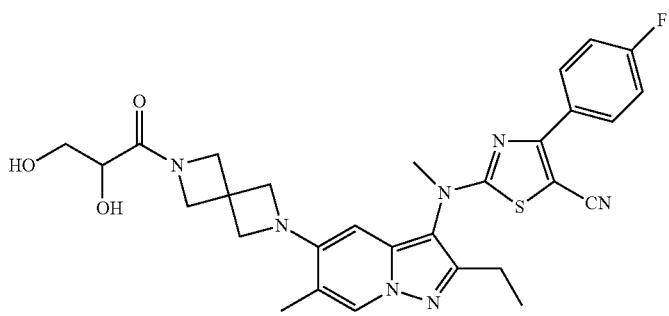 [SMILES: CCc1nn2cc(C)c(N3CC4(CN(C(=O)C(O)CO)C4)C3)cc2c1N(C)c1nc(-c2ccc(F)cc2)c(C#N)s1] |
| 100 | 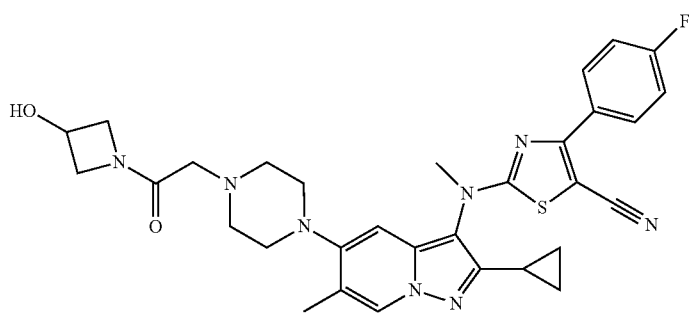 [SMILES: Cc1cn2nc(C3CC3)c(N(C)c3nc(-c4ccc(F)cc4)c(C#N)s3)c2cc1N1CCN(CC(=O)N2CC(O)C2)CC1] |

-continued

| Ex. | Structure |
|---|---|
| 101 | 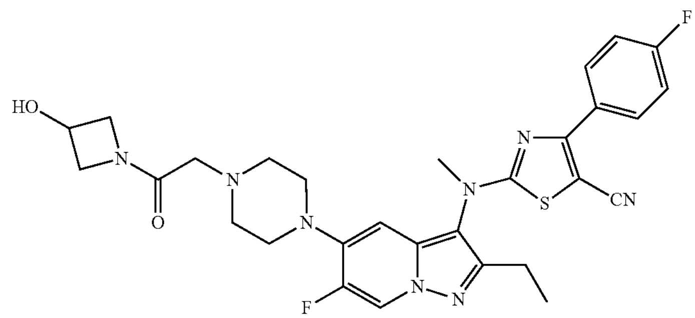 [SMILES: CCc1nn2cc(F)c(N3CCN(CC(=O)N4CC(O)C4)CC3)cc2c1N(C)c1nc(-c2ccc(F)cc2)c(C#N)s1] |
| 102 | 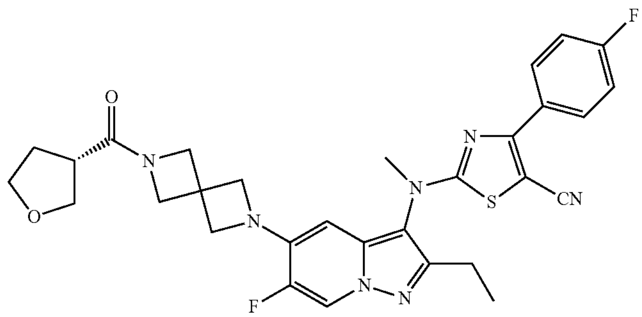 [SMILES: CCc1nn2cc(F)c(N3CC4(CN(C(=O)[C@H]5CCOC5)C4)C3)cc2c1N(C)c1nc(-c2ccc(F)cc2)c(C#N)s1] |
| 103 | 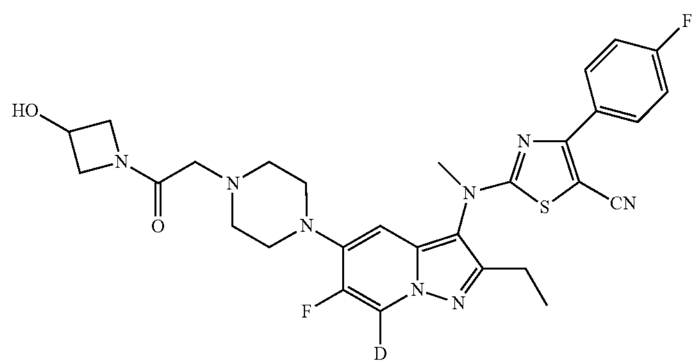 [SMILES: [2H]c1c(F)c(N2CCN(CC(=O)N3CC(O)C3)CC2)cc2c(N(C)c3nc(-c4ccc(F)cc4)c(C#N)s3)c(CC)nn12] |
| 104 | 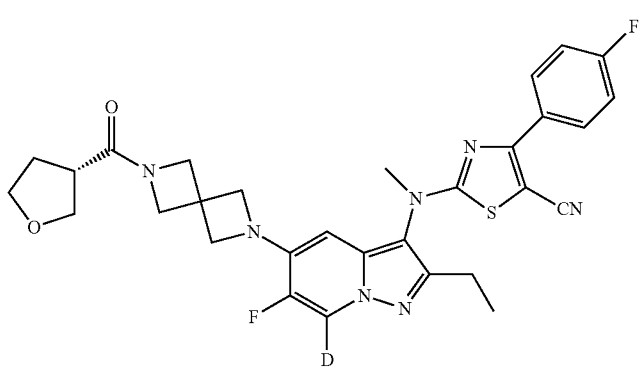 [SMILES: [2H]c1c(F)c(N2CC3(CN(C(=O)[C@H]4CCOC4)C3)C2)cc2c(N(C)c3nc(-c4ccc(F)cc4)c(C#N)s3)c(CC)nn12] |

-continued
| Ex. | Structure |
|---|---|
| 105 | 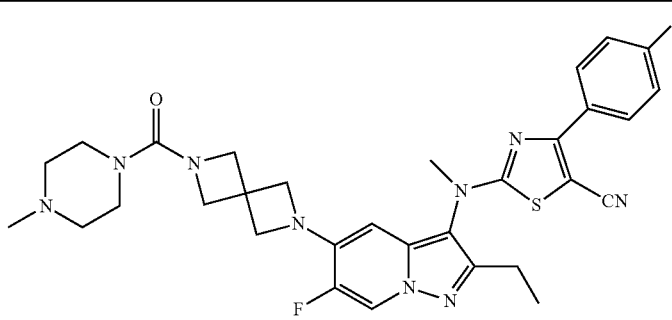 |
| 106 | 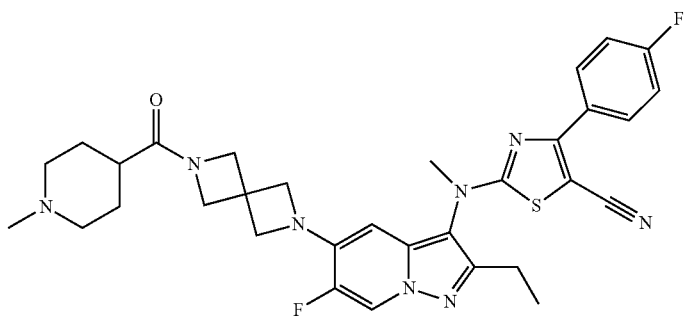 [SMILES: CCc1nn2cc(F)c(N3CC4(CN(C(=O)C5CCN(C)CC5)C4)C3)cc2c1N(C)c1nc(-c2ccc(F)cc2)c(C#N)s1] |
| 107 | 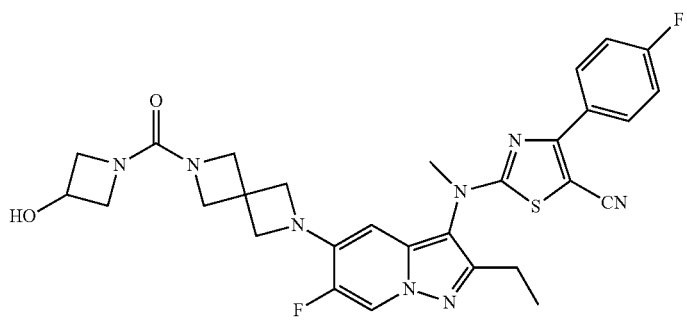 [SMILES: CCc1nn2cc(F)c(N3CC4(CN(C(=O)N5CC(O)C5)C4)C3)cc2c1N(C)c1nc(-c2ccc(F)cc2)c(C#N)s1] |
| 108 | 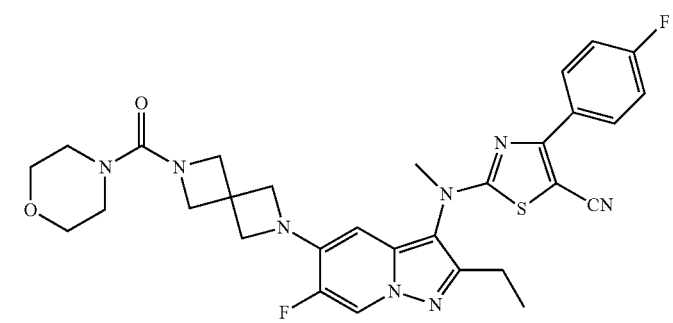 [SMILES: CCc1nn2cc(F)c(N3CC4(CN(C(=O)N5CCOCC5)C4)C3)cc2c1N(C)c1nc(-c2ccc(F)cc2)c(C#N)s1] |
| 109 | 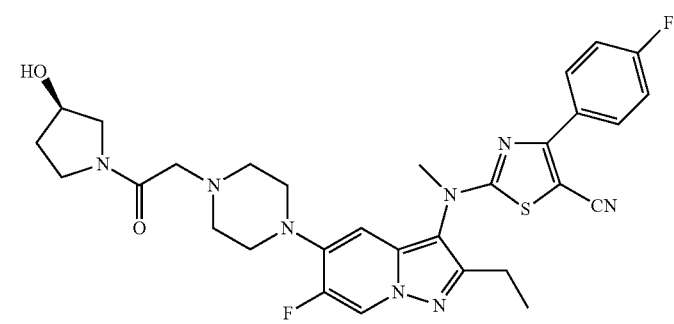 [SMILES: CCc1nn2cc(F)c(N3CCN(CC(=O)N4CC[C@@H](O)C4)CC3)cc2c1N(C)c1nc(-c2ccc(F)cc2)c(C#N)s1] |

-continued
| Ex. | Structure |
|---|---|
| 110 | 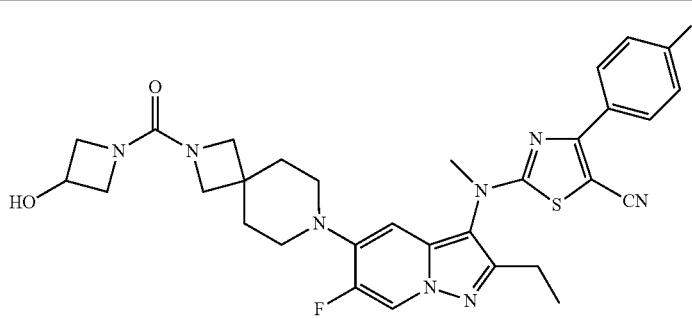 |
| 111 | 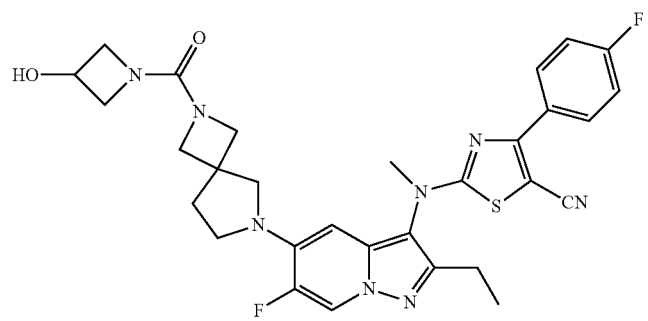 [SMILES: CCc1nn2cc(F)c(N3CCC4(CN(C(=O)N5CC(O)C5)C4)C3)cc2c1N(C)c1nc(-c2ccc(F)cc2)c(C#N)s1] |
| 112 | 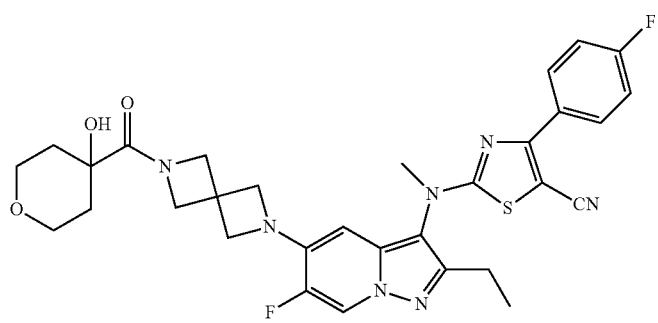 [SMILES: CCc1nn2cc(F)c(N3CC4(CN(C(=O)C5(O)CCOCC5)C4)C3)cc2c1N(C)c1nc(-c2ccc(F)cc2)c(C#N)s1] |
| 113 | 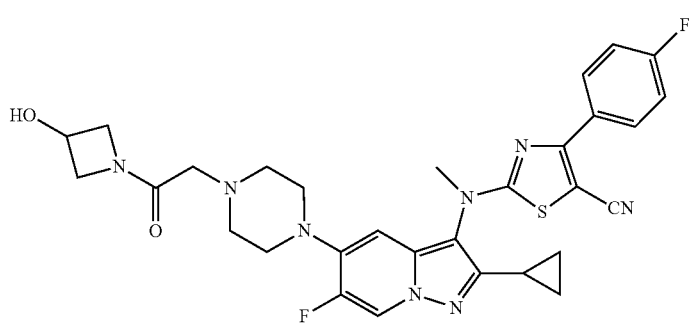 [SMILES: CN(c1nc(-c2ccc(F)cc2)c(C#N)s1)c1c(C2CC2)nn2cc(F)c(N3CCN(CC(=O)N4CC(O)C4)CC3)cc12] |
| 114 | 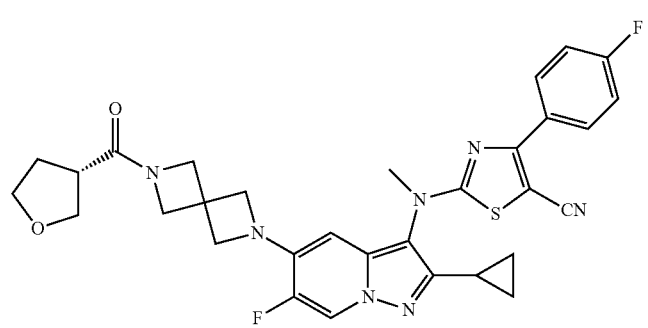 [SMILES: CN(c1nc(-c2ccc(F)cc2)c(C#N)s1)c1c(C2CC2)nn2cc(F)c(N3CC4(CN(C(=O)[C@H]5CCOC5)C4)C3)cc12] |

-continued
| Ex. | Structure |
|---|---|
| 115 | 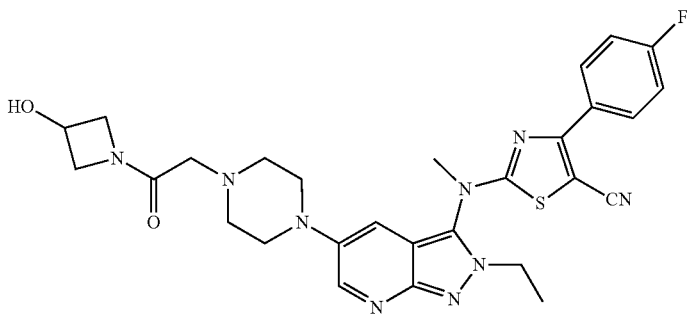 [SMILES: CCn1nc2ncc(N3CCN(CC(=O)N4CC(O)C4)CC3)cc2c1N(C)c1nc(-c2ccc(F)cc2)c(C#N)s1] |
| 116 | 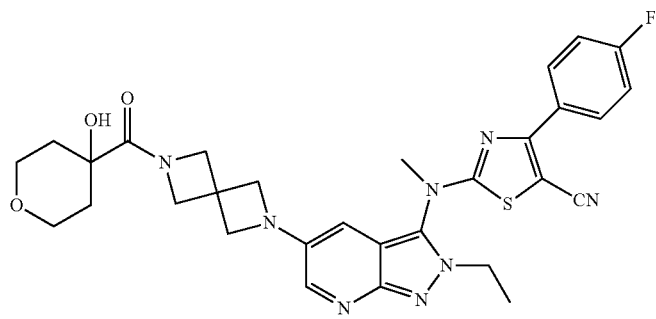 [SMILES: CCn1nc2ncc(N3CC4(CN(C(=O)C5(O)CCOCC5)C4)C3)cc2c1N(C)c1nc(-c2ccc(F)cc2)c(C#N)s1] |
| 117 | 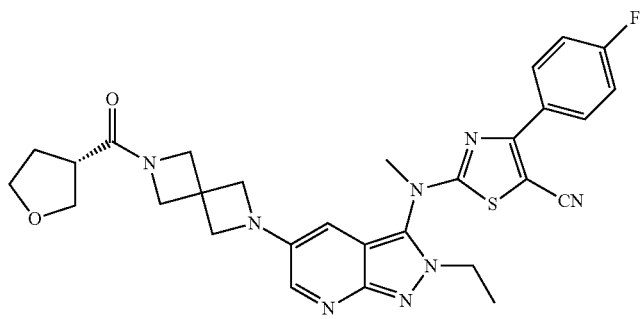 [SMILES: CCn1nc2ncc(N3CC4(CN(C(=O)[C@H]5CCOC5)C4)C3)cc2c1N(C)c1nc(-c2ccc(F)cc2)c(C#N)s1] |
| 118 | 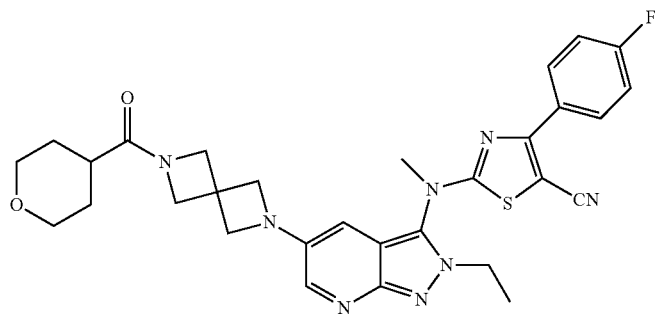 [SMILES: CCn1nc2ncc(N3CC4(CN(C(=O)C5CCOCC5)C4)C3)cc2c1N(C)c1nc(-c2ccc(F)cc2)c(C#N)s1] |

-continued
| Ex. | Structure |
|---|---|
| 119 | 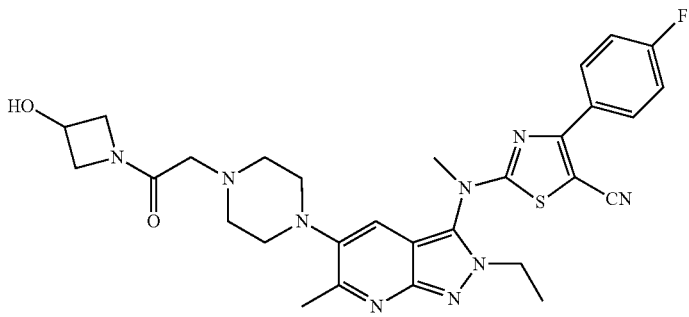 [SMILES: CCn1nc2nc(C)c(N3CCN(CC(=O)N4CC(O)C4)CC3)cc2c1N(C)c1nc(-c2ccc(F)cc2)c(C#N)s1] |
| 120 | 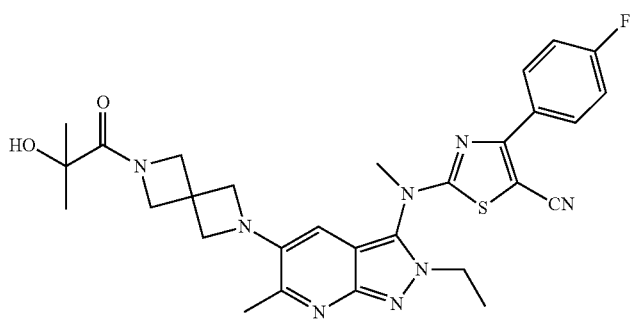 [SMILES: CCn1nc2nc(C)c(N3CC4(CN(C(=O)C(C)(C)O)C4)C3)cc2c1N(C)c1nc(-c2ccc(F)cc2)c(C#N)s1] |
| 121 | 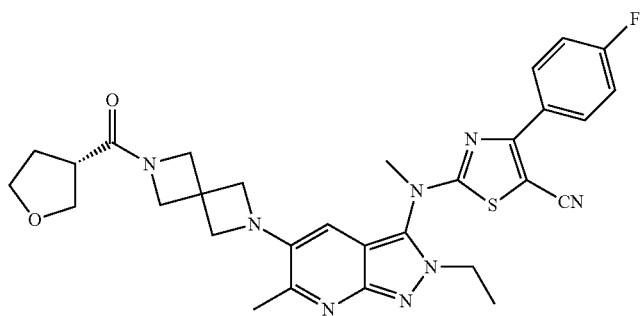 [SMILES: CCn1nc2nc(C)c(N3CC4(CN(C(=O)[C@H]5CCOC5)C4)C3)cc2c1N(C)c1nc(-c2ccc(F)cc2)c(C#N)s1] |
| 122 | 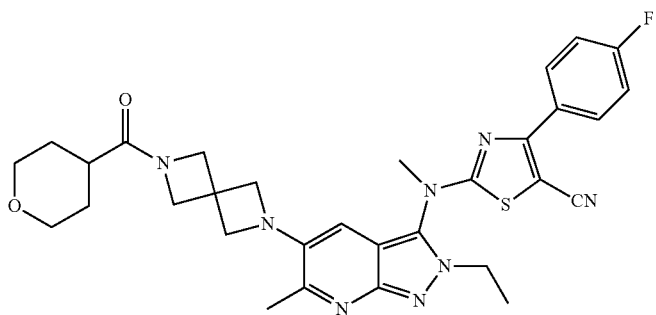 [SMILES: CCn1nc2nc(C)c(N3CC4(CN(C(=O)C5CCOCC5)C4)C3)cc2c1N(C)c1nc(-c2ccc(F)cc2)c(C#N)s1] |

| Ex. | Structure |
|---|---|
| 125 | 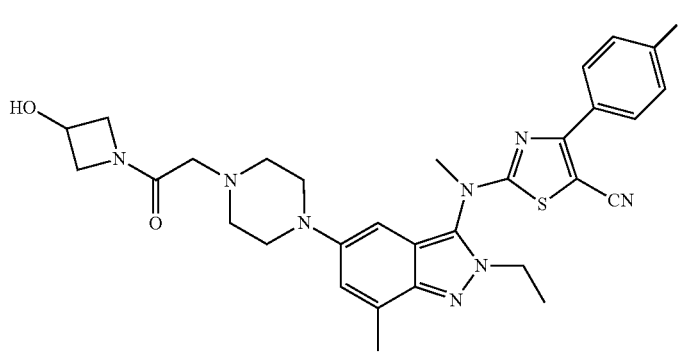 |
In some embodiments, the compound or a pharmaceutically acceptable salt, solvate, or stereoisomer thereof is:
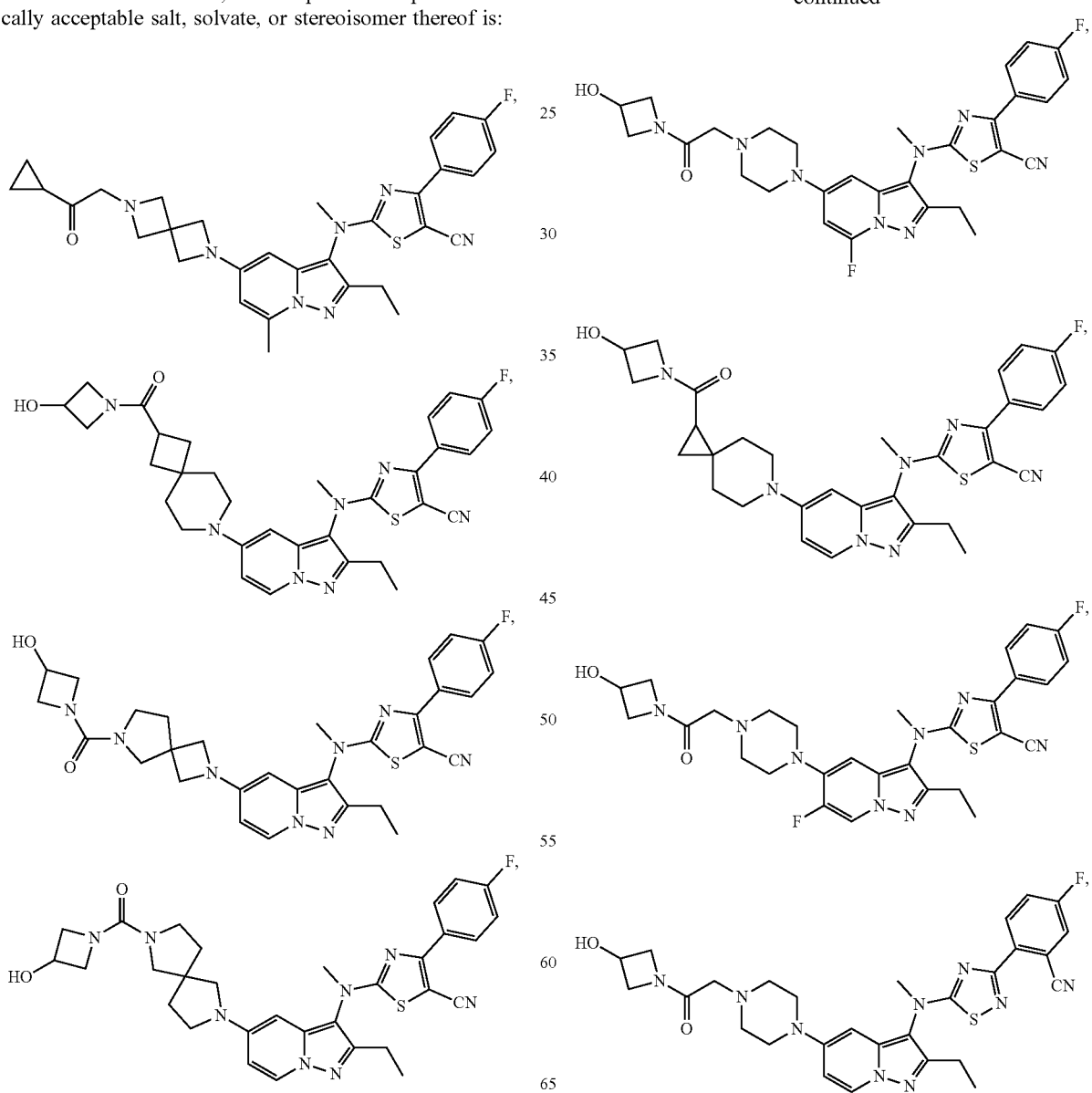

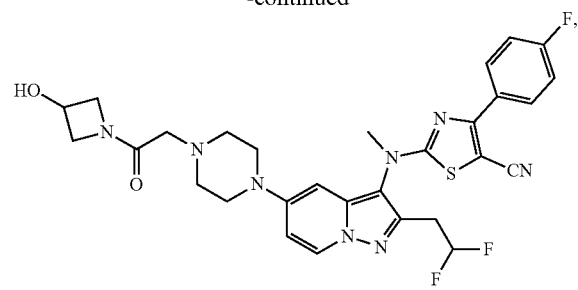
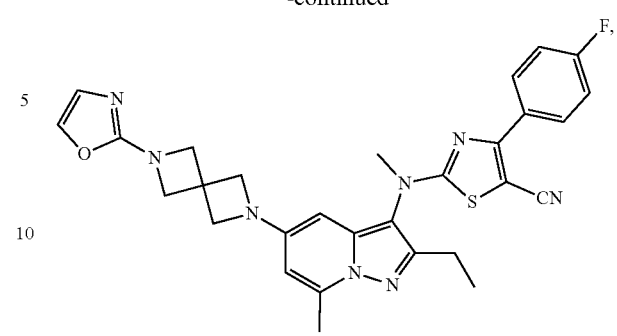
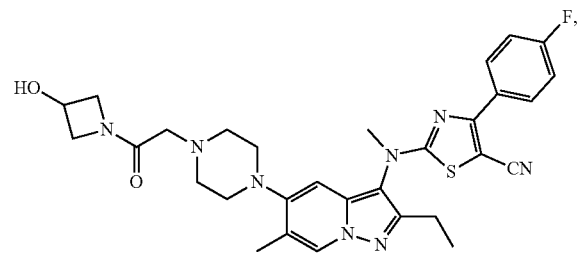
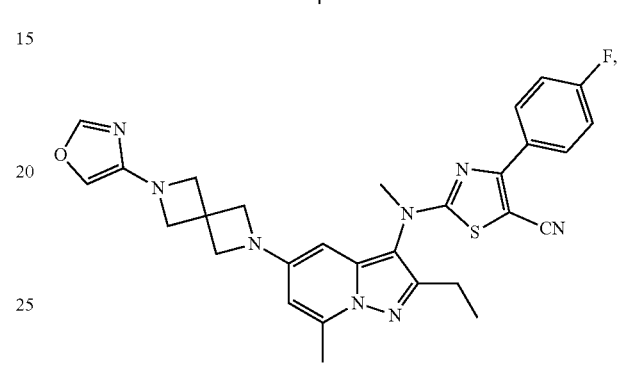
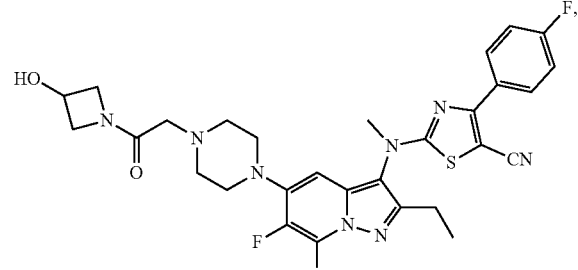
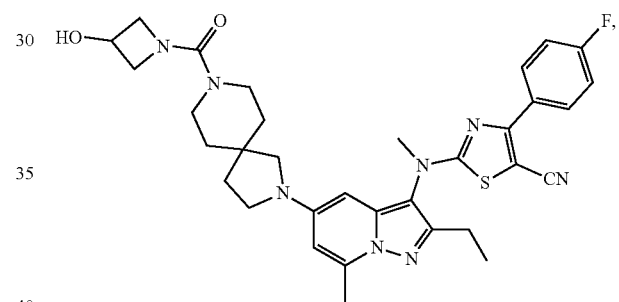
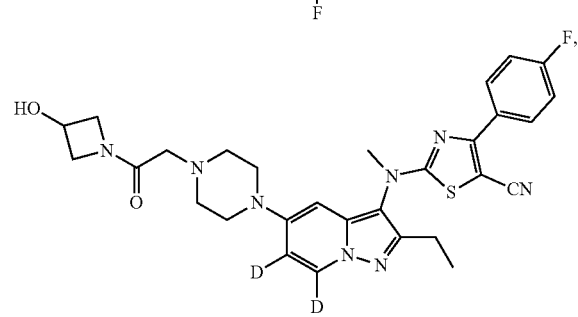
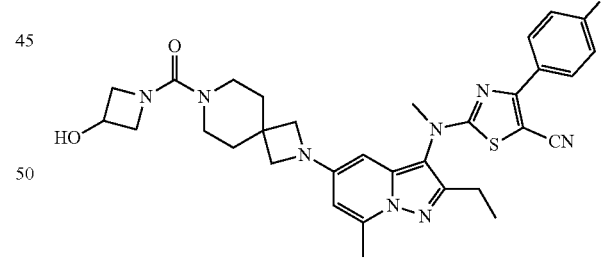
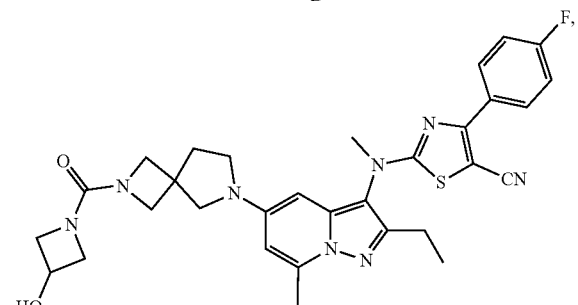
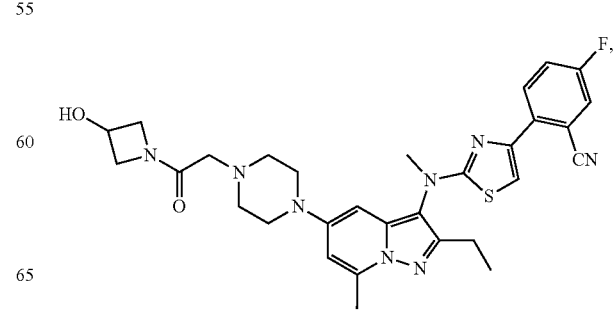

95
-continued
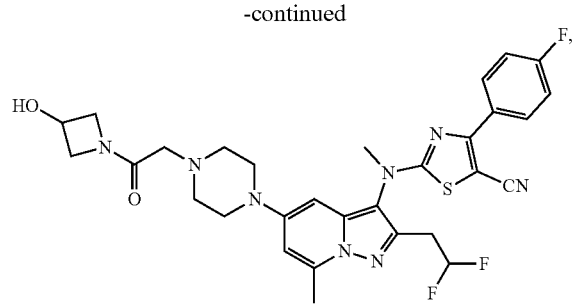
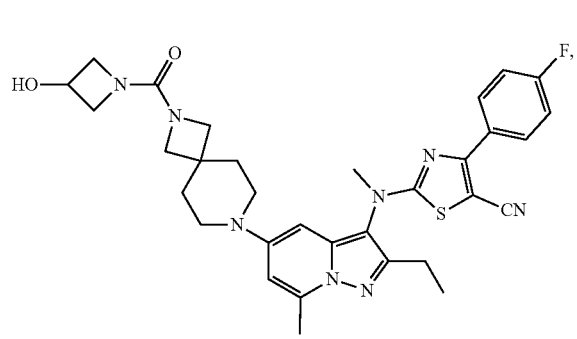
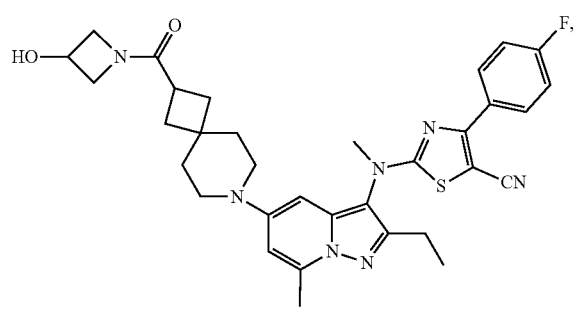
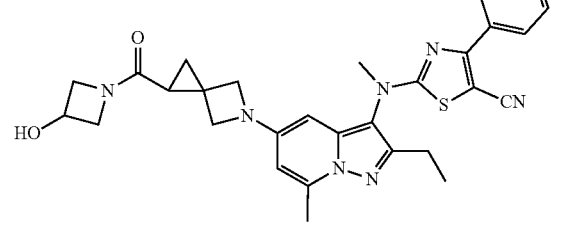
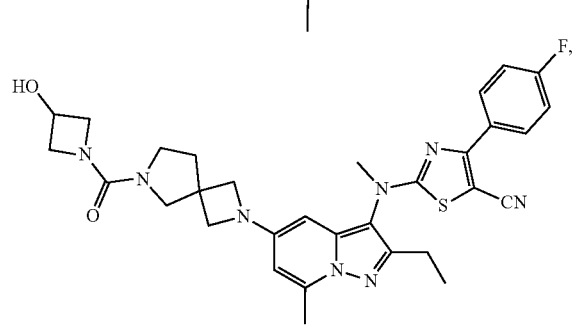
96
-continued
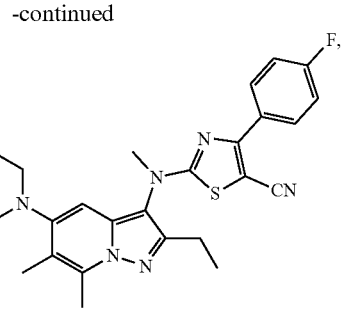
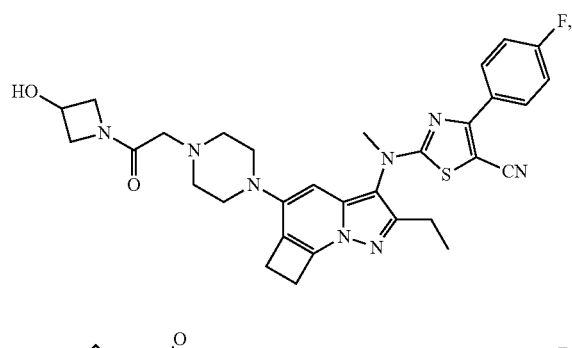
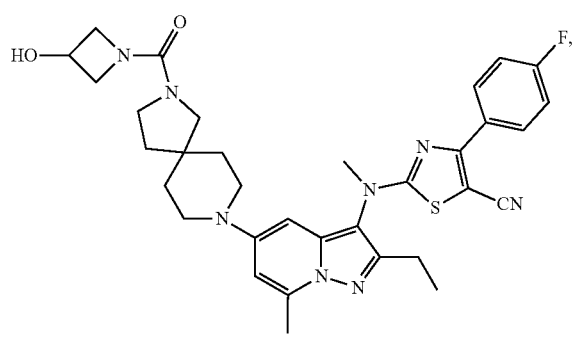
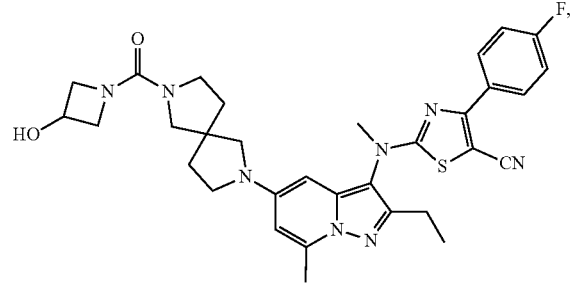
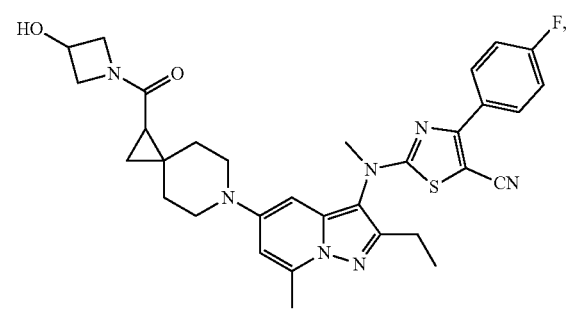

97
-continued
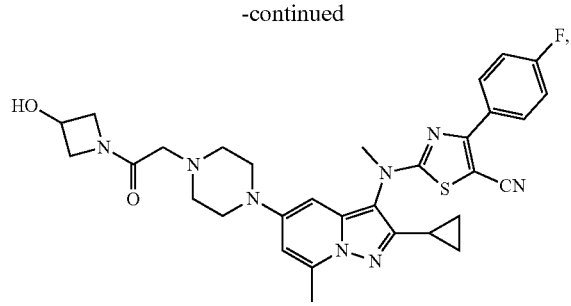
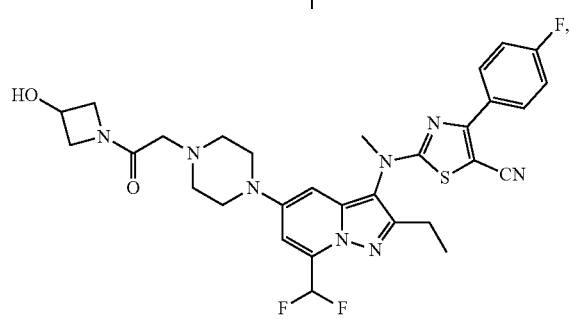
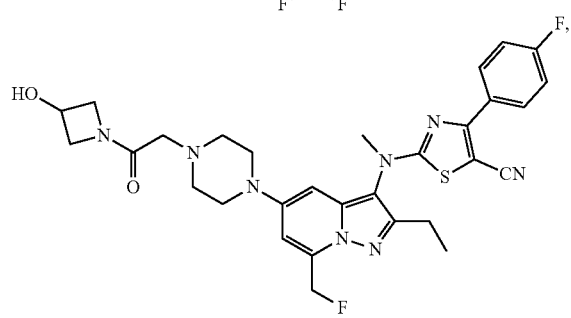
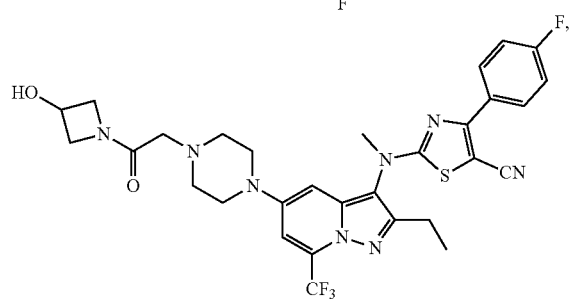
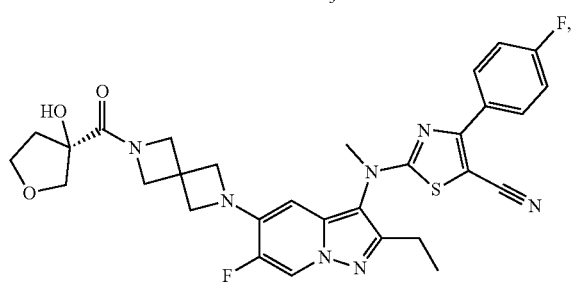
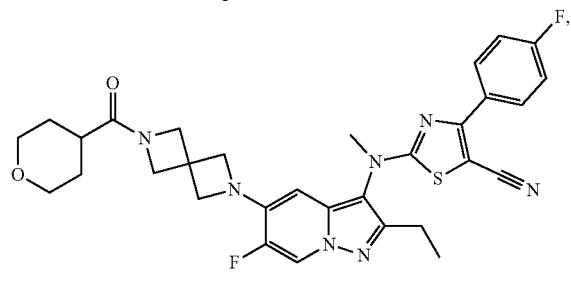
98
-continued
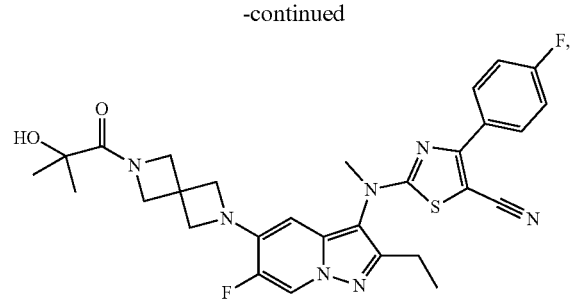
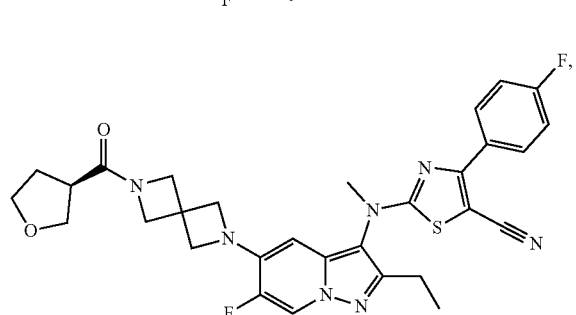
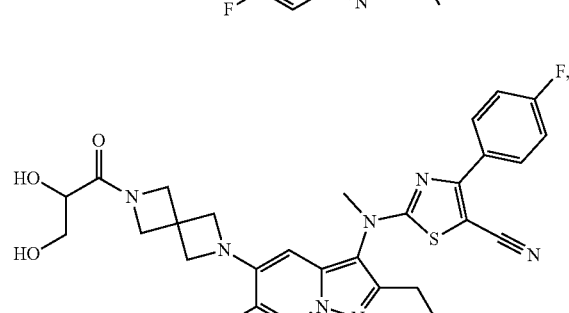
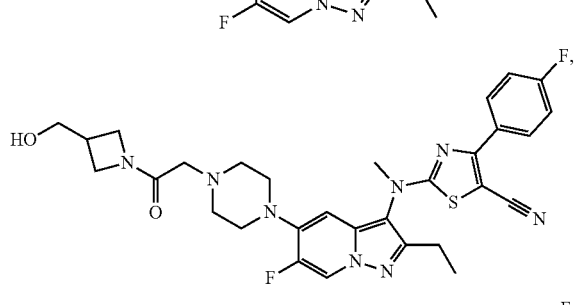
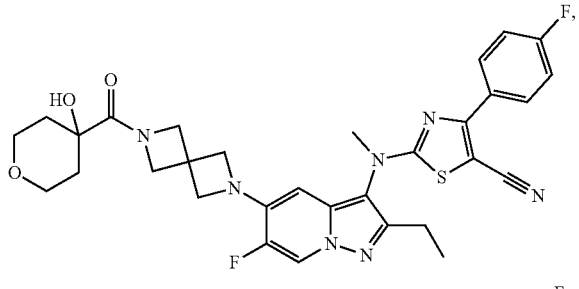
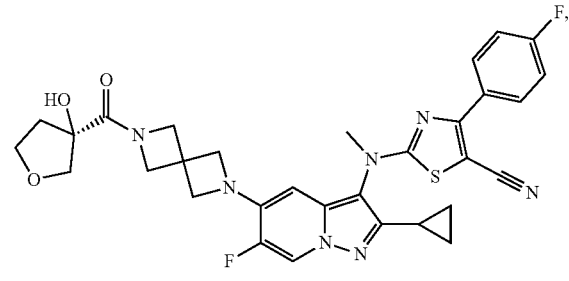

99
-continued
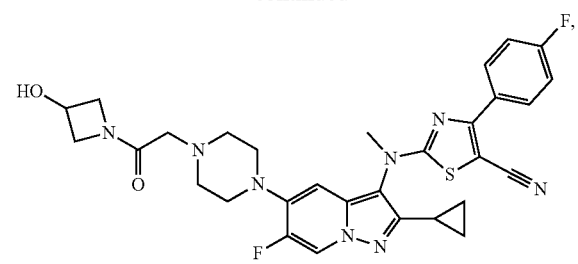
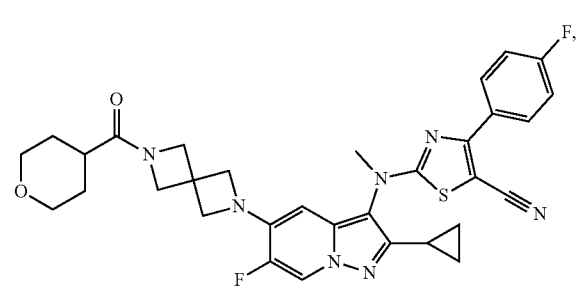
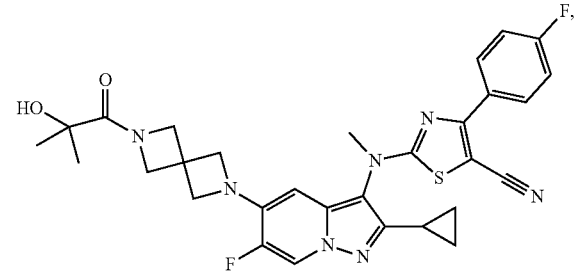
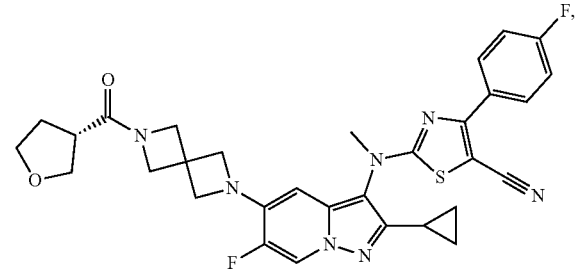
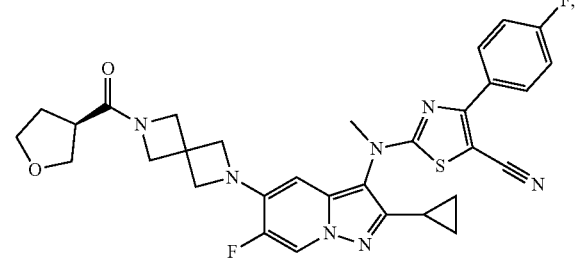
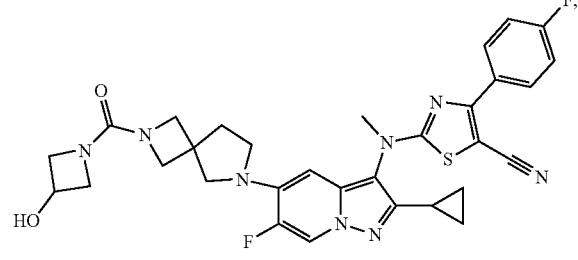
100
-continued
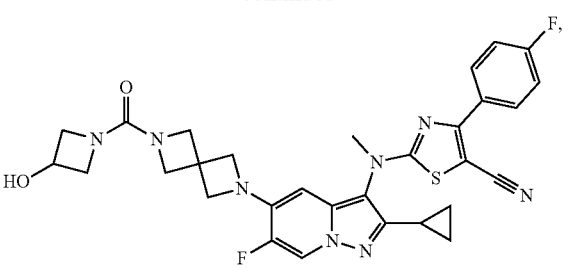
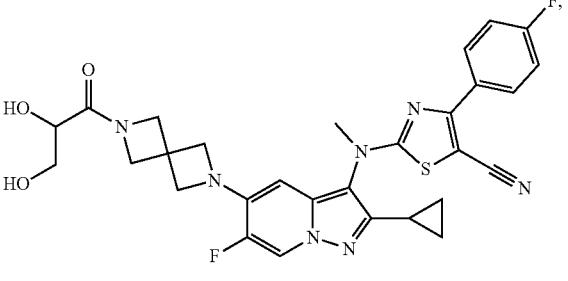
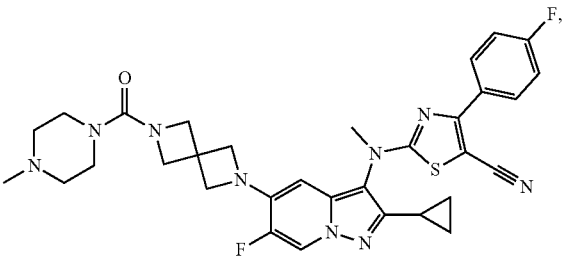
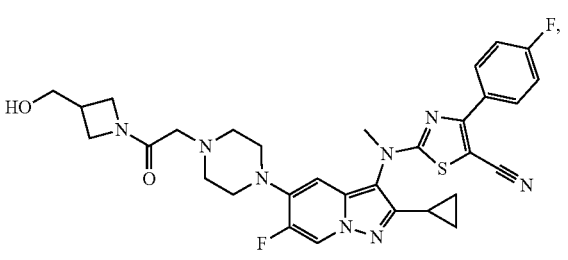
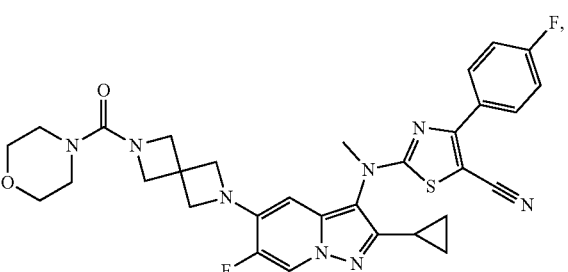
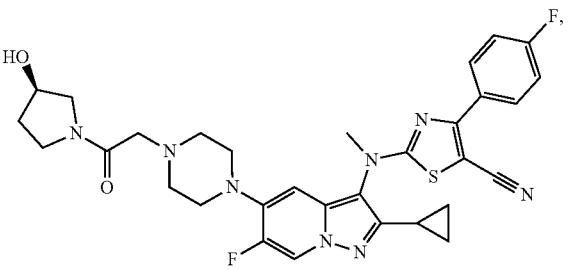

101
-continued
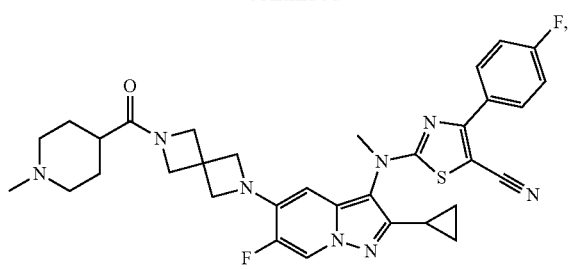
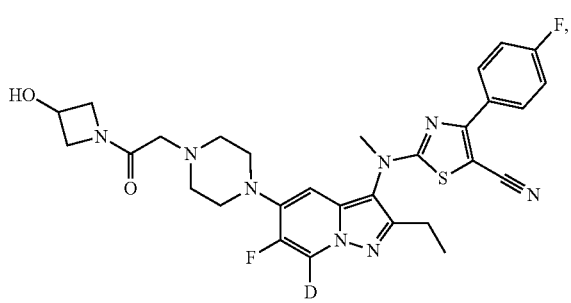
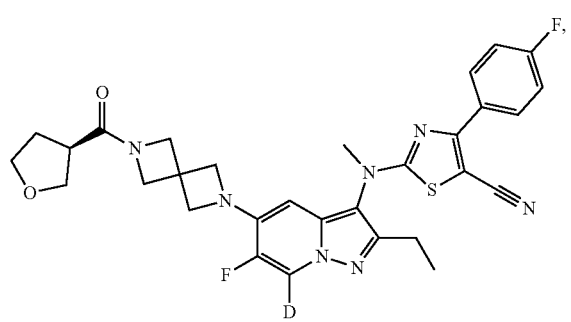
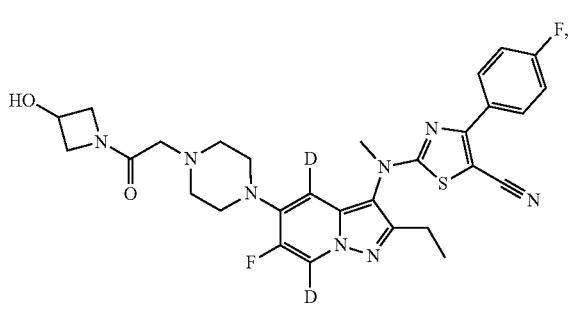
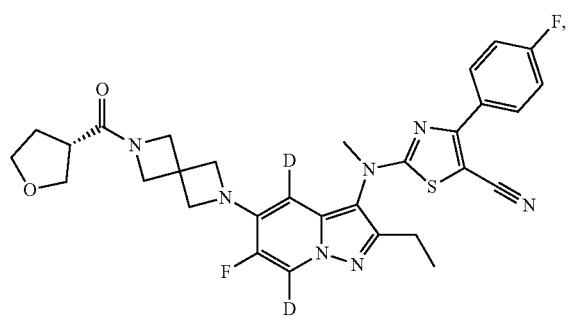
102
-continued
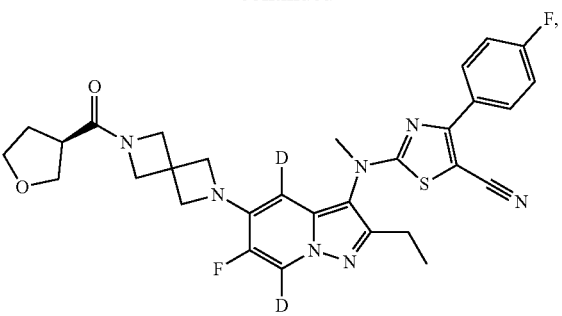
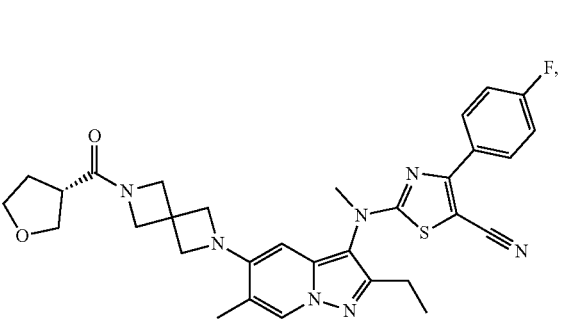
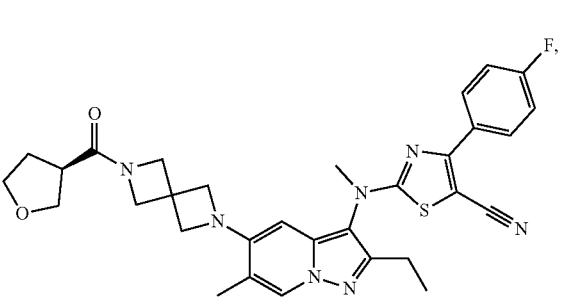
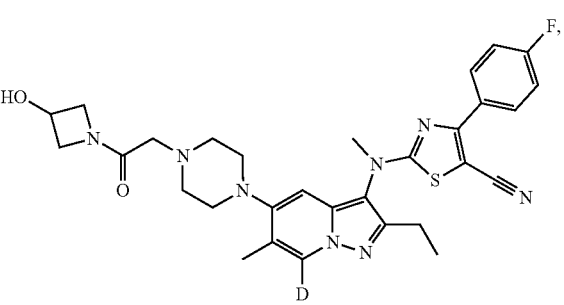
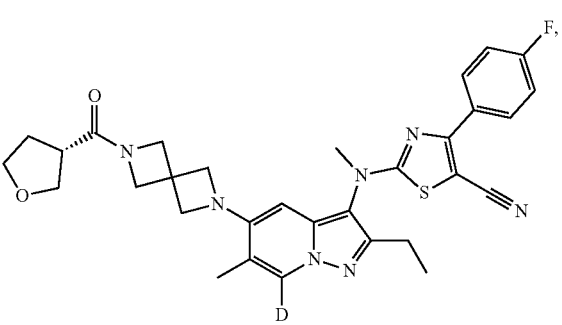

103
-continued
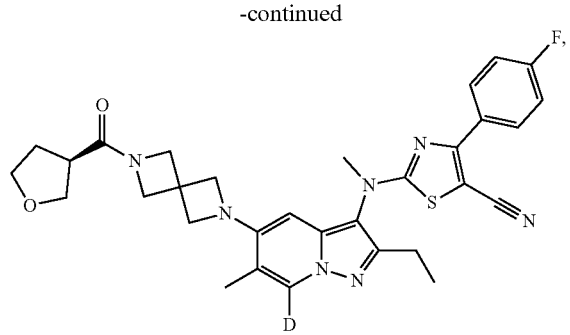
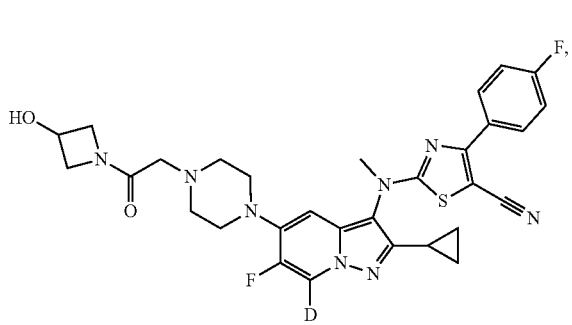
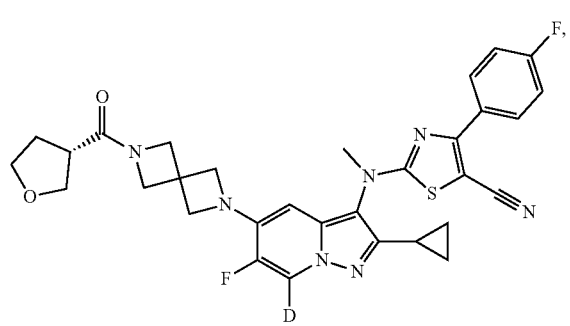
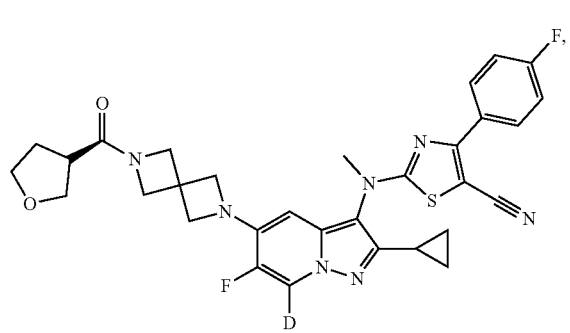
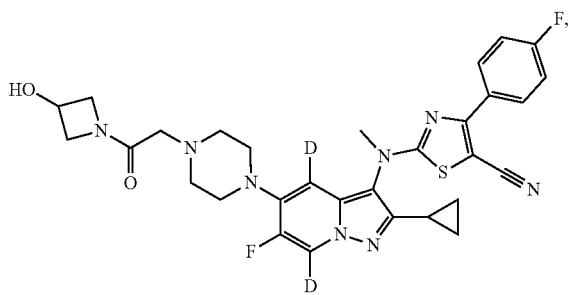
104
-continued
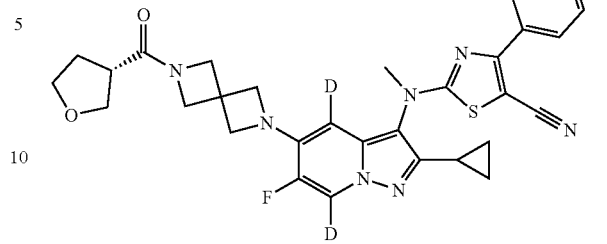
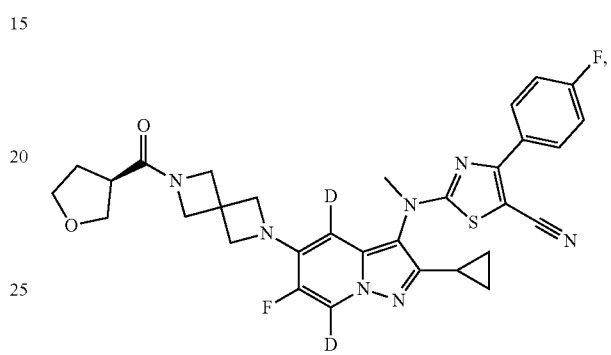
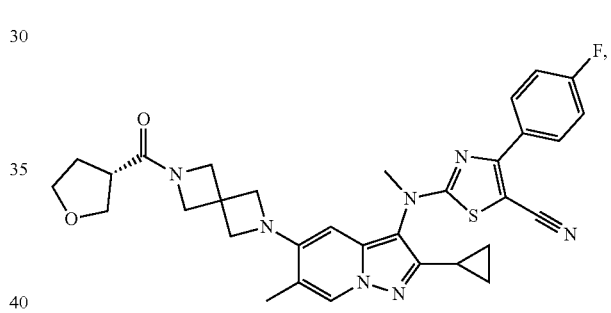
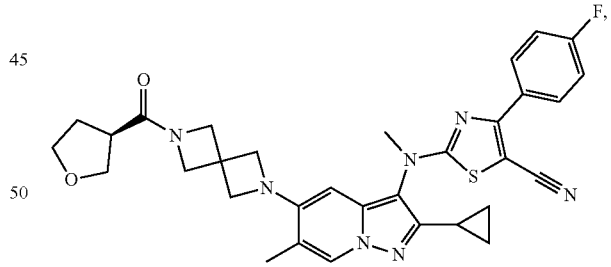
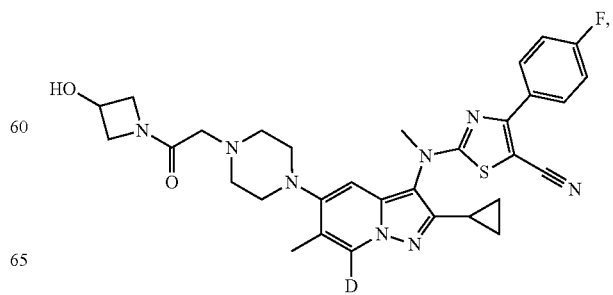

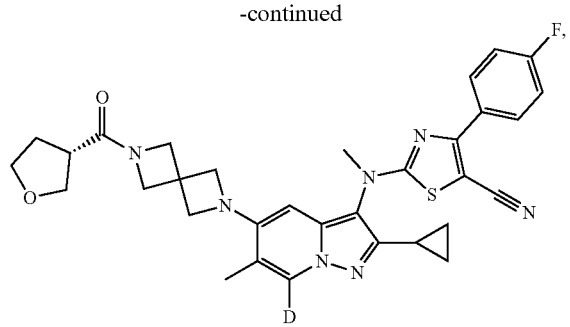
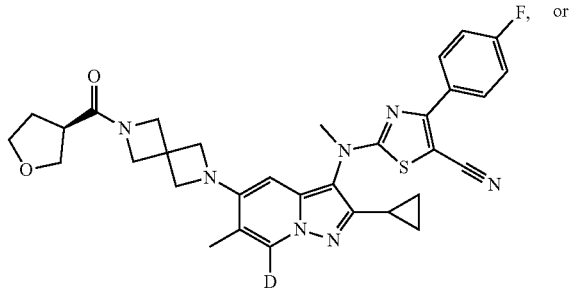
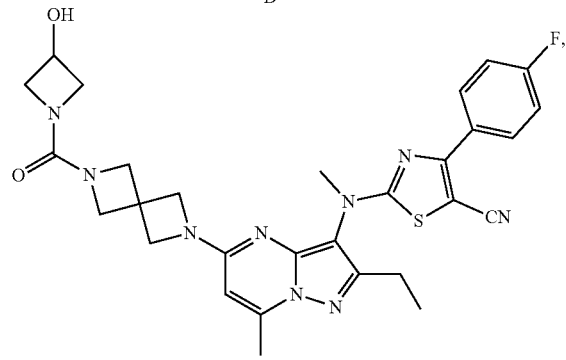
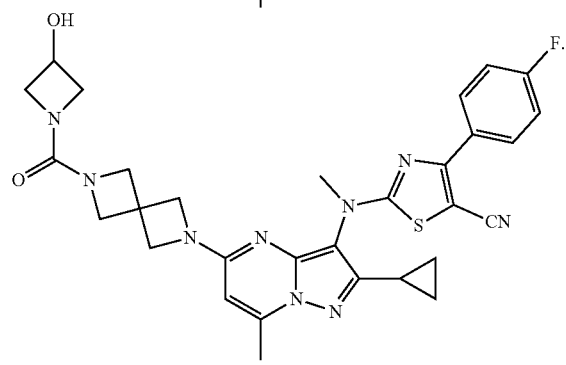
In some embodiments, the compound or a pharmaceutically acceptable salt, solvate, or stereoisomer thereof is:
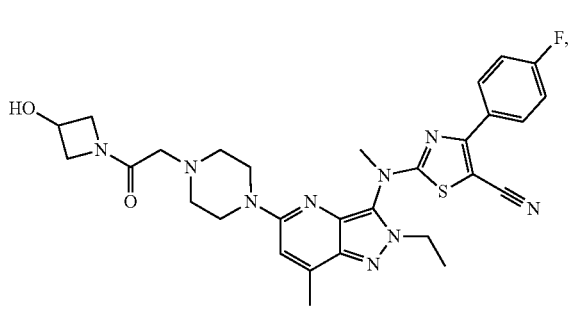
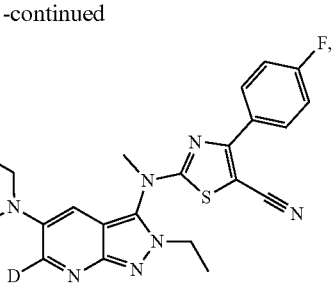
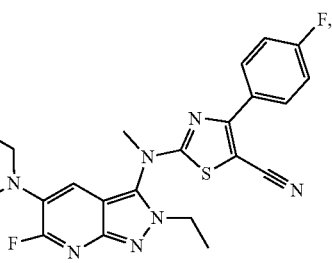
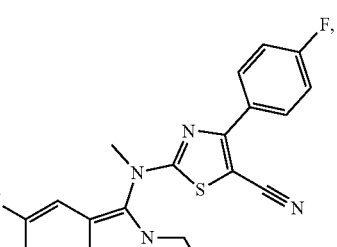
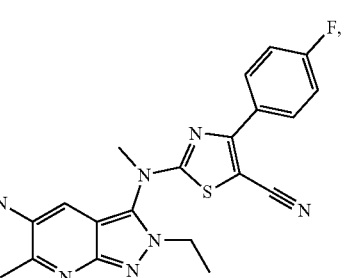
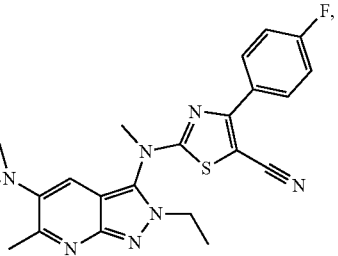
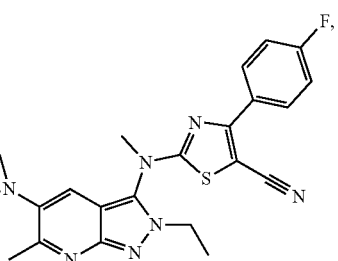

107
-continued
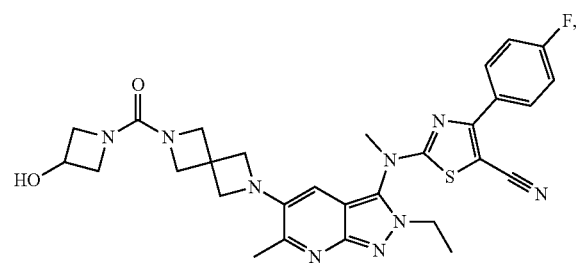
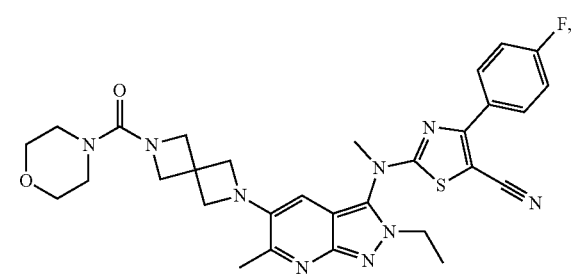
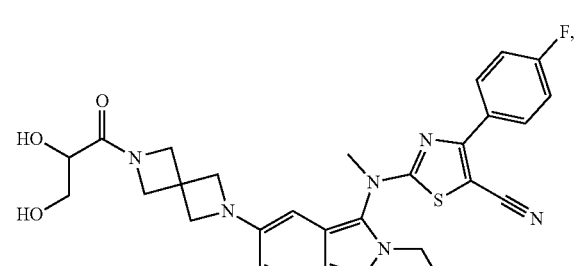
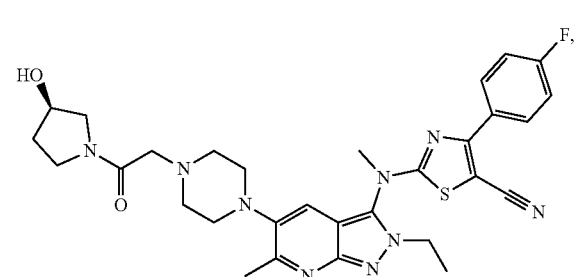
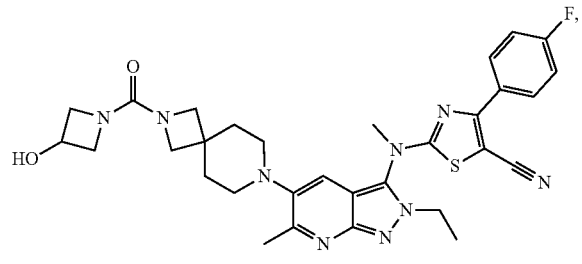
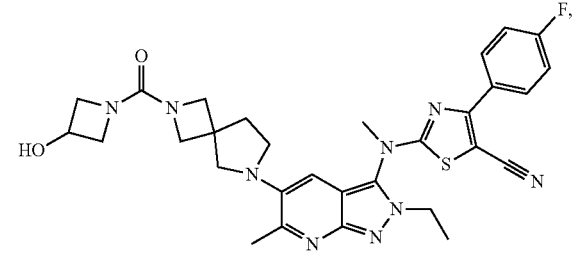
108
-continued
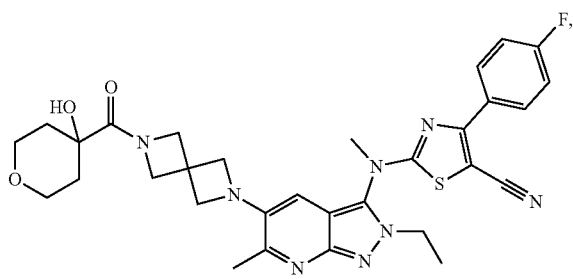
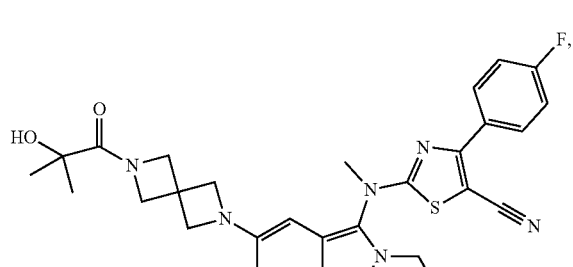
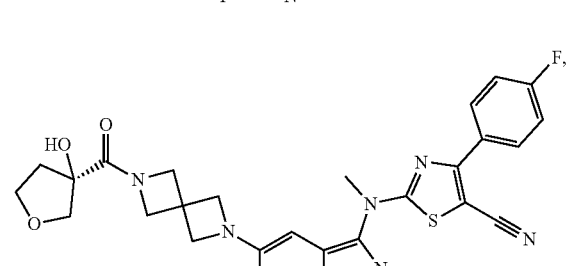
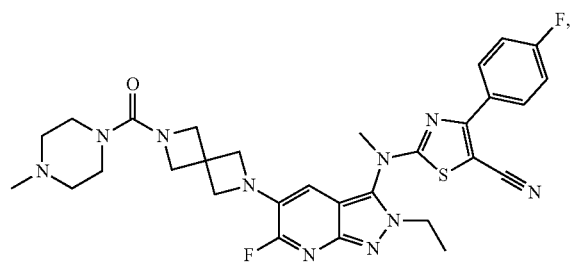
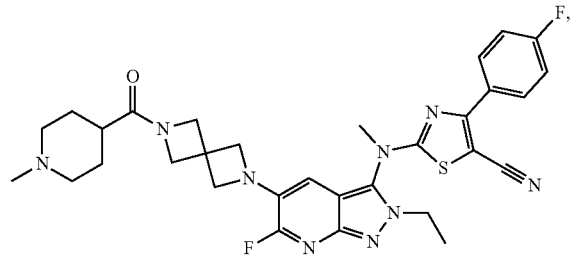
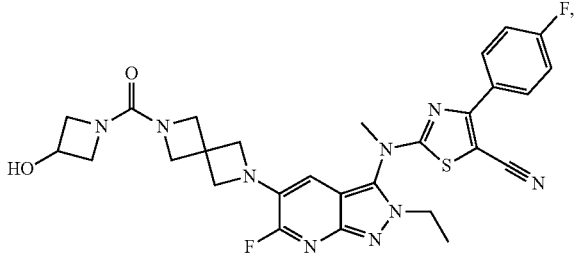

109
-continued
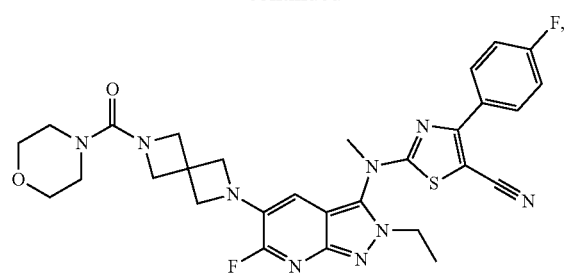
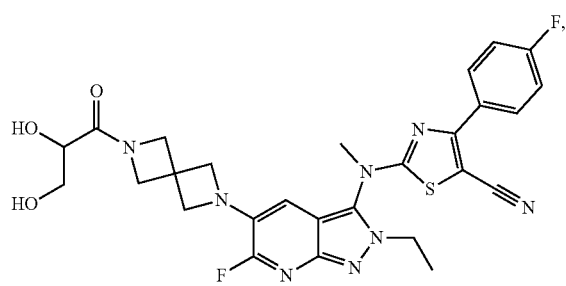
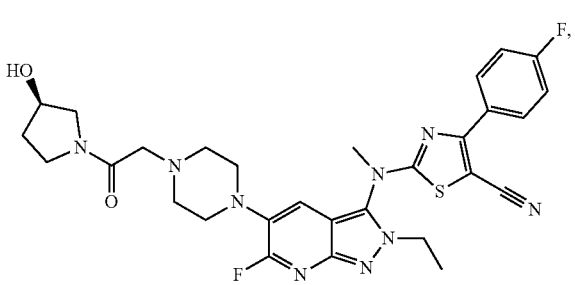
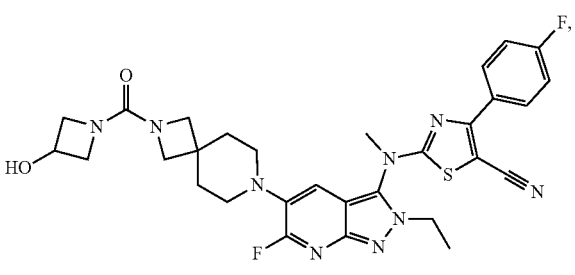
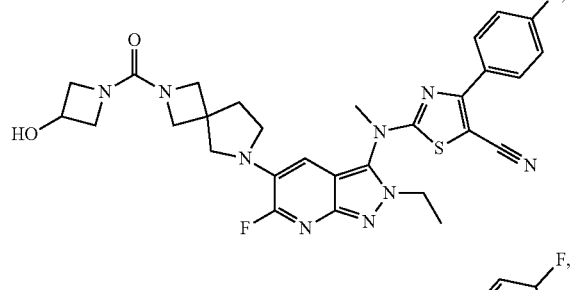
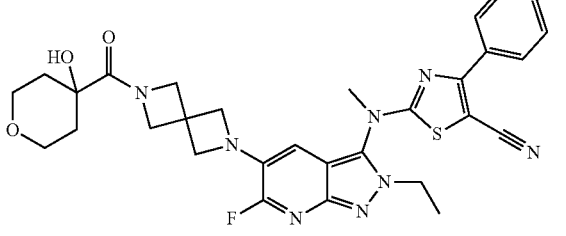
110
-continued
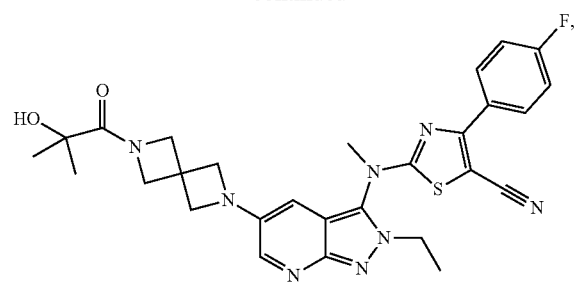
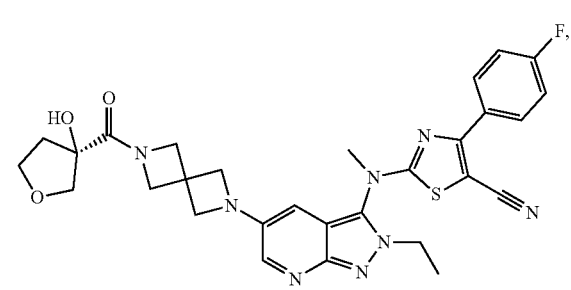
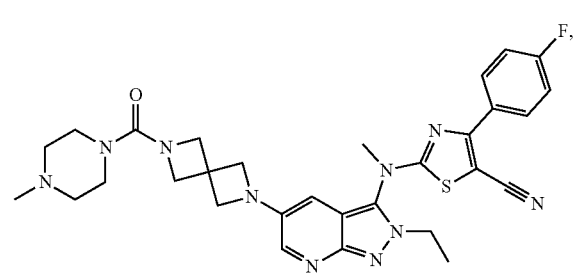
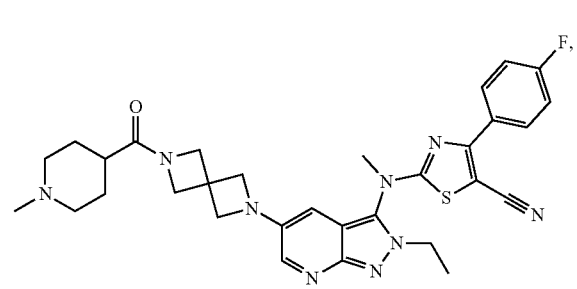
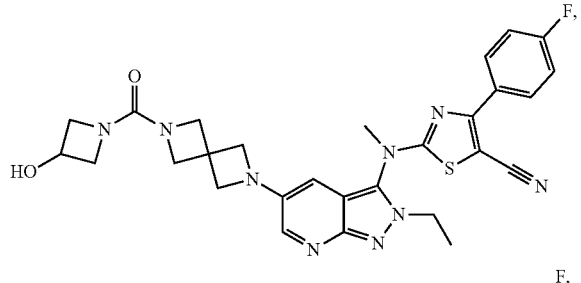
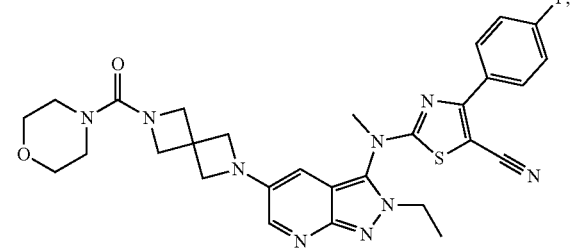

111
-continued
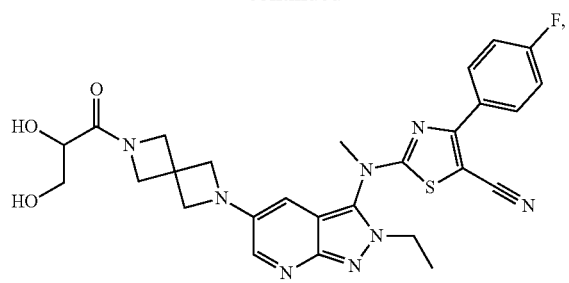
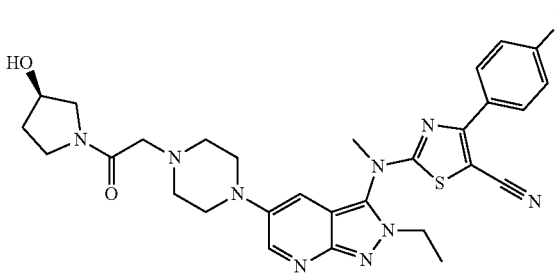
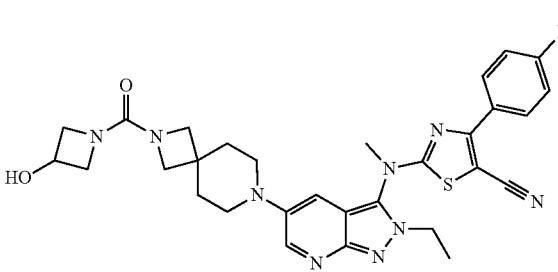
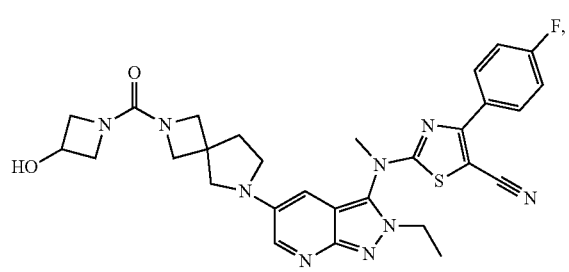
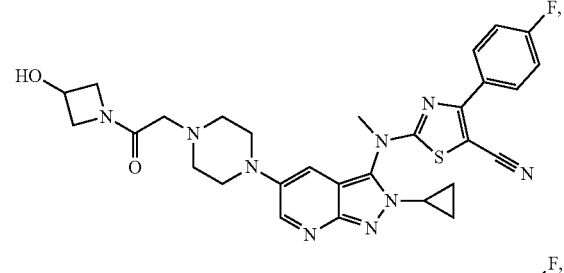
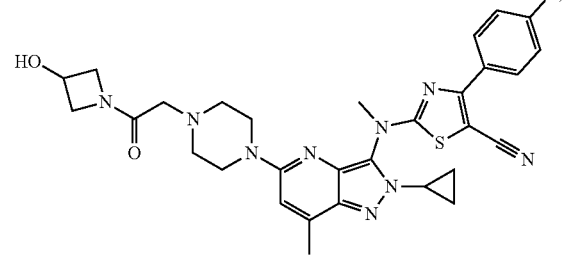
112
-continued
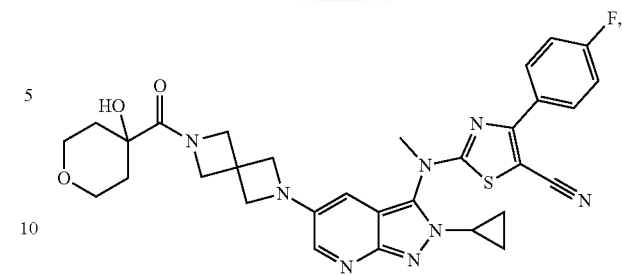
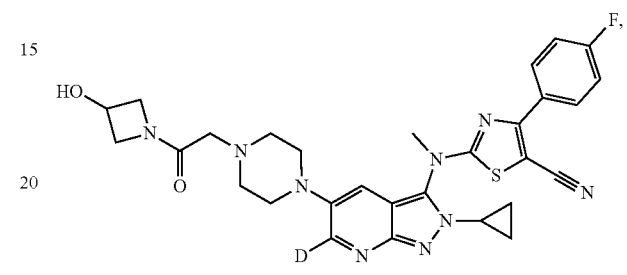

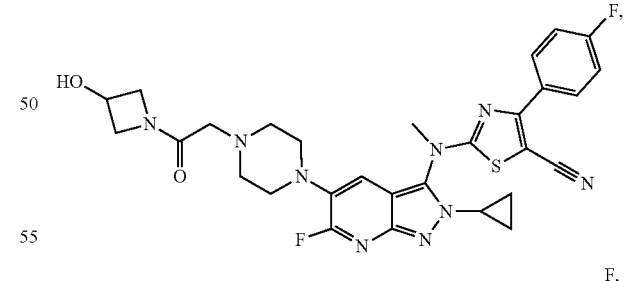
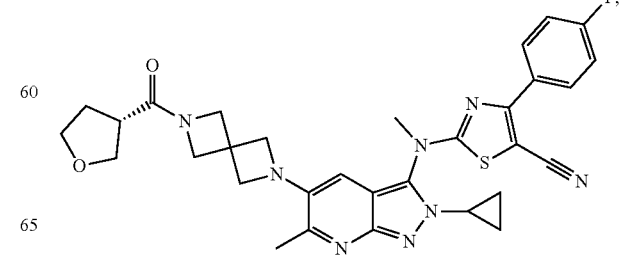

113
-continued
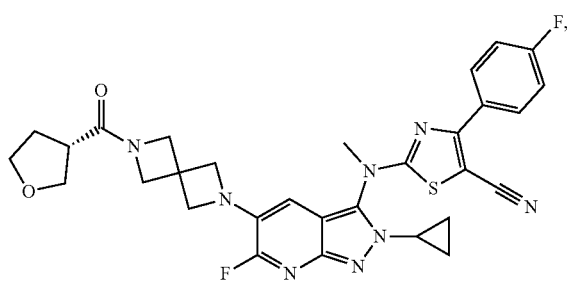
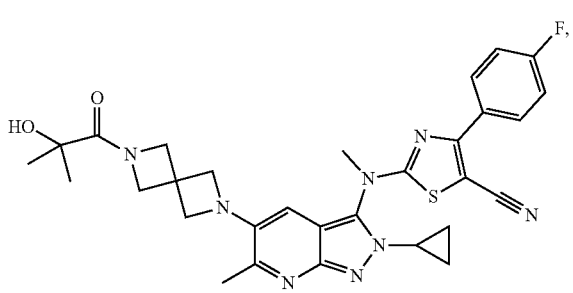
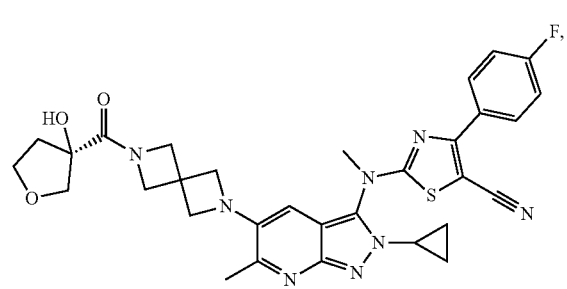
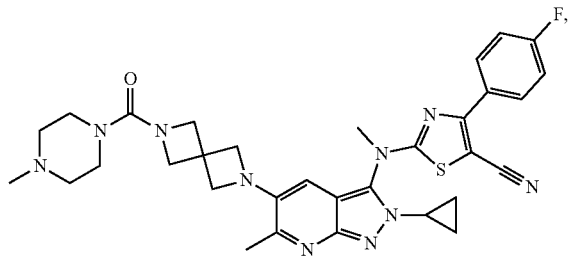
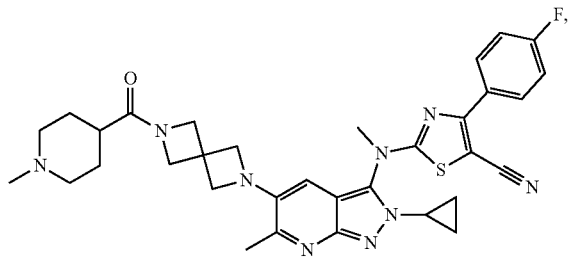
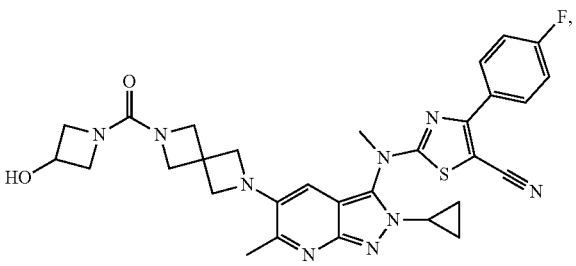
114
-continued
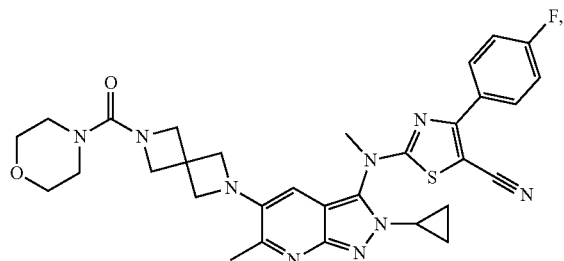
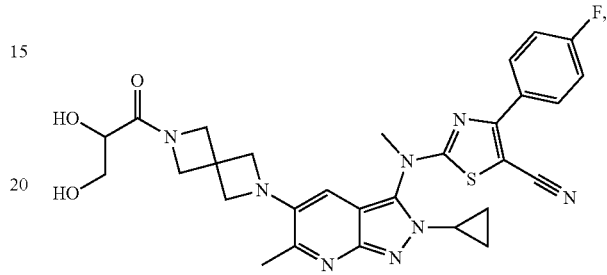
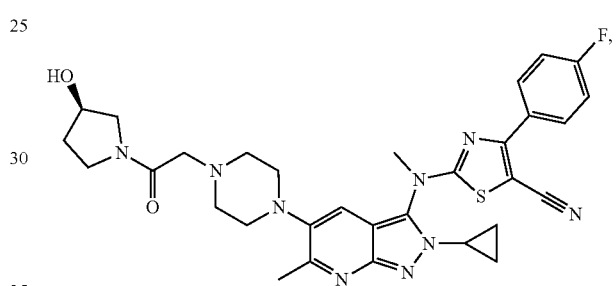

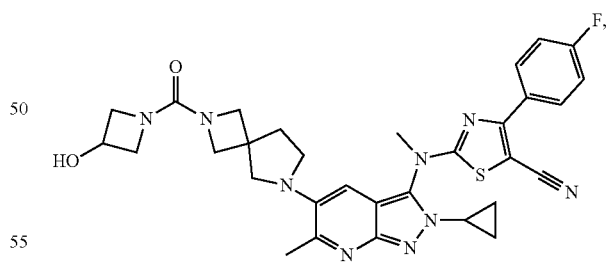
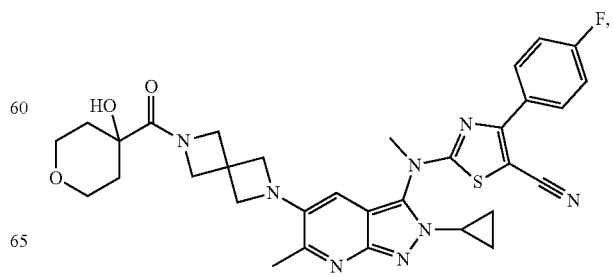

115
-continued
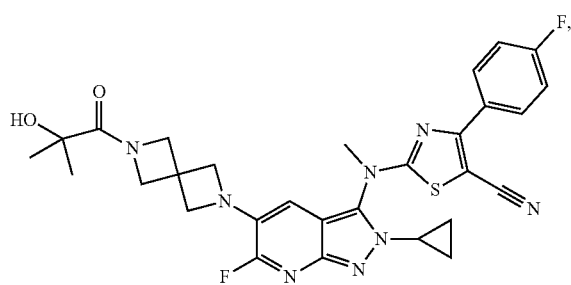
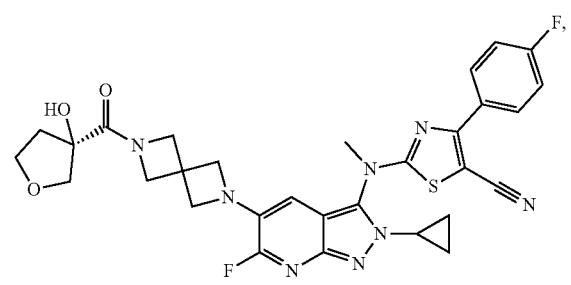
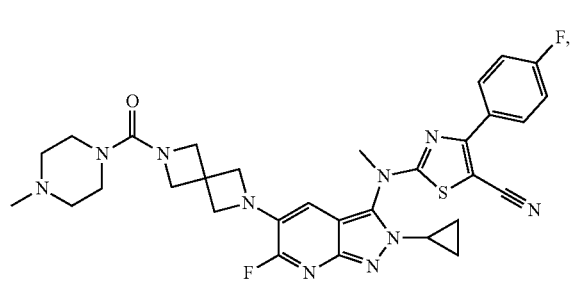
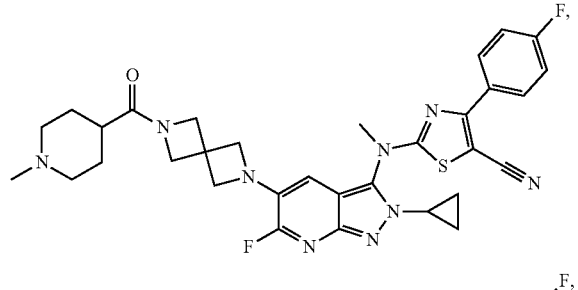
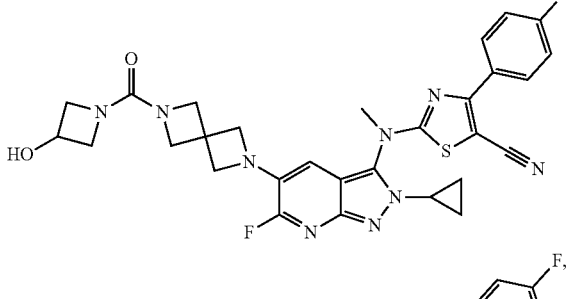
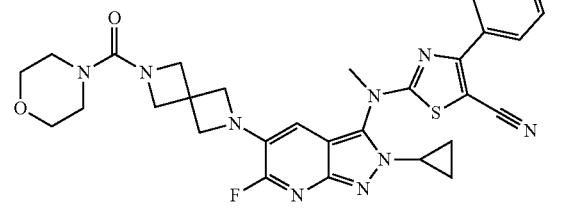
116
-continued
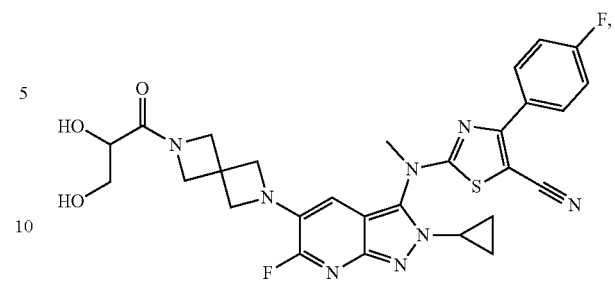
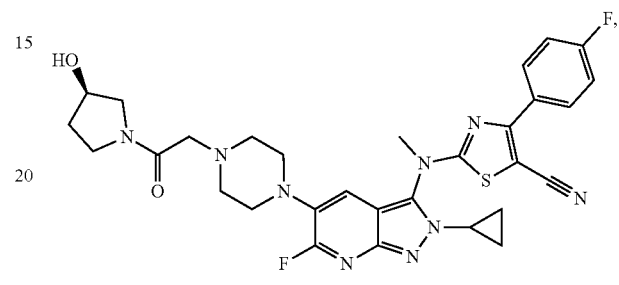
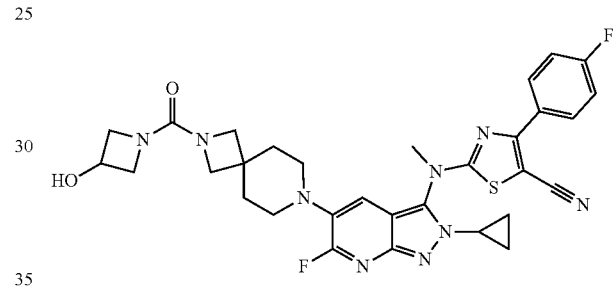
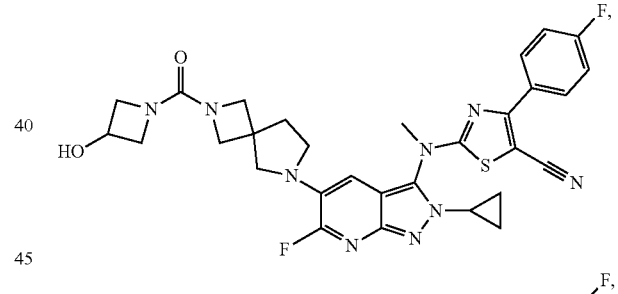
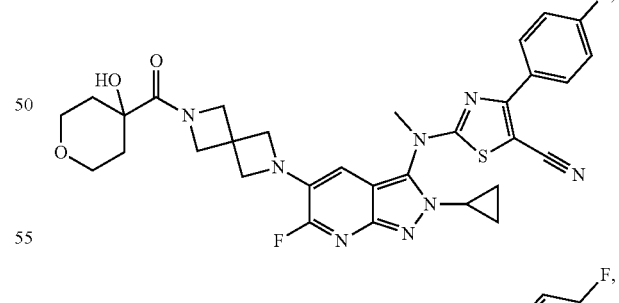
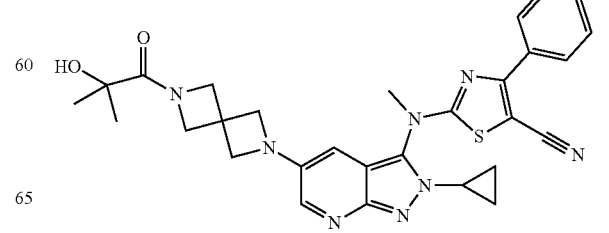

-continued

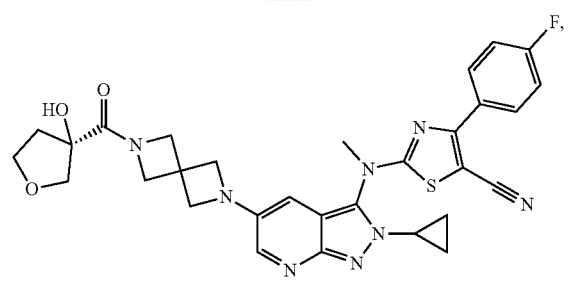
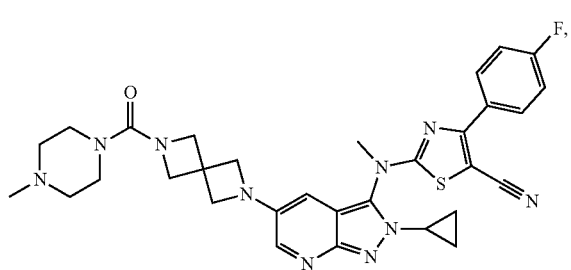
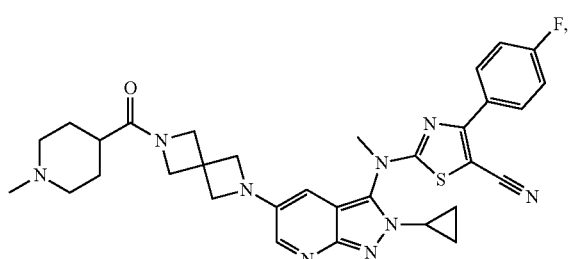
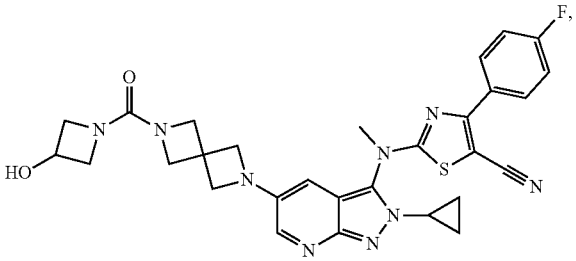
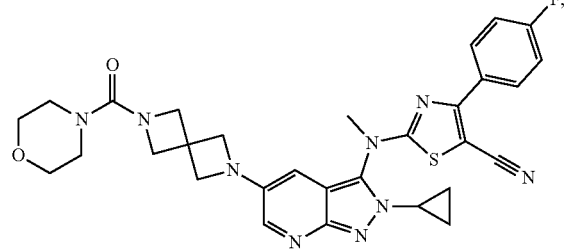
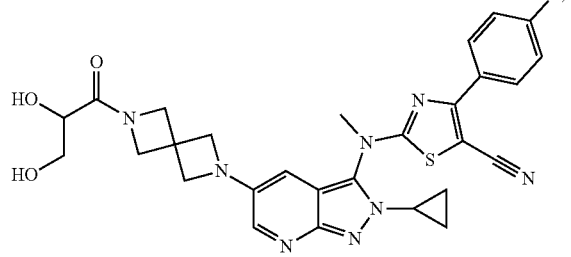

-continued

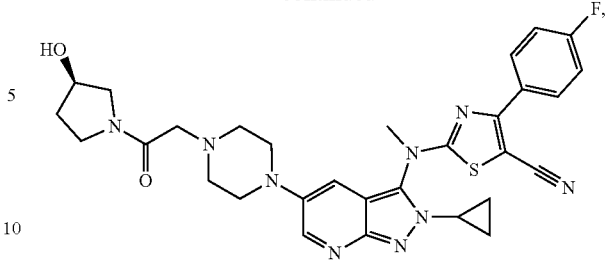
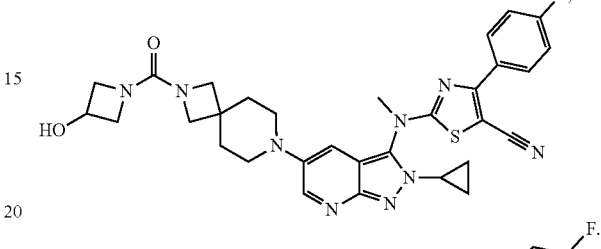
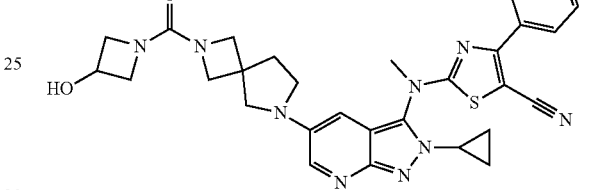

Further Forms of Compounds Disclosed Herein
Isomers/Stereoisomers

In some embodiments, the compounds described herein exist as geometric isomers. In some embodiments, the compounds described herein possess one or more double bonds. The compounds presented herein include all cis, trans, syn, anti, entgegen (E), and zusammen (Z) isomers as well as the corresponding mixtures thereof In some situations, the compounds described herein possess one or more chiral centers and each center exists in the R configuration, or S configuration. The compounds described herein include all diastereomeric, enantiomeric, and epimeric forms as well as the corresponding mixtures thereof. In additional embodiments of the compounds and methods provided herein, mixtures of enantiomers and/or diastereoisomers, resulting from a single preparative step, combination, or interconversion are useful for the applications described herein. In some embodiments, the compounds described herein are prepared as their individual stereoisomers by reacting a racemic mixture of the compound with an optically active resolving agent to form a pair of diastereoisomeric compounds, separating the diastereomers and recovering the optically pure enantiomers. In some embodiments, dissociable complexes are preferred. In some embodiments, the diastereomers have distinct physical properties (e.g., melting points, boiling points, solubilities, reactivity, etc.) and are separated by taking advantage of these dissimilarities. In some embodiments, the diastereomers are separated by chiral chromatography, or preferably, by separation/resolution techniques based upon differences in solubility. In some embodiments, the optically pure enantiomer is then recovered, along with the resolving agent.

Labeled Compounds

In some embodiments, the compounds described herein exist in their isotopically-labeled forms. In some embodiments, the methods disclosed herein include methods of treating diseases by administering such isotopically-labeled compounds. In some embodiments, the methods disclosed herein include methods of treating diseases by administering such isotopically-labeled compounds as pharmaceutical compositions. Thus, in some embodiments, the compounds disclosed herein include isotopically-labeled compounds, which are identical to those recited herein, but for the fact that one or more atoms are replaced by an atom having an atomic mass or mass number different from the atomic mass or mass number usually found in nature. Examples of isotopes that can be incorporated into compounds described herein, or a solvate, or stereoisomer thereof, include isotopes of hydrogen, carbon, nitrogen, oxygen, phosphorous, sulfur, fluorine, and chloride, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Compounds described herein, and the metabolites, pharmaceutically acceptable salts, esters, prodrugs, solvate, hydrates or derivatives thereof which contain the aforementioned isotopes and/or other isotopes of other atoms are within the scope of this invention. Certain isotopically-labeled compounds, for example those into which radioactive isotopes such as $^3H$ and $^{14}C$ are incorporated, are useful in drug and/or substrate tissue distribution assays. Tritiated, i.e., $^3H$ and carbon-14, i.e., $^{14}C$, isotopes are particularly preferred for their ease of preparation and detectability. Further, substitution with heavy isotopes such as deuterium, i.e., $^2H$, produces certain therapeutic advantages resulting from greater metabolic stability, for example increased in vivo half-life or reduced dosage requirements. In some embodiments, the isotopically labeled compound or a pharmaceutically acceptable salt, solvate, or stereoisomer thereof is prepared by any suitable method.

In some embodiments, the compounds described herein are labeled by other means, including, but not limited to, the use of chromophores or fluorescent moieties, bioluminescent labels, or chemiluminescent labels.

Pharmaceutically Acceptable Salts

In some embodiments, the compounds described herein exist as their pharmaceutically acceptable salts. In some embodiments, the methods disclosed herein include methods of treating diseases by administering such pharmaceutically acceptable salts. In some embodiments, the methods disclosed herein include methods of treating diseases by administering such pharmaceutically acceptable salts as pharmaceutical compositions.

In some embodiments, the compounds described herein possess acidic or basic groups and therefor react with any of a number of inorganic or organic bases, and inorganic and organic acids, to form a pharmaceutically acceptable salt. In some embodiments, these salts are prepared in situ during the final isolation and purification of the compounds disclosed herein, or by separately reacting a purified compound in its free form with a suitable acid or base, and isolating the salt thus formed.

Examples of pharmaceutically acceptable salts include those salts prepared by reaction of the compounds described herein with a mineral, organic acid, or inorganic base, such salts including acetate, acrylate, adipate, alginate, aspartate, benzoate, benzenesulfonate, bisulfate, bisulfate, bromide, butyrate, butyn-1,4-dioate, camphorate, camphorsulfonate, caproate, caprylate, chlorobenzoate, chloride, citrate, cyclopentanepropionate, decanoate, digluconate, dihydrogenphosphate, dinitrobenzoate, dodecylsulfate, ethanesulfonate, formate, fumarate, glucoheptanoate, glycerophosphate, glycolate, hemisulfate, heptanoate, hexanoate, hexyne-1,6-dioate, hydroxybenzoate, γ-hydroxybutyrate, hydrochloride, hydrobromide, hydroiodide, 2-hydroxyethanesulfonate, iodide, isobutyrate, lactate, maleate, malonate, methanesulfonate, mandelate metaphosphate, methanesulfonate, methoxybenzoate, methylbenzoate, monohydrogenphosphate, 1-napthalenesulfonate, 2-napthalenesulfonate, nicotinate, nitrate, palmoate, pectinate, persulfate, 3-phenylpropionate, phosphate, picrate, pivalate, propionate, pyrosulfate, pyrophosphate, propiolate, phthalate, phenylacetate, phenylbutyrate, propanesulfonate, salicylate, succinate, sulfate, sulfite, succinate, suberate, sebacate, sulfonate, tartrate, thiocyanate, tosylateundeconate, and xylenesulfonate.

Further, the compounds described herein can be prepared as pharmaceutically acceptable salts formed by reacting the free base form of the compound with a pharmaceutically acceptable inorganic or organic acid, including, but not limited to, inorganic acids such as hydrochloric acid, hydrobromic acid, sulfuric acid, nitric acid, phosphoric acid metaphosphoric acid, and the like; and organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, p-toluenesulfonic acid, tartaric acid, trifluoroacetic acid, citric acid, benzoic acid, 3-(4-hydroxybenzoyl)benzoic acid, cinnamic acid, mandelic acid, arylsulfonic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, and muconic acid.

In some embodiments, those compounds described herein which comprise a free acid group react with a suitable base, such as the hydroxide, carbonate, bicarbonate, sulfate, of a pharmaceutically acceptable metal cation, with ammonia, or with a pharmaceutically acceptable organic primary, secondary, tertiary, or quaternary amine. Representative salts include the alkali or alkaline earth salts, like lithium, sodium, potassium, calcium, and magnesium, and aluminum salts and the like. Illustrative examples of bases include sodium hydroxide, potassium hydroxide, choline hydroxide, sodium carbonate, $N^+(C_{1-4}\text{ alkyl})_4$, and the like.

Representative organic amines useful for the formation of base addition salts include ethylamine, diethylamine, ethylenediamine, ethanolamine, diethanolamine, piperazine, and the like. It should be understood that the compounds described herein also include the quaternization of any basic nitrogen-containing groups they contain. In some embodiments, water or oil-soluble or dispersible products are obtained by such quaternization.

Solvates

In some embodiments, the compounds described herein exist as solvates. The invention provides for methods of treating diseases by administering such solvates. The invention further provides for methods of treating diseases by administering such solvates as pharmaceutical compositions.

Solvates contain either stoichiometric or non-stoichiometric amounts of a solvent, and, in some embodiments, are formed during the process of crystallization with pharmaceutically acceptable solvents such as water, ethanol, and the like. Hydrates are formed when the solvent is water, or alcoholates are formed when the solvent is alcohol. Solvates of the compounds described herein can be conveniently prepared or formed during the processes described herein. In addition, the compounds provided herein can exist in unsolvated as well as solvated forms. In general, the solvated forms are considered equivalent to the unsolvated forms for the purposes of the compounds and methods provided herein.

Tautomers

In some situations, compounds exist as tautomers. The compounds described herein include all possible tautomers within the formulas described herein. Tautomers are compounds that are interconvertible by migration of a hydrogen atom, accompanied by a switch of a single bond and adjacent double bond. In bonding arrangements where tautomerization is possible, a chemical equilibrium of the tautomers will exist. All tautomeric forms of the compounds disclosed herein are contemplated. The exact ratio of the tautomers depends on several factors, including temperature, solvent, and pH.

Pharmacokinetics and Pharmacodynamics

In some embodiments, the compounds described herein exhibit specific pharmacokinetic/pharmacodynamic parameters.

In some embodiments, the compound of Formula (I) or (II), or a pharmaceutically acceptable salt, solvate, or stereoisomer thereof, exhibits a Cmax between about 50 ng/mL and about 1000 ng/mL. In some embodiments, the compound of Formula (I) or (II), or a pharmaceutically acceptable salt, solvate, or stereoisomer thereof, exhibits a Cmax between about 50 ng/mL and about 1000 ng/mL when orally dosed in rats. In some embodiments, the compound of Formula (I) or (II), or a pharmaceutically acceptable salt, solvate, or stereoisomer thereof, exhibits a Cmax between about 50 ng/mL and about 1000 ng/mL when orally in beagle dogs. In some embodiments, the compound of Formula (I) or (II), or a pharmaceutically acceptable salt, solvate, or stereoisomer thereof, exhibits a Cmax between about 50 ng/mL and about 1000 ng/mL when orally dosed in cynomolgus monkeys. In some embodiments, the compound of Formula (I) or (II), or a pharmaceutically acceptable salt, solvate, or stereoisomer thereof, exhibits a Cmax between about 100 ng/mL and about 500 ng/mL. In some embodiments, the compound of Formula (I) or (II), or a pharmaceutically acceptable salt, solvate, or stereoisomer thereof, exhibits a Cmax between about 100 ng/mL and about 500 ng/mL when orally dosed in rats. In some embodiments, the compound of Formula (I) or (II), or a pharmaceutically acceptable salt, solvate, or stereoisomer thereof, exhibits a Cmax between about 100 ng/mL and about 500 ng/mL when orally dosed in beagle dogs. In some embodiments, the compound of Formula (I) or (II), or a pharmaceutically acceptable salt, solvate, or stereoisomer thereof, exhibits a Cmax between about 100 ng/mL and about 500 ng/mL when orally dosed in cynomolgus monkeys.

In some embodiments, the compound of Formula (I) or (II), or a pharmaceutically acceptable salt, solvate, or stereoisomer thereof, exhibits a AUC between about 500 $h \cdot ng \cdot mL^{-1}$ and about 9000 $h \cdot ng \cdot mL^{-1}$. In some embodiments, the compound of Formula (I) or (II), or a pharmaceutically acceptable salt, solvate, or stereoisomer thereof, exhibits a AUC between about 500 $h \cdot ng \cdot mL^{-1}$ and about 9000 $h \cdot ng \cdot mL^{-1}$ when orally dosed in rats. In some embodiments, the compound of Formula (I) or (II), or a pharmaceutically acceptable salt, solvate, or stereoisomer thereof, exhibits a AUC between about 500 $h \cdot ng \cdot mL^{-1}$ and about 9000 $h \cdot ng \cdot mL^{-1}$ when orally dosed in beagle dogs. In some embodiments, the compound of Formula (I) or (II), or a pharmaceutically acceptable salt, solvate, or stereoisomer thereof, exhibits a AUC between about 500 $h \cdot ng \cdot mL^{-1}$ and about 9000 $h \cdot ng \cdot mL^{-1}$ when orally dosed in cynomolgus monkeys. In some embodiments, the compound of Formula (I) or (II), or a pharmaceutically acceptable salt, solvate, or stereoisomer thereof, exhibits a AUC between about 1000 $h \cdot ng \cdot mL^{-1}$ and about 5000 $h \cdot ng \cdot mL^{-1}$. In some embodiments, the compound of Formula (I) or (II), or a pharmaceutically acceptable salt, solvate, or stereoisomer thereof, exhibits a AUC between about 1000 $h \cdot ng \cdot mL^{-1}$ and about 5000 $h \cdot ng \cdot mL^{-1}$ when orally dosed in rats. In some embodiments, the compound of Formula (I) or (II), or a pharmaceutically acceptable salt, solvate, or stereoisomer thereof, exhibits a AUC between about 1000 $h \cdot ng \cdot mL^{-1}$ and about 5000 $h \cdot ng \cdot mL^{-1}$ when orally dosed in beagle dogs. In some embodiments, the compound of Formula (I) or (II), or a pharmaceutically acceptable salt, solvate, or stereoisomer thereof, exhibits a AUC between about 1000 $h \cdot ng \cdot mL^{-1}$ and about 5000 $h \cdot ng \cdot mL^{-1}$ when orally dosed in cynomolgus monkeys.

In some embodiments, the compound of Formula (I) or (II), or a pharmaceutically acceptable salt, solvate, or stereoisomer thereof, exhibits a T½ between about 1 h and about 20 h. In some embodiments, the compound of Formula (I) or (II), or a pharmaceutically acceptable salt, solvate, or stereoisomer thereof, exhibits a T½ between about 1 h and about 20 h when orally dosed in rats. In some embodiments, the compound of Formula (I) or (II), or a pharmaceutically acceptable salt, solvate, or stereoisomer thereof, exhibits a T½ between about 1 h and about 20 h when orally dosed in beagle dogs. In some embodiments, the compound of Formula (I) or (II), or a pharmaceutically acceptable salt, solvate, or stereoisomer thereof, exhibits a T½ between about 1 h and about 20 h when orally dosed in cynomolgus monkeys. In some embodiments, the compound of Formula (I) or (II), or a pharmaceutically acceptable salt, solvate, or stereoisomer thereof, exhibits a T½ between about 2 h and about 5 h. In some embodiments, the compound of Formula (I) or (II), or a pharmaceutically acceptable salt, solvate, or stereoisomer thereof, exhibits a T½ between about 2 h and about 5 h when orally dosed in rats. In some embodiments, the compound of Formula (I) or (II), or a pharmaceutically acceptable salt, solvate, or stereoisomer thereof, exhibits a T½ between about 2 h and about 5 h when orally dosed in beagle dogs. In some embodiments, the compound of Formula (I) or (II), or a pharmaceutically acceptable salt, solvate, or stereoisomer thereof, exhibits a T½ between about 2 h and about 5 h when orally dosed in cynomolgus monkeys.

Preparation of the Compounds

The compounds used in the reactions described herein are made according to organic synthesis techniques known to those skilled in this art, starting from commercially available chemicals and/or from compounds described in the chemical literature. "Commercially available chemicals" are obtained from standard commercial sources including Acros Organics (Pittsburgh, Pa.), Aldrich Chemical (Milwaukee, Wis., including Sigma Chemical and Fluka), Apin Chemicals Ltd. (Milton Park, UK), Avocado Research (Lancashire, U.K.), BDH Inc. (Toronto, Canada), Bionet (Cornwall, U.K.), Chemservice Inc. (West Chester, Pa.), Crescent Chemical Co. (Hauppauge, N.Y.), Eastman Organic Chemicals, Eastman Kodak Company (Rochester, N.Y.), Fisher Scientific Co. (Pittsburgh, Pa.), Fisons Chemicals (Leicestershire, UK), Frontier Scientific (Logan, Utah), ICN Biomedicals, Inc. (Costa Mesa, Calif.), Key Organics (Cornwall, U.K.), Lancaster Synthesis (Windham, N.H.), Maybridge Chemical Co. Ltd. (Cornwall, U.K.), Parish Chemical Co. (Orem, Utah), Pfaltz & Bauer, Inc. (Waterbury, Conn.), Polyorganix (Houston, Tex.), Pierce Chemical Co. (Rockford, Ill.), Riedel de Haen AG (Hanover, Germany), Spectrum Quality Product, Inc. (New Brunswick, N.J.), TCI America (Portland, Oreg.), Trans World Chemicals, Inc. (Rockville, Md.), and Wako Chemicals USA, Inc. (Richmond, Va.).

Suitable reference books and treatise that detail the synthesis of reactants useful in the preparation of compounds described herein, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Additional suitable reference books and treatise that detail the synthesis of reactants useful in the preparation of compounds described herein, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

Specific and analogous reactants are optionally identified through the indices of known chemicals prepared by the Chemical Abstract Service of the American Chemical Society, which are available in most public and university libraries, as well as through on-line. Chemicals that are known but not commercially available in catalogs are optionally prepared by custom chemical synthesis houses, where many of the standard chemical supply houses (e.g., those listed above) provide custom synthesis services. A reference for the preparation and selection of pharmaceutical salts of the compounds described herein is P. H. Stahl & C. G. Wermuth "Handbook of Pharmaceutical Salts", Verlag Helvetica Chimica Acta, Zurich, 2002.

Pharmaceutical Compositions

In certain embodiments, the compound described herein is administered as a pure chemical. In some embodiments, the compound described herein is combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in *Remington: The Science and Practice of Pharmacy* (Gennaro, 21S' Ed. Mack Pub. Co., Easton, Pa. (2005)).

Accordingly, provided herein is a pharmaceutical composition comprising a compound described herein, or a pharmaceutically acceptable salt, solvate, tautomer, or stereoisomer thereof, and a pharmaceutically acceptable excipient.

In certain embodiments, the compound provided herein is substantially pure, in that it contains less than about 5%, or less than about 1%, or less than about 0.1%, of other organic small molecules, such as unreacted intermediates or synthesis by-products that are created, for example, in one or more of the steps of a synthesis method.

Pharmaceutical compositions are administered in a manner appropriate to the disease to be treated (or prevented). An appropriate dose and a suitable duration and frequency of administration will be determined by such factors as the condition of the patient, the type and severity of the patient's disease, the particular form of the active ingredient, and the method of administration. In general, an appropriate dose and treatment regimen provides the composition(s) in an amount sufficient to provide therapeutic and/or prophylactic benefit (e.g., an improved clinical outcome, such as more frequent complete or partial remissions, or longer disease-free and/or overall survival, or a lessening of symptom severity. Optimal doses are generally determined using experimental models and/or clinical trials. The optimal dose depends upon the body mass, weight, or blood volume of the patient.

In some embodiments, the pharmaceutical composition is formulated for oral, topical (including buccal and sublingual), rectal, vaginal, transdermal, parenteral, intrapulmonary, intradermal, intrathecal and epidural and intranasal administration. Parenteral administration includes intramuscular, intravenous, intraarterial, intraperitoneal, or subcutaneous administration. In some embodiments, the pharmaceutical composition is formulated for intravenous injection, oral administration, inhalation, nasal administration, topical administration, or ophthalmic administration. In some embodiments, the pharmaceutical composition is formulated for oral administration. In some embodiments, the pharmaceutical composition is formulated for intravenous injection. In some embodiments, the pharmaceutical composition is formulated as a tablet, a pill, a capsule, a liquid, an inhalant, a nasal spray solution, a suppository, a suspension, a gel, a colloid, a dispersion, a suspension, a solution, an emulsion, an ointment, a lotion, eye drop, or an ear drop. In some embodiments, the pharmaceutical composition is formulated as a tablet.

Suitable doses and dosage regimens are determined by conventional range-finding techniques known to those of ordinary skill in the art. Generally, treatment is initiated with smaller dosages that are less than the optimum dose of the compound disclosed herein. Thereafter, the dosage is increased by small increments until the optimum effect under the circumstances is reached. In some embodiments, the present method involve the administration of about 0.1 µg to about 50 mg of at least one compound of the invention per kg body weight of the subject. For a 70 kg patient, dosages of from about 10 µg to about 200 mg of the compound disclosed herein would be more commonly used, depending on a subject's physiological response.

By way of example only, the dose of the compound described herein for methods of treating a disease as described herein is about 0.001 to about 1 mg/kg body weight of the subject per day, for example, about 0.001 mg, about 0.002 mg, about 0.005 mg, about 0.010 mg, 0.015 mg, about 0.020 mg, about 0.025 mg, about 0.050 mg, about 0.075 mg, about 0.1 mg, about 0.15 mg, about 0.2 mg, about 0.25 mg, about 0.5 mg, about 0.75 mg, or about 1 mg/kg body weight per day. In some embodiments, the dose of compound described herein for the described methods is about 1 to about 1000 mg/kg body weight of the subject being treated per day, for example, about 1 mg, about 2 mg, about 5 mg, about 10 mg, about 15 mg, about 20 mg, about 25 mg, about 50 mg, about 75 mg, about 100 mg, about 150 mg, about 200 mg, about 250 mg, about 500 mg, about 750 mg, or about 1000 mg per day.

Methods of Treatment

The compounds disclosed herein, or a pharmaceutically acceptable salt, solvate, or stereoisomer thereof, are useful as autotaxin inhibitors, therefore, useful in the treatment of diseases or disorders in which it is believed autotaxin activity plays a role.

Disclosed herein are methods of treating an autotaxin associated disease or disorder in a subject in need thereof comprising the step of administering to the subject an effective amount of a compound disclosed herein, or a pharmaceutically acceptable salt, solvate, or stereoisomer thereof.

The autotaxin associated disease or disorder is, for example, a fibrotic disease, cancer, an inflammatory disease, an autoimmune disease, a respiratory disease, a cardiovascular disease, a neurological disease, a metabolic disorder, pain, pruritus, or hepatitis.

The autotaxin associated disease or disorder is, for example, a fibrotic disease, cancer, an inflammatory disease, an autoimmune disease, a respiratory disease, a cardiovascular disease, or a neurological disease.

Cancer

ATX is widely expressed, with highest mRNA levels detected in lymph nodes, brain, kidney, testis, pancreas, lung and liver. ATX is found overexpressed in several common human cancers, while many established tumour cell lines express ATX to varying levels. Expression is also detected in stromal cells, including macrophages, fibroblasts, and endothelial cells. ATX is an attractive target for the treatment of cancer because it acts extracellularly and stimulates the metastatic cascade at multiple levels. In addition, ATX has been implicated in inflammatory processes by regulating lymphocyte homing. ATX is thought to act in an autocrine/paracrine manner to promote tumour progression, i.e., by providing an invasive and angiogenic microenvironment for malignant cells. A causal link between the ATX-LPA axis and cancer is supported by a growing number of studies. Overexpressed ATX promotes tumour aggressiveness, metastasis and angiogenesis in mice. ATX is overexpressed in various human cancers, including glioblastoma, lung and breast cancer, renal cell carcinoma and Hodgkin lymphoma. Furthermore, ATX is upregulated in stromal cells from cancer patients. ATX mediates the EBV-induced growth and survival of Hodgkin lymphoma cells, while ATX knockdown reduces lymphoma cell growth and viability. Inducible overexpression of LPA1 receptors in breast carcinoma cells promotes tumour growth and bone metastasis, while LPA1 knockdown reduces tumour progression. ATX and LPA receptors have transforming potential both in vitro and in mice. Inhibition of the LPA1 receptor reduces metastasis and metastatic dormancy in breast cancer. Serum ATX levels in patients with B-cell neoplasms, especially follicular lymphoma (FL), are higher than those in healthy subjects. Serum ATX in FL patients was associated with tumour burden and changed in parallel with the patients' clinical courses. Plasma LPA levels in FL patients correlated well with ATX levels. Since tumour cells from FL patients expressed ATX, secreted ATX from lymphoma cells probably underlies the increase in serum ATX. Thus, serum ATX is a promising marker for FL. ATX/lysoPLD activity is also significantly elevated in malignant effusions from ovarian cancer patients. Furthermore, serum ATX activity decreases after prostate cancer surgery and may reflect postoperative damage or nutritional status. Dual ATX and pan-LPA receptor inhibitors inhibit breast cancer cell migration and invasion and cause tumour regression in breast cancer xenograft model. Overexpression of ATX or LPA receptors in breast cancer epithelium causes high frequency of late-onset mammary carcinomas. LPA2 knockout mice have reduced incidence of chemically induced colon carcinoma.

In one aspect, described herein is a method for treating or preventing cancer in a mammal comprising administering a therapeutically effective amount of an autotaxin inhibitor described herein, or a pharmaceutically acceptable salt, solvate, or stereoisomer thereof, to the mammal. Non-limiting examples of cancers include, acute lymphoblastic leukemia, acute myeloid leukemia, adrenocortical carcinoma, anal cancer, appendix cancer, astrocytomas, atypical teratoid/rhabdoid tumor, basal cell carcinoma, bile duct cancer, bladder cancer, bone cancer (osteosarcoma and malignant fibrous histiocytoma), brain stem glioma, brain tumors, brain and spinal cord tumors, breast cancer, bronchial tumors, Burkitt lymphoma, cervical cancer, chronic lymphocytic leukemia, chronic myelogenous leukemia, colon cancer, colorectal cancer, craniopharyngioma, cutaneous T-Cell lymphoma, desmoid tumors, embryonal tumors, endometrial cancer, ependymoblastoma, ependymoma, esophageal cancer, ewing sarcoma family of tumors, eye cancer, retinoblastoma, gallbladder cancer, gastric (stomach) cancer, gastrointestinal carcinoid tumor, gastrointestinal stromal tumor (GIST), gastrointestinal stromal cell tumor, germ cell tumor, glioma, hairy cell leukemia, head and neck cancer, hepatocellular (liver) cancer, Hodgkin lymphoma, hypopharyngeal cancer, intraocular melanoma, islet cell tumors (endocrine pancreas), Kaposi sarcoma, kidney cancer, Langerhans cell histiocytosis, laryngeal cancer, leukemia, Acute lymphoblastic leukemia, acute myeloid leukemia, chronic lymphocytic leukemia, chronic myelogenous leukemia, hairy cell leukemia, liver cancer, non-small cell lung cancer, small cell lung cancer, Burkitt lymphoma, cutaneous T-cell lymphoma, Hodgkin lymphoma, non-Hodgkin lymphoma, lymphoma, Waldenstrom macroglobulinemia, medulloblastoma, medulloepithelioma, melanoma, mesothelioma, mouth cancer, chronic myelogenous leukemia, myeloid leukemia, multiple myeloma, nasopharyngeal cancer, neuroblastoma, non-Hodgkin lymphoma, non-small cell lung cancer, oral cancer, oropharyngeal cancer, osteosarcoma, malignant fibrous histiocytoma of bone, ovarian cancer, ovarian epithelial cancer, ovarian germ cell tumor, ovarian low malignant potential tumor, pancreatic cancer, papillomatosis, parathyroid cancer, penile cancer, pharyngeal cancer, pineal parenchymal tumors of intermediate differentiation, pineoblastoma and supratentorial primitive neuroectodermal tumors, pituitary tumor, plasma cell neoplasm/multiple myeloma, pleuropulmonary blastoma, primary central nervous system lymphoma, prostate cancer, rectal cancer, renal cell (kidney) cancer, retinoblastoma, rhabdomyosarcoma, salivary gland cancer, sarcoma, Sezary syndrome, skin cancer, small cell lung cancer, small intestine cancer, soft tissue sarcoma, squamous cell carcinoma, stomach (gastric) cancer, supratentorial primitive neuroectodermal tumors, T-cell lymphoma, testicular cancer, throat cancer, thymoma and thymic carcinoma, thyroid cancer, urethral cancer, uterine cancer, uterine sarcoma, vaginal cancer, vulvar cancer, Waldenstrom macroglobulinemia, and Wilms tumor.

In some embodiments, the autotaxin inhibitor described herein, or a pharmaceutically acceptable salt, solvate, or stereoisomer thereof, is used in the treatment of ovarian cancer, prostate cancer, breast cancer, lung cancer, melanoma, head and neck cancer, bowel cancer (colorectal cancer), thyroid cancer, glioblastoma, follicular lymphoma, renal cancer, Hodgkin lymphoma, hepatocellular carcinoma, pancreatic cancer or melanoma. In some embodiments, the autotaxin inhibitor described herein, or a pharmaceutically acceptable salt, solvate, or stereoisomer thereof, is used in the treatment of bone metastases.

In some embodiments, the autotaxin inhibitor described herein, or a pharmaceutically acceptable salt, solvate, or stereoisomer thereof, is used in the treatment of oral cancer, prostate cancer, rectal cancer, non-small cell lung cancer, lip and oral cavity cancer, liver cancer, lung cancer, anal cancer, kidney cancer, vulvar cancer, breast cancer, oropharyngeal cancer, nasal cavity and paranasal sinus cancer, nasopharyngeal cancer, urethra cancer, small intestine cancer, bile duct cancer, bladder cancer, ovarian cancer, laryngeal cancer, hypopharyngeal cancer, gallbladder cancer, colon cancer, colorectal cancer, head and neck cancer, parathyroid cancer, penile cancer, vaginal cancer, thyroid cancer, pancreatic cancer, esophageal cancer, Hodgkin's lymphoma, leukemia-related disorders, mycosis fungoides, or myelodysplastic syndrome.

In some embodiments, the autotaxin inhibitor described herein, or a pharmaceutically acceptable salt, solvate, or stereoisomer thereof, is used in the treatment of non-small cell lung cancer, pancreatic cancer, breast cancer, ovarian cancer, colorectal cancer, or head and neck cancer.

In some embodiments, the autotaxin inhibitor described herein, or a pharmaceutically acceptable salt, solvate, or stereoisomer thereof, is used in the treatment of a carcinoma, a tumor, a neoplasm, a lymphoma, a melanoma, a glioma, a sarcoma, or a blastoma.

In some embodiments, the carcinoma is selected from the group consisting of: carcinoma, adenocarcinoma, adenoid cystic carcinoma, adenosquamous carcinoma, adrenocortical carcinoma, well differentiated carcinoma, squamous cell carcinoma, serous carcinoma, small cell carcinoma, invasive squamous cell carcinoma, large cell carcinoma, islet cell carcinoma, oat cell carcinoma, squamous carcinoma, undifferentiatied carcinoma, verrucous carcinoma, renal cell carcinoma, papillary serous adenocarcinoma, merkel cell carcinoma, hepatocellular carcinoma, soft tissue carcinomas, bronchial gland carcinomas, capillary carcinoma, bartholin gland carcinoma, basal cell carcinoma, carcinosarcoma, papilloma/carcinoma, clear cell carcinoma, endometrioid adenocarcinoma, mesothelial, metastatic carcinoma, mucoepidermoid carcinoma, cholangiocarcinoma, actinic keratoses, cystadenoma, and hepatic adenomatosis.

In some embodiments, the tumor is selected from the group consisting of: astrocytic tumors, malignant mesothelial tumors, ovarian germ cell tumor, supratentorial primitive neuroectodermal tumors, Wilm's tumor, pituitary tumors, extragonadal germ cell tumor, gastrinoma, germ cell tumors, gestational trophoblastic tumor, brain tumors, pineal and supratentorial primitive neuroectodermal tumors, pituitary tumor, somatostatin-secreting tumor, endodermal sinus tumor, carcinoids, central cerebral astrocytoma, glucagonoma, hepatic adenoma, insulinoma, medulloepithelioma, plasmacytoma, vipoma, and pheochromocytoma.

In some embodiments, the neoplasm is selected from the group consisting of: intaepithelial neoplasia, multiple myeloma/plasma cell neoplasm, plasma cell neoplasm, interepithelial squamous cell neoplasia, endometrial hyperplasia, focal nodular hyperplasia, hemangioendothelioma, lymphangioleio myomatosis and malignant thymoma.

In some embodiments, the lymphoma is selected from the group consisting of: nervous system lymphoma, AIDS-related lymphoma, cutaneous T-cell lymphoma, non-Hodgkin's lymphoma, mantle cell lymphoma, follicular lymphoma and Waldenstrom's macroglobulinemia.

In some embodiments, the melanoma is selected from the group consisting of: acral lentiginous melanoma, superficial spreading melanoma, uveal melanoma, lentigo maligna melanomas, melanoma, intraocular melanoma, adenocarcinoma nodular melanoma, and hemangioma.

In some embodiments, the sarcoma is selected from the group consisting of: adenomas, adenosarcoma, chondosarcoma, endometrial stromal sarcoma, Ewing's sarcoma, Kaposi's sarcoma, leiomyosarcoma, rhabdomyosarcoma, sarcoma, uterine sarcoma, osteosarcoma, and pseudosarcoma.

In some embodiments, the glioma is selected from the group consisting of: glioma, brain stem glioma, and hypothalamic and visual pathway glioma.

In some embodiments, the blastoma is selected from the group consisting of: pulmonary blastoma, pleuropulmonary blastoma, retinoblastoma, neuroblastoma, medulloblastoma, glioblastoma, and hemangiblastomas.

In some embodiments, the method further comprises administering a second therapeutic agent to the mammal in addition to the autotaxin inhibitor, or a pharmaceutically acceptable salt, solvate, or stereoisomer thereof. In one aspect, described herein is a method for the treatment or prevention of cancer in a mammal, the method comprising administering to the mammal a therapeutically effective amount of an autotaxin inhibitor, or a pharmaceutically acceptable salt, solvate, or stereoisomer thereof and a second anti-cancer agent or therapy.

Inflammation

High ATX expression is found in the high endothelial venules (HEVs) of lymphoid organs and in venules at sites of chronic inflammation, where it may play a role in T cell trafficking across the endothelial walls during inflammation. Intravenous injection of enzymatically inactive ATX attenuated the homing of T cells to lymphoid tissues, probably through competition with endogenous ATX. These results suggest that ATX is a potential target for anti-inflammatory therapy. Investigators recently showed that injection of neutralizing monoclonal antibodies against ATX into mice reduced plasma LPA levels to zero. It thus appears that plasma LPA can be depleted by targeting ATX. These results suggest that ATX is a potential target for anti-inflammatory therapy.

In another aspect, described herein is a method of treating or preventing an inflammatory disease or condition in a mammal comprising administering a therapeutically effective amount of an autotaxin inhibitor described herein, or a pharmaceutically acceptable salt, solvate, or stereoisomer thereof, to the mammal. In some embodiments, the inflammatory disease or condition is psoriasis, rheumatoid arthritis, vasculitis, inflammatory bowel disease, dermatitis, osteoarthritis, asthma, inflammatory muscle disease, allergic rhinitis, vaginitis, interstitial cystitis, scleroderma, eczema, lupus erythematosus, dermatomyositis, Sjogren's syndrome, thyroiditis, myasthenia gravis, autoimmune hemolytic anemia, multiple sclerosis, cystic fibrosis, chronic relapsing hepatitis, primary biliary cirrhosis, primary sclerosing cholangitis, allergic conjunctivitis or atopic dermatitis.

In one aspect, described herein is a method for treating or preventing an inflammatory disease or condition in a mammal, the method comprising administering to the mammal a therapeutically effective amount of an autotaxin inhibitor, or a pharmaceutically acceptable salt, solvate, or stereoisomer thereof, and an anti-inflammatory drug. In some embodiments, the anti-inflammatory drug comprises a non-steroidal anti-inflammatory drug.

Metabolic Disorders

ATX expression is significantly up-regulated in adipose tissue from patients exhibiting both insulin resistance and impaired glucose tolerance. This suggests that ATX may serve as a therapeutic target in obesity-associated type 2 diabetes.

In another aspect, described herein is a method of treating or preventing a metabolic disorder in a mammal comprising administering a therapeutically effective amount of an autotaxin inhibitor described herein, or a pharmaceutically acceptable salt, solvate, or stereoisomer thereof, to the mammal. In some embodiments, disclosed herein are methods of treating metabolic disorders and conditions associated with metabolic disorders, comprising administering an autotaxin inhibitor. As used herein, a "metabolic disorder" refers to any pathological condition resulting from an alteration in a subject's metabolism. Such disorders include those resulting from an alteration in glucose homeostasis and/or insulin dysfunction. Metabolic disorders, include but are not limited to, metabolic syndrome, elevated blood glucose levels, insulin resistance, glucose intolerance, type 2 diabetes, type 1 diabetes, pre-diabetes, non-alcoholic fatty liver disease, nonalcoholic steatohepatitis (NASH), and obesity. In some embodiments, the metabolic disorder is nonalcoholic steatohepatitis (NASH).

Metabolic disorders are inter-related and can result in disorders across various systems. Addressing the core metabolic disorder can reduce the severity of related conditions in a patient, including, for example, cardiovascular disorders (including, e.g., ischemic heart disease, angina and myocardial infarction, congestive heart failure, high blood pressure, abnormal cholesterol levels, deep vein thrombosis, and pulmonary embolism), neurological disorders (including, e.g., stroke, meralgia paresthetica, migraines, idiopathic, and intracranial hypertension, depression and social stigmatism), rheumatological and orthopedic disorders (including, e.g., gout, poor mobility, osteoarthritis, and lower back pain), dermatological disorders (including, e.g., stretch marks, acanthosis nigricans, lymphedema, cellulitis), gastrointestinal disorders (including, e.g., gastroesophageal reflux disease (GERD) and cholelithiasis (gallstones)), respiratory disorders (including, e.g., obstructive sleep apnea, obesity hypoventilation syndrome, asthma, and increased complications during general anaesthesia), urology and nephrology disorders (including, e.g., erectile dysfunction, urinary incontinence, chronic renal failure, and hypogonadism).

In some embodiments, administering an autotaxin inhibitor described herein to an individual with a metabolic disorder has a variety of desirable outcomes which include, but are not limited to, reducing blood glucose levels, decreasing plasma lysophosphatidic acid levels, improving insulin sensitivity, increasing insulin secretion, improving glucose tolerance, and decreasing adipose tissue expansion. Any of these outcomes can treat, delay or prevent the onset of a metabolic disorder, wherein such metabolic disorders include, but are not limited to, metabolic syndrome, elevated blood glucose levels, insulin resistance, glucose intolerance, type 2 diabetes, type 1 diabetes, pre-diabetes, non-alcoholic fatty liver disease, nonalcoholic steatohepatitis, and obesity.

In some embodiments, methods disclosed herein comprise administering an autotaxin inhibitor described herein to a subject with elevated blood glucose levels. In some embodiments, the autotaxin inhibitor is used to treat an underlying metabolic disorder. In some embodiments, the metabolic disorder is treated by reducing blood glucose levels. In some embodiments, the subject is overweight or obese. In some embodiments, the subject has type 2 diabetes. In some embodiments, the subject has non-alcoholic fatty liver disease and/or nonalcoholic steatohepatitis. In some embodiments, the subject does not have a metabolic disorder. In some embodiments, the autotaxin inhibitor delays or prevents the onset of the metabolic disorder by reducing elevated blood glucose levels.

In some embodiments, methods disclosed herein comprise reducing plasma lysophosphatidic acid levels in an individual by administering an autotaxin inhibitor. In some embodiments, the plasma lysophosphatidic acid levels in the individual are elevated relative to a control. In some embodiments, the control is a person without a metabolic disorder. In some embodiments, the elevated plasma lysophosphatidic acid levels in the individual contribute to or increase the risk for developing a metabolic disorder.

In some embodiments, disclosed herein are methods comprising administering an autotaxin inhibitor to a subject with elevated plasma lysophosphatidic acid levels relative to a control. In some embodiments, disclosed herein are methods for improving insulin sensitivity comprising administering an autotaxin inhibitor to an individual sensitive to insulin. In some embodiments, disclosed herein are methods comprising the administration of an autotaxin inhibitor to a subject with insulin resistance. In some embodiments, disclosed herein are methods comprising the administration of an autotaxin inhibitor to improve insulin secretion in an individual. In some embodiments, disclosed herein are methods comprising the administration of an autotaxin inhibitor to improve glucose tolerance in an individual with impaired glucose tolerance. In some embodiments, disclosed herein are methods for decreasing adipose tissue expansion in a subject comprising administering to the subject an autotaxin inhibitor. In some embodiments, disclosed herein are methods for the treatment of a metabolic disorder in a subject that is overweight or obese comprising administering to the subject an autotaxin inhibitor.

In another aspect, described herein is a method of treating or preventing drug induced hyperglycemia in a mammal comprising administering a therapeutically effective amount of an autotaxin inhibitor described herein, or a pharmaceutically acceptable salt, solvate, or stereoisomer thereof, to the mammal. In some embodiments, administration of an autotaxin inhibitor to a subject treats, prevents, or ameliorates the symptoms of drug induced hyperglycemia. In some embodiments, administration of an autotaxin inhibitor to a subject treats, prevents, or ameliorates the symptoms of drug induced hyperglycemia by reducing blood glucose levels. Pharmacological agents can affect glucose homeostasis that can result in hyperglycemia. In some embodiments, the hyperglycemia occurs in the absence of a diagnosis of diabetes. If left untreated, the elevated blood glucose levels can lead to a medical emergency. Symptoms include, but are not limited to fatigue, weakness, fruity odor of the breath, confusion, lack of concentration, shortness of breath, nausea, vomiting, dry skin, and flushing of the skin. Common drug categories that are associated with contributing to hyperglycemia include, but are not limited to: antibiotics, such as fluoroquinolones including gatifloxacin; beta-blockers, such as propranolol, metoprolol or atenolol; thiazide, such as hydrochlorothiazide, and thiazide-like diuretics, and thiazide-like drugs (metolazone); second-generation antipsychotics (SGAs) or "atypical antipsychotics" such as olanzapine or clozapine; corticosteroids; calcinuerin inhibitors such as cyclosporine, sirolimus or tarcrolimus; and protease inhibitors such as ritonavir.

In another aspect, described herein is a method of treating or preventing stress induced hyperglycemia in a mammal comprising administering a therapeutically effective amount of an autotaxin inhibitor described herein, or a pharmaceutically acceptable salt, solvate, or stereoisomer thereof, to the mammal. some embodiments, administration of an autotaxin inhibitor to a subject treats or prevents or delays the onset of stress induced hyperglycemia. In some embodiments, administration of an autotaxin inhibitor to a subject treats or prevents or delays the onset of stress induced hyperglycemia by reducing blood glucose levels. Stressed induced hyperglycemia (SIH) is a transient increase in plasma glucose levels higher than 200 mg/dL which occurs during an acute illness or injury. In some embodiments, the hyperglycemia occurs in the absence of a diagnosis of diabetes. The SIFT results from an excess of glucose production relative glucose clearance. SIH has been associated with conditions including, but not limited to, myocardial infarction, stroke, and trauma. SIH has been associated with increase mortality and a higher incidence of congestive heart failure and cardiogenic shock in patients after myocardial infarction. Stroke victims have higher mortality associated with SIH and worse odds of desirable neurological outcomes as glucose levels increase with SIH. Hyperglycemia was also shown to be a predictor of infectious complications in the form of pneumonia, urinary tract infections, wound infections and bacteria. Overall, published studies have consistently shown higher morbidity and higher mortality rates in those patients that present with SIFT.

Fibrotic Disorders

Mice lacking the LPA1 receptor are markedly protected from pulmonary fibrosis and mortality. The absence of LPA1 leads to reduced fibroblast recruitment and vascular leak, two responses that are excessive when injury leads to fibrosis rather than to repair. Thus, the ATX-LPA axis represents a therapeutic target for diseases in which aberrant responses to injury contribute to fibrosis, such as idiopathic pulmonary fibrosis, as well as renal interstitial fibrosis, hepatic fibrosis and skin fibrosis.

In one aspect, described herein is a method for the treatment or prevention of fibrosis in a mammal comprising administering a therapeutically effective amount of an autotaxin inhibitor described herein, or a pharmaceutically acceptable salt, solvate, or stereoisomer thereof, to the mammal. In some embodiments, accumulation of extracellular matrix or the rate of accumulation of extracellular matrix in a tissue having fibrosis is reduced following administration of the autotaxin inhibitor, or a pharmaceutically acceptable salt, solvate, or stereoisomer thereof. In some embodiments, the fibrosis comprises peritoneal fibrosis, lung fibrosis, liver fibrosis, kidney fibrosis, ocular fibrosis or cutaneous fibrosis. In some embodiments, the fibrosis is idiopathic pulmonary fibrosis (IPF). As an example, the method comprises administering an autotaxin inhibitor to a mammal having liver fibrosis. In some instances, the onset of cirrhosis or liver failure is delayed or prevented following administration of the autotaxin inhibitor, or a pharmaceutically acceptable salt, or solvate thereof. In some instances, the accumulation of fibrogenic cells and/or the deposition of extracellular matrix proteins within the liver is attenuated or prevented following administration of the autotaxin inhibitor, or a pharmaceutically acceptable salt, or solvate thereof. In one example, the method comprises administering an autotaxin inhibitor to a mammal having kidney fibrosis. In some instances, administration of an autotaxin inhibitor to the mammal prevents renal failure. As another example, the method comprises administering an autotaxin inhibitor to a mammal having peritoneal fibrosis. As a further example, the method comprises administering an autotaxin inhibitor to a mammal having skin fibrosis.

In one aspect, described herein is a method for the treatment or prevention of fibrosis in a mammal comprising administering to the mammal a therapeutically effective amount of an autotaxin inhibitor, or a pharmaceutically acceptable salt, solvate, or stereoisomer thereof, and a second therapeutic agent. In some embodiments, the second therapeutic agent comprises an angiotensin inhibitor, colchicine, corticosteroid, an endothelin inhibitor, interferon-alpha, interleukin 10, an antioxidant, a hepatic stellate cell (HSC) inhibitor, an ACE inhibitor, an ADAM inhibitor, a metalloenzyme, pirfenidone, tranilast, fluorofenidone, an anti-inflammatory agent, an immunosuppressant, or a combination thereof.

Pain

Mice lacking the LPA1 receptor are also protected against injury-induced neuropathic pain and related behaviour. Heterozygous Enpp2(+/−) mice, which have 50% ATX protein compared to wild-type mice, show approx. 50% recovery of nerve injury-induced neuropathic pain (see, e.g., Inoue et al., 2008). Therefore, targeting ATX (and its downstream LPA signaling pathways) represents a novel way to prevent nerve injury-induced neuropathic pain.

In one aspect, described herein is a method for the treatment of neuropathic pain in a mammal comprising administering a therapeutically effective amount of an autotaxin inhibitor described herein, or a pharmaceutically acceptable salt, solvate, or stereoisomer thereof, to the mammal.

Neuropathic pain results from injury to a nerve. In contrast to immediate pain caused by tissue injury, in some embodiments, neuropathic pain develops days or months after a traumatic injury. In addition, neuropathic pain frequently is long-lasting or chronic and can occur spontaneously or as a result of stimulation that normally is not painful.

In one aspect, described herein is a method for the treatment of neuropathic pain in a mammal comprising administering to the mammal a therapeutically effective amount of an autotaxin inhibitor, or a pharmaceutically acceptable salt, solvate, or stereoisomer thereof, and a second therapeutic agent for the treatment of neuropathic pain.

Pruritus

Serum ATX levels have been reported to correlate with pruritus of cholestasis (Kremer et al., 2012). Serum ATX levels have also been shown to correlate with pruritus in patients with atopic dermatitis (Nakao et al., 2014). This suggests that targeting ATX (and its downstream LPA signaling pathways) represents a useful method for the treatment of pruritus.

In one aspect, described herein is a method for treating or preventing pruritus in a mammal comprising administering a therapeutically effective amount of an autotaxin inhibitor described herein, or a pharmaceutically acceptable salt, solvate, or stereoisomer thereof, to the mammal. In some embodiments, the pruritus is associated with dermatitis herpetiformis, dermatomyositis, pemphigoid, Sjögren's syndrome, Darier's disease, Hailey-Hailey disease, Ichthyoses, Sjögren-Larsson syndrome, dermatophytosis, folliculitis, impetigo and other bacterial infections, insect bites, pediculosis, scabies, viral infection, asteatosis, atopic eczema, contact dermatitis, drug reaction, lichen planus, lichen simplex chronicus, mastocytosis (urticaria pigmentosa), miliaria, psoriasis, scar(s), urticaria, cutaneous T-cell lymphoma or mycosis fungoides, cutaneous B-cell lymphoma, leukemia cutis, pemphigoid gestationis, polymorphic eruption of pregnancy or prurigo gestationis. In one aspect, described herein is a method for treating or preventing cholestatic pruritus in a mammal comprising administering a therapeutically effective amount of an autotaxin inhibitor described herein, or a pharmaceutically acceptable salt, solvate, or stereoisomer thereof, to the mammal in need thereof.

In one aspect, described herein is a method for the treatment or prevention of a pruritus in a mammal, the method comprising administering to the mammal a therapeutically effective amount of an autotaxin inhibitor, or a pharmaceutically acceptable salt, solvate, or stereoisomer thereof, and a second therapeutic agent. In some embodiments, the second therapeutic agent comprises topical capsaicin.

Hepatitis C and B/Hepatocellular Carcinoma

Serum ATX activity and plasma LPA levels are increased in chronic hepatitis C (HCV) in association with liver fibrosis. ATX and genes related to ATX signalling pathway were up regulated in human hepatocellular carcinoma (HCC) patients co-infected with HCV. It has recently been reported that ATX expression in tumour cells is specifically associated with HCV and that ATX plays a key role in HCV replication. Recent studies have also reported the ATX-LPA signalling axis to play an essential role in the lifecycle of both chronic hepatitis B (HBV) and chronic hepatitis C (HCV). Thus, ATX-LPA is also a potential therapeutic target for the treatment of hepatitis B and hepatitis C.

In one aspect, described herein is a method for treating or preventing hepatitis in a mammal comprising administering a therapeutically effective amount of an autotaxin inhibitor described herein, or a pharmaceutically acceptable salt, solvate, or stereoisomer thereof, to the mammal. In some embodiments, the hepatitis is hepatitis B or hepatitis C. In one aspect, described herein is a method for treating or preventing hepatocellular carcinoma in a mammal comprising administering a therapeutically effective amount of an autotaxin inhibitor described herein, or a pharmaceutically acceptable salt, solvate, or stereoisomer thereof, to the mammal.

In one aspect, described herein is a method for the treatment or prevention of hepatitis in a mammal, the method comprising administering to the mammal a therapeutically effective amount of an autotaxin inhibitor, or a pharmaceutically acceptable salt, solvate, or stereoisomer thereof, and a second therapeutic agent. In some embodiments, the second therapeutic agent comprises HCV polymerase inhibitor, HBV polymerase inhibitor, immunomodulatory agents, pegylated interferon, viral entry inhibitor, viral maturation inhibitor, capsid assembly modulator, reverse transcriptase inhibitor (such as Zidovudine, Didanosine, Zalcitabine, ddA, Stavudine, Lamivudine, Abacavir, Emtricitabine, Entecavir, Apricitabine, Atevirapine, ribavirin, acyclovir, famciclovir, valacyclovir, ganciclovir, valganciclovir, Tenofovir, Adefovir, PMPA, cidofovir, Efavirenz, Nevirapine, Delavirdine, and Etravirine), a cyclophilin/TNF inhibitor, a TLR-agonist, or a combination thereof.

Neurological Diseases

In one aspect, described herein is a method for treating or preventing a neurological disease in a mammal comprising administering a therapeutically effective amount of an autotaxin inhibitor described herein, or a pharmaceutically acceptable salt, solvate, or stereoisomer thereof, to the mammal. In some embodiments, the neurological disease is multiple sclerosis. In some instances, the neurological disease is caused by a genetic disorder. In some instances, the neurological disease is developmental, for example, spina bifida. In some instances, the neurological disease is a degenerative disease, for example, Parkinson's disease or Alzheimer's disease. In some instances, the neurological disease results from a stroke. Neurological diseases, conditions and disorders or characteristics of neurological diseases, conditions and disorders suitable for treatment with an ATX inhibitor include, without limitation, Amyotrophic lateral sclerosis (ALS), Arteriovenous malformations (AVMs), brain aneurysm, brain tumor, Dural arteriovenous fistulae, epilepsy, headache, memory disorders, Parkinson's disease, peripheral neuropathy, post-herpetic neuralgia, spinal cord tumor and stroke. In certain instances, autotaxin activity is increased in CSF (cerebrospinal fluid) and serum of relapse/remitting multiple sclerosis patients compared to patients with other neurological diseases.

In some embodiments, the mutiple sclerosis is relapsing-remitting multiple sclerosis, relapsing multiple sclerosis, primary-progressive multiple sclerosis, or secondary-progressive multiple sclerosis.

In some embodiments, the mutiple sclerosis is relapsing-remitting multiple sclerosis (RRMS). People with this type of MS have clearly defined attacks of worsening neurologic function. These attacks are followed by partial or complete recovery periods called remissions. During remission, symptoms often improve and there is no apparent worsening or progression of disease. About 85% of people with MS are initially diagnosed with RRMS.

In some embodiments, the mutiple sclerosis is relapsing multiple sclerosis (RMS). RMS includes several forms of MS that have relapsing features, including relapsing-remitting MS, progressive-relapsing MS, and secondary-progressive MS.

In some embodiments, the mutiple sclerosis is primary-progressive multiple sclerosis (PPMS). This form has a steady worsening of neurologic functioning, but without any distinct relapses or periods of remission. A person's rate of progression may vary over time—with occasional plateaus or temporary improvements—but the progression is continuous. 10% of people are diagnosed with this type of MS.

In some embodiments, the mutiple sclerosis is secondary-progressive multiple sclerosis (SPMS). Following an initial period of relapsing-remitting MS (RRMS), many people transition to SPMS. The disease begins to worsen more steadily, with or without occasional relapses, remissions, or plateaus.

In some embodiments, disclosed herein are methods of treating a nervous system injury in a subject, for example, injury to the brain, spinal cord and/or nerve tissue, the methods comprising the administration of an autotaxin inhibitor to the subject.

In some embodiments, disclosed herein are methods for the treatment of a cancer affecting the nervous system of a subject, the methods comprising the administration of an autotaxin inhibitor to the subject. In some examples, the cancer is brain cancer.

In some embodiments, disclosed herein are methods of treating injury-induced demyelination in a subject, the methods comprising the administration of an autotaxin inhibitor to the subject.

In some embodiments, disclosed herein are methods of treating an infection of the nervous system in a subject, the methods comprising the administration of an autotaxin inhibitor to the subject. In some examples, the nervous system infection includes meningitis.

In some embodiments, disclosed herein are methods of preventing or treating a sign, symptom and/or complication of a neurological disease, disorder or condition, the methods comprising administration of an autotaxin inhibitor. In some embodiments, disclosed herein are methods of preventing or treating a sign, symptom and/or complication of multiple sclerosis in a subject, the methods comprising administering an autotaxin inhibitor to the subject. Signs and symptoms of multiple sclerosis include, without limitation, numbness or weakness in one or more limbs, partial or complete loss of vision, double vision, blurring of vision, tingling sensation, electric-shock sensations, tremors, lack of coordination, unsteady gait, slurred speech, fatigue, dizziness, and changes in bowel and/or bladder function. Examples of multiple sclerosis complications include, without limitation, muscle stiffness, muscle spasms, paralysis, mental changes such as forgetfulness and mood swings, depression and epilepsy.

In some embodiments, disclosed herein are methods of decreasing the frequency, severity and/or duration of a relapse of a neurological disease, disorder or condition, the methods comprising administration of an autotaxin inhibitor. In some embodiments, disclosed herein are methods of decreasing the frequency, severity and/or duration of a relapse of multiple sclerosis, the methods comprising administration of an autotaxin inhibitor. In some instances, administration of an autotaxin inhibitor decreases or stops the progression of one or more symptoms in a patient having multiple sclerosis. In some instances, administration of an autotaxin inhibitor prevents or delays the onset of multiple sclerosis symptoms.

Neurological diseases, conditions and disorders or characteristics of neurological diseases, conditions and disorders suitable for treatment with an autotaxin inhibitor include, without limitation, absence of the septum pellucidum, acid lipase disease, acid maltase deficiency, acquired epileptiform aphasia, acute disseminated encephalomyelitis, ADHD, Adie's pupil, Adie's syndrome, adrenoleukodystrophy, agenesis of the corpus callosum, agnosia, aicardi syndrome, neurological complications from AIDS, Alexander disease, Alpers' disease, alternating hemiplegia, Alzheimer's disease, amyotrophic lateral sclerosis (ALS), anencephaly, aneurysm, angelman syndrome, angiomatosis, anoxia, antiphospholipid syndrome, aphasia, apraxia, arachnoid cysts, arachnoiditis, Arnold-Chiari malformation, arteriovenous malformation, Asperger syndrome, ataxia, stroke, Barth syndrome, batten disease, Becker's myotonia, Behcet's disease, Bell's palsy, benign essential blepharospasm, benign focal amyotrophy, benign intracranial hypertension, Bernhardt-Roth syndrome, Binswanger's disease, blepharospasm, Bloch-Sulzberger syndrome, brachial plexus injuries, Bradbury-Eggleston syndrome, brain aneurysm, brain injury, Brown-Sequard syndrome, CADASIL, canavan disease, causalgia, cavernomas, cavernous angioma, cavernous malformation, central cord syndrome, central pain syndrome, central pontine myelinolysis, cephalic disorders, ceramidase deficiency, cerebellar degeneration, cerebellar hypoplasia, cerebral aneurysms, cerebral arteriosclerosis, cerebral atrophy, cerebral beriberi, cerebral cavernous malformation, cerebral gigantism, cerebral hypoxia, cerebral palsy, cerebro-oculo-facio-skeletal syndrome, chiari malformation, chorea, choreoacanthocytosis, chronic inflammatory demyelinating polyneuropathy (CIDP), chronic orthostatic intolerance, cockayne syndrome type II, Coffin Lowry syndrome, colpocephaly, coma, complex regional pain syndrome, congenital facial diplegia, congenital myasthenia, congenital myopathy, congenital vascular cavernous malformations, corticobasal degeneration, cranial arteritis, craniosynostosis, cree encephalitis, Creutzfeldt-Jakob disease, cumulative trauma disorders, Cushing's syndrome, cytomegalic inclusion body disease, cytomegalovirus infection, Dandy-Walker syndrome, Dawson disease, De Morsier's syndrome, Dejerine-Klumpke palsy, dementia, dentate cerebellar ataxia, dentatorubral atrophy, dermatomyositis, developmental dyspraxia, Devic's syndrome, diabetic neuropathy, diffuse sclerosis, dravet syndrome, dysautonomia, dysgraphia, dysphagia, dyspraxia, dyssynergia cerebellaris, dystonias, bulbospinal muscular atrophy, encephalopathy, empty sella syndrome, encephalitis, encephaloceles, encephalotrigeminal angiomatosis, epilepsy, Erb-Duchenne and Dejerine-Klumpke Palsies, Erb's palsy, extrapontine myelinolysis, fabry disease, Fahr's syndrome, familial dysautonomia, familial hemangioma, familial idiopathic basal ganglia calcification, familial periodic paralyses, familial spastic paralysis, Farber's Disease, febrile seizures, fibromuscular dysplasia, fisher syndrome, Friedreich's ataxia, and frontotemporal dementia.

In one aspect, described herein is a method for the treatment or prevention of neurological disorder such as multiple sclerosis in a mammal, the method comprising administering to the mammal a therapeutically effective amount of an autotaxin inhibitor, or a pharmaceutically acceptable salt, solvate, or stereoisomer thereof, and a second therapeutic agent. Second therapeutic agent, without limitation, plasma exchange, physical therapy, muscle relaxants, exercise, rest, and administration of one or more of the following: corticosteroids, beta interferons, glatiramer acetate, dimethyl fumarate, fingolimod, teriflunomide, natalizumab, mitoxantrone; and combinations thereof.

Autoimmune Diseases

In one aspect, described herein is a method for treating or preventing an autoimmune disease in a mammal comprising administering a therapeutically effective amount of an autotaxin inhibitor described herein, or a pharmaceutically acceptable salt, solvate, or stereoisomer thereof, to the mammal. Examples of autoimmune diseases include, but are not limited to, Alopecia Areata, Lupus, Ankylosing Spondylitis, Meniere's Disease, Antiphospholipid Syndrome, Mixed Connective Tissue Disease, Autoimmune Addison's Disease, Autoimmune Hemolytic Anemia, Myasthenia Gravis, Autoimmune Hepatitis, Pemphigus Vulgaris, Behcet's Disease, Pernicious Anemia, Bullous Pemphigoid, Polyarthritis Nodosa, Cardiomyopathy, Polychondritis, Celiac Sprue-Dermatitis, Polyglandular Syndromes, Chronic Fatigue Syndrome (CFIDS), Polymyalgia Rheumatica, Chronic Inflammatory Demyelinating, Polymyositis and Dermatomyositis, Chronic Inflammatory Polyneuropathy, Primary Agammaglobulinemia, Churg-Strauss Syndrome, Primary Biliary Cirrhosis, Cicatricial Pemphigoid, Psoriasis, CREST Syndrome, Raynaud's Phenomenon, Cold Agglutinin Disease, Reiter's Syndrome, Crohn's Disease, Rheumatic Fever, Discoid Lupus, Multiple Sclerosis, Rheumatoid Arthritis, Essential Mixed, Cryoglobulinemia Sarcoidosis, Fibromyalgia, Scleroderma, Grave's Disease, Sjögren's Syndrome, Guillain-Barre, Stiff-Man Syndrome, Hashimoto's Thyroiditis, Takayasu Arteritis, Idiopathic Pulmonary Fibrosis (IPF), Temporal Arteritis/Giant Cell Arteritis, Idiopathic Thrombocytopenia Purpura (ITP), Ulcerative Colitis, IgA Nephropathy, Uveitis, Insulin Dependent Diabetes (Type I), Diabetes (Type II), Vasculitis, Lichen Planus, and Vitiligo. In some embodiments, the autoimmune disease is scleroderma. In some embodiments, the autoimmune disease is Idiopathic Pulmonary Fibrosis (IPF).

In some embodiments, the methods for the treatment, reduction of risk, and delaying the onset of an autoimmune disease or disorder further comprise the administration of an immunosuppressant. Immunosuppressants include, without limitation, glucocorticoids, cytostatics, antibodies and drugs that act on immunophilins. Examples of glucocorticoids include cortisol, cortisone, prednisone, prednisolone, methylprednisolone, dexamethasone, betamethasone, triamcinolone, beclometasone, fludrocortisone, deoxycorticosterone, and aldosterone. Examples of cytostatics include alkylating agents (e.g., nitrogen mustards such as cyclophosphamide, nitrosoureas, platinum compounds) and antimetabolites (e.g., folic acid analogues such as methotrexate, purine analogues such as azathioprine and mercaptopurine, pyrimidine analogues such as fluorouracil, protein synthesis inhibitors). Examples of drugs for use in the methods described include ciclosporin, tacrolimus, sirolimus, interferons, opioids, TNF binding proteins, mycophenolate, and fingolimod. Examples of antibodies useful for co-administration with an autotaxin inhibitor in a method described herein include Antithymocyte globulin, 1D09C3, Adalimumab/D2E7 (Humira; Trudexa), Afelimomab, Afutuzumab/GA101 (type II), Alemtuzumab/Campath-1H (MabCampath), Apolizumab/Hu1D10, Aselizumab, Atlizumab, Basiliximab (Simulect), Bectumomab/IMMU-LL2, Belimumab (Benlysta, LymphoStat-B), Bertilimumab, BL22/CAT-3888, Brentuximab/cAC10/SGN-35, Briakinumab/ABT-874, Canakinumab/ACZ885 (Ilaris), Certolizumab pegol/CDP870 (Cimzia), Clenoliximab, Dacetuzumab/SGN-40, Daclizumab (Zenapax), Eculizumab/5G1.1 (Soliris), Efalizumab (Raptiva, formerly Xanelim), Epratuzumab/hLL2/IMMU-102 (Lymphocyde©), Fontolizumab, Fresolimumab/GC-1008, Galiximab/IDEC-114, Gavilimomab/ABX-CBL, Gemtuzumab, Golimumab/CNTO148 (Simponi), HL2434P (IMMU-114), Ibritumomab tiuxetan (MXDPTA)/IDEC Y2B8 (Zevalin), Infliximab/chimeric A2 (cA2) (Remicade), Inolimomab/BT563, Inotuzumab, Keliximab/IDEC CE9.1, Lerdelimumab/CAT-152, Lintuzumab/HuM195 (Zamyl), LMB-2, Lorvotuzumab mertansine, Lumiliximab/IDEC-152, Lym-1 (Oncolym), MDX-060, Mepolizumab/SB-240563, Metelimumab/CAT-192, Mogamulizumab/KW-0761/AMG-761, Moxetumomab pasudotox/CAT-8015/HA22, Muromonab-CD3 (Orthoclone OKT3), Natalizumab (Tysabri, Antegren), Nerelimomab/CDP571, Ocrelizumab/PRO70769 (type I), Odulimomab, Ofatumumab/2F2/HuMax-CD20 (Arzerra) (type I), Omalizumab (Xolair), Otelixizumab/TRX4, Pascolizumab/SB 240683, Reslizumab/SCH 55700 (Cinquil), Rituximab/chimeric 2B8 (IDEC-C2B8) (Rituxan, MabThera) (type I), Ruplizumab (Antova), SAR-3419, Secukinumab/AIN-457, SGN30, Siplizumab/MEDI-507, Teplizumab/MGA031/hOKT3γ1 (Ala-Ala), Tocilizumab (Actemra), Tositumomab (type II), Ustekinumab/CNTO 1275 (Stelara), Vedolizumab/MNL-0002, Veltuzumab/IMMU-106/hA20 (type I), Visilizumab (Nuvion), Zanolimumab/HuMax-CD4, Zolimomab aritox/H65, Abatacept/CTLA4-Ig/BMS-188667 (Orencia), Belatacept/LEA29Y, Atacicept/BLyS/APRIL-Ig, Etanercept/TNFR-Ig (Enbrel), Pegsunercept/pegylated TNFR-Ig, Alefacept (Amevive), and Rilonacept (Arcalyst). Immunosuppressive antibodies include antibodies that target complement-dependent proteins and interleukins.

Respiratory Diseases

In one aspect, described herein is a method for treating or preventing a respiratory disease in a mammal comprising administering a therapeutically effective amount of an autotaxin inhibitor described herein, or a pharmaceutically acceptable salt, solvate, or stereoisomer thereof, to the mammal. Respiratory disease refers to diseases affecting the organs that are involved in breathing, such as the nose, throat, larynx, eustachian tubes, trachea, bronchi, lungs, related muscles (e.g., diaphram and intercostals), and nerves. In particular, examples of respiratory diseases include asthma, adult respiratory distress syndrome and allergic (extrinsic) asthma, non-allergic (intrinsic) asthma, acute severe asthma, chronic asthma, clinical asthma, nocturnal asthma, allerGen-induced asthma, aspirin-sensitive asthma, exercise-induced asthma, isocapnic hyperventilation, child onset asthma, adult-onset asthma, cough-variant asthma, occupational asthma, steroid-resistant asthma, seasonal asthma, seasonal allergic rhinitis, perennial allergic rhinitis, chronic obstructive pulmonary disease, including chronic bronchitis or emphysema, pulmonary hypertension, interstitial lung fibrosis and/or airway inflammation, cystic fibrosis, and hypoxia.

Cardiovascular Diseases

In one aspect, described herein is a method for treating or preventing a cardivascular disease in a mammal comprising administering a therapeutically effective amount of an autotaxin inhibitor described herein, or a pharmaceutically acceptable salt, solvate, or stereoisomer thereof, to the mammal. Cardiovascular disease refers to diseases affecting the heart or blood vessels or both. In particular, cardiovascular disease includes arrhythmia (atrial or ventricular or both); atherosclerosis and its sequelae; angina; cardiac rhythm disturbances; myocardial ischemia; myocardial infarction; cardiac or vascular aneurysm; vasculitis, stroke; peripheral obstructive arteriopathy of a limb, an organ, or a tissue; reperfusion injury following ischemia of the brain, heart, kidney or other organ or tissue; endotoxic, surgical, or traumatic shock; hypertension, valvular heart disease, heart failure, abnormal blood pressure, vasoconstriction (including that associated with migraines); vascular abnormality, inflammation, insufficiency limited to a single organ or tissue.

Combination Therapy

In certain instances, the compound described herein, or a pharmaceutically acceptable salt, solvate, tautomer, or stereoisomer thereof, is administered in combination with a second therapeutic agent.

In some embodiments, the benefit experienced by a patient is increased by administering one of the compounds described herein with a second therapeutic agent (which also includes a therapeutic regimen) that also has therapeutic benefit.

In one specific embodiment, a compound described herein, or a pharmaceutically acceptable salt, solvate, tautomer, or stereoisomer thereof, is co-administered with a second therapeutic agent, wherein the compound described herein, or a pharmaceutically acceptable salt, solvate, or stereoisomer thereof, and the second therapeutic agent modulate different aspects of the disease, disorder or condition being treated, thereby providing a greater overall benefit than administration of either therapeutic agent alone.

In any case, regardless of the disease, disorder or condition being treated, the overall benefit experienced by the patient is simply additive of the two therapeutic agents or the patient experiences a synergistic benefit.

In certain embodiments, different therapeutically-effective dosages of the compounds disclosed herein will be utilized in formulating a pharmaceutical composition and/or in treatment regimens when the compounds disclosed herein are administered in combination with a second therapeutic agent. Therapeutically-effective dosages of drugs and other agents for use in combination treatment regimens are optionally determined by means similar to those set forth hereinabove for the actives themselves. Furthermore, the methods of prevention/treatment described herein encompasses the use of metronomic dosing, i.e., providing more frequent, lower doses in order to minimize toxic side effects. In some embodiments, a combination treatment regimen encompasses treatment regimens in which administration of a compound described herein, or a pharmaceutically acceptable salt, solvate, tautomer, or stereoisomer thereof, is initiated prior to, during, or after treatment with a second agent described herein, and continues until any time during treatment with the second agent or after termination of treatment with the second agent. It also includes treatments in which a compound described herein, or a pharmaceutically acceptable salt, solvate, or stereoisomer thereof, and the second agent being used in combination are administered simultaneously or at different times and/or at decreasing or increasing intervals during the treatment period. Combination treatment further includes periodic treatments that start and stop at various times to assist with the clinical management of the patient.

It is understood that the dosage regimen to treat, prevent, or ameliorate the condition(s) for which relief is sought, is modified in accordance with a variety of factors (e.g. the disease, disorder or condition from which the subject suffers; the age, weight, sex, diet, and medical condition of the subject). Thus, in some instances, the dosage regimen actually employed varies and, in some embodiments, deviates from the dosage regimens set forth herein.

For combination therapies described herein, dosages of the co-administered compounds vary depending on the type of co-drug employed, on the specific drug employed, on the disease or condition being treated, and so forth. In additional embodiments, when co-administered with a second therapeutic agent, the compound provided herein is administered either simultaneously with the second therapeutic agent, or sequentially.

In combination therapies, the multiple therapeutic agents (one of which is one of the compounds described herein) are administered in any order or even simultaneously. If administration is simultaneous, the multiple therapeutic agents are, by way of example only, provided in a single, unified form, or in multiple forms (e.g., as a single pill or as two separate pills).

The compounds described herein, or a pharmaceutically acceptable salt, solvate, or stereoisomer thereof, as well as combination therapies, are administered before, during or after the occurrence of a disease or condition, and the timing of administering the composition containing a compound varies. Thus, in one embodiment, the compounds described herein are used as a prophylactic and are administered continuously to subjects with a propensity to develop conditions or diseases in order to prevent the occurrence of the disease or condition. In another embodiment, the compounds and compositions are administered to a subject during or as soon as possible after the onset of the symptoms. In specific embodiments, a compound described herein is administered as soon as is practicable after the onset of a disease or condition is detected or suspected, and for a length of time necessary for the treatment of the disease. In some embodiments, the length required for treatment varies, and the treatment length is adjusted to suit the specific needs of each subject. For example, in specific embodiments, a compound described herein or a formulation containing the compound is administered for at least 2 weeks, about 1 month to about 5 years.

In some embodiments, the compound of described herein, or a pharmaceutically acceptable salt, solvate, or stereoisomer thereof, is administered in combination with an adjuvant. In one embodiment, the therapeutic effectiveness of one of the compounds described herein is enhanced by administration of an adjuvant (i.e., by itself the adjuvant has minimal therapeutic benefit, but in combination with another therapeutic agent, the overall therapeutic benefit to the patient is enhanced).

EXAMPLES

Intermediate 1: 2-((5-bromo-2-ethylpyrazolo[1,5-a]pyridin-3-yl)(methypamino)-4-(4-fluorophenyl)thiazole-5-carbonitrile

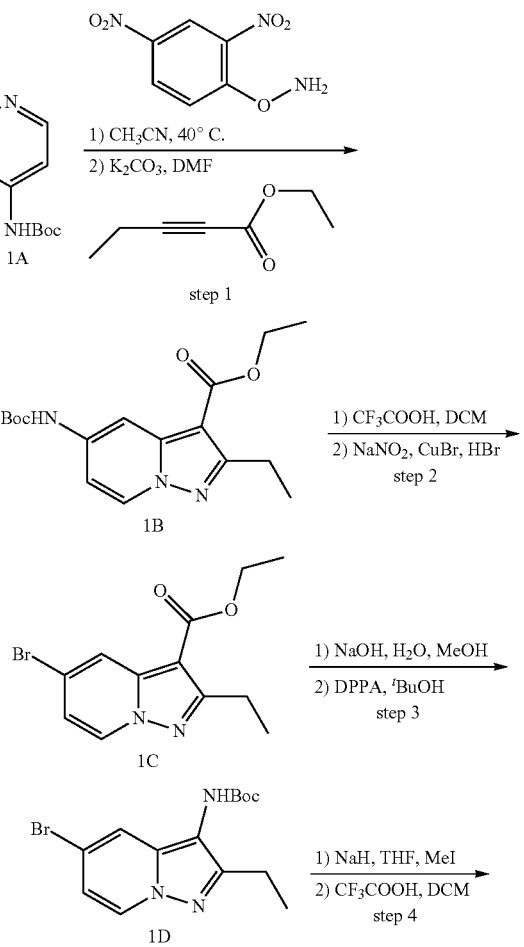

-continued

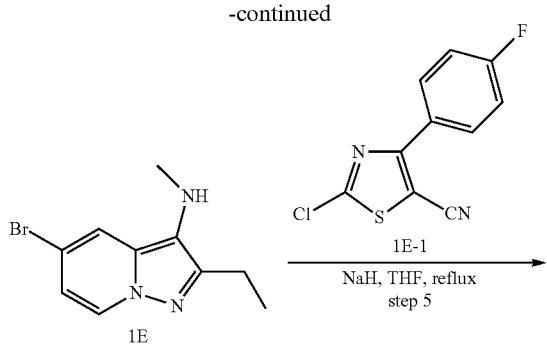

(19.9 g, 0.1 mol) dissolved in acetonitrile (250 mL). The resulting solution was heated at 40° C. for 18 h. The mixture solution was evaporated to dryness, redissolved in DMF (200 mL). Then ethyl ethyl 2-pentynoate (12.6 g, 0.1 mol) and $K_2CO_3$ (27.6 g, 0.2 mol) were added to the solution in room temperature. After 18 h, the solution mixture was diluted with EA (1000 mL), washed with water (2×500 mL) and brine (250 mL), dried with $Na_2SO_4$ and concentrated. The crude product was purified by flash chromatography to afford the title compound 1B (12.0 g, 36%) as a yellow solid. LC-MS (ESI): m/z=334.2 $[M+H]^+$.

Step 2: ethyl 5-bromo-2-ethylpyrazolo[1,5-a]pyridine-3-carboxylate (1C)

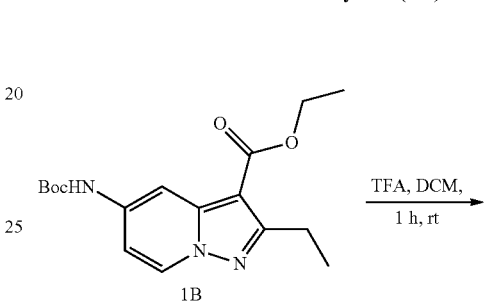

Step 1: ethyl 5-((tert-butoxycarbonyl)amino)-2-ethylnyrazolo[1,5-a]pyridine-3-carboxylate (1B)

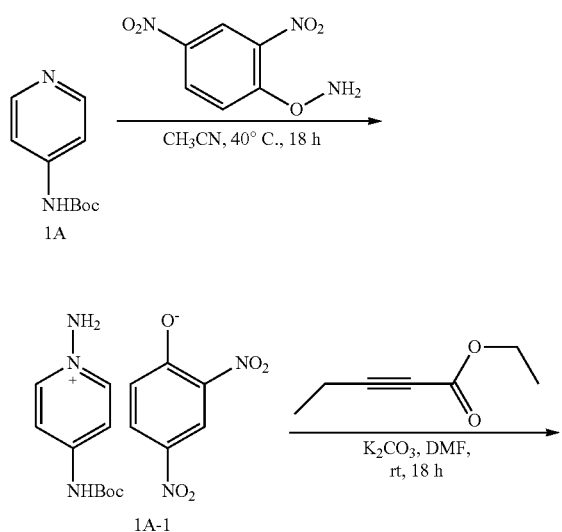

4-(Boc-amino)pyridine (19.4 g, 0.1 mol) was added to a stirred solution of O-(2,4-dinitrophenyl)hydroxylamine

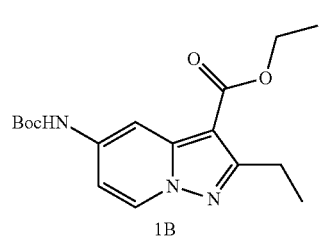

A solution of 1B (3.33 g, 10.0 mmol) and trifluoroacetic acid (10 ml) in DCM (100 mL) was stirred at room temperature for 1 h. The solvents were removed in vacuo to leave the the trifluoroacetate salt 1B-1 as a brown solid. A solution of $NaNO_2$ (1.0 g, 15.0 mmol) in water (15 mL) was added dropwise to a solution of the trifluoroacetate salt 1B-1 in concentrated HBr (10 mL) at 0° C. over 2 min. After 10 min, a solution of CuBr (2.8 g, 20.0 mmol) in concentrated HBr (10 mL) was added, then the reaction mixture heated to 50° C. for 15 min until gas evolution ceased. Then the reaction mixture was diluted with water (50 mL) and extracted twice with EA (2×200 mL). The combined extracts were dried ($Na_2SO_4$) and the solvent removed in vacuo. The residue was purified by flash column chromatography to yield 1C as a yellow solid (1.9 g, 64%). LC-MS (ESI): m/z=297.1 $[M+H]^+$.

Step 3: tert-butyl (5-bromo-2-ethylpyrazolo[1,5-a]pyridin-3-yl)carbamate (1D)

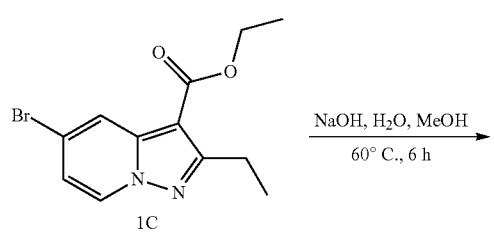

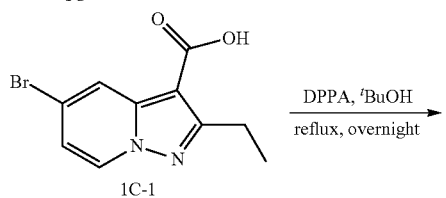

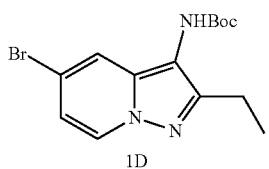

To a solution of 1C (1.9 g, 6.4 mmol) in tetrahydrofuran (10 mL) and methanol (10 mL) was added 8N aqueous sodium hydroxide solution (5 mL), and the mixture was stirred at 70° C. for 6 hr. The reaction solution was cooled to room temperature, tetrahydrofuran and methanol were evaporated under reduced pressure, Then the reaction mixture was acided to pH 4 with 3N Hydrochloric acid, and the mixture was diluted with water (30 mL). The resulting white precipitate was collected by filtration, washed with water (30 mL), and dried to give the 1C-1 (1.6 g, 94%) as a white solid. $^1$H-NMR (DMSO-d6, 400 MHz) δ 12.54 (br, 1H), 8.69-8.73 (m, 1H) 8.15-8.16 (m, 1H), 7.21-7.23 (m, 1H), 2.98-3.02 (m, 2H), 1.24-1.28 (m, 3H).

1C-1 (1.6 g, 6.0 mmol) and triethylamine (2.5 mL) were dissolved in tert-butanol (25 mL). Diphenyl phosphoryl azide (DPPA, 3.1 mL) was added via a syringe. The reaction mixture was stirred at ambient temperature for overnight followed by heat-up at reflux for 24 hours. The reaction mixture was concentrated and purified by flash column chromatography to yield 1D as a yellow solid (0.73 g, 36%). $^1$H NMR (400 MHz, CDCl3) δ 8.19 (d, 1H), 7.57 (s, 1H), 6.76 (d, 1H), 5.83 (s, 1H), 2.78 (q, 2H), 1.51 (s, 9H), 1.33 (t, 3H). LC-MS (ESI): m/z=342.0 [M+H]$^+$.

Step 4: 5-bromo-2-ethyl-N-methylpyrazolo[1,5-a]pyridin-3-amine (1E)

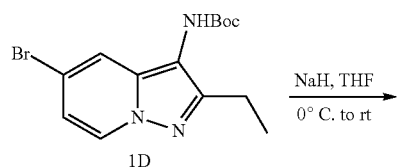

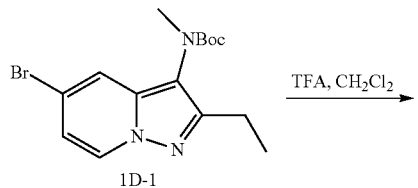

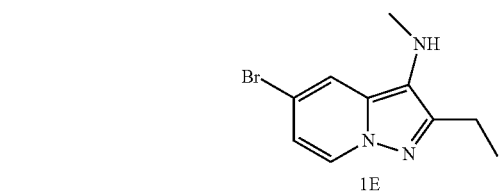

To a solution of 1D (0.73 g, 2.1 mmol) in THF (20 mL) were added NaH (0.1 g, 60%, 1.2 equiv, 2.5 mmol) at 0° C. After 20 min, MeI (0.36 g, 2.5 mmol) was added, then the reaction mixture was warmed to rt. After being stirred at room temperature for 1 h, the reaction mixture was poured into water and then the product was extracted with EA (2×100 mL), dried over Na$_2$SO$_4$, and concentrated in vacuo. The crude product (1D-1) was used for next step without further pufication.

A solution of 1D-1 and trifluoroacetic acid (3 mL) in DCM (10 mL) was stirred at room temperature for 1 h. Solvent was evaporated, and the crude product was partitioned between water and DCM. The aqueous layer was basified with NaHCO$_3$ and extracted with DCM. Combined organic layers were washed with brine, dried over sodium sulfate, filtered, and evaporated to give 1E (0.4 g, 76%) that was used in the next step without further purification.

Step 5: 5-bromo-2-ethyl-N-methylpyrazolo[1,5-a]pyridin-3-amine2-((5-bromo-2-ethylpyrazolo[1,5-a]pyridin-3-yl)(methyl)amino)-4-(4-fluorophenyl)thiazole-5-carbonitrile (Intermediate 1)

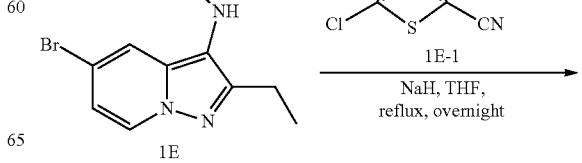

145
-continued

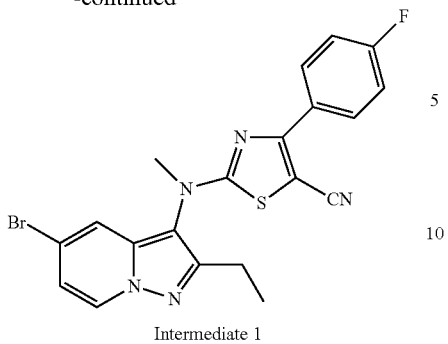

Intermediate 1

To a solution compound 1E (0.40 g, 1.6 mmol) in THF (10 mL) under argon was slowly added NaH (60% in oil suspension, 0.13 g, 3.2 mmol). The reaction mixture was heated at 70° C. for 30 min and then cooled to 40° C. before adding 2-chloro-4-(4-fluorophenyl)thiazole-5-carbonitrile (1E-1) (0.76 g, 3.2 mmol). The reaction mixture was stirred at 70° C. overnight. After cooling to room temperature, the mixture was slowly quenched by addition of water and then diluted with EtOAc. The organic layer was separated and the aqueous layer extracted with EtOAc. The combined organic layers were then washed with water and brine, dried over $Na_2SO_4$, filtered, and concentrated in vacuo. The residue was purified by flash chromatography to afford Intermediate 1 (0.20 g, 28%) as a yellow solid. $^1$H NMR (400 MHz, $CDCl_3$) δ 8.25 (d, 1H), 8.14-8.08 (m, 2H), 7.48 (d, 1H), 7.17-7.10 (m, 2H), 6.89 (d, 1H), 3.57 (s, 3H), 2.75 (m, 2H), 1.32 (t, 3H).

Intermediate 2: 5-bromo-2-ethyl-7-methyl-3-nitro-pyrazolo[1,5-a]pyridine

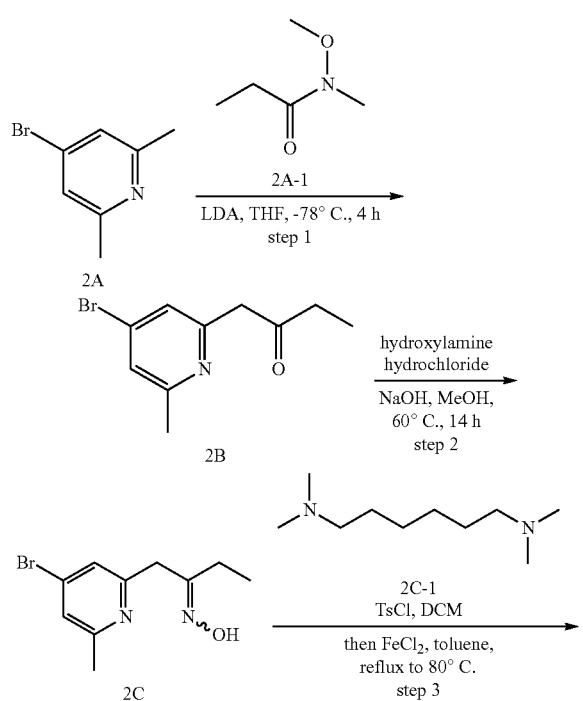

146
-continued

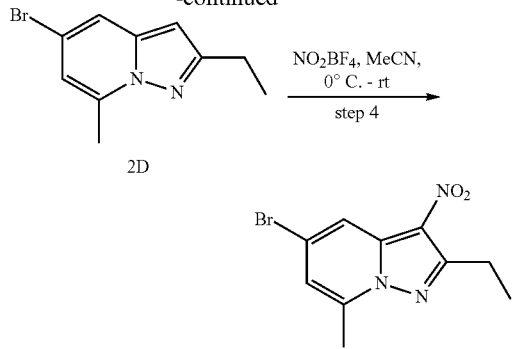

Intermediate 2

Step 1: 1-(4-bromo-6-methylpyridin-2-yl)butan-2-one (2B)

To a solution of 4-bromo-2,6-dimethylpyridine (2A) (25.5 g, 137.0 mmol) in anhydrous tetrahydrofuran (500 mL) was added lithium diisopropylamide (2M in tetrahydrofuran, 102.4 mL, 204.9 mmol) dropwise over 30 minutes via a dropping addition funnel at −78° C. under nitrogen. The mixture was stirred for 2 h at −78° C. and N-methoxy-N-methylpropionamide (2A-1) (8.0 g, 68.3 mmol, dissolved in 20 mL THF) was added dropwise over 15 minutes. Then the reaction mixture was stirred for 1 h at −78° C. and then quenched with addition of water. The mixture was warmed to rt, and then concentrated in vacuo. The residue was diluted with EtOAc and $H_2O$. The organic layer was separated and the aqueous layer extracted with EtOAc. The combined organic layers were then washed with water and brine, dried over $Na_2SO_4$, concentrated in vacuo. The residue was purified by flash chromatography to afford 2B (14 g, 85%). $^1$H NMR (400 MHz, $CDCl_3$) δ 7.26-7.23 (m, 1H), 7.23-7.19 (m, 1H), 3.84 (s, 2H), 2.56 (q, J=7.3 Hz, 2H), 2.50 (s, 3H), 1.06 (t, J=7.3 Hz, 3H). LC-MS (ESI): m/z=244.1 [M+H]$^+$.

Step 2: 1-(4-bromo-6-methylpyridin-2-yl)butan-2-one oxime (2C)

To a solution of 1-(4-bromo-6-methylpyridin-2-yl)butan-2-one (2B) (0.22 g, 0.91 mmol) in methanol (5 mL) was added hydroxylamine hydrochloride (0.32 g, 4.5 mmol) to give a thick slurry. The mixture was treated with sodium hydroxide (0.18 g, 4.5 mmol), heated at 60° C. for 6 hours, cooled and concentrated to a paste. The paste was treated with 100 mL of water and extracted with ethyl acetate. The organic layer was washed with brine, dried ($Na_2SO_4$), filtered and concentrated to give a white solid as title compound 2C (0.16 g, 70%). LC-MS (ESI): m/z=257.1 [M+H]$^+$.

Step 3: 5-bromo-2-ethyl-7-methylpyrazolo[1,5-a]pyridine (2D)

To a solution of 1-(4-bromo-6-methylpyridin-2-yl)butan-2-one oxime (0.5 g, 2 mmol) and $N^1,N^1,N^6,N^6$-tetramethylhexane-1,6-diamine (2C-1) (0.4 g, 2.4 mmol) in dichloromethane (20 mL) at 0° C. under nitrogen was treated dropwise with 4-methylbenzene-1-sulfonyl chloride (0.5 g, 2.3 mmol) over 10 minutes to give a solution that was stirred at ambient temperature for 90 minutes, concentrated in vacuo. The residue was dissolved in toluene (40 ml), refluxed for 2 h, then treated with ferrous chloride (0.025 g, 0.19 mmol), heated at 80° C. for 3 hours and cooled to give a dark colored slurry. The mixture was suspended in water (100 mL), stirred for 20 minutes, filtered, and the filtrate was extracted with ethyl acetate (100 mL). The organic layer was dried over Sodium sulfate, filtered, and concentrated in vacuo. The residue was purified by column chromatography on silica gel (n-hexane:ethyl acetate=3:2) to give the title compound 2D (0.3 g, 64%). $^1$H NMR (400 MHz, CDCl$_3$) δ 7.58-7.43 (m, 1H), 6.70-6.57 (m, 1H), 6.30 (s, 1H), 2.88 (q, J=7.6 Hz, 2H), 2.71 (s, 3H), 1.35 (t, J=7.6 Hz, 3H). LC-MS (ESI): m/z=241.1 [MAH]$^+$.

Step 4: 5-bromo-2-ethyl-7-methyl-3-nitropyrazolo [1,5-a]pyridine (Intermediate 2)

To a solution of 2D (1.0 g, 4.2 mmol) in acetonitrile (10 mL) was added nitronium tetrafluoroborate (0.67 g, 5.1 mmol) under cooling with ice water, and the reaction mixture was allowed to warm to rt and stirred for 1.5 h. The reaction mixture was then poured into crashed ice, and was extracted with ethyl acetate. The organic layer was dried over magnesium sulfate, filtered, and concentrated in vacuo. The residue was purified by column chromatography on silica gel (n-hexane:ethyl acetate=3:2) to give the title compound 6 (0.94 g, 79%). $^1$H NMR (400 MHz, CDCl$_3$) δ 8.37 (s, 1H), 7.22-7.14 (m, 1H), 3.79-3.48 (m, 2H), 1.63 (t, J=7.2 Hz, 3H).

Intermediate 3: 2-((5-bromo-2-ethyl-6-fluoropyrazolo[1,5-a]pyridin-3-yl)(methyl)amino)-4-(4-fluorophenyl)thiazole-5-carbonitrile

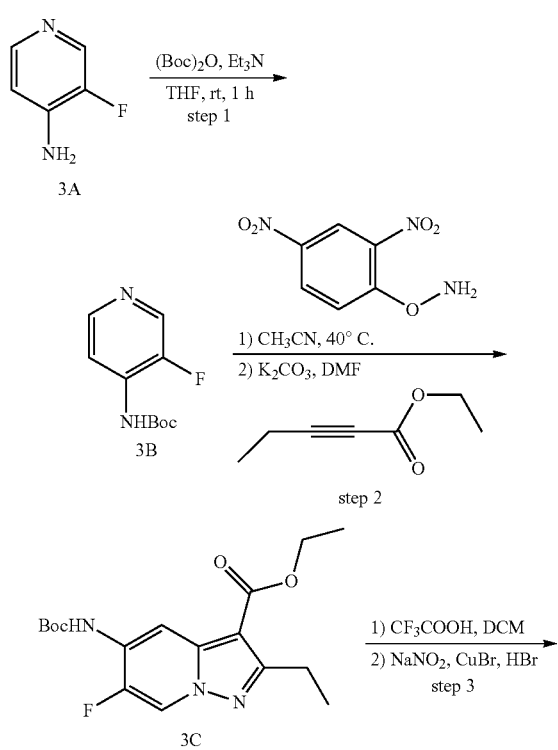

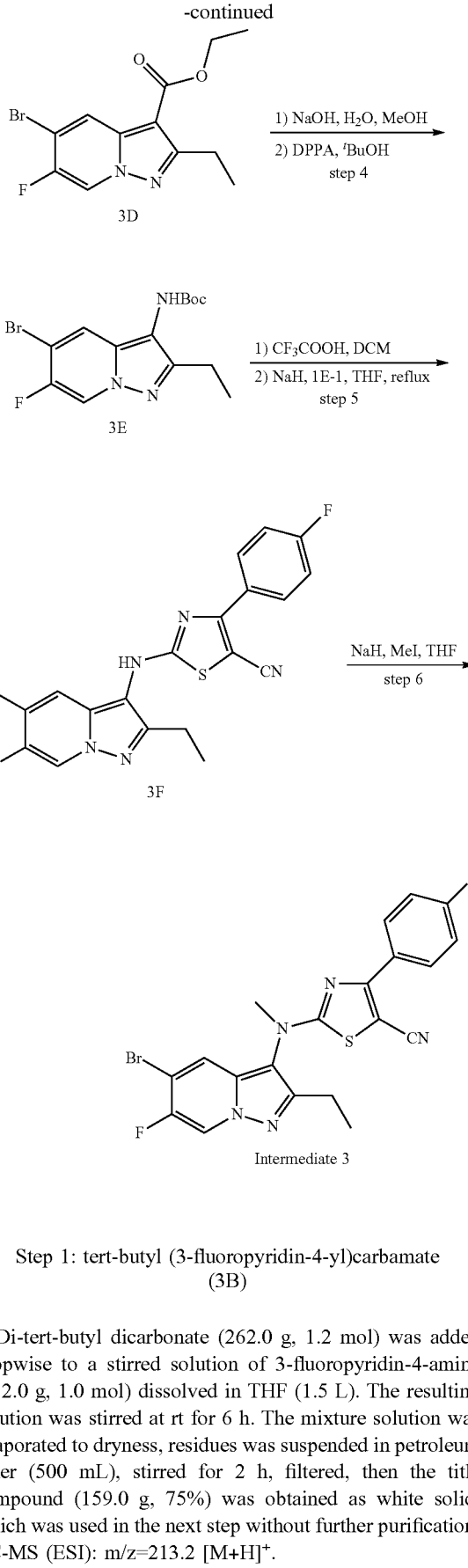

Step 1: tert-butyl (3-fluoropyridin-4-yl)carbamate (3B)

Di-tert-butyl dicarbonate (262.0 g, 1.2 mol) was added dropwise to a stirred solution of 3-fluoropyridin-4-amine (112.0 g, 1.0 mol) dissolved in THF (1.5 L). The resulting solution was stirred at rt for 6 h. The mixture solution was evaporated to dryness, residues was suspended in petroleum ether (500 mL), stirred for 2 h, filtered, then the title compound (159.0 g, 75%) was obtained as white solid, which was used in the next step without further purification. LC-MS (ESI): m/z=213.2 [M+H]$^+$.

Step 2: 5-((tert-butoxycarbonyl)amino)-2-ethyl-6-fluoropyrazolo[1,5-a]pyridine-3-carboxylate (3C)

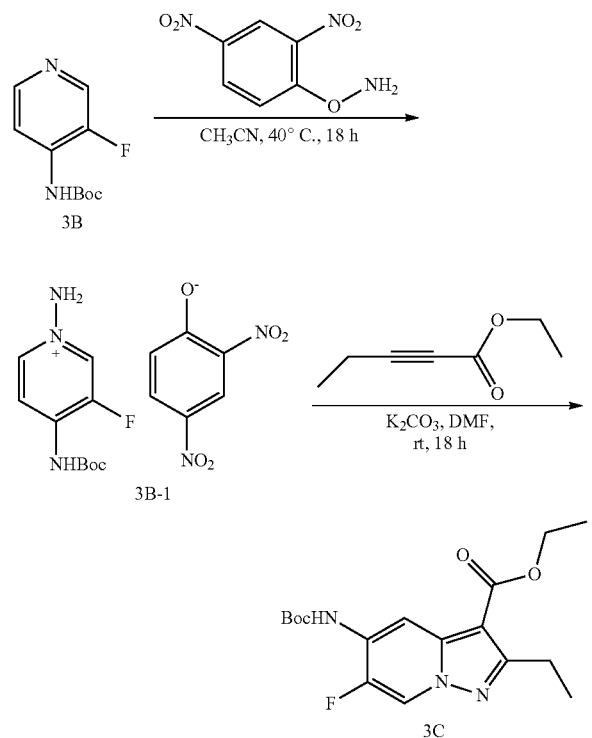

Tert-butyl (3-fluoropyridin-4-yl)carbamate (3B) (21.2 g, 0.1 mol) was added to a stirred solution of O-(2,4-dinitrophenyl)hydroxylamine (19.9 g, 0.1 mol) dissolved in acetonitrile (250 mL). The resulting solution was heated at 40° C. for 18 h. The mixture solution was evaporated to dryness, redissolved in DMF (200 mL). Then ethyl ethyl 2-pentynoate (12.6 g, 0.1 mol) and K₂CO₃ (27.6 g, 0.2 mol) were added to the solution in room temperature. After 18 h, the solution mixture was diluted with EA (1000 mL), washed with water (2×500 mL) and brine (250 mL), dried with Na₂SO₄ and concentrated. The crude product was purified by flash chromatography to afford the title compound (3.5 g, 10%) as a yellow solid. LC-MS (ESI): m/z=352.2 [M+H]⁺.

Step 3: ethyl 5-bromo-2-ethyl-6-fluoropvrazolo[1,5-a]pyridine-3-carboxylate (3D)

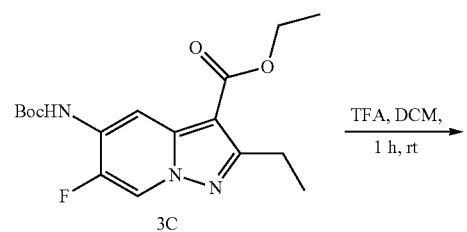

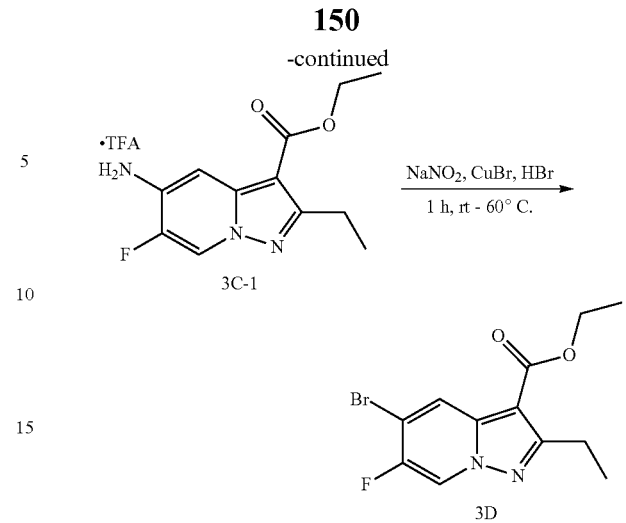

A solution of 3C (3.5 g, 10.0 mmol) and trifluoroacetic acid (10 mL) in DCM (100 mL) was stirred at room temperature for 1 h. The solvents were removed in vacuo to leave the the trifluoroacetate salt 3C-1 as a brown solid.

A solution of NaNO₂ (1.0 g, 15.0 mmol) in water (15 mL) was added dropwise to a solution of the trifluoroacetate salt 3C-1 in concentrated HBr (10 mL) at 0° C. over 2 min. After 10 min, a solution of CuBr (2.8 g, 20.0 mmol) in concentrated HBr (10 mL) was added, then the reaction mixture heated to 50° C. for 15 min until gas evolution ceased. Then the reaction mixture was diluted with water (50 mL) and extracted twice with EA (2×200 mL). The combined extracts were dried (Na₂SO₄) and the solvent removed in vacuo. The crude product was purified by flash chromatography to afford the title compound 3D as a yellow solid (1.3 g, 40%). LC-MS (ESI): m/z=315.1/317.1 [M+H]⁺.

Step 4: tert-butyl (5-bromo-2-ethyl-6-fluoropyrazolo[1,5-a]pyridin-3-yl)carbamate (3E)

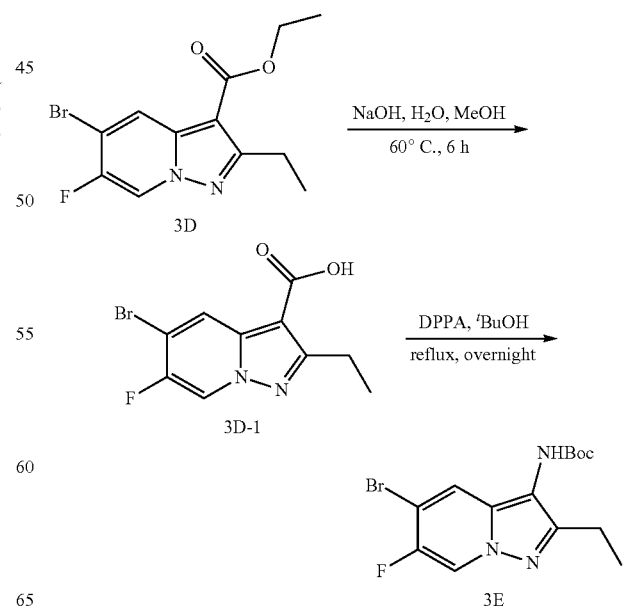

To a solution of 3D (1.3 g, 4.0 mmol) in THF (10 mL) and methanol (10 mL) was added 8N aqueous sodium hydroxide solution (3 mL), and the mixture was stirred at 70° C. for 6 hr. The reaction solution was cooled to room temperature, THF and MeOH were evaporated under reduced pressure, Then the reaction mixture was acided to pH 4 with 3N Hydrochloric acid, and the mixture was diluted with water (30 mL). The resulting white precipitate was collected by filtration, washed with water (30 mL), and dried to give the 3D-1 (1.0 g, 90%) as a white solid. LC-MS (ESI): m/z=287.0/289.0 [M+H]$^+$.

3D-1 (1.0 g, 3.6 mmol) and triethylamine (1.5 mL) were dissolved in tert-butanol (25 mL). Diphenyl phosphoryl azide (DPPA, 1.8 mL) was added via a syringe. The reaction mixture was stirred at ambient temperature for overnight followed by heat-up at reflux for 24 hours. The reaction mixture was concentrated and purified by flash column chromatography to yield 3E as a yellow solid (1.2 g, 90%). LM-MS: m/z=358.1/360.1[M+H]$^+$ Step 5: 5-bromo-2-ethyl-6-fluoro-N-methylpyrazolo[1,5-a]pyridin-3-amine (3F)

A solution of 3E (1.2 g, 3.4 mmol) and trifluoroacetic acid (3 mL) in DCM (10 mL) was stirred at room temperature for 1 h. Solvent was evaporated, and the crude product was partitioned between water and DCM. The aqueous layer was basified with NaHCO$_3$ and extracted with DCM. Combined organic layers were washed with brine, dried over sodium sulfate, filtered, and evaporated to give 3E-1 (0.78 g, 90%) that was used in the next step without further purification. To a solution of compound 3E-1 (0.78 g, 3.0 mmol) in DMF (10 mL) under argon was added 1E-1 (0.71 g, 3.0 mmol). The reaction mixture was heated at 120° C. for 1 h. After cooling to room temperature, the mixture was quenched with water and then diluted with EtOAc. The organic layer was separated and the aqueous layer extracted with EtOAc. The combined organic layers were then washed with water and brine, dried over Na$_2$SO$_4$, filtered, and evaporated to give 3F (0.75 g, 54%) that was used in the next step without further purification.

Step 6: 5-bromo-2-ethyl-N-methylpyrazolo[1,5-a]pyridin-3-amine2-((5-bromo-2-ethylpyrazolo[1,5-a]pyridin-3-yl)(methypamino)-4-(4-fluorophenyl)thiazole-5-carbonitrile (Intermediate 3)

To a solution of 3F (0.75 g, 1.6 mmol) in THF (20 mL) were added NaH (0.077 g, 60%, 1.2 equiv, 1.9 mmol) at 0° C. After 20 min, MeI (0.27 g, 1.9 mmol) was added, then the reaction mixture was warmed to rt. After being stirred at room temperature for 1 h, the reaction mixture was poured into water and then the product was extracted with EA (2×100 mL), dried over Na$_2$SO$_4$, and concentrated in vacuo. The residue was purified by flash chromatography to afford the title compound (0.68 g, 90%) as a yellow solid. $^1$H NMR (400 MHz, CDCl$_3$) δ 8.42 (d, J=3.5 Hz, 1H), 8.16-8.11 (m, 2H), 7.59 (d, J=6.5 Hz, 1H), 7.19-7.12 (m, 2H), 3.60 (s, 3H), 2.77 (q, J=7.6 Hz, 2H), 1.34 (t, J=7.6 Hz, 3H).

Intermediate 4: 2-((5-bromo-2-cyclopropyl-7-methylpyrazolo[1,5-a]pyridin-3-yl)(methyl)amino)-4-(4-fluorophenyl)thiazole-5-carbonitrile

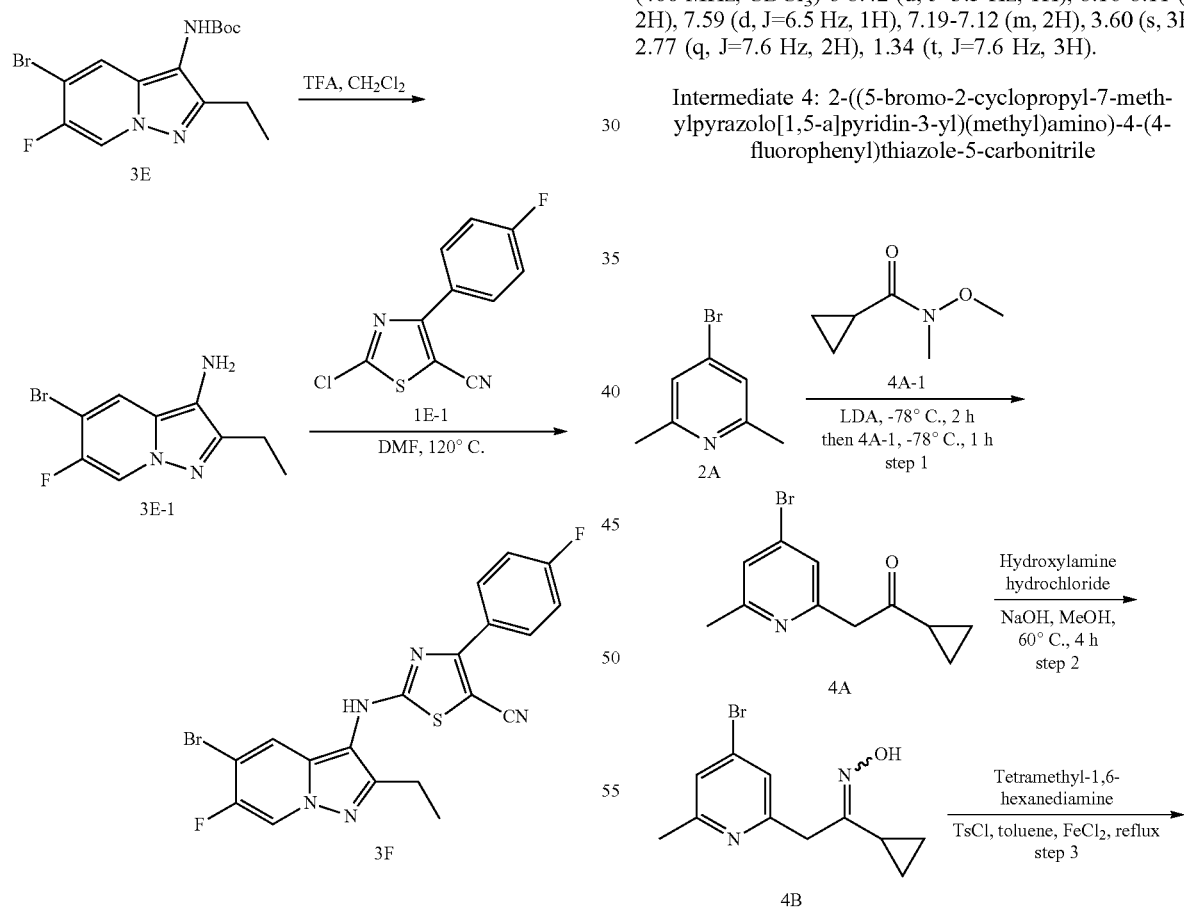

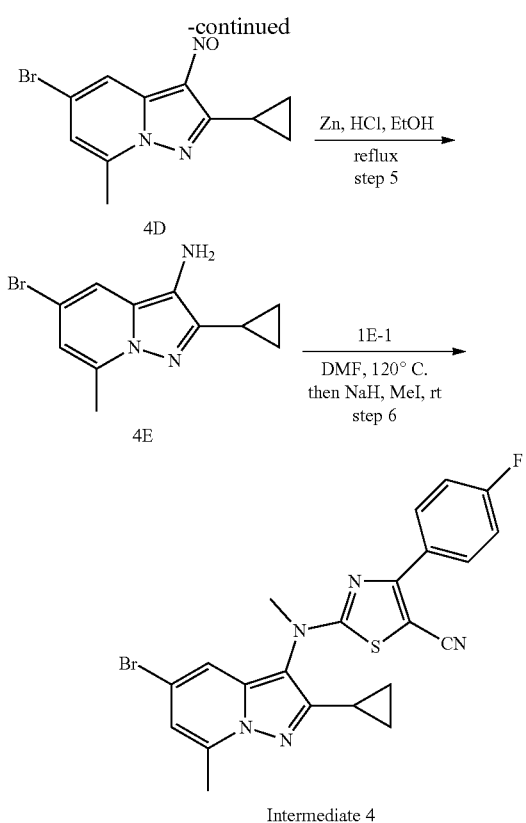

Intermediate 4

Step 1: 2-(4-bromo-6-methylpyridin-2-yl)-1-cyclopropylethan-1-one (4A)

To a solution of 4-bromo-2,6-dimethylpyridine (2A) (18.6 g, 0.1 mol) in THF (300 mL) was added LDA (2M in THF, 75 mL, 0.15 mol) dropwise over 30 minutes via a dropping addition funnel at −78° C. under nitrogen. The mixture was stirred for 2 h at −78° C. and N-methoxy-N-methylcyclopropanecarboxamide (4A-1) (12.9 g, 0.1 mol, dissolved in 100 mL THF) was added dropwise over 15 minutes. Then the reaction mixture was stirred for 1 h at −78° C. and then quenched with addition of water. The mixture was warmed to rt, and then concentrated in vacuo. The residue was diluted with EtOAc and H$_2$O. The organic layer was separated and the aqueous layer extracted with EtOAc. The combined organic layers were then washed with water and brine, dried over Na$_2$SO$_4$, concentrated in vacuo. The residue was purified by flash chromatography to afford the title compound 4A (22.9 g, 90%). LC-MS (ESI): m/z=256.1 [M+H]$^+$.

Step 2: 2-(4-bromo-6-methylpyridin-2-yl)-1-cyclopropylethan-1-one oxime (4B)

To a solution of 4A (12.7 g, 0.05 mol) in methanol (150 mL) was added hydroxylamine hydrochloride (17.4 g, 0.25 mmol), sodium hydroxide (10.0 g, 0.25 mmol), and the mixture was stirred at 60° C. for 4 hr. The cooled reaction mixture was diluted with H$_2$O, extracted with EtOAc. The organic layer was washed with brine, dried over Na$_2$SO$_4$, and concentrated under vacuum. The residue was purified by flash chromatography to afford the title compound 4B (12.1 g, 90%) as a white solid. LC-MS (ESI): m/z=271.1 [M+H]$^+$.

Step 3: 5-bromo-2-cyclopropyl-7-methylpyrazolo[1,5-a]pyridine (4C)

To a solution of 4B (8.1 g, 30.0 mmol) and N$^1$, N$^1$, N$^6$, N$^6$-tetramethylhexane-1,6-diamine (6.2 g, 36.0 mmol) in CH$_2$Cl$_2$ (100 mL) at 0° C. under nitrogen was added the solution of TsCl (6.8 g, 36.0 mmol) in CH$_2$Cl$_2$ (50 mL) over 10 minutes, the reaction mixture was stirred at ambient temperature for 1.5 h and then concentrated in vacuo. The residue was diluted with toluene (200 mL), after refluxed for 2 h, the reaction mixture was treated with FeCl$_2$ (0.38 g, 3.0 mmol), heated at 80° C. for 3 h. The cooled reaction mixture was quenched with water (200 mL), stirred for 30 min, filtered, and the filtrate was extracted with ethyl acetate. The organic layer was dried over Sodium sulfate, filtered, and concentrated in vacuo. The organic layer was washed with brine, dried over Na$_2$SO$_4$, and concentrated under vacuum. The residue was purified by flash chromatography to afford the title compound 4C (2.9 g, 38%). LC-MS (ESI): m/z=253.1 [M+H]$^+$.

Step 4: 5-bromo-2-cyclopropyl-7-methyl-3-nitrosopyrazolo[1,5-a]pyridine (4D)

To a solution of 4C (2.5 g, 10.0 mmol) in AcOH (8 mL) at 0° C. under nitrogen was added NaNO$_2$ (1.0 g, 15.0 mmol) in H$_2$O (5 mL) over 10 minutes, then the reaction mixture was stirred at 0° C. for 1.5 h. The cooled reaction mixture was quenched with water (50 mL), extracted with CH$_2$Cl$_2$. The organic layer was dried over Sodium sulfate, filtered, and concentrated in vacuo. The organic layer was washed with brine, dried over Na$_2$SO$_4$, and concentrated under vacuum. The residue solid (4D, 2.2 g, 80%) was used in the next step without further purification. LC-MS (ESI): m/z=282.0 [M+H]$^+$.

Step 5: 5-bromo-2-cyclopropyl-7-methyl-3-nitrosopyrazolo[1,5-a]pyridine (4E)

To a solution of 4D (1.4 g, 5.0 mmol) and Zn (0.65 g, 10.0 mmol) in EtOH (30 mL) was added concentrated HCl (3 mL) dropwise, the reaction mixture was stirred at reflux for 2 h. The cooled reaction mixture was diluted with water (100 mL), then basified with NaHCO$_3$ and extracted with EtOAc. Combined organic layers were washed with brine, dried over sodium sulfate, filtered, and concentrated under vacuum. The residue was purified by flash chromatography to afford the title compound 4E (1.1 g, 84%). LC-MS (ESI): m/z=268.1 [M+H]$^+$.

Step 6: 2-((5-bromo-2-cyclopropyl-7-methylpyrazolo[1,5-a]pyridin-3-yl)(methylamino)-4-(4-fluorophenyl)thiazole-5-carbonitrile (Intermediate 4)

A solution of 4E (1.3 g, 5.0 mmol) and 1E-1 (1.2 g, 5.0 mmol) in DMF (10 mL) was stirred 100° C. for 4 h. Then the reaction mixture was cooled to 0° C., NaH (60%, 0.3 g, 7.5 mmol) was added and stirred at 0° C. about 30 min, followed by the addition of MeI (1.4 g, 10 mmol) dropwise. This mixture was stirred at 0° C. for 30 min, then quenched with water, extracted with EtOAc. The organic layer was dried over Sodium sulfate, filtered, and concentrated in vacuo. The residue was purified by column chromatography to give the title compound Intermediate 4 (1.5 g, 62%). $^1$H NMR (400 MHz, CDCl$_3$) δ 8.16-8.12 (m, 2H), 7.37 (s, 1H), 7.18-7.14 (m, 2H), 6.77 (s, 1H), 3.64 (s, 3H), 2.69 (s, 3H), 1.92-1.88 (m, 1H), 1.14-1.02 (m, 4H).

Intermediate 5: 2-((5-bromo-2-ethyl-7-methylpyrazolo[1,5-a]pyridin-3-yl)(methyl)amino)-4-(4-fluorophenyl)thiazole-5-carbonitrile

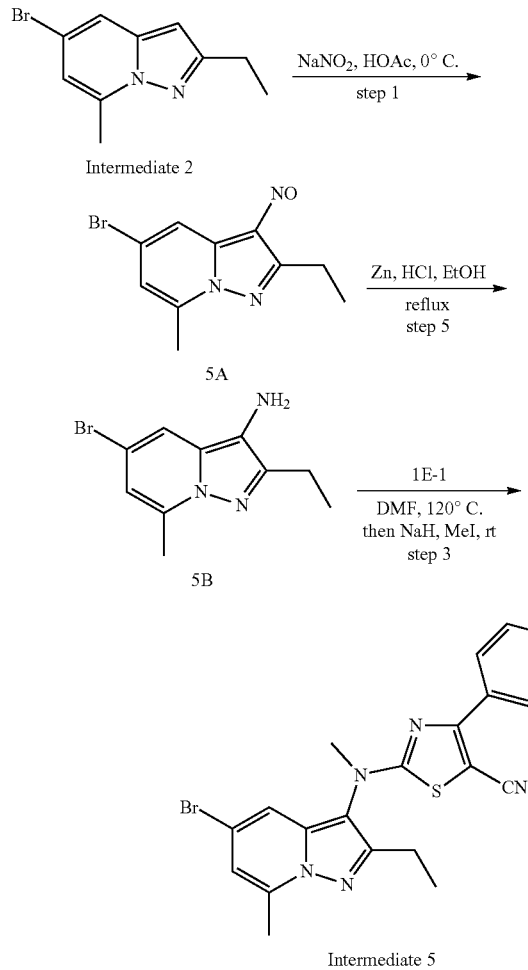

Step 1: 5-bromo-2-ethyl-7-methyl-3-nitrosopyrazolo[1,5-a]pyridine (5A)

Starting from Intermediate 2 and proceeding in analogy to preparation 4D afford the title 5A (80% yield). LC-MS (ESI): m/z=271.0 [M+H]$^+$.

Step 2: 5-bromo-2-ethyl-7-methylpyrazolo[1,5-a]pyridin-3-amine (5B)

Starting from 5A and proceeding in analogy to preparation 4E afford the title 5B (56% yield). $^1$H NMR (400 MHz, CDCl$_3$) δ 7.37 (s, 1H), 6.48 (s, 1H), 2.84-2.79 (m, 2H), 2.60 (s, 3H), 1.34-1.30 (m, 3H).

Step 3: 2-((5-bromo-2-ethyl-7-methylpyrazolo[1,5-a]pyridin-3-yl)(methyl)amino)-4-(4-fluorophenyl)thiazole-5-carbonitrile (Intermediate 5)

Starting from 5B and proceeding in analogy to preparation of Intermediate 4 afford the title Intermediate 5 (33% yield). $^1$H NMR (400 MHz, CDCl$_3$) δ 8.16-8.12 (m, 2H), 7.41 (s, 1H), 7.18-7.14 (m, 2H), 6.81 (s, 1H), 3.60 (s, 3H), 2.83-2.77 (m, 2H), 2.75 (s, 3H), 1.37-1.33 (m, 3H).

Intermediate 6: 2-((5-bromo-2-ethyl-6-methylpyrazolo[1,5-a]pyridin-3-yl)(methyl)amino)-4-(4-fluorophenyl)thiazole-5-carbonitrile

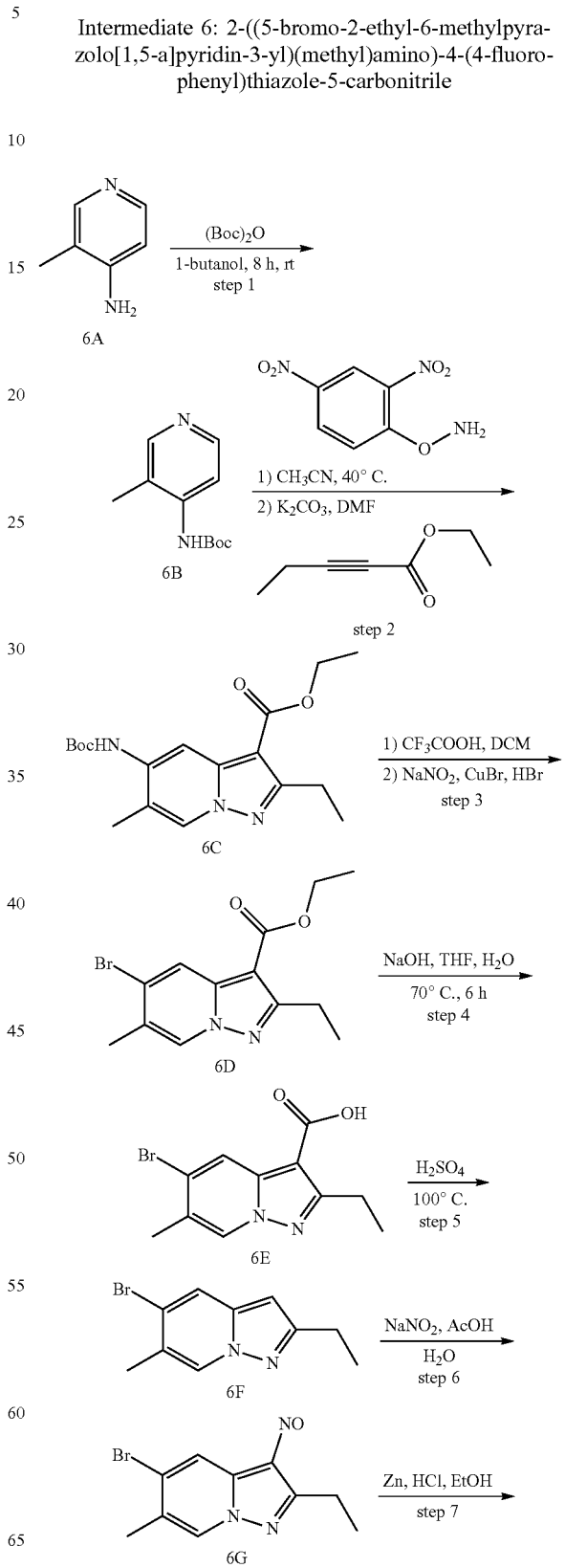

-continued

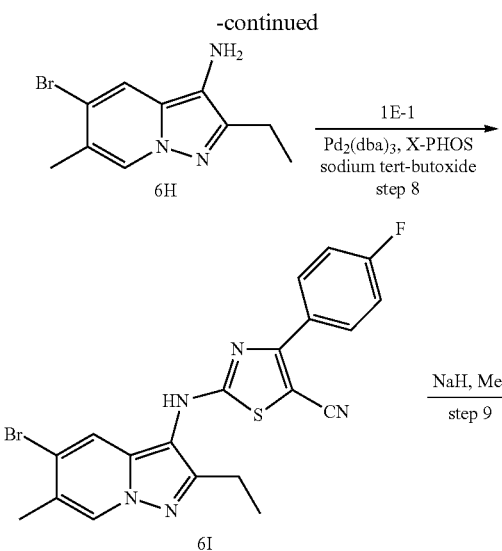

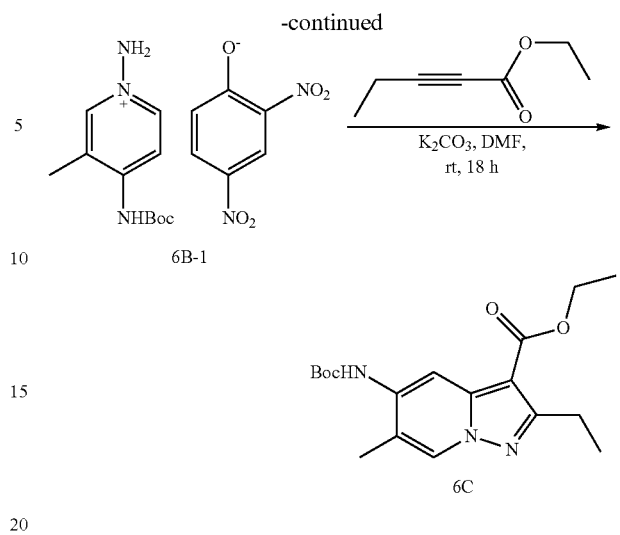

tert-butyl (3-methylpyridin-4-yl)carbamate (19.4 g, 0.09 mol) was added to a stirred solution of O-(2,4-dinitrophenyl)hydroxylamine (19.9 g, 0.1 mol) dissolved in acetonitrile (250 mL). The resulting solution was heated at 40° C. for 18 h. The mixture solution was evaporated to dryness, redissolved in DMF (200 mL). Then ethyl ethyl 2-pentynoate (12.6 g, 0.1 mol) and $K_2CO_3$ (27.6 g, 0.2 mol) were added to the solution in room temperature. After 18 h, the solution mixture was diluted with EA (1000 mL), washed with water (2×500 mL) and brine (1×250 mL), dried with $Na_2SO_4$ and concentrated. The crude product was purified by flash chromatography to afford the title compound 6C (12.0 g, 36%) as a yellow solid. LC-MS (ESI): m/z 348.2 [M+H]$^+$.

Step 3: ethyl 5-bromo-2-ethylpyrazolo[1,5-a]pyridine-3-carboxylate (6D)

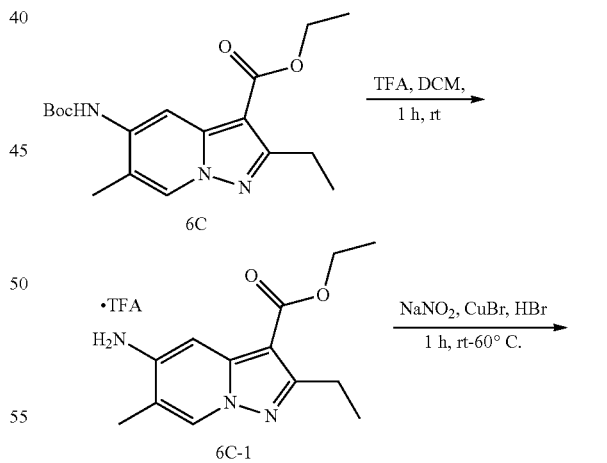

Step 1: tert-butyl (3-methylpyridin-4-yl)carbamate (6B)

To a solution of 3-methylpyridin-4-amine (6A) (38.0 g, 0.35 mol) in 1-butanol (300 mL) was added (Boc)$_2$O (84.3 g, 0.38 mol). The mixture solution was stirred at r.t. for 8 hours. Then the solution mixture was diluted with EA (1000 mL), washed with water (2×500 mL) and brine (1×250 mL), dried with Na$_2$SO$_4$ and concentrated. The crude product was purified by flash chromatography to afford the title compound 6B (73.0 g, 99%) as a white solid.

Step 2: ethyl-5-((tert-butoxycarbonyl)amino)-2-ethyl-6-methylpyrazolo[1,5-a]pyridine-3-carboxylate (6C)

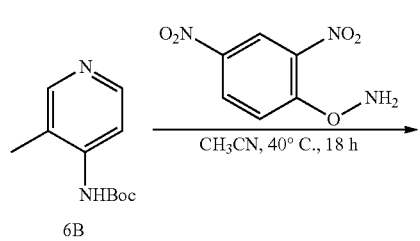

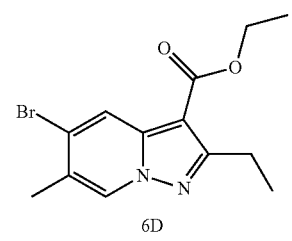

A solution of 6C (3.33 g, 9.6 mmol) and trifluoroacetic acid (10 mL) in DCM (100 mL) was stirred at room temperature for 1 h. The solvents were removed in vacuo to leave the the trifluoroacetate salt 6C-1 as a brown solid. A solution of NaNO$_2$ (1.0 g, 15.0 mmol) in water (15 mL) was added dropwise to a solution of the trifluoroacetate salt 6C-1 in concentrated HBr (10 mL) at 0° C. over 2 min. After 10 min, a solution of CuBr (2.8 g, 20.0 mmol) in concentrated HBr (10 mL) was added, then the reaction mixture heated to 50° C. for 15 min until gas evolution ceased. Then the reaction mixture was diluted with water (50 mL) and extracted twice with EA (2×200 mL). The combined extracts were dried (Na$_2$SO$_4$) and the solvent removed in vacuo. The crude product was purified by flash chromatography to afford the title compound 6D (1.9 g, 64%) as a yellow solid. LC-MS (ESI): m/z=311.0 [M+H]$^+$.

Step 4: 5-bromo-2-ethyl-6-methylpyrazolo[1,5-a]pyridine-3-carboxylic acid (6E)

To a solution of 6D (1.9 g, 6.1 mmol) in tetrahydrofuran (10 mL) and methanol (10 mL) was added 8N aqueous sodium hydroxide solution (5 mL), and the mixture was stirred at 70° C. for 6 hr. The reaction solution was cooled to room temperature, tetrahydrofuran and methanol were evaporated under reduced pressure, Then the reaction mixture was acided to pH 4 with 3N Hydrochloric acid, and the mixture was diluted with water (30 mL). The resulting white precipitate was collected by filtration, washed with water (30 mL), and dried to give the 6E (1.6 g, 91.0%) as a white solid. LC-MS (ESI): m/z=282.0 [M+H]$^+$.

Step 5: 5-bromo-2-ethyl-6-methylpyrazolo[1,5-a]pyridine (6F)

To a solution of 6E (1.6 g, 5.7 mmol) in 40% sulfuric acid (150 mL), and the mixture was stirred at 100° C. for 6 hr. The reaction solution was cooled to room temperature, the reaction solution was diluted with water (500 mL) and extracted twice with EA (2×500 mL). The combined extracts were dried (Na$_2$SO$_4$) and the solvent removed in vacuo to give the 6F (1.2 g, 88.90%) as a white solid. LC-MS (ESI): m/z=238.0 [M+H]$^+$.

Step 6: 5-bromo-2-ethyl-6-methyl-3-nitrosopyrazolo[1,5-a]pyridine (6G)

To a solution of 6F (1.2 g, 5.0 mmol) in acetic acid (25 mL) was added the solution of sodium nitrite (0.6 g, 8.7 mmol) dissolved in water (2 mL) at 0° C. Then the mixture was stirred at room temperature for 2 hr. The reaction solution was diluted with water (200 mL) and extracted twice with EA (2×200 mL). The combined extracts were dried (Na$_2$SO$_4$) and the solvent was removed in vacuo to give the 6G (1.0 g, 74.6%) as a brown solid. LC-MS (ESI): m/z=267.0 [M+H]$^+$.

Step 7: 5-bromo-2-ethyl-6-methylpyrazolo[1,5-a]pyridin-3-amine (6H)

To a solution of 6G (1.0 g, 3.7 mmol) in ethanol (25 mL) was added zinc powder (0.5 g, 7.7 mmol). Then hydrochloric acid (1 mL) was added at 0° C. and the mixture was stirred at 80° C. for 6 hr. The cooled reaction solution was filtered and the filtrate was diluted with aqueous sodium bicarbonate solution (200 mL) and extracted twice with EA (2×200 mL). The combined extracts were dried (Na$_2$SO$_4$) and the solvent was removed in vacuo to give the 6H (1.0 g, 94.8%) as a brown solid. LC-MS (ESI): m/z=253.0 [M+H]$^+$.

Step 8: 2-((5-bromo-2-ethyl-6-methylpyrazolo[1,5-a]pyridin-3-yl)amino)-4-(4-fluorophenyl)thiazole-5-carbonitrile (6I)

6H (180 mg, 0.39 mmol), Pd$_2$(dba)$_3$ (37 mg, 0.04 mmol), X-PHOS (38.4 mg, 0.08 mmol), and sodium tert-butoxide (96.9 mg, 1.01 mmol) were added to a screw capped test tube. The tube was evacuated and back filled with argon. 2-chloro-4-(4-fluorophenyl)thiazole-5-carbonitrile (1E-1) (96.3 mg, 0.40 mmol) and toluene (10 mL) were added successively by syringe at room temperature. The tube was sealed with a Teflon-lined cap, and the reaction mixture was heated at 95° C. for 2.5 h. After cooling to room temperature, the suspension was diluted with dichloromethane and filtered through celite. The solvent was removed with the aid of a rotary evaporator to give a brown residue which was purified by column chromatography on silica gel (n-hexane:ethyl acetate=3:1) to give the title compound 6I (104.2 mg, 32.0%). LC-MS (ESI): m/z=457.0 [M+H]$^+$.

Step 9: 2-((5-bromo-2-ethyl-6-methylpyrazolo[1,5-a]pyridin-3-yl)(methypamino)-4-(4-fluorophenyl)thiazole-5-carbonitrile (Intermediate 6)

To a solution of 6I (0.3 g, 0.66 mmol) and iodomethane (0.1 g, 0.8 mmol) in tetrahydrofuran (10 mL) was added sodium hydride (60%, 0.04 g, 1 mmol) under cooling with ice water, and the reaction mixture was stirred for 40 min at room temperature. The reaction mixture was then poured into crashed ice, and was extracted with ethyl acetate. The organic layer was dried over magnesium sulfate, filtered, and concentrated in vacuo. The residue was purified by column chromatography on silica gel (n-hexane:ethyl acetate=3:1) to give the title compound (Intermediate 6) (0.28 g, 90%). LC-MS (ESI): m/z=471.0 [M+H]$^+$.

Intermediate 7: 2-((5-bromo-2-cyclopropylpyrazolo[1,5-a]pyridin-3-yl)(methyl)amino)-4-(4-fluorophenyl)thiazole-5-carbonitrile

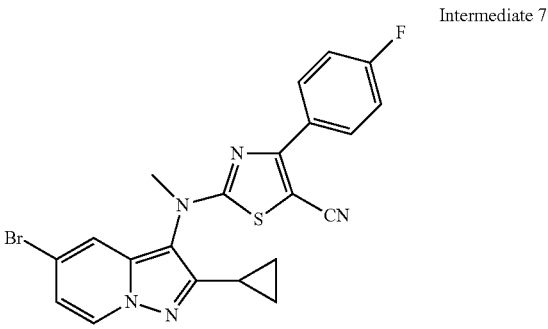 [SMILES: CN(c1nc(-c2ccc(F)cc2)c(C#N)s1)c1c(C2CC2)nn2ccc(Br)cc12]

Intermediate 7

Intermediate 7 was prepared from 1A and ethyl 3-cyclopropylpropiolate in a manner analogous to Intermediate 1 over 5 steps and was isolated as a yellow foam.

Intermediate 8: 2-((5-bromo-2-cyclopropyl-6-methylpyrazolo[1,5-a]pyridin-3-yl)(methyl)amino)-4-(4-fluorophenyl)thiazole-5-carbonitrile

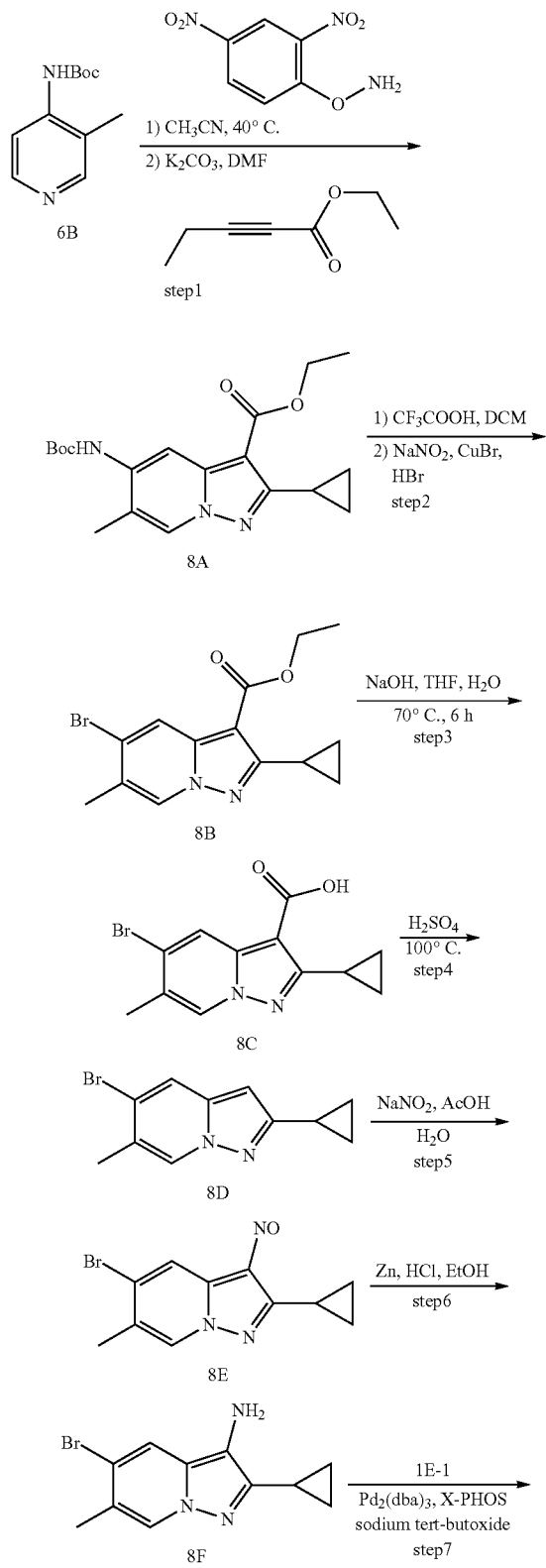

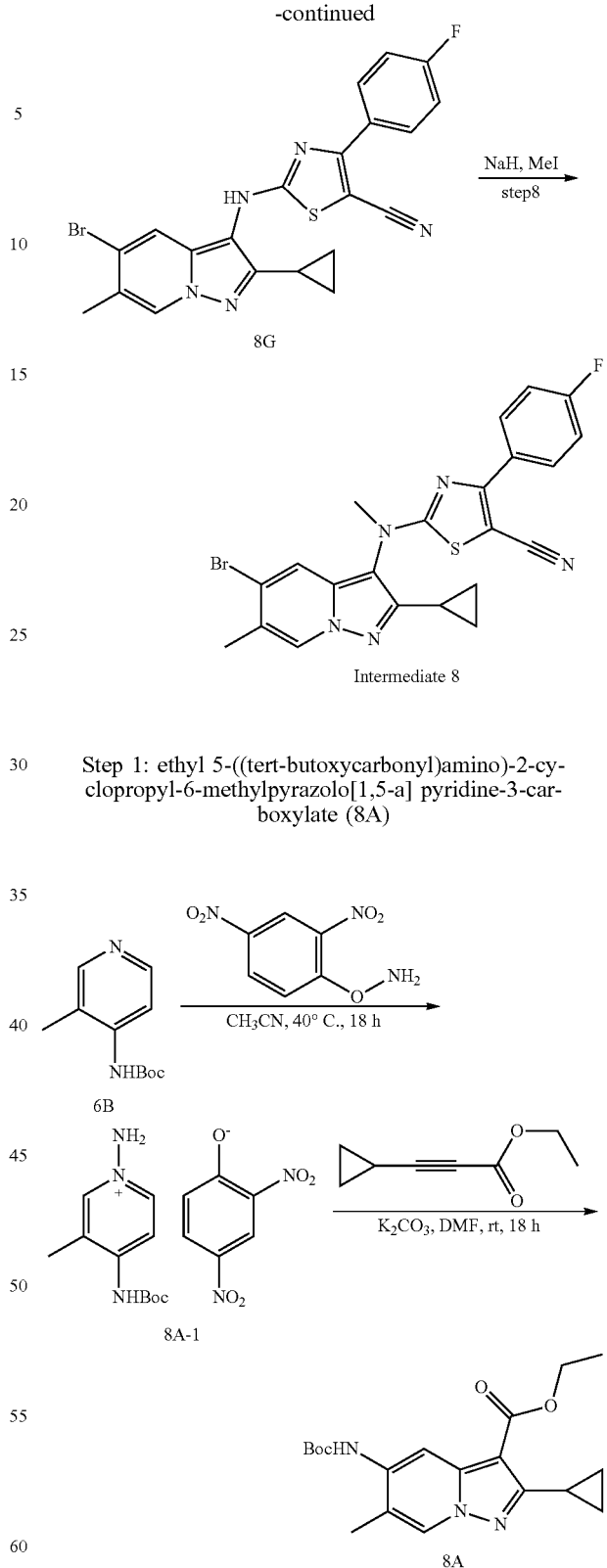

Step 1: ethyl 5-((tert-butoxycarbonyl)amino)-2-cyclopropyl-6-methylpyrazolo[1,5-a] pyridine-3-carboxylate (8A)

tert-butyl (3-methylpyridin-4-yl)carbamate (64.0 g, 0.3 mol) was added to a stirred solution of O-(2,4-dinitrophenyl) hydroxylamine (61.2 g, 0.3 mol) dissolved in acetonitrile (1000 mL). The resulting solution was heated at 40° C. for 18 h. The mixture solution was evaporated to dryness, redissolved in DMF (800 mL). Then ethyl 3-cyclopropyl-propiolate (42.5 g, 0.3 mol) and K$_2$CO$_3$ (85.0 g, 0.6 mol) were added to the solution at room temperature. After 18 h, the solution mixture was diluted with EA (1000 mL), washed with water (2×500 mL) and brine (1×250 mL), dried with Na$_2$SO$_4$ and concentrated. The crude product was purified by flash chromatography to afford 8A (7.4 g) as a yellow solid. LC-MS (ESI): m/z 360.2 [M+H]$^+$.

Step 2: ethyl 5-bromo-2-cyclopropyl-6-methylpyrazolo[1,5-a]pyridine-3-carboxylate (8B)

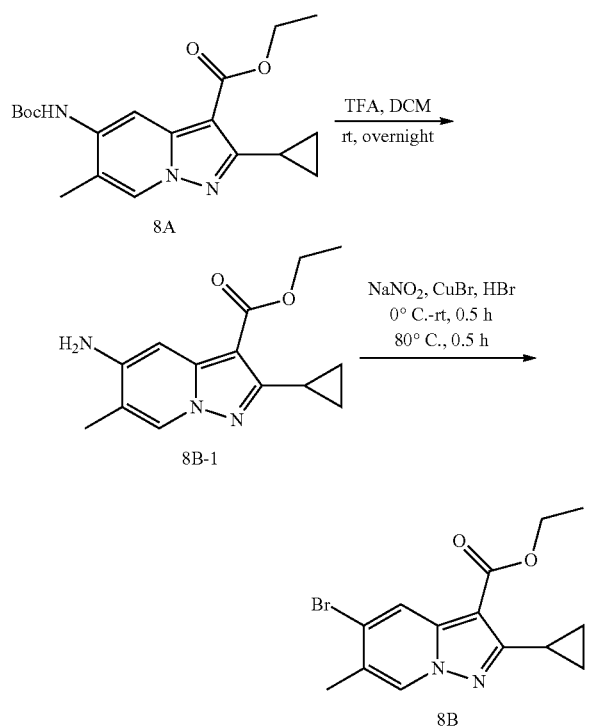

A solution of 8A (7.4 g, 20.6 mmol) and trifluoroacetic acid (20 mL) in DCM (60 mL) was stirred at room temperature for 1 h. The solvents were concentrated in vacuo to afford 8B-1 as a brown solid.

A solution of NaNO$_2$ (3.11 g, 45.7 mmol) in water (45 mL) was added dropwise to a solution of the trifluoroacetate salt 8B-1 in concentrated HBr (50 mL) at 0° C. over 2 min. After 10 min, a solution of CuBr (4.73 g, 33.0 mmol) in concentrated HBr (10 mL) was added, and then the reaction mixture heated to 80° C. for 15 min until gas evolution ceased. Then the reaction mixture was diluted with water (150 mL) and extracted twice with EA (2×200 mL). The combined extracts were dried by Na$_2$SO$_4$ and the solvent concentrated in vacuo, purified by column Chromatography to afford 8B (5.0 g, 45%) as a yellow solid. LC-MS (ESI): m/z=260.2 [M+H]$^+$.

Step 3: 5-bromo-2-cyclopropyl-6-methylpyrazolo[1,5-a]pyridine-3-carboxylic acid (8C)

To a solution of 8B (1.70 g, 5.3 mmol) in THF (10 mL) and methanol (10 mL) was added 8N aqueous sodium hydroxide solution (5 mL), The mixture was stirred at 70° C. for 6 hr, cooled to room temperature, concentrated under reduced pressure to remove MeOH and THF, acidfied to pH 4 with 3N Hydrochloric acid, diluted with water (30 mL). The resulting white precipitate was collected by filtration, washed with water (30 mL), and dried to give the 8C (1.5 g, 97.0%) as a white solid. LC-MS (ESI): m/z=295.0 [M+H]$^+$.

Step 4: 5-bromo-2-cyclopropyl-6-methylpyrazolo[1,5-a]pyridine (8D)

A solution of 8C (1.7 g, 5.8 mmol) in 40% sulfuric acid (20 mL) was stirred at 100° C. for 6 hr. The reaction solution was cooled to room temperature, diluted with water (100 mL) and extracted twice with EA (2×100 mL). The combined extracts were dried by Na$_2$SO$_4$, concentrated in vacuo to give 8D (1.4 g, 97%) as a white solid. LC-MS (ESI): m/z=252.0 [M+H]$^+$.

Step 5: 5-bromo-2-cyclopropyl-6-methyl-3-nitrosopyrazolo[1,5-a]pyridine (8E)

To a solution of 8D (0.65 g, 2.6 mmol) in acetic acid (25 mL) was added sodium nitrite (0.27 g, 3.9 mmol) in water (2 ml) at 0° C. The mixture was stirred at room temperature for 0.5 hr., diluted with water (50 mL) and extracted twice with EA (2×30 mL). The combined extracts were dried by Na$_2$SO$_4$, concentrated in vacuo to give 8E (0.70 g) as a brown solid.

Step 6: 5-bromo-2-cyclopropyl-6-methylpyrazolo[1,5-a]pyridin-3-amine (8F)

To a solution of 8E (0.7 g, 2.5 mmol) in ethanol (25 mL) was added zinc powder (0.33 g, 5.0 mmol), hydrochloric acid (1 ml) at 0° C. and the mixture was stirred at 80° C. for 6 hr. The reaction solution was filtered and the filtrate was diluted with sodium bicarbonate (20 mL) and extracted twice with EA (2×20 mL). The combined extracts were dried (Na$_2$SO$_4$), concentrated in vacuo to give 8F (0.62 g, 93%) as a brown solid. LC-MS (ESI): m/z=266.2 [M+H]$^+$.

Step 7: 2-((5-bromo-2-cyclopropyl-6-methylpyrazolo[1,5-a]pyridin-3-yl)amino)-4-(4-fluorophenyl)thiazole-5-carbonitrile (8G)

To a solution 8F (0.67 g, 2.5 mmol) in DMF (10 mL) under argon was added 1E-1 (0.60 g, 2.5 mmol). The reaction mixture was heated at 100° C. overnight. After cooling to room temperature, the mixture was diluted with water and EtOAc. The organic layer was separated and the aqueous layer extracted with EtOAc. The combined organic layers were then washed with water and brine, dried over Na$_2$SO$_4$, filtered, and concentrated in vacuo. The residue was purified by flash chromatography to afford 8G (0.56 g, 48%) as a yellow solid. LC-MS (ESI): m/z=468.0[M+H]$^+$.

Step 8: 2-((5-bromo-2-cyclopropyl-6-methylpyrazolo[1,5-a]pyridin-3-yl)(methyl)amino)-4-(4-fluorophenyl)thiazole-5-carbonitrile (Intermediate 8)

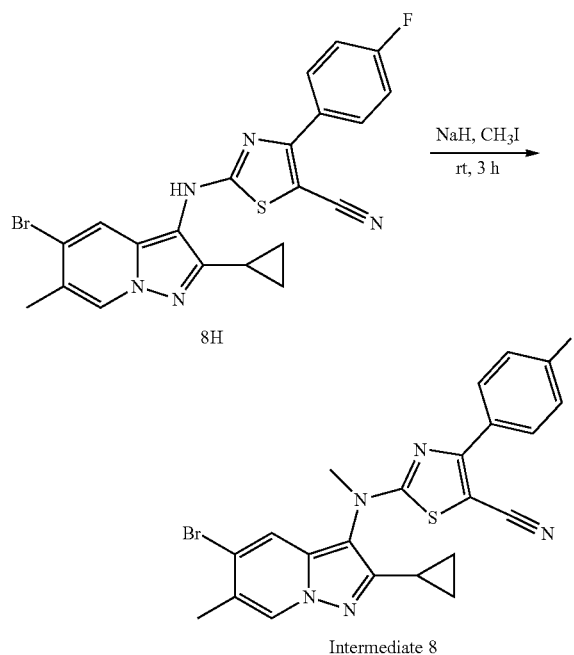

To a solution of 8G (0.56 g, 1.2 mmol) in THF (5 mL) were added NaH (72 mg, 60%, 1.5 equiv, 1.8 mmol) at 0° C. After 20 min, MeI (0.25 g, 1.8 mmol) was added, then the reaction mixture was warmed to rt. After being stirred at room temperature 3 h, the reaction mixture was poured into water and then the residue was extracted with EA (2×10 mL), dried over $Na_2SO_4$, and concentrated in vacuo to afford Intermediate 8 (0.57 g) as a yellow solid. LC-MS (ESI): m/z=482.1[M+Na]$^+$

Example 1: 2-((2-ethyl-5-(4-(2-(3-hydroxyazetidin-1-yl)-2-oxoethyl)piperazin-1-yl)pyrazolo[1,5-a]pyridin-3-yl)(methyl)amino)-4-(4-fluorophenyl)thiazole-5-carbonitrile (Compound 1)

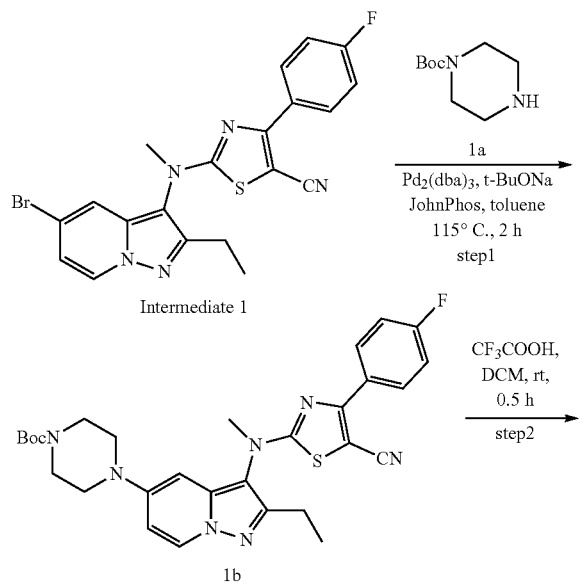

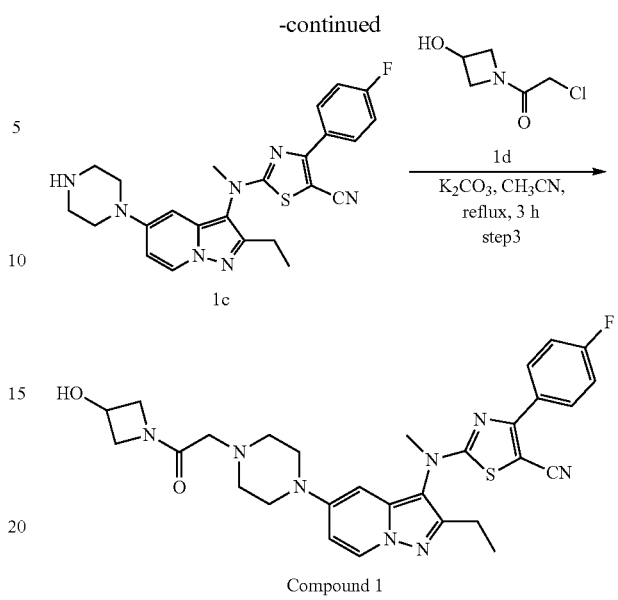

Step 1: tert-butyl 4-(3-((5-cyano-4-(4-fluorophenyl)thiazol-2-yl)(methyl)amino)-2-ethylpyrazolo[1,5-a]pyridin-5-yl)piperazine-1-carboxylate (1b)

To a solution Intermediate 1 (0.92 g, 2.0 mmol) in toluene (15 mL) under argon was successively added N-Boc piperazine (0.58 g, 3.0 mmol), sodium tert-butoxide (0.38 g, 4.0 mmol) and then JohnPhos (0.06 g, 0.2 mmol) and $Pd_2(dba)_3$ (0.09 g, 0.1 mmol). The reaction mixture was heated at 115° C. for 2 h. After cooling to room temperature, the mixture was diluted with water and EtOAc. The organic layer was separated and the aqueous layer extracted with EtOAc. The combined organic layers were then washed with water and brine, dried over $Na_2SO_4$, filtered, and concentrated in vacuo. The residue was purified by flash chromatography to afford 1b (0.70 g, 62%) as a yellow solid. $^1$H NMR (400 MHz, DMSO) δ 8.45 (d, 1H), 8.13-8.05 (m, 2H), 7.44-7.37 (m, 2H), 6.86-6.80 (m, 1H), 6.63 (d, 1H), 3.54 (s, 3H), 3.48-3.40 (m, 4H), 3.26 (d, 4H), 2.63 (q, 2H), 1.40 (s, 9H), 1.23 (t, 3H).

Step 2: 2-((2-ethyl-5-(piperazin-1-yl)pyrazolo[1,5-a]pyridin-3-yl)(methyl)amino)-4-(4-fluorophenyl)thiazole-5-carbonitrile (1c)

A solution of 1b (0.70 g, 1.2 mmol) and trifluoroacetic acid (3 mL) in DCM (10 mL) was stirred at room temperature for 0.5 h. Solvent was evaporated, and the crude product was partitioned between water and DCM. The aqueous layer was basified with $NaHCO_3$ and extracted with DCM. Combined organic layers were washed with brine, dried over sodium sulfate, filtered, and evaporated to give 1c (0.55 g, 100%) that was used in the next step without further purification.

Step 3: 2-((2-ethyl-5-(4-(2-(3-hydroxyazetidin-1-yl)-2-oxoethyl)piperazin-1-yl)pyrazolo[1,5-a]pyridin-3-yl)(methyl)amino)-4-(4-fluorophenyl)thiazole-5-carbonitrile (Compound 1)

To a solution of 1c (0.55 g, 1.2 mmol) in MeCN (15 mL) were added $K_2CO_3$ (0.33 g, 2.4 mmol) and 2-chloro-1-(3- hydroxyazetidin-1-yl)ethanone (1d) (0.22 g, 1.5 mmol). The reaction mixture was refluxed for 3 h. After cooling to room temperature, the mixture was diluted with water and EtOAc. The organic layer was separated and the aqueous layer extracted with EtOAc. The combined organic layers were then washed with water and brine, dried over Na$_2$SO$_4$, filtered, and concentrated in vacuo. The residue was was purified by flash chromatography to afford Compound 1 (0.32 g, 46%) as a yellow solid. $^1$H NMR (400 MHz, DMSO) δ 8.42 (d, 1H), 8.09 (d, 2H), 7.40 (t, 2H), 6.83 (d, 1H), 6.59 (d, 1H), 4.50-4.38 (m, 2H), 4.39-4.25 (m, 2H), 4.11-3.99 (m, 2H), 3.99-3.83 (m, 3H), 3.66-3.56 (m, 2H), 3.27 (s, 3H), 3.01 (d, 2H), 2.69-2.58 (m, 3H), 2.57-2.51 (m, 2H), 1.23 (m, 3H). LC-MS (ESI): m/z=288.2 [M/2+H]$^+$.

Example 2: (S)-2-((2-ethyl-5-(4-(2-(3-hydroxypyrrolidin-1-yl)-2-oxoethyl)piperazin-1-yl)pyrazolo[1,5-a]pyridin-3-yl)(methyl)amino)-4-(4-fluorophenyl)thiazole-5-carbonitrile (Compound 2)

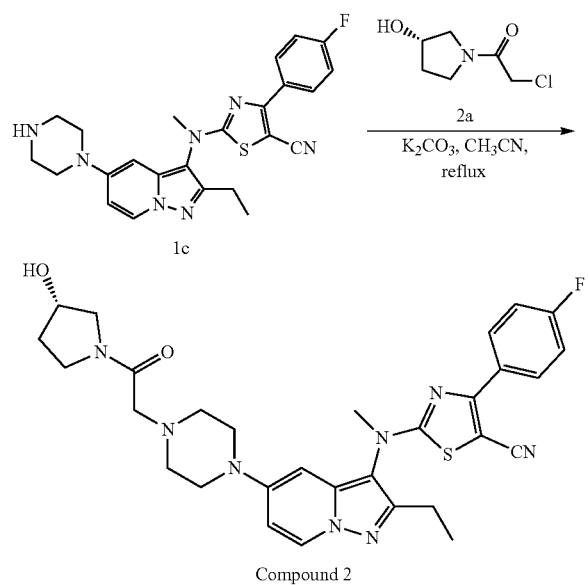

Compound 2

Compound 2 was prepared from 1c and (S)-2-chloro-1-(3-hydroxypyrrolidin-1-yl)ethan-1-one (2a) in a manner analogous to step 3 (Example 1) and was isolated as a yellow foam. $^1$H NMR (400 MHz, DMSO) δ 8.42 (d, 1H), 8.09 (m, 2H), 7.40 (m, 2H), 6.83 (m, 1H), 6.59 (d, 1H), 5.75 (s, 1H), 4.91 (m, 1H), 4.30-4.21 (m, 1H), 3.57-3.51 (m, 4H), 3.37-3.33 (m, 1H), 3.29-3.24 (m, 5H), 3.19-3.09 (m, 2H), 2.69-2.54 (m, 6H), 1.84-1.78 (m, 1H), 1.77-1.63 (m, 1H), 1.25-1.21 (m, 3H).

Example 3: (R)-2-((2-ethyl-5-(4-(2-(3-hydroxypyrrolidin-1-yl)-2-oxoethyl)piperazin-1-yl)pyrazolo[1,5-a]pyridin-3-yl)(methyl)amino)-4-(4-fluorophenyl)thiazole-5-carbonitrile (Compound 3)

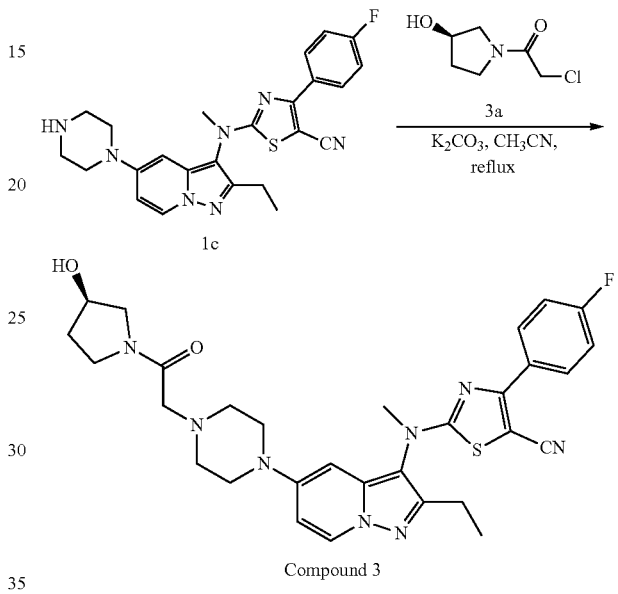

Compound 3

Compound 3 was prepared from 1c and (R)-2-chloro-1-(3-hydroxypyrrolidin-1-yl)ethan-1-one (3a) in a manner analogous to Step 3 (Example 1) and was isolated as a yellow foam. $^1$H NMR (400 MHz, CDCl$_3$) δ 8.23-8.11 (m, 3H), 7.15 (d, 2H), 6.59-6.52 (m, 1H), 6.30 (s, 1H), 4.61-4.45 (m, 1H), 3.74-3.48 (m, 6H), 3.44-3.23 (m, 5H), 2.94-2.81 (m, 3H), 2.71 (q, 2H), 2.18-1.89 (m, 5H), 1.40-1.19 (m, 3H). LC-MS (ESI): m/z=589.3 [M+H]$^+$ Example 4: 2-((2-ethyl-5-(4-(2-(3-(hydroxymethyl)azetidin-1-yl)-2-oxoethyl)piperazin-1-yl)pyrazolo[1,5-a]pyridin-3-yl)(methyl)amino)-4-(4-fluorophenyl)thiazole-5-carbonitrile (Compound 4)

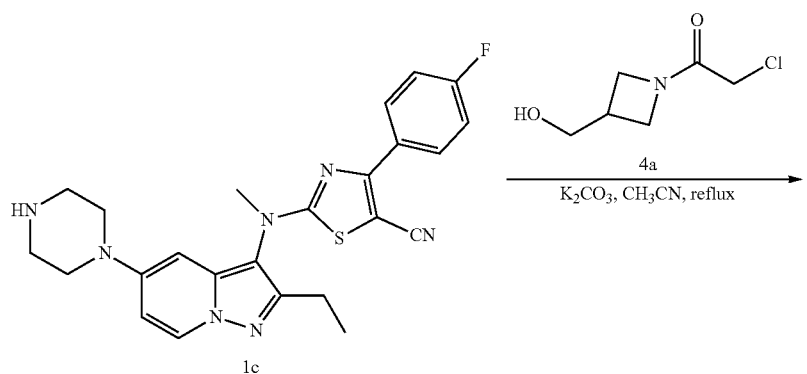

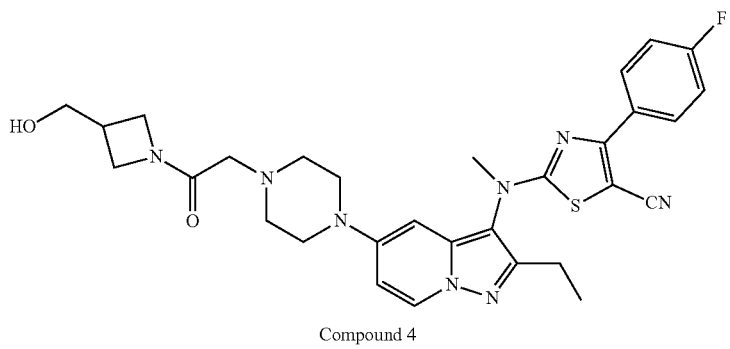

Compound 4

Compound 4 was prepared from 1c and 2-chloro-1-(3-(hydroxymethyl)azetidin-1-yl)ethan-1-one (4a) in a manner analogous to Step 3 (Example 1) and was isolated as a yellow foam. $^1$H NMR (400 MHz, DMSO) δ 8.42 (d, 1H), 8.09 (m, 2H), 7.46-7.36 (m, 2H), 6.83 (m, 1H), 6.59 (d, 1H), 4.76 (t, 1H), 4.18 (t, 1H), 3.90 (m, 1H), 3.83 (t, 1H), 3.60-3.47 (m, 6H), 3.30 (s, 5H), 3.28-3.25 (m, 3H), 3.00 (s, 2H), 2.67-2.58 (m, 3H), 1.26-1.20 (m, 3H).

Example 5: 2-(4-(3-((5-cyano-4-(4-fluorophenyl)thiazol-2-yl)(methyl)amino)-2-ethylpyrazolo[1,5-a]pyridin-5-yl)piperazin-1-yl)-N,N-dimethylacetamide (Compound 5)

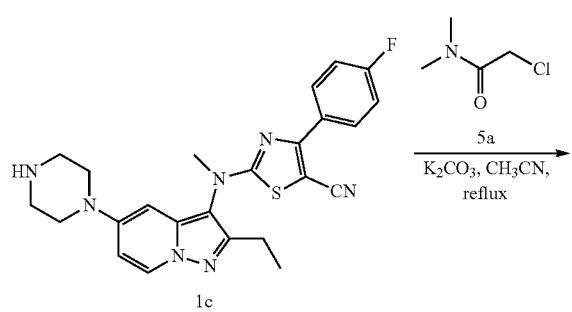

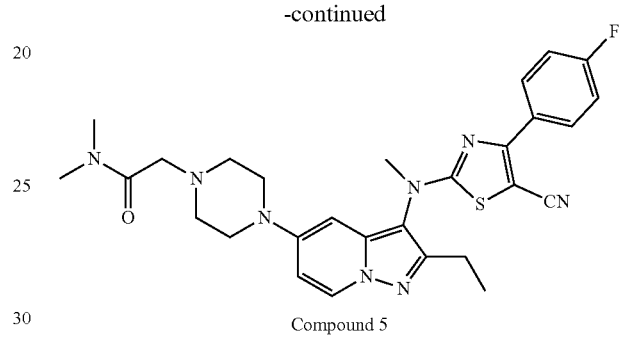

Compound 5

Compound 5 was prepared from 1c and 2-chloro-N,N-dimethylacetamide (5a) in a manner analogous to Step 3 (Example 1) and was isolated as a yellow foam. $^1$H NMR (400 MHz, CDCl$_3$) δ 8.22-8.11 (m, 3H), 7.20-7.12 (m, 2H), 6.56 (d, 1H), 6.29 (d, 1H), 3.58 (s, 3H), 3.36-3.25 (m, 6H), 3.07 (s, 3H), 2.97 (s, 3H), 2.84-2.67 (m, 6H), 1.33 (t, 3H). LC-MS (ESI): m/z=547.3 [M+H]$^+$ Example 6: 2-[[2-ethyl-5-[2-(3-hydroxyazetidine-1-carbonyl)-7-azaspiro[3.5]nonan-7-yl]pyrazolo[1,5-a]pyridin-3-yl]-methyl-amino]-4-(4-fluorophenyl)thiazole-5-carbonitrile (Compound 6)

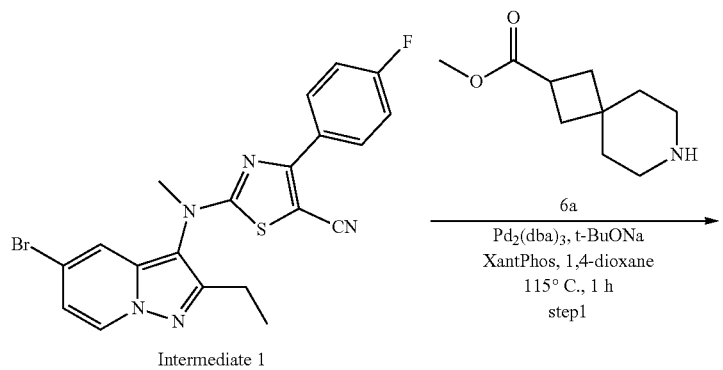

Intermediate 1

-continued

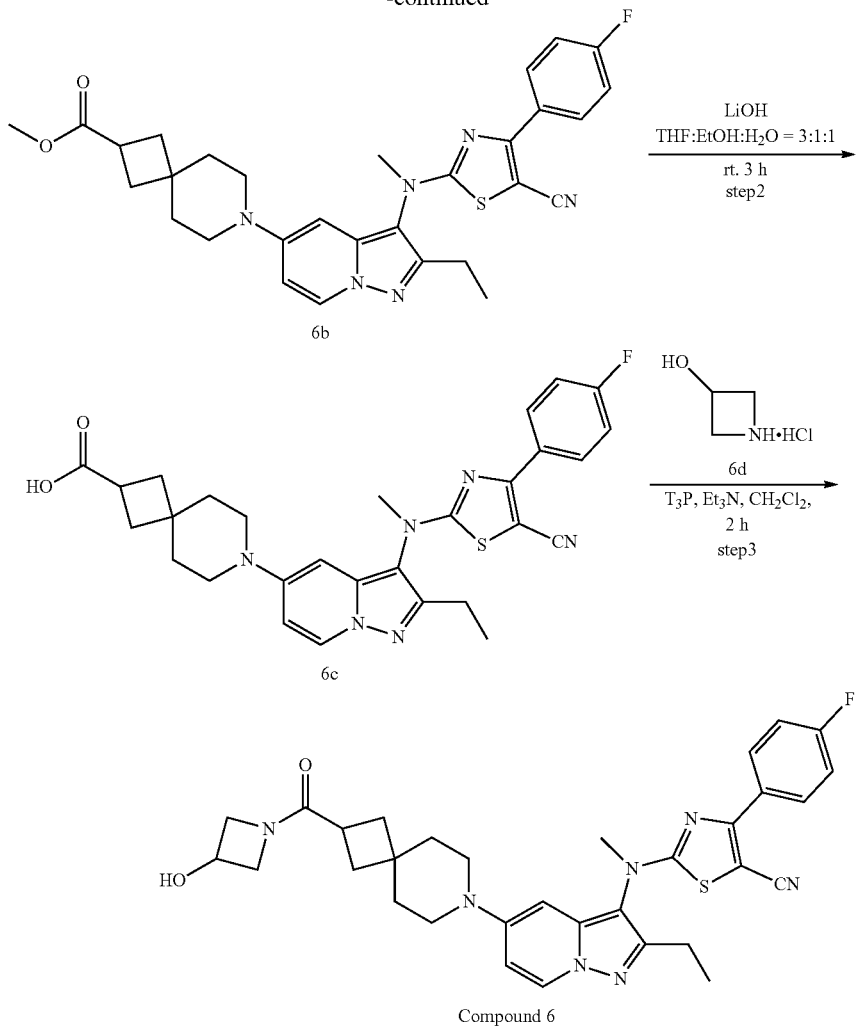

Compound 6

Step 1: methyl 7-(3-((5-cyano-4-(4-fluorophenyl)thiazol-2-yl)(methyl)amino)-2-ethylpyrazolo[1,5-a]pyridin-5-yl)-7-azaspiro[3.5]nonane-2-carboxylate (6b)

To a solution of Intermediate 1 (0.12 g, 0.27 mmol) in 1,4-dioxane (10 mL) under argon were successively added methyl 7-azaspiro[3.5]nonane-2-carboxylate (6a) (91 mg, 0.50 mmol), sodium tert-butoxide (52 mg, 0.54 mmol), XantPhos (23 mg, 0.04 mmol) and $Pd_2dba_3$ (18 mg, 0.02 mmol). The reaction mixture was heated at 115° C. for 1 h. After cooling to room temperature, the reaction was filtered on Clarcel, the cake was washed with DCM and the filtrate was then concentrated in vacuo. The crude product was purified by chromatography on silica gel (elution EA/PE: 1/3 to 1/1) to afford 6b (56 mg, 38%).

Step 2: 7-(3-((5-cyano-4-(4-fluorophenyl)thiazol-2-yl)(methyl)amino)-2-ethylpyrazolo[1,5-a]pyridin-5-yl)-7-azaspiro[3.5]nonane-2-carboxylic acid (6c)

6b (56 mg, 0.10 mmol) was dissolved in THF:EtOH:$H_2O$=3:1:1 (10 mL), then treated with LiOH.$H_2O$ (21 mg, 0.5 mmol) and stirred for 3 h at RT. After completion of the reaction, the resulting mixture was diluted with $H_2O$ and acidified to pH=3 with 2N HCl. The aqueous layer was extracted with EtOAc (30 mL) and this ethyl acetate layer was washed with brine, dried over anhydrous $Na_2SO_4$, filtered and concentrated in vacuo to give 6c (42 mg, 77%). LC-MS (ESI): m/z=545.3 [M+H]$^+$

Step 3: 2-[[2-ethyl-5-[2-(3-hydroxyazetidine-1-carbonyl)-7-azaspiro[3.5]nonan-7-yl]pyrazolo[1,5-a]pyridin-3-yl]-methyl-amino]-4-(4-fluorophenyl)thiazole-5-carbonitrile (Compound 6)

1-Propanephosphonic acid cyclic anhydride (1.57 M solution in THF, 0.1 mL) was added to a solution of 6c (42 mg, 0.077 mmol), 3-Hydroxyazetidine hydrochloride (11 mg, 0.1 mmol) and triethylamine (30 mg, 0.3 mmol in DCM (10 mL) and the resulting mixture stirred for 2 h. The reaction mixture was poured into water (20 mL) and extracted with dichloromethane (2×20 mL). The combined organic solutions were washed with brine (20 mL), dried over $Na_2SO_4$, filtered and evaporated in vacuo. Purification was by silica gel chromatography to give the subtitled compound as a pale yellow solid. $^1$H NMR (400 MHz, CDCl$_3$) δ 8.28 (d, 1H), 8.19-8.11 (m, 2H), 7.21-7.11 (m, 2H), 6.64 (d, 1H), 6.39 (s, 1H), 4.71-4.62 (m, 1H), 4.30-4.20 (m, 2H), 3.95-3.81 (m, 2H), 3.58 (s, 3H), 3.29-3.21 (m, 2H), 3.21-3.15 (m, 2H), 2.98 (d, 1H), 2.73 (q, 2H), 2.20-2.10 (m, 1H), 2.07-1.94 (m, 3H), 1.85-1.71 (m, 5H), 1.34 (t, 3H). LC-MS (ESI): m/z=600.3 [M+H]⁺

Example 7: 2-((2-ethyl-5-(1-(3-hydroxyazetidine-1-carbonyl)-5-azaspiro[2.3]hexan-5-yl)pyrazolo[1,5-a]pyridin-3-yl)(methyl)amino)-4-(4-fluorophenyl)thiazole-5-carbonitrile (Compound 7)

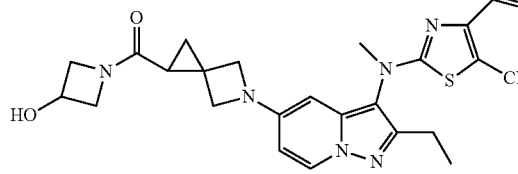

The title compound was prepared by the method substantially similar to that mentioned in Example 6, using methyl 5-azaspiro[2.3]hexane-2-carboxylate to afford Compound 7 as a pale yellow solid. ¹H NMR (400 MHz, CDCl₃) δ 8.24 (d, 1H), 8.19-8.10 (m, 2H), 7.16 (d, 2H), 6.14 (d, 1H), 5.87 (s, 1H), 4.78-4.66 (m, 1H), 4.47 (s, 1H), 4.33-4.19 (m, 1H), 4.17-3.97 (m, 5H), 3.87 (s, 1H), 2.72 (q, 2H), 1.71-1.64 (m, 1H), 1.46-1.37 (m, 2H), 1.36-1.28 (m, 3H), 1.28-1.24 (m, 3H). LC-MS (ESI): m/z=558.2 [M+H]⁺.

Example 8: 2-[[2-ethyl-5-[6-(3-hydroxyazetidine-1-carbonyl)-2-azaspiro[3.3]heptan-2-yl]pyrazolo[1,5-a]pyridin-3-yl]-methyl-amino]-4-(4-fluorophenyl)thiazole-5-carbonitrile (Compound 8)

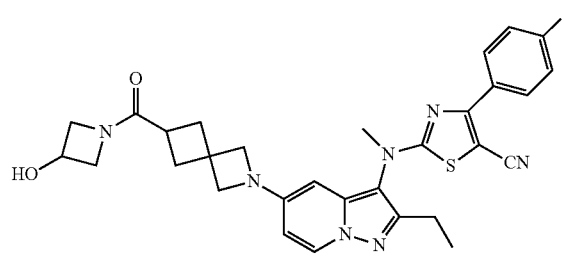

The title compound was prepared by the method substantially similar to that mentioned in Example 6, using methyl 2-azaspiro[3.3]hexane-6-carboxylate to afford Compound 8 as a pale yellow solid. ¹H NMR (400 MHz, CDCl₃) δ 8.22 (d, 1H), 8.20-8.12 (m, 2H), 7.21-7.13 (m, 2H), 6.11 (d, 1H), 5.83 (d, 1H), 4.74-4.63 (m, 1H), 4.34-4.20 (m, 2H), 4.03-3.90 (m, 5H), 3.90-3.81 (m, 1H), 3.57 (s, 3H), 2.99-2.88 (m, 1H), 2.72 (q, 2H), 2.60-2.48 (m, 2H), 2.47-2.33 (m, 2H), 1.34 (t, 3H). LC-MS (ESI): m/z=572.3 [M+H]⁺

Example 9: (R)-2-((2-ethyl-5-(6-(tetrahydrofuran-3-carbonyl)-2,6-diazaspiro[3.3]heptan-2-yl)pyrazolo[1,5-a]pyridin-3-yl)(methyl)amino)-4-(4-fluorophenyl)thiazole-5-carbonitrile (Compound 9)

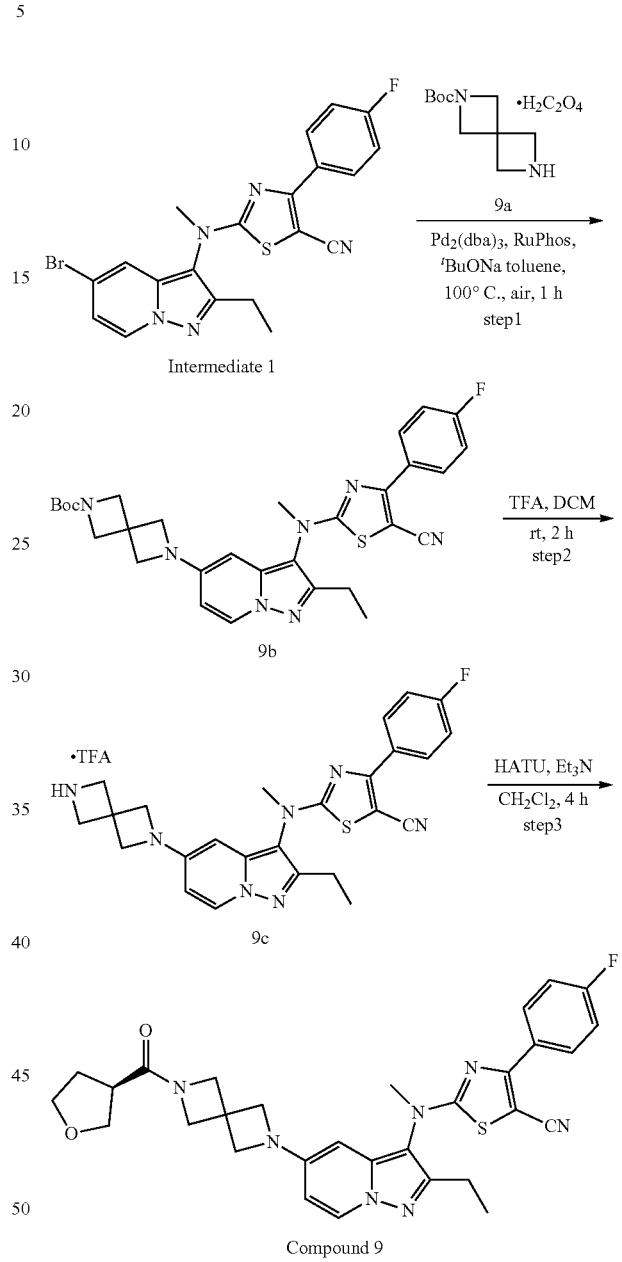

Step 1: tert-butyl 6-(3-((5-cyano-4-(4-fluorophenyl)thiazol-2-yl)(methyl)amino)-2-ethylpyrazolo[1,5-a]pyridin-5-yl)-2,6-diazaspiro[3.3]heptane-2-carboxylate (9b)

To a solution of intermediate 1 (0.40 g, 0.9 mmol) in toluene (10 mL) under air were successively added 9a (0.28 g, 1.4 mmol), sodium tert-butoxide (0.43 g, 4.5 mmol), RuPhos (90 mg, 0.2 mmol), and Pd₂(dba)₃ (91 mg, 0.1 mmol). The reaction mixture was heated at 100° C. for 1 h. After cooling to room temperature, the reaction was concentrated in vacuo. The residue was purified by chromatography on silica gel to afford 9b (0.40 g, 80%) as a brown solid. ¹H NMR (400 MHz, CDCl₃) δ 8.20-8.14 (m, 3H), 7.18-7.14-7.20 (m, 2H), 6.13-6.10 (m, 1H), 5.87 (d, J=2.4 Hz, 1H), 4.11 (s, 4H), 4.06 (s, 4H), 3.57 (s, 3H), 2.74-2.68 (m, 2H), 1.44 (s, 9H), 1.32 (t, J=7.6 Hz, 3H).

Step 2: 6-(3-((5-cyano-4-(4-fluorophenyl)thiazol-2-yl)(methyl)amino)-2-ethylpyrazolo[1,5-a]pyridin-5-yl)-2,6-diazaspiro[3.3]heptan-2-ium 2,2,2-trifluoroacetate (9c)

A solution of 9b (85 mg, 0.15 mmol) and trifluoroacetic acid (2 mL) in DCM (5 mL) was stirred at room temperature for 2 h. The reaction was concentrated in vacuo to afford the crude product (9c), and it was used for next step without further purification.

Step 3: (R)-2-((2-ethyl-5-(6-(tetrahydrofuran-3-carbonyl)-2,6-diazaspiro[3.3]heptan-2-yl)pyrazolo[1,5-a]pyridin-3-yl)(methyl)amino)-4-(4-fluorophenyl)thiazole-5-carbonitrile (Compound 9)

To a solution of 9c (58 mg, 0.1 mmol) in DCM (10 mL) were successively added (R)-tetrahydrofuran-3-carboxylic acid (20 mg, 0.16 mmol), HATU (60 mg, 0.16 mmol) and Et₃N (0.5 mL, 3.6 mmol). The reaction mixture was stirred at room temperature for 4 h, then the mixture was diluted with water (10 mL) and extracted with DCM (10 mL×3). The combined organic layers were then washed with water (10 mL×2) and brine (5 mL×1), dried over Na₂SO₄, filtered, and concentrated in vacuo. The residue was purified by flash chromatography to afford the title compound 9 (50 mg, 85%) as a light brown solid. ¹H NMR (400 MHz, CDCl₃) δ 8.22 (d, J=7.6 Hz, 1H), 8.17-8.13 (m, 2H), 7.18-7.13 (m, 2H), 6.18-6.16 (m, 1H), 5.90 (d, J=2.4 Hz, 1H), 4.41-4.35 (m, 2H), 4.20 (s, 2H), 4.12 (s, 4H), 4.00-3.93 (m, 1H), 3.91-3.89 (m 1H), 3.83-3.78 (m, 2H), 3.57 (s, 3H), 3.26-3.20 (m, 2H), 2.96-2.92 (m, 1H), 2.75-2.69 (m, 2H), 1.38 (t, J=7.2 Hz, 3H). LC-MS: m/z=572.3 [M+H]⁺

Example 10: (S)-2-((2-ethyl-5-(6-(tetrahydrofuran-3-carbonyl)-2,6-diazaspiro[3.3]heptan-2-yl)pyrazolo[1,5-a]pyridin-3-yl)(methyl)amino)-4-(4-fluorophenyl)thiazole-5-carbonitrile (Compound 10)

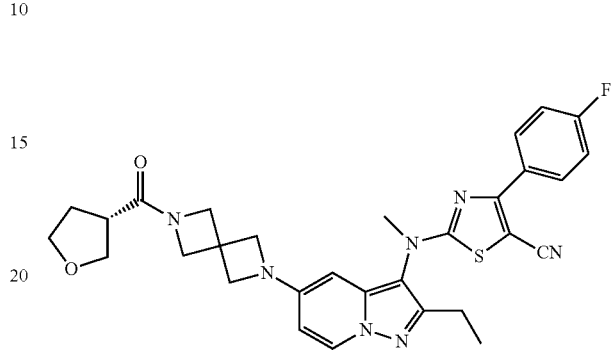

The title compound was prepared was prepared from 9c (58 mg, 0.1 mmol) and (S)-tetrahydrofuran-3-carboxylic acid in a manner analogous to Example 9. The Compound 10 was isolated as a light brown solid (50 mg, 85%) and the spectra were the same as Compound 9.

Example 11: 2-((2-ethyl-5-(6-(3-hydroxyazetidine-1-carbonyl)-2,6-diazaspiro[3.3]heptan-2-yl)pyrazolo[1,5-a]pyridin-3-yl)(methyl)amino)-4-(4-fluorophenyl)thiazole-5-carbonitrile (Compound 11)

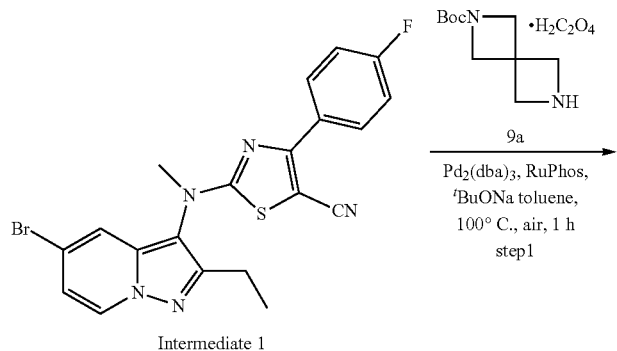

Intermediate 1

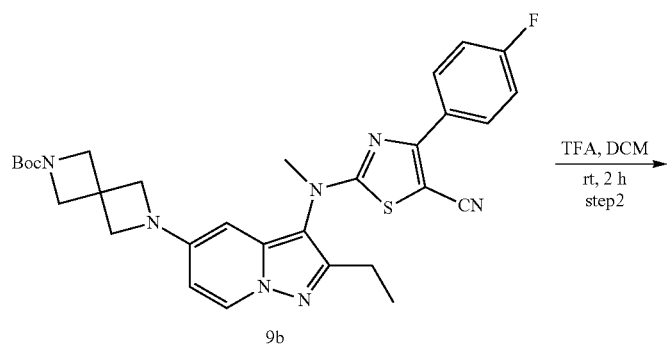

9b

-continued

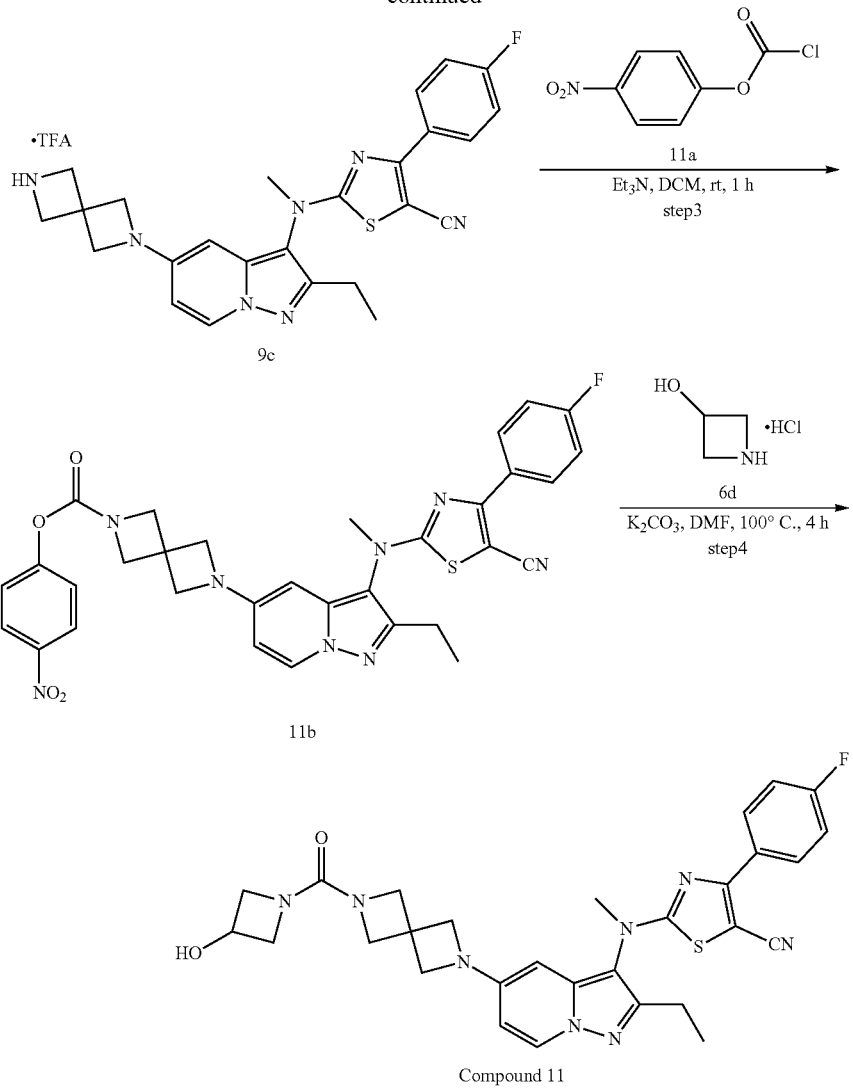

Step 1: tert-butyl 6-(3-((5-cyano-4-(4-fluorophenyl)thiazol-2-yl)(methyl)amino)-2-ethylpyrazolo[1,5-a]pyridin-5-yl)-2,6-diazaspiro[3.3]heptane-2-carboxylate (9b)

See Example 9, step 1.

Step 2: 6-(3-((5-cyano-4-(4-fluorophenyl)thiazol-2-yl)(methyl)amino)-2-ethylpyrazolo[1,5-a]pyridin-5-yl)-2,6-diazaspiro[3.3]heptan-2-ium 2,2,2-trifluoroacetate (9c)

See Example 9, step 2.

Step 3: 4-nitrophenyl 6-(3-((5-cyano-4-(4-fluorophenyl)thiazol-2-yl)(methyl)amino)-2-ethylpyrazolo[1,5-a]pyridin-5-yl)-2,6-diazaspiro[3.3]heptane-2-carboxylate (11b)

To a solution of 9c in DCM (10 mL) were successively added Et$_3$N (0.5 mL, 6.8 mmol) and 4-Nitrophenyl chloroformate (40 mg, 0.2 mmol). The reaction mixture was stirred at room temperature for 1 h. The reaction mixture was washed with water (5 mL×3) and brine (5 mL×1), dried over Na$_2$SO$_4$, filtered, and concentrated in vacuo to afford the crude product (11b) and it was used for next step without further purification.

Step 4: 2-((2-ethyl-5-(6-(3-hydroxyazetidine-1-carbonyl)-2,6-diazaspiro[3.3]heptan-2-yl)pyrazolo[1,5-a]pyridin-3-yl)(methyl)amino)-4-(4-fluorophenyl)thiazole-5-carbonitrile (Compound 11)

To a solution of 11b in DMF (10 mL) were successively added 3-Hydroxyazetidine hydrochloride (6d) (22 mg, 0.2 mmol) and K$_2$CO$_3$ (97 mg, 0.7 mmol). The reaction mixture was stirred at 100° C. for 4 h. After cooling to room temperature, the mixture was diluted with water (10 mL) and extracted with EtOAc (10 mL×3). The combined organic layers were then washed with water (10 mL×2) and brine (5 mL×1), dried over Na$_2$SO$_4$, filtered, and concentrated in vacuo. The residue was purified by flash chromatography to afford the title Compound 11 (35 mg, 41% over 4 steps) as a yellow solid. $^1$H NMR (400 MHz, CDCl$_3$) δ 8.23 (d, J=7.6 Hz, 1H), 8.17-8.13 (m, 2H), 7.19-7.13 (m, 2H), 6.13-6.10 (m, 1H), 5.87 (d, J=2.0 Hz, 1H), 4.64-4.59 (m, 1H), 4.18-

4.14 (m, 2H), 4.12 (s, 4H), 4.06 (s, 4H), 3.84-3.80 (m, 2H), 3.57 (s, 3H), 2.71 (q, J=7.6 Hz, 2H), 1.33 (t, J=7.6, 3H). LC-MS: m/z=573.3 [M+H]$^+$.

Example 12: 2-((2-ethyl-5-(2-(3-hydroxyazetidine-1-carbonyl)-2,7-diazaspiro[3.5]nonan-7-yl)pyrazolo[1,5-a]pyridin-3-yl)(methyl)amino)-4-(4-fluorophenyl)thiazole-5-carbonitrile (Compound 12)

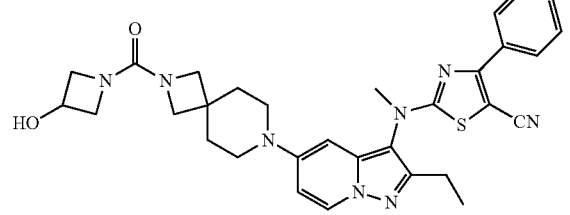

The title compound was prepared by the method substantially similar to that mentioned in Example 11, using methyl tert-butyl 2,7-diazaspiro[3.5]nonane-2-carboxylate to afford Compound 12 as a pale yellow solid. $^1$H NMR (400 MHz, CDCl$_3$) δ 8.24 (d, 1H), 8.20-8.08 (m, 2H), 7.22-7.09 (m, 2H), 6.58 (d, 1H), 6.32 (d, 1H), 4.66-4.54 (m, 1H), 4.20-4.10 (m, 2H), 3.85-3.80 (m, 2H), 3.71 (s, 4H), 3.58 (s, 3H), 3.26-3.17 (m, 4H), 2.72 (q, 2H), 1.93-1.85 (m, 4H), 1.33 (t, 3H). LC-MS (ESI): m/z=301.2 [M/2+H]$^+$ Example 13: 2-[[2-ethyl-5-[7-(3-hydroxyazetidine-1-carbonyl)-2,7-diazaspiro[3.5]nonan-2-yl]pyrazolo[1,5-a]pyridin-3-yl[-methyl-amino]-4-(4-fluorophenyl)thiazole-5-carbonitrile (Compound 13)

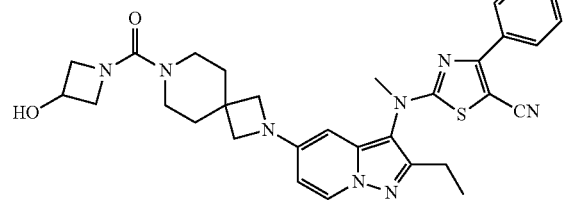

The title compound was prepared by the method substantially similar to that mentioned in Example 11, using tert-butyl 2,7-diazaspiro[3.5] nonane-7-carboxylate to afford Compound 13 as a pale yellow solid. $^1$H NMR (400 MHz, CDCl$_3$) δ 8.21 (d, 1H), 8.18-8.11 (m, 2H), 7.22-7.10 (m, 2H), 6.12 (d, 1H), 5.84 (d, 1H), 4.64-4.55 (m, 1H), 4.25-4.15 (m, 2H), 3.88-3.81 (m, 2H), 3.70 (s, 4H), 3.56 (s, 3H), 3.33-3.23 (m, 4H), 2.71 (m, 2H), 2.00 (s, 1H), 1.85-1.74 (m, 4H), 1.33 (t, 3H). LC-MS (ESI): m/z=601.3 [M+H]$^+$ Example 14: 2-((2-ethyl-5-(6-(4-methylpiperazine-1-carbonyl)-2,6-diazaspiro[3.3]heptan-2-yl)pyrazolo[1,5-a]pyridin-3-yl)(methyl)amino)-4-(4-fluorophenyl)thiazole-5-carbonitrile (Compound 14)

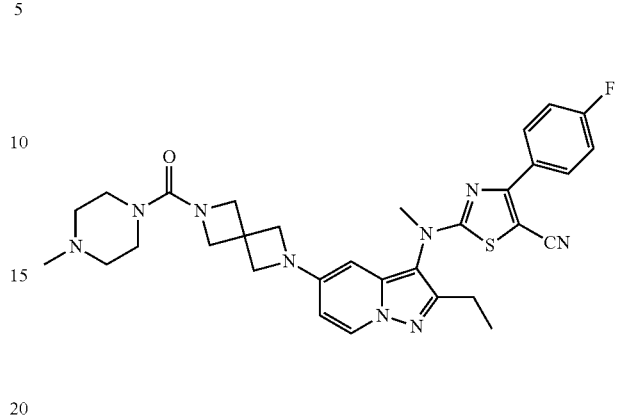

Starting from 11b (58 mg, 0.1 mmol) and proceeding in analogy to preparation Example 9, using 1-methylpiperazine to afford Compound 14 (20 mg, 37% yield over 4 steps) as a pale yellow solid. $^1$H NMR (400 MHz, CDCl$_3$) δ 8.18-8.14 (m, 3H), 7.18-7.14 (m, 2H), 6.12-6.09 (m, 1H), 5.86 (d, J=2.4 Hz, 1H), 4.16 (s, 4H), 4.06 (s, 4H), 3.57 (s, 3H), 3.39-3.36 (m, 4H), 2.73-2.68 (m, 2H), 2.40-2.37 (m, 4H), 2.30 (s, 3H), 1.32 (t, J=7.2 Hz, 3H). LC-MS: m/z=601.3 [M+H]$^+$.

Example 15: 2-((2-ethyl-5-(6-(3-hydroxyazetidine-1-carbonyl)-2,6-diazaspiro[3.4]octan-2-yl)pyrazolo[1,5-a]pyridin-3-yl)(methyl)amino)-4-(4-fluorophenyl)thiazole-5-carbonitrile (Compound 15)

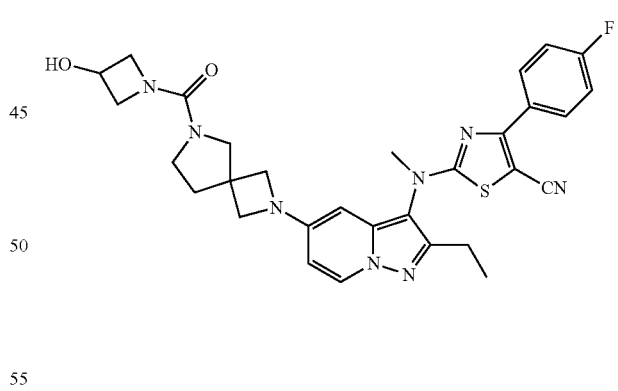

Starting from intermediate 1 (100 mg, 0.22 mmol) and proceeding in analogy to preparation Example 11, using tert-butyl 2,6-diazaspiro[3.4]octane-6-carboxylate to afford the title Compound 15 (70 mg, 55% over 4 steps) as a pale brown solid. $^1$H NMR (400 MHz, CDCl$_3$) δ 8.51-8.50 (d, J=7.6 Hz, 1H), 8.16-8.13 (m, 2H), 7.18-7.14 (m, 2H), 6.20 (d, J=7.6 Hz, 1H), 5.89 (s, 1H), 4.62-4.59 (m, 1H), 4.28-4.14 (m, 2H), 3.96-3.89 (m, 4H), 3.86-3.83 (m, 2H), 3.57 (s, 3H), 3.44 (t, J=6.8 Hz, 2H), 2.77 (q, J=7.6 Hz, 2H), 2.15 (t, J=6.8 Hz, 2H), 1.43-1.23 (m, 5H). LC-MS: m/z=587.3 [M+H]$^+$.

Example 16: 2-((2-ethyl-5-(2-(3-hydroxyazetidine-1-carbonyl)-2,6-diazaspiro[3.4]octan-6-yl)pyrazolo[1,5-a]pyridin-3-yl)(methyl)amino)-4-(4-fluorophenyl)thiazole-5-carbonitrile (Compound 16)

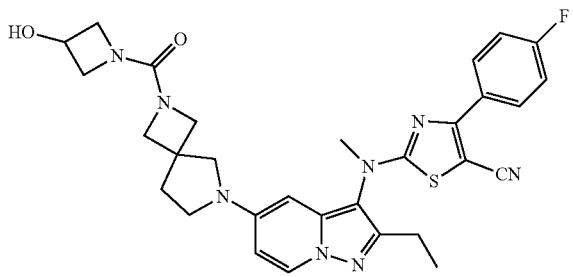 [SMILES: CCc1nn2ccc(N3CCC4(CN(C(=O)N5CC(O)C5)C4)C3)cc2c1N(C)c1nc(-c2ccc(F)cc2)c(C#N)s1]

Starting from intermediate 1 (100 mg, 0.22 mmol) and proceeding in analogy to preparation Example 11, using tert-butyl 2,6-diazaspiro[3.4]octane-2-carboxylate to afford the title Compound 16 (35 mg, 25% over 4 steps) as a pale yellow solid. $^1$H NMR (400 MHz, CDCl$_3$) δ 8.24 (d, J=7.6 Hz, 1H), 8.17-8.14 (m, 2H), 7.18-7.14 (m, 2H), 6.32-6.29 (m, 1H), 5.91 (d, J=2.4 Hz, 1H), 4.64-4.59 (m, 1H), 4.18-4.14 (m, 2H), 3.95-3.89 (m, 4H), 3.83-3.80 (m, 2H), 3.58 (s, 3H), 3.42 (t, J=6.8 Hz, 2H), 2.72 (q, J=7.6 Hz, 2H), 2.24 (t, J=6.8 Hz, 2H), 1.33 (t, J=7.6 Hz, 3H), 1.28-1.23 (m, 2H). LC-MS: m/z=294.2 [M/2+H]$^+$.

Example 17: 2-((2-ethyl-5-(8-(3-hydroxyazetidine-1-carbonyl)-2,8-diazaspiro[4.5]decan-2-yl)pyrazolo[1,5-a]pyridin-3-yl)(methyl)amino)-4-(4-fluorophenyl)thiazole-5-carbonitrile (Compound 17)

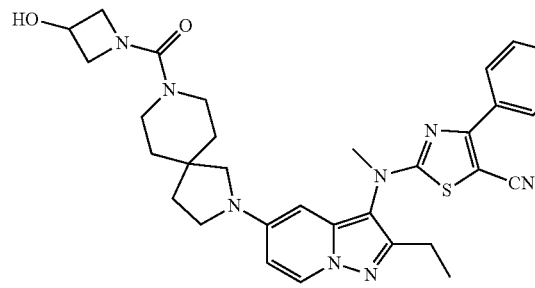

Starting from Intermediate 1 (100 mg, 0.22 mmol) and proceeding in analogy to preparation Example 11, using tert-butyl 2,8-diazaspiro[4.5]decane-8-carboxylate to afford the title Compound 17 (35 mg, 37% over 4 steps) as a pale yellow solid. $^1$H NMR (400 MHz, CDCl$_3$) δ 8.21 (d, J=7.4 Hz, 1H), 8.18-8.13 (m, 2H), 7.18-7.13 (m, 2H), 6.33-6.31 (m, 1H), 5.88 (d, J=2.4 Hz, 1H), 4.61-4.58 (m, 1H), 4.21-4.17 (m, 2H), 3.86-3.83 (m, 2H), 3.58 (s, 3H), 3.45-3.35 (m, 4H), 3.32-3.20 (m, 2H), 3.20 (s, 2H), 2.74-2.69 (m, 2H), 1.93 (t, J=7.6 Hz, 2H), 1.61-1.58 (m, 4H), 1.33 (t, J=7.6 Hz, 3H).

Example 18: 2-((2-ethyl-5-(2-(3-hydroxyazetidine-1-carbonyl)-2,8-diazaspiro[4.5]decan-8-yl)pyrazolo[1,5-a]pyridin-3-yl)(methyl)amino)-4-(4-fluorophenyl)thiazole-5-carbonitrile (Compound 18)

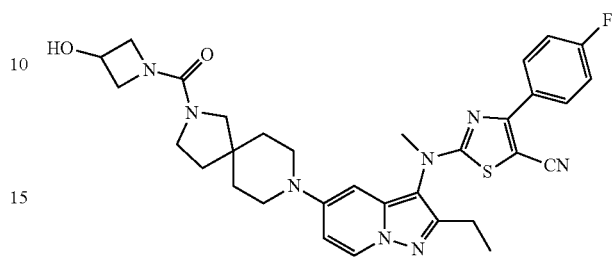

Starting from Intermediate 1 (100 mg, 0.22 mmol) and proceeding in analogy to preparation Example 11, using tert-butyl 2,8-diazaspiro[4.5]decane-2-carboxylate to afford the title Compound 18 (40 mg, 30% over 4 steps) as a pale yellow solid. $^1$H NMR (400 MHz, CDCl$_3$) δ 8.38 (d, J=7.4 Hz, 1H), 8.17-8.13 (m, 2H), 7.18-7.13 (m, 2H), 6.68 (d, J=7.4 Hz, 1H), 6.42 (s, 1H), 4.63-4.58 (m, 2H), 4.22-4.18 (m, 2H), 3.86-3.82 (m, 2H), 3.59 (s, 3H), 3.45-3.37 (m, 4H), 3.31-3.21 (m, 4H), 2.78-2.72 (m, 2H), 1.83-1.74 (m, 6H), 1.35 (t, J=7.6 Hz, 3H).

Example 19: 2-((2-ethyl-5-(4-(2-(3-hydroxyazetidin-1-yl)-2-oxoethyl)piperazin-1-yl)pyrazolo[1,5-a]pyridin-3-yl)(methyl)amino)-4-(4-fluorophenyl)thiazole-5-carbonitrile (Compound 19)

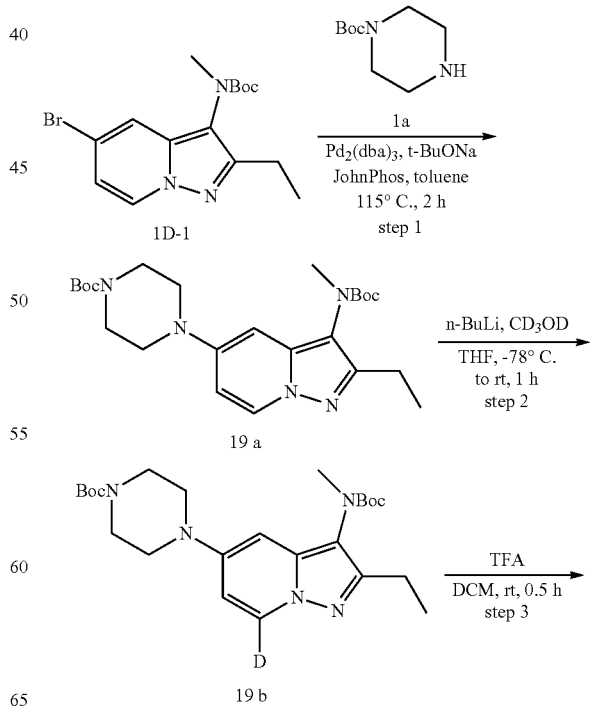

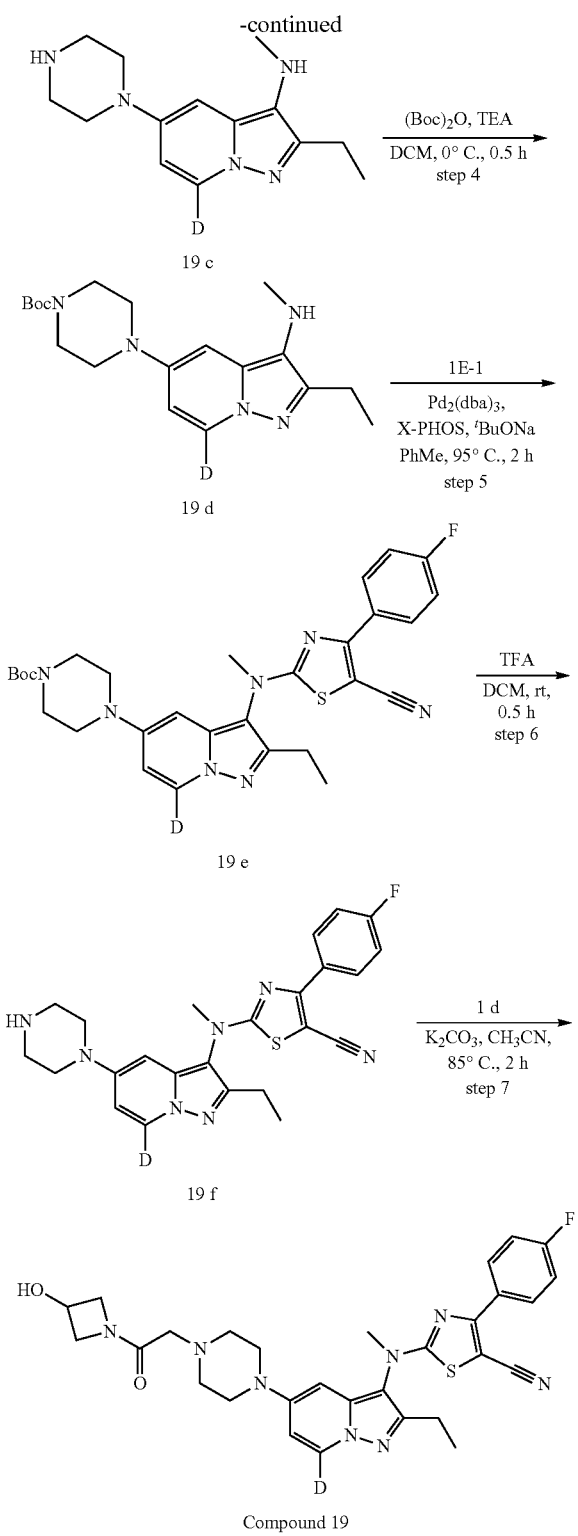

then JohnPhos (0.06 g, 0.2 mmol) and Pd$_2$(dba)$_3$ (0.09 g, 0.1 mmol). The reaction mixture was heated at 115° C. for 2 h. After cooling to room temperature, the mixture was diluted with water and EtOAc. The organic layer was separated and the aqueous layer extracted with EtOAc. The combined organic layers were then washed with water and brine, dried over Na$_2$SO$_4$, filtered, and concentrated in vacuo. The residue was purified by flash chromatography to afford 19a (0.58 g, 62%) as a yellow solid. LC-MS (ESI): m/z=460.3 [M+H]$^-$ Step 2: tert-butyl 4-(3-((tert-butoxycarbonyl)(methyl)amino)-2-ethylpyrazolo[1,5-a]pyridin-5-yl-7-d)piperazine-1-carboxylate (19b)

To a solution of 19a (0.5 g, 1.1 mmol) in THF (30 mL) was added n-BuLi (2.5 M THF solution, 2.2 mL, 5.5 mmol) dropwise at −78° C. under a nitrogen atmosphere, and the reaction mixture was further stirred for 1 h at the same temperature. CD$_3$OD (2 mL) was added dropwise to the reaction mixture, the mixture was warmed to rt, and then concentrated in vacuo. The residue was purified by column chromatography on silica gel to afford 19b (0.33 g, 66%) as a yellow oil. $^1$H NMR (400 MHz, CDCl$_3$) δ 6.42 (s, 1H), 6.31 (d, J=2.7 Hz, 1H), 3.57 (d, J=5.4 Hz, 4H), 3.15 (d, J=4.5 Hz, 8H), 2.66 (q, J=7.6 Hz, 2H), 1.46 (s, 9H), 1.38-1.16 (m, 12H).
LC-MS (ESI): m/z=461.2 [M+H]$^+$.

Step 3: 2-ethyl-N-methyl-5-(piperazin-1-yl)pyrazolo[1,5-a]pyridin-7-d-3-amine (19c)

A solution of 2 (0.33 g, 0.72 mmol) and trifluoroacetic acid (3 mL) in DCM (6 mL) was stirred at room temperature for 0.5 h. Solvent was evaporated, and the crude product was partitioned between water and DCM. The aqueous layer was basified with NaHCO$_3$ and extracted with DCM. Combined organic layers were washed with brine, dried over sodium sulfate, filtered, and evaporated to give 19c (0.19 g, 100%) that was used in the next step without further purification. LC-MS (ESI): m/z=261.3 [M+H]$^+$ Step 4: tert-butyl 4-(2-ethyl-3-(methylamino)pyrazolo[1,5-a]pyridin-5-yl-7-d)piperazine-1-carboxylate (19d)

To a solution 19c (0.19 g, 0.72 mmol) in DCM (10 mL) under argon was successively added TEA (0.08 g, 0.77 mmol), Di-tert-butyl dicarbonate (0.17 g, 0.76 mmol) at 0° C. The reaction mixture was further stirred for 30 min. then the mixture was concentrated in vacuo. The residue was purified by flash chromatography to afford 19d (0.15 g, 58%) as a yellow solid. LC-MS (ESI): m/z=361.2 [M+H]$^+$.

Step 5: tert-butyl 4-(3-((5-cyano-4-(4-fluorophenyl)thiazol-2-yl)(methyl)amino)-2-ethylpyrazolo[1,5-a]pyridin-5-yl-7-d)piperazine-1-carboxylate (19e)

To a solution 19d (0.15 g, 0.42 mmol) in toluene (10 mL) under argon was successively added chloro-4-(4-fluorophenyl)thiazole-5-carbonitrile (1E-1) (0.1 g, 0.42 mmol), sodium tert-butoxide (0.12 g, 1.26 mmol) and then X-Phos (38 mg, 0.08 mmol) and Pd$_2$(dba)$_3$ (37 mg, 0.04 mmol). The reaction mixture was heated at 95° C. for 2 h. After cooling to room temperature, the mixture was concentrated in vacuo. The residue was purified by flash chromatography to afford 19e (0.11 g, 47%) as a yellow solid. $^1$H NMR (400 MHz, CDCl₃) δ 8.20-8.05 (m, 2H), 7.19-7.12 (m, 2H), 6.56 (d, J=2.7 Hz, 1H), 6.30 (d, J=2.7 Hz, 1H), 3.59 (q, J=3.7 Hz, 7H), 3.22 (t, J=5.4 Hz, 4H), 2.72 (q, J=7.6 Hz, 2H), 1.47 (s, 9H), 1.38 (m, 3H). LC-MS (ESI): m/z=563.7 [M+H]⁺.

Step 6: 2-((2-ethyl-5-(piperazin-1-yl)pyrazolo[1,5-a]pyridin-3-yl-7-d)(methyl)amino)-4-(4-fluorophenyl)thiazole-5-carbonitrile (19f)

A solution of 19e (0.11 g, 0.20 mmol) and trifluoroacetic acid (3 mL) in DCM (6 mL) was stirred at room temperature for 0.5 h. Solvent was evaporated, and the crude product was partitioned between water and DCM. The aqueous layer was basified with NaHCO₃ and extracted with DCM. Combined organic layers were washed with brine, dried over sodium sulfate, filtered, and evaporated to give 19f (92 mg, 100%) that was used in the next step without further purification. LC-MS (ESI): m/z=463.3 [M+H]⁺.

Step 7: 2-((2-ethyl-5-(4-(2-(3-hydroxyazetidin-1-yl)-2-oxoethyl)piperazin-1-yl)pyrazolo[1,5-a]pyridin-3-yl-7-d)(methyl)amino)-4-(4-fluorophenyl)thiazole-5-carbonitrile (Compound 19)

To a solution of 19f (92 mg, 0.20 mmol) in MeCN (5 mL) were added potassium carbonate (0.28 g, 2.0 mmol) and 2-chloro-1-(3-hydroxyazetidin-1-yl)ethanone (1d) (90 mg, 0.60 mmol). The reaction mixture was refluxed for 2 h. After cooling to room temperature, the mixture was diluted with water and EtOAc. The organic layer was separated and the aqueous layer extracted with EtOAc. The combined organic layers were then washed with water and brine, dried over Na₂SO₄, filtered, and concentrated in vacuo. The residue was purified by flash chromatography to afford Compound 19 (60 mg, 52%) as a yellow solid. ¹H NMR (400 MHz, CDCl₃) δ 8.09 (d, 2H), 7.40 (t, 2H), 6.83 (d, 1H), 6.59 (d, 1H), 4.50-4.38 (m, 2H), 4.39-4.25 (m, 2H), 4.11-3.99 (m, 2H), 3.99-3.83 (m, 3H), 3.66-3.56 (m, 2H), 3.27 (s, 3H), 3.01 (d, 2H), 2.69-2.58 (m, 3H), 2.57-2.51 (m, 2H), 1.23 (m, 3H). LC-MS (ESI): m/z=288.8 [M/2+H]⁺

Example 20: 2-((2-ethyl-5-(7-(3-hydroxyazetidine-1-carbonyl)-2,7-diazaspiro[4.4]nonan-2-yl)pyrazolo[1,5-a]pyridin-3-yl)(methyl)amino)-4-(4-fluorophenyl)thiazole-5-carbonitrile (Compound 20)

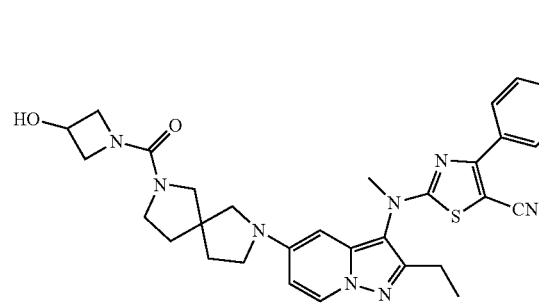

Starting from intermediate 1 and proceeding in analogy to preparation Example 11, using tert-butyl 2,7-diazaspiro[4.4]nonane-2-carboxylate to afford the title compound as a yellow solid. ¹H NMR (400 MHz, DMSO-D6) δ 8.39 (d, J=7.6 Hz, 1H), 8.13-8.05 (m, 2H), 7.44-7.36 (m, 2H), 6.53-6.45 (m, 1H), 5.54-5.46 (m, 1H), 4.39-431 (m, 1H), 4.05-4.38 (m, 2H), 3.66-3.56 (m, 2H), 3.53 (s, 3H), 3.47-3.37 (m, 2H), 3.38-3.30 (m, 2H), 3.28-3.17 (m, 4H), 2.61 (q, J=7.5 Hz, 2H), 1.99-1.89 (m, 2H), 1.89-1.79 (m, 2H), 1.18 (t, J=7.5 Hz, 3H). LC-MS: m/z=601.3 [M+H]⁺.

Example 21: 2-((2-cyclopropyl-5-(4-(2-(3-hydroxyazetidin-1-yl)-2-oxoethyl)piperazin-1-yl)pyrazolo[1,5-a]pyridin-3-yl)(methyl)amino)-4-(4-fluorophenyl)thiazole-5-carbonitrile (Compound 21)

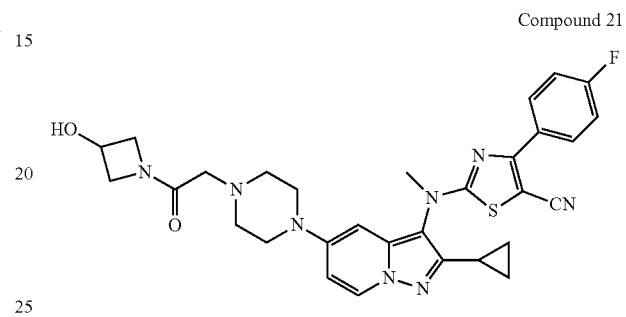

Compound 21

The title compound was prepared by the method substantially similar to that mentioned in Example 1, using Intermediate 7 afford Compound 21 as a white solid. ¹H NMR (400 MHz, CDCl₃) δ 8.15 (m, 3H), 7.22-7.05 (m, 2H), 6.52 (dd, 1H), 6.27 (d, 1H), 4.67 (m, 1H), 4.49-4.38 (m, 1H), 4.28 (m, 1H), 4.10 (d, 1H), 3.90 (m, 1H), 3.63 (s, 3H), 3.36-3.22 (m, 4H), 3.13 (d, 2H), 2.73 (d, 4H), 1.26 (s, 1H), 1.03 (m, 4H). LC-MS (ESI): m/z=587.2 [M+H]⁺

Example 22: (S)-2-((2-cyclopropyl-5-(6-(tetrahydrofuran-3-carbonyl)-2,6-diazaspiro[3.3]heptan-2-yl)pyrazolo[1,5-a]pyridin-3-yl)(methyl)amino)-4-(4-fluorophenyl)thiazole-5-carbonitrile (Compound 22)

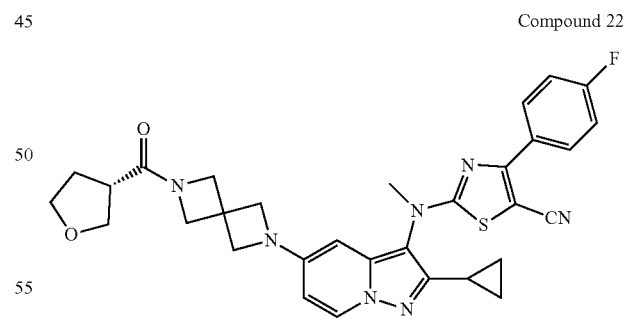

Compound 22

The title compound was prepared by the method substantially similar to that mentioned in Example 10, using Intermediate 7 afford Compound 22 as a white solid. ¹H NMR (400 MHz, CDCl3) δ 8.20-8.09 (m, 3H), 7.21-7.11 (m, 2H), 6.10 (dd, 1H), 5.87 (d, 1H), 4.35 (q, 2H), 4.20 (s, 2H), 4.11 (d, 4H), 3.98 (t, 1H), 3.94-3.76 (m, 3H), 3.62 (s, 3H), 2.92 (dt, 1H), 2.16 (dt, 1H), 2.10-2.01 (m, 1H), 1.86 (dd, 1H), 1.03 (dd, 2H), 0.87 (dd, J=7.8, 2.8 Hz, 2H). LC-MS (ESI): m/z=584.3 [M+H]⁺

187

Example 23: 2-((2-ethyl-5-(4-(2-(3-hydroxyazetidin-1-yl)-2-oxoethyl)piperazin-1-yl)-7-methylpyrazolo[1,5-a]pyridin-3-yl)(methyl)amino)-4-(4-fluorophenyl)thiazole-5-carbonitrile (Compound 23)

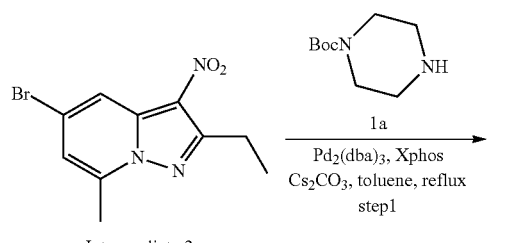

Intermediate 2

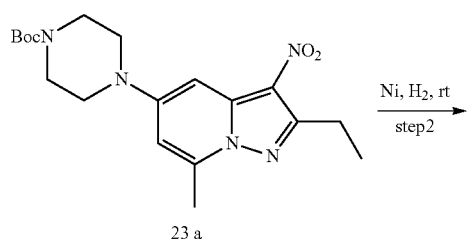

23 a

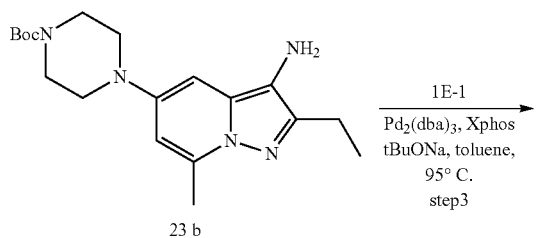

23 b

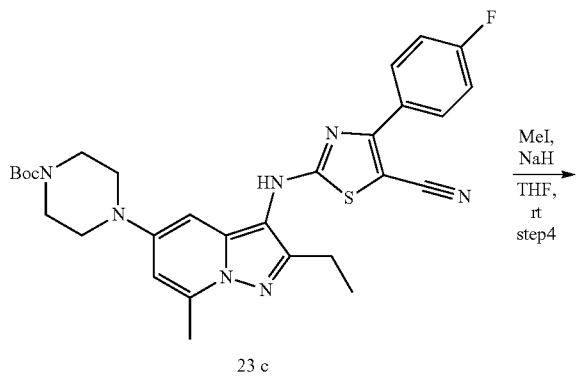

23 c

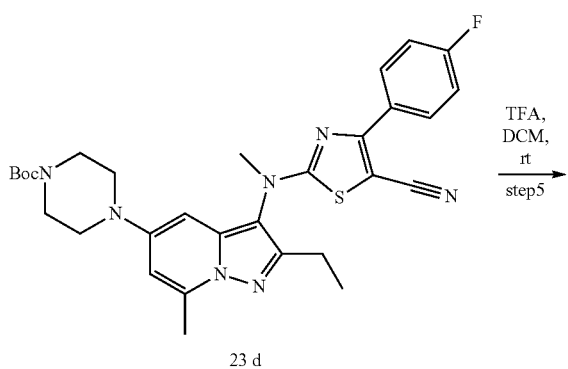

23 d

188

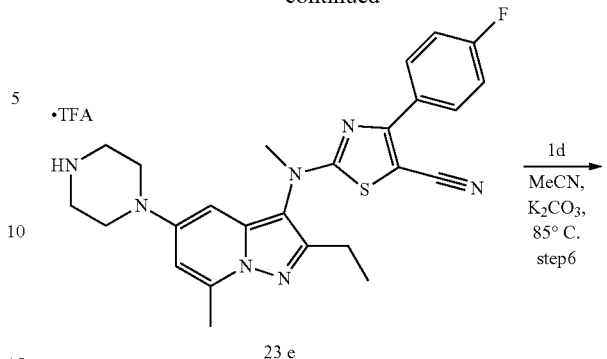

23 e

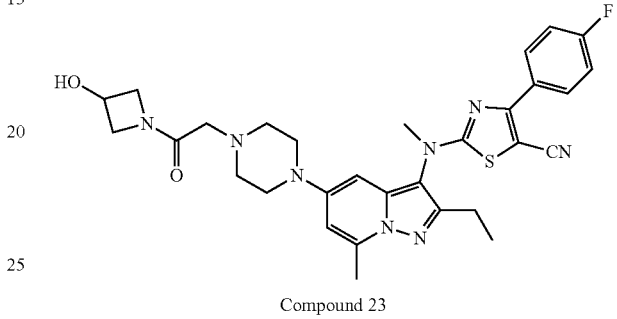

Compound 23

Step 1: tert-butyl 4-(2-ethyl-7-methyl-3-nitropyrazolo[1,5-a]pyridin-5-yl)piperazine-1-carboxylate (23a)

Intermediate 2 (2.5 g, 8.8 mmol), Pd$_2$(dba)$_3$ (0.81 g, 0.88 mmol), X-PHOS (0.84 g, 1.8 mmol), and cesium carbonate (8.6 g, 26 mmol) were added to a screw capped test tube. The tube was evacuated and back filled with argon. tert-butyl piperazine-1-carboxylate (1a) (2.5 g, 13 mmol) and toluene (10 mL) were added successively by syringe at room temperature. The tube was sealed with a Teflon-lined cap, and the reaction mixture was heated at 120° C. for 10 h. After cooling to room temperature, the suspension was diluted with dichloromethane and filtered through Celite. The solvent was removed with the aid of a rotary evaporator to give a brown residue which was purified by column chromatography on silica gel (n-hexane: ethyl acetate=3:2) to give the title 23a (1.5 g, 44%). NMR (400 MHz, CDCl$_3$) δ 7.47-7.35 (m, 1H), 6.61-6.41 (m, 1H), 3.72-3.55 (m, 4H), 3.54-3.38 (m, 4H), 3.15 (q, J=7.4 Hz, 2H), 2.71 (s, 3H), 1.50 (s, 9H), 1.36 (t, J=7.4 Hz, 3H).

Step 2: tert-butyl 4-(3-amino-2-ethyl-7-methylpyrazolo[1,5-a]pyridin-5-yl)piperazine-1-carboxylate (23b)

22a (0.16 g, 0.40 mmol) was dissolved in methanol (10 mL), Raney-Nickel (0.16 g) was added and the mixture was stirred under hydrogen (balloon) for 4 h at room temperature. Then the mixture was filtered and diluted with methanol (2×10 mL). The organic filtrate was concentrated under reduced pressure, the residue was directly used for the next step without purification.

Step 3: tert-butyl 4-(3-((5-cyano-4-(4-fluorophenyl)thiazol-2-yl)amino)-2-ethyl-7-methylpyrazolo[1,5-a]pyridin-5-yl)piperazine-1-carboxylate (23c)

(23b) (145 mg, 0.40 mmol), Pd$_2$(dba)$_3$ (37 mg, 0.04 mmol), X-PHOS (38.4 mg, 0.08 mmol), and sodium tert-butoxide (96.9 mg, 1.01 mmol) were added to a screw capped test tube. The tube was evacuated and back filled with argon. 2-chloro-4-(4-fluorophenyl)thiazole-5-carbonitrile (1E-1) (96.3 mg, 0.40 mmol) and toluene (10 mL) were added successively by syringe at room temperature. The tube was sealed with a Teflon-lined cap, and the reaction mixture was heated at 95° C. for 2.5 h. After cooling to room temperature, the suspension was diluted with dichloromethane and filtered through Celite. The solvent was removed with the aid of a rotary evaporator to give a brown residue which was purified by column chromatography on silica gel (n-hexane:ethyl acetate=3:1) to give the title compound 23c (104.2 mg, 46%). $^1$H NMR (400 MHz, CDCl$_3$) δ 8.11-7.95 (m, 2H), 7.14-6.97 (m, 2H), 6.42 (s, 1H), 6.33 (s, 1H), 3.64-3.49 (m, 4H), 3.30-3.08 (m, 4H), 2.77 (q, J=7.4 Hz, 2H), 2.71 (s, 3H), 1.47 (s, 9H), 1.31 (t, J=7.6 Hz, 3H).

Step 4: tert-butyl 4-(3-((5-cyano-4-(4-fluorophenyl)thiazol-2-yl)(methyl)amino)-2-ethyl-7-methylpyrazolo[1,5-a]pyridin-5-yl)piperazine-1-carboxylate (23d)

To a solution of 23c (0.3 g, 0.5 mmol) and iodomethane (0.1 g, 0.8 mmol) in tetrahydrofuran (10 mL) was added sodium hydride (60%, 0.04 g, 1 mmol) under cooling with ice water, and the reaction mixture was stirred for 40 min at room temperature. The reaction mixture was then poured into crashed ice, and was extracted with ethyl acetate. The organic layer was dried over magnesium sulfate, filtered, and concentrated in vacuo. The residue was purified by column chromatography on silica gel (n-hexane:ethyl acetate=3:1) to give the title compound (23d) (0.28 g, 90%). $^1$H NMR (400 MHz, CDCl$_3$) δ 8.21-8.10 (m, 2H), 7.16 (t, J=8.7 Hz, 2H), 6.42 (s, 1H), 6.31-6.20 (m, 1H), 3.61-3.50 (m, 7H), 3.28-3.11 (m, 4H), 2.75 (q, J=7.6 Hz, 2H), 2.71 (s, 3H), 1.47 (s, 9H), 1.32 (t, J=7.6 Hz, 3H).

Step 5: 2-((2-ethyl-7-methyl-5-(piperazin-1-yl)pyrazolo[1,5-a]pyridin-3-yl)(methyl)amino)-4-(4-fluorophenyl)thiazole-5-carbonitrile (23e)

To a solution of (23d) (0.3 g, 0.5 mmol) in dichloromethane (6 mL) was added TFA (3 mL) at room temperature, The reaction mixture was stirred for 3 h and concentrated, the residue was directly used for the next step without purification. LC-MS (ESI): m/z=476.3 [M+H]$^+$ Step 6: 2-((2-ethyl-5-(4-(2-(3-hydroxyazetidin-1-yl)-2-oxoethyl)piperazin-1-yl)-7-methyl pyrazolo[1,5-a]pyridin-3-yl)(methyl)amino)-4-(4-fluorophenyl)thiazole-5-carbonitrile (Compound 23)

To a solution of (23e) (0.25 g, 0.53 mmol) in acetonitrile (10 mL) was added potassium carbonate (2.2 g, 16 mmol) and 1d (0.31 g, 2.1 mmol). The reaction mixture was refluxed for 3.5 h and then filtered, and the solid was washed with acetonitrile. The filtrate was then suspended in 50 mL of water, extracted with ethyl acetate, the organic layer was dried over magnesium sulfate, filtered, and concentrated in vacuo. The residue was purified by column chromatography on silica gel (n-hexane:ethyl acetate=1:1) to give the Compound 23 (0.2 g, 65%). $^1$H NMR (400 MHz, DMSO) δ 8.31-7.89 (m, 2H), 7.63-7.26 (m, 2H), 6.81 (s, 1H), 6.62-6.34 (m, 1H), 5.66 (br, 1H), 4.38-4.25 (m, 1H), 4.10-3.97 (m, 1H), 3.91 (dd, J=9.3, 4.1 Hz, 1H), 3.76-3.45 (m, 5H), 3.29-3.15 (m, 4H), 3.09-2.93 (m, 2H), 2.71-2.62 (m, 3H), 2.61 (s, 3H), 2.58-2.52 (m, 3H), 1.24 (t, J=7.6 Hz, 3H). LC-MS (ESI): m/z=589.2 [M+H]$^+$ Example 24: 2-(4-(3-((5-cyano-4-(4-fluorophenyl)thiazol-2-yl)(methyl)amino)-2-ethyl-7-methylpyrazolo[1,5-a]pyridin-5-yl)piperazin-1-yl)-N,N-dimethylacetamide (Compound 24)

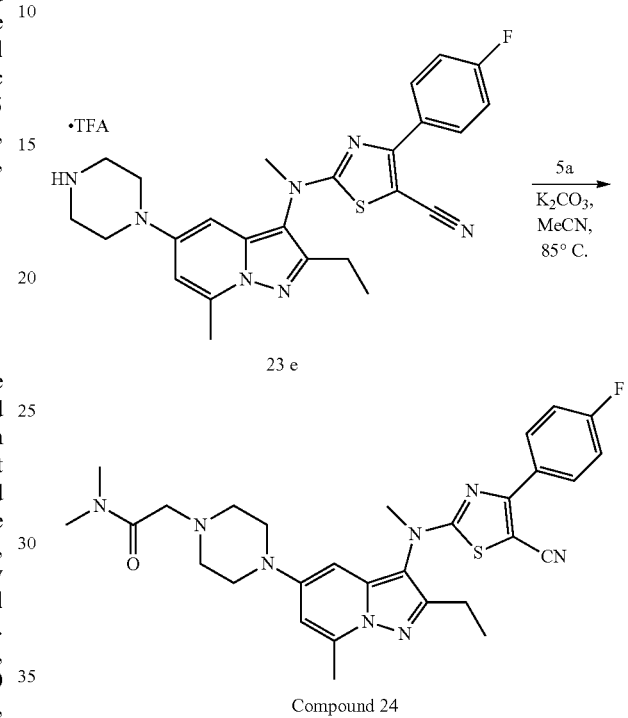

Compound 24 was prepared from 23e and 2-chloro-N,N-dimethylacetamide (5a) in a manner analogous to Step 6 (Example 23) and was isolated as a yellow foam. $^1$H NMR (400 MHz, CDCl$_3$) δ 8.28-7.93 (m, 2H), 7.24-7.02 (m, 2H), 6.47-6.37 (m, 1H), 6.31-6.17 (m, 1H), 3.59 (s, 3H), 3.43-3.19 (m, 6H), 3.08 (s, 3H), 2.96 (s, 3H), 2.82-2.57 (m, 9H), 1.32 (t, J=7.6 Hz, 3H). LC-MS (ESI): m/z=561.3 [M+H]$^+$ Example 25: (R)-2-((2-ethyl-5-(4-(2-(3-hydroxypyrrolidin-1-yl)-2-oxoethyl)piperazin-1-yl)-7-methylpyrazolo[1,5-a]pyridin-3-yl)(methyl)pamino)-4-(4-fluorophenyl)thiazole-5-carbonitrile (Compound 25)

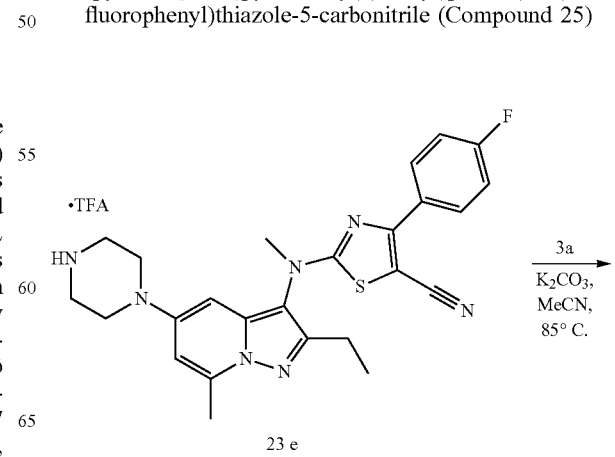

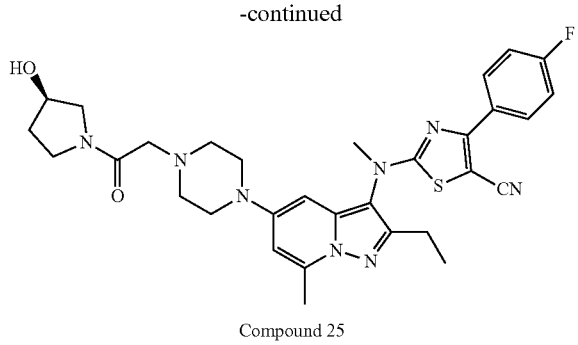

Compound 25

Compound 25 was prepared from 23e and (R)-2-chloro-1-(3-hydroxypyrrolidin-1-yl)ethan-1-one (3a) in a manner analogous to Step 6 (Example 25) and was isolated as a yellow foam. $^1$H NMR (400 MHz, CDCl$_3$) δ 8.23-8.04 (m, 2H), 7.16 (t, 2H), 6.39 (s, 1H), 6.29 (s, 1H), 4.53 (d, 1H), 3.93-3.40 (m, 12H), 3.26 (s, 4H), 2.75 (m, 2H), 2.72 (s, 3H), 2.03 (d, 3H), 1.32 (t, 3H). LC-MS: m/z (ESI): 603.2 [M+H]$^+$ Example 26: (S)-2-((2-ethyl-5-(4-(2-(3-hydroxypyr-rolidin-1-yl)-2-oxoethyl)piperazin-1-yl)-7-methyl-pyrazolo[1,5-a]pyridin-3-yl)(methyl)amino)-4-(4-fluorophenyl)thiazole-5-carbonitrile (Compound 26)

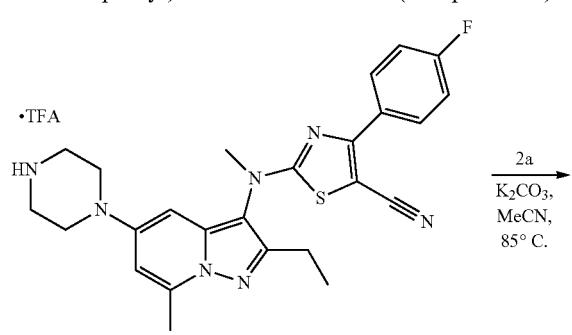

23 e

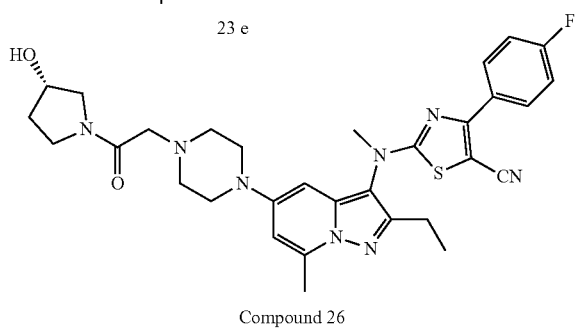

Compound 26

Compound 26 was prepared from 23e and (S)-2-chloro-1-(3-hydroxypyrrolidin-1-yl)ethan-1-one (2a) in a manner analogous to Step 6 (Example 23) and was isolated as a yellow foam. $^1$H NMR (400 MHz, CDCl$_3$) δ 8.20-8.09 (m, 2H), 7.15 (t, 2H), 6.42 (s, 1H), 6.24 (d1H), 4.51 (m, 1H), 3.72-3.47 (m, 7H), 3.30 (s, 4H), 3.26-3.17 (m, 2H), 2.82-2.71 (m, 6H), 2.70 (s, 3H), 2.19 (s, 2H), 2.03 (m, 1H), 2.01-1.89 (m, 1H), 1.32 (t, 3H). LC-MS (ESI): m/z=603.4 [M+H]$^+$ Example 27: 2-((2-ethyl-5-(4-(2-(3-(hydroxymethyl)azetidin-1-yl)-2-oxoethyl)piperazin-1-yl)-7-methyl-pyrazolo[1,5-a]pyridin-3-yl)(methyl)amino)-4-(4-fluorophenyl)thiazole-5-carbonitrile (Compound 27)

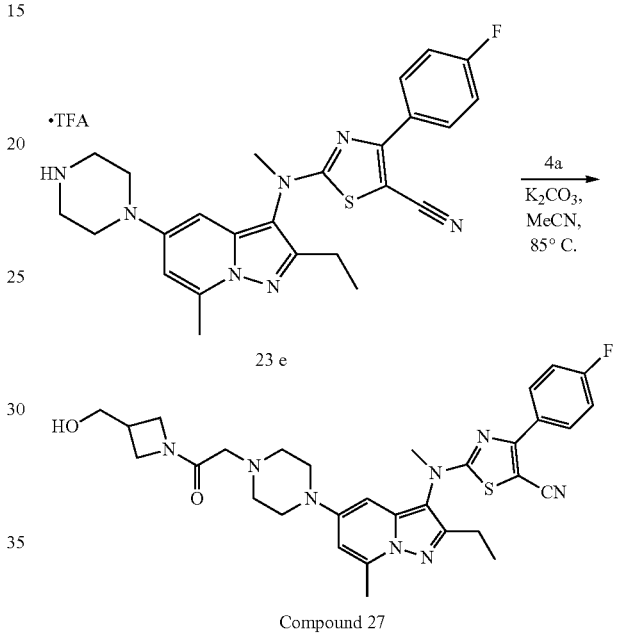

Compound 27

Compound 27 was prepared from 23e and 2-chloro-1-(3-(hydroxymethyl)azetidin-1-yl)ethan-1-one (4a) in a manner analogous to Step 6 (Example 23) and was isolated as a yellow foam. $^1$H NMR (400 MHz, CDCl$_3$) δ 8.26-8.04 (m, 2H), 7.16 (m, 2H), 6.40 (s, 1H), 6.27 (s, 1H), 4.28 (t, 1H), 4.20-4.03 (m, 2H), 3.95-3.69 (m, 3H), 3.59 (s, 3H), 3.49-3.18 (m, 6H), 3.00 (s, 3H), 2.85-2.62 (m, 5H), 1.32 (t, 5H). LC-MS (ESI): m/z=603.7 [M+H]$^+$ Example 28: 2-((2-ethyl-5-(6-(3-hydroxyazetidine-1-carbonyl)-2,6-diazaspiro[3.3]heptan-2-yl)-7-methylpyrazolo[1,5-a]pyridin-3-yl)(methyl)amino)-4-(4-fluorophenyl)thiazole-5-carbonitrile (Compound 28)

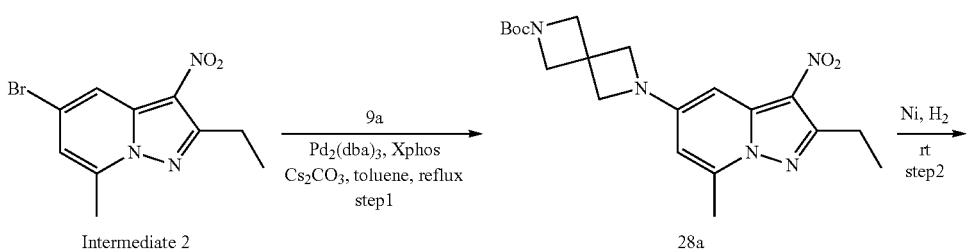

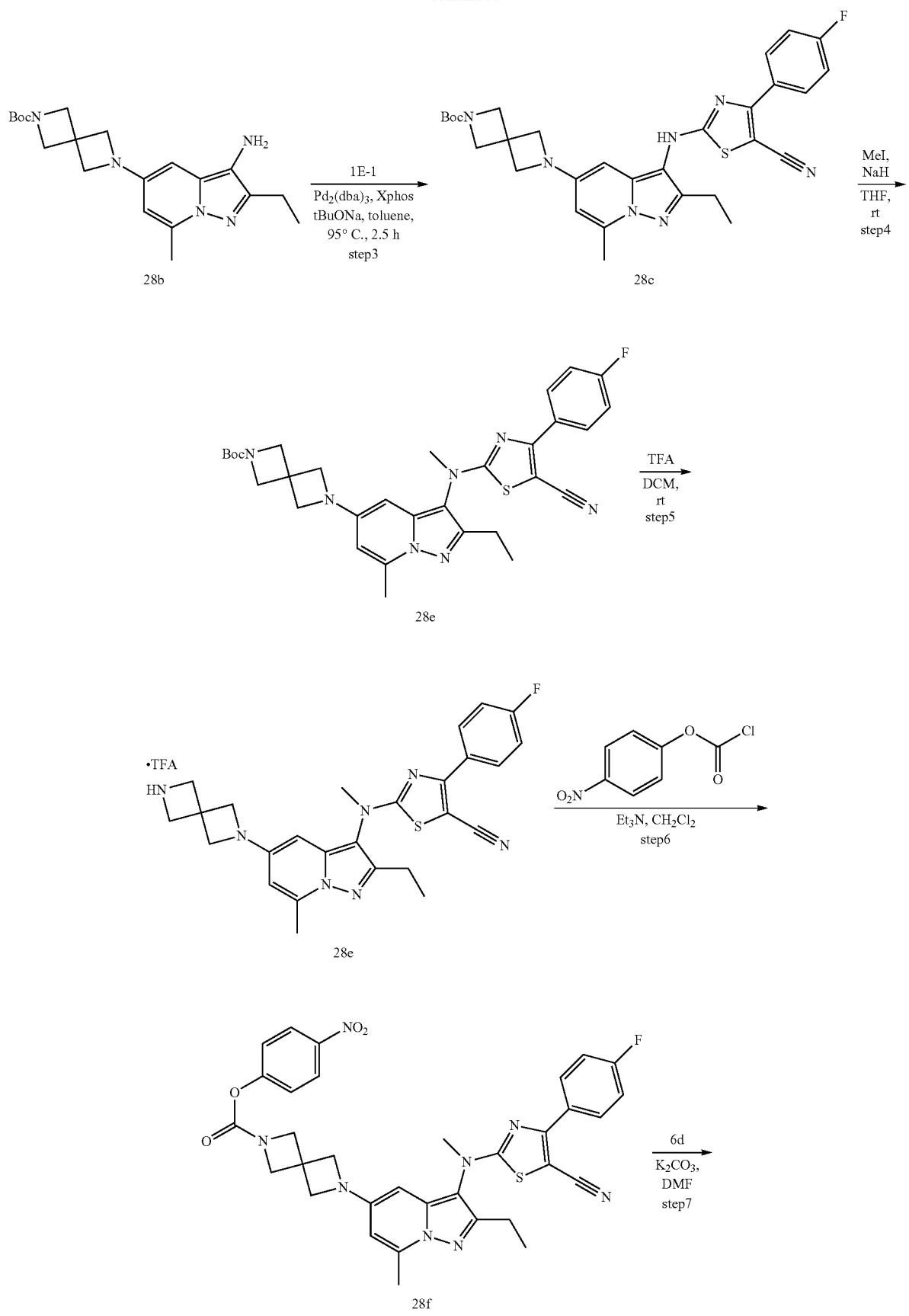

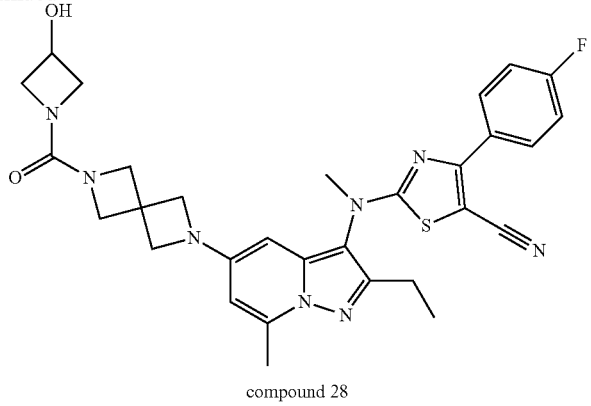 [SMILES: CCc1nn2c(C)cc(N3CC4(CN(C(=O)N5CC(O)C5)C4)C3)cc2c1N(C)c1nc(-c2ccc(F)cc2)c(C#N)s1]

compound 28

Step 1: tert-butyl 6-(2-ethyl-7-methyl-3-nitropyrazolo[1,5-a]pyridin-5-yl)-2,6-diazaspiro[3.3]heptane-2-carboxylate (28a)

Intermediate 2 (100 mg, 0.35 mmol), $Pd_2(dba)_3$ (32 mg, 0.035 mmol), X-PHOS (33.6 mg, 0.07 mmol), and $Cs_2CO_3$ (573 mg, 1.76 mmol) were added to a screw capped test tube. The tube was evacuated and back filled with argon. 9a (152 mg, 0.53 mmol) and toluene (10 mL) were added successively by syringe at room temperature. The tube was sealed with a Teflon-lined cap, and the reaction mixture was heated at 112° C. for 10 h. After cooling to room temperature, the suspension was diluted with dichloromethane and filtered through Celite. The solvent was removed with the aid of a rotary evaporator to give a brown residue which was purified by column chromatography on silica gel to give the title compound 28a (0.09 g, 66%). $^1H$ NMR (400 MHz, $CDCl_3$) δ 6.90-6.75 (m, 1H), 6.05-5.89 (m, 1H), 4.19 (s, 4H), 4.16 (s, 4H), 3.09 (q, J=7.4 Hz, 2H), 2.63 (s, 3H), 1.46 (s, 9H), 1.34 (t, J=7.4 Hz, 3H).

Step 2: tert-butyl 6-(3-amino-2-ethyl-7-methylpyrazolo[1,5-a]pyridin-5-yl)-2,6-diazaspiro[3.3]heptane-2-carboxylate (28b)

28a (200 mg, 0.5 mol) was dissolved in methanol (5 mL), then Raney-Nickel (0.2 g) was added and the mixture was stirred under hydrogen (balloon) for 4 h at room temperature. Then the mixture was filtered and diluted with methanol (2×10 mL). The organic filtrate was concentrated, the residue was directly used for the next step without purification.

Step 3: tert-butyl 6-(3-((5-cyano-4-(4-fluorophenyl)thiazol-2-yl)amino)-2-ethyl-7-methyl pyrazolo[1,5-a]pyridin-5-yl)-2,6-diazaspiro[3.3]heptane-2-carboxylate (28c)

28b (185 mg, 0.50 mmol), $Pd_2(dba)_3$ (46 mg, 0.05 mmol), X-PHOS (47 mg, 0.1 mmol), and sodium tert-butoxide (120 mg, 1.25 mmol) were added to a screw capped test tube. The tube was evacuated and back filled with argon. 1E-1 (107 mg, 0.45 mmol) and toluene (10 mL) were added successively by syringe at room temperature. The tube was sealed with a Teflon-lined cap, and the reaction mixture was heated at 95 for 2.5 h. After cooling to room temperature, the suspension was diluted with dichloromethane and filtered through Celite. The solvent was removed with the aid of a rotary evaporator to give a brown residue which was purified by column chromatography on silica gel to give the title compound 28c (129 mg, 45%). $^1H$ NMR (400 MHz, $CDCl_3$) δ 7.99-7.90 (m, 2H), 7.82 (br, 1H), 7.12-6.82 (m, 2H), 6.03-5.90 (m, 1H), 5.90-5.81 (m, 1H), 4.11 (s, 4H), 4.02 (s, 4H), 2.73 (q, J=7.6 Hz, 2H), 2.69 (s, 3H), 1.44 (s, 9H), 1.27 (t, J=7.3 Hz, 3H). LC-MS (ESI): m/z=574.3 $[M+H]^+$

Step 4: tert-butyl 6-(3-((5-cyano-4-(4-fluorophenyl)thiazol-2-yl)(methyl)amino)-2-ethyl-7-methylpyrazolo[1,5-a]pyridin-5-yl)-2,6-diazaspiro[3.3]heptane-2-carboxylate (28d)

To a solution of 28c (50 mg, 0.087 mmol) and iodomethane (111 mg, 0.78 mmol) in THF (5 mL) was added sodium hydride (60%, 35 mg, 0.87 mmol) under cooling with ice water, and the reaction mixture was stirred for 40 min at room temperature. The reaction mixture was then poured into crashed ice, and was extracted with ethyl acetate. The organic layer was dried over magnesium sulfate, filtered, and concentrated in vacuo. The residue was purified by column chromatography on silica gel to give the title compound 28d (43 mg, 85%). $^1H$ NMR (400 MHz, $CDCl_3$) δ 8.35-7.89 (m, 2H), 7.21-7.00 (m, 2H), 6.17-5.88 (m, 1H), 5.90-5.64 (m, 1H), 4.10 (s, 4H), 4.05 (s, 4H), 3.57 (s, 3H), 2.76 (q, J=7.6 Hz, 2H), 2.72 (s, 3H), 1.44 (s, 9H), 1.33 (t, J=7.6 Hz, 3H). LC-MS (ESI): m/z=588.3 $[M+H]^+$

Step 5: 2-((2-ethyl-7-methyl-5-(2,6-diazaspiro[3.3]heptan-2-yl)pyrazolo[1,5-a]pyridin-3-yl)(methyl)amino)-4-(4-fluorophenyl)thiazole-5-carbonitrile 2,2,2-trifluoroacetate (28e)

To a solution of 28d (160 mg, 4 0.27 mmol) in dichloromethane (6 mL) was added TFA (3 mL) at room temperature, The reaction mixture was stirred for 3 h and concentrated, the residue was directly used for the next step without purification.

Step 6: 4-nitrophenyl 6-(3-((5-cyano-4-(4-fluorophenyl)thiazol-2-yl)(methyl)amino)-2-ethyl-7-methylpyrazolo[1,5-a]pyridin-5-yl)-2,6-diazaspiro[3.3]heptane-2-carboxylate (28f)

Triethylamine (138 mg, 1.36 mmol) and p-nitrophenyl chloroformate (33 mg, 0.16 mmol) were added to a room temperature solution of 28e (66 mg, 0.136 mmol) in dry dichloromethane (5 mL) under an argon atmosphere. After 2 h, the reaction mixture was quenched with water, diluted with ethyl acetate (50 mL), washed with water (2×50 mL), and brine (100 mL). All volatiles were removed under reduced pressure and the residue directly used for the next step without purification.

Step 7: 2-((2-ethyl-5-(6-(3-hydroxyazetidine-1-carbonyl)-2,6-diazaspiro[3.3]heptan-2-yl)-7-methylpyrazolo[1,5-a]pyridin-3-yl)(methyl)amino)-4-(4-fluorophenyl)thiazole-5-carbonitrile (Compound 28)

To a solution of 28f (400 mg, 0.61 mmol) in DMF (5 mL) was added K$_2$CO$_3$ (339 mg, 2.45 mmol) and 6d (133 mg, 1.23 mmol). The reaction mixture was heated to 100° C. for 2 h and then filtered, and the solid was washed with ethyl acetate. The filtrate was then suspended in 50 mL of water, extracted with ethyl acetate, the organic layer was dried over magnesium sulfate, filtered, and concentrated in vacuo. The residue was purified by column chromatography on silica gel to give the title compound 28 (210 mg, 58%). $^1$H NMR (400 MHz, CDCl$_3$) δ 8.26-8.01 (m, 2H), 7.22-7.06 (m, 2H), 6.01 (s, 1H), 5.83 (s, 1H), 4.63 (br, 1H), 4.23-3.95 (m, 10H), 3.86-3.73 (m, 2H), 3.68-3.42 (m, 4H), 3.02-2.65 (m, 5H), 1.35 (t, J=7.6 Hz, 3H). LC-MS (ESI): m/z=587.3 [M+H]$^+$ Example 29: 2-((2-ethyl-5-(6-(2-hydroxyacetyl)-2,6-diazaspiro[3.3]heptan-2-yl)-7-methylpyrazolo[1,5-a]pyridin-3-yl)(methyl)amino)-4-(4-fluorophenyl)thiazole-5-carbonitrile (Compound 29)

Step 1: 2-((5-(6-(2-((tert-butyldimethylsilyl)oxy)acetyl)-2,6-diazaspiro[3.3]heptan-2-yl)-2-ethyl-7-methylpyrazolo[1,5-a]pyridin-3-yl)(methyl)amino)-4-(4-fluorophenyl)thiazole-5-carbonitrile (29a)

To a solution of 2-((tert-butyldimethylsilyl)oxy)acetic acid (59 mg, 0.31 mmol) and HATU (117 mg, 0.31 mmol) in DCM (5 mL) was added triethylamine (0.4 mL, 2.66 mmol) and Compound 28e (125 mg, 0.26 mmol) at rt. After 2 h, the reaction mixture was quenched with water, diluted with DCM (50 mL), washed with water (2×50 mL), and brine (100 mL). All volatiles were removed under reduced pressure. The residue was directly used for the next step without purification. LC-MS (ESI): m/z=660.3 [M+H]$^+$ Step 2: 2-((2-ethyl-5-(6-(2-hydroxyacetyl)-2,6-diazaspiro[3.3]heptan-2-yl)-7-methylpyrazolo[1,5-a]pyridin-3-yl)(methyl)amino)-4-(4-fluorophenyl)thiazole-5-carbonitrile (Compound 29)

To a solution of compound 29a (168 mg, 0.31 mmol) in THF (5 mL) was added TBAF (136 mg, 0.52 mmol) at rt.

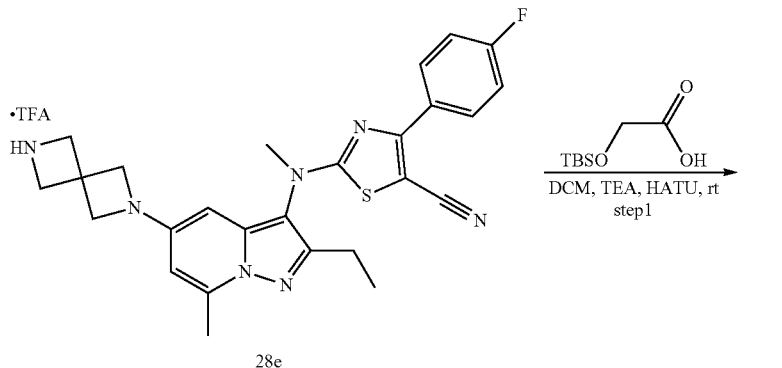

28e

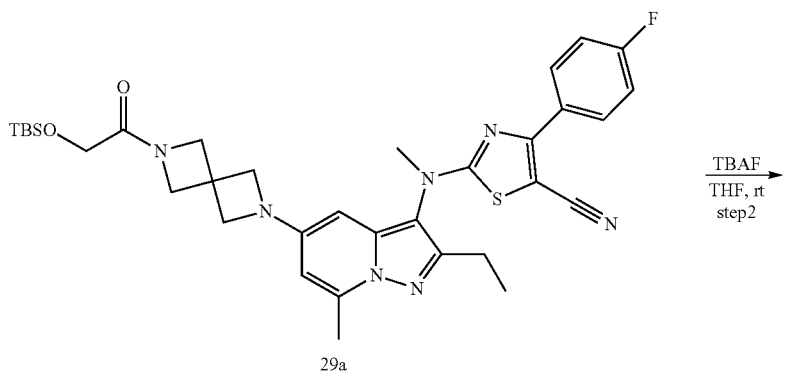

29a

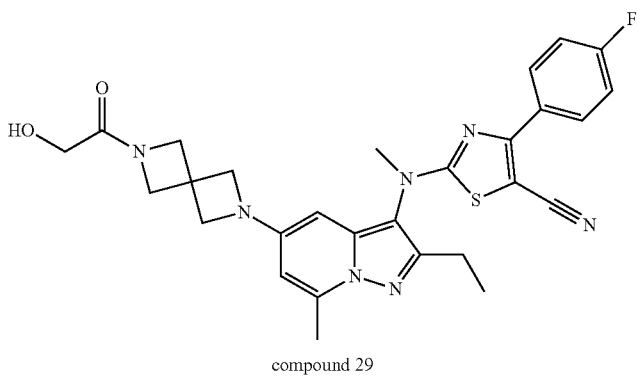

compound 29

After 2 h, the reaction mixture was quenched with water, diluted with ethyl acetate (50 mL), washed with water (2×50 mL), and brine (100 mL). All volatiles were removed under reduced pressure. The residue was purified by column chromatography on silica gel to give the title Compound 29 (90 mg, 63%). $^1$H NMR (400 MHz, CDCl$_3$) δ 8.26-8.06 (m, 2H), 7.22-7.07 (m, 2H), 5.97 (s, 1H), 5.85 (s, 1H), 4.28 (s, 4H), 4.08 (s, 4H), 4.00 (s, 2H), 3.57 (s, 3H), 2.75 (d, 2H), 2.70 (s, 3H), 1.32 (t, 3H). LC-MS (ESI): m/z=546.2 [M+H]$^+$ Example 30: 2-((2-ethyl-5-(6-(2-hydroxy-2-methyl-propanoyl)-2,6-diazaspiro[3.3]heptan-2-yl)-7-methylpyrazolo[1,5-a]pyridin-3-yl)(methyl)amino)-4-(4-fluorophenyl)thiazole-5-carbonitrile (Compound 30)

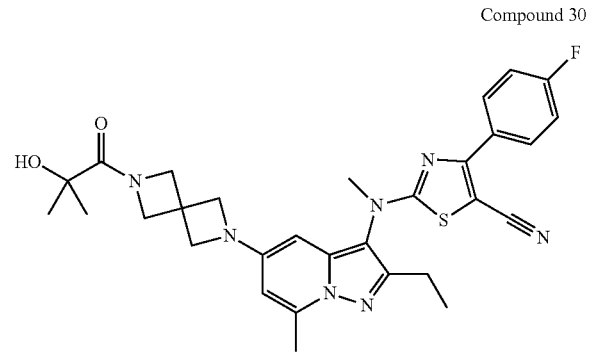 [SMILES: CCc1nn2c(C)cc(N3CC4(CN(C(=O)C(C)(C)O)C4)C3)cc2c1N(C)c1nc(-c2ccc(F)cc2)c(C#N)s1]

Compound 30

To a solution of 28e (70 mg, 0.14 mmol) in dichloromethane (5 mL) was added HATU (65 mg, 0.17 mmol), triethylamine (58 mg, 0.57 mmol) and 2-hydroxy-2-methylpropanoic acid (25 mg, 0.21 mmol). The reaction mixture was stirred at room temperature for 3 h and then the reaction mixture was quenched with water, extracted with ethyl acetate, the organic layer was washed with water (3×15 mL) and then dried over magnesium sulfate, filtered, and concentrated in vacuo. The residue was purified by column chromatography on silica gel to give the title Compound 30 (0.045 g, 51%). $^1$H NMR (400 MHz, CDCl3) δ 8.20-8.10 (m, 2H), 7.22-7.10 (m, 2H), 5.98 (d, 1H), 5.84 (d, 1H), 4.56 (s, 2H), 4.24 (s, 2H), 4.08 (s, 4H), 3.57 (s, 3H), 2.76 (q, 2H), 2.71 (s, 3H), 1.41 (s, 6H), 1.32 (t, 3H). MS m/z (ESI): 574.2[M+H$^+$]

Example 31: 2-((2-ethyl-7-methyl-5-(6-(oxetane-3-carbonyl)-2,6-diazaspiro[3.3]heptan-2-yl)pyrazolo[1,5-a]pyridin-3-yl)(methyl)amino)-4-(4-fluorophenyl)thiazole-5-carbonitrile (Compound 31)

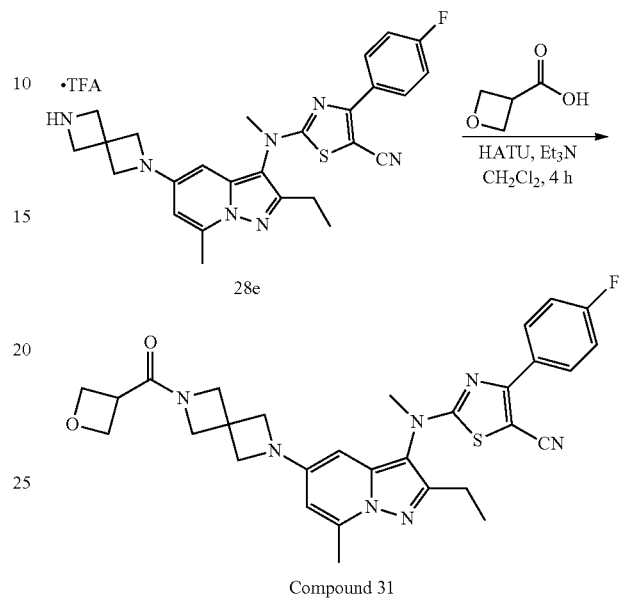

Compound 31

To a solution of 28e (71 mg, 0.145 mmol) in DCM (10 mL) were successively added oxetane-3-carboxylic acid (17.8 mg, 0.174 mmol), HATU (67 mg, 0.174 mmol) and Et$_3$N (0.5 mL, 3.6 mmol). The reaction mixture was stirred at room temperature for 1 h, then the mixture was diluted with water (10 mL) and extracted with DCM (10 mL×3). The combined organic layers were then washed with water (10 mL×2) and brine (5 mL×1), dried over Na$_2$SO$_4$, filtered, and concentrated in vacuo. The residue was purified by flash chromatography to afford the title Compound 31 (50 mg, 85%) as a light brown solid. $^1$H NMR (400 MHz, CDCl$_3$) δ 8.15 (dd, 2H), 7.17 (t, 2H), 6.07 (s, 1H), 5.87 (s, 1H), 4.89 (t, 2H), 4.74 (dd, 2H), 4.19 (d, 7H), 3.85-3.74 (m, 2H), 3.56 (d, 3H), 2.90 (d, 5H), 1.38 (t, 3H). LC-MS: m/z=572.3 [M+H]$^+$.

Example 32: 2-((2-ethyl-7-methyl-5-(6-(4-methyl-piperazine-1-carbonyl)-2,6-diazaspiro[3.3]heptan-2-yl)pyrazolo[1,5-a]pyridin-3-yl)(methyl)amino)-4-(4-fluorophenyl)thiazole-5-carbonitrile (Compound 32)

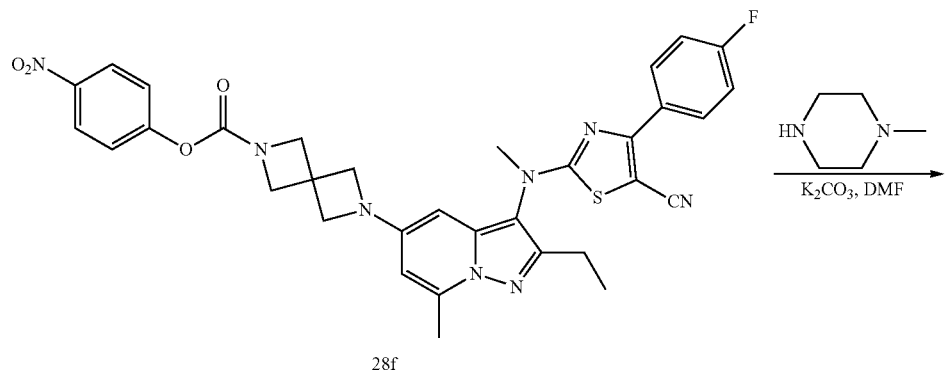

28f

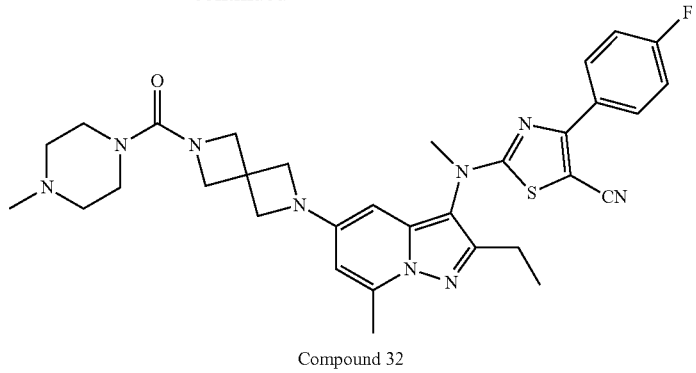

Compound 32

To a solution of 28f (89 mg, 0.136 mmol) in DMF (5 mL) was added K₂CO₃ (75 mg, 0.55 mmol) and 1-methylpiperazine (27 mg, 0.27 mmol). The reaction mixture was heated to 100° C. for 2 h and then filtered, and the solid was washed with ethyl acetate. The filtrate was then suspended in 50 mL of water, extracted with ethyl acetate, the organic layer was dried over magnesium sulfate, filtered, and concentrated in vacuo. The residue was purified by column chromatography on silica gel to give the title Compound 32 (28 mg, 33%). ¹H NMR (400 MHz, CDCl₃) δ 8.22-8.06 (m, 2H), 7.20-7.09 (m, 2H), 5.95 (s, 1H), 5.87-5.79 (m, 1H), 4.18 (s, 4H), 4.04 (s, 4H), 3.98-3.82 (m, 2H), 3.82-3.64 (m, 3H), 3.57 (s, 3H), 3.44-3.34 (m, 2H), 2.83-2.70 (m, 6H), 2.69 (s, 3H), 1.32 (t, J=7.6 Hz, 3H). LC-MS: m/z=614.3 [M+H]⁺.

Example 33: 2-((2-ethyl-7-methyl-5-(6-(1-methylpiperidine-4-carbonyl)-2,6-diazaspiro[3.3]heptan-2-yl)pyrazolo[1,5-a]pyridin-3-yl)(methyl)amino)-4-(4-fluorophenyl)thiazole-5-carbonitrile (Compound 33)

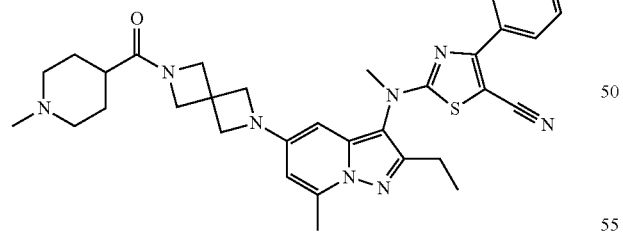

Compound 33

The title compound was prepared by the method substantially similar to that mentioned in Example 31, using 1-methylpiperidine-4-carboxylic acid to afford Compound 33 as a pale yellow solid. ¹H NMR (400 MHz, CDCl₃) δ 8.19-8.12 (m, 2H), 7.16 (t, 2H), 5.97 (s, 1H), 5.84 (d, 1H), 4.36 (s, 2H), 4.20 (s, 2H), 4.09 (s, 4H), 3.57 (s, 3H), 3.40 (s, 3H), 2.75 (dq, 8H), 2.50 (s, 5H), 1.32 (t, 4H). LC-MS (ESI): m/z=613.3 [M+H]⁺

Example 34: tetrahydrofuran-3-yl 6-(3-((5-cyano-4-(4-fluorophenyl)thiazol-2-yl)(methyl)amino)-2-ethyl-7-methylpyrazolo[1,5-a]pyridin-5-yl)-2,6-diazaspiro[3.3]heptane-2-carboxylate (Compound 34)

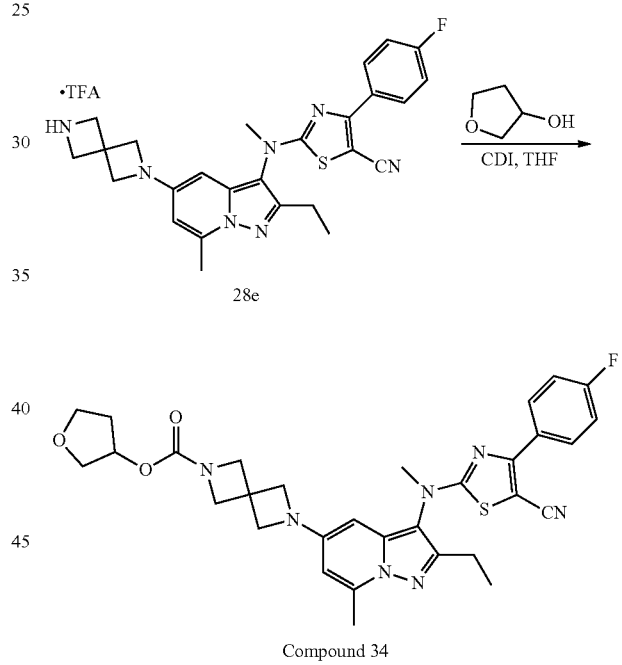

Compound 34

To a solution of tetrahydrofuran-3-ol (120 mg, 1.36 mmol) in THF (10 mL) at r.t. under N₂ (g) was added 1,1'-carbonylbis(1H-imidazole) (218 mg, 1.36 mmol) in THF (10 mL). The mixture was stirred for 1 h, then 28e was added, and the reaction was stirred overnight at 70° C. The solvent was removed, and the residue was purified by column chromatography on silica gel to give the title Compound 34 (28 mg, 34%). ¹H NMR (400 MHz, CDCl₃) δ 8.25-8.02 (m, 2H), 7.16 (t, J=8.7 Hz, 2H), 5.98 (s, 1H), 5.84 (s, 1H), 5.30-5.09 (m, 1H), 4.17 (s, 4H), 4.06 (s, 4H), 3.97-3.73 (m, 4H), 3.57 (s, 3H), 2.82-2.61 (m, 5H), 2.30-2.08 (m, 2H), 1.33 (t, J=7.6 Hz, 3H). LC-MS (ESI): m/z=602.2 [M+H]⁺

Example 35: 2-((2-ethyl-7-methyl-5-(6-(oxazol-2-yl)-2,6-diazaspiro[3.3]heptan-2-yl)pyrazolo[1,5-a]pyridin-3-yl)(methyl)amino)-4-(4-fluorophenyl)thiazole-5-carbonitrile (Compound 35)

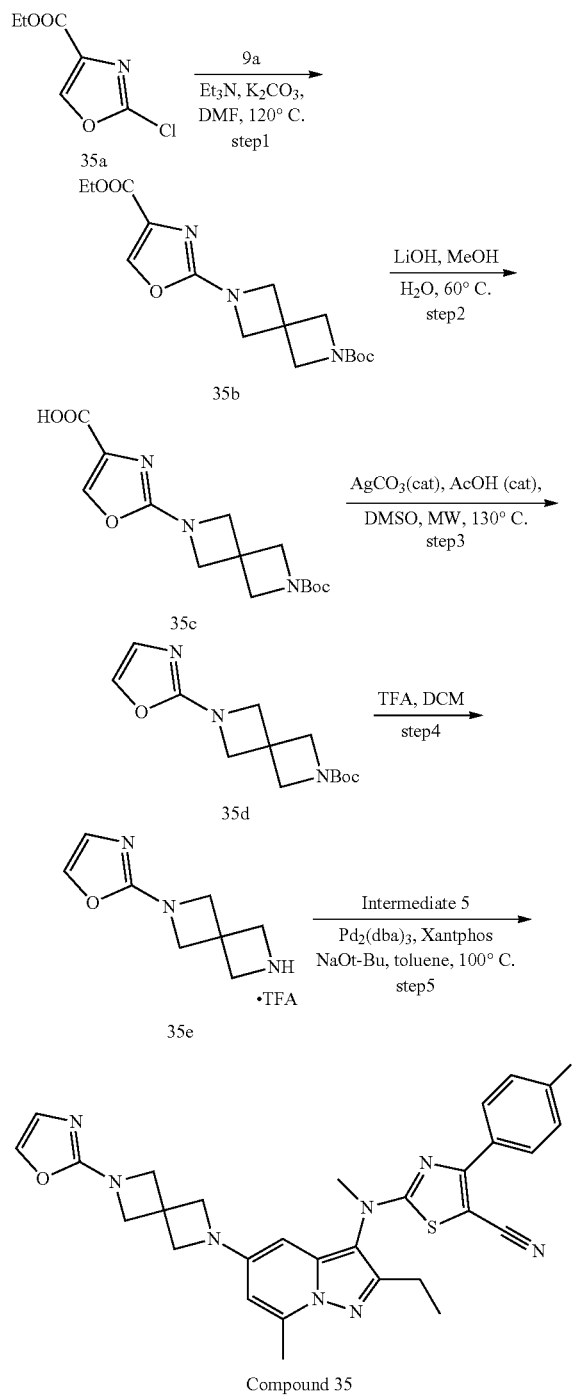

Compound 35

Step 1: ethyl 2-(6-(tert-butoxycarbonyl)-2,6-diazaspiro[3.3]heptan-2-yl)oxazole-4-carboxylate (35b)

To a solution of ethyl 2-chlorooxazole-4-carboxylate (5.0 g, 28.00 mmol) in DMF (50 ml) was added 9a (12.0 g, 43.0 mmol), $K_2CO_3$ (12.0 g, 85.0 mmol), triethylamine (5.8 g, 57.0 mmol). The mixture was stirred for 2 h at 120° C. After cooling to room temperature, then the reaction mixture was partitioned between ethyl acetate (100 ml) and water (150 ml). The organic layer was washed with brine, dried ($Na_2SO_4$), filtered and concentrated under reduced pressure, the residue was directly used for the next step without purification. $^1$H NMR (400 MHz, $CDCl_3$) δ 7.77 (s, 1H), 4.35 (q, 2H), 4.27 (d, 4H), 4.08 (d, 4H), 1.44 (s, 9H), 1.35 (m, 3H). LC-MS (ESI): m/z=338.2 [M+H]$^+$ Step 2: 2-(6-(tert-butoxycarbonyl)-2,6-diazaspiro[3.3]heptan-2-yl)oxazole-4-carboxylic acid (35c)

To a solution of 35b (9.5 g, 28.0 mmol) in methanol (150 mL), water (50 mL) was added lithium hydroxide (3.4 g, 140.0 mmol). The mixture was stirred for 2 h at 60° C. After cooling to room temperature, and concentrated. The paste was treated with 50 mL of water, diluted with hydrochloric acid PH=3~4, and was extracted with ethyl acetate, The organic layer was washed with brine, dried ($Na_2SO_4$), filtered and concentrated under reduced pressure, the residue was directly used for the next step without purification. $^1$H NMR (400 MHz, $CDCl_3$) δ 7.88 (s, 1H), 4.31 (s, 4H), 4.12 (s, 4H), 1.46 (s, 9H). LC-MS (ESI): m/z=310.2 [M+H]$^+$ Step 3: tert-butyl 6-(oxazol-2-yl)-2,6-diazaspiro[3.3]heptane-2-carboxylate (35d)

To a solution of 35c (0.2 g, 0.6 mmol) in DMSO (6 mL) was added silver carbonate (40 mg, 0.1 mmol) and acetic acid (4 mg, 0.06 mmol). The resulting mixture was submitted to microwave irradiation at 130° C. for 15 min at a maximum power of 150 W and subsequently air-jet cooled to room temperature. The reaction mixture was then poured into water and extracted repeatedly with ethyl acetate. The organic layer was dried over magnesium sulfate, filtered, and concentrated in vacuo. The residue was purified by column chromatography on silica gel to give 35d (50 mg, 30%). $^1$H NMR (400 MHz, $CDCl_3$) δ 7.21 (d, 1H), 6.81 (s, 1H), 4.24 (s, 4H), 4.09 (s, 4H), 1.44 (s, 9H). LC-MS (ESI): m/z=266.2 [M+H]$^+$ Step 4: 2-(2,6-diazaspiro[3.3]heptan-2-yl)oxazole trifluoroacetate (35e)

To a solution of 35d (50 mg, 0.18 mmol) in dichloromethane (6 mL) was added TFA (3 mL) at room temperature, The reaction mixture was stirred for 1 h and concentrated, the residue was directly used for the next step without purification. LC-MS (ESI): m/z=166.2 [M+H]$^+$ Step 5: 2-((2-ethyl-7-methyl-5-(6-(oxazol-2-yl)-2,6-diazaspiro[3.3]heptan-2-yl)pyrazolo[1,5-a]pyridin-3-yl)(methyl)amino)-4-(4-fluorophenyl)thiazole-5-carbonitrile (Compound 35)

35e (53 mg, 0.2 mmol) was added trimethylamine in toluene (5 mL) until PH=7~8, the resulting mixture was added Intermediate 5 (91 mg, 0.2 mmol), $Pd_2(dba)_3$ (17 mg, 0.02 mmol), XantPhos (0.2 g, 0.04 mmol), sodium tert-butoxide (0.22 g, 2.4 mmol) and the tube was evacuated and back filled with argon. The reaction mixture was heated at 100° C. for 4 h. After cooling to room temperature, the suspension was diluted with dichloromethane and filtered through Celite. The solvent was removed to give a brown residue which was purified by flash chromatography on a silica give the Compound 35 (50 mg, 46%). $^1$H NMR (400 MHz, CDCl$_3$) δ 8.22-8.06 (m, 2H), 7.23 (d, 1H), 7.16 (t, 2H), 6.85 (s, 1H), 5.97 (s, 1H), 5.84 (d, 1H), 4.36 (s, 4H), 4.21-4.02 (m, 4H), 3.57 (s, 3H), 2.74 (q, 2H), 2.69 (s, 3H), 1.32 (t, 3H). LC-MS (ESI): m/z=555.2 [M+H]$^+$
Example 36: 2-((2-ethyl-5-(2-(3-hydroxyazetidine-1-carbonyl)-2,6-diazaspiro[3.4]octan-6-yl)-7-methyl-pyrazolo[1,5-a]pyridin-3-yl)(methypamino)-4-(4-fluorophenyl)thiazole-5-carbonitrile
(Compound 36)
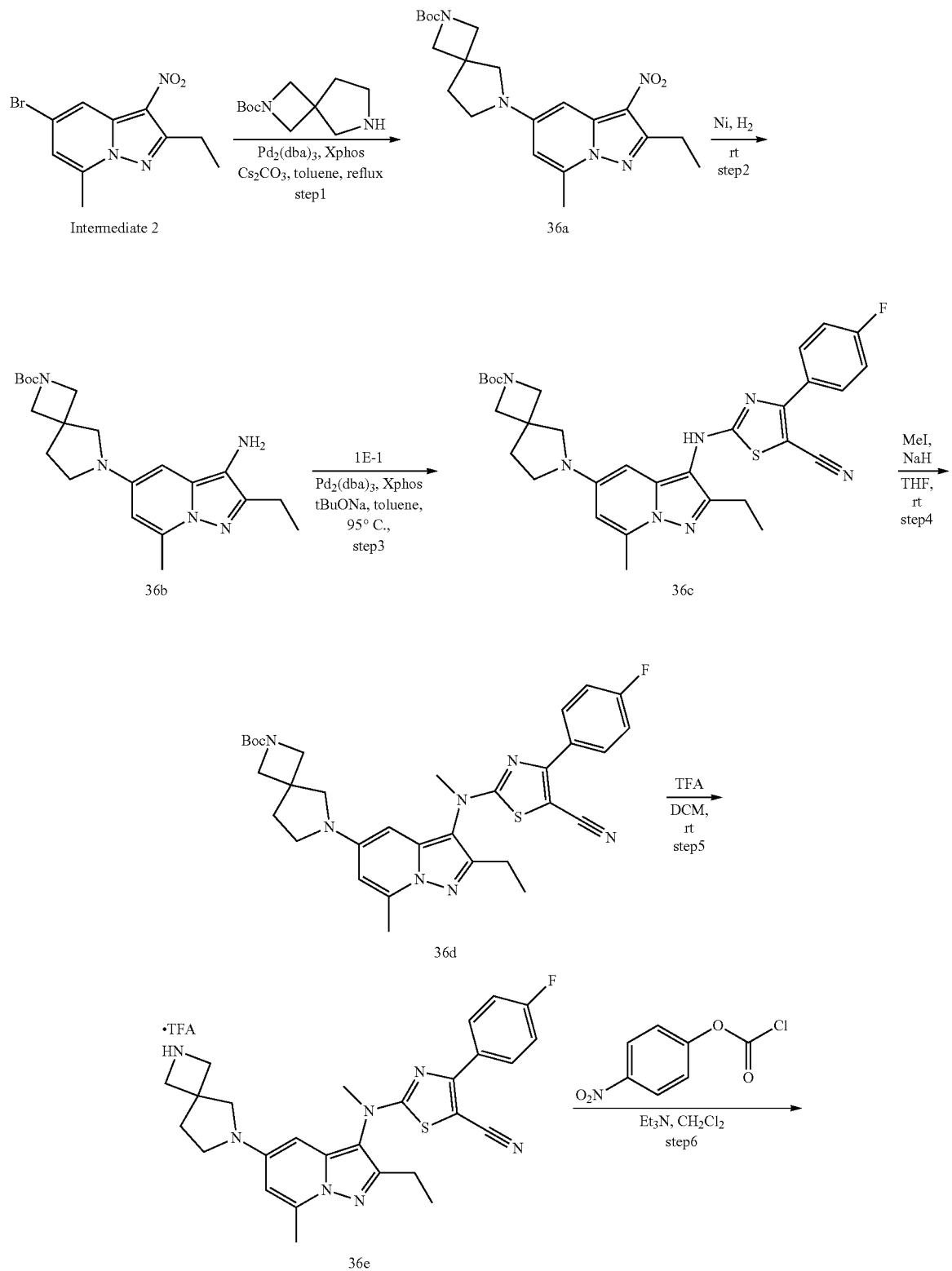

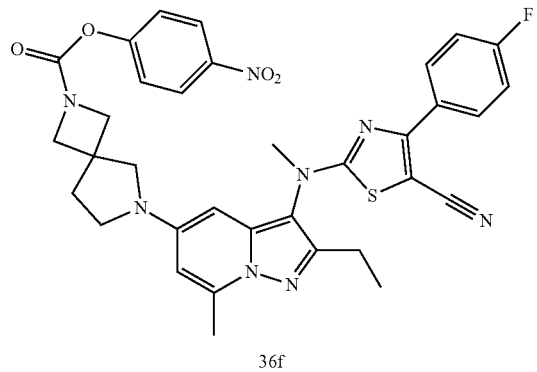

36f

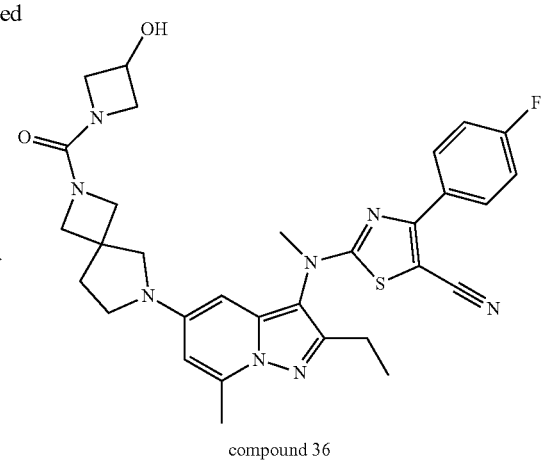

compound 36

6d
K₂CO₃,
DMF
step7

Step 1: tert-butyl 6-(2-ethyl-7-methyl-3-nitropyrazolo[1,5-a]pyridin-5-yl)-2,6-diazaspiro[3.4]octane-2-carboxylate (36a)

Intermediate 2 (940 mg, 3.3 mmol), Pd₂(dba)₃ (303 mg, 0.33 mmol), X-PHOS (315 mg, 0.66 mmol), and Cs₂CO₃ (5.4 g, 16.5 mmol) were added to a screw capped test tube. The tube was evacuated and back filled with argon. tert-butyl 2,6-diazaspiro[3.4]octane-2-carboxylate (1.1 g, 5.0 mmol) and toluene (40 mL) were added successively by syringe at room temperature. The tube was sealed with a Teflon-lined cap, and the reaction mixture was heated at 112° C. for 20 h. After cooling to room temperature, the suspension was diluted with dichloromethane and filtered through Celite. The solvent was removed with the aid of a rotary evaporator to give a brown residue which was purified by column chromatography on silica gel to give the title compound 36a (630 mg, 46%). ¹H NMR (400 MHz, CDCl₃) δ 7.59-7.43 (m, 1H), 6.30-6.08 (m, 1H), 3.92 (q, J=8.7 Hz, 4H), 3.60 (s, 2H), 3.50 (t, J=6.9 Hz, 2H), 3.39 (q, J=7.6 Hz, 2H), 2.72 (s, 3H), 2.29 (t, J=6.9 Hz, 2H), 1.55 (t, J=7.6 Hz, 3H), 1.45 (s, 9H).

Step 2: tert-butyl 6-(3-amino-2-ethyl-7-methylpyrazolo[1,5-a]pyridin-5-yl)-2,6-diazaspiro [3.4]octane-2-carboxylate (36b)

36a (630 mg, 1.52 mmol) was dissolved in methanol (10 mL), then Raney-Nickel (600 mg) was added and the mixture was stirred under hydrogen (balloon) for 4 h at room temperature. Then the mixture was filtered and diluted with methanol (2×10 mL). The organic filtrate was concentrated under reduced pressure, the residue was directly used for the next step without purification. LC-MS (ESI): m/z=386.3 [M+H]⁺

Step 3: tert-butyl 6-(3-((5-cyano-4-(4-fluorophenyl) thiazol-2-yl)amino)-2-ethyl-7-methyl pyrazolo[1,5-a]pyridin-5-yl)-2,6-diazaspiro[3.4]octane-2-carboxylate (36c)

36b (585 mg, 1.52 mmol), Pd₂(dba)₃ (139 mg, 0.15 mmol), X-PHOS (145 mg, 0.30 mmol), and sodium tert-butoxide (365 mg, 3.79 mmol) were added to a screw capped test tube. The tube was evacuated and back filled with argon. 1E-1 (362 mg, 1.52 mmol) and toluene (50 mL) were added successively by syringe at room temperature. The tube was sealed with a Teflon-lined cap, and the reaction mixture was heated at 95 for 2.5 h. After cooling to room temperature, the suspension was diluted with dichloromethane and filtered through Celite. The solvent was removed with the aid of a rotary evaporator to give a brown residue which was purified by column chromatography on silica gel to give the title compound 36c (485 mg, 54%). ¹H NMR (400 MHz, CDCl₃) δ 8.09-7.98 (m, 2H), 7.16-6.98 (m, 2H), 6.26-6.08 (m, 1H), 6.03-5.82 (m, 1H), 3.90 (dd, J=18.7, 8.7 Hz, 4H), 3.50 (s, 2H), 3.40 (t, J=6.8 Hz, 2H), 2.78 (q, J=7.5 Hz, 2H), 2.72 (s, 3H), 2.23 (t, J=6.8 Hz, 2H), 1.44 (s, 9H), 1.31 (t, J=7.6 Hz, 3H). LC-MS (ESI): m/z=588.3 [M+H]⁺

Step 4: tert-butyl 6-(3-((5-cyano-4-(4-fluorophenyl) thiazol-2-yl)(methyl)amino)-2-ethyl-7-methylpyrazolo[1,5-a]pyridin-5-yl)-2,6-diazaspiro[3.4]octane-2-carboxylate (36d)

To a solution of 36c (485 mg, 0.83 mmol) and iodomethane (351 mg, 2.48 mmol) in THF (10 mL) was added sodium hydride (60%, 99 mg, 2.48 mmol) under cooling with ice water, and the reaction mixture was stirred for 40 min at room temperature. The reaction mixture was then poured into crashed ice, and was extracted with ethyl acetate. The organic layer was dried over magnesium sulfate, filtered, and concentrated in vacuo. The residue was purified by column chromatography on silica gel to give the title compound 36d (390 mg, 79%). ¹H NMR (400 MHz, CDCl₃) δ 8.21-8.04 (m, 2H), 7.21-7.04 (m, 2H), 6.29-6.11 (m, 1H), 5.99-5.78 (m, 1H), 3.98-3.78 (m, 4H), 3.58 (s, 3H), 3.51 (s, 2H), 3.41 (t, J=6.8 Hz, 2H), 2.83-2.68 (m, 5H), 2.23 (t, J=6.8 Hz, 2H), 1.44 (s, 9H), 1.33 (t, J=7.6 Hz, 3H).

Step 5: 2-((2-ethyl-7-methyl-5-(2,6-diazaspiro[3.4] octan-6-yl)pyrazolo[1,5-a]pyridin-3-yl)(methyl) amino)-4-(4-fluorophenyl)thiazole-5-carbonitrile 2,2,2-trifluoroacetate (36e)

To a solution of 36d (390 mg, 0.65 mmol) in dichloromethane (6 mL) was added TFA (3 mL) at room temperature, The reaction mixture was stirred for 3 h and concentrated, the residue was directly used for the next step without purification.

Step 6: 4-nitrophenyl 6-(3-((5-cyano-4-(4-fluorophenyl)thiazol-2-yl)(methyl)amino)-2-ethyl-7-methylpyrazolo[1,5-a]pyridin-5-yl)-2,6-diazaspiro[3.4]octane-2-carboxylate (36f)

Triethylamine (656 mg, 6.48 mmol) and p-nitrophenyl chloroformate (157 mg, 0.78 mmol) were added to a solution of 36e (325 mg, 0.65 mmol) in dry dichloromethane (5 mL) at room temperature under an argon atmosphere. After 2 h, the reaction mixture was quenched with water, diluted with ethyl acetate (50 mL), washed with water (2×50 mL), and brine (100 mL). All volatiles were removed under reduced pressure and the residue was directly used for the next step without purification. LC-MS (ESI): m/z=667.3 [M+H]$^+$ Step 7: 2-((2-ethyl-5-(2-(3-hydroxyazetidine-1-carbonyl)-2,6-diazaspiro[3.4]octan-6-yl)-7-methylpyrazolo[1,5-a]pyridin-3-yl)(methyl)amino)-4-(4-fluorophenyl)thiazole-5-carbonitrile (Compound 36)

To a solution of 36f (432 mg, 0.65 mmol) in DMF (5 mL) was added K$_2$CO$_3$ (537 mg, 3.88 mmol) and azetidin-3-ol hydrochloride (211 mg, 1.94 mmol). The reaction mixture was heated to 100° C. for 2 h and then filtered, and the solid was washed with ethyl acetate. The filtrate was then suspended in 50 mL of water, extracted with ethyl acetate, the organic layer was dried over magnesium sulfate, filtered, and concentrated in vacuo. The residue was purified by column chromatography on silica gel to give the title compound 36 (210 mg, 54%). $^1$H NMR (400 MHz, CDCl$_3$) δ 8.31-7.96 (m, 2H), 7.15 (t, J=8.7 Hz, 2H), 6.15 (s, 1H), 5.98-5.76 (m, 1H), 4.70-4.45 (m, 1H), 4.22-4.05 (m, 2H), 3.91 (q, J=8.5 Hz, 4H), 3.81 (dd, J=9.1, 4.5 Hz, 2H), 3.58 (s, 3H), 3.50 (s, 2H), 3.39 (t, J=6.8 Hz, 2H), 2.81-2.63 (m, 5H), 2.21 (t, J=6.8 Hz, 2H), 1.32 (t, J=7.6 Hz, 3H). LC-MS (ESI): m/z=601.3 [M+H]$^+$ Example 37: 2-((2-ethyl-5-(2-(3-hydroxyazetidine-1-carbonyl)-2,8-diazaspiro[4.5]decan-8-yl)-7-methylpyrazolo[1,5-a]pyridin-3-yl)(methyl)amino)-4-(4-fluorophenyl)thiazole-5-carbonitrile (Compound 37)

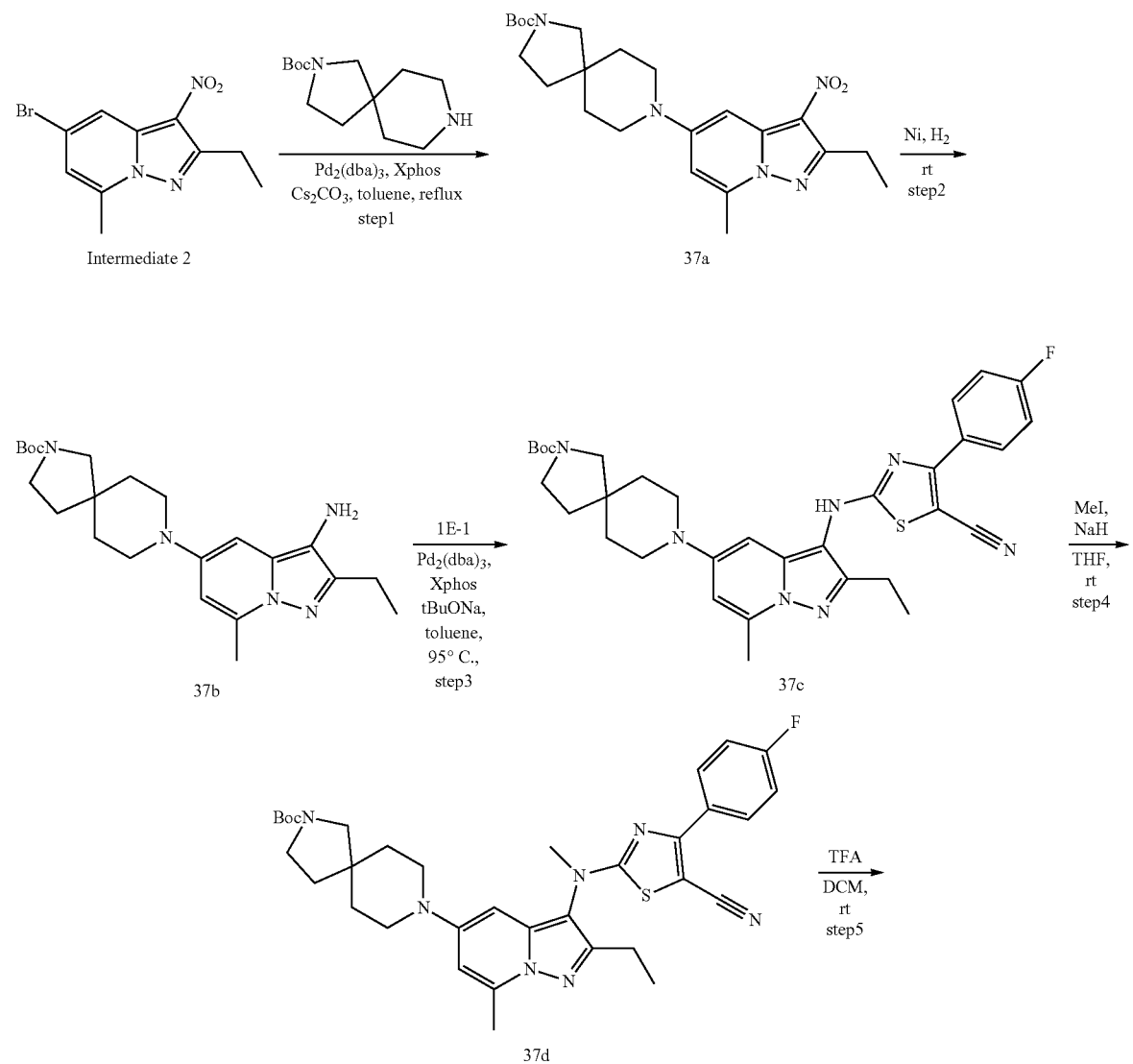

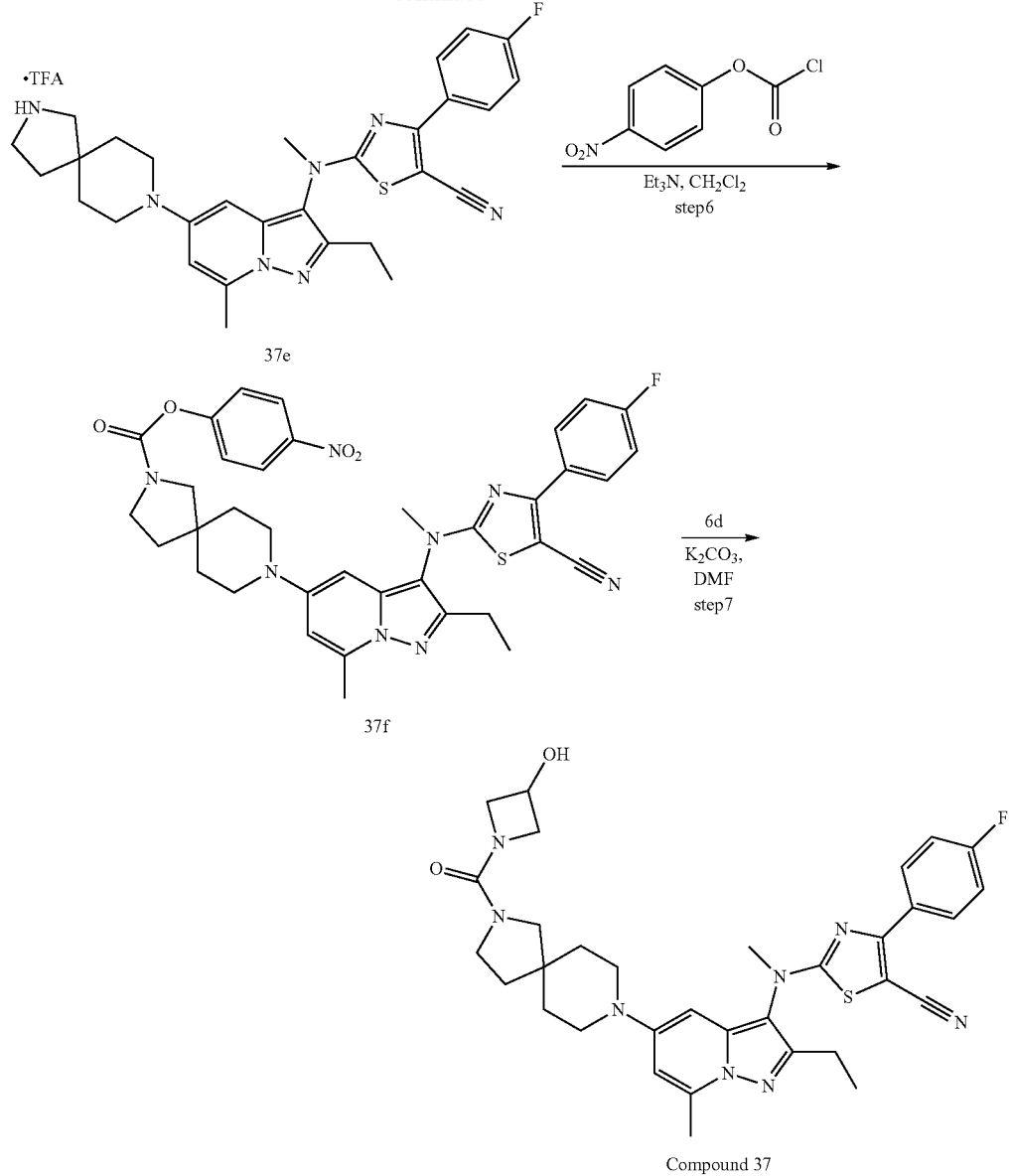

Compound 37

Step 1: tert-butyl 8-(2-ethyl-7-methyl-3-nitropyrazolo[1,5-a]pyridin-5-yl)-2,8-diazaspiro[4.5]decane-2-carboxylate (37a)

Intermediate 2 (0.7 g, 2.0 mmol), $Pd_2(dba)_3$ (0.2 g, 0.2 mmol), X-PHOS (0.2 g, 0.5 mmol), and $Cs_2CO_3$ (2.0 g, 7.0 mmol) were added to a screw capped test tube. The tube was evacuated and back filled with argon. tert-butyl 2,8-diazaspiro[4.5]decane-2-carboxylate (0.9 g, 4.0 mmol) and toluene (30 mL) were added successively by syringe at room temperature. The tube was sealed with a Teflon-lined cap, and the reaction mixture was heated at 100° C. for 5 h. After cooling to room temperature, the suspension was diluted with dichloromethane and filtered through Celite. The solvent was removed with the aid of a rotary evaporator to give a brown residue which was purified by column chromatography on silica gel to give the title compound 37a (0.24 g, 20%).

Step 2: tert-butyl 8-(3-amino-2-ethyl-7-methylpyrazolo[1,5-a]pyridin-5-yl)-2,8-diazaspiro [4.5]decane-2-carboxylate (37b)

37a (0.24 g, 0.54 mmol) was dissolved in methanol (10 mL), then Raney Ni (0.2 g) was added and the mixture was stirred under hydrogen (balloon) for 1 h at room temperature. Then the mixture was filtered and diluted with methanol (2×10 mL). The organic filtrate was concentrated under reduced pressure, the residue was directly used for the next step without purification.

Step 3: tert-butyl 8-(3-((5-cyano-4-(4-fluorophenyl) thiazol-2-yl)amino)-2-ethyl-7-methylpyrazolo[1,5-a] pyridin-5-yl)-2,8-diazaspiro[4.5]decane-2-carboxylate (37c)

37b (220 mg, 0.53 mmol), X-PHOS (51 mg, 0.11 mmol), and sodium tert-butoxide (150 mg, 1.6 mmol) were added to a screw capped test tube. The tube was evacuated and back filled with argon. 2-chloro-4-(4-fluorophenyl)thiazole-5-carbonitrile (100 mg, 0.43 mmol) and toluene (5 mL) were added successively by syringe at room temperature. The tube was sealed with a Teflon-lined cap, and the reaction mixture was heated at 100° C. for 3 h. After cooling to room temperature, the suspension was diluted with dichloromethane and filtered through Celite. The solvent was removed with the aid of a rotary evaporator to give a brown residue which was purified by column chromatography on silica gel, eluting with dichloromethane and then (dichloromethane/methanol=30:1) to give the title compound 37c (95 mg, 29%). LC-MS: m/z (ESI): 616.3[M+H$^+$].

Step 4: tert-butyl 8-(3-((5-cyano-4-(4-fluorophenyl)thiazol-2-yl)(methypamino)-2-ethyl-7-methylpyrazolo[1,5-a]pyridin-5-yl)-2,8-diazaspiro[4.5]decane-2-carboxylate (37d)

To a solution of 37c (95 mg, 0.15 mmol) and iodomethane (109 mg, 0.77 mmol) in THF (5 mL) was added sodium hydride (60%, 11 mg, 0.45 mmol) under cooling with ice water, and the reaction mixture was stirred for 1 hour at room temperature. The reaction mixture was then poured into crashed ice, and was extracted with ethyl acetate. The organic layer was dried over sodium sulfate, filtered, and concentrated in vacuo, the residue was directly used for the next step without purification.

Step 5: 2-((2-ethyl-7-methyl-5-(2,8-diazaspiro[4.5]decan-8-yl)pyrazolo[1,5-a]pyridin-3-yl)(methyl)amino)-4-(4-fluorophenyl)thiazole-5-carbonitrile (37e)

To a solution of 37d (98 mg, 0.15 mmol) in dichloromethane (3 mL) was added TFA (3 mL) at room temperature, The reaction mixture was stirred for 3 h and concentrated, the residue was directly used for the next step without purification. LC-MS: m/z (ESI): 530.2[M+H$^+$].

Step 6: 4-nitrophenyl 8-(3-((5-cyano-4-(4-fluorophenyl)thiazol-2-yl)(methyl)amino)-2-ethyl-7-methylpyrazolo[1,5-a]pyridin-5-yl)-2,8-diazaspiro[4.5]decane-2-carboxylate (37f)

Triethylamine (153 mg, 1.5 mmol) and p-nitrophenyl chloroformate (46 mg, 0.23 mmol) were added to a solution of 37e (80 mg, 0.15 mmol) in dry dichloromethane (5 mL) under an argon atmosphere at room temperature. After 2 h, the reaction mixture was quenched with water, diluted with dichloromethane (20 mL), washed with water (3×15 mL). All volatiles were removed under reduced pressure and the residue was directly used for the next step without purification.

Step 7: 2-((2-ethyl-5-(2-(3-hydroxyazetidine-1-carbonyl)-2,8-diazaspiro[4.5]decan-8-yl)-7-methylpyrazolo[1,5-a]pyridin-3-yl)(methyl)amino)-4-(4-fluorophenyl)thiazole-5-carbonitrile (Compound 37)

To a solution of 37f (100 mg, 0.14 mmol) in DMF (4 mL) was added K$_2$CO$_3$ (60 mg, 0.43 mmol) and azetidin-3-ol hydrochloride (21 mg, 0.29 mmol), the reaction mixture was heated at 110° C. for 3 h, then filtered, and the solid was washed with ethyl acetate. The filtrate was then suspended in 30 mL water, extracted with ethyl acetate, the organic layer was dried over sodium sulfate, filtered, and concentrated in vacuo. The residue was purified by column chromatography on silica gel to give the title Compound 37 (26 mg, 29%). $^1$H NMR (400 MHz, CDCl$_3$) δ 8.19-8.11 (m, 2H), 7.19-7.12 (m, 2H), 6.53 (s, 1H), 6.40 (s, 1H), 4.64-4.54 (m, 1H), 4.20 (m, 2H), 3.84 (m, 2H), 3.59 (s, 3H), 3.42 (t, 2H), 3.32 (s, 2H), 3.28 (s, 2H), 3.20 (d, 2H), 2.81-2.74 (m, 2H), 2.72 (s, 3H), 1.80 (t, 3H), 1.73 (s, 4H), 1.33 (t, 3H), 1.26 (s, 1H). LC-MS m/z (ESI): 629.3[M+H$^+$].

Example 38: 2-((2-ethyl-7-methyl-5-(6-(tetrahydrofuran-2-carbonyl)-2,6-diazaspiro[3.3]heptan-2-yl)pyrazolo[1,5-a]pyridin-3-yl)(methyl)amino)-4-(4-fluorophenyl)thiazole-5-carbonitrile (Compound 38)

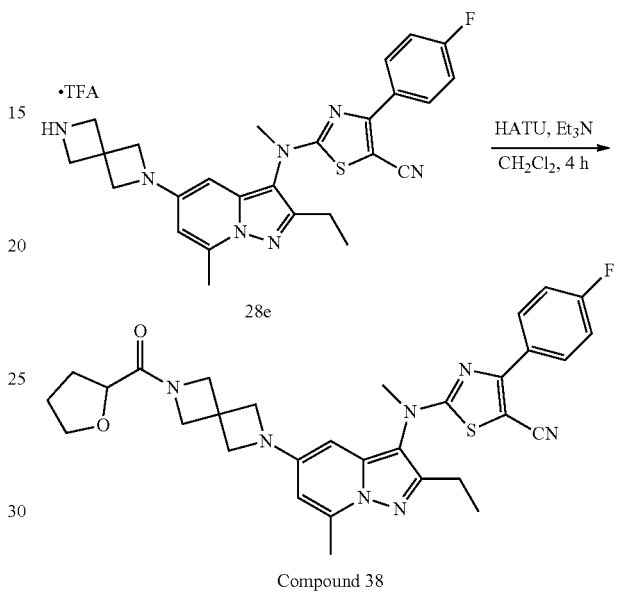

To a solution of 28e (58 mg, 0.1 mmol) in DCM (10 mL) were successively added tetrahydrofuran-2-carboxylic acid (20 mg, 0.16 mmol), HATU (60 mg, 0.16 mmol) and Et$_3$N (0.5 mL, 3.6 mmol). The reaction mixture was stirred at room temperature for 4 h, then the mixture was diluted with water (10 mL) and extracted with DCM (10 mL×3). The combined organic layers were then washed with water (10 mL×2) and brine (5 mL×1), dried over Na$_2$SO$_4$, filtered, and concentrated in vacuo. The residue was purified by flash chromatography to afford the title Compound 38 (50 mg, 85%) as a light brown solid. $^1$H NMR (400 MHz, CDCl$_3$) δ 8.20-8.10 (m, 2H), 7.17 (dd, 2H), 6.07 (s, 1H), 5.86 (s, 1H), 4.53 (d, 1H), 4.46-4.32 (m, 1H), 4.18 (d, 2H), 3.95-3.78 (m, 3H), 3.56 (d, 2H), 2.89 (dd, 3H), 2.24-2.06 (m, 3H), 2.01-1.82 (m, 3H), 1.43-1.33 (m, 3H). LC-MS: m/z=572.3 [M+H]$^+$.

Example 39: (S)-2-((2-ethyl-7-methyl-5-(6-(tetrahydrofuran-3-carbonyl)-2,6-diazaspiro[3.3]heptan-2-yl)pyrazolo[1,5-a]pyridin-3-yl)(methyl)amino)-4-(4-fluorophenyl)thiazole-5-carbonitrile (Compound 39)

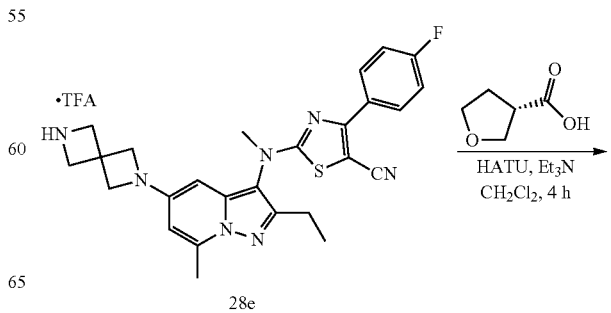

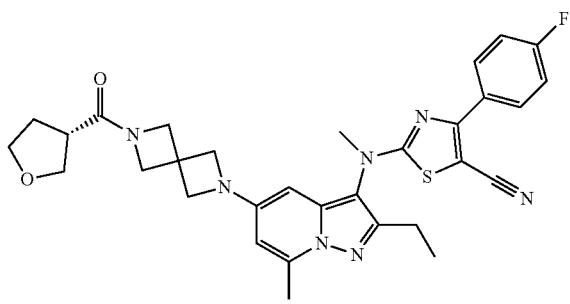

Compound 39

To a solution of 28e (70 mg, 0.14 mmol) in dichloromethane (5 mL) was added HATU (65 mg, 0.17 mmol), triethylamine (58 mg, 0.57 mmol) and (S)-tetrahydrofuran-3-carboxylic acid (25 mg, 0.21 mmol). The reaction mixture was stirred at room temperature for 3 h and then the reaction mixture was quenched with water, extracted with ethyl acetate, the organic layer was washed with water (3×15 mL) and then dried over magnesium sulfate, filtered, and concentrated in vacuo. The residue was purified by column chromatography on silica gel to give the title Compound 39 (37 mg, 44%). $^1$H NMR (400 MHz, CDCl$_3$) δ 8.20-8.10 (m, 2H), 7.20-7.09 (m, 2H), 5.97 (s, 1H), 5.85 (d, J=2.1 Hz, 1H), 4.35 (dd, J=17.0, 9.1 Hz, 2H), 4.20 (s, 2H), 4.09 (d, J=15.1 Hz, 4H), 3.99 (t, J=8.2 Hz, 1H), 3.93-3.76 (m, 3H), 3.57 (s, 3H), 2.98-2.86 (m, 1H), 2.75 (q, J=7.6 Hz, 2H), 2.70 (s, 3H), 2.17 (dd, J=12.3, 6.8 Hz, 1H), 2.09-2.02 (m, 1H), 1.32 (t, J=7.6 Hz, 3H). LC-MS: m/z=586.2 [M+H]$^+$ Example 40: (R)-2-((2-ethyl-7-methyl-5-(6-(tetrahydrofuran-3-carbonyl)-2,6-diazaspiro[3.3]heptan-2-yl)pyrazolo[1,5-a]pyridin-3-yl)(methyl)amino)-4-(4-fluorophenyl)thiazole-5-carbonitrile (Compound 40)

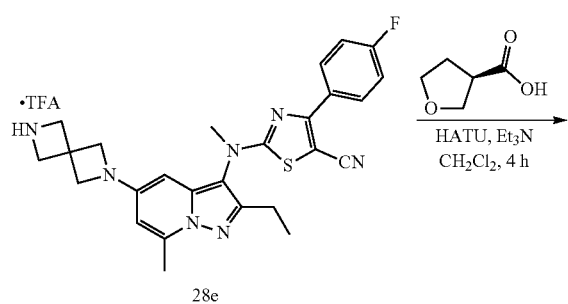

28e

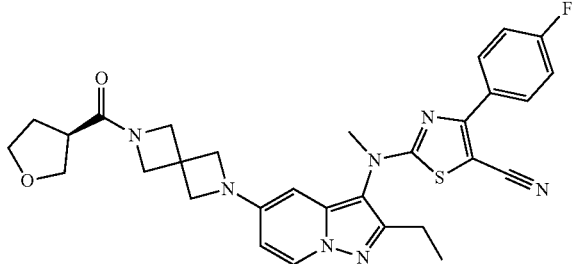

Compound 40

To a solution of 28e (70 mg, 0.14 mmol) in dichloromethane (5 mL) was added HATU (65 mg, 0.17 mmol), triethylamine (58 mg, 0.57 mmol) and (S)-tetrahydrofuran-3-carboxylic acid (25 mg, 0.21 mmol). The reaction mixture was stirred at room temperature for 3 h and then the reaction mixture was quenched with water, extracted with ethyl acetate, the organic layer was washed with water (3×15 mL) and then dried over magnesium sulfate, filtered, and concentrated in vacuo. The residue was purified by column chromatography on silica gel to give the title Compound 40 (32 mg, 38%). $^1$H NMR (400 MHz, CDCl$_3$) δ 8.19-8.10 (m, 2H), 7.21-7.09 (m, 2H), 5.97 (d, J=1.3 Hz, 1H), 5.85 (d, J=2.2 Hz, 1H), 4.35 (q, J=9.1 Hz, 2H), 4.21 (d, J=11.6 Hz, 2H), 4.12-4.03 (m, 4H), 3.99 (t, J=8.2 Hz, 1H), 3.86 (dddd, J=25.8, 18.9, 12.1, 7.1 Hz, 3H), 3.57 (s, 3H), 2.92 (dt, J=15.2, 7.4 Hz, 1H), 2.75 (q, J=7.6 Hz, 2H), 2.70 (s, 3H), 2.17 (td, J=14.0, 7.2 Hz, 1H), 2.10-2.02 (m, 1H), 1.32 (t, J=7.6 Hz, 3H). LC-MS: m/z=586.2 [M+H]$^+$ Example 41: 2-((2-ethyl-7-methyl-5-(6-(tetrahydro-2H-pyran-4-carbonyl)-2,6-diazaspiro[3.3]heptan-2-yl)pyrazolo[1,5-a]pyridin-3-yl)(methyl)amino)-4-(4-fluorophenyl)thiazole-5-carbonitrile (Compound 41)

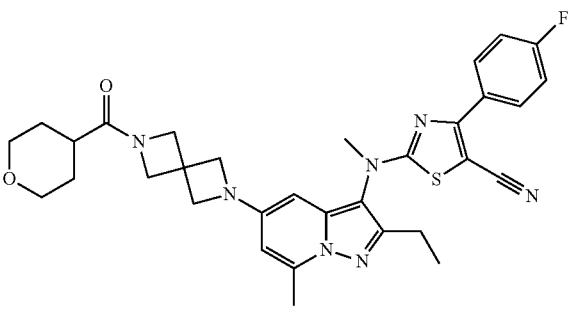

Compound 41

The title compound was prepared by the method substantially similar to that mentioned in Example 31, using tetrahydro-2H-pyran-4-carboxylic acid to afford Compound 41 as a pale yellow solid. $^1$H NMR (400 MHz, CDCl$_3$) δ 8.19-8.11 (m, 2H), 7.20-7.09 (m, 2H), 5.99 (s, 1H), 5.85 (d, J=2.1 Hz, 1H), 4.27 (d, J=62.4 Hz, 4H), 4.08 (s, 3H), 4.01 (d, J=10.1 Hz, 2H), 3.57 (s, 3H), 3.41 (td, J=11.7, 2.0 Hz, 2H), 2.77 (q, J=7.6 Hz, 2H), 2.73 (s, 3H), 2.39 (ddd, J=15.0, 7.5, 3.8 Hz, 1H), 2.01 (d, J=7.3 Hz, 1H), 1.86 (ddd, J=15.7, 12.2, 4.5 Hz, 2H), 1.58 (d, J=11.5 Hz, 2H), 1.33 (t, J=7.6 Hz, 3H). LC-MS: m/z=600.2[M+H]$^+$ Example 42: 4-nitrophenyl 6-(3-((5-cyano-4-(4-fluorophenyl)thiazol-2-yl)(methyl)amino)-2-ethyl-7-methylpyrazolo[1,5-a]pyridin-5-yl)-2,6-diazaspiro[3.3]heptane-2-carboxylate (Compound 42)

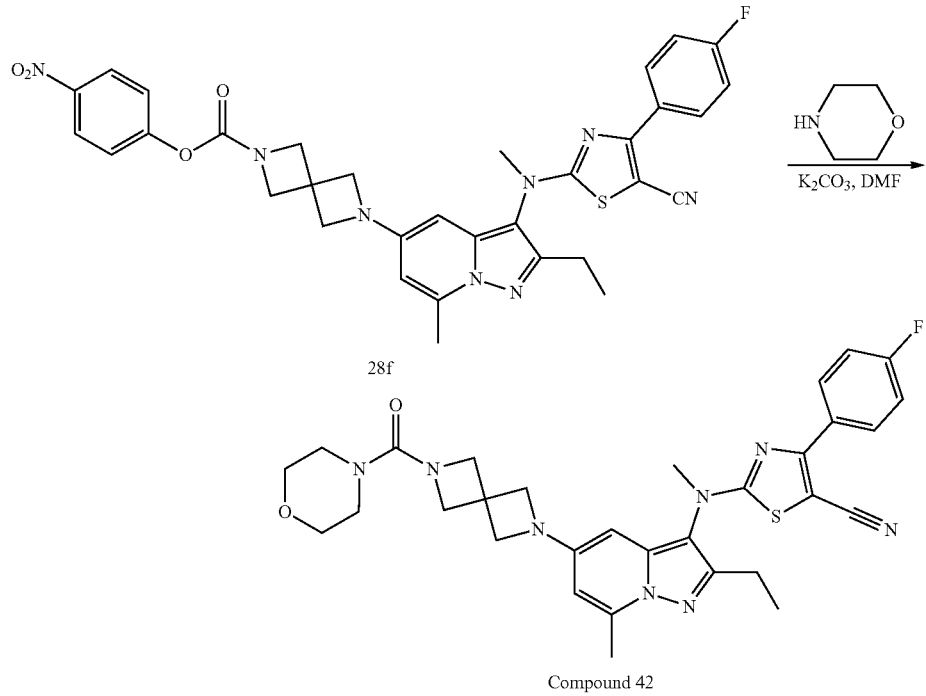

To a solution of 28f (110 mg, 0.17 mmol) in DMF (4 mL) was added $K_2CO_3$ (71 mg, 0.51 mmol) and morpholine (30 mg, 0.34 mmol). The reaction mixture was heated at 110° C. for 3 h and then filtered, and the solid was washed with ethyl acetate. The filtrate was then suspended in 30 mL of water, extracted with ethyl acetate, the organic layer was dried over magnesium sulfate, filtered, and concentrated in vacuo. The residue was purified by column chromatography on silica gel to give the title Compound 42 (24 mg, 23%). $^1$H NMR (400 MHz, CDCl3) δ 8.20-8.11 (m, 2H), 7.19-7.11 (m, 2H), 5.97 (d, J=1.4 Hz, 1H), 5.82 (d, J=2.3 Hz, 1H), 4.16 (s, 4H), 4.05 (s, 4H), 3.68-3.61 (m, 4H), 3.57 (s, 3H), 3.37-3.29 (m, 4H), 2.76 (q, J=7.6 Hz, 2H), 2.71 (s, 3H), 1.32 (t, J=7.6 Hz, 3H). LC-MS: m/z=601.2 [M+H]$^+$ Example 43: 2-((2-ethyl-7-methyl-5-(2-(tetrahydro-2H-pyran-4-carbonyl)-2,6-diazaspiro[3.4]octan-6-yl)pyrazolo[1,5-a]pyridin-3-yl)(methyl)amino)-4-(4-fluorophenyl)thiazole-5-carbonitrile (Compound 43)

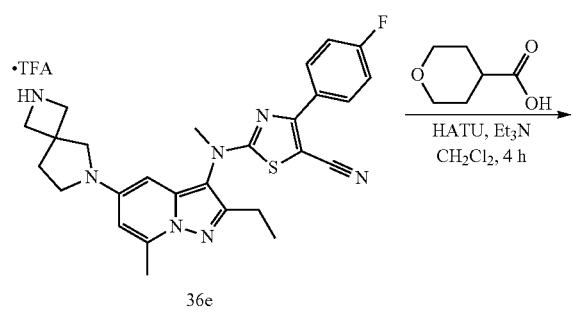

-continued

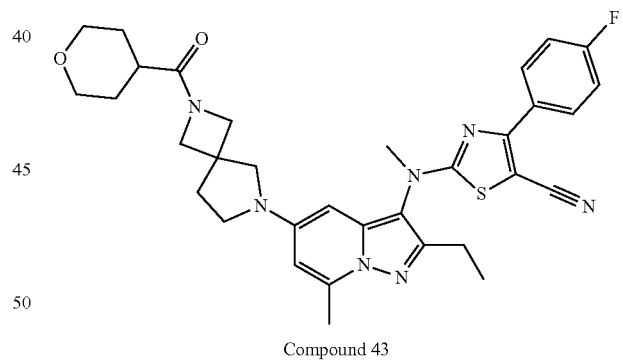

Compound 43

Compound 43 was prepared from 36e and tetrahydro-2H-pyran-4-carboxylic acid in a manner analogous to Example 31. $^1$H NMR (400 MHz, CDCl$_3$) δ 8.15 (dd, 2H), 7.17 (t, 2H), 6.27 (s, 1H), 5.92 (s, 1H), 4.01 (d, 3H), 3.59 (s, 5H), 3.48 (s, 2H), 3.39 (t, 3H), 2.96-2.84 (m, 4H), 2.39 (d, 2H), 2.30 (t, 2H), 1.94-1.80 (m, 3H), 1.58 (d, 3H), 1.39 (t, 3H). LC-MS (ESI): m/z=614.3 [M+H]$^+$

Example 44: 2-((2-ethyl-7-methyl-5-(6-(tetrahydro-2H-pyran-4-carbonyl)-2,6-diazaspiro[3.4]octan-2-yl)pyrazolo[1,5-a]pyridin-3-yl)(methyl)amino)-4-(4-fluorophenyl)thiazole-5-carbonitrile (Compound 44)

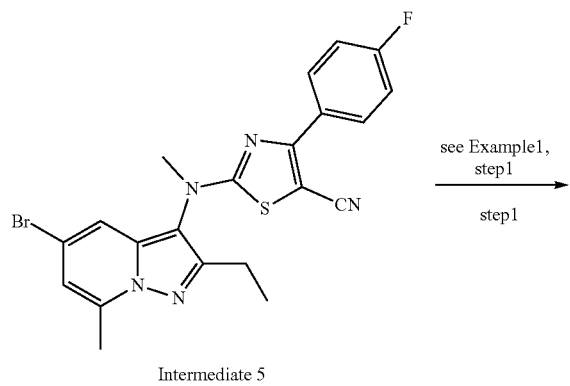

Step 1: tert-butyl 2-(3-((5-cyano-4-(4-fluorophenyl)thiazol-2-yl)(methyl)amino)-2-ethyl-7-methylpyrazolo[1,5-a]pyridin-5-yl)-2,6-diazaspiro[3.4]octane-6-carboxylate (44a)

44a was prepared from Intermediate 5 in a manner analogous to Step 1, Example 1 and was isolated as a yellow foam.

Step 2: 2-((2-ethyl-7-methyl-5-(2,6-diazaspiro[3.4]octan-2-yl)pyrazolo[1,5-a]pyridin-3-yl)(methyl)amino)-4-(4-fluorophenyl)thiazole-5-carbonitrile TFA salt (44b)

To a solution of 44a (80 mg, 0.13 mmol) in DCM (8 mL) was successively added trifluoroacetic acid (4 mL). The reaction mixture was stirred at room temperature for 1 h. The mixture was concentrated in vacuo. The residue was used for the next reaction without purification (65 mg, 97.0%) as a yellow oil.

Step 3: 2-((2-ethyl-7-methyl-5-(6-(tetrahydro-2H-pyran-4-carbonyl)-2,6-diazaspiro[3.4]octan-2-yl)pyrazolo[1,5-a]pyridin-3-yl)(methyl)amino)-4-(4-fluorophenyl)thiazole-5-carbonitrile (Compound 44)

To a solution of 44b (65 mg, 0.13 mmol) in DMF (10 mL) was successively added tetrahydropyran-4-carboxylic acid (34 mg, 0.26 mmol) HATU (98 mg, 0.25 mmol) Et$_3$N (0.13 g, 1.30 mmol). The reaction mixture was heated at 40° C. for 2 h. After cooling to room temperature, the mixture was diluted with water and EtOAc. The organic layer was separated and the aqueous layer extracted with EtOAc. The residue was purified by column chromatography on silica gel to give Compound 44 (13 mg, 16.3%) as a yellow solid. $^1$H NMR (400 MHz, CDCl$_3$) δ 8.21-8.07 (m, 2H), 7.16 (t, 2H), 6.05 (s, 1H), 5.85 (s, 1H), 4.07-3.86 (m, 5H), 3.73 (d, 2H), 3.56 (d, 5H), 3.42 (t, 2H), 2.84 (d, 4H), 2.56 (s, 1H), 2.26 (d, 2H), 2.18 (d, 2H), 1.92 (dd, 3H), 1.61 (d, 2H), 1.36 (t, 3H). LC-MS (ESI): m/z=614.3 [M+H]$^+$

Example 45: (S)-2-((2-ethyl-7-methyl-5-(6-(tetrahydrofuran-3-carbonyl)-2,6-diazaspiro[3.4]octan-2-yl)pyrazolo[1,5-a]pyridin-3-yl)(methyl)amino)-4-(4-fluorophenyl)thiazole-5-carbonitrile (Compound 45)

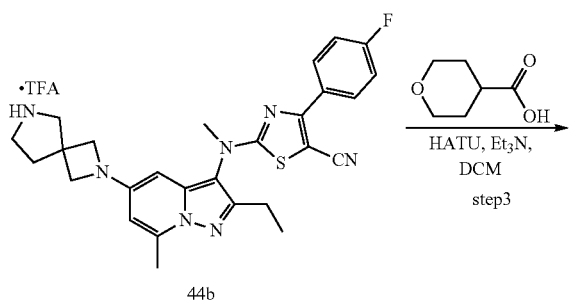

Compound 45 was prepared from 44b and (S)-tetrahydrofuran-3-carboxylic acid in a manner analogous to Example 31. $^1$H NMR (400 MHz, CDCl$_3$) δ 8.15 (dd, J=8.8, 5.4 Hz, 2H), 7.15 (t, J=8.6 Hz, 2H), 5.98 (s, 1H), 5.84 (dd, J=6.6, 2.1 Hz, 1H), 4.03 (t, J=8.1 Hz, 1H), 3.94-3.80 (m, 7H), 3.72 (dt, J=15.8, 11.0 Hz, 2H), 3.65-3.51 (m, 5H), 3.17-3.04 (m, 1H), 2.74 (q, J=7.6 Hz, 2H), 2.69 (d, J=2.5 Hz, 3H), 2.27 (t, J=6.9 Hz, 1H), 2.24-2.07 (m, 3H), 1.32 (t, J=7.6 Hz, 3H). LC-MS (ESI): m/z=600.2 [M+H]$^+$ Example 46: (R)-2-((2-ethyl-7-methyl-5-(6-(tetrahydrofuran-2-carbonyl)-2,6-diazaspiro[3.4]octan-2-yl)pyrazolo[1,5-a]pyridin-3-yl)(methyl)amino)-4-(4-fluorophenyl)thiazole-5-carbonitrile (Compound 46)

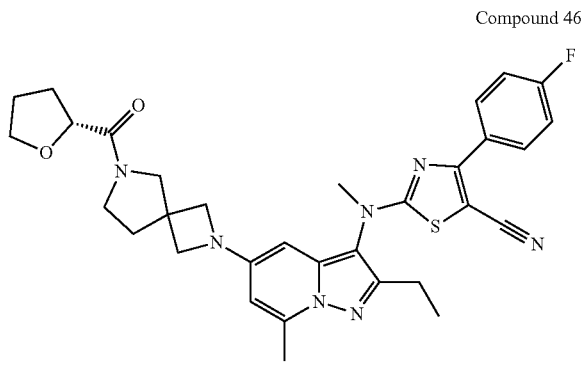 [SMILES: CCc1nn2c(C)cc(N3CC4(CCN(C(=O)[C@H]5CCCO5)C4)C3)cc2c1N(C)c1nc(-c2ccc(F)cc2)c(C#N)s1]

Compound 46

Compound 46 was prepared from 44b and (R)-tetrahydrofuran-2-carboxylic acid in a manner analogous to Example 31. $^1$H NMR (400 MHz, CDCl$_3$) δ 8.19-8.11 (m, 2H), 7.16 (t, 2H), 6.08 (s, 1H), 5.86 (s, 1H), 4.53-4.43 (m, 1H), 4.02-3.52 (m, 13H), 2.87 (s, 5H), 2.34-1.83 (m, 6H), 1.38 (t, 3H). LC-Ms m/z (ESI): 600.2 [M+H$^+$]

Example 47: 2-((2-ethyl-7-methyl-5-(6-(1-methylazetidine-3-carbonyl)-2,6-diazaspiro[3.4]octan-2-yl)pyrazolo[1,5-a]pyridin-3-yl)(methyl)amino)-4-(4-fluorophenyl)thiazole-5-carbonitrile (Compound 47)

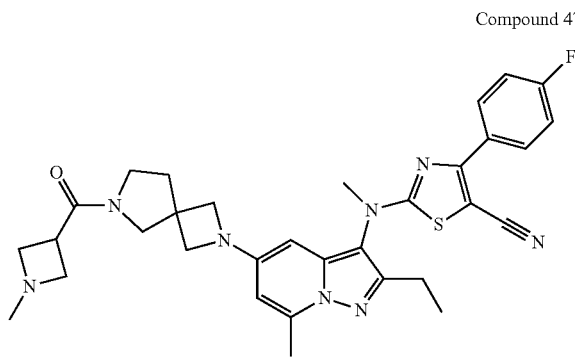

Compound 47

Compound 47 was prepared from 44b and 1-methylazetidine-3-carboxylic acid in a manner analogous to Example 31. $^1$H NMR (400 MHz, CDCl$_3$) δ 8.15 (dd, J=8.6, 5.5 Hz, 2H), 7.15 (t, J=8.6 Hz, 2H), 5.97 (s, 1H), 5.83 (d, J=2.6 Hz, 1H), 3.91-3.81 (m, 6H), 3.69 (s, 1H), 3.56 (t, J=5.9 Hz, 6H), 3.48-3.40 (m, 3H), 2.78-2.71 (m, 2H), 2.69 (d, J=2.1 Hz, 3H), 2.45 (d, J=4.1 Hz, 3H), 2.24 (t, J=6.9 Hz, 1H), 2.14 (t, J=7.0 Hz, 1H), 1.35-1.28 (m, 3H). LC-MS (ESI): m/z=599.3 [M+H]$^+$ Example 49: (R)-2-((2-ethyl-7-methyl-5-(2-(tetrahydrofuran-2-carbonyl)-2,6-diazaspiro[3.4]octan-6-yl)pyrazolo[1,5-a]pyridin-3-yl)(methyl)amino)-4-(4-fluorophenyl)thiazole-5-carbonitrile (Compound 49)

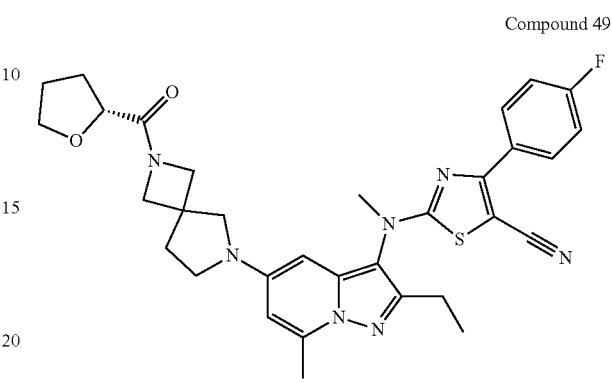

Compound 49

Starting from 36e and proceed in analogy to preparation Example 31, using (R)-tetrahydrofuran-2-carboxylic acid to afford the title compound 49 as a pale yellow solid. $^1$H NMR (400 MHz, CDCl$_3$) δ 8.15 (dd, 2H), 7.16 (t, 2H), 6.25 (s, 1H), 5.91 (s, 1H), 4.35 (ddd, 2H), 4.00 (d, 2H), 3.84 (dd, 3H), 3.57 (d, 5H), 3.45 (s, 2H), 2.91-2.79 (m, 5H), 2.27 (t, 2H), 2.22-2.07 (m, 2H), 1.98-1.84 (m, 2H), 1.37 (t, 3H). LC-MS m/z (ESI): 600.2 [M+H$^+$]

Example 50: 2-((2-ethyl-7-methyl-5-(2-methyl-1-oxo-2,8-diazaspiro[4.5]decan-8-yl)pyrazolo[1,5-a]pyridin-3-yl)(methyl)amino)-4-(4-fluorophenyl)thiazole-5-carbonitrile (Compound 50)

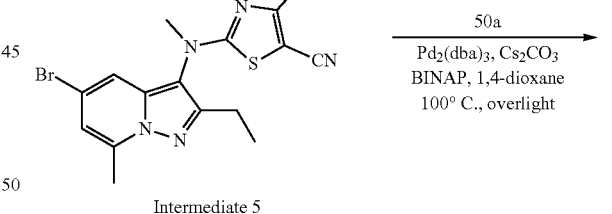

Intermediate 5

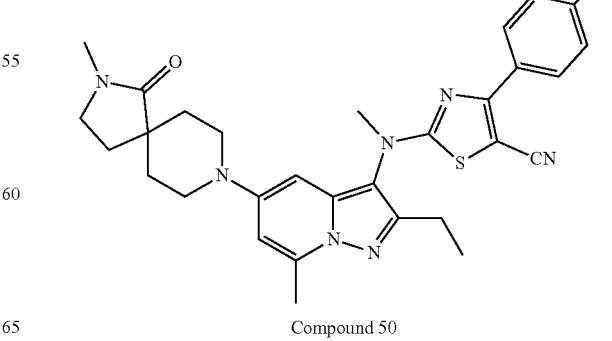

Compound 50

To a solution Intermediate 5 (0.12 g, 0.25 mmol) in 1,4-dioxane (5 mL) under argon was successively added 2-methyl-2,8-diazaspiro[4.5]decan-1-one (50a)(84 mg, 0.5 mmol), Cs$_2$CO$_3$ (0.33 g, 1.0 mmol) and then BINAP (31 mg, 0.05 mmol), Pd$_2$(dba)$_3$ (23 mg, 0.025 mmol). The reaction mixture was heated at 100° C. overnight. After cooling to room temperature, the mixture was diluted with water and EtOAc. The organic layer was separated and the aqueous layer extracted with EtOAc. The combined organic layers were then washed with water and brine, dried over Na$_2$SO$_4$, filtered, and concentrated in vacuo. The residue was purified by flash chromatography to afford Compound 50 (80 mg, 56%) as a yellow solid. $^1$H NMR (400 MHz, CDCl$_3$) δ 8.22-8.10 (m, 2H), 7.20-7.11 (m, 2H), 6.51 (s, 1H), 6.34 (s, 1H), 3.85-3.65 (m, 2H), 3.58 (s, 3H), 3.34 (t, J=6.9 Hz, 2H), 3.04 (s, 2H), 2.86 (s, 3H), 2.79-2.66 (m, 5H), 2.09-1.96 (m, 4H), 1.58 (s, 2H), 1.36-1.20 (m, 3H). LC-MS (ESI): m/z=558.3 [M+H]$^+$.

Example 51: (S)-2-((2-ethyl-7-methyl-5-(2-(tetrahydrofuran-3-carbonyl)-2,6-diazaspiro[3.4]octan-6-yl)pyrazolo[1,5-a]pyridin-3-yl)(methyl)amino)-4-(4-fluorophenyl)thiazole-5-carbonitrile (Compound 51)

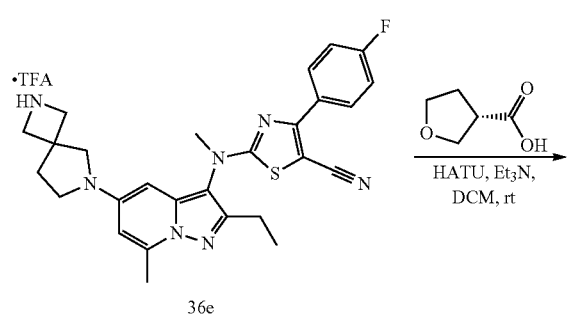

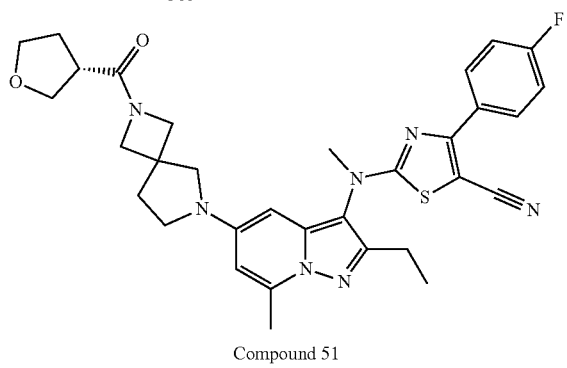

Compound 51

To a solution of (3S)-tetrahydrofuran-3-carboxylic acid (90 mg, 0.78 mmol) and HATU (296 mg, 0.78 mmol) in DCM (5 mL) was added triethylamine (0.9 mL, 6.48 mmol) and 36e (325 mg, 0.65 mmol) at rt. After 2 h, the reaction mixture was quenched with water, diluted with DCM (50 mL), washed with water (2×50 mL), and brine (100 mL). All volatiles were removed under reduced pressure. The residue was purified by column chromatography on silica gel to give the title Compound 51 (120 mg, 31%). $^1$H NMR (400 MHz, CDCl$_3$) δ 8.26-8.02 (m, 2H), 7.21-7.07 (m, 2H), 6.21 (s, 1H), 5.90 (s, 1H), 4.05-3.94 (m, 3H), 3.93-3.75 (m, 4H), 3.64-3.51 (m, 5H), 3.45 (s, 2H), 2.99-2.86 (m, 1H), 2.86-2.72 (m, 5H), 2.28 (t, 2H), 2.25-2.12 (m, 2H), 2.12-1.93 (m, 1H), 1.35 (t, J=7.6 Hz, 3H). LC-MS (ESI): m/z=600.3 [M+H]$^+$.

Example 52: 2-((2-ethyl-5-(2-(2-hydroxyacetyl)-2,6-diazaspiro[3.4]octan-6-yl)-7-methylpyrazolo[1,5-a]pyridin-3-yl)(methyl)amino)-4-(4-fluorophenyl)thiazole-5-carbonitrile (Compound 52)

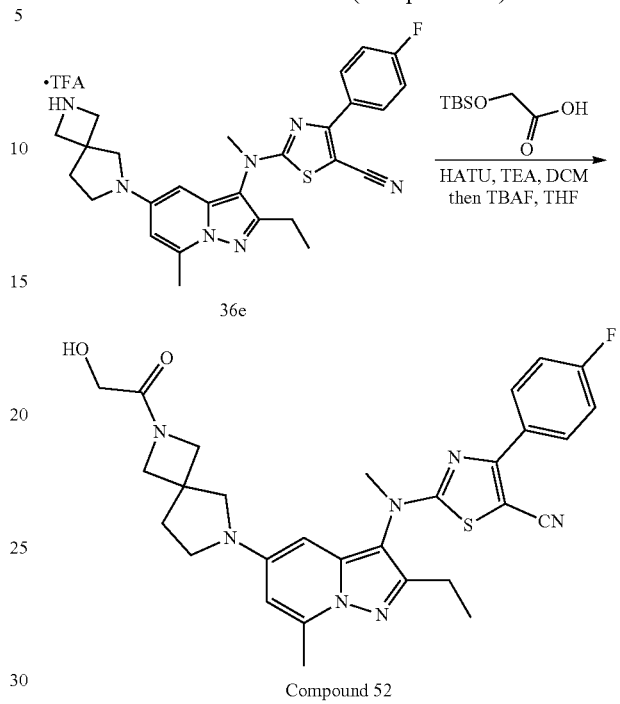

Compound 52

To a solution of 36e (100 mg, 0.2 mmol) in DCM (10 mL) were successively added 2-((tert-butyldimethylsilyl)oxy)acetic acid (47 mg, 0.24 mmol), HATU (100 mg, 0.15 mmol) and TEA (60 mg, 0.6 mmol). The reaction mixture was stirred at room temperature for 4 h, then the mixture was diluted with water (10 mL) and extracted with DCM (10 mL×3). The combined organic layers were then washed with water (100 mL×2) and brine (50 mL×1), dried over sodium sulfate, filtered, and concentrated in vacuo to give the crude product. To a solution of crude product in THF (4 mL) were successively added TBAF (52 mg, 0.4 mmol) was stirred at room temperature for 5 h. The residue was purified by flash chromatography to afford the title compound 52 (50 mg, 45%) as a light white solid. LC-MS (ESI): m/z=560.2 [M+H]$^+$.

Example 53: 2-((2-ethyl-5-(6-(2-hydroxy-2-methylpropanoyl)-2,6-diazaspiro[3.4]octan-2-yl)-7-methylpyrazolo[1,5-a]pyridin-3-yl)(methyl)amino)-4-(4-fluorophenyl)thiazole-5-carbonitril (Compound 53)

Compound 53

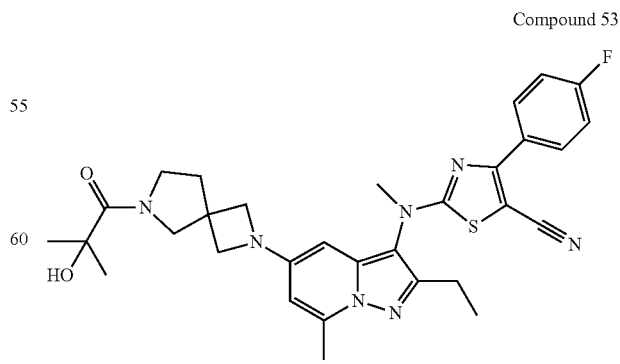

Compound 53 was prepared from 44b and 2-hydroxy-2-methylpropanoic acid in a manner analogous to Example 31.

$^1$H NMR (400 MHz, CDCl$_3$) δ 8.20-8.09 (m, 2H), 7.21-7.10 (m, 2H), 5.98 (d, J=1.3 Hz, 1H), 5.84 (d, J=2.2 Hz, 1H), 3.87 (s, 5H), 3.73 (dd, J=30.2, 23.7 Hz, 3H), 3.57 (s, 3H), 2.75 (q, J=7.6 Hz, 2H), 2.70 (s, 3H), 2.31-2.10 (m, 2H), 1.47 (s, 6H), 1.32 (t, J=7.6 Hz, 3H). LC-MS (ESI): m/z=588.3 [M+H]$^+$.

Example 54: 2-((2-ethyl-5-(2-(1-hydroxycyclopropane-1-carbonyl)-2,6-diazaspiro[3.4]octan-6-yl)-7-methylpyrazolo[1,5-a]pyridin-3-yl)(methyl)amino)-4-(4-fluorophenyl)thiazole-5-carbonitrile (Compound 54)

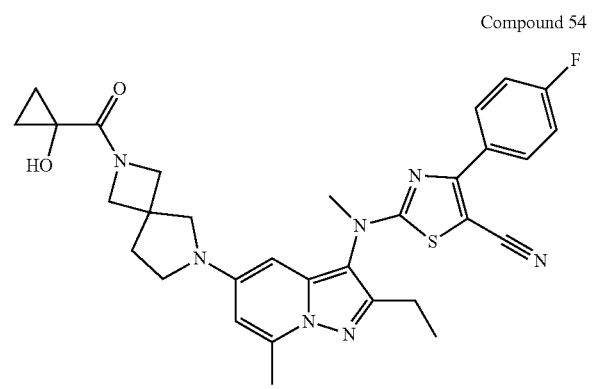 [SMILES: CCc1nn2c(C)cc(N3CCC4(CN(C(=O)C5(O)CC5)C4)C3)cc2c1N(C)c1nc(-c2ccc(F)cc2)c(C#N)s1]

Compound 54

Compound 54 was prepared from 44b and 1-hydroxycyclopropane-1-carboxylic acid in a manner analogous to Example 31. $^1$H NMR (400 MHz, CDCl3) δ 8.19-8.10 (m, 2H), 7.21-7.09 (m, 2H), 5.97 (d, J=1.3 Hz, 1H), 5.85 (d, J=2.2 Hz, 1H), 4.35 (q, J=9.1 Hz, 2H), 4.21 (d, J=11.6 Hz, 2H), 4.12-4.03 (m, 4H), 3.99 (t, J=8.2 Hz, 1H), 3.86 (dddd, J=25.8, 18.9, 12.1, 7.1 Hz, 3H), 3.57 (s, 3H), 2.92 (dt, J=15.2, 7.4 Hz, 1H), 2.75 (q, J=7.6 Hz, 2H), 2.70 (s, 3H), 2.17 (td, J=14.0, 7.2 Hz, 1H), 2.10-2.02 (m, 1H), 1.32 (t, J=7.6 Hz, 3H). LC-MS (ESI): m/z=586.2 [M+H]$^+$.

Example 55: 2-((5-(2-(2,3-dihydroxypropyl)-2,6-diazaspiro[3.4]octan-6-yl)-2-ethyl-7-methylpyrazolo[1,5-a]pyridin-3-yl)(methyl)amino)-4-(4-fluorophenyl)thiazole-5-carbonitrile (Compound 55)

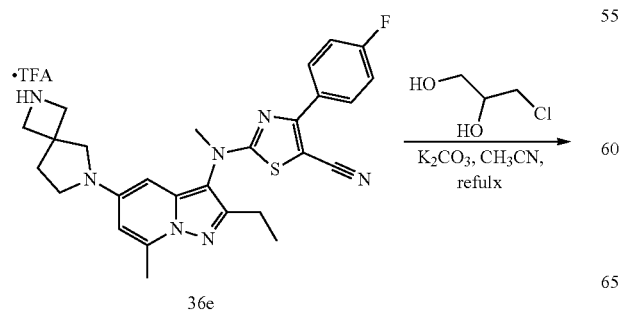

36e

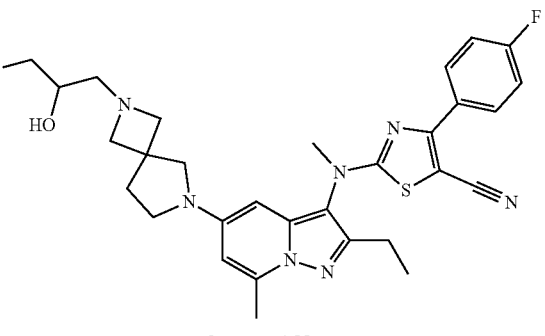

Compound 55

Compound 55 was prepared from 36e and 3-chloropropane-1,2-diol. $^1$H NMR (400 MHz, CDCl$_3$) δ 8.16 (dd, 2H), 7.15 (t, 2H), 6.15 (s, 1H), 5.85 (d, 1H), 3.88 (dd, 1H), 3.68 (dt, 5H), 3.58 (s, 3H), 3.55-3.44 (m, 3H), 3.38 (t, 2H), 2.97 (dd, 1H), 2.85 (dd, 1H), 2.79-2.71 (m, 2H), 2.70 (s, 3H), 2.27 (t, J=6.8 Hz, 2H), 1.32 (t, J=7.6 Hz, 3H). LC-MS (ESI): m/z=576.2 [M+H]$^+$.

Example 56: 2-((2-ethyl-7-methyl-5-(6-(oxazole-5-carbonyl)-2,6-diazaspiro[3.3]heptan-2-yl)pyrazolo[1,5-a]pyridin-3-yl)(methyl)amino)-4-(4-fluorophenyl)thiazole-5-carbonitrile (Compound 56)

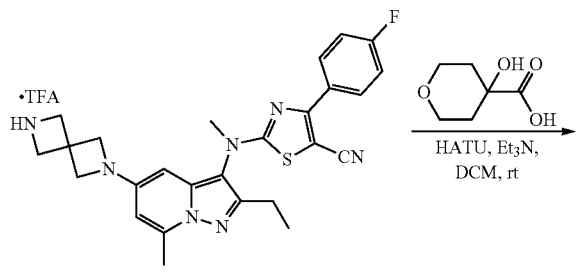

28e

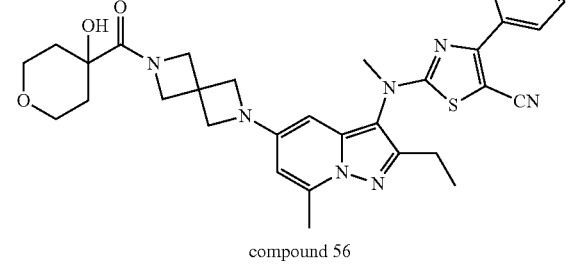

compound 56

To a solution of 4-hydroxytetrahydro-2H-pyran-4-carboxylic acid (90 mg, 0.61 mmol) and HATU (233 mg, 0.61 mmol) in DCM (5 mL) was added triethylamine (0.7 mL, 5.1 mmol) and 28e (249 mg, 0.51 mmol) at rt. After 2 h, the reaction mixture was quenched with water, diluted with DCM (50 mL), washed with water (2×50 mL), and brine (100 mL). All volatiles were removed under reduced pressure. The residue was purified by column chromatography on silica gel to give the title Compound 56 (150 mg, 48%). $^1$H NMR (400 MHz, CDCl$_3$) δ 8.23-8.07 (m, 2H), 7.20-7.11 (m, 2H), 5.97 (s, 1H), 5.84 (s, 1H), 4.63 (s, 2H), 4.25 (s, 2H), 4.08 (s, 4H), 3.91-3.71 (m, 4H), 3.57 (s, 3H), 2.75 (q, J=7.6 Hz, 2H), 2.70 (s, 3H), 2.14-2.03 (m, 2H), 1.50 (d, J=12.9 Hz, 2H), 1.32 (t, J=7.6 Hz, 3H). LC-MS (ESI): m/z=616.3 [M+H]$^+$.

Example 57: 2-((2-ethyl-7-methyl-5-(6-(oxazole-5-carbonyl)-2,6-diazaspiro[3.3]heptan-2-yl)pyrazolo[1,5-a]pyridin-3-yl)(methyl)amino)-4-(4-fluorophenyl)thiazole-5-carbonitrile (Compound 57)

Example 59: 2-((2-ethyl-5-(6-(4-hydroxytetrahydrofuran-3-carbonyl)-2,6-diazaspiro[3.3]heptan-2-yl)-7-methylpyrazolo[1,5-a]pyridin-3-yl)(methyl)amino)-4-(4-fluorophenyl)thiazole-5-carbonitrile (Compound 59 and Compound 74)

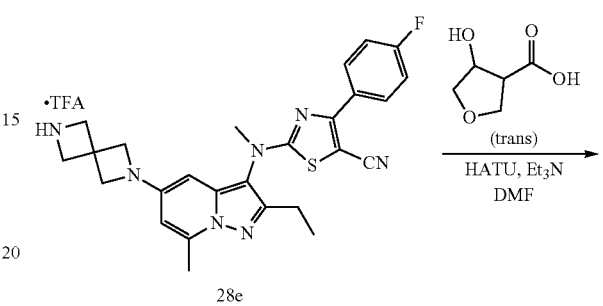

28e

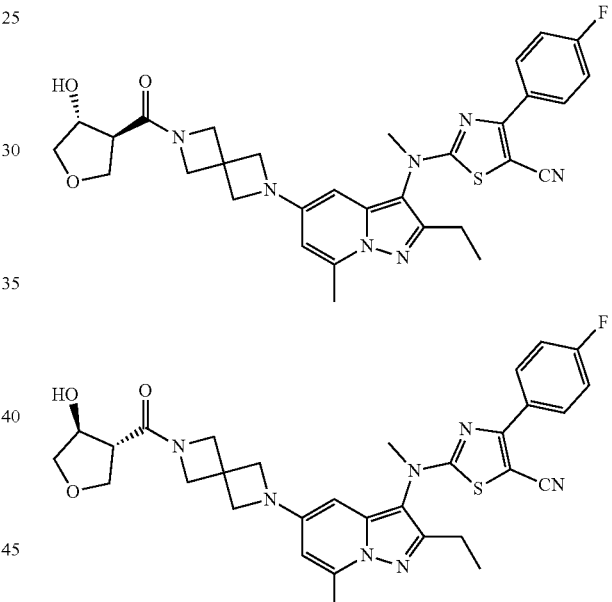

compound 59 and compound 74

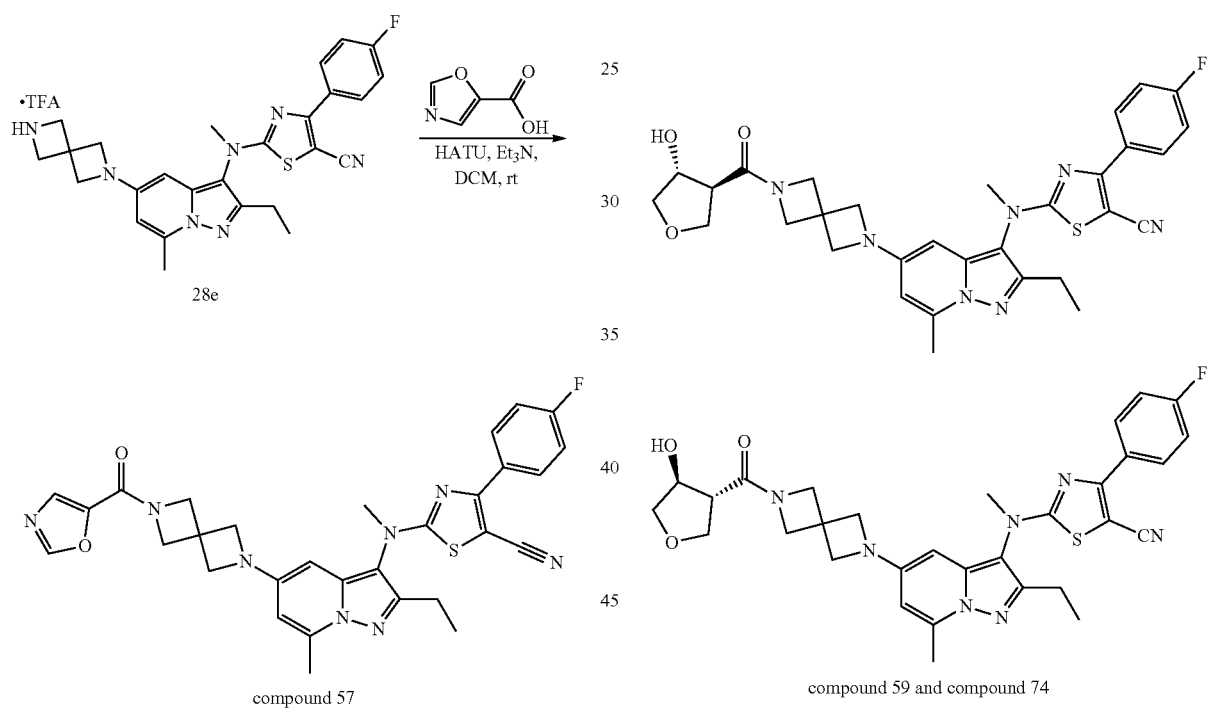

compound 57

To a solution of oxazole-5-carboxylic acid (69 mg, 0.61 mmol) and HATU (233 mg, 0.61 mmol) in DCM (5 mL) was added triethylamine (0.7 mL, 5.1 mmol) and 28e (249 mg, 0.51 mmol) at rt. After 2 h, the reaction mixture was quenched with water, diluted with DCM (50 mL), washed with water (2×50 mL), and brine (100 mL). All volatiles were removed under reduced pressure. The residue was purified by column chromatography on silica gel (n-hexane:ethyl acetate=1:1) to give the title Compound 57 (150 mg, 51%). $^1$H NMR (400 MHz, CDCl$_3$) δ 8.15 (m, 2H), 7.97 (s, 1H), 7.70 (s, 1H), 7.16 (m, 2H), 6.09 (s, 1H), 5.89 (s, 1H), 4.72 (s, 2H), 4.40 (s, 2H), 4.18 (s, 4H), 3.58 (s, 3H), 2.81 (q, 2H), 2.76 (s, 3H), 1.34 (t, 3H). LC-MS (ESI): m/z=583.2 [M+H]$^+$.

To a solution of 4-hydroxytetrahydrofuran-3-carboxylic acid (24 mg, 0.18 mmol) in DMF (5 mL) were successively added HATU (68 mg, 0.18 mmol) and Et$_3$N (36 mg, 0.36 mmol). The reaction mixture was stirred at room temperature for 0.5 h, then the mixture was added 28e (58 mg, 0.12 mmol) and stirred at room temperature for 3 h. The mixture was diluted with water (10 mL) and extracted with DCM (10 mL×3). The combined organic layers were then washed with water (10 mL×2) and brine (5 mL×1), dried over Na$_2$SO$_4$, filtered, and concentrated in vacuo. The residue was purified by HPLC (chiral AD column n-hexane/ethanol=80/20 50 min) to afford compound 59 and 74. Compound 59 LC-MS (ESI): m/z=602.2 [M+H]$^+$. Compound 74 LC-MS (ESI): m/z=602.2 [M+H]$^+$.

Example 60: 2-((5-(6-(2,3-dihydroxypropanoyl)-2,6-diazaspiro[3.3]heptan-2-yl)-2-ethyl-7-methylpyrazolo[1,5-a]pyridin-3-yl)(methyl)amino)-4-(4-fluorophenyl)thiazole-5-carbonitrile (Compound 60)

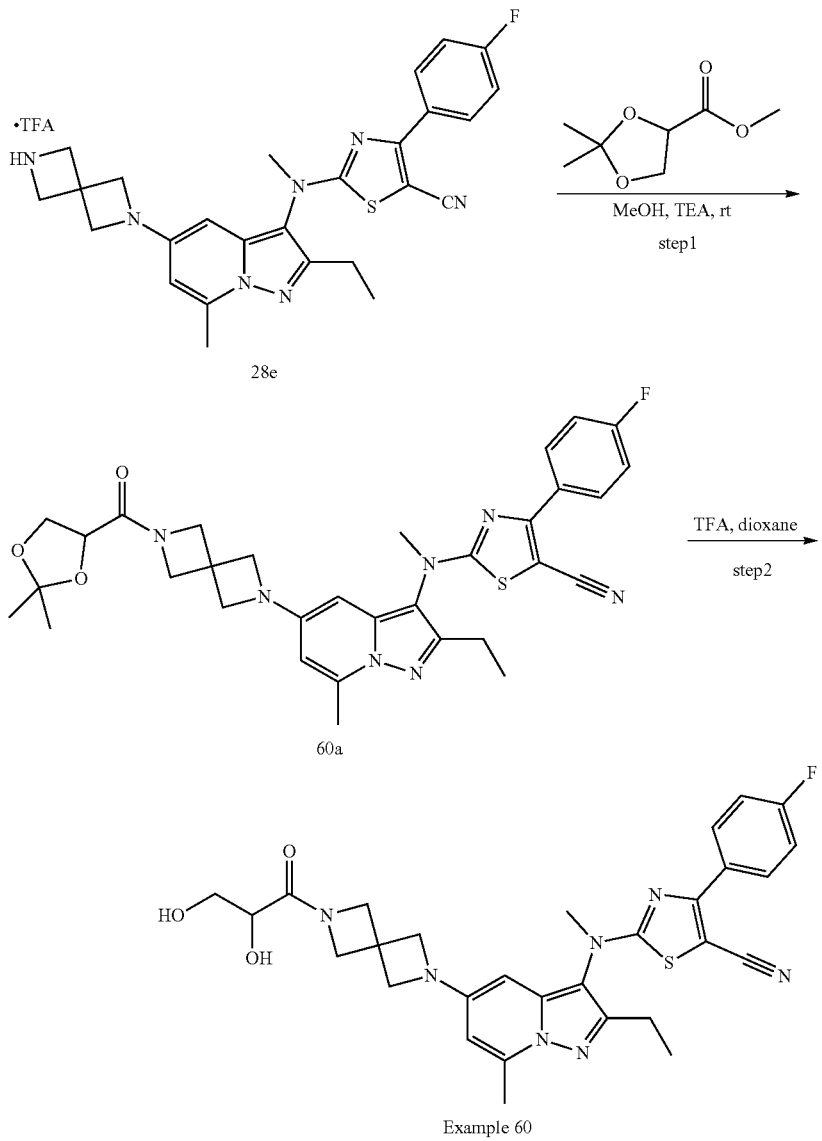

Step 1: 2-((5-(6-(2,2-dimethyl-1,3-dioxolane-4-carbonyl)-2,6-diazaspiro[3.3]heptan-2-yl)-2-ethyl-7-methylpyrazolo[1,5-a]pyridin-3-yl)(methyl)amino)-4-(4-fluorophenyl)thiazole-5-carbonitrile (60a)

To a solution of compound 28e (249 mg, 0.51 mmol) in MeOH (5 mL) was added triethylamine (0.7 mL, 5.1 mmol) and methyl 2,2-dimethyl-1,3-dioxolane-4-carboxylate (98 mg, 0.61 mmol) at rt. The reaction mixture was stirred overnight, quenched with water, diluted with DCM (50 mL), washed with water (2×50 mL), and brine (100 mL). All volatiles were removed under reduced pressure. The residue was directly used for the next step without purification. LC-MS (ESI): m/z=616.3 [M+H]+

Step 2

2-((5-(6-(2,3-dihydroxypropanoyl)-2,6-diazaspiro[3.3]heptan-2-yl)-2-ethyl-7-methylpyrazolo[1,5-a]pyridin-3-yl)(methyl)amino)-4-(4-fluorophenyl)thiazole-5-carbonitrile (Compound 60)

To a solution of 60a (314 mg, 0.51 mmol) in 1,4-dioxane (4 mL) was added TFA (2 mL) at 0° C. The reaction mixture was allowed to warm to rt, and stirred overnight, quenched with water, diluted with DCM (50 mL), washed with water (2×50 mL), and brine (100 mL). All volatiles were removed under reduced pressure. The residue was purified by column chromatography on silica gel to give the title Compound 60 (121 mg, 41%). $^1$H NMR (400 MHz, CDCl$_3$) δ 8.29-8.01 (m, 2H), 7.22-7.06 (m, 2H), 5.98 (s, 1H), 5.85 (s, 1H), 4.54-4.38 (m, 2H), 4.28 (d, 2H), 4.19 (t, 1H), 4.15-3.99 (m, 4H), 3.87-3.64 (m, 2H), 3.57 (s, 3H), 2.76 (q, 2H), 2.71 (s, 3H), 1.32 (t, J=7.6 Hz, 3H). LC-MS (ESI): m/z=576.2 [M+H]$^+$ Example 61: 2-((2-ethyl-5-(6-(1-hydroxycyclopropane-1-carbonyl)-2,6-diazaspiro[3.3]heptan-2-yl)-7-methylpyrazolo[1,5-a]pyridin-3-yl)(methyl)amino)-4-(4-fluorophenyl)thiazole-5-carbonitrile (Compound 61)

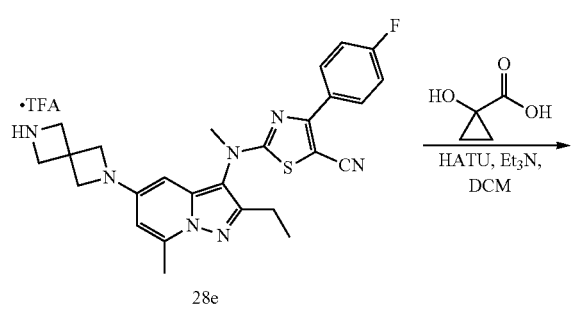
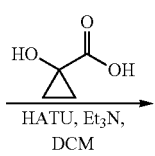

28e

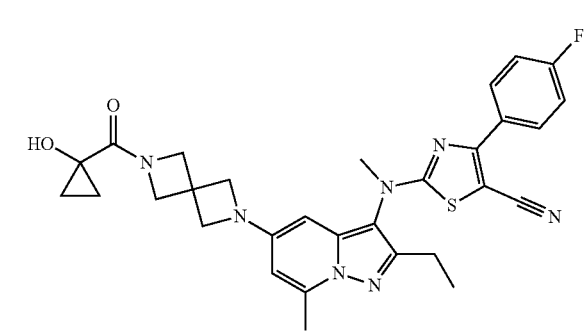

Compound 61

To a solution of 28e (160 mg, 0.33 mmol) in dichloromethane (10 mL) was added HATU (150 mg, 0.39 mmol), triethylamine (130 mg, 1.3 mmol) and 1-hydroxycyclopropane-1-carboxylic acid (50 mg, 0.49 mmol). The reaction mixture was stirred at room temperature for 3 h and then the reaction mixture was quenched with water, extracted with ethyl acetate, the organic layer was washed with water (3×15 mL) and then dried over magnesium sulfate, filtered, and concentrated in vacuo. The residue was purified by column chromatography on silica gel to give the title Compound 61 (0.10 g, 53%). $^1$H NMR (400 MHz, CDCl$_3$) δ 8.14 (dd, 2H), 7.16 (t, 2H), 6.04 (s, 1H), 5.86 (s, 1H), 4.70 (s, 2H), 4.34 (s, 1H), 4.29 (d, 2H), 4.11 (s, 4H), 3.58 (s, 3H), 2.76 (q, 2H), 2.70 (s, 3H), 1.32 (dd, 5H), 1.03-0.94 (m, 2H). MS m/z (ESI): 572.21[M+H$^+$].

Example 62: (S)-2-((2-ethyl-5-(6-(2-hydroxypropanoyl)-2,6-diazaspiro[3.3]heptan-2-yl)-7-methylpyrazolo[1,5-a]pyridin-3-yl)(methyl)amino)-4-(4-fluorophenyl)thiazole-5-carbonitrile (Compound 62)

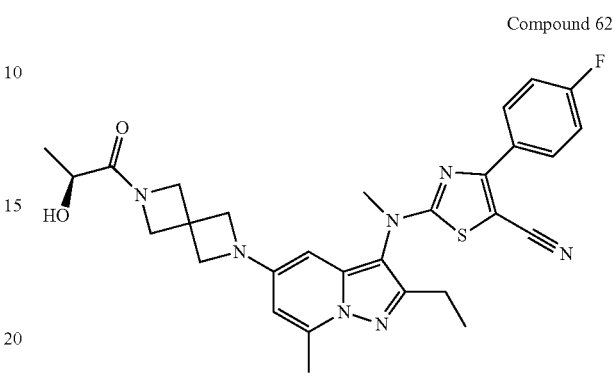

Compound 62

The title compound was prepared by the method substantially similar to that mentioned in Example 30, using methyl (S)-2-hydroxypropanoic acid to afford Compound 62 as a pale yellow solid. $^1$H NMR (400 MHz, CDCl$_3$) δ 8.15 (dd, 2H), 7.17 (t, 2H), 6.08 (s, 1H), 5.88 (s, 1H), 4.53-4.03 (m, 9H), 3.56 (d, 3H), 2.87 (dd, 5H), 1.52-1.27 (m, 6H). LC-MS (ESI): m/z=560.2 [M+H]$^+$ Example 63: (R)-2-((2-ethyl-5-(6-(2-hydroxypropanoyl)-2,6-diazaspiro[3.3]heptan-2-yl)-7-methylpyrazolo[1,5-a]pyridin-3-yl)(methyl)amino)-4-(4-fluorophenyl)thiazole-5-carbonitrile (Compound 63)

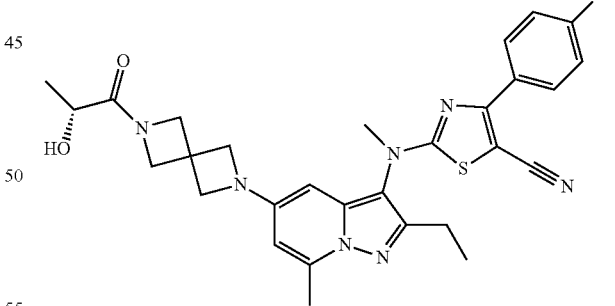

The title compound was prepared by the method substantially similar to that mentioned in Example 30, using methyl (R)-2-hydroxypropanoic acid to afford Compound 63 as a pale yellow solid. $^1$H NMR (400 MHz, CDCl$_3$) δ 8.23-8.05 (m, 2H), 7.21-7.09 (m, 2H), 5.97 (s, 1H), 5.85 (s, 1H), 4.47-4.15 (m, 5H), 4.15-3.98 (m, 4H), 3.57 (s, 3H), 2.74 (q, J=7.6 Hz, 2H), 2.69 (s, 2H), 2.65 (s, 1H), 1.36-1.27 (m, 6H). LC-MS (ESI): m/z=560.2 [M+H]$^+$

Example 64: (3S)—N-(3-(3-((5-cyano-4-(4-fluorophenyl)thiazol-2-yl)(methyl)amino)-2-ethyl-7-methylpyrazolo[1,5-a]pyridin-5-yl)-3-azabicyclo[3.1.0]hexan-6-yl)tetrahydrofuran-3-carboxamide (Compound 64)

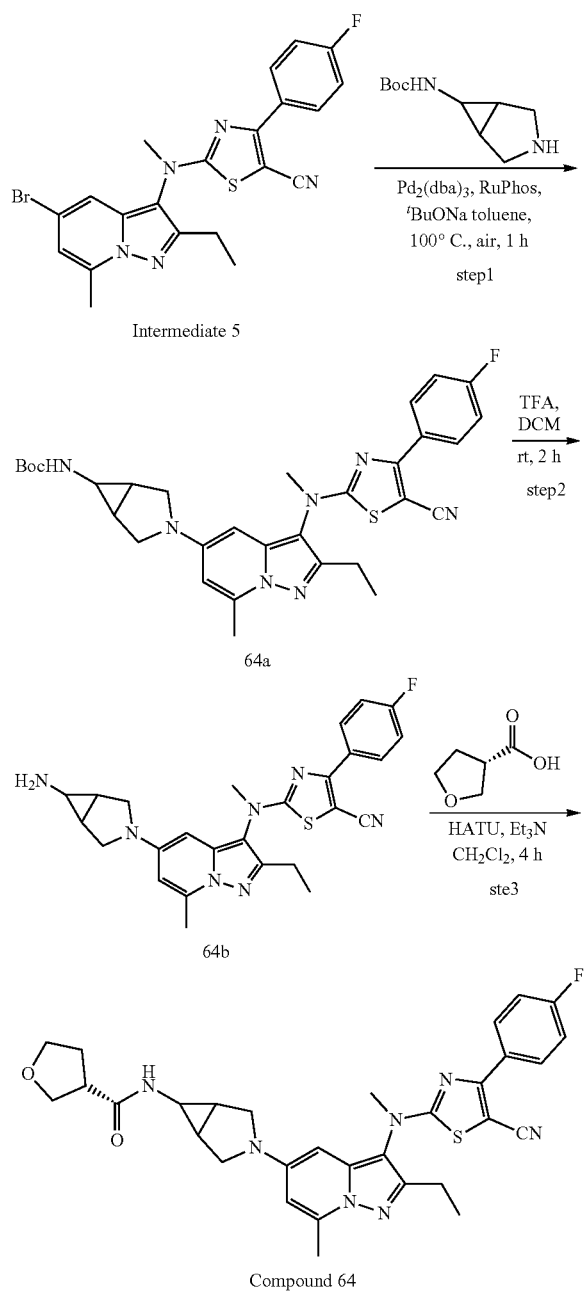

Step 1: tert-butyl (3-(3-((5-cyano-4-(4-fluorophenyl)thiazol-2-yl)(methyl)amino)-2-ethyl-7-methylpyrazolo[1,5-a]pyridin-5-yl)-3-azabicyclo[3.1.0]hexan-6-yl)carbamate (64a)

To a solution of Intermediate 5 (0.40 g, 0.9 mmol) in toluene (10 mL) under air were successively added tert-butyl 3-azabicyclo[3.1.0]hexan-6-ylcarbamate (0.28 g, 1.4 mmol), sodium tert-butoxide (0.43 g, 4.5 mmol), RuPhos (90 mg, 0.2 mmol), and $Pd_2(dba)_3$ (91 mg, 0.1 mmol). The reaction mixture was heated at 100° C. for 1 h. After cooling to room temperature, the reaction was concentrated in vacuo. The residue was purified by chromatography on silica gel to afford 64a (0.40 g, 80%) as a brown solid.

Step 2: 2-((2-ethyl-6-methyl-5-(2,6-diazaspiro[3.3]heptan-2-yl)pyrazolo[1,5-a]pyridin-3-yl)(methyl)amino)-4-(4-fluorophenyl)thiazole-5-carbonitrile (64b)

A solution of 64a (85 mg, 0.15 mmol) and TFA (2 mL) in DCM (5 mL) was stirred at room temperature for 2 h. The reaction was concentrated in vacuo to afford the crude product (64b), and it was used for next step without further purification.

Step 3: (3S)—N-(3-(3-((5-cyano-4-(4-fluorophenyl)thiazol-2-yl)(methyl)amino)-2-ethyl-7-methylpyrazolo[1,5-a]pyridin-5-yl)-3-azabicyclo[3.1.0]hexan-6-yl)tetrahydrofuran-3-carboxamide (Compound 64)

To a solution of 64b (54 mg, 0.11 mmol) in DCM (10 mL) were successively added (S)-tetrahydrofuran-3-carboxylic acid (15 mg, 0.13 mmol), HATU (65 mg, 0.17 mmol) and TEA (33 mg, 0.33 mmol). The reaction mixture was stirred at room temperature for 4 h, then the mixture was diluted with water (10 mL) and extracted with DCM (10 mL×3). The combined organic layers were then washed with water (10 mL×2) and brine (5 mL×1), dried over sodium sulfate, filtered, and concentrated in vacuo. The residue was purified by flash chromatography to afford the title compound 64 (50 mg, 72%) as a light brown solid. LC-MS (ESI): m/z=586.2 $[M+H]^+$

Example 66: 2-((2-ethyl-5-(6-(furan-2-carbonyl)-2,6-diazaspiro[3.3]heptan-2-yl)-7-methylpyrazolo[1,5-a]pyridin-3-yl)(methyl)amino)-4-(4-fluorophenyl)thiazole-5-carbonitrile (Compound 66)

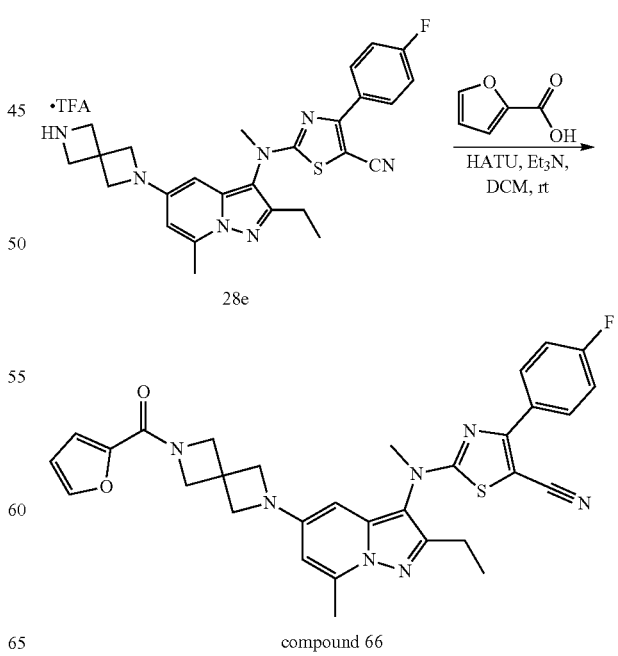

To a solution of furan-2-carboxylic acid (10 mg, 0.1 mmol) and HATU (50 mg, 0.1 mmol) in DCM (5 mL) was added triethylamine (0.1 mL, 0.8 mmol) and Compund 13 (40 mg, 0.08 mmol) at rt. After 2 h, the reaction mixture was quenched with water, diluted with DCM (50 mL), washed with water (2×50 mL), and brine (100 mL). All volatiles were removed under reduced pressure. The residue was purified by column chromatography on silica gel to give the title compound 66 (20 mg, 40%). $^1$H NMR (400 MHz, CDCl$_3$) δ 8.15 (m, 2H), 7.49 (s, 1H), 7.16 (t, 2H), 7.09 (m, 1H), 6.49 (m, 1H), 6.00 (s, 1H), 5.86 (s, 1H), 4.71 (s, 2H), 4.36 (s, 2H), 4.12 (s, 4H), 3.58 (s, 3H), 2.76 (q, 2H), 2.72 (s, 3H), 1.33 (t, 3H). LC-MS (ESI): m/z=582.2 [M+H]$^+$.

Example 67: 2-((2-ethyl-5-(4-(2-(3-hydroxyazetidin-1-yl)-2-oxoethyl)piperazin-1-yl)pyrazolo[1,5-a]pyridin-3-yl)(methyl)amino)-4-(4-fluorophenyl)thiazole-5-carbonitrile (Compound 67)

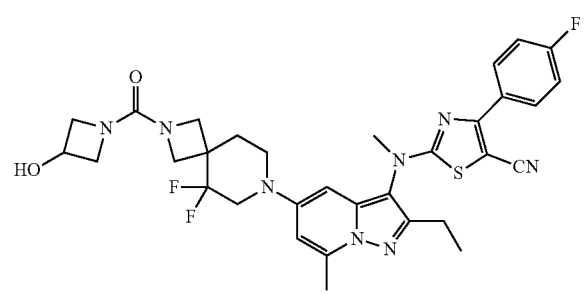 [SMILES: CCc1nn2c(C)cc(N3CCC4(CN(C(=O)N5CC(O)C5)C4)C(F)(F)C3)cc2c1N(C)c1nc(-c2ccc(F)cc2)c(C#N)s1]

The title compound was prepared by the method substantially similar to that mentioned in Example 48, using tert-butyl 5,5-difluoro-2,7-diazaspiro[3.5]nonane-2-carboxylate to afford Compound 67 as a pale yellow solid. $^1$H NMR (400 MHz, CDCl$_3$) δ 8.200-8.107 (m, 2H), 7.215-7.114 (m, 2H), 5.960 (dd, J=2.5, 1.1 Hz, 1H), 5.829 (d, J=2.4 Hz, 1H), 4.416 (s, 2H), 4.185 (s, 2H), 4.117-4.011 (m, 4H), 3.573 (s, 3H), 2.793-2.643 (m, 5H), 2.462 (s, 1H), 2.102 (s, 6H), 1.317 (t, J=7.6 Hz, 3H). LC-MS: m/z=650.2 [M+H]$^+$ Example 68: (S)-2-((5-(2-(2,3-dihydroxypropyl)-2,6-diazaspiro[3.4]octan-6-yl)-2-ethyl-7-methylpyrazolo[1,5-a]pyridin-3-yl)(methyl)amino)-4-(4-fluorophenyl)thiazole-5-carbonitrile (Compound 68)

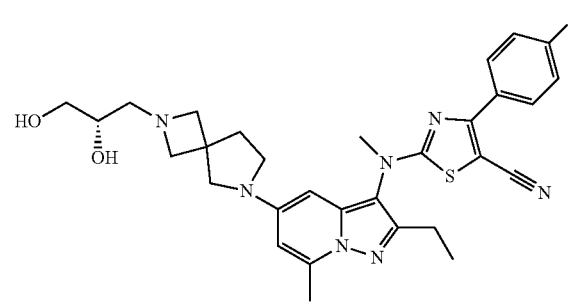

Compound 68 was prepared from Compound 55 (Example 55) by SFC. $^1$H NMR (400 MHz, CDCl$_3$) δ 8.16 (dd, 2H), 7.15 (t, 2H), 6.15 (s, 1H), 5.85 (d, 1H), 3.88 (dd, 1H), 3.68 (dt, 5H), 3.58 (s, 3H), 3.55-3.44 (m, 3H), 3.38 (t, 2H), 2.97 (dd, 1H), 2.85 (dd, 1H), 2.79-2.71 (m, 2H), 2.70 (s, 3H), 2.27 (t, J=6.8 Hz, 2H), 1.32 (t, J=7.6 Hz, 3H). LC-MS (ESI): m/z=576.2 [M+H]$^+$.

Example 69: (R)-2-((5-(2-(2,3-dihydroxypropyl)-2,6-diazaspiro[3.4]octan-6-yl)-2-ethyl-7-methylpyrazolo[1,5-a]pyridin-3-yl)(methyl)amino)-4-(4-fluorophenyl)thiazole-5-carbonitrile (Compound 69)

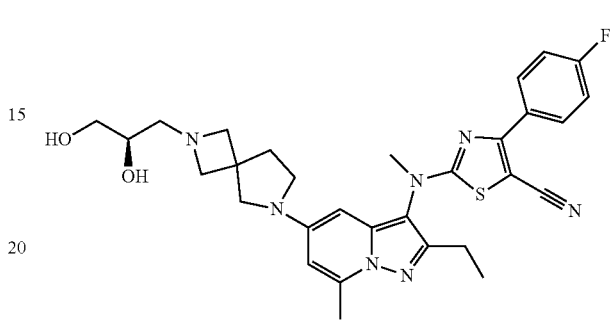

Compound 69 was prepared from Compound 55 (Example 55) by SFC. $^1$H NMR (400 MHz, CDCl3) δ 8.16 (dd, 2H), 7.15 (t, 2H), 6.15 (s, 1H), 5.85 (d, 1H), 3.88 (dd, 1H), 3.68 (dt, 5H), 3.58 (s, 3H), 3.55-3.44 (m, 3H), 3.38 (t, 2H), 2.97 (dd, 1H), 2.85 (dd, 1H), 2.79-2.71 (m, 2H), 2.70 (s, 3H), 2.27 (t, J=6.8 Hz, 2H), 1.32 (t, J=7.6 Hz, 3H). LC-MS (ESI): m/z=576.2 [M+H]$^+$.

Example 70: 2-((2-ethyl-5-(6-(isoxazole-3-carbonyl)-2,6-diazaspiro[3.3]heptan-2-yl)-7-methylpyrazolo[1,5-a]pyridin-3-yl)(methyl)amino)-4-(4-fluorophenyl)thiazole-5-carbonitrile (Compound 70)

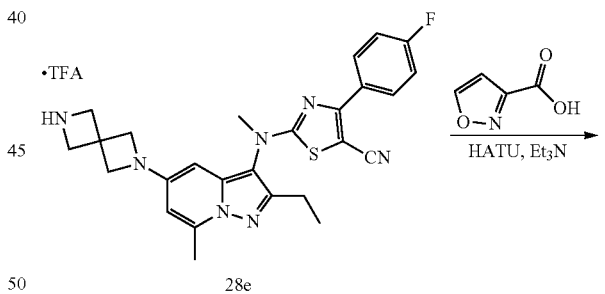

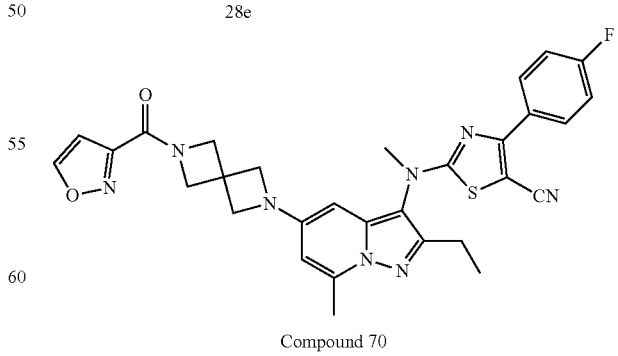

Compound 70

To a solution of 28e (0.14 g, 0.29 mmol) in DMF (10 mL) was successively added tetrahydropyran-4-carboxylic acid (65 mg, 0.57 mmol), HATU (0.22 g, 0.57 mmol), Et$_3$N (0.29 g, 2.90 mmol). The reaction mixture was heated at 40° C. for 2 h. After cooling to room temperature, the mixture was diluted with water and EtOAc. The organic layer was separated and the aqueous layer extracted with EtOAc. The residue was purified by column chromatography on silica gel to give Compound 70 (16 mg, 9.6%) as a yellow solid. $^1$H NMR (400 MHz, CDCl$_3$) δ 8.22-8.06 (m, 2H), 7.23 (d, 1H), 7.16 (t, 2H), 6.85 (s, 1H), 5.97 (s, 1H), 5.84 (d, 1H), 4.36 (m, 4H), 4.21-4.02 (m, 4H), 3.57 (s, 3H), 2.74 (q, 2H), 2.69 (s, 3H), 1.32 (t, 3H). LC-MS (ESI): m/z=583.2 [M+H]$^+$ Example 71: 2-((2-ethyl-5-(6-(furan-2-carbonyl)-2,6-diazaspiro[3.3]heptan-2-yl)-7-methylpyrazolo[1,5-a]pyridin-3-yl)(methyl)amino)-4-(4-fluorophenyl)thiazole-5-carbonitrile (Compound 71)

Example 72: (R)-2-((5-(1-(2,3-dihydroxypropyl)-1H-pyrazol-4-yl)-2-ethyl-7-methylpyrazolo[1,5-a]pyridin-3-yl)(methyl)amino)-4-(4-fluorophenyl)thiazole-5-carbonitrile (Compound 72)

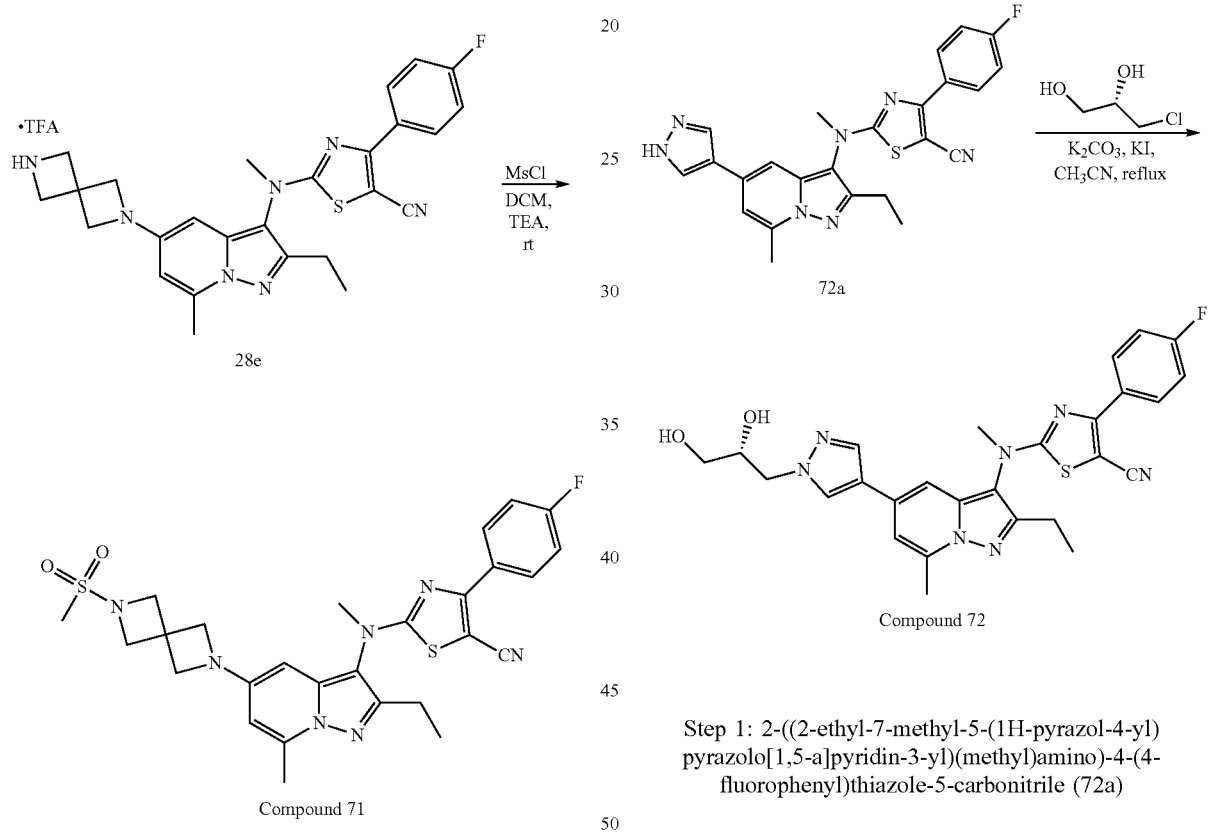

Compound 71

Compound 72

Step 1: 2-((2-ethyl-7-methyl-5-(1H-pyrazol-4-yl)pyrazolo[1,5-a]pyridin-3-yl)(methyl)amino)-4-(4-fluorophenyl)thiazole-5-carbonitrile (72a)

To a solution of 28e (125 mg, 0.26 mmol) in DCM (5 mL) was added triethylamine (0.4 mL, 2.6 mmol) and MsCl (0.2 mL, 2.6 mmol) at 0° C. The reaction mixture was allowed to warm to rt and stirred for 1 h, then quenched with water, diluted with DCM (50 mL), washed with water (2×50 mL), and brine (100 mL). All volatiles were removed under reduced pressure. The residue was purified by column chromatography on silica gel to give the title Compound 71 (110 mg, 75%). $^1$H NMR (400 MHz, CDCl$_3$) δ 8.28-7.98 (m, 2H), 7.22-7.05 (m, 2H), 5.97 (s, 1H), 5.84 (d, 1H), 4.11 (s, 4H), 4.06 (s, 4H), 3.57 (s, 3H), 2.87 (s, 3H), 2.75 (q, 2H), 2.70 (s, 3H), 1.32 (t, 3H). LC-MS (ESI): m/z=566.2 [M+H]$^+$ To a solution Intermediate 5 (0.20 g, 0.43 mmol) in 1,4-dioxane (4 mL) under argon was successively added 4-(4,4,5,5-tetramethyl-1,3,2-dioxaborolan-2-yl)-1H-pyrazole (0.12 g, 0.64 mmol), K$_2$CO$_3$ (0.18 g, 1.28 mmol) and then Pd(dppf)Cl$_2$ (0.062 g, 0.085 mmol) and H$_2$O (1.0 mL). The reaction mixture was heated at 90° C. for 4 h. After cooling to room temperature, the mixture was diluted with water and EtOAc. The organic layer was separated and the aqueous layer extracted with EtOAc. The combined organic layers were then washed with water and brine, dried over Na$_2$SO$_4$, filtered, and concentrated in vacuo. The residue was was purified by flash chromatography to afford 72a (0.10 g, 51%) as a yellow solid. LC-MS (ESI): m/z=458.2 [M+H]$^+$ Step 2: (R)-2-((5-(1-(2,3-dihydroxypropyl)-1H-pyrazol-4-yl)-2-ethyl-7-methylpyrazolo[1,5-a]pyridin-3-yl)(methyl)amino)-4-(4-fluorophenyl)thiazole-5-carbonitrile (Compound 72)

To a solution of 72a (0.10 g, 0.22 mmol) in acetonitrile (10 mL) was added K₂CO₃ (0.15 g, 1.0 mmol), KI (0.11 g, 0.66 mmol) and (S)-3-chloropropane-1,2-diol (0.097 g, 0.87 mmol). The reaction mixture was refluxed for 3.5 h and then filtered, and the solid was washed with acetonitrile. The filtrate was then suspended in 50 mL of water, extracted with ethyl acetate, the organic layer was dried over magnesium sulfate, filtered, and concentrated in vacuo. The residue was purified by column chromatography on silica gel to give the Compound 72 (0.035 g, 30%) as a white solid. MS m/z (ESI): 532.2[M+H⁺].

Example 73: 2-(4-(3-((5-cyano-4-(4-fluorophenyl)thiazol-2-yl) (methyl) amino)-2-ethylpyrazolo [1,5-a]pyridin-5-yl) piperazin-1-yl)-N, N-dimethylacetamide (Compound 73)

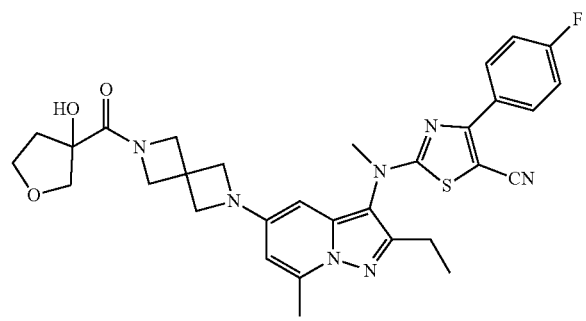 [SMILES: CCc1nn2c(C)cc(N3CC4(CN(C(=O)C5(O)CCOC5)C4)C3)cc2c1N(C)c1nc(-c2ccc(F)cc2)c(C#N)s1]

The title compound was prepared by the method substantially similar to that mentioned in Example 31, using 3-hydroxytetrahydrofuran-3-carboxylic acid to afford Compound 73 as a white solid. ¹H NMR (400 MHz, Chloroform-d) δ 8.206-8.112 (m, 2H), 7.215-7.114 (m, 2H), 5.971 (s, 1H), 5.837 (d, J=2.3 Hz, 1H), 4.561 (d, J=16.6 Hz, 2H), 4.268 (s, 2H), 4.112-3.923 (m, 7H), 3.735 (d, J=9.8 Hz, 1H), 3.573 (s, 3H), 3.401 (s, 1H), 2.809-2.684 (m, 5H), 2.417 (ddd, J=12.5, 9.2, 7.6 Hz, 1H), 2.117-1.973 (m, 1H), 1.368-1.231 (m, 4H). LC-MS (ESI): m/z=601.2 [M+H]⁺

Example 75 and Example 76

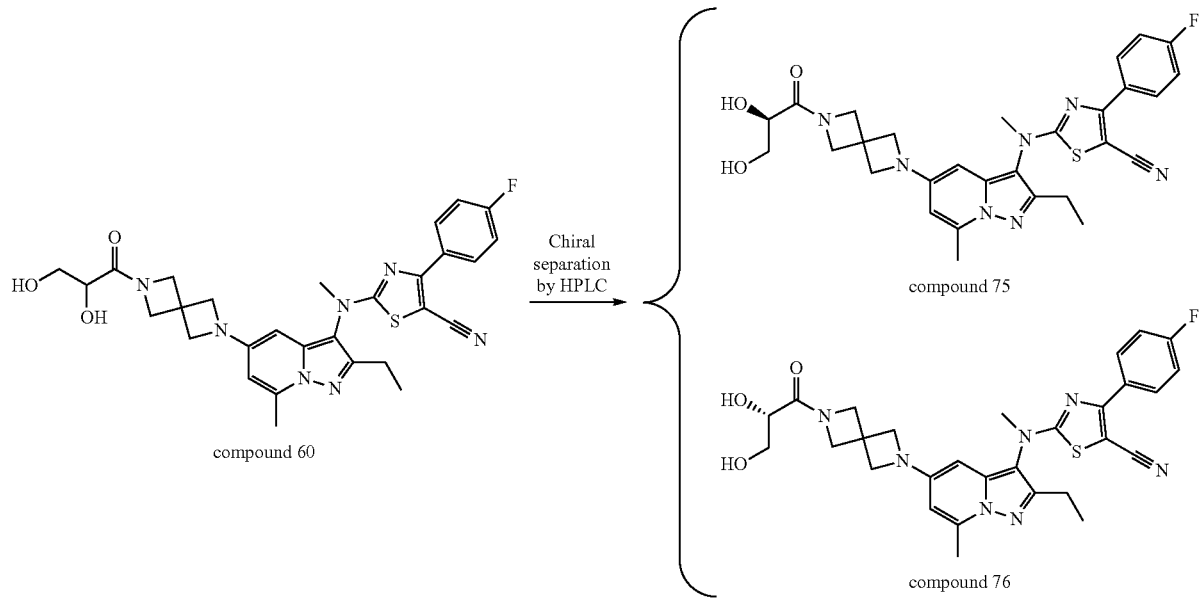 [SMILES: CCc1nn2c(C)cc(N3CC4(CN(C(=O)C(O)CO)C4)C3)cc2c1N(C)c1nc(-c2ccc(F)cc2)c(C#N)s1 ; CCc1nn2c(C)cc(N3CC4(CN(C(=O)[C@@H](O)CO)C4)C3)cc2c1N(C)c1nc(-c2ccc(F)cc2)c(C#N)s1 ; CCc1nn2c(C)cc(N3CC4(CN(C(=O)[C@H](O)CO)C4)C3)cc2c1N(C)c1nc(-c2ccc(F)cc2)c(C#N)s1]

Example 75 and Example 76 were separated from Example 60 (by SFC on ChiralPak AS column). The conditions of separation were as follows: Instrument: Waters UPC2 analytical SFC (SFC-H)

Column: ChiralPak AS, 150×4.6 mm I.D., 3 μm; Mobile phase: A for CO2 and B for Ethanol (0.05% DEA); Gradient: B 5-40%; Flow rate: 2.5 mL/min; Back pressure: 100 bar; Column temperature: 35° C.; Wavelength: 220 nm.

The peak 1 was compound 75 (4.72 min). The absolute configuration was not confirmed. NMR (400 MHz, CDCl₃) δ 8.29-8.01 (m, 2H), 7.22-7.06 (m, 2H), 5.98 (s, 1H), 5.85 (s, 1H), 4.54-4.38 (m, 2H), 4.28 (d, 2H), 4.19 (t, 1H), 4.15-3.99 (m, 4H), 3.87-3.64 (m, 2H), 3.57 (s, 3H), 2.76 (q, 2H), 2.71 (s, 3H), 1.32 (t, J=7.6 Hz, 3H). LC-MS (ESI): m/z=576.2 [M+H]⁺

The peak 2 was compound 76 (4.94 min). The absolute configuration was not confirmed. NMR (400 MHz, CDCl₃) δ 8.29-8.01 (m, 2H), 7.22-7.06 (m, 2H), 5.98 (s, 1H), 5.85 (s, 1H), 4.54-4.38 (m, 2H), 4.28 (d, 2H), 4.19 (t, 1H), 4.15-3.99 (m, 4H), 3.87-3.64 (m, 2H), 3.57 (s, 3H), 2.76 (q, 2H), 2.71 (s, 3H), 1.32 (t, J=7.6 Hz, 3H). LC-MS (ESI): m/z=576.2 [M+H]⁺

Example 77: 2-((2-cyclopropyl-5-(6-(2-hydroxy-2-methylpropanoyl)-2,6-diazaspiro[3.3]heptan-2-yl)-7-methylpyrazolo[1,5-a]pyridin-3-yl)(methyl)amino)-4-(4-fluorophenyl)thiazole-5-carbonitrile (Comnound 77)

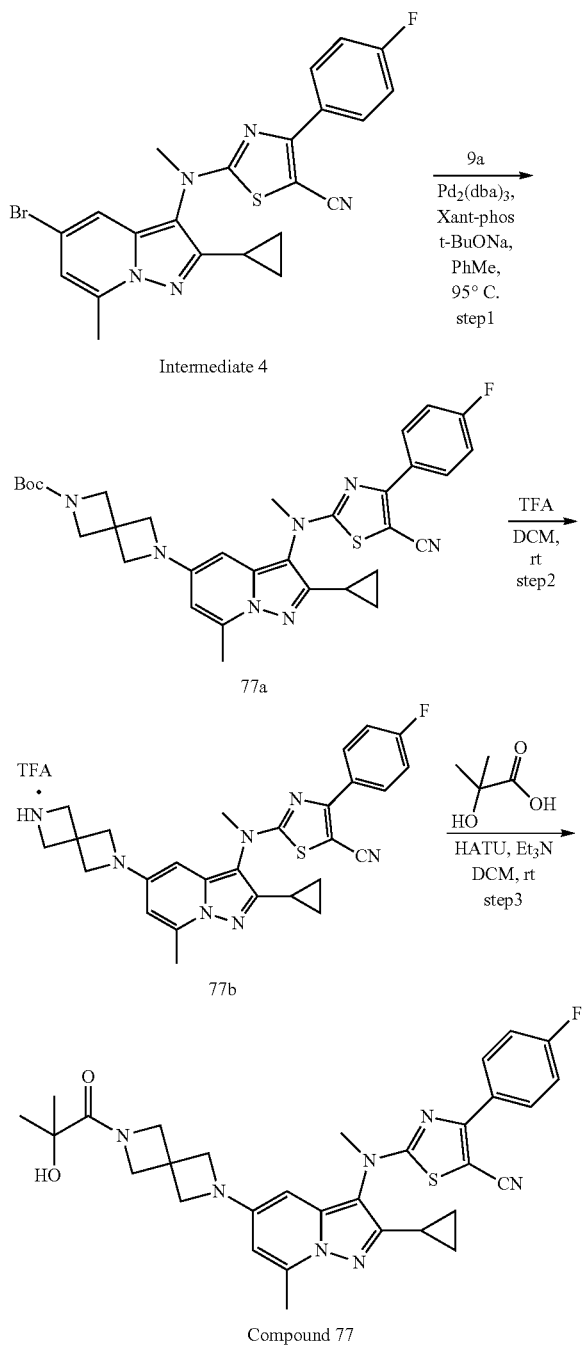

Step 1: tert-butyl 6-(3-((5-cyano-4-(4-fluorophenyl)thiazol-2-yl)(methyl)amino)-2-cyclopropyl-7-methylpyrazolo[1,5-a]pyridin-5-yl)-2,6-diazaspiro[3.3]heptane-2-carboxylate (77a)

To a solution of Intermediate 4 (500 mg, 1.04 mmol) in toluene (10 mL) under argon were successively added 9a (359 mg, 1.24 mmol), sodium tert-butoxide (598 mg, 6.22 mmol), XantPhos (120 mg, 0.20 mmol) and Pd$_2$dba$_3$ (95 mg, 0.10 mmol). The reaction mixture was heated at 100° C. for 4 h. After cooling to room temperature, the reaction was filtered on Celite, the cake was washed with DCM and the filtrate was then concentrated in vacuo. The crude product was purified by chromatography on silica gel to afford 78a (500 mg, 84%). LC-MS (ESI): m/z=600.3 [M+H]$^+$ Step 2: 2-((2-cyclopropyl-7-methyl-5-(2,6-diazaspiro[3.3]heptan-2-yl)pyrazolo[1,5-a]pyridin-3-yl)(methyl)amino)-4-(4-fluorophenyl)thiazole-5-carbonitrile (77b)

To a solution of 77a (200 mg, 0.33 mmol) in dichloromethane (5 mL) was added TFA (5 mL) at room temperature, the reaction mixture was stirred for 3 h and concentrated, the residue was directly used for the next step without purification. LC-MS (ESI): m/z=500.2 [M+H]$^+$ Step 3: 2-((2-cyclopropyl-5-(6-(2-hydroxy-2-methylpropanoyl)-2,6-diazaspiro[3.3]heptan-2-yl)-7-methylpyrazolo[1,5-a]pyridin-3-yl)(methyl)amino)-4-(4-fluorophenyl)thiazole-5-carbonitrile (Compound 77)

To a solution of 77b (80 mg, 0.16 mmol) in dichloromethane (10 mL) was added N,N-diethylethanamine (65 mg, 0.64 mmol), HATU (73 mg, 0.19 mmol) and 2-hydroxy-2-methyl-propanoic acid (25 mg, 0.24 mmol). The reaction mixture was stirred at room temperature for 3 h and then the reaction mixture was quenched with water, extracted with ethyl acetate, the organic layer was washed with water (3×15 mL) and then dried over magnesium sulfate, filtered, and concentrated in vacuo. The residue was purified by column chromatography on silica gel to give Compound 77 (35 mg, 37%) as a yellow solid. $^1$H NMR (400 MHz, CDCl3) δ 8.21-8.12 (m, 2H), 7.20-7.11 (m, 2H), 5.93 (d, 1H), 5.82 (d, 1H), 4.55 (s, 2H), 4.24 (s, 2H), 4.06 (s, 4H), 3.61 (s, 3H), 2.63 (s, 3H), 1.87 (m, 1H), 1.41 (s, 6H), 1.11-0.94 (m, 4H). LC-MS (ESI): m/z=586.2 [M+H]$^+$ Example 78: (S)-2-((2-cyclopropyl-7-methyl-5-(6-(tetrahydrofuran-3-carbonyl)-2,6-diazaspiro[3.3]heptan-2-yl)pyrazolo[1,5-a]pyridin-3-yl)(methyl)amino)-4-(4-fluorophenyl)thiazole-5-carbonitrile (Compound 78)

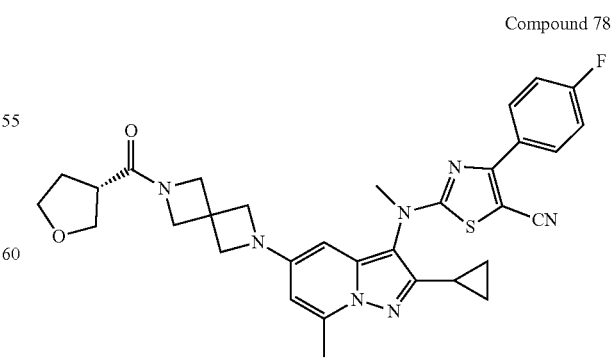

Compound 78

The title compound was prepared by the method substantially similar to that mentioned in Step 3 (Example 77), using (S)-tetrahydrofuran-3-carboxylic acid afford Compound 78 as a white solid. ¹H NMR (400 MHz, CDCl3) δ 8.20-8.11 (m, 2H), 7.19-7.11 (m, 2H), 5.94 (d, 1H), 5.83 (d, 1H), 4.34 (q, 2H), 4.23-4.13 (m, 2H), 4.13-4.02 (m, 4H), 3.98 (t, 1H), 3.93-3.77 (m, 3H), 3.61 (s, 3H), 2.97-2.86 (m, 1H), 2.63 (s, 3H), 2.16 (dt, 1H), 2.10-2.00 (m, 1H), 1.87 (m, 1H), 1.12-0.93 (m, 4H). LC-MS (ESI): m/z=598.2 [M+H]⁺

Example 79: 2-(4-(3-((5-cyano-4-(4-fluorophenyl) thiazol-2-yl) (methyl) amino)-2-ethylpyrazolo [1, 5-a] pyridin-5-yl) piperazin-1-yl) acetamide (Compound 79)

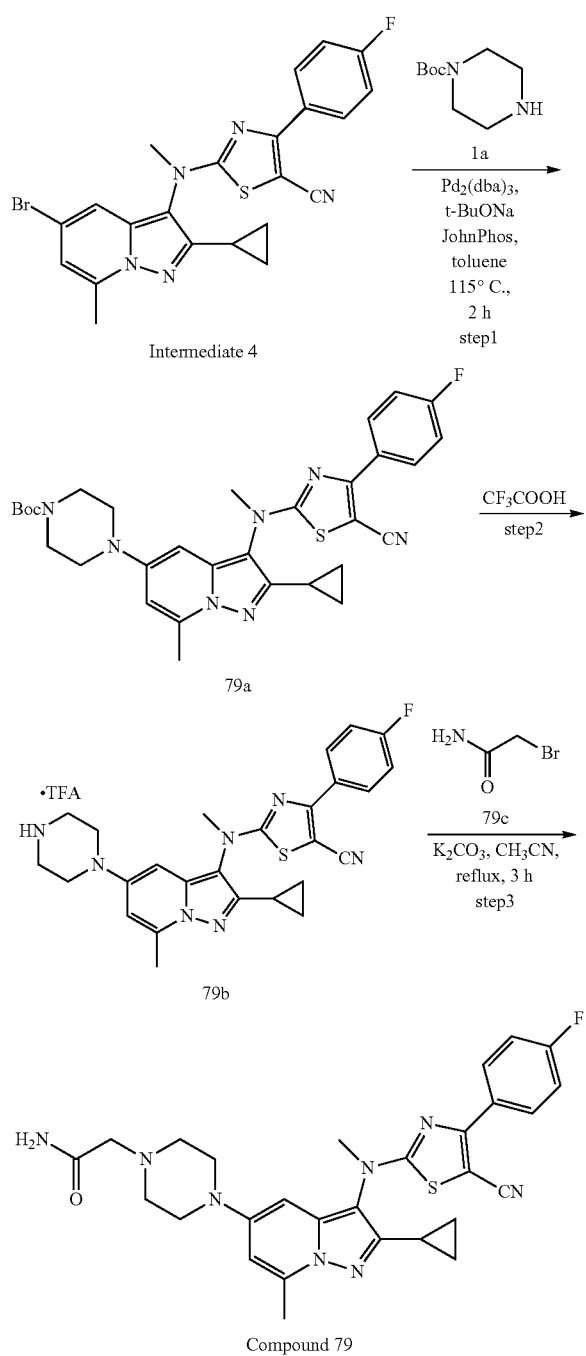

Step 1: tert-butyl 4-(3-((5-cyano-4-(4-fluorophenyl) thiazol-2-yl)(methyl)amino)-2-cyclopropyl-7-methylpyrazolo[1,5-a]pyridin-5-yl)piperazine-1-carboxylate (79b)

To a solution Intermediate 4 (0.92 g, 2.0 mmol) in toluene (15 mL) under argon was successively added N-Boc piperazine (0.58 g, 3.0 mmol), sodium tert-butoxide (0.38 g, 4.0 mmol) and then JohnPhos (0.06 g, 0.2 mmol) and Pd₂(dba)₃ (0.09 g, 0.1 mmol). The reaction mixture was heated at 115° C. for 2 h. After cooling to room temperature, the mixture was diluted with water and EtOAc. The organic layer was separated and the aqueous layer extracted with EtOAc. The combined organic layers were then washed with water and brine, dried over Na₂SO₄, filtered, and concentrated in vacuo. The residue was purified by flash chromatography to afford 79b (0.70 g, 62%) as a yellow solid. ¹H NMR (400 MHz, DMSO) δ 7.641-7.567 (m, 2H), 7.467 (d, J=1.4 Hz, 1H), 7.155-7.075 (m, 2H), 6.860 (p, J=1.4 Hz, 1H), 3.966 (s, 2H), 3.551 (t, J=5.3 Hz, 4H), 3.217 (dt, J=11.5, 5.3 Hz, 2H), 3.126 (dt, J=11.7, 5.2 Hz, 2H), 2.582 (d, J=1.3 Hz, 3H), 2.439 (p, J=5.9 Hz, 1H), 1.465 (s, 7H), 0.748-0.652 (m, 2H), 0.671-0.575 (m, 2H).

Step 2: 2-((2-cyclopropyl-7-methyl-5-(piperazin-1-yl) pyrazolo [1,5-a] pyridin-3-yl) (methyl) amino)-4-(4-fluorophenyl) thiazole-5-carbonitrile (79c)

A solution of 79b (0.70 g, 1.2 mmol) and trifluoroacetic acid (3 mL) in DCM (10 mL) was stirred at room temperature for 0.5 h. Solvent was evaporated, and the crude product was partitioned between water and DCM. The aqueous layer was basified with NaHCO₃ and extracted with DCM. Combined organic layers were washed with brine, dried over sodium sulfate, filtered, and evaporated to give 79c (0.55 g, 100%) that was used in the next step without further purification.

Step 3: 2-(4-(3-((5-cyano-4-(4-fluorophenyl) thiazol-2-yl) (methyl) amino)-2-ethylpyrazolo [1, 5-a] pyridin-5-yl) piperazin-1-yl) acetamide (Compound 79)

To a solution of 79c (0.55 g, 1.2 mmol) in MeCN (15 mL) were added potassium carbonate (0.33 g, 2.4 mmol) and 2-bromoacetamide (79d) (0.22 g, 1.5 mmol). The reaction mixture was refluxed for 3 h. After cooling to room temperature, the mixture was diluted with water and EtOAc. The organic layer was separated and the aqueous layer extracted with EtOAc. The combined organic layers were then washed with water and brine, dried over Na₂SO₄, filtered, and concentrated in vacuo. The residue was was purified by flash chromatography to afford Compound 79 (0.33 g, 48%) as a white solid. ¹H NMR (400 MHz, CDCl₃) δ 14.372 (s, OH), 8.363 (d, J=5.4 Hz, 4H), 7.440 (d, J=1.8 Hz, 4H), 7.372 (dd, J=5.4, 1.8 Hz, 5H), 7.090 (s, 1H), 3.896 (s, 9H), 3.681 (s, 1H), 3.181 (s, 1H), 2.575 (q, J=7.3 Hz, 10H), 2.447 (q, J=7.4 Hz, 1H), 2.302 (q, J=7.5 Hz, 1H), 1.257 (s, 1H), 1.160 (dt, J=17.3, 7.5 Hz, 2H), 1.075 (t, J=7.3 Hz, 14H). LC-MS: m/z=545.3 [M+H]⁺

Example 80: 2-(4-(3-((5-cyano-4-(4-fluorophenyl)thiazol-2-yl)(methyl)amino)-2-cyclopropyl-7-methylpyrazolo[1,5-a]pyridin-5-yl)piperazin-1-yl)acetic acid (Compound 80)

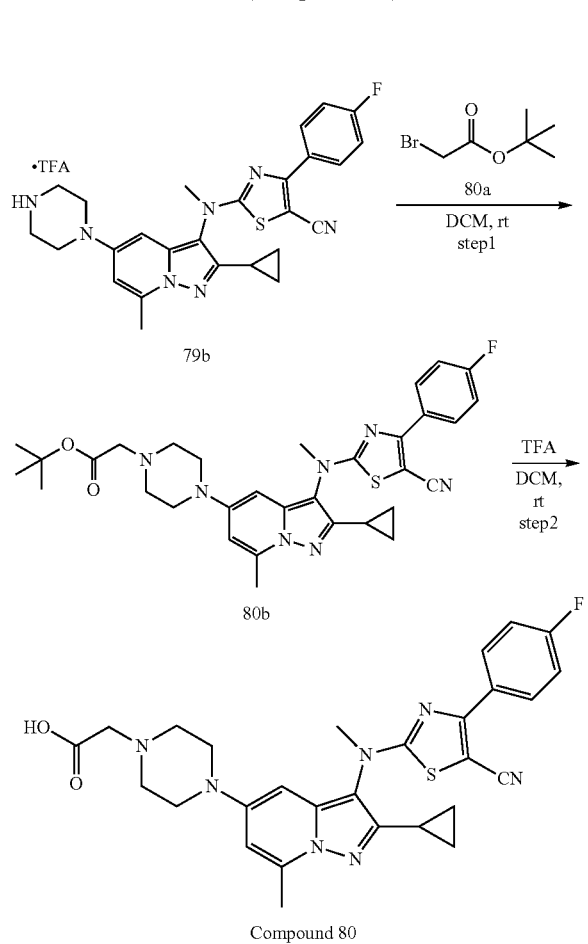

Step 1: tert-butyl 2-(4-(3-((5-cyano-4-(4-fluorophenyl)thiazol-2-yl)(methyl)amino)-2-cyclopropyl-7-methylpyrazolo[1,5-a]pyridin-5-yl)piperazin-1-yl)acetate (80b)

See Example 48, Step 3. $^1$H NMR (400 MHz, CDCl$_3$) δ 7.636-7.563 (m, 2H), 7.450 (d, J=1.4 Hz, 1H), 7.155-7.075 (m, 2H), 6.674 (p, J=1.3 Hz, 1H), 3.968 (s, 2H), 3.397-3.283 (m, 4H), 3.119 (s, 1H), 2.665-2.576 (m, 4H), 2.552 (d, J=1.2 Hz, 3H), 2.439 (p, J=5.9 Hz, 1H), 1.420 (s, 6H), 0.696-0.544 (m, 4H). LC-MS (ESI): m/z=602.3 [M+H]$^+$ Step 2: 2-(4-(3-((5-cyano-4-(4-fluorophenyl)thiazol-2-yl)(methyl)amino)-2-cyclopropyl-7-methylpyrazolo[1,5-a]pyridin-5-yl)piperazin-1-yl)acetic acid (Compound 80)

See Example 48, Step 2. $^1$H NMR (400 MHz, Chloroform-d) δ 8.116 (dd, J=8.7, 5.4 Hz, 2H), 7.112 (t, J=8.6 Hz, 2H), 6.302 (d, J=15.4 Hz, 2H), 3.686 (s, 2H), 3.608 (s, 3H), 3.457 (s, 4H), 3.320 (s, 4H), 2.935 (s, 15H), 2.628 (s, 3H), 1.873 (ddd, J=13.7, 8.3, 5.1 Hz, 1H), 1.297 (s, 2H), 1.086 (d, J=4.8 Hz, 1H), 1.093-0.944 (m, 4H). LC-MS (ESI): m/z=546.2 [M+H]$^+$

Example 82: (R)-2-((2-cyclopropyl-5-(4-(2,3-dihydroxypropyl)piperazin-1-yl)-7-methylpyrazolo[1,5-a]pyridin-3-yl)(methyl)amino)-4-(4-fluorophenyl)thiazole-5-carbonitrile (Compound 82)

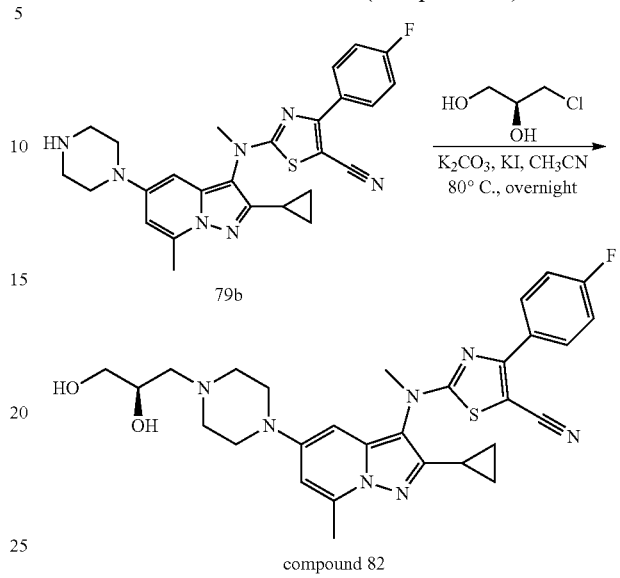

To a solution of 79b (0.15 g, 0.3 mmol) in MeCN (5 mL) were added K$_2$CO$_3$ (0.13 g, 0.9 mmol), KI (51 mg, 0.3 mmol) and (S)-3-chloropropane-1,2-diol (68 mg, 0.6 mmol). The reaction mixture was refluxed overnight. After cooling to room temperature, the mixture was diluted with water and EtOAc. The organic layer was separated and the aqueous layer extracted with EtOAc. The combined organic layers were then washed with water and brine, dried over Na$_2$SO$_4$, filtered, and concentrated in vacuo. The residue was purified by flash chromatography to afford Compound 82 (20 mg, 12%) as a white solid. $^1$H NMR (400 MHz, CDCl$_3$) δ 8.18-8.14 (m, 2H), 7.18-7.14 (m, 2H), 6.38 (s, 1H), 6.24 (s, 1H), 3.94-3.91 (m, 1H), 3.79-3.75 (m, 1H), 3.62 (s, 3H), 3.62-3.52 (m, 1H), 3.31 (brs, 4H), 2.89-2.88 (m, 2H), 2.72-2.64 (m, 6H), 2.53-2.49 (m, 2H), 1.88-1.86 (m, 1H), 1.09-0.96 (m, 4H). LC-MS (ESI): m/z=562.2 [M+H]$^+$

Example 83: (S)-2-((2-cyclopropyl-5-(4-(2,3-dihydroxypropyl)piperazin-1-yl)-7-methylpyrazolo[1,5-a]pyridin-3-yl)(methyl)amino)-4-(4-fluorophenyl)thiazole-5-carbonitrile (Compound 83)

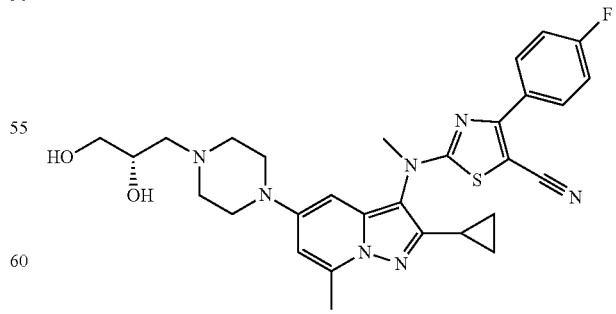

Compound 83 was prepared from Intermediate 79b and (S)-3-chloropropane-1,2-diol in a manner analogous to Compound 82 and was isolated as a reddish brown solid. $^1$H NMR (400 MHz, CDCl$_3$) δ 8.18-8.14 (m, 2H), 7.18-7.14 (m, 2H), 6.38 (s, 1H), 6.24 (s, 1H), 3.94-3.91 (m, 1H), 3.79-3.75 (m, 1H), 3.62 (s, 3H), 3.62-3.52 (m, 1H), 3.31 (brs, 4H), 2.89-2.88 (m, 2H), 2.72-2.64 (m, 6H), 2.53-2.49 (m, 2H), 1.88-1.86 (m, 1H), 1.09-0.96 (m, 4H). LC-MS (ESI): m/z=562.2 [M+H]$^+$ Example 84: 2-((2-cyclopropyl-7-methyl-5-(6-(1-methylazetidine-3-carbonyl)-2,6-diazaspiro[3.3]heptan-2-yl)pyrazolo[1,5-a]pyridin-3-yl)(methyl)amino)-4-(4-fluorophenyl)thiazole-5-carbonitrile (Compound 84)

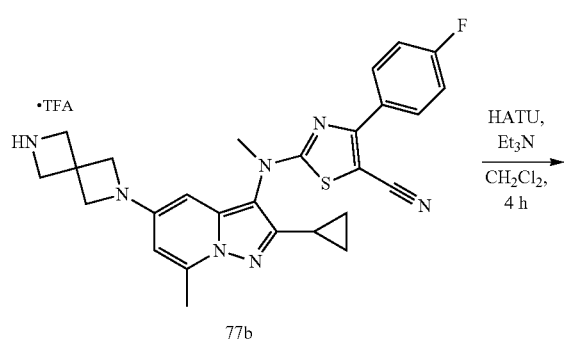

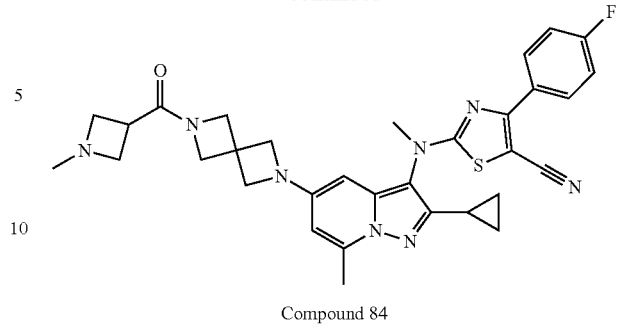

Compound 84

The title compound was prepared by the method substantially similar to that mentioned in Step 3 (Example 77), using 1-methylazetidine-3-carboxylic acid afford Compound 84 as a yellow solid. $^1$H NMR (400 MHz, CDCl$_3$) δ 8.21-8.11 (m, 2H), 7.16 (t, 2H), 5.92 (s, 1H), 5.81 (d, 1H), 4.27 (s, 2H), 4.18 (s, 2H), 4.10-3.98 (m, 4H), 3.89 (t, 2H), 3.61 (s, 3H), 3.44 (dt, 3H), 2.62 (s, 3H), 2.50 (s, 3H), 1.93-1.78 (m, 1H), 1.12-0.88 (m, 4H). LC-Ms m/z (ESI): 597.3[M+H$^+$]

Example 85: 2-((2-cyclopropyl-7-methyl-5-(6-(1-methylpyrrolidine-3-carbonyl)-2,6-diazaspiro[3.3]heptan-2-yl)pyrazolo[1,5-a]pyridin-3-yl)(methyl)amino)-4-(4-fluorophenyl)thiazole-5-carbonitrile (Compound 85)

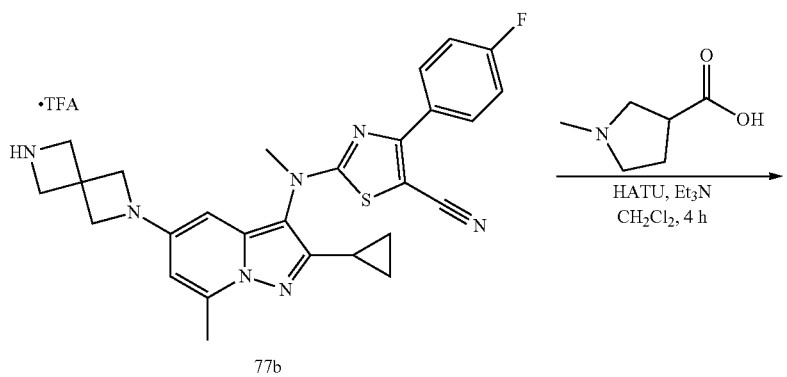

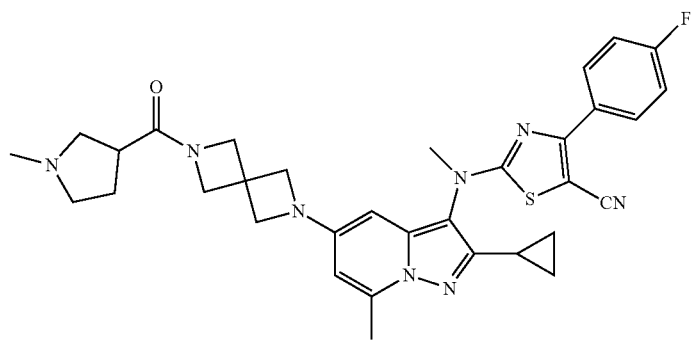

Compound 85

To a solution of 77b (54 mg, 0.11 mmol) in DCM (10 mL) were successively added 1-methylpyrrolidine-3-carboxylic acid (15 mg, 0.13 mmol), HATU (65 mg, 0.17 mmol) and TEA (33 mg, 0.33 mmol). The reaction mixture was stirred at room temperature for 4 h, then the mixture was diluted with water (10 mL) and extracted with DCM (10 mL×3). The combined organic layers were then washed with water (10 mL×2) and brine (5 mL×1), dried over sodium sulfate, filtered, and concentrated in vacuo. The residue was purified by flash chromatography to afford the title compound 85 (50 mg, 72%) as a light brown solid. $^1$H NMR (400 MHz, CDCl$_3$) δ 8.15 (s, 2H), 7.30 (s, 2H), 6.50 (d, 1H), 5.80 (d, 1H), 3.76 (d, 4H), 3.46 (d, 4H), 2.96 (d, 3H), 2.70 (d, 3H), 2.37-2.62 (m, 11H), 1.96-2.07 (m, 2H), 0.99-1.24 (m, 4H). LC-MS (ESI): m/z=611.2 [M+H]$^+$

Example 86: (S)-2-((2-cyclopropyl-7-methyl-5-(2-(tetrahydrofuran-3-carbonyl)-2,6-diazaspiro[3.4]octan-6-yl)pyrazolo[1,5-a]pyridin-3-yl)(methyl)amino)-4-(4-fluorophenyl)thiazole-5-carbonitrile (Compound 86)

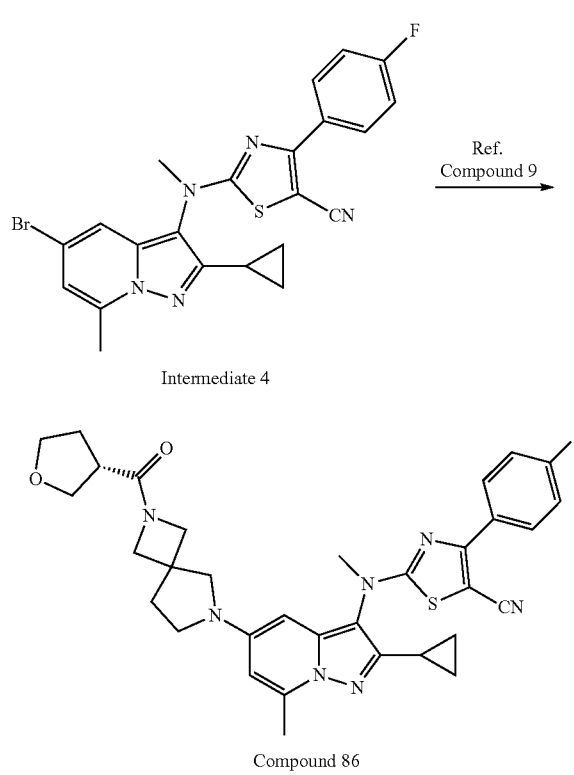

Compound 86 was prepared from Intermediate 4 in a manner analogous to Compound 9 and was isolated as a tawny solid. 1H NMR (400 MHz, CDCl$_3$) δ 8.18-8.14 (m, 2H), 7.18-7.14 (m, 2H), 6.13 (d, J=2.4 Hz, 1H), 5.85 (d, J=2.4 Hz, 1H), 4.17-4.09 (m, 2H), 4.03-3.97 (m, 3H), 3.94-3.90 (m, 1H), 3.85-3.80 (m, 2H), 3.61 (s, 3H), 3.55-3.53 (m, 1H), 3.45-3.43 (m, 2H), 2.95-2.87 (m, 2H), 2.66 (s, 3H), 2.27 (t, J=6.8 Hz, 2H), 2.18-2.14 (m, 1H), 2.08-2.05 (m, 1H), 1.92-1.86 (m, 1H), 1.09-1.03 (m, 2H), 1.01-0.96 (m, 2H). LC-MS (ESI): m/z=612.3 [M+H]$^+$

Example 87: 2-[[2-cyclopropyl-5-(3-hydroxyazetidin-1-yl)-7-methyl-pyrazolo[1,5-a]pyridin-3-yl]-methyl-amino]-4-(4-fluorophenyl)thiazole-5-carbonitrile (Compound 87)

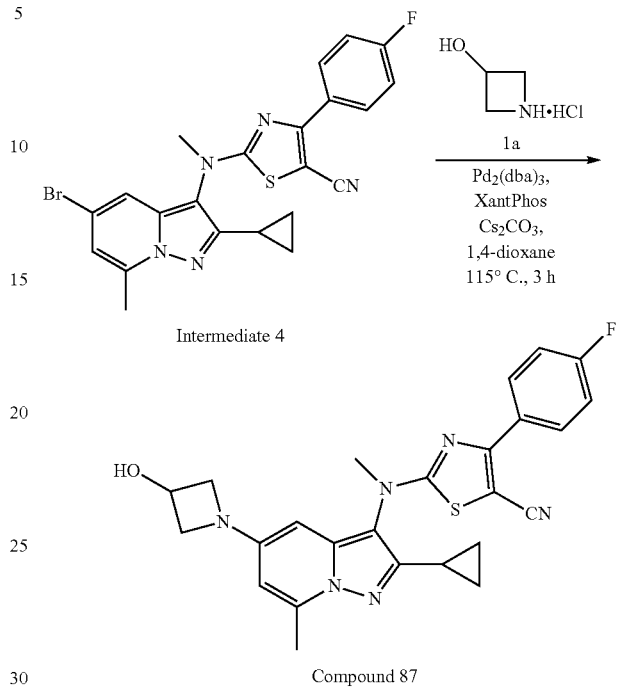

To a solution Intermediate 4 (0.12 g, 0.25 mmol) in 1,4-dioxane (5 mL) under argon was successively added 3-Hydroxyazetidine hydrochloride (55 mg, 0.5 mmol), Cesium Carbonate (0.33 g, 1.0 mmol) and then XantPhos (29 mg, 0.05 mmol) and Pd$_2$(dba)$_3$ (23 mg, 0.025 mmol). The reaction mixture was heated at 115° C. for 3 h. After cooling to room temperature, the mixture was diluted with water and EtOAc. The organic layer was separated and the aqueous layer extracted with EtOAc. The combined organic layers were then washed with water and brine, dried over Na$_2$SO$_4$, filtered, and concentrated in vacuo. The residue was was purified by flash chromatography to afford Compound 87 (62 mg, 53%) as a yellow solid. $^1$H NMR (400 MHz, CDCl$_3$) δ 8.20-8.104 (m, 2H), 7.20-7.12 (m, 2H), 5.96 (s, 1H), 5.82 (d, J=2.4 Hz, 1H), 4.83-4.73 (m, 1H), 4.24-4.18 (m, 2H), 3.76-3.74 (m, 2H), 3.62 (s, 3H), 2.62 (d, J=9.2 Hz, 3H), 1.92-1.83 (m, 1H), 1.11-0.95 (m, 4H). LC-MS (ESI): m/z=475.1 [M+H]$^+$.

Example 88: 2-[[5-(3-cyanoazetidin-1-yl)-2-cyclopropyl-7-methyl-pyrazolo[1,5-a]pyridin-3-yl]-methyl-amino]-4-(4-fluorophenyl)thiazole-5-carbonitrile (Compound 88)

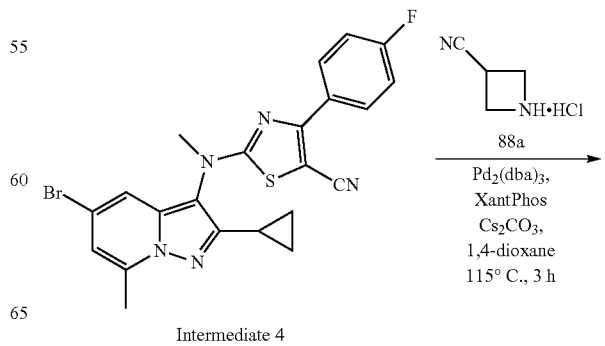

-continued

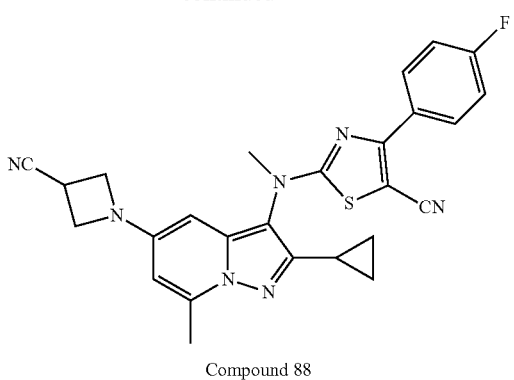

Compound 88

Compound 88 was prepared from Intermediate 4 and 3-Azetidinecarbonitrile hydrochloride (88a) in a manner analogous to Example 87 and was isolated as a yellow foam. $^1$H NMR (400 MHz, CDCl$_3$) δ 8.21-8.13 (m, 2H), 7.20-7.12 (m, 2H), 5.94 (d, J=1.4 Hz, 1H), 5.87 (d, J=2.4 Hz, 1H), 4.29-4.21 (m, 2H), 4.20-4.11 (m, 2H), 3.63 (s, 3H), 2.65 (s, 3H), 1.94-1.84 (m, 1H), 1.57 (s, 1H), 1.15-0.95 (m, 4H). LC-MS (ESI): m/z=484.2 [M+H]$^+$.

Example 90: 2-((2-cyclopropyl-5-(6-(4-hydroxytetrahydro-2H-pyran-4-carbonyl)-2,6-diazaspiro[3.3]heptan-2-yl)-7-methylpyrazolo[1,5-a]pyridin-3-yl)(methyl)amino)-4-(4-fluorophenyl)thiazole-5-carbonitrile (Compound 90)

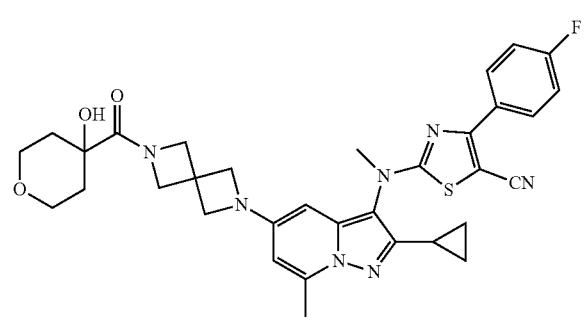 [SMILES: Cc1cc(N2CC3(CN(C(=O)C4(O)CCOCC4)C3)C2)cc2c(N(C)c3nc(-c4ccc(F)cc4)c(C#N)s3)c(C3CC3)nn12]

The title compound was prepared by the method substantially similar to that mentioned in Step 3 (Example 77), using 4-hydroxytetrahydro-2H-pyran-4-carboxylic acid afford Compound 90 as a white solid. $^1$H NMR (400 MHz, CDCl$_3$) δ 8.20-8.11 (m, 2H), 7.21-7.09 (m, 2H), 5.94 (d, J=1.4 Hz, 1H), 5.82 (d, 1H), 4.62 (s, 2H), 4.25 (s, 2H), 4.07 (s, 4H), 3.82 (q, 4H), 3.61 (s, 3H), 2.63 (s, 3H), 2.06 (d, 2H), 1.91-1.80 (m, 1H), 1.50 (d, 2H), 1.10-0.95 (m, 4H). LC-MS (ESI): m/z=628.3 [M+H]$^+$.

Example 91: 2-((5-(6-(bicyclo[1.1.1]pentane-1-carbonyl)-2,6-diazaspiro[3.3]heptan-2-yl)-2-cyclopropyl-7-methylpyrazolo[1,5-a]pyridin-3-yl)(methyl)amino)-4-(4-fluorophenyl)thiazole-5-carbonitrile (Compound 91)

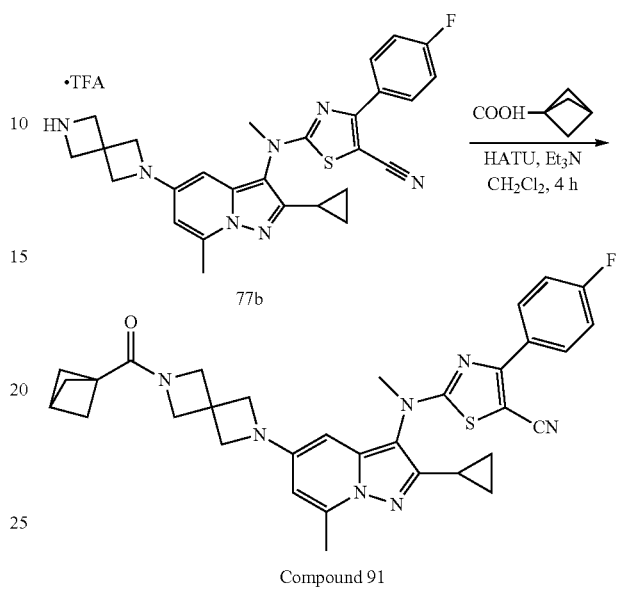

Compound 91

To a solution of 77b (58 mg, 0.1 mmol) in DCM (10 mL) were successively added bicycle [1.1.1] pentane-1-carboxylic acid (20 mg, 0.16 mmol), HATU (60 mg, 0.16 mmol) and Et$_3$N (0.5 mL, 3.6 mmol). The reaction mixture was stirred at room temperature for 4 h, then the mixture was diluted with water (10 mL) and extracted with DCM (10 mL×3). The combined organic layers were then washed with water (10 mL×2) and brine (5 mL×1), dried over Na$_2$SO$_4$, filtered, and concentrated in vacuo. The residue was was purified by flash chromatography to afford Compound 91 (50 mg, 85%) as a white solid. $^1$H NMR (400 MHz, CDCl$_3$) δ 8.200-8.107 (m, 2H), 7.215-7.107 (m, 2H), 6.407 (dd, J=2.6, 1.1 Hz, 1H), 6.273 (d, J=2.6 Hz, 1H), 4.620 (d, J=3.9 Hz, 1H), 4.225-4.087 (m, 4H), 3.835 (dd, J=9.3, 4.4 Hz, 2H), 3.676 (d, J=8.5 Hz, 2H), 3.587 (s, 3H), 3.406 (td, J=11.1, 5.7 Hz, 2H), 3.323-3.174 (m, 2H), 2.804-2.685 (m, 5H), 2.429 (s, 1H), 2.177-2.059 (m, 2H), 1.321 (t, J=7.6 Hz, 4H). LC-MS: m/z=580.3 [M+H]$^+$.

Example 92: 2-((2-ethyl-5-(6-(isoxazole-3-carbonyl)-2,6-diazaspiro[3.3]heptan-2-yl)-7-methylpyrazolo[1,5-a]pyridin-3-yl)(methyl)amino)-4-(4-fluorophenyl)thiazole-5-carbonitrile (Compound 92)

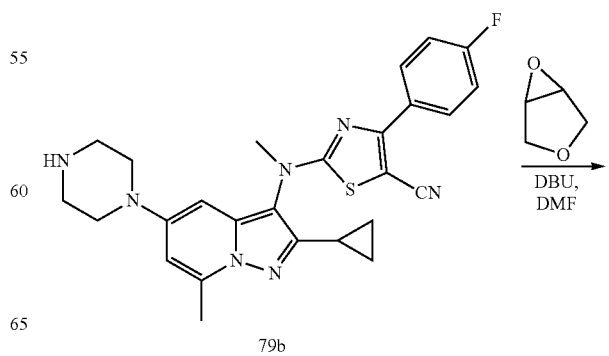

79b

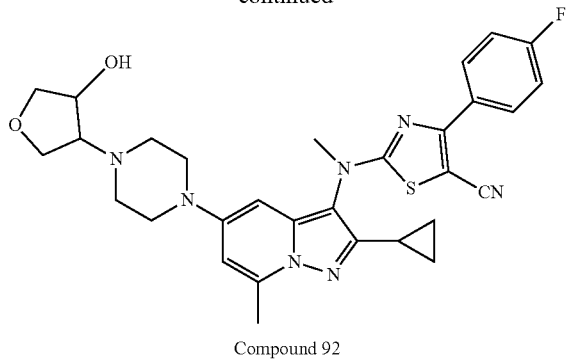

Compound 92

To a solution of 79b (100 mg, 0.21 mmol) in DMF (5 mL) was successively added 3,6-dioxabicyclo[3.1.0]hexane (0.18 g, 2.1 mmol), DBU (0.31 g, 2.1 mmol). The reaction mixture was heated at 115° C. for 2 h. After cooling to room temperature, the mixture was diluted with water and EtOAc. The organic layer was separated and the aqueous layer extracted with EtOAc. The residue was purified by column chromatography on silica gel to give Compound 92 (6 mg, 5.1%) as a yellow solid. $^1$H NMR (400 MHz, CDCl$_3$) δ 8.15 (dd, 2H), 7.16 (t, 2H), 6.32 (s, 2H), 4.93 (s, 1H), 4.30-4.18 (m, 1H), 4.13 (d, 1H), 4.08-3.99 (m, 1H), 3.72 (s, 1H), 3.68-3.52 (m, 7H), 3.35 (s, 2H), 3.25 (s, 2H), 2.66 (s, 3H), 1.93-1.84 (m, 1H), 1.26 (d, 2H), 1.15-0.92 (m, 4H). LC-MS (ESI): m/z=574.3 [M+H]$^+$ Example 93: 2-((2-cyclopropyl-5-(4-(3-hydroxyazetidin-1-yl)piperidin-1-yl)-7-methylpyrazolo[1,5-a]pyridin-3-yl)(methyl)amino)-4-(4-fluorophenyl)thiazole-5-carbonitrile (Compound 93)

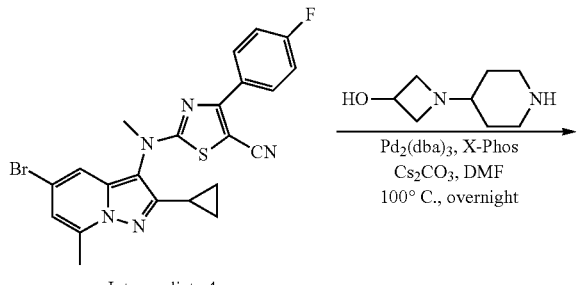

Intermediate 4

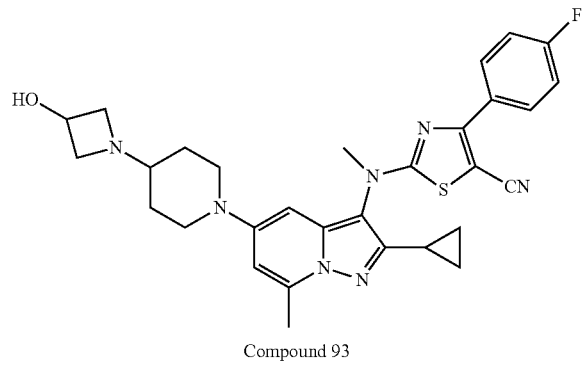

Compound 93

To a solution Intermediate 4 (80 mg, 0.17 mmol) in DMF (10 mL) under nitrogen was successively added 1-(4-piperidyl)azetidin-3-ol (39 mg, 0.25 mmol), Cesium Carbonate (162 mg, 0.50 mmol) and then X-Phos (16 mg, 0.033 mmol) and Pd$_2$(dba)$_3$ (15 mg, 0.016 mmol). The reaction mixture was heated at 100° C. overnight. After cooling to room temperature, the mixture was diluted with water and DCM (50 mL), washed with water (2×50 mL), and brine (100 mL). All volatiles were removed under reduced pressure. The residue was purified by column chromatography on silica gel to give the title Compound 93 (25 mg, 27%). $^1$H NMR (400 MHz, CDCl$_3$) δ 8.20-8.03 (m, 2H), 7.16 (t, J=8.7 Hz, 2H), 6.35 (s, 1H), 6.22 (s, 1H), 4.76-4.57 (m, 1H), 3.85-3.64 (m, 4H), 3.62 (s, 3H), 2.89-2.72 (m, 4H), 2.63 (s, 4H), 2.06-2.01 (m, 1H), 1.89-1.82 (m, 2H), 1.80-1.70 (m, 2H), 1.10-1.01 (m, 2H), 1.01-0.95 (m, 2H). LC-MS (ESI): m/z=558.3 [M+H]$^+$ Example 94: 2-((2-cyclopropyl-7-methyl-5-(4-(oxetan-3-yl)piperazin-1-yl)pyrazolo[1,5-a]pyridin-3-yl)(methyl)amino)-4-(4-fluorophenyl)thiazole-5-carbonitrile (Compound 94)

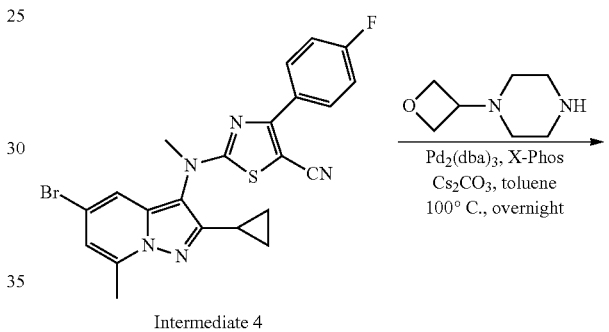

Intermediate 4

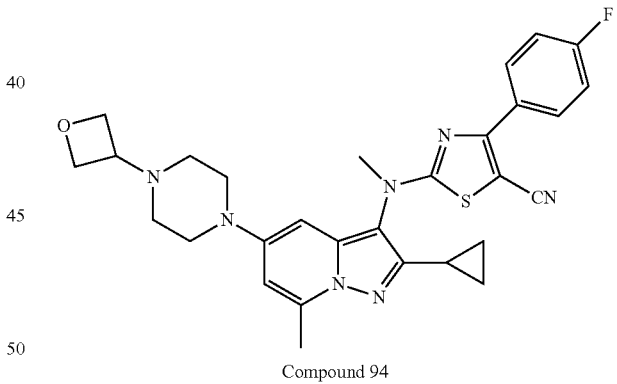

Compound 94

To a solution Intermediate 4 (80 mg, 0.17 mmol) in toluene (10 mL) under nitrogen was successively added 1-(oxetan-3-yl)piperazine (35 mg, 0.25 mmol), Cesium Carbonate (162 mg, 0.50 mmol) and then X-Phos (16 mg, 0.033 mmol) and Pd$_2$(dba)$_3$ (15 mg, 0.016 mmol). The reaction mixture was heated at 100° C. overnight. After cooling to room temperature, the mixture was diluted with water and DCM (50 mL), washed with water (2×50 mL), and brine (100 mL). All volatiles were removed under reduced pressure. The residue was purified by column chromatography on silica gel (DCM:MeOH=20:1) to give the title Compound 94 (25 mg, 27%). $^1$H NMR (400 MHz, CDCl$_3$) δ 8.25-7.97 (m, 2H), 7.23-7.01 (m, 2H), 6.39 (s, 1H), 6.24 (s, 1H), 4.68 (dt, 4H), 3.63 (s, 3H), 3.61-3.51 (m, 1H), 3.37-3.20 (m, 4H), 2.64 (s, 3H), 2.58-2.43 (m, 4H), 1.92-1.82 (m, 1H), 1.12-1.00 (m, 2H), 1.00-0.95 (m, 2H). LC-MS (ESI): m/z=544.2 [M+H]+

Example 95: 2-((2-ethyl-5-(4-(2-(3-hydroxyazetidin-1-yl)-2-oxoethyl)piperazin-1-yl)-7-methylpyrazolo[1,5-a]pyrimidin-3-yl)(methyl)amino)-4-(4-fluorophenyl)thiazole-5-carbonitrile (Compound 95)

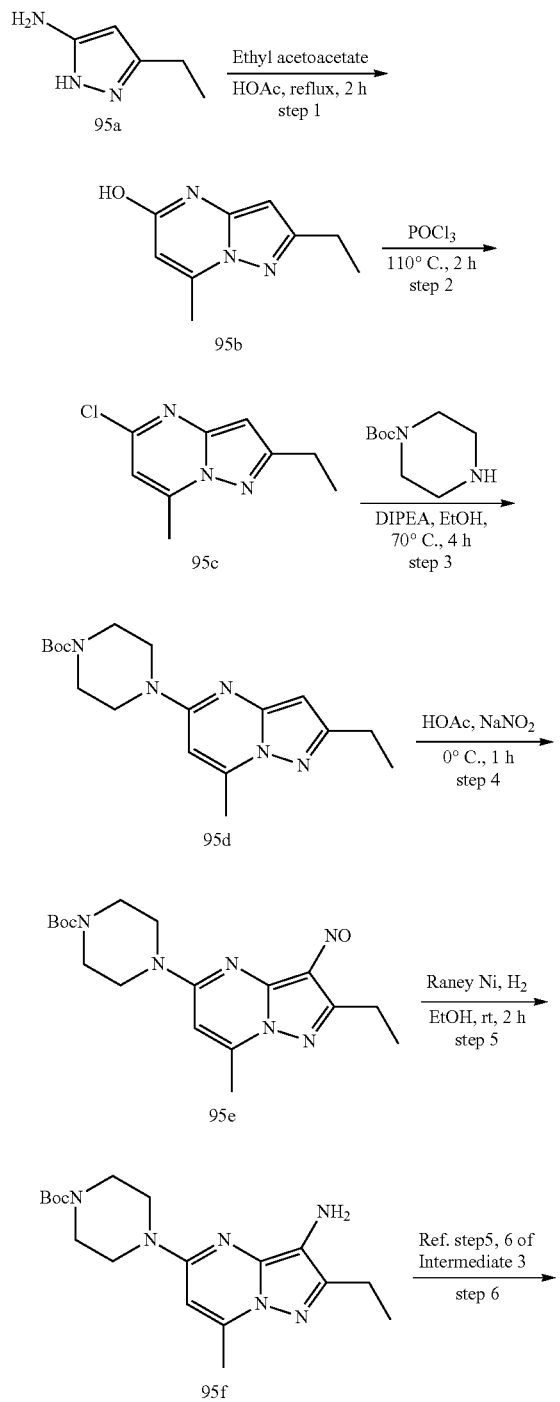

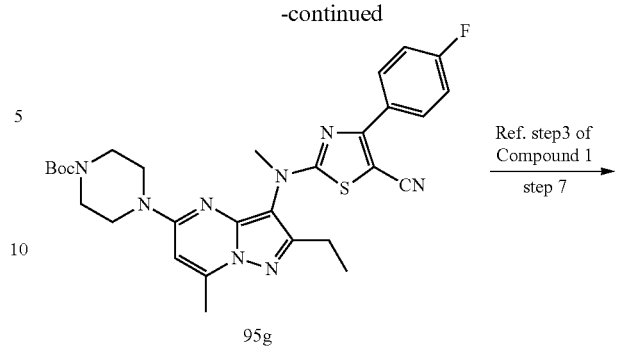

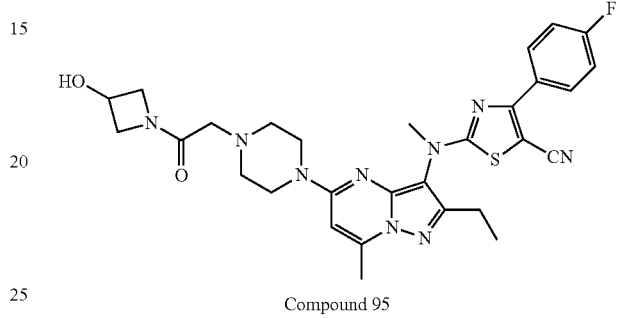

Compound 95

Step 1: 2-ethyl-7-methylpyrazolo[1,5-a]pyrimidin-5-ol (95b)

To a solution of 95a (1.11 g, 10.0 mmol) in AcOH (10 mL) was added ethyl acetoacetate (1.40 g, 10.8 mmol), and reflux for 2 h. After cooling to room temperature, the reaction mixture was concentrated in vacuo. The residue was purified by chromatography on silica gel to afford 95b (0.90 g, 51%) as a yellow solid. LC-MS (ESI): m/z=178.1 [M+H]+

Step 2: 5-chloro-2-ethyl-7-methylpyrazolo[1,5-a]pyrimidine (95c)

95b (0.80 g, 4.5 mmol) and POCl3 (5.0 mL, 54 mmol) were refluxed for 1 h. After cooling to room temperature, the reaction mixture was concentrated in vacuo. The residue (95c) (1.50 g) was used to next step without further purification.

Step 3: tert-butyl 4-(2-ethyl-7-methylpyrazolo[1,5-a]pyrimidin-5-yl)piperazine-1-carboxylate (95d)

95c (1.50 g, 4.5 mmol) was dissolved in EtOH (20 mL), then DIPEA (2.5 mL, 15 mmol) was added dropwise to the solution, N-Boc piperazine (1.26 g, 6.8 mmol) was added to the reaction mixture after 5 min at room temperature, and warmed to 70° C. for 4 h. After cooling to room temperature, the reaction mixture was concentrated in vacuo. The resdue was purified by chromatography on silica gel to afford 95d (0.75 g, 48%) as a brown foam. LC-MS (ESI): m/z=346.3 [M+H]+

Step 4: tert-butyl 4-(2-ethyl-7-methyl-3-nitrosopyrazolo[1,5-a]pyrimidin-5-yl)piperazine-1-carboxylate (95e)

To a solution of 95d (0.66 g, 2.0 mmol) in HOAc (4 mL) was slowly added coled NaNO2 aqueous solution (0.15 g dissolved in 4 mL water, 2.2 mmol) at 0° C., and stirred for 1 h. 5 mL water was added to the reaction mixture, filtered, washed with water (2 mL×3), and the filter cake was dried in vacuo to afford crude product 95e as a dark green solid. LC-MS (ESI): m/z=375.2 [M+H]$^+$

Step 5: tert-butyl 4-(3-amino-2-ethyl-7-methylpyrazolo[1,5-a]pyrimidin-5-yl)piperazine-1-carboxylate (95f)

95e and Raney Ni (50 mg) were added to MeOH (5 mL) at rt, and the mixture stirred under H$_2$ (1 atm) atmosphere for 3 h. The reaction mixture was concentrated in vacuo and purified by chromatography on silica gel to afford 95f (0.49 g, 71%) as a yellow solid. LC-MS (ESI): m/z=361.3 [M+H]+

Step 6: tert-butyl 4-(3-amino-2-ethyl-7-methylpyrazolo[1,5-a]pyrimidin-5-yl)piperazine-1-carboxylate (95g)

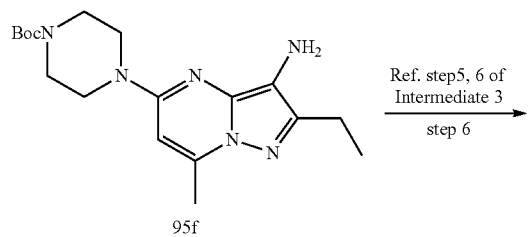

95f

Ref. step5, 6 of Intermediate 3
step 6

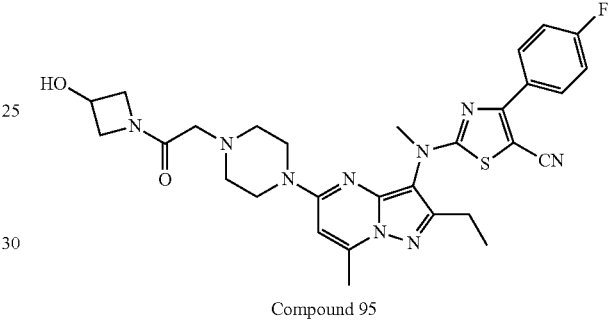

95g

Step 7: 2-((2-ethyl-5-(4-(2-(3-hydroxyazetidin-1-yl)-2-oxoethyl)piperazin-1-yl)-7-methylpyrazolo[1,5-a]pyrimidin-3-yl)(methyl)amino)-4-(4-fluorophenyl)thiazole-5-carbonitrile (Compound 95)

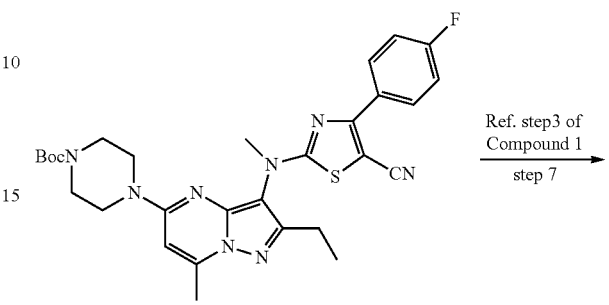

95g

Ref. step3 of Compound 1
step 7

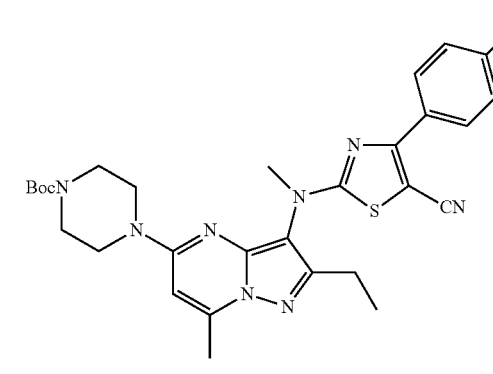

Compound 95

Compound 95 was prepared from 95f according to the synthesis of Intermediate 3 and Compound 1 and was isolated as a white solid. $^1$H NMR (400 MHz, CDCl$_3$) δ 8.14-8.10 (m, 2H), 7.16-7.12 (m, 2H), 6.03 (s, 1H), 4.73-4.70 (m, 1H), 4.50-4.46 (m, 1H), 4.35-4.30 (m, 1H), 4.18-4.16 (m, 1H), 3.98-3.88 (m, 5H), 3.63 (s, 3H), 3.27-3.20 (m, 2H), 2.95-3.05 (m, 4H), 2.79-2.74 (m, 2H), 2.51 (s, 3H), 1.33 (t, J=7.6 Hz, 3H). LC-MS (ESI): m/z=590.3 [M+H]$^+$

Example 96: 2-((2-ethyl-5-(4-(2-(3-hydroxyazetidin-1-yl)-2-oxoethyl)piperazin-1-yl)-6-methylpyrazolo[1,5-a]pyridin-3-yl)(methyl)amino)-4-(4-fluorophenyl)thiazole-5-carbonitrile (Compound 96)

Intermediate 6

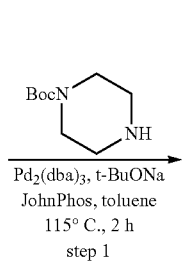

Pd$_2$(dba)$_3$, t-BuONa
JohnPhos, toluene
115° C., 2 h
step 1

259
-continued

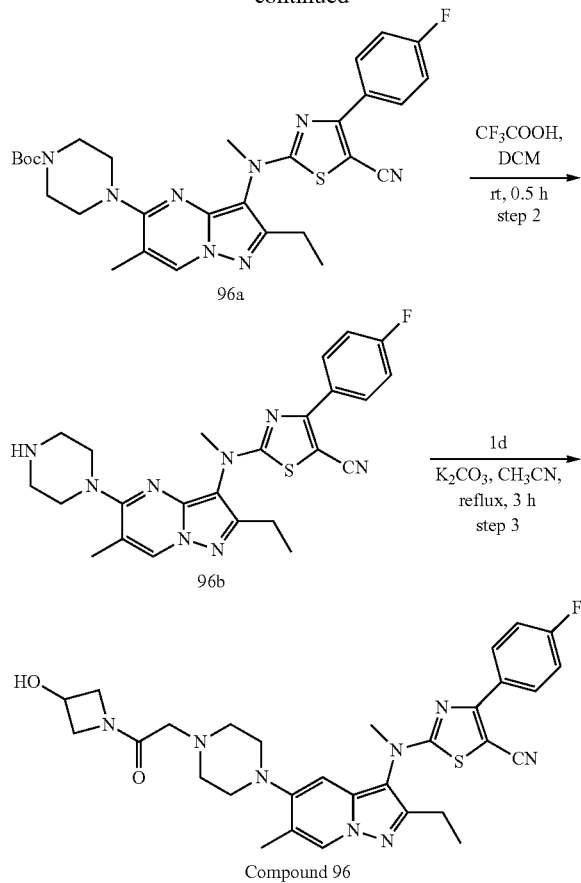

Step 3: 2-((2-ethyl-5-(4-(2-(3-hydroxyazetidin-1-yl)-2-oxoethyl)piperazin-1-yl)-6-methylpyrazolo[1,5-a]pyridin-3-yl)(methyl)amino)-4-(4-fluorophenyl)thiazole-5-carbonitrile (Compound 96)

To a solution of 96b (0.55 g, 1.2 mmol) in MeCN (15 mL) were added potassium carbonate (0.33 g, 2.4 mmol) and 2-chloro-1-(3-hydroxyazetidin-1-yl)ethanone (0.22 g, 1.5 mmol). The reaction mixture was refluxed for 3 h. After cooling to room temperature, the mixture was diluted with water and EtOAc. The organic layer was separated and the aqueous layer extracted with EtOAc. The combined organic layers were then washed with water and brine, dried over $Na_2SO_4$, filtered, and concentrated in vacuo. The residue was purified by flash chromatography to afford Compound 96 (0.32 g, 46%) as a yellow solid. $^1$H NMR (400 MHz, CDCl3) δ 8.23 (d, 1H), 8.15 (d, 2H), 7.17 (t, 2H), 6.74 (d, 1H), 3.59 (d, 4H), 3.31 (d, 4H), 2.96 (s, 8H), 2.71-2.86 (m, 3H), 2.27 (s, 3H), 1.3-1.34 (m, 3H), 1.26 (d, 1H). LC-MS (ESI): m/z=589.2 [M+H]$^+$.

Example 97: (S)-2-((2-ethyl-6-methyl-5-(6-(tetrahydrofuran-3-carbonyl)-2,6-diazaspiro[3.3]heptan-2-yl)pyrazolo[1,5-a]pyridin-3-yl)(methyl)amino)-4-(4-fluorophenyl)thiazole-5-carbonitrile (Compound 97)

Step 1: tert-butyl 4-(3-((5-cyano-4-(4-fluorophenyl)thiazol-2-yl)(methyl)amino)-2-ethyl-6-methylpyrazolo[1,5-a]pyridin-5-yl)piperazine-1-carboxylate (96a)

To a solution Intermediate 6 (0.92 g, 2.0 mmol) in toluene (15 mL) under argon was successively added N-Boc piperazine (0.58 g, 3.0 mmol), sodium tert-butoxide (0.38 g, 4.0 mmol) and then JohnPhos (0.06 g, 0.2 mmol) and Pd$_2$(dba)$_3$ (0.09 g, 0.1 mmol). The reaction mixture was heated at 115° C. for 2 h. After cooling to room temperature, the mixture was diluted with water and EtOAc. The organic layer was separated and the aqueous layer extracted with EtOAc. The combined organic layers were then washed with water and brine, dried over $Na_2SO_4$, filtered, and concentrated in vacuo. The residue was purified by flash chromatography to afford 96a (0.70 g, 62%) as a yellow solid. LC-MS (ESI): m/z=576.2 [M+H]$^+$ Step 2:

A solution of 96a (0.70 g, 1.2 mmol) and trifluoroacetic acid (3 mL) in DCM (10 mL) was stirred at room temperature for 0.5 h. Solvent was evaporated, and the crude product was partitioned between water and DCM. The aqueous layer was basified with NaHCO$_3$ and extracted with DCM. Combined organic layers were washed with brine, dried over sodium sulfate, filtered, and evaporated to give 96b (0.55 g, 100%) that was used in the next step without further purification.

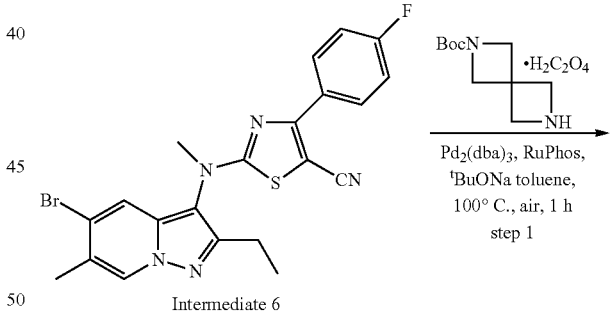

Intermediate 6

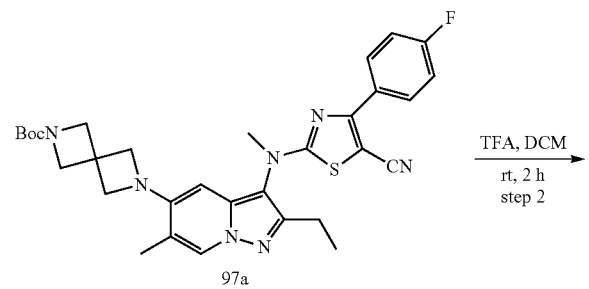

97a

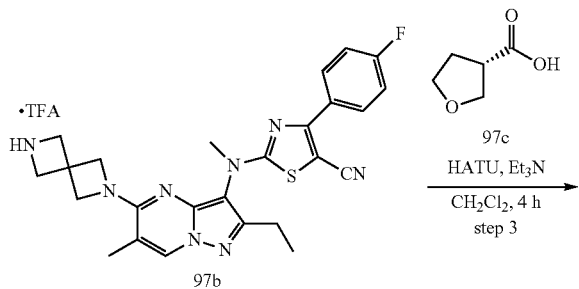

97c

HATU, Et₃N
CH₂Cl₂, 4 h
step 3

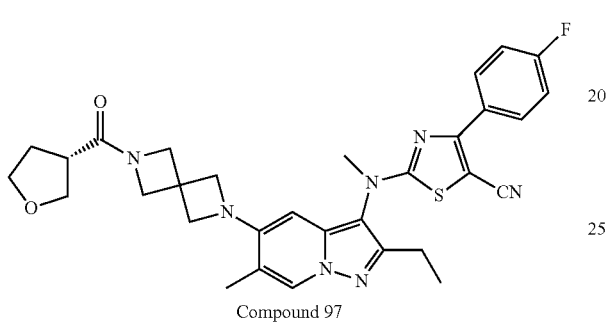

Compound 97

Step 1: tert-butyl 6-(3-((5-cyano-4-(4-fluorophenyl)thiazol-2-yl)(methyl)amino)-2-ethyl-6-methylpyrazolo[1,5-a]pyridin-5-yl)-2,6-diazaspiro[3.3]heptane-2-carboxylate (97a)

To a solution of Intermediate 1 (0.40 g, 0.9 mmol) in toluene (10 mL) under air were successively added tert-butyl 2,6-diazaspiro[3.3]heptane-2-carboxylate (9a) (0.28 g, 1.4 mmol), sodium tert-butoxide (0.43 g, 4.5 mmol), RuPhos (90 mg, 0.2 mmol), and Pd₂(dba)₃ (91 mg, 0.1 mmol). The reaction mixture was heated at 100° C. for 1 h. After cooling to room temperature, the reaction was concentrated in vacuo. The residue was purified by chromatography on silica gel to afford 97a (0.40 g, 80%) as a brown solid.

Step 2: 2-((2-ethyl-6-methyl-5-(2,6-diazaspiro[3.3]heptan-2-yl)pyrazolo[1,5-a]pyridin-3-yl)(methyl)amino)-4-(4-fluorophenyl)thiazole-5-carbonitrile (97b)

A solution of 97a (85 mg, 0.15 mmol) and TFA (2 mL) in DCM (5 mL) was stirred at room temperature for 2 h. The reaction was concentrated in vacuo to afford the crude product (97b), and it was used for next step without further purification.

Step 3: (S)-2-((2-ethyl-6-methyl-5-(6-(tetrahydrofuran-3-carbonyl)-2,6-diazaspiro[3.3]heptan-2-yl)pyrazolo[1,5-a]pyridin-3-yl)(methyl)amino)-4-(4-fluorophenyl)thiazole-5-carbonitrile (Compound 97)

To a solution of 97b (54 mg, 0.11 mmol) in DCM (10 mL) were successively added 1c (15 mg, 0.13 mmol), HATU (65 mg, 0.17 mmol) and TEA (33 mg, 0.33 mmol). The reaction mixture was stirred at room temperature for 4 h, then the mixture was diluted with water (10 mL) and extracted with DCM (10 mL×3). The combined organic layers were then washed with water (10 mL×2) and brine (5 mL×1), dried over sodium sulfate, filtered, and concentrated in vacuo. The residue was purified by flash chromatography to afford the title Compound 97 (50 mg, 77%) as a light brown solid. ¹H NMR (400 MHz, CDCl3) δ 8.20 (d, 1H), 8.15 (d, 2H), 7.3 (d, 2H), 6.6 (d, 1H), 4.12 (d, 2H), 3.76-4.12 (d, 8H), 3.46-3.5 (s, 4H), 3.0-3.07 (m, 5H), 2.79 (s, 1H), 2.21 (s, 2H), 1.87-1.96 (s, 3H). 1.27-1.36 (s, 3H). LC-MS (ESI): m/z=586.2 [M+H]⁺

Example 98: 2-((2-ethyl-5-(6-(2-hydroxy-2-methylpropanoyl)-2,6-diazaspiro[3.3]heptan-2-yl)-6-methylpyrazolo[1,5-a]pyridin-3-yl)(methyl)amino)-4-(4-fluorophenyl)thiazole-5-carbonitrile (Compound 98)

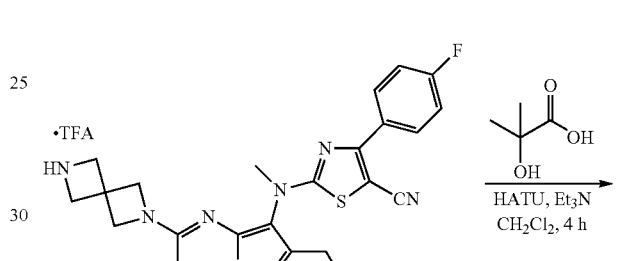

HATU, Et₃N
CH₂Cl₂, 4 h

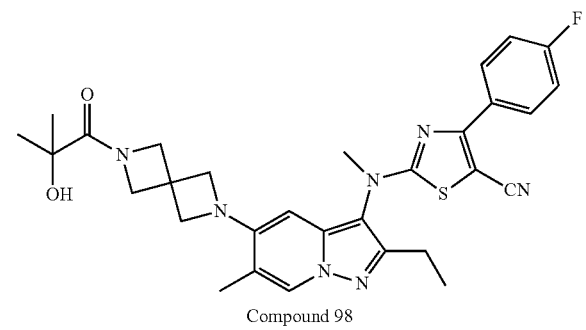

Compound 98

To a solution of 97b (50 mg, 0.1 mmol) in DCM (10 mL) were successively added 2-hydroxy-2-methylpropanoic acid (17 mg, 0.12 mmol), HATU (70 mg, 0.15 mmol) and TEA (40 mg, 0.33 mmol). The reaction mixture was stirred at room temperature for 4 h, then the mixture was diluted with water (10 mL) and extracted with DCM (10 mL×3). The combined organic layers were then washed with water (100 mL×2) and brine (50 mL×1), dried over sodium sulfate, filtered, and concentrated in vacuo. The residue was purified by flash chromatography to afford the title Compound 98 (50 mg, 85%) as a light brown solid. LC-MS (ESI): m/z=574.2 [M+H]⁺

Example 99: 2-((5-(6-(2,3-dihydroxypropanoyl)-2,6-diazaspiro[3.3]heptan-2-yl)-2-ethyl-6-methylpyrazolo[1,5-a]pyridin-3-yl)(methyl)amino)-4-(4-fluorophenyl)thiazole-5-carbonitrile (Compound 99)

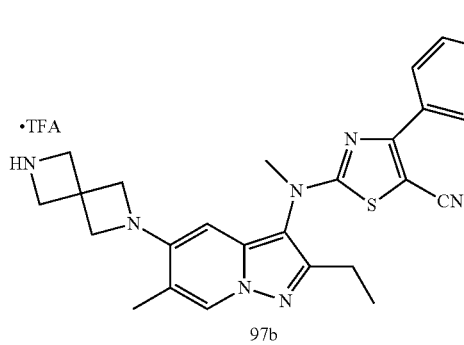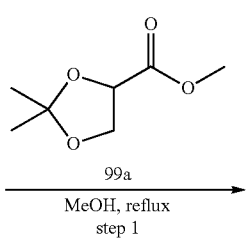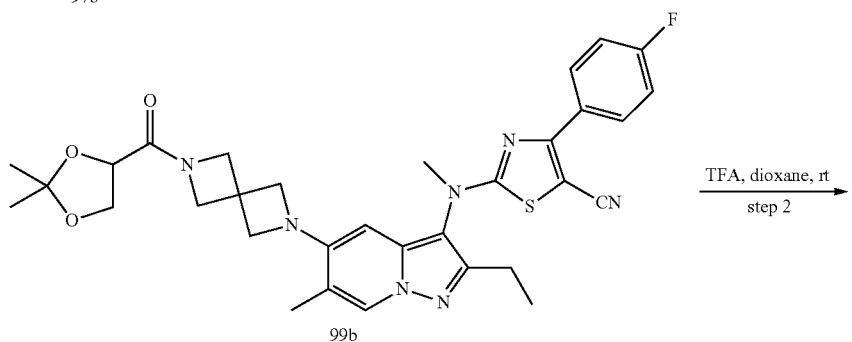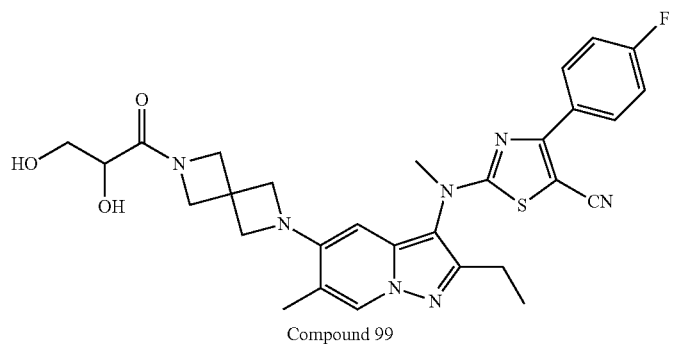

reaction was concentrated in vacuo, and the residue was purified by flash chromatography to afford the title Compound 99 (30 mg, 46%) as a light white solid. LC-MS (ESI): m/z=576.2 [M+H]$^+$ Step 1: 2-((5-(6-(2,2-dimethyl-1,3-dioxolane-4-carbonyl)-2,6-diazaspiro[3.3]heptan-2-yl)-2-ethyl-6-methylpyrazolo[1,5-a]pyridin-3-yl)(methyl)amino)-4-(4-fluorophenyl)thiazole-5-carbonitrile (99b)

To a solution of 97b (70 mg, 0.14 mmol) in MeOH (10 mL) were successively added 99a (112 mg, 0.7 mmol), The reaction mixture was stirred reflux for 4 h, then the mixture was concentrated in vacuo to afford the crude product (99b), and it was used for next step without further purification. LC-MS (ESI): m/z=616.2 [M+H]$^+$ Step 2: 2-((5-(6-(2,3-dihydroxypropanoyl)-2,6-diazaspiro[3.3]heptan-2-yl)-2-ethyl-6-methylpyrazolo[1,5-a]pyridin-3-yl)(methyl)amino)-4-(4-fluorophenyl)thiazole-5-carbonitrile (Compound 99)

A solution of 99b (70 mg, 0.11 mmol) and TFA (2 mL) in dioxane (5 mL) was stirred at room temperature for 2 h. The Example 100: 2-((2-cyclopropyl-5-(4-(2-(3-hydroxyazetidin-1-yl)-2-oxoethyl)piperazin-1-yl)-6-methylpyrazolo[1,5-a]pyridin-3-yl)(methyl)amino)-4-(4-fluorophenyl)thiazole-5-carbonitrile (Compound 100)

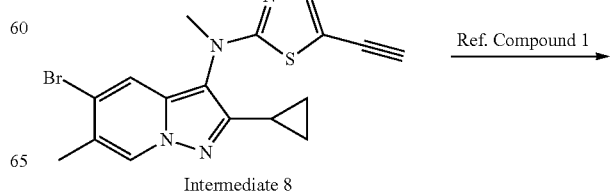

Intermediate 8

-continued

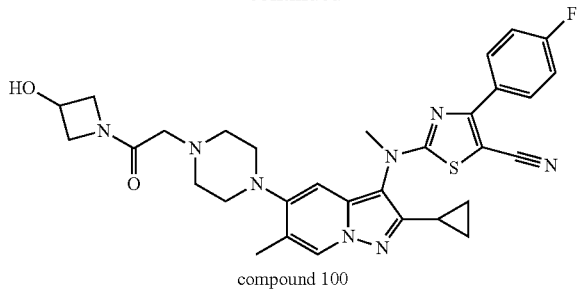

compound 100

Compound 100 was prepared from Intermediate 8 according to the synthesis of Compound 1 over 3 steps and was isolated as a white solid (10% yield). $^1$H NMR (400 MHz, CDCl$_3$) δ 8.18-8.13 (m, 2H), 8.09 (s, 1H), 7.18-7.13 (m, 2H), 6.59 (s, 1H), 4.70-4.65 (m, 1H), 4.49-4.45 (m, 1H), 4.30-4.26 (m, 1H), 4.14 (brs, 1H), 3.92-3.89 (m, 1H), 3.64 (s, 3H), 3.24-3.13 (m, 2H), 3.03 (brs, 4H), 2.80 (brs, 4H), 2.26 (s, 3H), 1.87-1.84 (m, 1H), 1.05-0.98 (m, 4H). LC-MS (ESI): m/z=601.3 [M+H]$^+$ Example 101: 2-[[2-ethyl-6-fluoro-5-[4-[2-(3-hydroxyazetidin-1-yl)-2-oxo-ethyl]piperazin-1-yl]pyrazolo[1,5-a]pyridin-3-yl]-methyl-amino]-4-(4-fluorophenyl)thiazole-5-carbonitrile (Compound 101)

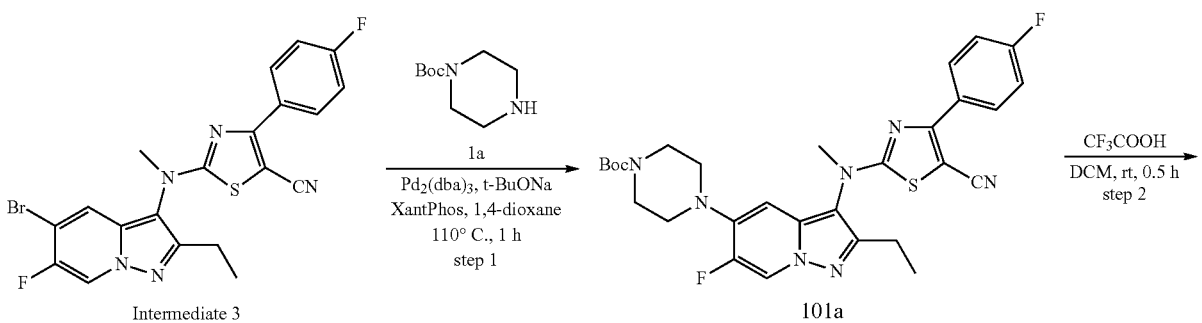

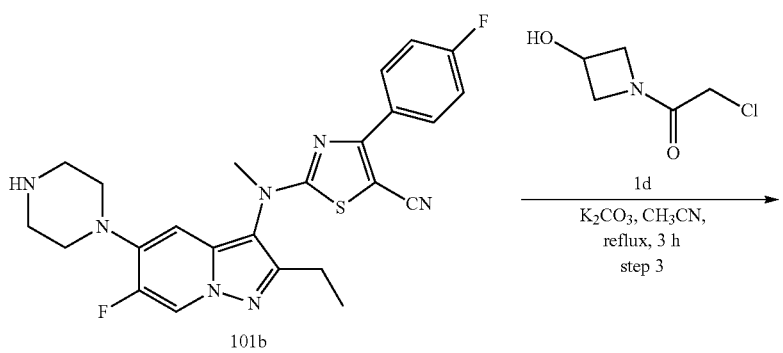

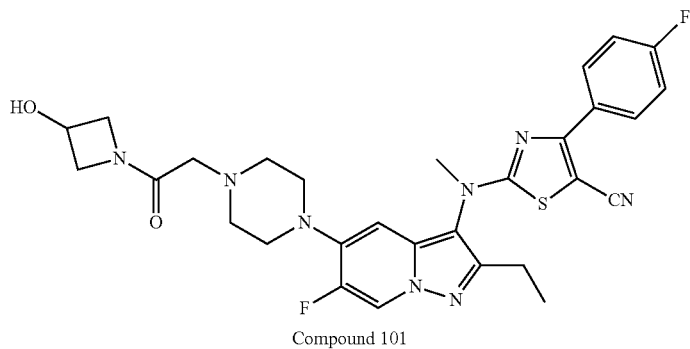

Compound 101

Step 1: tert-butyl 4-[3-[[5-cyano-4-(4-fluorophenyl)thiazol-2-yl]-methyl-amino]-2-ethyl-6-fluoro-pyrazolo[1,5-a]pyridin-5-yl]piperazine-1-carboxylate (101a)

To a solution Intermediate 3 (0.48 g, 1.0 mmol) in 1,4-dioxane (15 mL) under argon was successively added N-Boc piperazine (0.29 g, 1.5 mmol), sodium tert-butoxide (0.19 g, 2.0 mmol) and then XantPhos (0.12 g, 0.2 mmol) and Pd$_2$(dba)$_3$ (0.09 g, 0.1 mmol). The reaction mixture was heated at 110° C. for 1 h. After cooling to room temperature, the mixture was diluted with water and EtOAc. The organic layer was separated and the aqueous layer extracted with EtOAc. The combined organic layers were then washed with water and brine, dried over Na$_2$SO$_4$, filtered, and concentrated in vacuo. The residue was purified by flash chromatography to afford 101a (0.34 g, 58%) as a yellow solid. LC-MS (ESI): m/z=524.2 [M-t-Bu+H]$^+$.

Step 2: 2-[[2-ethyl-5-[ethyl-[2-(methylamino)ethyl]amino]-6-fluoro-pyrazolo[1,5-a]pyridin-3-yl]-methyl-amino]-4-(4-fluorophenyl)thiazole-5-carbonitrile (101b)

A solution of 101a (0.34 g, 0.58 mmol) and trifluoroacetic acid (3 mL) in DCM (10 mL) was stirred at room temperature for 0.5 h. Solvent was evaporated, and the crude product was partitioned between water and DCM. The aqueous layer was basified with NaHCO$_3$ and extracted with DCM. Combined organic layers were washed with brine, dried over sodium sulfate, filtered, and evaporated to give 101b (0.24 g, 86%) that was used in the next step without further purification. LC-MS (ESI): m/z=480.2 [M+H]$^+$.

Step 3: 2-[[2-ethyl-6-fluoro-5-[4-[2-(3-hydroxyazetidin-1-yl)-2-oxo-ethyl]piperazin-1-yl]pyrazolo[1,5-a]pyridin-3-yl]-methyl-amino]-4-(4-fluorophenyl)thiazole-5-carbonitrile (Compound 101)

To a solution of 101b (96 mg, 0.2 mmol) in MeCN (5 mL) were added K$_2$CO$_3$ (55 mg, 0.4 mmol) and 2-chloro-1-(3-hydroxyazetidin-1-yl)ethanone (1d) (45 mg, 0.3 mmol). The reaction mixture was refluxed for 3 h. After cooling to room temperature, the mixture was diluted with water and EtOAc. The organic layer was separated and the aqueous layer extracted with EtOAc. The combined organic layers were then washed with water and brine, dried over Na$_2$SO$_4$, filtered, and concentrated in vacuo. The residue was was purified by flash chromatography to afford Compound 101 (70 mg, 59%) as a yellow solid. $^1$H NMR (400 MHz, CDCl$_3$) δ 8.27 (d, J=6.9 Hz, 1H), 8.19-8.10 (m, 2H), 7.20-7.11 (m, 2H), 6.45 (d, J=8.2 Hz, 1H), 4.71-4.62 (m, 1H), 4.50-4.40 (m, 1H), 4.32-4.22 (m, 1H), 4.17-4.05 (m, 1H), 3.95-3.85 (m, 1H), 3.58 (s, 3H), 3.33-3.09 (m, 6H), 2.89-2.77 (m, 4H), 2.72 (q, J=7.6 Hz, 2H), 1.32 (t, J=7.6 Hz, 3H). LC-MS (ESI): m/z=593.3 [M+H]$^+$.

Example 102: 2-[[2-ethyl-6-fluoro-5-[2-[(3S)-tetrahydrofuran-3-carbonyl]-2,6-diazaspiro[3.3]heptan-6-yl]pyrazolo[1,5-a]pyridin-3-yl]-methyl-amino]-4-(4-fluorophenyl)thiazole-5-carbonitrile (Compound 102)

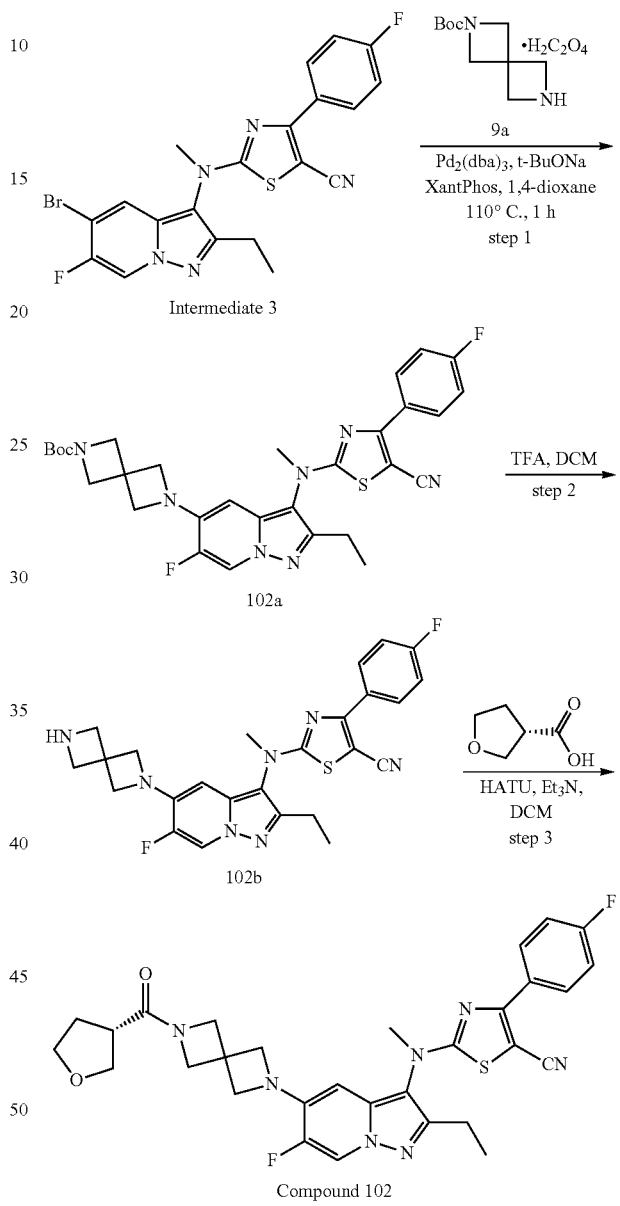

Step 1: tert-butyl tert-butyl 6-[3-[[5-cyano-4-(4-fluorophenyl)thiazol-2-yl]-methyl-amino]-2-ethyl-6-fluoro-pyrazolo[1,5-a]pyridin-5-yl]-2,6-diazaspiro[3.3]heptane-2-carboxylate (102a)

To a solution Intermediate 3 (0.48 g, 1.0 mmol) in 1,4-dioxane (15 mL) under argon was successively added tert-butyl 2,6-diazaspiro[3.3]heptane-2-carboxylate oxalate (9a) (0.43 g, 1.5 mmol), sodium tert-butoxide (0.57 g, 6 mmol) and then XantPhos (0.12 g, 0.2 mmol) and Pd$_2$(dba)$_3$ (0.09 g, 0.1 mmol). The reaction mixture was heated at 110°

C. for 1 h. After cooling to room temperature, the mixture was diluted with water and EtOAc. The organic layer was separated and the aqueous layer extracted with EtOAc. The combined organic layers were then washed with water and brine, dried over Na$_2$SO$_4$, filtered, and concentrated in vacuo. The residue was was purified by flash chromatography to afford 102a (0.41 g, 68%) as a yellow solid.

Step 2: 2-[[5-(2,6-diazaspiro[3.3]heptan-2-yl)-2-ethyl-6-fluoro-pyrazolo[1,5-a]pyridin-3-yl[-methyl-amino]-4-(4-fluorophenyl)thiazole-5-carbonitrile (102b)

A solution of 102a (0.41 g, 0.69 mmol) and trifluoroacetic acid (3 mL) in DCM (10 mL) was stirred at room temperature for 0.5 h. Solvent was evaporated, and the crude product was partitioned between water and DCM. The aqueous layer was basified with NaHCO$_3$ and extracted with DCM. Combined organic layers were washed with brine, dried over sodium sulfate, filtered, and evaporated to give 102b (0.32 g, 94%) that was used in the next step without further purification. LC-MS (ESI): m/z=492.2 [M+H]$^+$.

Step 3: 2-[[2-ethyl-6-fluoro-5-[2-[(3S)-tetrahydrofuran-3-carbonyl]-2,6-diazaspiro[3.3]heptan-6-yl]pyrazolo[1,5-a]pyridin-3-yl]-methyl-amino]-4-(4-fluorophenyl)thiazole-5-carbonitrile (Compound 102)

To a solution of 102b (60 mg, 0.12 mmol) in DCM (10 mL) were successively added (S)-tetrahydrofuran-3-carboxylic acid (21 mg, 0.18 mmol), HATU (68 mg, 0.18 mmol) and Et$_3$N (36 mg, 0.36 mmol). The reaction mixture was stirred at room temperature for 4 h, then the mixture was diluted with water (10 mL) and extracted with DCM (10 mL×3). The combined organic layers were then washed with water (10 mL×2) and brine (5 mL×1), dried over Na$_2$SO$_4$, filtered, and concentrated in vacuo. The residue was was purified by flash chromatography to afford the title Compound 102 (32 mg, 45%) as a yellow solid. $^1$H NMR (400 MHz, CDCl$_3$) δ 8.20 (d, J=6.5 Hz, 1H), 8.18-8.12 (m, 2H), 7.20-7.12 (m, 2H), 5.90 (d, J=8.5 Hz, 1H), 4.42-4.29 (m, 2H), 4.29-4.15 (m, 6H), 3.99 (t, J=8.2 Hz, 1H), 3.93-3.76 (m, 3H), 3.56 (s, 3H), 2.97-2.86 (m, 1H), 2.70 (q, J=7.6 Hz, 2H), 2.23-2.11 (m, 1H), 2.10-2.00 (m, 1H), 1.31 (t, J=7.6 Hz, 3H). LC-MS (ESI): m/z=590.2 [M+H]$^+$.

Example 103: 2-((2-ethyl-6-fluoro-5-(4-(2-(3-hydroxyazetidin-1-yl)-2-oxoethyl)piperazin-1-yl)pyrazolo[1,5-a]pyridin-3-yl-7-d)(methyl)amino)-4-(4-fluorophenyl)thiazole-5-carbonitrile (Compound 103)

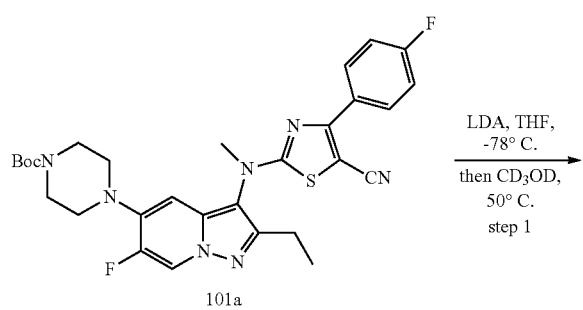

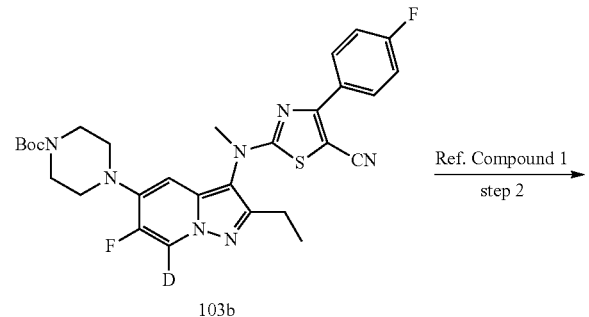

103b

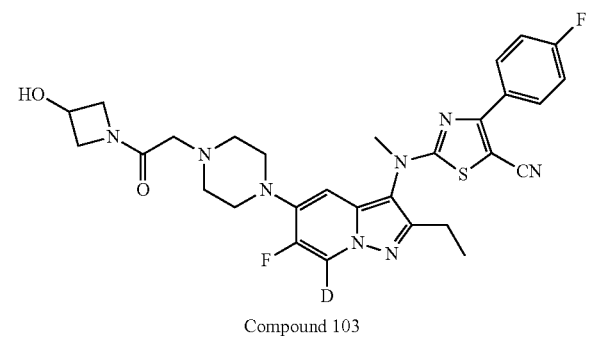

Compound 103

Step 1: tert-butyl-4-(3-((5-cyano-4-(4-fluorophenyl)thiazol-2-yl)(methyl)amino)-2-ethyl-6-fluoropyrazolo[1,5-a]pyridin-5-yl-7-d)piperazine-1-carboxylate (103a)

To a solution of 101a (0.15 g, 0.26 mmol) in THF (5 mL) was added LDA (2.0 M n-hexane solution, 1.0 mL, 2.0 mmol) dropwise at −78° C. under a nitrogen atmosphere, and the reaction mixture was further stirred for 1 h at the same temperature. CD$_3$OD (2 mL) was added dropwise to the reaction mixture, the mixture was warmed to 50° C. for 10 min, and then concentrated in vacuo. The residue was purified by column chromatography on silica gel to afford 103a (75 mg, 50%) as a yellow foam. $^1$H NMR (400 MHz, DMSO-d$_6$) δ 8.11-8.08 (m, 2H), 7.43-7.39 (m, 2H), 6.98-6.96 (d, J=8.4 Hz, 1H), 3.55 (s, 3H), 3.54-3.47 (m, 4H), 3.09-3.06 (m, 4H), 2.68-2.62 (m, 2H), 1.41 (s, 9H), 1.23 (t, J=7.6 Hz, 3H).

Step 2: 2-((2-ethyl-6-fluoro-5-(4-(2-(3-hydroxyazetidin-1-yl)-2-oxoethyl)piperazin-1-yl)pyrazolo[1,5-a]pyridin-3-yl-7-d)(methyl)amino)-4-(4-fluorophenyl)thiazole-5-carbonitrile (Compound 103)

Compound 103 was prepared from 103a in a manner analogous to preparation of Compound 1 and was isolated as a white solid. $^1$H NMR (400 MHz, DMSO-d$_6$) δ 8.1-8.09 (m, 2H), 7.43-7.39 (m, 2H), 6.91 (d, J=8.8 Hz, 1H), 5.65 (d, J=6 Hz, 1H), 4.45-4.42 (m, 1H), 4.38-4.34 (m, 1H), 4.05-4.01 (m, 1H), 3.93-3.90 (m, 1H), 3.59-3.57 (m, 1H), 3.56 (s, 3H), 3.13-3.11 (m, 4H), 3.04-3.02 (m, 2H), 2.67-2.62 (m, 2H), 2.57-2.58 (m, 4H), 1.23 (t, J=7.6 Hz, 3H). LC-MS (ESI): m/z=595.3 [M+H]$^+$ Example 104: 2-((2-ethyl-6-fluoro-5-(6-(3-hydroxyazetidine-1-carbonyl)-2,6-diazaspiro[3.3]heptan-2-yl)pyrazolo[1,5-a]pyridin-3-yl-7-d)(methyl)amino)-4-(4-fluorophenyl)thiazole-5-carbonitrile (Compound 104)

Step 1: tert-butyl 6-(3-((5-cyano-4-(4-fluorophenyl)thiazol-2-yl)(methyl)amino)-2-ethyl-6-fluoropyrazolo[1,5-a]pyridin-5-yl-7-d)-2,6-diazaspiro[3.3]heptane-2-carboxylate (103a)

Compound 104a was prepared from 102a in a manner analogous to preparation of Compound 103a and was isolated as a yellow solid. $^1$H NMR (400 MHz, DMSO-$d_6$) δ 8.11-8.07 (m, 2H), 7.43-7.38 (m, 2H), 6.31 (d, J=8.0 Hz, 1H), 4.15 (s, 4H), 4.02 (s, 4H), 3.52 (s, 3H), 2.64-2.58 (m, 2H), 1.37 (s, 9H), 1.21 (d, J=7.6 Hz, 3H).

Step 2: 2-((2-ethyl-6-fluoro-5-(6-(3-hydroxyazetidine-1-carbonyl)-2,6-diazaspiro[3.3]heptan-2-yl)pyrazolo[1,5-a]pyridin-3-yl-7-d)(methyl)amino)-4-(4-fluorophenyl)thiazole-5-carbonitrile (Compound 104)

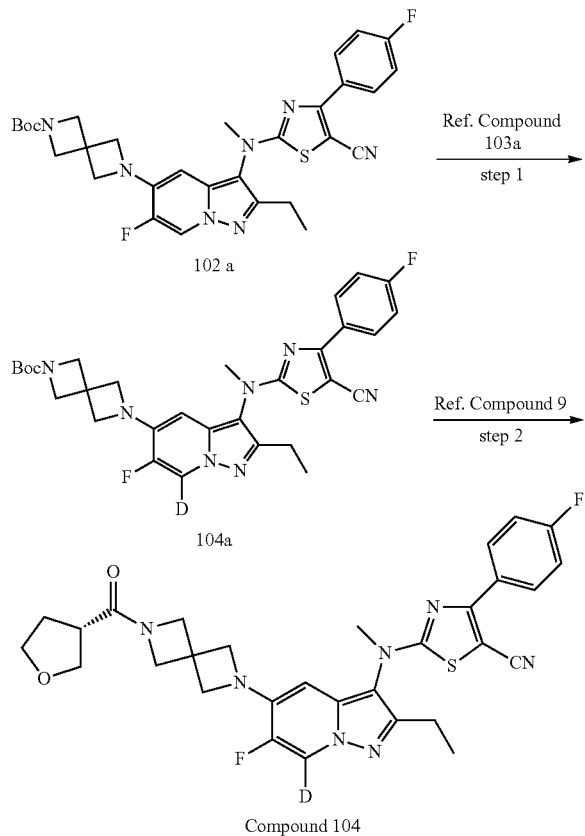

Compound 104 was prepared from 104a in a manner analogous to preparation of Compound 9 and was isolated as a pale yellow solid. $^1$H NMR (400 MHz, DMSO-$d_6$) δ 8.11-8.09 (m, 2H), 7.44-7.39 (m, 2H), 6.33 (d, J=8.4 Hz, 1H), 4.35-4.31 (m, 1H), 4.18 (s, 4H), 4.04 (s, 1H), 3.85-3.82 (m, 1H), 3.71-3.57 (m, 4H), 3.53 (s, 3H), 2.97-2.93 (m, 1H), 2.70-2.69 (m, 2H), 2.62-2.59 (m, 2H), 1.99-1.91 (m, 1H), 1.22 (t, J=7.6 Hz, 3H). LC-MS (ESI): m/z=591.3 [M+H]$^+$ Example 105: 2-((2-ethyl-6-fluoro-5-(6-(4-methylpiperazine-1-carbonyl)-2,6-diazaspiro[3.3]heptan-2-yl)pyrazolo[1,5-a]pyridin-3-yl)(methyl)amino)-4-(4-fluorophenyl)thiazole-5-carbonitrile (Compound 105)

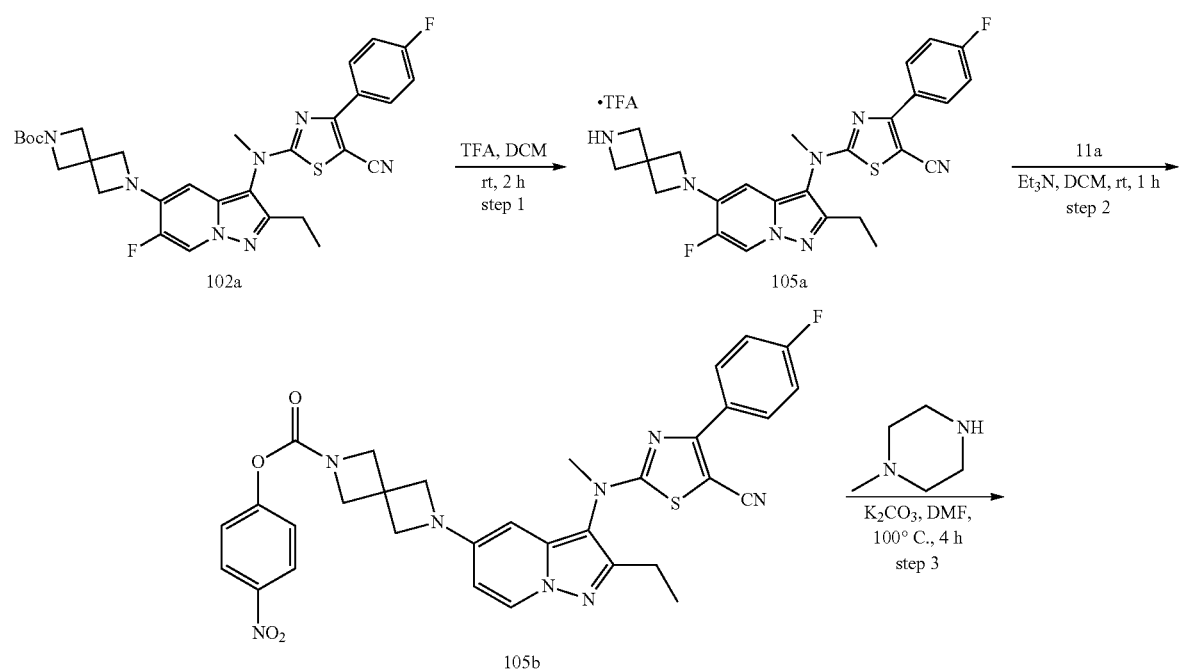

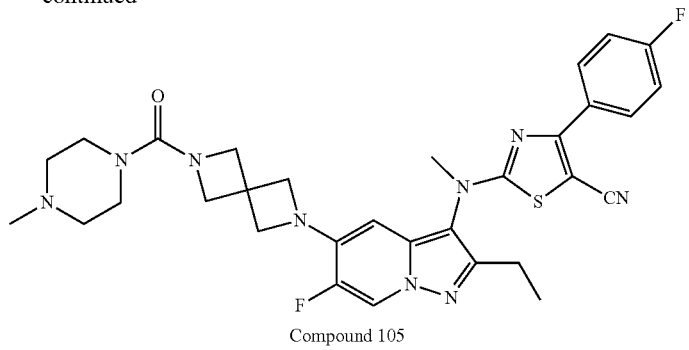

Compound 105

Step 1: 2-((2-ethyl-6-fluoro-5-(2,6-diazaspiro[3.3]heptan-2-yl)pyrazolo[1,5-a]pyridin-3-yl)(methyl)amino)-4-(4-fluorophenyl)thiazole-5-carbonitrile TFA Salt (105a)

Starting from 102a and proceeding in analogy to preparation 9c afford the title compound 105a.

Step 2: 4-nitrophenyl 6-(3-((5-cyano-4-(4-fluorophenyl)thiazol-2-yl)(methyl)amino)-2-ethylpyrazolo[1,5-a]pyridin-5-yl)-2,6-diazaspiro[3.3]heptane-2-carboxylate (105b)

Starting from 105a and proceeding in analogy to preparation 11b afford the title compound 105b.

Step 3: 2-((2-ethyl-6-fluoro-5-(6-(4-methylpiperazine-1-carbonyl)-2,6-diazaspiro[3.3]heptan-2-yl)pyrazolo[1,5-a]pyridin-3-yl)(methyl)amino)-4-(4-fluorophenyl)thiazole-5-carbonitrile (Compound 105)

Starting from 105b and proceeding in analogy to preparation Compound 11, using 1-methylpiperazine to afford the title Compound 105. LC-MS: m/z=618.3 [M+H]⁺.

Example 106: 2-((2-ethyl-6-fluoro-5-(6-(1-methylpiperidine-4-carbonyl)-2,6-diazaspiro[3.3]heptan-2-yl)pyrazolo[1,5-a]pyridin-3-yl)(methyl)amino)-4-(4-fluorophenyl)thiazole-5-carbonitrile (Compound 106)

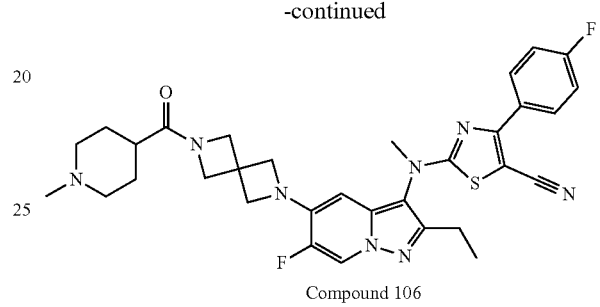

Compound 106

To a solution of 1-methylpiperidine-4-carboxylic acid (35 mg, 0.244 mmol) in DMF (5 mL) were successively added HATU (92 mg, 0.244 mmol) and Et₃N (50 mg, 0.5 mmol). The reaction mixture was stirred at room temperature for 0.5 h, then the mixture was added 102b (100 mg, 0.2 mmol) and stirred at room temperature for 3 h. The mixture was diluted with water (10 mL) and extracted with DCM (10 mL×3). The combined organic layers were then washed with water (10 mL×2) and brine (5 mL×1), dried over Na₂SO₄, filtered, and concentrated in vacuo. The residue was purified by flash chromatography to afford the title Compound 106 (40 mg, 32%) as a pale yellow solid. ¹H NMR (400 MHz, CDCl₃) δ 8.21 (d, J=4 Hz, 1H), 8.17-8.13 (m, 2H), 7.19-7.14 (m, 2H), 5.89 (d, J=4.8 Hz, 1H), 4.36 (s, 2H), 4.19 (m, 6H), 3.56 (s, 3H), 3.21 (s, 2H), 2.70 (q, J=7.6 Hz, 2H), 2.61-2.43 (m, 3H), 2.15-1.87 (m, 4H), 1.31 (t, J=7.6 Hz, 3H), 1.25 (s, 3H). LC-MS (ESI): m/z=617.3 [M+H]⁺.

Example 107: 2-((2-ethyl-6-fluoro-5-(6-(3-hydroxyazetidine-1-carbonyl)-2,6-diazaspiro[3.3]heptan-2-yl)pyrazolo[1,5-a]pyridin-3-yl)(methyl)amino)-4-(4-fluorophenyl)thiazole-5-carbonitrile (Compound 107)

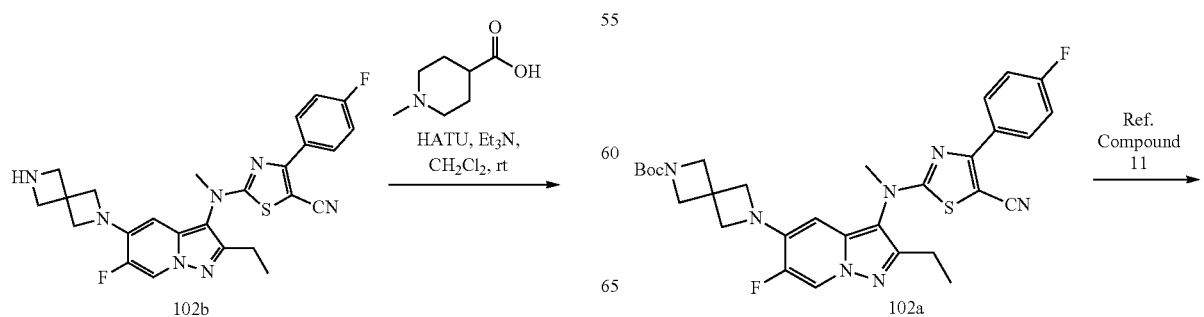

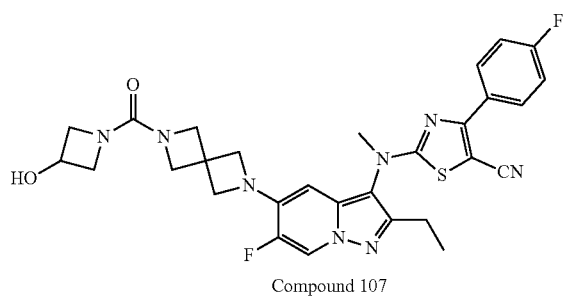

Compound 107

Compound 107 was prepared from 102a in a manner analogous to preparation of Compound 11 and was isolated as a white solid. LC-MS (ESI): m/z=591.3 [M+H]$^+$ Example 108: 2-((2-ethyl-6-fluoro-5-(6-(morpholine-4-carbonyl)-2,6-diazaspiro[3.3]heptan-2-yl)pyrazolo[1,5-a]pyridin-3-yl)(methyl)amino)-4-(4-fluorophenyl)thiazole-5-carbonitrile (Compound 108)

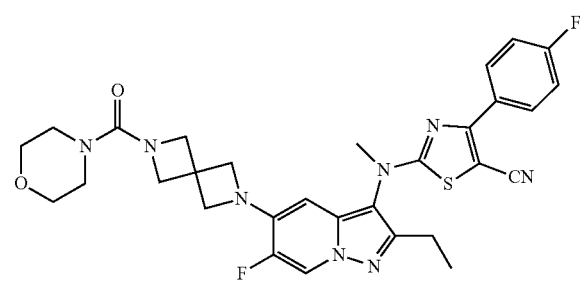 [SMILES: CCc1nn2cc(F)c(N3CC4(CN(C(=O)N5CCOCC5)C4)C3)cc2c1N(C)c1nc(-c2ccc(F)cc2)c(C#N)s1]

The title compound was prepared by the method substantially similar to that mentioned in Example 11, using morpholine to afford Compound 108 as a pale yellow solid. LC-MS (ESI): m/z=605.3 [M+H]$^+$ Example 109: (R)-2-((2-ethyl-6-fluoro-5-(4-(2-(3-hydroxypyrrolidin-1-yl)-2-oxoethyl)piperazin-1-yl)pyrazolo[1,5-a]pyridin-3-yl)(methyl)amino)-4-(4-fluorophenyl)thiazole-5-carbonitrile (Compound 109)

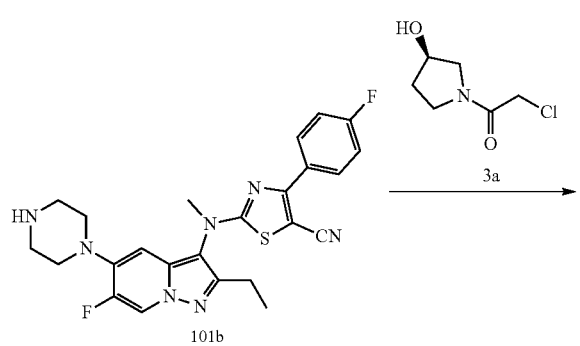

Compound 109 was prepared from 101b and (R)-2-chloro-1-(3-hydroxypyrrolidin-1-yl)ethan-1-one (3a) in a manner analogous to preparation of Compound 1 and was isolated as a white solid. LC-MS (ESI): m/z=607.3 [M+H]$^+$ Example 110: 2-((2-ethyl-6-fluoro-5-(2-(3-hydroxyazetidine-1-carbonyl)-2,7-diazaspiro[3.5]nonan-7-yl)pyrazolo[1,5-a]pyridin-3-yl)(methyl)amino)-4-(4-fluorophenyl)thiazole-5-carbonitrile (Compound 110)

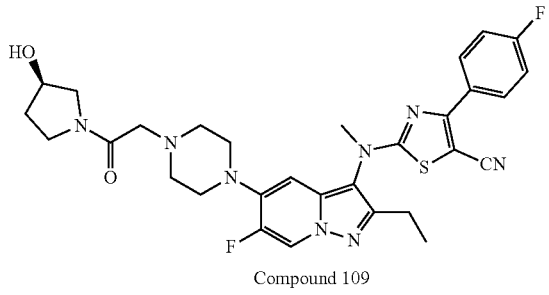

Compound 109

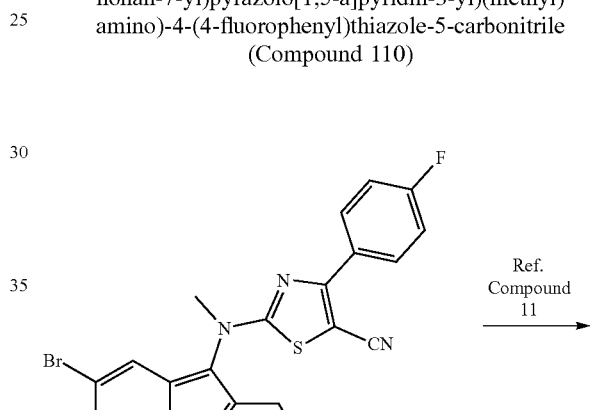

Intermediate 3

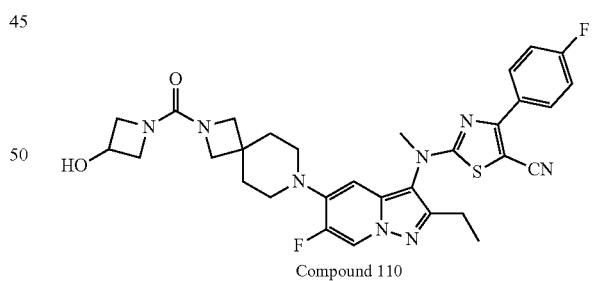

Compound 110

Compound 110 was prepared from Intermediate 3 in a manner analogous to preparation of Compound 11 and was isolated as a white solid. $^1$H NMR (400 MHz, CDCl$_3$) δ 8.30 (d, J=6.8 Hz, 1H), 8.17-8.13 (m, 2H), 7.19-7.14 (m, 2H), 6.46 (d, J=8.0 Hz, 1H), 4.63-4.59 (m, 1H), 4.19-4.15 (m, 2H), 3.84-3.81 (m, 2H), 3.58 (s, 3H), 3.10-3.06 (m, 4H), 2.75-2.69 (m, 2H), 1.95-1.93 (m, 4H), 1.84 (s, 4H), 1.32 (t, J=7.6 Hz, 3H). LC-MS (ESI): m/z=619.3 [M+H]$^+$ Example 111: 2-((2-ethyl-6-fluoro-5-(2-(3-hydroxyazetidine-1-carbonyl)-2,6-diazaspiro[3.4]octan-6-yl)pyrazolo[1,5-a]pyridin-3-yl)(methyl)amino)-4-(4-fluorophenyl)thiazole-5-carbonitrile (Compound 111)

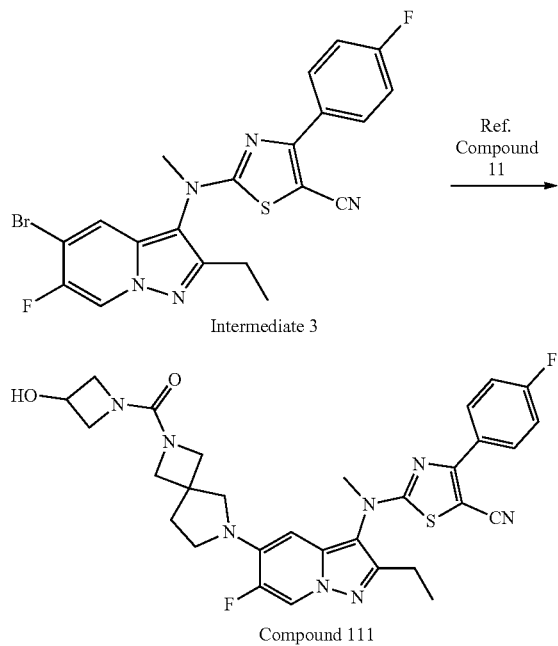

Compound 111 was prepared from Intermediate 3 in a manner analogous to preparation of Compound 11 and was isolated as a white solid. $^1$H NMR (400 MHz, CDCl$_3$) δ 8.21 (d, J=7.6 Hz, 1H), 8.17-8.14 (m, 2H), 7.18-7.14 (m, 2H), 5.97 (d, J=8.4 Hz, 1H), 4.63-4.59 (m, 1H), 4.18-4.14 (m, 2H), 3.95-3.88 (m, 4H), 3.83-3.80 (m, 2H), 3.63 (d, J=2.8 Hz, 1H), 3.57 (s, 3H), 3.55-3.50 (m, 2H), 2.72-2.66 (m, 2H), 1.56 (s, 4H), 1.31 (t, J=7.6 Hz, 3H). LC-MS (ESI): m/z=605.3 [M+H]$^+$ Example 112: 2-[[2-ethyl-6-fluoro-5-[2-(4-hydroxytetrahydropyran-4-carbonyl)-2,6-diazaspiro[3.3]heptan-6-yl]pyrazolo[1,5-a]pyridin-3-yl]-methyl-amino]-4-(4-fluorophenyl)thiazole-5-carbonitrile (Compound 112)

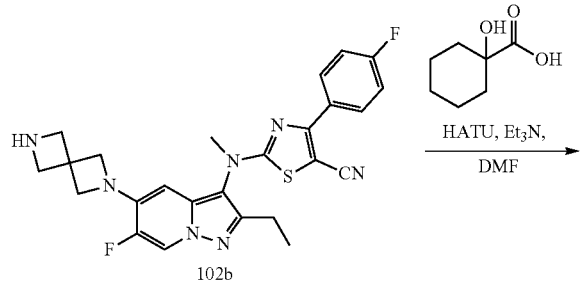

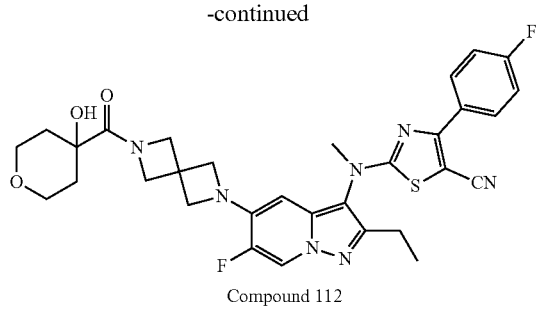

To a solution of 4-hydroxytetrahydropyran-4-carboxylic acid (26 mg, 0.18 mmol) in DMF (5 mL) were successively added HATU (68 mg, 0.18 mmol) and Et$_3$N (36 mg, 0.36 mmol). The reaction mixture was stirred at room temperature for 0.5 h, then the mixture was added 102b (60 mg, 0.12 mmol) and stirred at room temperature for 3 h. The mixture was diluted with water (10 mL) and extracted with DCM (10 mL×3). The combined organic layers were then washed with water (10 mL×2) and brine (5 mL×1), dried over Na$_2$SO$_4$, filtered, and concentrated in vacuo. The residue was was purified by flash chromatography to afford the title Compound 112 (32 mg, 45%) as a yellow solid. $^1$H NMR (400 MHz, CDCl$_3$) δ 8.22 (d, J=6.5 Hz, 1H), 8.18-8.11 (m, 2H), 7.18-7.12 (m, 2H), 5.90 (d, J=8.5 Hz, 1H), 4.64 (s, 2H), 4.28-4.16 (m, 5H), 3.90-3.69 (m, 4H), 3.57 (s, 3H), 2.70 (q, J=7.6 Hz, 2H), 2.14-2.04 (m, 2H), 2.00 (s, 1H), 1.50 (d, J=12.7 Hz, 2H), 1.31 (t, J=7.6 Hz, 3H). LC-MS (ESI): m/z=620.3 [M+H]$^+$.

Example 113: 2-((2-cyclopropyl-6-fluoro-5-(4-(2-(3-hydroxyazetidin-1-yl)-2-oxoethyl)piperazin-1-yl)pyrazolo[1,5-a]pyridin-3-yl)(methyl)amino)-4-(4-fluorophenyl)thiazole-5-carbonitrile (Compound 113)

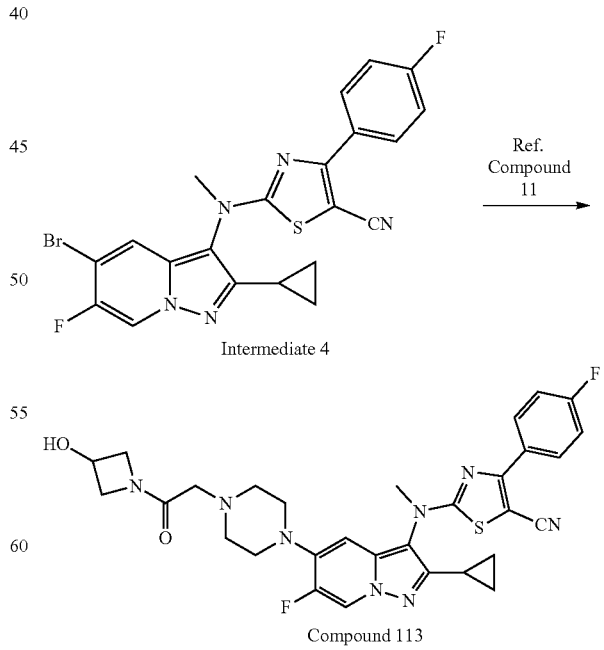

Compound 113 was prepared from Intermediate 4 in a manner analogous to preparation of Compound 1 and was isolated as a yellow solid. 1H NMR (400 MHz, DMSO-$d_6$) δ 8.86 (d, J=7.6 Hz, 1H), 8.12-8.08 (m, 2H), 7.43-7.39 (m, 2H), 6.89 (d, J=8.4 Hz, 1H), 5.66 (d, J=6.0 Hz, 1H), 4.49-4.40 (m, 2H), 4.37-4.33 (m, 1H), 4.11-4.08 (m, 2H), 4.05-4.01 (m, 1H), 3.93-3.90 (m, 1H), 3.58 (s, 3H), 3.12-3.02 (m, 4H), 2.62-2.53 (m, 4H), 1.91-1.85 (m, 1H), 0.98-0.95 (m, 2H), 0.91-0.88 (m, 2H). LC-MS (ESI): m/z=605.2 [M+H]$^+$ Example 114: (S)-2-((2-cyclopropyl-6-fluoro-5-(6-(tetrahydrofuran-3-carbonyl)-2,6-diazaspiro[3.3]heptan-2-yl)pyrazolo[1,5-a]pyridin-3-yl)(methyl)amino)-4-(4-fluorophenyl)thiazole-5-carbonitrile (Compound 114)

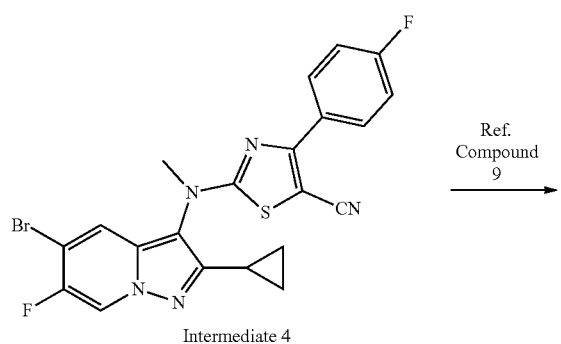

Intermediate 4

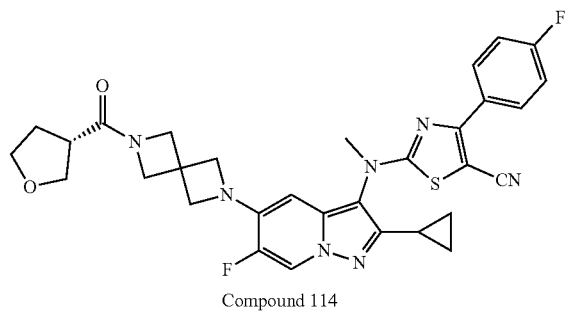

Compound 114

Compound 114 was prepared from Intermediate 4 in a manner analogous to preparation of Compound 9 and was isolated as a brown solid. $^1$H NMR (400 MHz, CDCl$_3$) δ 8.18-8.14 (m, 2H), 7.26-7.14 (m, 2H), 5.88 (d, J=8.0 Hz, 1H), 4.36-4.35 (m, 2H), 4.23-4.19 (m, 4H), 4.03-3.77 (m, 2H), 3.61 (s, 3H), 2.81 (s, 4H), 2.22-2.17 (m, 2H), 2.14-1.96 (m, 2H), 1.86-1.80 (m, 1H), 1.05-0.98 (m, 4H). LC-MS (ESI): m/z=602.3 [M+H]$^+$ Example 115: 2-((2-ethyl-5-(4-(2-(3-hydroxyazetidin-1-yl)-2-oxoethyl)piperazin-1-yl)-2H-pyrazolo[3,4-b]pyridin-3-yl)(methyl)amino)-4-(4-fluorophenyl)thiazole-5-carbonitrile (Compound 115)

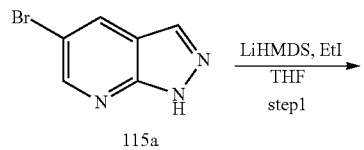

115a

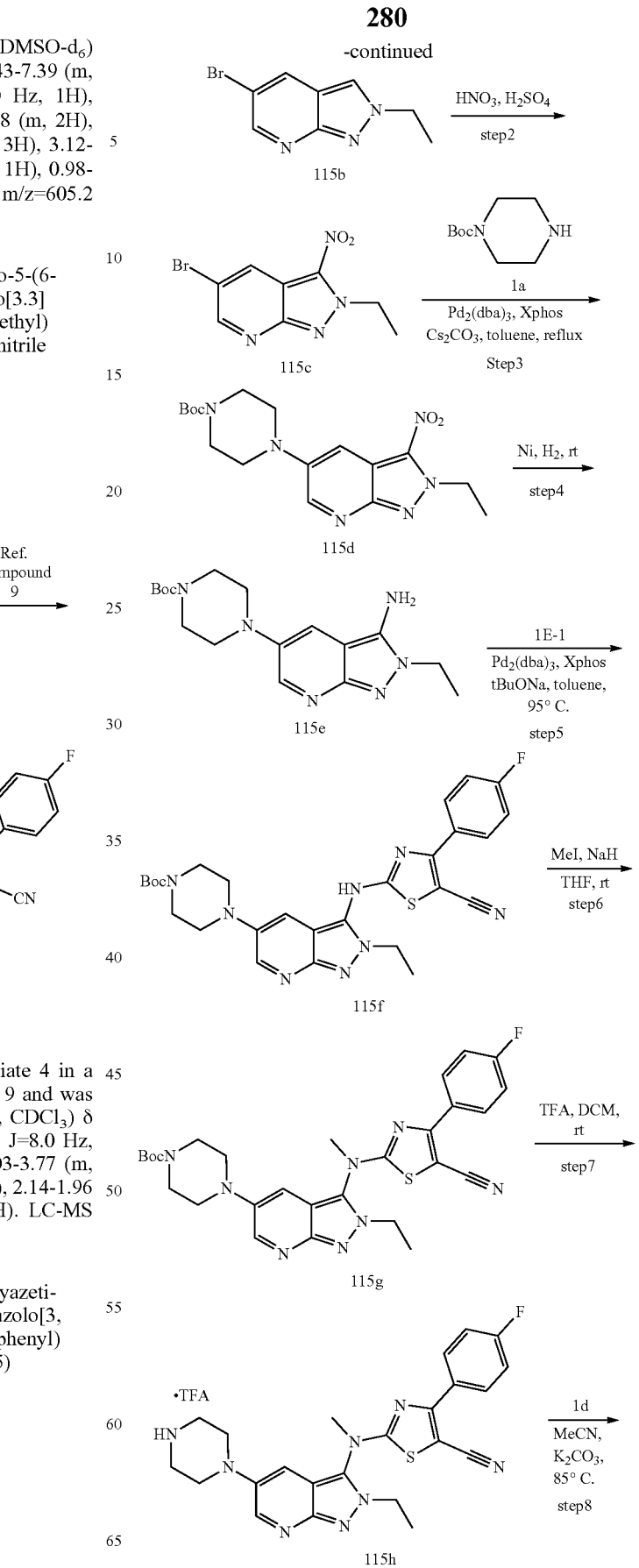

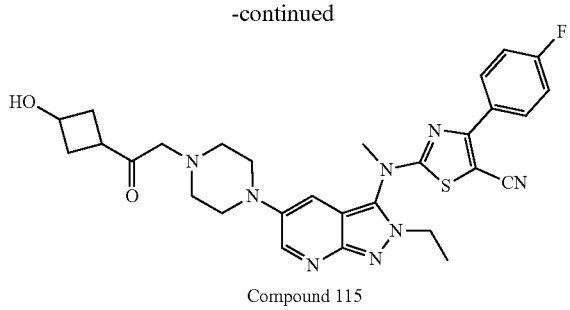

Compound 115

Step 1: 5-bromo-2-ethyl-2H-pyrazolo[3,4-b]pyridine (115b)

To a solution of 115a (5 g, 25.3 mmol) in anhydrous THF (80 mL) was added LiHMDS (2M in THF, 16 mL, 32.9 mmol) dropwise over 30 minutes via a dropping addition funnel at 0° C. under nitrogen. Then iodoethane was added. The mixture was stirred at room temperature overnight. Then quenched with addition of water, and extracted with ethyl acetate. The combined organic layers were then washed with water and brine, dried over $Na_2SO_4$, concentrated in vacuo. The residue was purified by flash chromatography to afford the 115b (3.43 g, 60%). $^1$H NMR (400 MHz, $CDCl_3$) δ 8.67 (d, J=2.3 Hz, 1H), 8.17 (d, J=2.3 Hz, 1H), 7.91 (s, 1H), 4.50 (q, J=7.3 Hz, 2H), 1.66 (t, J=7.3 Hz, 3H). LC-MS (ESI): m/z 226.0 $[M+H]^+$

Step 2: 5-bromo-2-ethyl-3-nitro-2H-pyrazolo[3,4-b]pyridine (115c)

To a solution of 115b (1.2 g, 5.3 mmol) in sulfuric acid (16 mL) was successively added nitric acid (4 mL) at 0° C. The reaction mixture was heated at 60° C. for 2 h. After cooling to room temperature, the mixture was diluted with water and EtOAc. The organic layer was separated and the aqueous layer extracted with EtOAc. The residue was purified by column chromatography on silica gel to give 115c as a yellow solid. $^1$H NMR (400 MHz, $CDCl_3$) δ 8.83 (d, J=1.9 Hz, 1H), 8.70 (d, J=2.3 Hz, 1H), 5.05 (q, J=7.2 Hz, 2H), 1.69 (t, J=7.2 Hz, 3H). LC-MS (ESI): m/z 271.0 $[M+H]^+$.

Step 3: tert-butyl 4-(2-ethyl-3-nitro-2H-pyrazolo[3,4-b]pyridin-5-yl)piperazine-1-carboxylate (115d)

115c (2 g, 7.38 mmol), $Pd_2(dba)_3$ (0.676 g, 0.738 mmol), X-PHOS (0.44 g, 1.476 mmol), and cesium carbonate (8.6 g, 22.14 mmol) were added to a screw capped test tube. The tube was evacuated and back filled with argon. tert-butyl piperazine-1-carboxylate (1a) (2.75 g, 14.76 mmol) and toluene (10 mL) were added successively by syringe at room temperature. The tube was sealed with a Teflon-lined cap, and the reaction mixture was heated at 120° C. for 10 h. After cooling to room temperature, the suspension was diluted with dichloromethane and filtered through Celite. The solvent was removed with the aid of a rotary evaporator to give a brown residue which was purified by column chromatography on silica gel to give 115d (1.39 g, 50%).

Step 4: tert-butyl 4-(3-amino-2-ethyl-2H-pyrazolo[3,4-b]pyridin-5-yl)piperazine-1-carboxylate (115e)

115d (1.39 g, 3.69 mmol) was dissolved in methanol (10 mL), Raney-Nickel (0.16 g) was added and the mixture was stirred under hydrogen (balloon) for 4 h at room temperature. Then the mixture was filtered and diluted with methanol (2×10 mL). The organic filtrate was concentrated under reduced pressure, the residue was directly used for the next step without purification.

Step 5: tert-butyl 4-(3-((5-cyano-4-(4-fluorophenyl)thiazol-2-yl)amino)-2-ethyl-2H-pyrazolo[3,4-b]pyridin-5-yl)piperazine-1-carboxylate (115f)

115e (1.8 g, 5.2 mmol), $Pd_2(dba)_3$ (480 mg, 0.52 mmol), X-PHOS (310 mg, 1mmol), and sodium tert-butoxide (5.1 mg, 16 mmol) were added to a screw capped test tube. The tube was evacuated and back filled with argon. 2-chloro-4-(4-fluorophenyl)thiazole-5-carbonitrile (1E-1) (96.3 mg, 0.40 mmol) and toluene (10 mL) were added successively by syringe at room temperature. The tube was sealed with a Teflon-lined cap, and the reaction mixture was heated at 95° C. for 2.5 h. After cooling to room temperature, the suspension was diluted with dichloromethane and filtered through Celite. The solvent was removed with the aid of a rotary evaporator to give a brown residue which was purified by column chromatography on silica gel to give the 115f (1.1 g, 40%).

Step 6: tert-butyl 4-(3-((5-cyano-4-(4-fluorophenyl)thiazol-2-yl)(methyl)amino)-2-ethyl-2H-pyrazolo[3,4-b]pyridin-5-yl)piperazine-1-carboxylate (115g)

To a solution of 115f (1.1 g, 2.1 mmol) and iodomethane (0.57 g, 4 mmol) in THF (10 mL) was added sodium hydride (60%, 0.16 g, 4 mmol) under cooling with ice water, and the reaction mixture was stirred for 40 min at room temperature. The reaction mixture was then poured into crashed ice, and was extracted with ethyl acetate. The organic layer was dried over magnesium sulfate, filtered, and concentrated in vacuo. The residue was purified by column chromatography on silica gel to give 115g (1 g, 90%).

Step 7: 2-((2-ethyl-5-(piperazin-1-yl)-2H-pyrazolo[3,4-b]pyridin-3-yl)(methyl)amino)-4-(4-fluorophenyl)thiazole-5-carbonitrile TFA Salt (115h)

To a solution of 115g (1 g, 1.8 mmol) in dichloromethane (12 mL) was added TFA (6 mL) at room temperature, The reaction mixture was stirred for 3 h and concentrated, the residue was directly used for the next step without purification.

Step 8: 2-((2-ethyl-5-(4-(2-(3-hydroxyazetidin-1-yl)-2-oxoethyl)piperazin-1-yl)-2H-pyrazolo[3,4-b]pyridin-3-yl)(methyl)amino)-4-(4-fluorophenyl)thiazole-5-carbonitrile (Compound 115)

To a solution of 115h (0.9 g, 2 mmol) in acetonitrile (10 mL) was added potassium carbonate (5 g, 40 mmol) and 2-chloro-1-(3-hydroxyazetidin-1-yl)ethanone (1d) (0.4 g, 3 mmol). The reaction mixture was refluxed for 3.5 h and then filtered, and the solid was washed with acetonitrile. The filtrate was then suspended in 50 mL of water, extracted with ethyl acetate, the organic layer was dried over magnesium sulfate, filtered, and concentrated in vacuo. The residue was purified by column chromatography on silica gel to give the Compound 115 (0.7 g, 66%). $^1$H NMR (400 MHz, $CDCl_3$) δ 8.63 (d, 1H), 8.20-8.08 (m, 2H), 7.22-7.13 (m, 2H), 6.99 (t, 1H), 4.68 (s, 1H), 4.53-4.42 (m, 1H), 4.38-4.26 (m, 3H), 4.21 (s, 1H), 4.00-3.92 (m, 1H), 3.66 (d, 3H), 3.43-3.21 (m, 6H), 3.05 (s, 5H), 1.62 (t, 3H). LC-MS (ESI): m/z=576.2 [M+H]$^+$ Example 116: 2-((2-ethyl-5-(6-(4-hydroxytetra-hydro-2H-pyran-4-carbonyl)-2,6-diazaspiro[3.3]heptan-2-yl)-2H-pyrazolo[3,4-b]pyridin-3-yl)(methyl)amino)-4-(4-fluorophenyl)thiazole-5-carbonitrile (Compound 116)

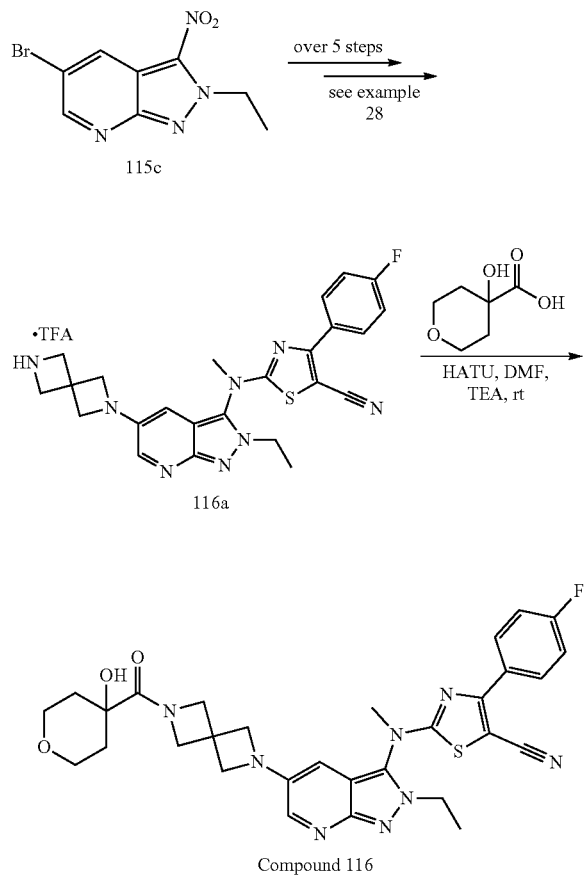

To a solution of 4-hydroxytetrahydro-2H-pyran-4-carboxylic acid (116 mg, 0.79 mmol) and HATU (300 mg, 0.79 mmol) in DMF (10 mL) was added triethylamine (0.73 mL, 5.27 mmol) and 116a (116a was prepared from 115c and 9a in a manner analogous to preparation of 115h over 5 steps) (250 mg, 0.43 mmol) at rt. After 2 h, the reaction mixture was quenched with water, diluted with DCM (50 mL), washed with water (2×50 mL), and brine (100 mL). All volatiles were removed under reduced pressure. The residue was purified by column chromatography on silica gel to give the title Compound 116 (120 mg, 47%). $^1$H NMR (400 MHz, CDCl$_3$) δ 8.31 (s, 1H), 8.13 (dd, 2H), 7.17 (t, 2H), 6.64 (s, 1H), 4.67 (s, 2H), 4.36 (dd, 3H), 4.27 (s, 2H), 4.16 (s, 4H), 3.83-3.78 (m, 2H), 3.68 (s, 4H), 2.19-2.03 (m, 2H), 1.62 (t, 3H), 1.52 (d, 2H). LC-MS (ESI): m/z=603.2 [M+H]$^+$ Example 117: 2-((2-ethyl-5-(6-(4-hydroxytetra-hydro-2H-pyran-4-carbonyl)-2,6-diazaspiro[3.3]heptan-2-yl)-2H-pyrazolo[3,4-b]pyridin-3-yl)(methyl)amino)-4-(4-fluorophenyl)thiazole-5-carbonitrile (Compound 117)

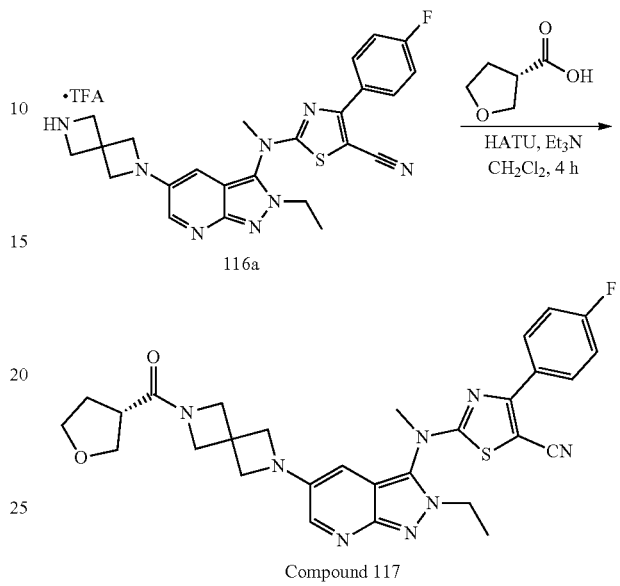

To a solution of 116a (0.1 g, 0.21 mmol) in DCM (10 mL) were successively added (S)-tetrahydrofuran-3-carboxylic acid (29.4 mg, 0.253 mmol), HATU (100 mg, 0.253 mmol) and Et$_3$N (0.5 mL, 3.6 mmol). The reaction mixture was stirred at room temperature for 1 h, then the mixture was diluted with water (10 mL) and extracted with DCM (10 mL×3). The combined organic layers were then washed with water (10 mL×2) and brine (5 mL×1), dried over Na$_2$SO$_4$, filtered, and concentrated in vacuo. The residue was purified by flash chromatography to afford the title Compound 117 (70 mg, 60%) as a light brown solid. $^1$H NMR (400 MHz, CDCl$_3$) δ 8.28 (s, 1H), 8.19-8.09 (m, 2H), 7.18 (t, J=8.7 Hz, 2H), 6.66 (s, 1H), 4.36 (dd, J=14.6, 7.3 Hz, 4H), 4.18 (d, J=30.2 Hz, 1H), 3.99 (t, J=8.2 Hz, 1H), 3.94-3.77 (m, 3H), 3.67 (s, 3H), 2.98-2.87 (m, 1H), 2.24-2.12 (m, 2H), 2.09 (d, J=5.4 Hz, 1H), 1.63 (t, J=7.3 Hz, 3H). LC-MS: m/z=573.2 [M+H]$^+$.

Example 118: 2-((2-ethyl-5-(6-(tetrahydro-2H-pyran-4-carbonyl)-2,6-diazaspiro[3.3]heptan-2-yl)-2H-pyrazolo[3,4-b]pyridin-3-yl)(methyl)amino)-4-(4-fluorophenyl)thiazole-5-carbonitrile (Compound 118)

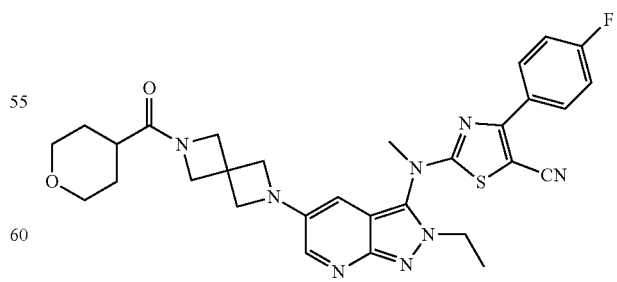

The title compound was prepared by the method substantially similar to that mentioned in Example 117, using tetrahydro-2H-pyran-4-carboxylic acid to afford Compound 118 (0.036 g, 47%) as a pale yellow solid. $^1$H NMR (400 MHz, CDCl$_3$) δ 8.24 (d, 1H), 8.19-8.10 (m, 2H), 7.18 (t, 2H), 6.50 (d, J=2.2 Hz, 1H), 4.34 (dd, 4H), 4.20 (s, 2H), 4.17-4.07 (m, 4H), 4.01 (d, J=9.7 Hz, 2H), 3.66 (s, 3H), 3.42 (dd, 2H), 2.41 (ddd, J=11.4, 7.6, 3.9 Hz, 1H), 1.87 (ddd, J=16.0, 12.6, 4.3 Hz, 2H), 1.67-1.51 (m, 5H). LC-MS (ESI): m/z=587.2 [M+H]$^+$ Example 119: 2-((2-ethyl-5-(4-(2-(3-hydroxyazetidin-1-yl)-2-oxoethyl)piperazin-1-yl)-6-methyl-2H-pyrazolo[3,4-b]pyridin-3-yl)(methyl)amino)-4-(4-fluorophenyl)thiazole-5-carbonitrile (Compound 119)

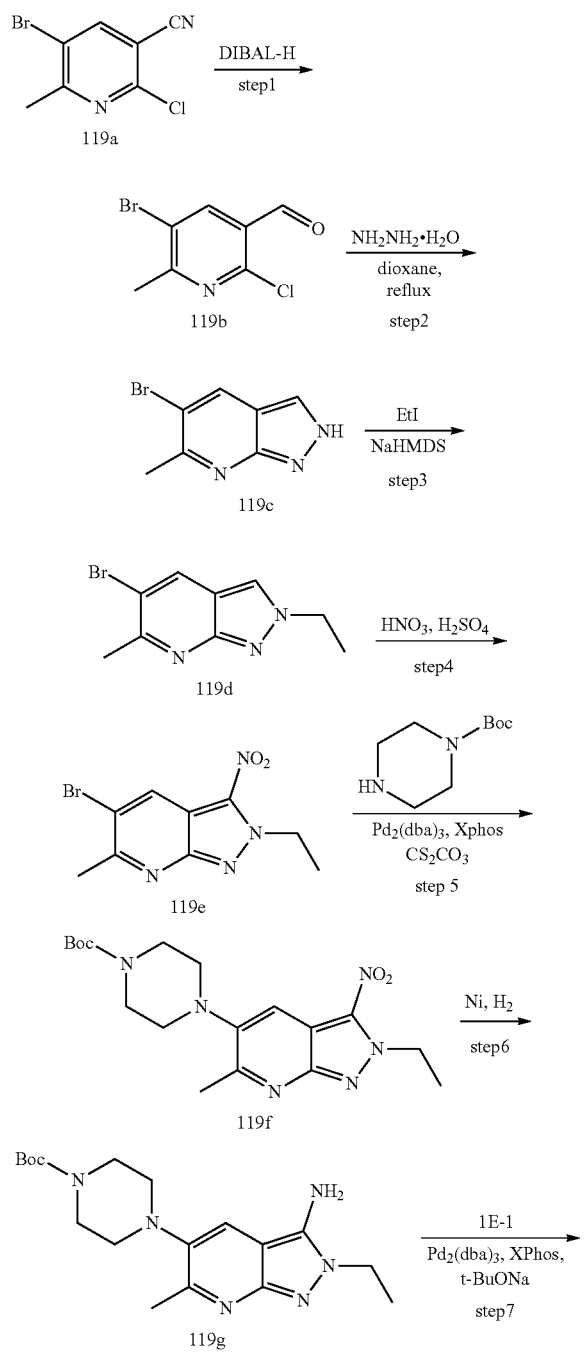

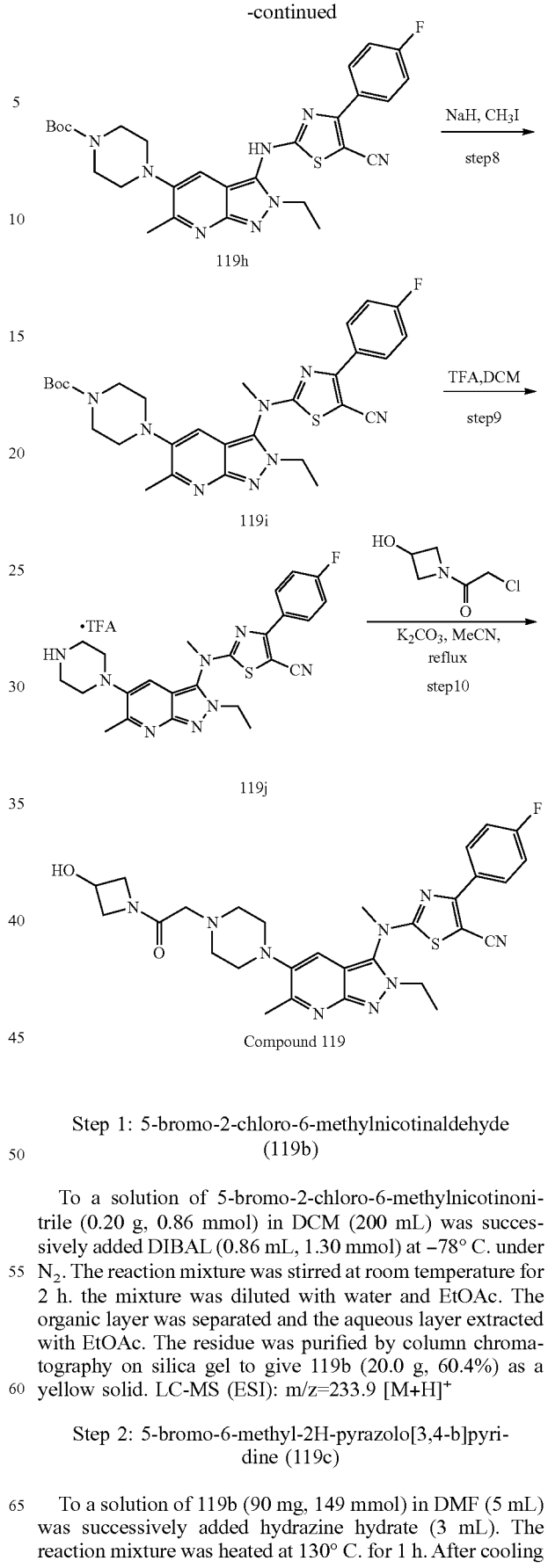

Step 1: 5-bromo-2-chloro-6-methylnicotinaldehyde (119b)

To a solution of 5-bromo-2-chloro-6-methylnicotinonitrile (0.20 g, 0.86 mmol) in DCM (200 mL) was successively added DIBAL (0.86 mL, 1.30 mmol) at −78° C. under N$_2$. The reaction mixture was stirred at room temperature for 2 h. the mixture was diluted with water and EtOAc. The organic layer was separated and the aqueous layer extracted with EtOAc. The residue was purified by column chromatography on silica gel to give 119b (20.0 g, 60.4%) as a yellow solid. LC-MS (ESI): m/z=233.9 [M+H]$^+$ Step 2: 5-bromo-6-methyl-2H-pyrazolo[3,4-b]pyridine (119c)

To a solution of 119b (90 mg, 149 mmol) in DMF (5 mL) was successively added hydrazine hydrate (3 mL). The reaction mixture was heated at 130° C. for 1 h. After cooling to room temperature, the mixture was diluted with water and EtOAc. The organic layer was separated and the aqueous layer extracted with EtOAc. The residue was purified by column chromatography on silica gel to give 119c (70 mg, 86.0%) as a yellow solid. LC-MS (ESI): m/z=211.9 [M+H]+

Step 3: 5-bromo-2-ethyl-6-methyl-2H-pyrazolo[3,4-b]pyridine (119d)

To a solution of 119c (1.2 g, 5.66 mmol) in THF (10 mL) under argon was successively added NaHMDS (4.24 mL, 8.49 mmol) at 0° C., then iodoethane (1.36 mL, 17.0 mmol) was added. The reaction mixture was stirred at room temperature for 2 h. The mixture was diluted with water and EtOAc. The organic layer was separated and the aqueous layer extracted with EtOAc. The combined organic layers were then washed with water and brine, dried over $Na_2SO_4$, filtered, and concentrated in vacuo. The residue was purified by flash chromatography to afford 119d (0.50 g, 37%) as a white solid. $^1$H NMR (400 MHz, $CDCl_3$) δ 8.19 (s, 1H), 7.84 (s, 1H), 4.47 (d, 2H), 2.79 (s, 3H), 1.65 (t, 3H). LC-MS (ESI): m/z=240.1 [M+H]+

Step 4: 5-bromo-2-ethyl-6-methyl-3-nitro-2H-pyrazolo[3,4-b]pyridine (119e)

To a solution of 119d (1.2 g, 5.0 mmol) in sulfuric acid (16 mL) was successively added nitric acid (4 mL) at 0° C. The reaction mixture was heated at 60° C. for 2 h. After cooling to room temperature, the mixture was diluted with water and EtOAc. The organic layer was separated and the aqueous layer extracted with EtOAc. The residue was purified by column chromatography on silica gel to give 119e as a yellow solid. $^1$H NMR (400 MHz, $CDCl_3$) δ 8.79 (s, 1H), 5.03 (q, 2H), 2.89 (s, 3H), 1.67 (t, 3H). LC-MS (ESI): m/z=285.0 [M+H]+

Step 5: tert-butyl 4-(2-ethyl-6-methyl-3-nitro-2H-pyrazolo[3,4-b]pyridin-5-yl)piperazine-1-carboxylate (119f)

To a solution of 119e (0.70 g, 2.0 mmol) in toluene (15 mL) under argon was successively added N-Boc piperazine (0.70 g, 4.0 mmol), cesium carbonate (2.0 g, 7.0 mmol) and then JohnPhos (0.2 g, 0.5 mmol) and $Pd_2(dba)_3$ (0.2 g, 0.2 mmol). The reaction mixture was heated at 115° C. for 2 h. After cooling to room temperature, the mixture was diluted with water and EtOAc. The organic layer was separated and the aqueous layer extracted with EtOAc. The combined organic layers were then washed with water and brine, dried over $Na_2SO_4$, filtered, and concentrated in vacuo. The residue was was purified by flash chromatography to afford 119f (0.40 g, 62%) as a yellow solid. LC-MS (ESI): m/z=391.2 [M+H]+

Step 6: tert-butyl 4-(3-amino-2-ethyl-6-methyl-2H-pyrazolo[3,4-b]pyridin-5-yl)piperazine-1-carboxylate (119g)

To a solution of 119f (50 mg, 0.12 mmol) in THF (4 mL) and MeOH (2 mL) under $H_2$ was successively added nickel (0.40 g). The reaction mixture was heated at 30° C. for 1 h. Then the mixture was filtered and diluted with methanol (2×20 mL). The organic filtrate was concentrated under reduced pressure, the residue was directly used for the next step without purification. LC-MS (ESI): m/z=361.2 [M+H]+

Step 7: tert-butyl 4-(3-((5-cyano-4-(4-fluorophenyl)thiazol-2-yl)amino)-2-ethyl-6-methyl-2H-pyrazolo[3,4-b]pyridin-5-yl)piperazine-1-carboxylate (119h)

To a solution of 119g (45 mg, 0.12 mmol) in toluene (5 mL) under argon was successively added 1E-1 (23 mg, 0.1 mmol), sodium tert-butoxide (4 mg, 0.4 mmol) and then JohnPhos (2 mg, 0.02 mmol) and $Pd_2(dba)_3$ (2 mg, 0.01 mmol). The reaction mixture was heated at 115° C. for 2 h. After cooling to room temperature, the mixture was diluted with water and EtOAc. The organic layer was separated and the aqueous layer extracted with EtOAc. The combined organic layers were then washed with water and brine, dried over $Na_2SO_4$, filtered, and concentrated in vacuo. The residue was was purified by flash chromatography to afford 119h (20 mg, 28.5%) as a yellow solid. LC-MS (ESI): m/z=563.2 [M+H]+

Step 8: tert-butyl 4-(3-((5-cyano-4-(4-fluorophenyl)thiazol-2-yl)(methyl)amino)-2-ethyl-6-methyl-2H-pyrazolo[3,4-b]pyridin-5-yl)piperazine-1-carboxylate (119i)

To a solution of 119h (0.42 g, 0.75 mmol) in THF (4 mL) under argon was successively added sodium hydride (72 mg, 1.5 mmol) at 0° C., then iodomethane (0.21 g, 1.5 mmol). The reaction mixture was heated at 30° C. for 3 h. The mixture was diluted with water and EtOAc. The organic layer was separated and the aqueous layer extracted with EtOAc. The combined organic layers were then washed with water and brine, dried over $Na_2SO_4$, filtered, and concentrated in vacuo. The residue was was purified by flash chromatography to afford 119i (0.22 g, 51%) as a yellow solid. LC-MS (ESI): m/z=577.3 [M+H]+

Step 9: 2-((2-ethyl-6-methyl-5-(piperazin-1-yl)-2H-pyrazolo[3,4-b]pyridin-3-yl)(methyl)amino)-4-(4-fluorophenyl)thiazole-5-carbonitrile TFA Salt (119j)

To a solution of 119i (30 mg, 0.05 mmol) in DCM (8 mL) was added trifluoroacetic acid (4 mL). The reaction mixture was stirred at room temperature for 1 h. The mixture was concentrated in vacuo. The residue was used for the next reaction without purification.

Step 10: 3-((2-ethyl-6-(4-(2-(3-hydroxyazetidin-1-yl)-2-oxoethyl)piperazin-1-yl)-8-methylimidazo[1,2-a]pyridin-3-yl)(methyl)amino)-1-(4-fluorophenyl)-1H-pyrazole-5-carbonitrile (Compound 119)

To a solution of 119j (30 mg, 0.05 mmol) in acetonitrile (10 mL) was added potassium carbonate (0.07 g, 0.5 mmol) and 1d (15 mg, 0.1 mmol). The reaction mixture was refluxed for 2 h and then filtered, and the solid was washed with acetonitrile. The filtrate was then suspended in 20 mL of water, extracted with ethyl acetate, the organic layer was dried over magnesium sulfate, filtered, and concentrated in vacuo. The residue was purified by column chromatography on silica gel to give Compound 119 as a yellow solid (0.15 g, 22%). $^1$H NMR (400 MHz, $CDCl_3$) δ 8.18-8.08 (m, 2H), 7.18 (dd, 3H), 4.73-4.61 (m, 1H), 4.54-4.41 (m, 1H), 4.35-4.24 (m, 3H), 4.14 (s, 1H), 3.90 (dd, 1H), 3.72-3.61 (m, 3H), 3.12 (s, 2H), 2.96 (s, 4H), 2.80-2.59 (m, 7H), 1.26 (s, 3H). LC-MS (ESI): m/z=590.2 [M+H]$^+$ Example 120: 2-((2-ethyl-5-(6-(2-hydroxy-2-methylpropanoyl)-2,6-diazaspiro[3.3]heptan-2-yl)-6-methyl-2H-pyrazolo[3,4-b]pyridin-3-yl)(methyl)amino)-4-(4-fluorophenyl)thiazole-5-carbonitrile (Compound 120)

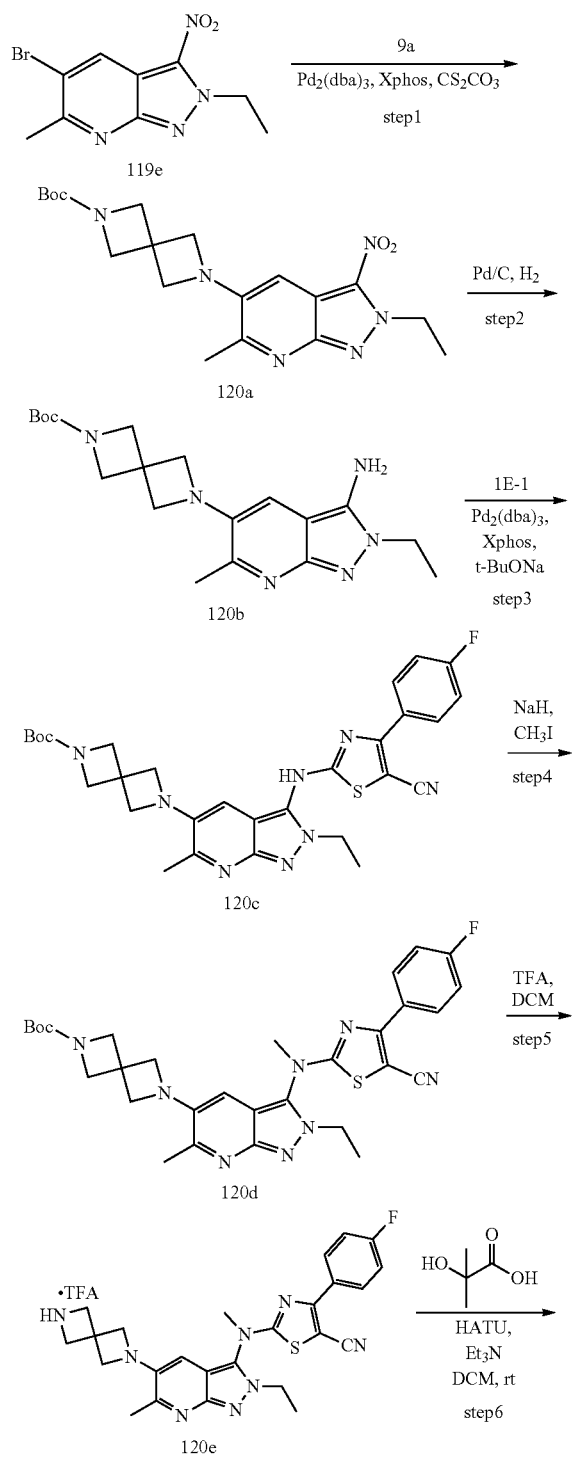

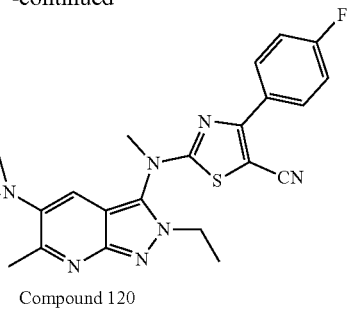

Compound 120

Step 1: tert-butyl 6-(2-ethyl-6-methyl-3-nitro-2H-pyrazolo[3,4-b]pyridin-5-yl)-2,6-diazaspiro[3.3]heptane-2-carboxylate (120a)

To a solution of 119e (1.5 g, 5.3 mmol) in toluene (20 mL) under argon was successively added 9a (2.3 g, 7.9 mmol), cesium carbonate (5.1 g, 16 mmol) and then JohnPhos (0.5 g, 1.1 mmol) and Pd$_2$(dba)$_3$ (0.5 g, 0.5 mmol). The reaction mixture was heated at 115° C. for 2 h. After cooling to room temperature, the mixture was diluted with water and EtOAc. The organic layer was separated and the aqueous layer extracted with EtOAc. The combined organic layers were then washed with water and brine, dried over Na$_2$SO$_4$, filtered, and concentrated in vacuo. The residue was purified by flash chromatography to afford 120a. LC-MS (ESI): m/z=391.2 [M+H]$^+$ Step 2: tert-butyl 4-(3-amino-2-ethyl-6-methyl-2H-pyrazolo[3,4-b]pyridin-5-yl)piperazine-1-carboxylate (120b)

To a solution of 120a (50 mg, 0.12 mmol) in THF (4 Ml) and MeOH (2 mL) under H$_2$ was successively added nickel (0.40 g). The reaction mixture was heated at 30° C. for 1 h. Then the mixture was filtered and diluted with methanol (2×20 mL). The organic filtrate was concentrated under reduced pressure, the residue was directly used for the next step without purification. LC-MS (ESI): m/z=361.2 [M+H]$^+$ Step 3: tert-butyl 4-(3-((5-cyano-4-(4-fluorophenyl)thiazol-2-yl)amino)-2-ethyl-6-methyl-2H-pyrazolo[3,4-b]pyridin-5-yl)piperazine-1-carboxylate (120c)

To a solution of 120b (45 mg, 0.12 mmol) in toluene (5 mL) under argon was successively added 1E-1 (23 mg, 0.1 mmol), sodium tert-butoxide (4 mg, 0.4 mmol) and then JohnPhos (2 mg, 0.02 mmol) and Pd$_2$(dba)$_3$ (2 mg, 0.01 mmol). The reaction mixture was heated at 115° C. for 2 h. After cooling to room temperature, the mixture was diluted with water and EtOAc. The organic layer was separated and the aqueous layer extracted with EtOAc. The combined organic layers were then washed with water and brine, dried over Na$_2$SO$_4$, filtered, and concentrated in vacuo. The residue was was purified by flash chromatography to afford 120c (20 mg, 28.5%) as a yellow solid. LC-MS (ESI): m/z=577.3 [M+H]$^+$ Step 4: tert-butyl 4-(3-((5-cyano-4-(4-fluorophenyl)thiazol-2-yl)(methyl)amino)-2-ethyl-6-methyl-2H-pyrazolo[3,4-b]pyridin-5-yl)piperazine-1-carboxylate (120d)

To a solution of 120c (0.42 g, 0.75 mmol) in THF (4 mL) under argon was successively added sodium hydride (72 mg, 1.5 mmol) at 0° C., then iodomethane (0.21 g, 1.5 mmol). The reaction mixture was heated at 30° C. for 3 h. The mixture was diluted with water and EtOAc. The organic layer was separated and the aqueous layer extracted with EtOAc. The combined organic layers were then washed with water and brine, dried over Na$_2$SO$_4$, filtered, and concentrated in vacuo. The residue was purified by flash chromatography to afford 120d (0.22 g, 51%) as a yellow solid. LC-MS (ESI): m/z=563.2 [M+H]$^+$ Step 5: 2-((2-ethyl-6-methyl-5-(piperazin-1-yl)-2H-pyrazolo[3,4-b]pyridin-3-yl)(methyl)amino)-4-(4-fluorophenyl)thiazole-5-carbonitrile (120e)

To a solution of 120d (30 mg, 0.05 mmol) in DCM (8 mL) was added trifluoroacetic acid (4 mL). The reaction mixture was stirred at room temperature for 1 h. The mixture was concentrated in vacuo. The residue was used for the next reaction without purification as a yellow oil.

Step 6: 3-((2-ethyl-6-(4-(2-(3-hydroxyazetidin-1-yl)-2-oxoethyl)piperazin-1-yl)-8-methylimidazo[1,2-a]pyridin-3-yl)(methyl)amino)-1-(4-fluorophenyl)-1H-pyrazole-5-carbonitrile (Compound 120)

To a solution of 120e (94 mg, 0.16 mmol) in dichloromethane (10 mL) was added N,N-diethylethanamine (65 mg, 0.64 mmol), HATU (73 mg, 0.19 mmol) and 2-hydroxy-2-methyl-propanoic acid (25 mg, 0.24 mmol). The reaction mixture was stirred at room temperature for 3 h and then the reaction mixture was quenched with water, extracted with ethyl acetate, the organic layer was washed with water (3×15 mL) and then dried over magnesium sulfate, filtered, and concentrated in vacuo. The residue was purified by column chromatography on silica gel to give the title Compound 120 (34 mg, 37%) as a yellow solid. $^1$H NMR (400 MHz, CDCl$_3$) δ 8.27-7.98 (m, 2H), 7.23-7.10 (m, 2H), 6.57 (s, 1H), 4.57 (s, 2H), 4.29 (dt, 4H), 4.03 (s, 4H), 3.66 (s, 3H), 3.03 (s, 1H), 2.59 (s, 3H), 1.60 (t, 3H), 1.42 (s, 6H). LC-MS (ESI): m/z=590.2 [M+H]$^+$ Example 121: (S)-2-((2-ethyl-6-methyl-5-(6-(tetrahydrofuran-3-carbonyl)-2,6-diazaspiro[3.3]heptan-2-yl)-2H-pyrazolo[3,4-b]pyridin-3-yl)(methyl)amino)-4-(4-fluorophenyl)thiazole-5-carbonitrile (Compound 121)

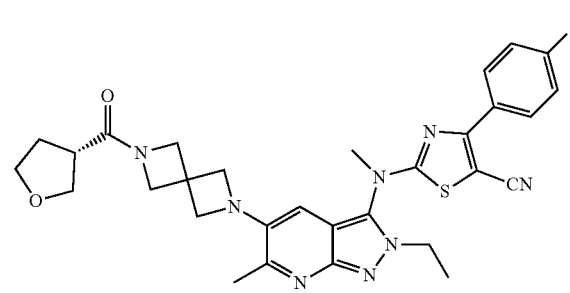

The title compound was prepared by the method substantially similar to that mentioned in Example 120, using (S)-tetrahydrofuran-3-carboxylic acid to afford Compound 121 as a pale yellow solid. $^1$H NMR (400 MHz, CDCl$_3$) δ 8.25-8.05 (m, 2H), 7.23-7.08 (m, 2H), 6.58 (s, 1H), 4.44-4.24 (m, 4H), 4.24-4.12 (m, 2H), 4.08-3.94 (m, 4H), 3.95-3.76 (m, 3H), 3.66 (s, 3H), 2.93 (dt, 1H), 2.59 (s, 3H), 2.22-1.96 (m, 3H), 1.60 (t, 3H). LC-MS (ESI): m/z=587.3 [M+H]$^+$ Example 122: 2-((2-ethyl-6-methyl-5-(6-(tetrahydro-2H-pyran-4-carbonyl)-2,6-diazaspiro[3.3]heptan-2-yl)-2H-pyrazolo[3,4-b]pyridin-3-yl)(methyl)amino)-4-(4-fluorophenyl)thiazole-5-carbonitrile (Compound 122)

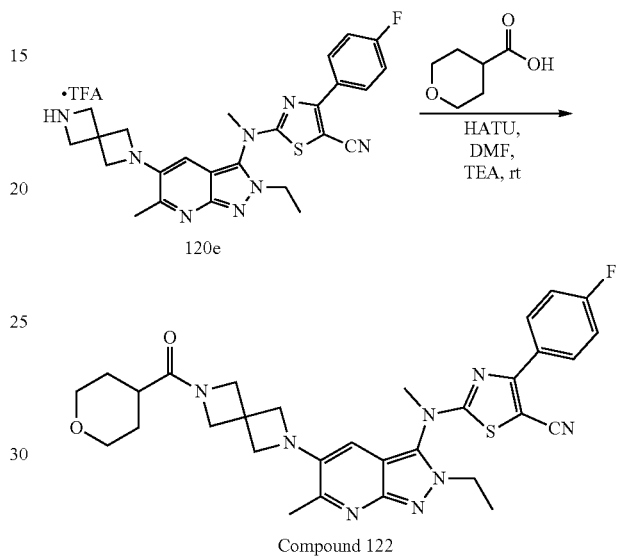

To a solution of tetrahydropyran-4-carboxylic acid (24 mg, 0.1 mmol) and HATU (71 mg, 0.19 mmol) in DMF (10 mL) was added triethylamine (0.17 mL, 1.25 mmol) and 120e (75 mg, 0.12 mmol) at rt. After 2 h, the reaction mixture was quenched with water, diluted with DCM (50 mL), washed with water (2×50 mL), and brine (100 mL). All volatiles were removed under reduced pressure. The residue was purified by column chromatography on silica gel to give the title Compound 122 (30 mg, 40%). $^1$H NMR (400 MHz, CDCl$_3$) δ 8.25-8.01 (m, 2H), 7.18 (t, 2H), 6.58 (s, 1H), 4.38 (s, 2H), 4.30 (q, 2H), 4.19 (s, 2H), 4.11-3.91 (m, 6H), 3.66 (s, 3H), 3.41 (td, 2H), 2.60 (s, 3H), 2.48-2.34 (m, 1H), 1.96-1.75 (m, 4H), 1.60 (t, 3H). LC-MS (ESI): m/z=601.3 [M+H]$^+$ Example 125: 2-((2-ethyl-5-(4-(2-(3-hydroxyazetidin-1-yl)-2-oxoethyl)piperazin-1-yl)-7-methyl-2H-indazol-3-yl)(methyl)amino)-4-(4-fluorophenyl)thiazole-5-carbonitrile (Compound 125)

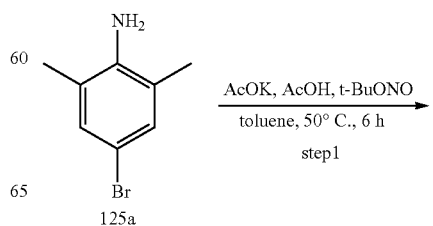

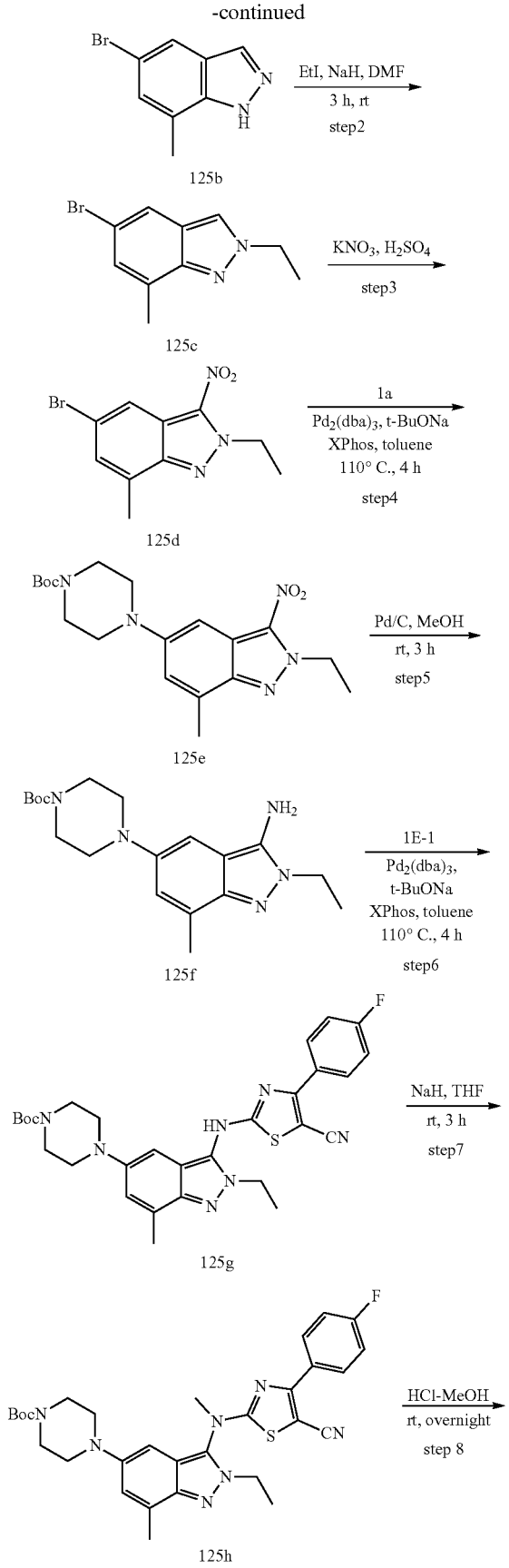

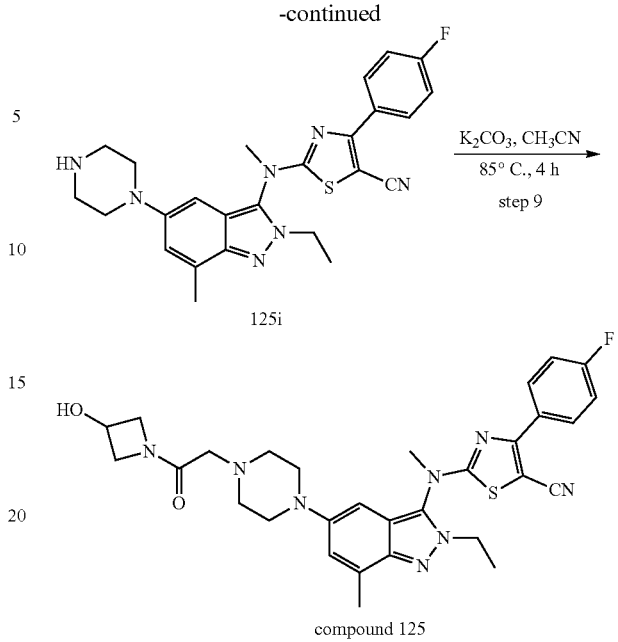

compound 125

Step 1: 5-bromo-7-methyl-1H-indazole (125b)

To a solution of 125a (78.2 g, 0.39 mol) and potassium acetate (33.5 g, 0.56 mol) in toluene (1 L) was added tert-butyl nitrite (44.4 g, 0.43 mol) at 0° C. for 6 hr. The mixture was diluted with EA (1000 mL), washed with water (2×500 mL) and brine (1×250 mL), dried with $Na_2SO_4$ and concentrated. The crude product was purified by flash chromatography to afford the title compound 125b (60.2 g, 99%) as a white solid. LC-MS (ESI): m/z=213.0 [M+H]$^+$.

Step 2: 5-bromo-2-ethyl-7-methyl-2H-indazole (125c)

To a solution of 125b (7 g, 29.3 mmol) in sulfuric acid (50 mL) was added potassium nitrate at 0° C. for 1hr. The mixture was diluted with EA (200 mL), washed with water (2×200 mL) and brine (1×250 mL), dried with $Na_2SO_4$ and concentrated. The crude product was purified by flash chromatography to afford the title compound 125c (6 g, 76.9%) as a brown solid. LC-MS (ESI): m/z=239.0 [M+H]$^+$.

Step 3: 5-bromo-2-ethyl-7-methyl-3-nitro-2H-indazole (125d)

To a solution of 125c (80 g, 0.38 mol) in DMF (500 mL) was added sodium hydride (60%, 13.6 g, 0.57 mol) under cooling with ice water, and the reaction mixture was stirred for 40 min at room temperature. Then iodoethane (118 g, 0.76 mol) was added to the mixture and stirred for another 2 hr. The reaction mixture was then poured into crashed ice, and extracted with ethyl acetate (2×1 L). The organic layer was dried over magnesium sulfate, filtered, and concentrated in vacuo. The residue was purified by column chromatography on silica gel to give the title compound 125d (73.6 g, 73.7%). LC-MS (ESI): m/z=284.0 [M+H]$^+$.

Step 4: tert-butyl 4-(2-ethyl-7-methyl-3-nitro-2H-indazol-5-yl)piperazine-1-carboxylate (125e)

To a solution 125d (7.00 g, 24.6 mmol) in toluene (70 mL) under argon was successively added N-Boc piperazine (5.97 g, 32.0 mmol), sodium tert-butoxide (4.74 g, 49.3 mmol) and then XPhos (2.35 g, 4.93 mmol) and Pd$_2$(dba)$_3$ (2.26 g, 2.46 mmol). The reaction mixture was heated at 80° C. for 2 h. After cooling to room temperature, the mixture was diluted with water and EtOAc. The organic layer was separated and the aqueous layer extracted with EtOAc. The combined organic layers were then washed with water and brine, dried over Na$_2$SO$_4$, filtered, and concentrated in vacuo. The residue was was purified by flash chromatography to afford 125e (1.90 g, 20%) as a yellow solid. LC-MS (ESI): m/z=390.3 [M+H]$^+$ Step 5: tert-butyl 4-(3-amino-2-ethyl-7-methyl-2H-indazol-5-yl)piperazine-1-carboxylate (125f)

To a solution 125e (1.90 g, 4.88 mmol) in MeOH (20 mL) was added Pd/C (0.5 g). The reaction mixture was stirred at room temperature under H$_2$ atmosphere for 2 h, and then filtered through celite. The filtrate was concentrated in vacuo to afford 125f (1.70 g, 97%) as a yellow solid. LC-MS (ESI): m/z=360.3 [M+H]$^+$ Step 6: tert-butyl 4-(3-((5-cyano-4-(4-fluorophenyl)thiazol-2-yl)amino)-2-ethyl-7-methyl-2H-indazol-5-yl)piperazine-1-carboxylate (125g)

To a solution 125f (1.20 g, 3.34 mmol) in toluene (12 mL) under argon was successively added 1E-1 (1.59 g, 6.68 mmol), sodium tert-butoxide (0.96 g, 10.00 mmol) and then XPhos (0.48 g, 1.00 mmol) and Pd$_2$(dba)$_3$ (0.46 g, 0.50 mmol). The reaction mixture was heated at 110° C. for 4 h. After cooling to room temperature, the mixture was diluted with water and EtOAc. The organic layer was separated and the aqueous layer extracted with EtOAc. The combined organic layers were then washed with water and brine, dried over Na$_2$SO$_4$, filtered, and concentrated in vacuo. The residue was purified by flash chromatography to afford 125g (0.68 g, 36%) as a yellow solid. $^1$H NMR (400 MHz, CDCl$_3$) δ 8.07-8.06 (m, 2H), 7.99 (s, 1H), 7.14 (t, J=8.4 Hz, 2H), 6.98 (s, 1H), 4.50 (q, J=7.2 Hz, 2H), 3.64 (brs, 4H), 2.95 (brs, 4H), 2.65 (s, 3H), 1.63 (t, J=7.2 Hz, 3H), 1.48 (s, 9H).

Step 7: tert-butyl 4-(3-((5-cyano-4-(4-fluorophenyl)thiazol-2-yl)(methyl)amino)-2-ethyl-7-methyl-2H-indazol-5-yl)piperazine-1-carboxylate (125h)

To a solution of 125g (0.65 g, 1.2 mmol) in THF (10 mL) were added NaH (93 mg, 60%, 2.0 equiv, 2.4 mmol) at 0° C. After 20 min, MeI (0.25 g, 1.7 mmol) was added, then the reaction mixture was warmed to rt. After being stirred at room temperature for 3 h, the reaction mixture was poured into water and then the product was extracted with EA (2×10 mL), dried over Na$_2$SO$_4$, and concentrated in vacuo, purified by flash chromatography to afford 125h (0.65 g, 98%) as a yellow solid. $^1$H NMR (400 MHz, CDCl$_3$) δ 8.17-8.13 (m, 2H), 7.72 (s, 1H), 7.16 (t, J=8.8 Hz, 2H), 6.96 (s, 1H), 4.47 (q, J=7.2 Hz, 2H), 3.65 (s, 3H), 3.47 (brs, 4H), 2.96 (brs, 4H), 2.65 (s, 3H), 1.63 (t, J=7.2 Hz, 3H), 1.46 (s, 9H).

Step 8: 2-((2-ethyl-7-methyl-5-(piperazin-1-yl)-2H-indazol-3-yl)(methyl)amino)-4-(4-fluorophenyl)thiazole-5-carbonitrile (125i)

A solution of 125h (0.65 g, 1.1 mmol) HCl—MeOH (10 mL) were stirred at room temperature overnight. The reaction mixture was concentrated in vacuo, poured into NaHCO$_3$ (sat.aq., 30 mL), extracted with EA (2×10 mL), dried over Na$_2$SO$_4$, and concentrated in vacuo to afford 125i (0.53 g, 99%) as a yellow solid. $^1$H NMR (400 MHz, CDCl$_3$) δ 9.66 (brs, 1H), 8.12-8.11 (m, 2H), 7.78 (s, 1H), 7.14 (t, J=8.6 Hz, 2H), 7.06 (s, 1H), 4.50 (q, J=7.2 Hz, 2H), 3.61 (s, 3H), 3.34 (brs, 8H), 2.66 (s, 3H), 1.64 (t, J=7.2 Hz, 3H). LC-MS (ESI): m/z=476.2 [M+H]$^+$ Step 9: 2-((2-ethyl-5-(4-(2-(3-hydroxyazetidin-1-yl)-2-oxoethyl)piperazin-1-yl)-7-methyl-2H-indazol-3-yl)(methyl)amino)-4-(4-fluorophenyl)thiazole-5-carbonitrile (Compound 125)

To a solution of 125i (0.53 g, 1.1 mmol) in MeCN (5 mL) were added potassium carbonate (0.31 g, 2.2 mmol) and 2-chloro-1-(3-hydroxyazetidin-1-yl) ethanone (1D) (0.22 g, 1.4 mmol). The reaction mixture was refluxed for 3 h. After cooling to room temperature, the mixture was diluted with water and EtOAc. The organic layer was separated and the aqueous layer extracted with EtOAc. The combined organic layers were then washed with water and brine, dried over Na$_2$SO$_4$, filtered, and concentrated in vacuo. The residue was purified by flash chromatography to afford Compound 125 (0.10 g, 15%) as a yellow solid. $^1$H NMR (400 MHz, CDCl$_3$) δ 8.16-8.13 (m, 2H), 7.70 (s, 1H), 7.16 (t, J=8.6 Hz, 2H), 7.00 (s, 1H), 4.66-4.64 (m, 1H), 4.49-4.45 (m, 3H), 4.36-4.25 (m, 1H), 4.23 (brs, 1H), 3.90-3.88 (m, 1H), 3.63 (s, 3H), 3.11 (brs, 6H), 2.72 (brs, 4H), 2.65 (s, 3H), 1.62 (t, J=7.4 Hz, 3H). LC-MS (ESI): m/z=589.3 [M+H]$^+$ Example A1: Biological In Vitro Assay Autotaxin is a plasma phosphodiesterase that converts lysophosphatidylcholine (LPC) into lysophosphatidic acid (LPA), therefore LPA formation was used to evaluate the potency of autotaxin inhibitors. The potency of compound was evaluated ex vivo in pooled human plasma.

Various concentrations of compound were incubated with plasma for 2 hours, and the LPA 18:2 and 20:4 concentration was measured by LC/MS/MS. To determine the LPA18:2 or 20:4 concentration in study plasma, a 10× calibration standard of LPA 18:2 or 20:4 were prepared by serial dilution in butyl alcohol: 20000, 10000, 5000, 2000, 1000, 500, 200, 100, 50, 20, and 10 ng/mL. 3 μL of calibration standard solution was added into 27.0 μL of blank plasma in 1.5-mL microcentrifuge tubes to generate 1× calibration standards. The 30.0 μL of standards or study plasma was added into 1.5-mL microcentrifuge tubes. 200 μL of butyl alcohol (containing 25.0 ng/mL LPA17:0 for internal control) was added into each 1.5-mL microcentrifuge tube containing study plasma or calibration standards. After vortexing for 1 minute and centrifuging at 10000 rpm for 10 min, 180 μL of supernatant was transferred into a 96-well plate and the LPA18:2 concentration in the plasma was quantitated using LC/MS/MS together with standards. Briefly, 8 μL of the solutions were injected for LC-MS/MS analysis using an ACQUITY UPLC BEH C18 column (2.1×50 mm, 1.7 μm) with mobile phase A [20 mM NH$_4$OAC in water (0.1% FA)] and phase B [5 mM NH$_4$OAC in water/0.2% FA in ACN=5:95]. Mass spectrometer parameters optimization for LPA18:2 were performed by Deprotonated molecular ion at m/z 433.2 ([M−H]$^−$) for LPA18:2, 457.2 for LPA20:4 and abundant product ion at m/z 152.8 for both LPA18:2 and LPA20:4 were obtained. Quantitative data were acquired in multiple reaction monitoring (MRM) negative electrospray ionization mode The inhibition rate of LPA formation was determined by comparing the levels of LPA in treated and non-treated plasma. The data was plotted against the corresponding concentration of compound and the $IC_{50}$ was calculated through non-linear regression fitting.

The table below listed the $IC_{50}$ (nM) of test compounds in inhibiting of LPA formation:

| Ex. | LPA formation (18:2) (IC50, nM) | LPA formation (20:4) (IC50, nM) |
| --- | --- | --- |
| 1 | A | A |
| 2 | A | A |
| 3 | A | A |
| 4 | A | A |
| 5 | A | A |
| 6 | A | A |
| 7 | B | B |
| 8 | B | B |
| 9 | B | B |
| 10 | A | A |
| 11 | A | A |
| 12 | A | A |
| 14 | A | A |
| 15 | A | A |
| 16 | A | A |
| 17 | A | A |
| 18 | A | A |
| 19 | A | A |
| 20 | A | A |
| 21 | A | A |
| 22 | A | A |
| 23 | B | B |
| 24 | B | A |
| 25 | A | A |
| 26 | B | B |
| 27 | A | A |
| 28 | A | A |
| 29 | B | C |
| 30 | A | A |
| 31 | B | B |
| 32 | A | A |
| 33 | A | B |
| 34 | B | B |
| 35 | B | B |
| 36 | A | A |
| 37 | A | A |
| 38 | A | A |
| 39 | A | A |
| 40 | A | A |
| 41 | A | A |
| 42 | A | A |
| 43 | A | A |
| 44 | A | A |
| 45 | A | A |
| 46 | B | B |
| 47 | A | B |
| 49 | A | A |
| 50 | D | D |
| 51 | A | A |
| 52 | B | B |
| 53 | A | A |
| 54 | C | C |
| 55 | B | B |
| 56 | A | A |
| 57 | A | A |
| 59 | B | B |
| 60 | A | B |
| 61 | B | B |
| 62 | B | B |
| 63 | B | B |
| 64 | B | B |
| 66 | A | A |
| 67 | B | B |
| 68 | B | B |
| 69 | B | B |
| 70 | B | B |
| 71 | B | B |
| 72 | D | D |
| 73 | A | A |
| 74 | B | B |
| 75 | B | B |
| 76 | A | B |
| 77 | A | A |
| 78 | A | A |
| 79 | C | C |
| 80 | D | D |
| 82 | B | B |
| 83 | C | C |
| 84 | A | A |
| 85 | B | B |
| 86 | A | A |
| 87 | D | D |
| 88 | D | D |
| 90 | A | A |
| 91 | B | B |
| 92 | B | B |
| 93 | B | B |
| 94 | B | C |
| 95 | D | D |
| 96 | A | A |
| 97 | A | A |
| 98 | B | B |
| 99 | A | A |
| 100 | A | A |
| 101 | A | A |
| 102 | A | A |
| 103 | A | A |
| 104 | A | A |
| 105 | A | A |
| 106 | A | A |
| 107 | A | A |
| 108 | A | A |
| 109 | A | A |
| 110 | A | A |
| 111 | A | A |
| 112 | A | A |
| 113 | A | A |
| 114 | A | A |
| 115 | A | A |
| 116 | A | A |
| 117 | A | A |
| 118 | A | A |
| 119 | A | A |
| 120 | A | A |
| 121 | A | A |
| 122 | A | A |
| 125 | C | C |

A is less or equal than 100 nM;
B is less or equal than 500 nM and more than 100 nM;
C is less or equal than 1000 nM and more than 500 nM; and
D is more than 1000 nM.

Example A2: Pharmacokinetics and Pharmacodynamics Studies

The pharmacokinetics and pharmacodynamics of test compounds after a single oral dose were investigated in SD rats, Beagle dog and Cynomolgus monkey. SD Rats (200-250 g) were purchased from Beijing Vital River Laboratory Animal Technology Co., Ltd. Male Beagle Dog, 6-9 kg, were purchased from Beijing Mashall. Male Cynomolgus monkeys, 3-5 kg, were purchased from Suzhou Xishan Zhongke Drugs Research and Development Co., Ltd. Following arrival, the animals were acclimated for 7 days in individual cages maintained at ambient temperature, 34 to 68% relative humidity, and 12-h light/dark cycles. Just prior to dose administration the rats were fasted overnight with free access to water. Animals were given 10 mL/kg of formulated compound in 0.5% methylcellulose (MC) by oral gavage, and the animals were fed four hours after dosing. The animals were manually restrained at the designated time points (pre-dose, 0.5, 1, 3, 6, 9, 12, and 24 h post-dose) to collect blood. Approximately 120 µL of blood was collected via orbital sinus into $K_2$EDTA tubes. The blood samples were centrifuged at 5000 rpm for 10 min at 4° C. to obtain plasma samples.

To determine the compound concentration in the plasma samples, a 10× calibration standard of compound were prepared by serial dilution in DMSO: 20000, 10000, 5000, 2000, 1000, 500, 200, 100, 50, 20, and 10 ng/mL. 3 µL of calibration standard solution was added into 27.0 µL of blank plasma in 1.5-mL microcentrifuge tubes to generate 1× calibration standards. The 30.0 µL of standards or study plasma was mixed with 200 µL of acetonitrile (containing 5 ng/mL verapamil for internal control) in a 1.5-mL microcentrifuge tube. After vertexing for 1 minute and centrifuging at 10000 rpm for 10 min, 180 µL of supernatant was transferred into a 96-well plate and the compound concentration in the plasma was quantitated using LC/MS/MS together with standards. Briefly, 1 µL of the solutions were injected for LC-MS/MS analysis using an Agilent Zorbax C18 column (50×2.1 mm, 3.5 µm) with mobile phase A [5 mM $NH_4Ac$ (0.1% FA)] and phase B [Methanol (0.1% FA)]. Mass spectrometer parameters optimization for compound was performed by infusing standard diluted at 1 µg/mL in water/methanol (1/1, v/v) directly in the ionization source at a flow of 10 µL/min. Quantitative data were acquired in multiple reaction monitoring (MRM) positive APCI mode.

Autotaxin is a secreted phosphodiesterase that converts lysophosphatidylcholine (LPC) into lysophosphatidic acid (LPA), and LPA 18:2 formation was used to evaluate the efficacy of autotaxin inhibitors. Therefore, the LPA 18:2 formation in response to drug administration was analyzed in each time point to assess the pharmacodynamics of test compounds. To determine the LPA18:2 concentration in study plasma, a 10× calibration standard of LPA 18:2 were prepared by serial dilution in butyl alcohol: 20000, 10000, 5000, 2000, 1000, 500, 200, 100, 50, 20, and 10 ng/mL. 3 µL of calibration standard solution was added into 27.0 µL of blank plasma in 1.5-mL microcentrifuge tubes to generate 1× calibration standards. The 30.0 µL of standards or study plasma was added into 1.5-mL microcentrifuge tubes. 200 µL of butyl alcohol (containing 25.0 ng/mL LPA17:0 for internal control) was added into each 1.5-mL microcentrifuge tube containing study plasma or calibration standards. After vortexing for 1 minute and centrifuging at 10000 rpm for 10 min, 180 µL of supernatant was transferred into a 96-well plate and the LPA18:2 concentration in the plasma was quantitated using LC/MS/MS together with standards. Briefly, 8 µL of the solutions were injected for LC-MS/MS analysis using an ACQUITY UPLC BEH C18 column (2.1×50 mm, 1.7 µm) with mobile phase A [20 mM $NH_4OAC$ in water (0.1% FA)] and phase B [5 mM $NH_4OAC$ in water/0.2% FA in ACN=5:95]. Mass spectrometer parameters optimization for LPA18:2 were performed by infusing standard diluted at 1 µg/mL in butyl Alcohol directly in the ionization source, at a flow of 10 µL/min. Deprotonated molecular ion at m/z 433.2 ([M–H]–) for LPA18:2, and abundant product ion at m/z 152.8 for LPA18:2 were obtained. Quantitative data were acquired in multiple reaction monitoring (MRM) negative electrospray ionization mode The percentage of LPA18:2 inhibition was plotted against the corresponding concentration of compound and the $IC_{50}$ was calculated through non-linear regression fitting.

Table 1 below lists the pharmacokinetic and pharmacodynamic parameters of test compounds in SD rats.

TABLE 1

| Ex. | Cmax (ng/mL) | AUC (h · ng · $mL^{-1}$) | T½ (h) | In vivo rat $IC_{50}$ (LPA 18:2) (ng/mL) |
|---|---|---|---|---|
| GLPG1690 | 889 ± 173 | 1257 ± 209 | 3.15 ± 1.8 | 28.46 |
| 97 | 336 ± 33.8 | 4689 ± 526 | 5.41 ± 1.7 | 11.73 |
| 101 | 268 ± 76 | 2048 ± 884 | 3.29 ± 0.25 | 5.12 |
| 102 | 732 ± 95 | 7522 ± 498 | 5.53 ± 0.2 | 5.22 |
| 103 | 209 ± 58 | 1085 ± 313 | 4.32 ± 1.5 | 28.86 |
| 104 | 408 ± 69 | 4333 ± 937 | 6.17 ± 0.87 | 69.30 |
| 106 | 29.2 ± 15 | 350 ± 156 | 7.21 ± 0.98 | 11.83 |
| 109 | 67.1 ± 24 | 269 ± 85 | 3.46 ± 0.21 | 6.09 |
| 112 | 460 ± 178 | 4750 ± 1426 | 3.77 ± 0.34 | 60.40 |
| 113 | 177 ± 99 | 963 ± 501 | 2.92 ± 0.31 | 8.96 |
| 114 | 140 ± 102 | 1464 ± 1123 | 3.72 ± 2.5 | 9.65 |
| 117 | 584 ± 265 | 2214 ± 704 | 4.36 ± 1.3 | 101.00 |
| 118 | 477 ± 250 | 2621 ± 1923 | 3.85 ± 1.3 | 7.31 |
| 119 | 96.2 ± 73 | 222 ± 160 | 1.64 ± 1.27 | 10.97 |
| 122 | 403 ± 341 | 1089 ± 544 | 2.99 ± 3.0 | 16.08 |

Table 2 below lists the nharmacokinetic narameters of test comnounds in beagle dogs.

TABLE 2

| | I.V. (1 mg/kg) | | | | P.O. (1 mg/kg) | | | |
|---|---|---|---|---|---|---|---|---|
| Ex. | C0 (ng/mL) | AUC (h · ng · $mL^{-1}$) | T1/2 (h) | Cl (ml/kg/min) | Cmax (ng/mL) | AUC (h · ng · $mL^{-1}$) | T1/2 (h) | F (%) |
| GLPG1690 | 5119 ± 1385 | 8647 ± 328 | 2.11 ± 1.23 | 1.91 ± 0.07 | 1133 ± 229 | 5755 ± 672 | 3.04 ± 0.77 | 66.2 ± 7.5 |
| 101 | 2288 ± 172 | 10738 ± 1807 | 5.06 ± 0.85 | 1.53 ± 0.27 | 425 ± 68 | 4020 ± 549 | 4.69 ± 0.17 | 36.1 ± 4.9 |
| 102 | 1073 ± 34.4 | 6478 ± 703 | 14.8 ± 0.57 | 1.85 ± 0.28 | 192 ± 26 | 2194 ± 325 | 20.4 ± 6.1 | 33.9 ± 5.0 |
| 118 | 786 ± 62 | 2193 ± 378 | 3.35 ± 0.60 | 7.68 ± 1.2 | 165 ± 40 | 900 ± 305 | 3.99 ± 0.89 | 40.7 ± 14 |

Table 3 below lists the pharmacokinetic parameters of test compounds in cynomolgus monkeys.

TABLE 3

| | I.V. (1 mg/kg) | | | | P.O. (1 mg/kg) | | | |
| --- | --- | --- | --- | --- | --- | --- | --- | --- |
| Ex. | C0 (ng/mL) | AUC (h · ng · mL$^{-1}$) | T1/2 (h) | Cl (ml/kg/min) | Cmax (ng/mL) | AUC (h · ng · mL$^{-1}$) | T1/2 (h) | F (%) |
| GLPG1690 | 4208 ± 1152 | 2774 ± 246 | 1.41 ± 0.19 | 6.02 ± 0.51 | 72.6 ± 38 | 244 ± 118 | 1.82 ± 0.63 | 4.51 ± 2.1 |
| 101 | 1225 ± 166 | 1992 ± 92 | 1.82 ± 0.1 | 8.21 ± 0.38 | 239 ± 119 | 1381 ± 904 | 2.49 ± 0.54 | 35.6 ± 22 |
| 118 | 993 ± 8.6 | 2640 ± 473 | 6.59 ± 1.5 | 6.06 ± 1.2 | 28.0 ± 3.0 | 153 ± 10 | 2.63 ± 0.85 | 2.90 ± 0.19 |

Example A3: CYP Inhibition in Human Liver Microsome

Test compounds were evaluated for CYP inhibition using human liver microsomes (HLM). Test compounds were 1:3 serially diluted starting at 50 µM to generate 7 different concentrations. After incubation of diluted test compounds with HLM, a substrate cocktail composed of phenacetin (10 µM), amodiaquine (2 µM), diclofenac (5 µM), s-mephenytoin (30 µM), dextromethorphan (5 µM), and midazolam (2 µM) was added to check the remaining CYP activity for CYP 1A2, 2C8, 2C9, 2C19, 2D6 and 3A4. The CYP activity was measured by detecting the peak area of individual metabolites of know CYP substrates using LC/MS/MS. A percentage of inhibition of CYP was calculated at each final concentration of test compound, through which an IC$_{50}$ was fitted to represent the inhibition potential.

TABLE 4

The IC$_{50}$ Values of test compounds in CYP isozymes 1A2, 2C8, 2C9, 2C19, 2D6 and 3A4.

| Ex. | 1A2 | 2C9 | 2C19 | 2D6 | 3A4 |
| --- | --- | --- | --- | --- | --- |
| GLPG1690 | >50 | 16.7 | 40.2 | >50 | 13.5 |
| 101 | >50 | 17.3 | 45.5 | >50 | >50 |
| 102 | 13.9 | 5.69 | 11.9 | >50 | >50 |
| 118 | >50 | 15.9 | >50 | >50 | >50 |

Example A4: Metabolic Stability (Half-Time) of Test Compounds in Liver Microsome of Human, Rat, Mouse, Dog and Monkey The metabolic stability was examined in human, rat, mouse, dog and cynomolgus monkey liver microsomes. Compound (1 µM) was mixed with diluted liver microsomes from each of the 5 species and a small aliquot was taken at 0, 5, 10, 20, 30 and 60 minutes for HPLC MS/MS analysis. Intrinsic clearance and half-life were calculated.

TABLE 5

Summary of the metabolic stability (halftime in minutes) of test compounds in human, SD rat, CD-1mouse, Beagle dog and Cynomolgus monkey liver microsomes

| | Human | Rat | Mouse | Dog | Monkey |
| --- | --- | --- | --- | --- | --- |
| GLPG1690 | 10.8 | 9.2 | 10.3 | 32.1 | 4.8 |
| 101 | 24.5 | 96.6 | 14.0 | 71.9 | 9.8 |
| 102 | 13.4 | 67.3 | 17.9 | 69.8 | 6.4 |
| 118 | 75.4 | >145 | 58.5 | >145 | 21.3 |

Example A5: Metabolic Stability (Half-Time) of Test Compounds in Human Hepatocytes The metabolic stability was examined in cryopreserved human hepatocytes. Compound (1 µM) was mixed with human hepatocytes at 0.5 million/mL, and a small aliquot was taken at 0, 15, 30, 60 and 90 minutes for LC/MS/MS analysis. Intrinsic clearance and half-time were calculated.

TABLE 6

Metabolic stability (half time in minutes) of test compounds in human hepatocytes

| | Human |
| --- | --- |
| GLPG1690 | 117.9 |
| 101 | >216.8 |
| 102 | 76.6 |
| 118 | >216.8 |

Example A6: Randomized, Double-Blind, Parallel-Group, Placebo-Controlled Multicenter Study to Evaluate the Efficacy and Safety of a Compound of Formula (I) or (II) in Subjects with Idiopathic Pulmonary Fibrosis The main purpose of this study is to see how a compound of Formula (I) or (II) works together on lung function and IPF disease in general. The study will also investigate how well a compound of Formula (I) or (II) is tolerated.

Study Type: Interventional (Clinical Trial)

Allocation: Randomized

Intervention Model: Parallel Assignment

Masking: Quadruple (Participant, Care Provider, Investigator, Outcomes Assessor) Primary Purpose: Treatment

| Arm | Intervention/treatment |
| --- | --- |
| Experimental: A compound of Formula (I) or (II) Administered for oral use once daily. | Drug: A compound of Formula (I) or (II) A compound of Formula (I) or (II) for oral use. |

Outcome Measures

Primary Outcome Measures:

Rate of decline of forced vital capacity (FVC) in mL. [Time Frame: From baseline through week 52]

To evaluate the efficacy of a compound of Formula (I) or (II) compared to placebo in subjects with Idiopathic Pulmonary Fibrosis (IPF) as evaluated by the rate of decline of FVC. Secondary Outcome Measures:

Disease progression defined as the composite endpoint of first occurrence of ≥10% absolute decline in percent predicted forced vital capacity (% FVC) or all-cause mortality. [Time Frame: At week 52]

To evaluate the impact of a compound of Formula (I) or (II) compared to placebo in subjects with Idiopathic Pulmonary Fibrosis (IPF) on disease progression defined as deterioration of FVC or all-cause mortality.

Time to first respiratory-related hospitalization until the end of the study [Time Frame: From screening through study completion, a minimum of 52 weeks]

To evaluate the impact of a compound of Formula (I) or (II) compared to placebo in subjects with Idiopathic Pulmonary Fibrosis (IPF) on respiratory-related hospitalization until the end of the study. Change from baseline in the St. George's Respiratory Questionnaire (SGRQ) total score. [Time Frame: At Week 52]

To evaluate the impact of a compound of Formula (I) or (II) compared to placebo in subjects with Idiopathic Pulmonary Fibrosis (IPF) on changes in quality of life (measured by SGRQ total score). The SGRQ is a 50-item questionnaire split into three domains: symptoms, activity and impact. Scores are weighted such that every domain score and the total score range from 0 to 100, with higher scores indicating a poorer health-related quality of life.

Eligibility Criteria
  Ages Eligible for Study: 40 Years and older (Adult, Older Adult)
  Sexes Eligible for Study: All
  Accepts Healthy Volunteers: No
Criteria
  Inclusion Criteria:
    Male or female subject aged ≥40 years on the day of signing the Informed Consent Form (ICF).
    A diagnosis of IPF within 5 years prior to the screening visit, as per applicable American Thoracic Society (ATS)/European Respiratory Society (ERS)/Japanese Respiratory Society (JRS)/Latin American Thoracic Association (ALAT) guidelines at the time of diagnosis.
    Chest high-resolution computed tomography (HRCT) historically performed within 12 months prior to the screening visit and according to the minimum requirements for IPF diagnosis by central review based on subject's HRCT only (if no lung biopsy (LB) available), or based on both HRCT and LB (with application of the different criteria in either situation). If an evaluable HRCT<12 months prior to screening is not available, an HRCT can be performed at screening to determine eligibility, according to the same requirements as the historical HRCT.
    Subjects receiving local standard of care for the treatment of IPF, defined as either pirfenidone or nintedanib at a stable dose for at least two months before screening, and during screening; or neither pirfenidone or nintedanib (for any reason). A stable dose is defined as the highest dose tolerated by the subject during those two months.
    The extent of fibrotic changes is greater than the extent of emphysema on the most recent HRCT scan (investigator-determined).
    Meeting all of the following criteria during the screening period: FVC≥45% predicted of normal, Forced expiratory volume in 1 second (FEV1)/FVC≥0.7, diffusing capacity of the lung for carbon monoxide (DLCO) corrected for Hb≥30% predicted of normal.
    Estimated minimum life expectancy of at least 30 months for non IPF related disease in the opinion of the investigator.
    Male subjects and female subjects of childbearing potential agree to use highly effective contraception/preventive exposure measures from the time of first dose of investigational medicinal product (IMP) (for the male subject) or the signing of the ICF (for the female subject), during the study, and until 90 days (male) or 30 days (female) after the last dose of IMP.
    Able to walk at least 150 meters during the 6-Minute Walk Test (6MWT) at screening Visit 1;
    without having a contraindication to perform the 6MWT or without a condition putting the subject at risk of falling during the test (investigator's discretion). The use of a cane is allowed, the use of a stroller is not allowed at all for any condition. At Visit 2, for the oxygen titration test, resting oxygen saturation (SpO2) should be ≥88% with maximum 6 L O2/minute; during the walk, SpO2 should be ≥83% with 6 L O2/minute or ≥88% with 0, 2 or 4 L O2/minute.
  Exclusion Criteria:
    History of malignancy within the past 5 years (except for carcinoma in situ of the uterine cervix, basal cell carcinoma of the skin that has been treated with no evidence of recurrence, prostate cancer that has been medically managed through active surveillance or watchful waiting, squamous cell carcinoma of the skin if fully resected, and Ductal Carcinoma In Situ).
    Acute IPF exacerbation within 6 months prior to screening and/or during the screening period. The definition of an acute IPF exacerbation is as follows: Previous or concurrent diagnosis of IPF; Acute worsening or development of dyspnea typically <1 month duration; Computed tomography with new bilateral ground-glass opacity and/or consolidation superimposed on a background pattern consistent with usual interstitial pneumonia pattern and deterioration not fully explained by cardiac failure or fluid overload.
    Lower respiratory tract infection requiring antibiotics within 4 weeks prior to screening and/or during the screening period.
    Interstitial lung disease associated with known primary diseases (e.g. sarcoidosis and amyloidosis), exposures (e.g. radiation, silica, asbestos, and coal dust), or drugs (e.g. amiodarone).
    Diagnosis of severe pulmonary hypertension (investigator-determined).
    Unstable cardiovascular, pulmonary (other than IPF), or other disease within 6 months prior to screening or during the screening period (e.g. acute coronary disease, heart failure, and stroke).
    Had gastric perforation within 3 months prior to screening or during screening, and/or underwent major surgery within 3 months prior to screening, during screening or have major surgery planned during the study period.
    Moderate to severe hepatic impairment (Child-Pugh B or C) and/or abnormal liver function test (LFT) at screening, defined as aspartate aminotransferase (AST), and/or alanine aminotransferase (ALT), and/or total bilirubin≥1.5× upper limit of the normal range (ULN), and/or gamma glutamyl transferase (GGT)≥3×ULN. Retesting is allowed once for abnormal LFT.
    Abnormal renal function defined as estimated creatinine clearance, calculated according to Cockcroft-Gault calculation (CCr) <30 mL/min. Retesting is allowed once.
    Use of any of the following therapies within 4 weeks prior to screening and during the screening period, or planned during the study: warfarin, imatinib, ambrisentan, azathioprine, cyclophosphamide, cyclosporine A, bosentan, methotrexate, sildenafil (except for occasional use), prednisone at steady dose >10 mg/day or equivalent.

Example A7: Randomized, Double-Blind, Placebo-Controlled, Multi-Center Study to Evaluate the Efficacy, Safety, and Tolerability of a Compound of Formula (I) or (II) in Subjects with Scleroderma The main purpose of the study is to see if a compound of Formula (I) or (II) helps (together with the standard of care treatment) in the treatment of the skin and other areas affected by scleroderma.

Study Design
   Study Type: Interventional (Clinical Trial)
   Allocation: Randomized
   Intervention Model: Parallel Assignment
   Masking: Quadruple (Participant, Care Provider, Investigator, Outcomes Assessor)
   Primary Purpose: Treatment
Arms and Interventions

| Arm | Intervention/treatment |
| --- | --- |
| Experimental: a compound of Formula (I) or (II) | Drug: a compound of Formula (I) or (II) A compound of Formula (I) or (II) for oral use |
| Placebo Comparator: Placebo | Drug: Placebo Matching placebo for oral use |

Outcome Measures
Primary Outcome Measures:
   Change from baseline in modified Rodnan skin score (mRSS) over 24 weeks [Time Frame: At screening and Week 24]
   To evaluate the efficacy of a compound of Formula (I) or (II) as evaluated by mRSS compared to placebo over 24 weeks for the treatment of subjects with systemic sclerosis. The 17-site mRSS will be used, with each body site assessed for skin thickness on a scale of 0 (uninvolved) to 3 (severe thickening) with a maximum score of 51.
Secondary Outcome Measures:
   Number of participants with adverse events (AEs) over 24 weeks as assessed by CTCAE version 5.0. [Time Frame: From screening until Week 24]
   To evaluate the safety and tolerability of a compound of Formula (I) or (II) compared to placebo over 24 weeks in the treatment of subjects with scleroderma.
Eligibility Criteria
   Ages Eligible for Study: 18 Years and older (Adult, Older Adult)
   Sexes Eligible for Study: All
   Accepts Healthy Volunteers: No
Criteria
   Inclusion Criteria:
   Able and willing to comply with the protocol requirements and to sign the informed consent form (ICF) as approved by the Independent Ethics Committee (IEC)/Institutional Review Board (IRB), prior to any screening evaluations.
   Male and female subjects≥18 years at the time of consent who meet the American College of Rheumatology (ACR)/EULAR 2013 diagnostic criteria for systemic sclerosis with diffuse cutaneous involvement (according to LeRoy's criteria) and ≤5 years since the onset of the first systemic sclerosis manifestation other than Raynaud's phenomenon.
mRSS>10 at screening.
Active disease at screening, as defined by: Worsening of skin thickening (≥2 mRSS points) as assessed by mRSS measured at screening versus a previous mRSS assessment made within 6 months prior to screening, or new areas of skin involvement within 6 months prior to screening as documented by physician note, or new-onset systemic sclerosis with symptoms or signs other than Raynaud's phenomenon within 2 years prior to screening, or ≥1 tendon friction rub (palpated in the finger flexors or extensors, wrist flexors or extensors, olecranon bursa, shoulders, knees, anterior or posterior ankles with active motion).
Subject must be able and willing to comply with restrictions on prior and concomitant medication as described in the protocol
Female subjects of childbearing potential must have a negative serum pregnancy test at screening.
Female subjects of childbearing potential or male subjects with female partners of childbearing potential must be willing to comply with the contraceptive methods described in the protocol prior to the first dose of the investigational medicinal product (IMP), during the clinical study, and for at least 90 days after the last dose of the IMP for male subjects and 30 days after the last dose of the IMP for female subjects.
A body mass index (BMI) between 18-35 kg/m$^2$, inclusive, at screening.
Judged to be in good health by the investigator based upon the results of a medical history, physical examination, vital signs, 12-lead ECG, and fasting clinical laboratory safety tests. Clinical laboratory safety test results must be within the reference ranges or test results that are outside the reference ranges need to be considered non-clinically significant in the opinion of the investigator.
Exclusion Criteria:
Known hypersensitivity to IMP ingredients or history of a significant allergic reaction to any drug as determined by the investigator, such as anaphylaxis requiring hospitalization.
Breastfeeding female or subject intending to become pregnant or breastfeed.
History of or a current immunosuppressive condition (e.g. human immunodeficiency virus [HIV] infection, congenital, acquired).
Positive serology for hepatitis B (surface antigen) or C (antibody), or any history of hepatitis from any cause. For hepatitis A, a history of infection within 12 weeks prior to screening. Positive serology for HIV-1 and HIV-2 (antibodies).
History of malignancy within the past 5 years (except for carcinoma in situ of the uterine cervix, basal cell carcinoma of the skin that has been treated with no evidence of recurrence, prostate cancer medically managed through active surveillance or watchful waiting, and squamous cell carcinoma of the skin if fully resected).
Clinically significant abnormalities detected on ECG at screening of either rhythm or conduction, QT interval corrected for heart rate using Fridericia's formula (QTcF)>450 ms, or a known long QT syndrome.

Unstable cardiovascular, pulmonary, or other disease (other than systemic sclerosis-related) within 6 months prior to the baseline visit (e.g. coronary heart disease, heart failure, stroke).

Severe pulmonary disease with forced vital capacity (FVC)≤45% of predicted within 6 months prior to the baseline visit.

Chronic or ongoing active infectious disease, including tuberculosis (requiring hospitalization or systemic treatment within 4 weeks prior to the baseline visit).

Abnormal liver function test (LFT) at screening, defined as aspartate aminotransferase (AST), and/or alanine aminotransferase (ALT), and/or bilirubin, and/or alkaline phosphatase>2× upper limit of normal (ULN). Retesting is allowed once.

Example B: Pharmaceutical Compositions

Example B1: Parenteral Composition

To prepare a parenteral pharmaceutical composition suitable for administration by injection, 100 mg of a water-soluble salt of a compound described herein is dissolved in DMSO and then mixed with 10 mL of 0.9% sterile saline. The mixture is incorporated into a dosage unit form suitable for administration by injection.

Example B2: Oral Composition

To prepare a pharmaceutical composition for oral delivery, 100 mg of a compound described herein is mixed with 750 mg of starch. The mixture is incorporated into an oral dosage unit for, such as a hard gelatin capsule, which is suitable for oral administration.

Example B3: Sublingual (Hard Lozenge) Composition

To prepare a pharmaceutical composition for buccal delivery, such as a hard lozenge, mix 100 mg of a compound described herein, with 420 mg of powdered sugar mixed, with 1.6 mL of light corn syrup, 2.4 mL distilled water, and 0.42 mL mint extract. The mixture is gently blended and poured into a mold to form a lozenge suitable for buccal administration.

The examples and embodiments described herein are for illustrative purposes only and in some embodiments, various modifications or changes are to be included within the purview of disclosure and scope of the appended claims.

What is claimed is:

1. A compound of Formula (I'), or a pharmaceutically acceptable salt, solvate, or stereoisomer thereof:

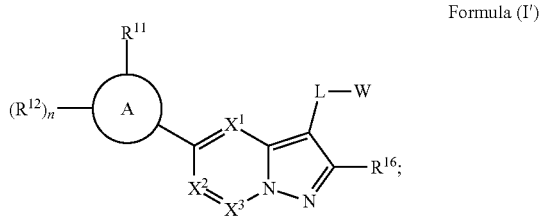

Formula (I')

wherein:
$X^1$ is $CR^{13}$;
$X^2$ is $CR^{14}$;
$X^3$ is N or $CR^{15}$;

W is

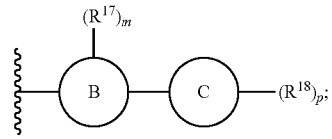

Ring A is cycloalkyl, heterocycloalkyl, aryl, or heteroaryl;
Ring B is cycloalkyl, heterocycloalkyl, aryl, or heteroaryl;
Ring C is cycloalkyl, heterocycloalkyl, aryl, or heteroaryl;
L is —O—, —S—, or —NR$^{19}$—;
$R^{11}$ is $L^1$-$R^{20}$;
$L^1$ is absent or $C_1$-$C_6$ alkylene optionally substituted with deuterium, halogen, —CN, —OR$^a$, —NR$^c$R$^d$, —C(=O)OR$^a$, or —C(=O)NR$^c$R$^d$;
$R^{20}$ is halogen, —CN, —OR$^{21}$, —SR$^{21}$, —S(=O)R$^{22}$, —S(=O)$_2$R$^{22}$, —NO$_2$, —NR$^{23}$R$^{24}$, —NR$^{21}$S(=O)$_2$R$^{22}$, —S(=O)$_2$NR$^{23}$R$^{24}$, —C(=O)R$^{22}$, —OC(=O)R$^{22}$, —C(=O)C(=O)R$^{22}$, —C(=O)OR$^{21}$, —C(=O)NR$^{21}$OR$^{21}$, —OC(=O)OR$^{21}$, —C(=O)NR$^{23}$R$^{24}$, —OC(=O)NR$^{23}$R$^{24}$, —NR$^{21}$C(=O)NR$^{23}$R$^{24}$—NR$^{21}$S(=O)$_2$NR$^{23}$R$^{24}$, —NR$^{21}$C(=O)R$^{22}$, —NR$^{21}$C(=O)OR$^{21}$, $C_1$-$C_6$ alkyl, cycloalkyl, heterocycloalkyl, aryl, or heteroaryl; wherein the alkyl, cycloalkyl, heterocycloalkyl, aryl, and heteroaryl are independently optionally substituted with one, two, or three $R^1$;
each $R^{21}$ is independently hydrogen, —CN, $C_1$-$C_6$ alkyl, cycloalkyl, heterocycloalkyl, aryl, or heteroaryl; wherein the alkyl, cycloalkyl, heterocycloalkyl, aryl, and heteroaryl are independently optionally substituted with one, two, or three $R^{1a}$;
$R^{22}$ is hydrogen, —CN, $C_1$-$C_6$ alkyl, cycloalkyl, heterocycloalkyl, aryl, or heteroaryl; wherein the alkyl, cycloalkyl, heterocycloalkyl, aryl, and heteroaryl are independently optionally substituted with one, two, or three $R^{1b}$;
$R^{23}$ and $R^{24}$ are independently hydrogen, $C_1$-$C_6$ alkyl, cycloalkyl, heterocycloalkyl, aryl, or heteroaryl; wherein the alkyl, cycloalkyl, heterocycloalkyl, aryl, and heteroaryl are independently optionally substituted with one, two, or three $R^{1c}$;
or $R^{23}$ and $R^{24}$ are taken together with the nitrogen atom to which they are attached to form a heterocycloalkyl optionally substituted with one, two, or three $R^{1d}$;
each $R^{12}$ is independently deuterium, halogen, —CN, —OR$^a$, —NR$^c$R$^d$, —C(=O)OR$^a$, —C(=O)NR$^c$R$^d$, $C_1$-$C_6$ alkyl, cycloalkyl, heterocycloalkyl, aryl, or heteroaryl; wherein the alkyl, cycloalkyl, heterocycloalkyl, aryl, and heteroaryl are independently optionally substituted with one, two, or three $R^2$;
or two $R^{12}$ on the same carbon are taken together to form an oxo;
$R^{13}$ is hydrogen, deuterium, halogen, —CN, —OR$^a$, —NR$^c$R$^d$, —C(=O)OR$^a$, —C(=O)NR$^c$R$^d$, $C_1$-$C_6$ alkyl, cycloalkyl, heterocycloalkyl, aryl, or heteroaryl; wherein the alkyl, cycloalkyl, heterocycloalkyl, aryl, and heteroaryl are independently optionally substituted with one, two, or three $R^3$;
$R^{14}$ is deuterium, halogen, —CN, —OR$^a$, —NR$^c$R$^d$, —C(=O)OR$^a$, —C(=O)NR$^c$R$^d$, $C_1$-$C_6$ alkyl, cycloalkyl, heterocycloalkyl, aryl, or heteroaryl; wherein the alkyl, cycloalkyl, heterocycloalkyl, aryl, and heteroaryl are independently optionally substituted with one, two, or three $R^4$;

$R^{15}$ is hydrogen, deuterium, halogen, —CN, —$OR^a$, —$NR^cR^d$, —C(=O)$OR^a$, —C(=O)$NR^cR^d$, $C_1$-$C_6$ alkyl, cycloalkyl, heterocycloalkyl, aryl, or heteroaryl; wherein the alkyl, cycloalkyl, heterocycloalkyl, aryl, and heteroaryl are independently optionally substituted with one, two, or three $R^5$;

or $R^{14}$ and $R^{15}$ are taken together to form a cycloalkyl or heterocycloalkyl; wherein the cycloalkyl and heterocycloalkyl are independently optionally substituted with one, two, or three $R^6$;

$R^{16}$ is hydrogen, deuterium, halogen, —CN, —$OR^a$, —$NR^cR^d$, —C(=O)$OR^a$, —C(=O)$NR^cR^d$, $C_1$-$C_6$ alkyl, cycloalkyl, heterocycloalkyl, aryl, or heteroaryl; wherein the alkyl, cycloalkyl, heterocycloalkyl, aryl, and heteroaryl are independently optionally substituted with one, two, or three $R^7$;

each $R^{17}$ is independently deuterium, halogen, —CN, —$OR^a$, —$NR^cR^d$, —C(=O)$R^a$, —C(=O)$OR^a$, —C(=O)$NR^cR^d$, —$NR^aC$(=O)$R^b$, $C_1$-$C_6$ alkyl, cycloalkyl, heterocycloalkyl, aryl, or heteroaryl; wherein the alkyl, cycloalkyl, heterocycloalkyl, aryl, and heteroaryl are independently optionally substituted with one, two, or three $R^8$;

or two $R^{17}$ on the same carbon are taken together to form an oxo;

each $R^{18}$ is independently deuterium, halogen, —CN, —$OR^a$, —$NR^cR^d$, —C(=O)$R^a$, —C(=O)$OR^a$, —C(=O)$NR^cR^d$, —$NR^aC$(=O)$R^b$, $C_1$-$C_6$ alkyl, cycloalkyl, heterocycloalkyl, aryl, or heteroaryl; wherein the alkyl, cycloalkyl, heterocycloalkyl, aryl, and heteroaryl are independently optionally substituted with one, two, or three $R^9$;

or two $R^{18}$ on the same carbon are taken together to form an oxo;

$R^{19}$ is hydrogen, —S(=O)$R^b$, —S(=O)$_2R^b$, —S(=O)$_2NR^cR^d$, —C(=O)$R^b$, —C(=O)$OR^a$, —C(=O)$NR^cR^d$, $C_1$-$C_6$ alkyl, $C_1$-$C_6$ haloalkyl, $C_1$-$C_6$ heteroalkyl, cycloalkyl, or heterocycloalkyl;

each $R^{1a}$, $R^{1b}$, $R^{1c}$, and $R^{1d}$ are independently oxo, halogen, —CN, —$OR^a$, —S(=O)$_2R^b$, —$NR^cR^d$, —S(=O)$_2NR^cR^d$, —C(=O)$R^b$, —OC(=O)$R^b$, —C(=O)$OR^a$, —OC(=O)$OR^a$, —C(=O)$NR^cR^d$, —OC(=O)$NR^cR^d$, —$NR^aC$(=O)$NR^cR^d$, —$NR^aC$(=O)$R^b$, $C_1$-$C_6$ alkyl, $C_1$-$C_6$ haloalkyl, $C_1$-$C_6$ hydroxyalkyl, or phenyl;

each $R^1$ is independently oxo, halogen, —CN, —$OR^a$, —$NR^cR^d$, —C(=O)$OR^a$, —C(=O)$R^a$, —C(=O)$NR^cR^d$, —S(=O)$_2R^b$, $C_1$-$C_6$ alkyl, cycloalkyl, heterocycloalkyl, or phenyl; wherein the alkyl, cycloalkyl, heterocycloalkyl, and phenyl are independently optionally substituted with one, two, or three halogen, —OH, —$NH_2$, $C_1$-$C_6$ alkyl, or phenyl;

each $R^2$, $R^3$, $R^4$, $R^5$, $R^6$, $R^7$, $R^8$, and $R^9$ are independently oxo, halogen, —CN, —$OR^a$, —$NR^cR^d$, —C(=O)$OR^a$, —C(=O)$R^a$, —C(=O)$NR^eR^d$, —S(=O)$_2R^b$, $C_1$-$C_6$ alkyl, cycloalkyl, heterocycloalkyl, or phenyl; wherein the alkyl, cycloalkyl, heterocycloalkyl, and phenyl are independently optionally substituted with one, two, or three halogen, —OH, —$NH_2$, $C_1$-$C_6$ alkyl, or phenyl;

each $R^a$ is independently hydrogen, $C_1$-$C_6$ alkyl, cycloalkyl, heterocycloalkyl, aryl, or heteroaryl; wherein the alkyl, cycloalkyl, heterocycloalkyl, aryl, and heteroaryl are independently optionally substituted with one, two, or three halogen, —OH, —$NH_2$, or $C_1$-$C_6$ alkyl;

each $R^b$ is independently $C_1$-$C_6$ alkyl, cycloalkyl, heterocycloalkyl, aryl, or heteroaryl; wherein the alkyl, cycloalkyl, heterocycloalkyl, aryl, and heteroaryl are independently optionally substituted with one, two, or three halogen, —OH, —$NH_2$, or $C_1$-$C_6$ alkyl;

each $R^c$ and $R^d$ are independently hydrogen, $C_1$-$C_6$ alkyl, cycloalkyl, heterocycloalkyl, aryl, or heteroaryl; wherein the alkyl, cycloalkyl, heterocycloalkyl, aryl, and heteroaryl are independently optionally substituted with one, two, or three halogen, —OH, —$NH_2$, or $C_1$-$C_6$ alkyl;

or $R^c$ and $R^d$ are taken together with the nitrogen atom to which they are attached to form a heterocycloalkyl optionally substituted with one, two, or three halogen, —OH, —$NH_2$, or $C_1$-$C_6$ alkyl;

n is 0-3;

m is 0-3; and p is 0-3.

2. The compound of claim 1, or a pharmaceutically acceptable salt, solvate, or stereoisomer thereof wherein:
$R^{13}$ is hydrogen, deuterium, halogen, —CN, —$OR^a$, —$NR^cR^d$, or $C_1$-$C_6$ alkyl optionally substituted with one, two, or three halogen.

3. The compound of claim 1, or a pharmaceutically acceptable salt, solvate, or stereoisomer thereof wherein:
$R^{14}$ is deuterium, halogen, —CN, —$OR^a$, —$NR^cR^d$, or $C_1$-$C_6$ alkyl optionally substituted with one, two, or three halogen.

4. The compound of claim 1, or a pharmaceutically acceptable salt, solvate, or stereoisomer thereof wherein:
$X^3$ is $CR^{15}$ and $R^{15}$ is hydrogen, deuterium, halogen, —CN, —$OR^a$, —$NR^cR^d$, or $C_1$-$C_6$ alkyl optionally substituted with one, two, or three halogen.

5. The compound of claim 1, or a pharmaceutically acceptable salt, solvate, or stereoisomer thereof wherein:
$R^{16}$ is $C_1$-$C_6$ alkyl.

6. The compound of claim 1, or a pharmaceutically acceptable salt, solvate, or stereoisomer thereof wherein:
L is —$NR^{19}$— and $R^{19}$ is hydrogen or $C_1$-$C_6$ alkyl.

7. The compound of claim 1, or a pharmaceutically acceptable salt, solvate, or stereoisomer thereof wherein:
Ring B is a 5-membered heteroaryl.

8. The compound of claim 1, or a pharmaceutically acceptable salt, solvate, or stereoisomer thereof wherein:
Ring C is aryl.

9. The compound of claim 1, or a pharmaceutically acceptable salt, solvate, or stereoisomer thereof wherein the compound is a compound of Formula (Ic):

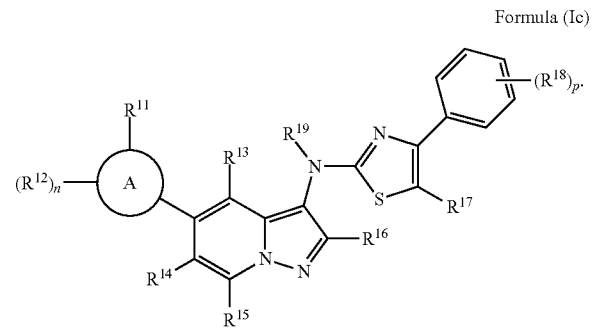

Formula (Ic)

10. The compound of claim 9, or a pharmaceutically acceptable salt, solvate, or stereoisomer thereof wherein:
$R^{17}$ is —CN.

11. The compound of claim 1, or a pharmaceutically acceptable salt, solvate, or stereoisomer thereof wherein:
  each $R^{18}$ is independently halogen, or $C_1$-$C_6$ alkyl optionally substituted with one, two, or three halogen.

12. The compound of claim 1, or a pharmaceutically acceptable salt, solvate, or stereoisomer thereof wherein:
  Ring A is heterocycloalkyl.

13. The compound of claim 1, or a pharmaceutically acceptable salt, solvate, or stereoisomer thereof wherein:
  $L^1$ is $C_1$-$C_6$ alkylene.

14. The compound of claim 1, or a pharmaceutically acceptable salt, solvate, or stereoisomer thereof wherein:
  $R^{20}$ is —CN, —S(=O)$_2$$R^{22}$, —C(=O)$R^{22}$, —C(=O)$OR^{21}$, —C(=O)N$R^{23}R^{24}$, heterocycloalkyl, or heteroaryl; wherein the heterocycloalkyl and heteroaryl are independently optionally substituted with one, two, or three $R^1$.

15. The compound of claim 1, or a pharmaceutically acceptable salt, solvate, or stereoisomer thereof wherein:
  $R^{20}$ is —C(=O)N$R^{23}R^{24}$.

16. The compound of claim 1, or a pharmaceutically acceptable salt, solvate, or stereoisomer thereof wherein:
  $R^{23}$ and $R^{24}$ are taken together with the nitrogen atom to which they are attached to form a heterocycloalkyl optionally substituted with one, two, or three oxo, halogen, —CN, —$OR^a$, —S(=O)$_2R^b$, —$NR^cR^d$, —S(=O)$_2NR^cR^d$, —C(=O)$R^b$, —OC(=O)$R^b$, —C(=O)$OR^a$, —OC(=O)$OR^a$, —C(=O)$NR^cR^d$, —OC(=O)$NR^cR^d$, —$NR^aC$(=O)$NR^cR^d$, —$NR^aC$(=O)$R^b$, $C_1$-$C_6$ alkyl, $C_1$-$C_6$ haloalkyl, or $C_1$-$C_6$ hydroxyalkyl.

17. The compound of claim 1, or a pharmaceutically acceptable salt, solvate, or stereoisomer thereof, selected from the group consisting of:

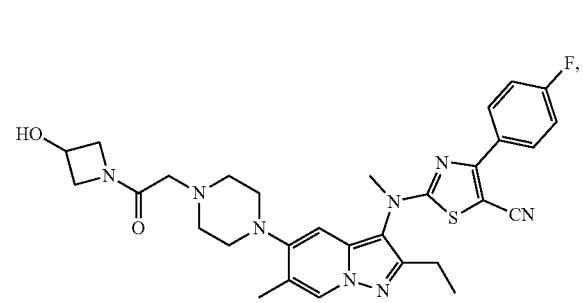

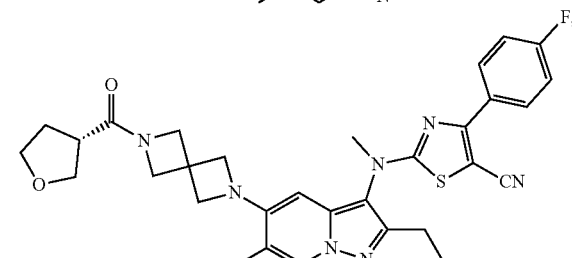

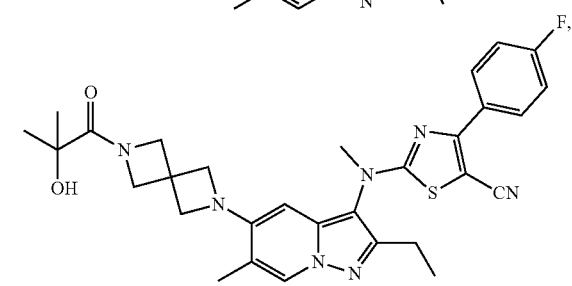

-continued

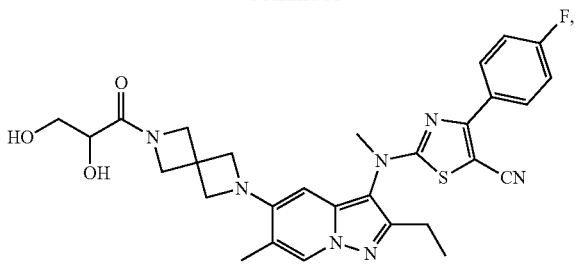

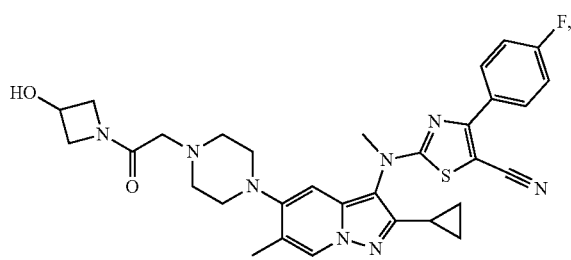

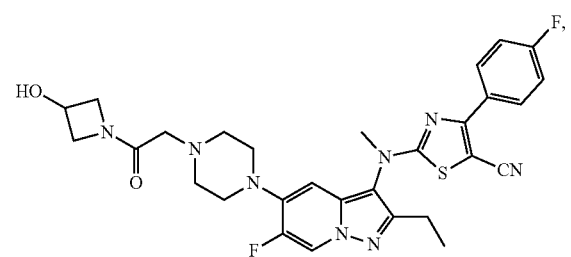

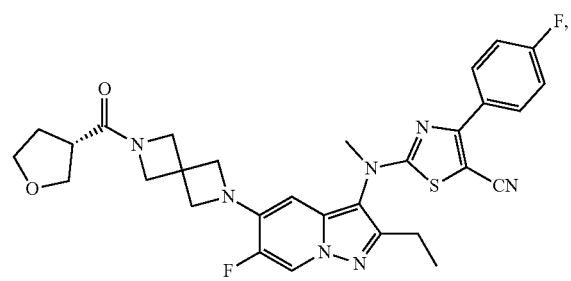 [SMILES: CN(c1nc(-c2ccc(F)cc2)c(C#N)s1)c1c(C2CC2)nn2cc(F)c(N3CC4(CN(C(=O)[C@H]5CCOC5)C4)C3)cc12]

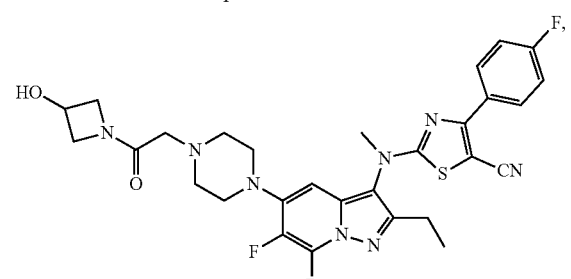

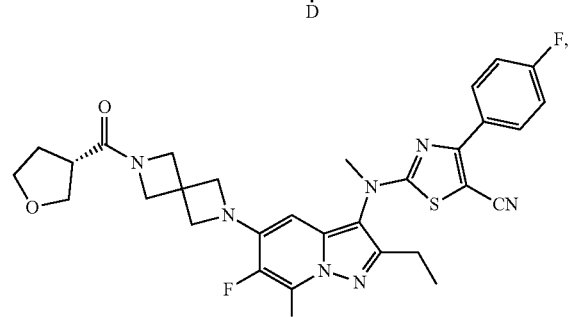

313
-continued

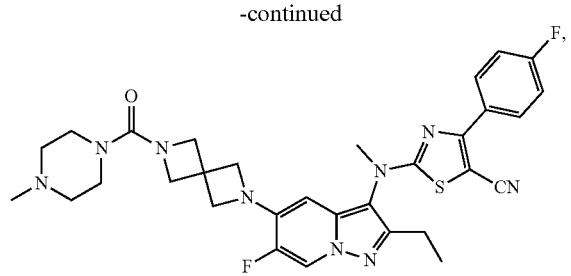

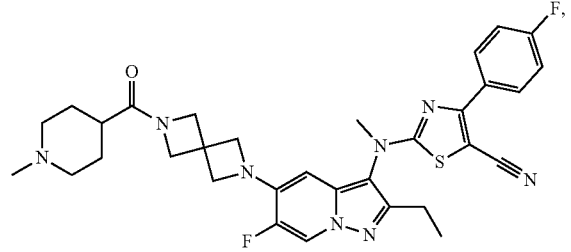

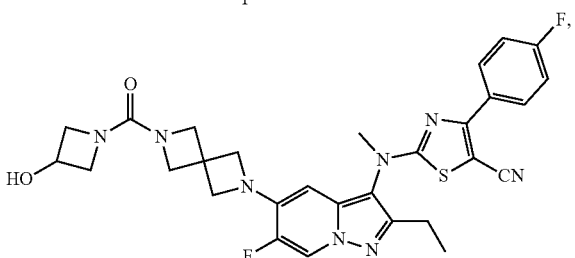

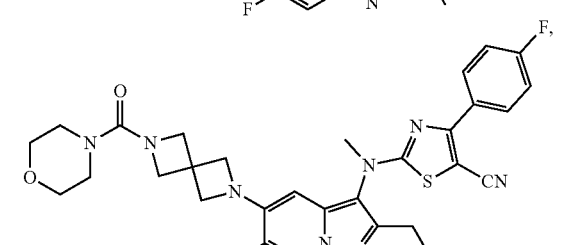

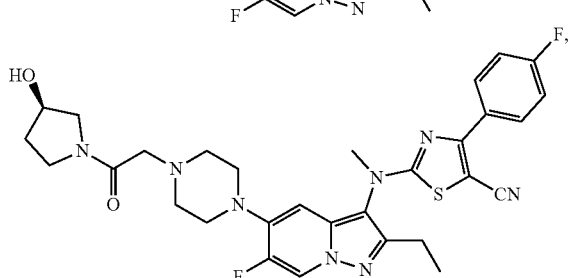

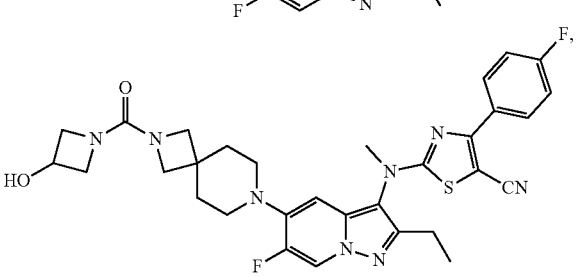

314
-continued

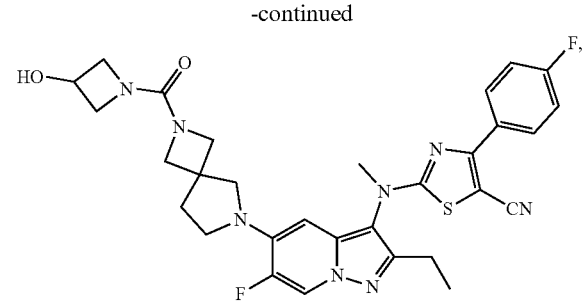

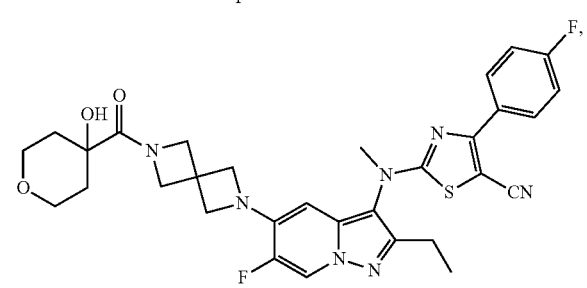

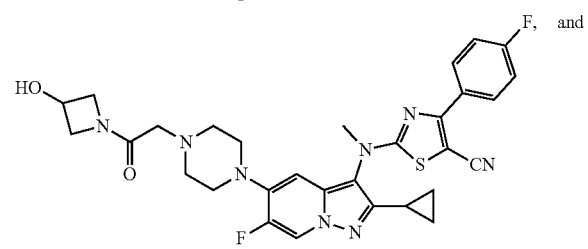

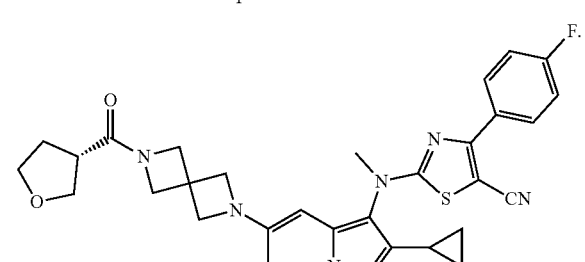

18. A pharmaceutical composition comprising a compound of claim 1, or a pharmaceutically acceptable salt, solvate, or stereoisomer thereof, and a pharmaceutically acceptable carrier or excipient.

19. A method of treating fibrotic diseases, cancers, inflammatory diseases, autoimmune diseases, respiratory diseases, cardiovascular diseases, neurological diseases, and metabolic diseases, the method comprising administering a therapeutic amount of a compound of claim 1.

20. A method of treating Idiopathic Pulmonary Fibrosis (IPF), scleroderma, or nonalcoholic steatohepatitis (NASH), the method comprising administering a therapeutic amount of a compound of claim 1.

\* \* \* \* \*

UNITED STATES PATENT AND TRADEMARK OFFICE
CERTIFICATE OF CORRECTION

PATENT NO. : 10,711,000 B2
APPLICATION NO. : 16/509300
DATED : July 14, 2020
INVENTOR(S) : Jin et al.

Page 1 of 1

It is certified that error appears in the above-identified patent and that said Letters Patent is hereby corrected as shown below:

In the Claims

Column 308; Lines 25-26; Claim 1, delete:
"-NR$^{21}$C(=)OR$^{21}$"
And replace with:
-- -NR$^{21}$C(=O)OR$^{21}$ --

Signed and Sealed this
Tenth Day of November, 2020

Andrei Iancu
*Director of the United States Patent and Trademark Office*